(12) United States Patent
Mulvihill et al.

(10) Patent No.: US 6,376,548 B1
(45) Date of Patent: Apr. 23, 2002

(54) ENHANCED PROPERTIED PESTICIDES

(75) Inventors: Mark Joseph Mulvihill, Ambler; Steven Howard Shaber, Horsham, both of PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/493,865

(22) Filed: Jan. 28, 2000

(51) Int. Cl.⁷ .................. A61K 31/16; C07D 241/00; C07D 413/00; C07D 231/00

(52) U.S. Cl. ............... 514/615; 514/252.1; 514/300; 514/317; 544/336; 544/398; 546/122; 546/192; 548/356.1; 548/531

(58) Field of Search ............... 514/613, 614, 514/615, 252.1, 300, 317; 560/123, 147; 548/356.1, 531; 546/122, 192; 544/336, 398

(56) References Cited

U.S. PATENT DOCUMENTS

| | | | |
|---|---|---|---|
| 4,760,057 A | 7/1988 | Alexander | 514/187 |
| 4,912,090 A | 3/1990 | Yani et al. | 514/30 |
| 4,916,230 A | 4/1990 | Alexander | 546/318 |
| 5,284,863 A | 2/1994 | Barnes et al. | 514/427 |
| 5,385,880 A | 1/1995 | Miyazaki et al. | 504/243 |
| 5,391,537 A | 2/1995 | Takabe et al. | 504/243 |
| 5,401,868 A | 3/1995 | Lund | 558/280 |
| 5,459,155 A | 10/1995 | Banks et al. | 514/395 |
| 5,684,018 A | 11/1997 | Alexander | |

FOREIGN PATENT DOCUMENTS

| | | |
|---|---|---|
| DE | 4343831 | 6/1995 |
| JP | 53-43571 | 11/1978 |
| JP | 54-1771 | 1/1979 |
| JP | 1-275565 | 11/1989 |
| WO | WO 91/00093 | 1/1991 |
| WO | WO 96/36613 | 11/1996 |
| WO | WO 98/16537 | 4/1998 |
| WO | WO 98/43970 | 10/1998 |
| WO | WO 99/35141 | 7/1999 |
| WO | WO 99/61017 | 12/1999 |
| WO | WO 00/29378 | 5/2000 |
| WO | WO 00/40582 | 7/2000 |

OTHER PUBLICATIONS

Harvey et. al., "The formation of anhydrides in the Mitsunobu reaction", Tetrahedron, (1997), vol. 53, No. 11, pp. 3933–3942.*

* cited by examiner

Primary Examiner—Richard L. Raymond
Assistant Examiner—Tamthom N. Truong
(74) Attorney, Agent, or Firm—Clark R. Carpenter

(57) ABSTRACT

This invention relates to enhanced propertied pesticides which can be used as fungicides, herbicides, insecticides, rodenticides or biocides, compositions comprising enhanced propertied pesticides, and the method of use of enhanced propertied pesticides and their compositions. It has been found that certain pesticidal compounds can be substituted with a moiety which comprises a substituent which enhances or changes the properties of the pesticidal compound. Additionally, some of the compounds of this invention may comprise two pesticidal components which can be different from one another. The invention relates also to pesticidal compositions comprising a pesticidal compound of this invention and an pesticidally acceptable carrier as well as methods of controlling a pest comprising applying a pesticidally effective amount of a composition comprising a compound of this invention and a pesticidally acceptable carrier to the pest, to the locus of the pest or to the growth medium of said pest.

22 Claims, No Drawings

ENHANCED PROPERTIED PESTICIDES

This invention relates to enhanced propertied pesticides which can be used as fungicides, herbicides, insecticides, rodenticides or biocides, compositions comprising enhanced propertied pesticides, and the method of use of enhanced propertied pesticides and their compositions. Although there are innumerable pesticides available for use, there is a continuing need for compounds which offer additional advantages to the end user.

Traditional pesticides may possess one or more deficiencies for the end user application. For instance, the pesticide may be slow acting and/or may have a limited spectrum of activity and/or may not possess a sufficiency of rain-fastness in the field to have a good residual activity. In order to be effective against the targeted pest, many pesticides must be applied in an undesirably high use rate from an environmental perspective. This can cause crop damage, especially with herbicides, because of lower than desired selectivity. Frequently the targeted pest builds up a resistance to the applied pesticide and requires larger amounts of it in order to be controlled. Many traditional tank mixes of pesticides cannot be accomplished because of their mutual incompatibility. Additionally, separately applied pesticide combinations arrive at the target pest at different rates, thus muting some of their mutual effectiveness. Some pesticides have adverse water solubilities for their intended application. Many pesticides are of the contact variety and hence possess no systemicity to completely protect the desired crop from the unwanted pest.

The compounds of the present invention overcome various deficiencies of traditional pesticides because they are substituted with a moiety comprising a substituent which enhances or changes the properties of the pesticidal compound. This substituent can be tailored in order to increase the rate of desired pesticidal action, to increase residual control against the pest, to decrease the overall use rate of the pesticide, increase the selectivity of the pesticide, change the water solubility of the pesticide, and increase the systemicity of the pesticide. Furthermore, the substituent on the pesticide may optionally comprise a pesticidal compound which may be the same as or different from the pesticidal compound on which the substituent occurs. This allows a combination of pesticides to be applied simultaneously as a single compound to the target pest or its locus. The application of such a compound provides many advantages such as a greater spectrum of activity against various pests, an attenuation of the build up of pest resistance since the pest is being controlled with two different modes of action, and the ability to combine two pesticidal compounds which would otherwise be incompatible with one another in a tank mix.

U.S. Pat. Nos. 4,916,230, 5,401,868, WO 99/61017 and WO 98/43970 all describe certain pharmaceutical compounds which are substituted with some of the moieties which are employed in the present invention. However, the use of these moieties to alter the properties of pesticides is neither disclosed nor suggested. JP 1275565 A2 and WO 9636613 A1 both disclose certain herbicidal compounds, some of which are substituted with some of the moieties which are employed in the present invention. However, the use of these moieties to alter the properties of herbicides and other pesticides is neither disclosed nor suggested.

In a first aspect of this invention, it has now been found that certain pesticidal compounds can be substituted with a moiety, said moiety comprising a substituent which enhances or changes the properties of the pesticidal compound.

The term "pesticidal compound" means any substance intended for preventing, destroying, repelling, or mitigating any insects, rodents, nematodes, fungi, or weeds, or any other forms of life declared to be pests; and any substance intended for use as a plant regulator, defoliant, or dessiccant. Therefore, "pesticidal compounds" include classes of compounds comprising fungicides, herbicides, insecticides, acaricides, nematicides, insect pheromones, rodenticides, biocides and microbicides.

The term "fungicide" means any agent which destroys fungi and/or inhibits their growth and is generally used on farm crops, preferably as a protective treatment rather than a curative treatment, by application to the surface of the plant in water suspensions or dusts before attack of a fungus. The term "herbicide" means any agent which destroys and/or inhibits the growth of undesirable plants and can be used in a preplanting, preemergence, postemergence or sterilant application. The term "insecticide" means any agent used primarily for the control of insects by preventing, destroying, repeling or mitigating any insects which may be present in any environment whatsoever. The term "acaricide" means any agent used primarily in the control of plant-feeding mites, especially spider mites. The term "nematicide" means any agent used primarily for the control of root-infesting nematodes on crop plants. The term "insect pheromone" means any agent used primarily for the control of behavioral responses of insects. The term "rodenticide" means any agent used primarily for the control of rodents, such as rats, mice, etc., and related animals such as rabbits. The term "biocide" means any agent used primarily to protect inanimate materials or industrial processes from biodeterioration by microorganisms and includes classes of compounds comprising microbicides, preservatives, disinfectants and antiseptics. The term "microbicide" includes compounds that are bactericides, fungicides, algicides, molluscicides and slimicides.

The fungicidal compounds which are suitable for use in this invention are those compounds which can be substituted with a moiety, said moiety comprising a substituent which enhances or changes the properties of the fungicidal compound, said fungicidal compounds said fungicidal compounds including, but not being limited to fenpropidin, triforine, piperalin, spiroxamine, cymoxanil, milneb, dazomat, dodine, dodicin, guazatine, iminoctadine, iminoctadine-tris, prothiocarb, flusulfamide, pyracarbolid, thifluzamide, ethoxabam, zarilamid, furametpyr, trichlamide, dicloran, bithionol, chloraniformethan, dichlorophen, benodanil, flutolanil, fenhexamid, mebenil, mepronil, tecloftalam, benomyl, carbendazim, chlorfenazole, cypendazole, debacarb, fuberidazole, thiabendazole, mecarbinzid, rabenzazole, diethofencarb, iprovalicarb, propamocarb, thiophanate, thiophanate-methyl, furophanate, azaconazole, bromuconazole, difenoconazole, epoxiconazole, etaconazole, fenbuconazole, fluotrimazole, fluquinconazole, flusilazole, furconazole, furconazole-cis, imibenconazole, myclobutanil, oxpoconazole, penconazole, propiconazole, quinconazole, sipconazole, tetraconazole, triadimefon, bitertanol, cyproconazole, diclobutrazole, diniconazole, flutriafol, hexaconazole, ipconazole, metconazole, tebuconazole, triadimenol, triticonazole, uniconazole, clotrimazole, fenapanil, imazalil, pefurazoate, prochloraz, triazoxide, triflumizole, fenamidone, glyodin, iprodione, azithiram, carbamorph, amobam, ferbam, mancozeb, maneb, metam, metiram, nabam, propineb, zineb, ziram, tecoram, cyclafuramid, fenfuram, methfuroxam, furcarbanil, aldimorph, dodemorph, fenpropimorph, tridemorph, fosetyl, fosetyl-aluminum, triamiphos, carboxin, oxycarboxin, drazoxolon, famoxadone, hymexazol, pencycuron, pyrifenox, pyroxychlor, pyroxyfur, fluazinam, bupirimate, cyprodinil, diflumetorim, dimethirimol, ethirimol, fenarimol, ferimzone, mepanipyrim, nuarimol, pyrimethanil, triarimol, quinoxyfen, 8-hydroxyquinoline sulfate, ethoxyquin, halacrinate, quinacetol, benquinox, metominostrobin, SSF-129, 2-[5-(4-chlorophenyl)-4-methyl-2,7-dioxa-3,6-diazaocta-3,5-dien-1-yl]-α-(methoxyimino)-N-methyl-benzeneacetamide, 2-[5-(4-fluorophenyl)-4-methyl-2,7-dioxa-3,6-diazaocta-3,5-dien-1-yl]-α-(methoxyimino)-N-methyl-benzeneacetamide, metsulfovax, methasulfocarb, anilazine, zoxamide, carpropamid, diclocymet, diclomezine, fenpiclonil, fludioxonil, silthiofam and AC382042. Preferred fungicides include, but are not limited to, fenpropidin, spiroxamine, cymoxanil, dodine, flusulfamide, thifluzamide, ethoxabam, zarilamid, furametpyr, dicloran, flutolanil, fenhexamid, benomyl, carbendazim, fuberidazole, thiabendazole, diethofencarb, propamocarb, thiophanate-methyl, iprovalicarb, epoxiconazole, flusilazole, propiconazole, penconazole, tebuconazole, cyproconazole, hexaconazole, triadimenol, fenbuconazole, myclobutanil, mancozeb, maneb, propineb, methfuroxam, fenamidone, iprodione, fenpropimorph, fosetyl, fosetyl-aluminum, carboxin, oxycarboxin, famoxadone, pencycuron, fluazinam, cyprodinil, fenarimol, ferimzone, pyrimethanil, quinoxyfen, 8-hydroxyquinoline sulfate, metominostrobin, SSF-129, 2-[5-(4-chlorophenyl)-4-methyl-2,7-dioxa-3,6-diazaocta-3,5-dien-1-yl]-α-(methoxyimino)-N-methyl-benzeneacetamide, 2-[5-(4-fluorophenyl)-4-methyl-2,7-dioxa-3,6-diazaocta-3,5-dien-1-yl]-α-(methoxyimino)-N-methyl-benzeneacetamide, metsulfovax, zoxamide, capropamid, diclocymet, methasulfocarb, fenpiclonil and fludioxonil.

The herbicidal compounds which are suitable for use in this invention are those compounds which can be substituted with a moiety, said moiety comprising a substituent which enhances or changes the properties of the herbicidal compound, said herbicidal compounds including, but not being limited to, pronamide, diflufenican, flumetsulam, propanil, clopyralid, asulam, chlorpropham, desmedipham, phenmedipham, sulcotrione, sethoxydim, trialkoxydim, trifluralin, hexazinone, pendimethalin, dinoseb, acifluorfen, aclonifen, fomesafen, imazaquin, imazethapyr, isoxaben, glyphosate, glyphosate-isopropylammonium, glyphosate-trimethylsulfonium, glufosinate, glufosinate-ammonium, 2,4-D, 2,4-DB, MCPA, fenoprop, fenoxaprop, fluazifop, haloxyfop, chloridazon, triclopyr, atrazine, terbuthylazine, terbumeton, ametryn, metribuzin, amitrole, bentazon, bromacil, chlorotoluron, diuron, fluometuron, isoproturon, linuron, chlorimuron-ethyl, chlorsulfuron, metsulfuron-methyl, nicosulfuron, bentazone, pyrazosulfuron ethyl, rimsufuron, thifensulfuron methyl, tribenuron methyl, bromoxynil, dicamba, metamitron, fluroxypyr-meptyl, clethodim, picloram, fomesafen and phenmedipham. Preferred herbicides include bromoxynil, 2,4-D, glyphosate, glyphosate-isopropylammonium, glyphosate-trimethylsulfonium, glufosinate, triclopyr, clopyralid, pronamide, diflufenican, flumetsulam, propanil, clopyralid, desmedipham, phenmedipham, sulcotrione, sethoxydim, trialkoxydim, trifluralin, hexazinone, pendimethalin, acifluorfen imazaquin, imazethapyr, fenoxaprop, fluazifop, atrazine, terbuthylazine, ametryn, metribuzin, amitrole, bentazon, bromacil, chlorotoluron, diuron, fluometuron, isoproturon, trifluralin, hexazinone, pendimethalin, chlorsulfuron, nicosulfuron, bentazone and rimsufuron.

The insecticidal compounds which are suitable for use in this invention are those compounds which can be substituted with a moiety, said moiety comprising a substituent which enhances or changes the properties of the insecticidal compound, said insecticidal compounds including, but not being limited to, chlorfluazuron, diflubenzuron, flucycloxuron, flufenoxuron, hexaflumuron, lufenuron, teflubenzuron, triflumuron, novaluron, aldicarb, bendiocarb, BPMC, carbaryl, carbofuran, cartap, ethiofencarb, fenoxycarb, formetanate, isoprocarb, methiocarb, methomyl, oxamyl, phosphocarb, promecarb, propoxur, tolfenpyrad, xylyl methylcarbamate, xylylcarb, abamectin, enamectin benzoate, milbemectin, acephate, dimethoate, fenamiphos, isofenphos, methamidophos, monocrotophos, omethoate, vamidothion, clothianidin, NTN-32692, imidacloprid, nidinotefuran, nitenpyram, oxamyl, chromafenozide, halofenozide, methoxyfenozide, tebufenozide, fluazuron, cyromazine, diafenthiuron, dicofol, fipronil, hexythiazox, pymetrozine, pyrimidifen, tebufenpyrad, carbofuran and fluvalinate. Preferred insecticides include, but are not limited to, abamectin, acephate, carbaryl, chlorfluazuron, chromafenozide, diflubenzuron, dimethoate, fipronil, fluvalinate, halofenozide, imidacloprid, methoxyfenozide and tebufenozide.

The acaricidal compounds which are suitable for use in this invention are those compounds which can be substituted with a moiety, said moiety comprising a substituent which enhances or changes the properties of the acaricidal compound, said acaricidal compounds including, but not being limited to, abamectin, aldicarb, bifenazate, bromopropylate, chlorobenzilate, chloropropylate, diafenthiuron, dicofol, dimethoate, fenothiocarb, fluazuron, flucycloxuron, flufenoxuron, fluvalinate, formetanate, hexythiazox, lufenuron, methamidophos, methiocarb, methomyl, milbemectin, monocrotophos, omethoate, oxamyl, pyrimidifen, tebufenpyrad, tolfenpyrad and vamidothion. Preferred miticides include, but are not limited to, bifenazate, dicofol, fluazuron and pyrimidifen.

The nematicidal compounds which are suitable for use in this invention are those compounds which can be substituted with a moiety, said moiety comprising a substituent which enhances or changes the properties of the nematicidal compound, said nematicidal compounds including, but not being limited to, aldicarb, fenamiphos, oxamyl and phosphocarb.

The insect pheromone compounds which are suitable for use in this invention are those compounds which can be substituted with a moiety, said moiety comprising a substituent which enhances or changes the properties of the insect pheromone compound, said pheromone compounds including, but not being limited to, (E,E)-8,10-dodecadienol, dodecane-1-ol, (E)-11-tetradecen-1-ol, (Z)-9-tetradecen-1-ol, (Z)-11-hexadecene-1-ol.

The rodenticidal compounds which are suitable for use in this invention are those compounds which can be substituted with a moiety, said moiety comprising a substituent which enhances or changes the properties of the rodenticidal compound, said rodenticidal compounds including, but not being limited to, difenacoum, brodifacoum, bromadiolone, coumatetrayl and warfarin. Preferred rodenticides include, but are not limited to, bromadiolone and warfarin.

The biocidal and microbicidal compounds which are suitable for use in this invention are those compounds which can be substituted with a moiety, said moiety comprising a substituent which enhances or changes the properties of the biocidal or microbicidal compound, said biocidal and microbicidal compounds including, but not being limited to, bronopol, 2-bromo-2-nitropropan-1-ol, 4,4-dimethyl-1,3-oxazolidine, 1-aza-3,7-dioxa-5-methylol-(3,3,0)-bicyclooctane, N-hydroxymethylchloroacetamide, 1-monomethylol-5,5-dimethylhydantoin, 1,3-dimethylol-5,5-dimethylhydantoin, 4-chloro-3,5-dimethylphenol, bis-(2-hydroxy-5-chlorophenyl)sulfide, dichlorophene, 2,4,4'-trichloro-2'-hydroxydiphenyl ether, 2-chloroacetamide, 2-bromoacetamide, 2-iodoacetamide, 2,2-dibromo-2-cyanoacetamide, benzisothiazolone, 4-isothiazolin-3-one, 5-chloro-4-isothiazolin-3-one, 4,5-dichloro-4-isothiazolin-3-one, 3-iodopropargyl-N-butylcarbamate, dodecylamine, parabens (esters of p-hydroxybenzoic acid), chlorhexidene (1,6-di(4-chlorophenyl-diguanide)hexane), 4,4'-dichloro-2-hydroxydiphenyl ether, salicylic acid and pyrithiones (2-mercapto derivatives of pyridine-N-oxides). Preferred biocidal and microbicidal compounds include, but are not limited to, 2-bromo-2-nitropropan-1-ol, 4,4-dimethyl-1,3-oxazolidine, 1,3-dimethylol-5,5-dimethylhydantoin, 4-chloro-3,5-dimethylphenol, salicylic acid and pyrithiones.

In a second aspect of this invention, it has been found that certain pesticidal compounds can be substituted with a moiety, said moiety comprising a substituent which comprises a second pesticidal component which may be the same as or different from the first pesticidal compound. In other words, some of the compounds of this invention may comprise two pesticidal components which can be different from one another. The components of the pesticidal compounds of this second aspect of this invention may be selected from the compounds listed hereinbefore for fungicides, herbicides, insecticides, acaricides, rodenticides, biocides and microbicides. When two pesticidal components are part of the pesticidal compounds of this invention, they may be independently selected from the various pesticidal classes noted above. For example, two insecticidal components may be selected in order to broaden the spectrum of activity against insects or to prevent resistance to one or the other insecticidal components. In another example, a fungicidal component and an insecticidal component may be selected in order to simultaneously prevent foliar damage by fungus and insects. In still another example, an insecticidal component and a herbicidal component may be selected in order to simultaneously enhance the locus of the desired growing plant by attenuating undesired insect species and undesired vegetation. The various combinations of pesticidal components which comprise the pesticidal compounds of this invention are advantageously selected by one skilled in the art using criteria such as rate of application, timing of application and the pest for which eradication is desired In both the first and second aspects of this invention, the pesticidal compounds are meant to encompass the pesticidally acceptable salts, isomers and enantiomers thereof.

Another aspect of this invention relates to pesticidal compositions comprising a pesticidal compound of this invention and an pesticidally acceptable carrier. Preferably, the composition contains from about 0.1% to about 99% by weight of said compound.

Still another aspect of this invention relates to a method of controlling a pest comprising applying a pesticidally effective amount of a compound or a composition comprising a compound of this invention and a pesticidally acceptable carrier to the pest, to the locus of the pest or to the growth medium of said pest.

More specifically, this invention relates to a pesticidal compound of formula (I)

$$Z^1(X^1)_m-\overset{\overset{G^{10}}{\|}}{C}-G^{11}-A \quad (I)$$

wherein

A is $$\underset{R^2}{\overset{R^1}{|}}C-(G^{21}-\overset{\overset{G^{20}}{\|}}{C})_t-(X^2)_q Z^2 \quad \text{or} \quad \underset{G^{21}\diagdown_{G^{20}}}{\overset{H\diagdown^{(CH_2)_n}\diagup R^1}{\diagup}_{R^2}}$$

$G^{10}$, $G^{11}$ and $G^{20}$ are each independently an oxygen atom or a sulfur atom, $G^{21}$ is an oxygen atom, a sulfur atom or $NR^3$, $X^1$ is an oxygen atom, a sulfur atom or a nitrogen atom attached to $Z^1$, $X^2$ is an oxygen atom, a sulfur atom, a nitrogen atom or a carbon atom attached to $Z^2$, m, q and t are each independently 0 or 1, n is 1 or 2, $Z^1(X^1)_m$ is a pesticidal moiety when m is 1 wherein $Z^1(X^1)_m$—H represents the pesticide, $Z^2(X^2)_q(C(=G^{20})G^{21})_t$ is a pesticidal moiety when q is 1 wherein $Z^2(X^2)_q(C(=G^{20})G^{21})_t$ or $Z^2(X^2)_q(C(=G^{20})G^{21})_t$—H represents the pesticide, $Z^1(X^1)_m$, when m is 0, is a hydrogen atom, halo, alkyl, alkylcarbonyloxyalkyl, alkylcarbonyl, hydroxyalkyl, alkylsulfonylalkyl, acetylaminoalkyl, haloalkyl, alkenyl, acetylaminoalkenyl, haloalkenyl, alkynyl, haloalkynyl, cycloalkyl, cycloalkenyl, carboxycycloalkyl, carboxycycloalkenyl, cycloalkylalkyl, cycloalkylalkenyl, cycloalkenylalkyl, cycloalkenylalkenyl, cycloalkylalkynyl, cycloalkenylalkynyl, carboxycycloalkylalkyl, carboxycycloalkylalkenyl, carboxycycloalkenylalkyl, carboxycycloalkenylalkenyl, carboxycycloalkylalkynyl, carboxycycloalkenylalkynyl, heterocyclyl, heterocyclylalkyl, heterocyclylalkenyl, heterocyclylalkynyl, alkoxyalkyl, alkoxyalkoxyalkyl, alkoxyalkenyl, alkoxyalkynyl, alkoxycarbonylalkyl, alkoxycarbonylalkenyl, alkoxycarbonylalkynyl, haloalkoxyalkyl, haloalkoxyalkenyl, haloalkoxyalkynyl, alkylthioalkyl, alkylthioalkenyl, alkylthioalkynyl, haloalkylthioalkyl, haloalkylthioalkenyl, haloalkylthioalkynyl, $NR^3R^4$, $SO_2NR^3R^4$, $OR^3$, $S(O)_jR^3$, carboxyalkyl, carboxyalkenyl, carboxyalkynyl, aryl, aryl substituted with one or more substituents independently selected from halo, nitro, hydroxy, cyano, thiocyanato, alkyl, alkylsulfonylalkyl, alkenyl, alkynyl, haloalkyl, haloalkenyl, haloalkynyl, alkoxy, haloalkoxy, $SO_2NR^3R^4$ and $NR^3R^4$, aralkyl, aralkenyl, aralkynyl, arcycloalkyl, aroxyalkyl, or aralkyl, aralkenyl, aralkynyl, arcycloalkyl, aroxyalkyl substituted with one or more substituents independently selected from halo, nitro, hydroxy, cyano, alkyl, cycloalkyl, alkenyl, alkynyl, haloalkyl, haloalkenyl, haloalkynyl, alkoxy, haloalkoxy, $SO_2NR^3R^4$ and $NR^3R^4$, heteroaryl, heteroaryl substituted with one or more substituents independently selected from halo, nitro, hydroxy, cyano, alkyl, alkenyl, alkynyl, haloalkyl, haloalkenyl, haloalkynyl, alkoxy, haloalkoxy, $SO_2NR^3R^4$ and $NR^3R^4$, heteroaralkyl, heteroaralkenyl, heteroaralkynyl, or heteroaralkyl, heteroaralkenyl, heteroaralkynyl substituted with one or more substituents independently selected from halo, hydroxy, cyano, nitro, alkyl, alkenyl, alkynyl, haloalkyl, haloalkenyl, haloalkynyl, alkoxy, haloalkoxy, $SO_2NR^3R^4$ and $NR^3R^4$, wherein j is 0, 1 or 2, $Z^2(X^2)_q$ is a hydrogen atom, alkyl, alkylcarbonyloxyalkyl, alkylcarbonyl, hydroxyalkyl, alkylsulfonylalkyl, acetylaminoalkyl, haloalkyl, alkenyl, acetylaminoalkenyl, haloalkenyl, alkynyl, haloalkynyl, cycloalkyl, cycloalkenyl, carboxycycloalkyl, carboxycycloalkenyl, cycloalkylalkyl, cycloalkylalkenyl, cycloalkenylalkyl, cycloalkenylalkenyl, cycloalkylalkynyl, cycloalkenylalkynyl, carboxycycloalkylalkyl, carboxycycloalkylalkenyl, carboxycycloalkenylalkyl, carboxycycloalkenylalkenyl, carboxycycloalkylalkynyl, carboxycycloalkenylalkynyl, heterocyclyl, heterocyclylalkyl, heterocyclylalkenyl, heterocyclylalkynyl, alkoxyalkyl, alkoxyalkoxyalkyl, alkoxyalkenyl, alkoxyalkynyl, alkoxycarbonylalkyl, alkoxycarbonylalkenyl, alkoxycarbonylalkynyl, haloalkoxyalkyl, haloalkoxyalkenyl, haloalkoxyalkynyl, alkylthioalkyl, alkylthioalkenyl, alkylthioalkynyl, haloalkylthioalkyl, haloalkylthioalkenyl, haloalkylthioalkynyl, $NR^3R^4$, $SO_2NR^3R^4$, carboxyalkyl, carboxyalkenyl, carboxyalkynyl, dialkoxyphosphorylalkyl, aryl, aryl substituted with one or more substituents independently selected from halo, nitro, hydroxy, cyano, thiocyanato, alkyl, alkylsulfonylalkyl, alkenyl, alkynyl, haloalkyl, haloalkenyl, haloalkynyl, alkoxy, haloalkoxy, $SO_2NR^3R^4$ and $NR^3R^4$, aralkyl, aralkenyl, aralkynyl, arcycloalkyl, aroxyalkyl, or aralkyl, aralkenyl, aralkynyl, arcycloalkyl, aroxyalkyl substituted with one or more substituents independently selected from halo, nitro, hydroxy, cyano, alkyl, cycloalkyl, alkenyl, alkynyl, haloalkyl, haloalkenyl, haloalkynyl, alkoxy, haloalkoxy, $SO_2NR^3R^4$ and $NR^3R^4$, heteroaryl, heteroaryl substituted with one or more substituents independently selected from halo, nitro, hydroxy, cyano, alkyl, alkenyl, alkynyl, haloalkyl, haloalkenyl, haloalkynyl, alkoxy, haloalkoxy, $SO_2NR^3R^4$ and $NR^3R^4$, heteroaralkyl, heteroaralkenyl, heteroaralkynyl, or heteroaralkyl, heteroaralkenyl, heteroaralkynyl substituted with one or more substituents independently selected from halo, hydroxy, nitro, cyano, alkyl, alkenyl, alkynyl, haloalkyl, haloalkenyl, haloalkynyl, alkoxy, haloalkoxy, $SO_2NR^3R^4$ and NR3R$^4$, when q is 0 and t is 1, $Z^2(X^2)_q$ halo, $NR^3R^4$, $\{(NR^3R^4R^5)^+M^-\}$, $OR^3$, $S(O)_jR^3$ or $SO_2NR^3R^4$ when both q and t are 0 wherein $M^-$ is halo, hydroxy, alkoxy or the anion of a carboxylic acid and j is 0, 1 or 2, $R^1$ and $R^2$ are each independently a hydrogen atom, alkyl, alkenyl, alkynyl, alkoxyalkyl, alkoxyalkenyl, alkoxyalkynyl, alkylthioalkyl, alkylthioalkenyl, alkylthioalkynyl, carboxy, carboxyalkyl, carboxyalkenyl, carboxyalkynyl, alkoxycarbonyl, alkoxycarbonylalkyl, alkoxycarbonylalkenyl, alkoxycarbonylalkynyl, alkylcarbonyl, alkenylcarbonyl, alkynylcarbonyl, cycloalkyl, cycloalkenyl, cycloalkylalkyl, cycloalkenylalkyl, cycloalkylalkenyl, cycloalkenylalkenyl, cycloalkylalkynyl, cycloalkenylalkynyl, heterocyclyl, heterocyclylalkyl, heterocyclylalkenyl, heterocyclylalkynyl, aryl, aryl substituted with one or more substituents independently selected from halo, hydroxy, cyano, nitro, alkyl, alkenyl, alkynyl, haloalkyl, haloalkenyl, haloalkynyl, alkoxy, haloalkoxy, $SO_2NR^3R^4$ and $NR^3R^4$, aralkyl, aralkenyl, aralkynyl, or aralkyl, aralkenyl, aralkynyl substituted with one or more substituents independently selected from halo, hydroxy, cyano, nitro, alkyl, alkenyl, alkynyl, haloalkyl, haloalkenyl, haloalkynyl, alkoxy, haloalkoxy, $SO_2NR^3R^4$ and $NR^3R^4$, heteroaryl, or heteroaryl substituted with one or more substituents independently selected from halo, hydroxy, cyano, nitro, alkyl, alkenyl, alkynyl, haloalkyl, haloalkenyl, haloalkynyl, alkoxy, haloalkoxy, $SO_2NR^3R^4$ and $NR^3R^4$, heteroaralkyl, heteroaralkenyl, heteroaralkynyl, or heteroaralkyl, heteroaralkenyl, heteroaralkynyl substituted with one or more substituents independently selected from halo, cyano, hydroxy, nitro, alkyl, alkenyl, alkynyl, haloalkyl, haloalkenyl, haloalkynyl, alkoxy, haloalkoxy, $SO_2NR^3R^4$ and $NR^3R^4$, or $R^1$ and $R^2$ taken together with the carbon atom to which they are attached form a 5–7 membered saturated or unsaturated ring, or $R^1$ may be a pesticidal moiety if $R^2$ is a hydrogen atom, $R^3$, $R^4$ and $R^5$ are each independently a hydrogen atom, alkyl, cycloalkyl, cycloalkenyl, cycloalkylalkyl, cycloalkylalkenyl, cycloalkylalkynyl, cycloalkenylalkyl, cycloalkenylalkenyl, cycloalkenylalkynyl, heterocyclyl, heterocyclylalkyl, heterocyclylalkenyl, heterocyclylalkynyl, alkoxyalkyl, alkenyl, alkynyl, or alkyl, cycloalkyl, cycloalkenyl, cycloalkylalkyl, cycloalkylalkenyl, cycloalkylalkynyl, cycloalkenylalkyl, cycloalkenylalkenyl, cycloalkenylalkynyl, heterocyclyl, heterocyclylalkyl, heterocyclylalkenyl, heterocyclylalkynyl, alkoxyalkyl, alkenyl or alkynyl substituted with one or more halo, aryl, aralkyl, aralkenyl, aralkynyl, or aryl, aralkyl, aralkenyl, aralkynyl substituted with one or more substituents independently selected from halo, alkyl, alkenyl, alkynyl, haloalkyl, haloalkenyl, haloalkynyl, alkoxy and haloalkoxy, heteroaryl, heteroaralkyl, heteroaralkenyl, heteroaralkynyl, or heteroaryl, heteroaralkyl, heteroaralkenyl, heteroaralkynyl substituted with one or more substituents independently selected from halo, alkyl, alkenyl, alkynyl, haloalkyl, haloalkenyl, haloalkynyl, alkoxy and haloalkoxy, or $R^3$ and $R^4$ taken together with the nitrogen atom to which they are attached form a 5- or 6-membered saturated or unsaturated heterocyclic ring, provided that when both m and q are 0, A is

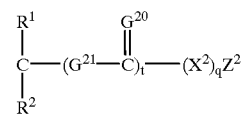

and $R^1$ is a pesticidal moiety, or the pesticidally acceptable salts, isomers and enantiomers thereof.

The term "alkyl" includes both branched and straight chain alkyl groups. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl, tetradecyl, hexadecyl, octadecyl, eicosyl and the like.

The term "halo" refers to fluoro, chloro, bromo or iodo.

The term "haloalkyl" refers to an alkyl group substituted with one or more halo groups, for example chloromethyl, 2-bromoethyl, 3-iodopropyl, trifluoromethyl, perfluoropropyl, 8-chlorononyl and the like.

The term "cycloalkyl" refers to a cyclic aliphatic ring structure, optionally substituted with alkyl, hydroxy and halo, such as cyclopropyl, methylcyclopropyl, cyclobutyl, 2-hydroxycyclopentyl, cyclohexyl, 4-chlorocyclohexyl, cycloheptyl, cyclooctyl and the like.

The term "alkylcarbonyloxyalkyl" refers to an ester moiety, for example acetoxymethyl, n-butyryloxyethyl and the like.

The term "alkynylcarbonyl" refers to an alkynylketo functionality, for example propynoyl and the like.

The term "hydroxyalkyl" refers to an alkyl group substituted with one or more hydroxy groups, for example hydroxymethyl, 2,3-dihydroxybutyl and the like.

The term "alkylsulfonylalkyl" refers to an alkyl group substituted with an alkylsulfonyl moiety, for example mesylmethyl, isopropylsulfonylethyl and the like.

The term "alkylsulfonyl" refers to a sulfonyl moiety substituted with an alkyl group, for example mesyl, n-propylsulfonyl and the like.

The term "acetylaminoalkyl" refers to an alkyl group substituted with an amide moiety, for example acetylaminomethyl and the like.

The term "acetylaminoalkenyl" refers to an alkenyl group substituted with an amide moiety, for example 2-(acetylamino)vinyl and the like.

The term "alkenyl" refers to an ethylenically unsaturated hydrocarbon group, straight or branched chain, having 1 or 2 ethylenic bonds, for example vinyl, allyl, 1-butenyl, 2-butenyl, isopropenyl, 2-pentenyl and the like.

The term "haloalkenyl" refers to an alkenyl group substituted with one or more halo groups.

The term "cycloalkenyl" refers to a cyclic aliphatic ring structure, optionally substituted with alkyl, hydroxy and halo, having 1 or 2 ethylenic bonds such as methylcyclopropenyl, trifluoromethylcyclopropenyl, cyclopentenyl, cyclohexenyl, 1,4-cyclohexadienyl and the like.

The term "alkynyl" refers to an unsaturated hydrocarbon group, straight or branched, having 1 or 2 acetylenic bonds, for example ethynyl, propargyl and the like.

The term "haloalkynyl" refers to an alkynyl group substituted with one or more halo groups.

The term "alkylcarbonyl" refers to an alkylketo functionality, for example acetyl, n-butyryl and the like.

The term "alkenylcarbonyl" refers to an alkenylketo functionality, for example, propenoyl and the like.

The term "aryl" refers to phenyl or naphthyl which may be optionally substituted. Typical aryl substituents include, but are not limited to, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl and 2-iodo-4-methylphenyl.

The term "heteroaryl" refers to a substituted or unsubstituted 5 or 6 membered unsaturated ring containing one, two or three heteroatoms, preferably one or two heteroatoms independently selected from oxygen, nitrogen and sulfur or to a bicyclic unsaturated ring system containing up to 10 atoms including one heteroatom selected from oxygen, nitrogen and sulfur. Examples of heteroaryls include, but is not limited to, 2-, 3- or 4-pyridinyl, pyrazinyl, 2-, 4-, or 5-pyrimidinyl, pyridazinyl, triazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl and isoquinolyl. The heterocyclic ring may be optionally substituted with up to two substituents.

The term "aralkyl" is used to describe a group wherein the alkyl chain can be branched or straight chain with the aryl portion, as defined hereinbefore, forming a terminal portion of the aralkyl moiety. Examples of aralkyl groups include, but are not limited to, optionally substituted benzyl, phenethyl, phenpropyl and phenbutyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)ethyl, 2-(2,4-dichlorophenyl)ethyl, 2-(3,5-dimethoxyphenyl)ethyl, 3-phenylpropyl, 3-(3-chlorophenyl)propyl, 3-(2-methylphenyl)propyl, 3-(4-methoxyphenyl)propyl, 3-(4-(trifluoromethyl)phenyl)propyl, 3-(2,4-dichlorophenyl)propyl, 4-phenylbutyl, 4-(4-chlorophenyl)butyl, 4-(2-methylphenyl)butyl, 4-(2,4-dichlorophenyl)butyl, 4-(2-methoxphenyl)butyl and 10-phenyldecyl.

The term "arcycloalkyl" is used to describe a group wherein the aryl group is attached to a cycloalkyl group, for example phenylcyclopentyl and the like.

The term "aralkenyl" is used to describe a group wherein the alkenyl chain can be branched or straight chain with the aryl portion, as defined hereinbefore, forming a terminal portion of the aralkenyl moiety, for example styryl (2-phenylvinyl), phenpropenyl and the like.

The term "aralkynyl" is used to describe a group wherein the alkynyl chain can be branched or straight chain with the aryl portion, as defined hereinbefore, forming a terminal portion of the aralkynyl moiety, for example 3-phenyl-1-propynyl and the like.

The term "aroxy" is used to describe an aryl group attached to a terminal oxygen atom. Typical aroxy groups include phenoxy, 3,4-dichlorophenoxy and the like.

The term "aroxyalkyl" is used to describe a group wherein an alkyl group is substituted with an aroxy group, for example pentafluorophenoxymethyl and the like.

The term "heteroaroxy" is used to describe an heteroaryl group attached to a terminal oxygen atom. Typical heteroaroxy groups include 4,6-dimethoxypyrimidin-2-yloxy and the like.

The term "heteroaralkyl" is used to describe a group wherein the alkyl chain can be branched or straight chain with the heteroaryl portion, as defined hereinbefore, forming a terminal portion of the heteroaralkyl moiety, for example 3-furylmethyl, thenyl, furfuryl and the like.

The term "heteroaralkenyl" is used to describe a group wherein the alkenyl chain can be branched or straight chain with the heteroaryl portion, as defined hereinbefore, forming a terminal portion of the heteroaralkenyl moiety, for example 3-(4-pyridyl)-1-propenyl.

The term "heteroaralkynyl" is used to describe a group wherein the alkynyl chain can be branched or straight chain with the heteroaryl portion, as defined hereinbefore, forming a terminal portion of the heteroaralkynyl moiety, for example 4-(2-thienyl)-1-butynyl.

The term "heterocyclyl" refers to a substituted or unsubstituted 5 or 6 membered saturated ring containing one, two or three heteroatoms, preferably one or two heteroatoms independently selected from oxygen, nitrogen and sulfur or to a bicyclic ring system containing up to 10 atoms including one heteroatom selected from oxygen, nitrogen and sulfur wherein the ring containing the heteroatom is saturated. Examples of heterocyclyls include, but are not limited to, tetrahydrofuryl, pyrrolidinyl, piperidinyl, tetrahydropyranyl, morpholinyl, piperazinyl, dioxolanyl, dioxanyl, indolinyl and 5-methyl-6-chromanyl.

The term "heterocyclylalkyl" is used to describe a group wherein the alkyl chain can be branched or straight chain with the heterocyclyl portion, as defined hereinabove, forming a terminal portion of the heterocyclylalkyl moiety, for example 3-piperidinylmethyl and the like.

The term "heterocyclylalkenyl" is used to describe a group wherein the alkenyl chain can be branched or straight chain with the heterocyclyl portion, as defined hereinbefore, forming a terminal portion of the heterocyclylalkenyl moiety, for example 2-morpholinyl-1-propenyl.

The term "heterocyclylalkynyl" is used to describe a group wherein the alkynyl chain can be branched or straight chain with the heterocyclyl portion, as defined hereinbefore, forming a terminal portion of the heterocyclylalkynyl moiety, for example 2-pyrrolidinyl-1-butynyl.

The term "carboxyalkyl" includes both branched and straight chain alkyl groups as defined hereinbefore attached to a carboxy (—COOH) group.

The term "carboxyalkenyl" includes both branched and straight chain alkenyl groups as defined hereinbefore attached to a carboxy group.

The term "carboxyalkynyl" includes both branched and straight chain alkynyl groups as defined hereinbefore attached to a carboxy group.

The term "carboxycycloalkyl" refers to a carboxy group attached to a cyclic aliphatic ring structure as defined hereinbefore.

The term "carboxycycloalkenyl" refers to a carboxy group attached to a cyclic aliphatic ring structure having 1 or 2 ethylenic bonds as defined hereinbefore.

The term "cycloalkylalkyl" refers to a cycloalkyl group as defined hereinbefore attached to an alkyl group, for example cyclopropylmethyl, cyclohexylethyl and the like.

The term "cycloalkylalkenyl" refers to a cycloalkyl group as defined hereinbefore attached to an alkenyl group, for example cyclohexylvinyl, cycloheptylallyl and the like.

The term "cycloalkylalkynyl" refers to a cycloalkyl group as defined hereinbefore attached to an alkynyl group, for example cyclopropylpropargyl, 4-cyclopentyl-2-butynyl and the like.

The term "cycloalkenylalkyl" refers to a cycloalkenyl group as defined hereinbefore attached to an alkyl group, for example 2-(cyclopenten-1-yl)ethyl and the like.

The term "cycloalkenylalkenyl" refers to a cycloalkenyl group as defined hereinbefore attached to an alkenyl group, for example 1-(cyclohexen-3-yl)allyl and the like.

The term "cycloalkenylalkynyl" refers to a cycloalkenyl group as defined hereinbefore attached to an alkynyl group, for example 1-(cyclohexen-3-yl)propargyl and the like.

The term "carboxycycloalkylalkyl" refers to a carboxy group attached to the cycloalkyl ring portion of a cycloalkylalkyl group as defined hereinbefore.

The term "carboxycycloalkylalkenyl" refers to a carboxy group attached to the cycloalkyl ring portion of a cycloalkylalkenyl group as defined hereinbefore.

The term "carboxycycloalkylalkynyl" refers to a carboxy group attached to the cycloalkyl ring portion of a cycloalkylalkynyl group as defined hereinbefore.

The term "carboxycycloalkenylalkyl" refers to a carboxy group attached to the cycloalkenyl ring portion of a cycloalkenylalkyl group as defined hereinbefore.

The term "carboxycycloalkenylalkenyl" refers to a carboxy group attached to the cycloalkenyl ring portion of a cycloalkenylalkenyl group as defined hereinbefore.

The term "carboxycycloalkenylalkynyl" refers to a carboxy group attached to the cycloalkenyl ring portion of a cycloalkenylalkynyl group as defined hereinbefore.

The term "alkoxy" includes both branched and straight chain alkyl groups attached to a terminal oxygen atom. Typical alkoxy groups include methoxy, ethoxy, n-propoxy, isopropoxy, tert-butoxy and the like.

The term "haloalkoxy" refers to an alkoxy group substituted with one or more halo groups, for example chloromethoxy, trifluoromethoxy, difluoromethoxy, perfluoroisobutoxy and the like.

The term "alkoxyalkoxyalkyl" refers to an alkyl group substituted with an alkoxy moiety which is in turn substituted with a second alkoxy moiety, for example methoxymethoxymethyl, isopropoxymethoxyethyl and the like.

The term "alkylthio" includes both branched and straight chain alkyl groups attached to a terminal sulfur atom, for example methylthio.

The term "haloalkylthio" refers to an alkylthio group substituted with one or more halo groups, for example trifluoromethylthio.

The term "alkoxyalkyl" refers to an alkyl group substituted with an alkoxy group, for example isopropoxymethyl.

The term "alkoxyalkenyl" refers to an alkenyl group substituted with an alkoxy group, for example 3-methoxyallyl.

The term "alkoxyalkynyl" refers to an alkynyl group substituted with an alkoxy group, for example 3-methoxypropargyl.

The term "alkoxycarbonylalkyl" refers to a straight chain or branched alkyl substituted with an alkoxycarbonyl, for example ethoxycarbonylmethyl, 2-(methoxycarbonyl)propyl and the like.

The term "alkoxycarbonylalkenyl" refers to a straight chain or branched alkenyl as defined hereinbefore substituted with an alkoxycarbonyl, for example 4-(ethoxycarbonyl)-2-butenyl and the like.

The term "alkoxycarbonylalkynyl" refers to a straight chain or branched alkynyl as defined hereinbefore substituted with an alkoxycarbonyl, for example 4-(ethoxycarbonyl)-2-butynyl and the like.

The term "haloalkoxyalkyl" refers to a straight chain or branched alkyl as defined hereinbefore substituted with a haloalkoxy, for example 2-chloroethoxymethyl, trifluoromethoxymethyl and the like.

The term "haloalkoxyalkenyl" refers to a straight chain or branched alkenyl as defined hereinbefore substituted with a haloalkoxy, for example 4-(chloromethoxy)-2-butenyl and the like.

The term "haloalkoxyalkynyl" refers to a straight chain or branched alkynyl as defined hereinbefore substituted with a haloalkoxy, for example 4-(2-fluoroethoxy)-2-butynyl and the like.

The term "alkylthioalkyl" refers to a straight chain or branched alkyl as defined hereinbefore substituted with an alkylthio group, for example methylthiomethyl, 3-(isobutylthio)heptyl and the like.

The term "alkylthioalkenyl" refers to a straight chain or branched alkenyl as defined hereinbefore substituted with an alkylthio group, for example 4-(methylthio)-2-butenyl and the like.

The term "alkylthioalkynyl" refers to a straight chain or branched alkynyl as defined hereinbefore substituted with an alkylthio group, for example 4-(ethylthio)-2-butynyl and the like.

The term "haloalkylthioalkyl" refers to a straight chain or branched alkyl as defined hereinbefore substituted with an haloalkylthio group, for example 2-chloroethylthiomethyl, trifluoromethylthiomethyl and the like.

The term "haloalkylthioalkenyl" refers to a straight chain or branched alkenyl as defined hereinbefore substituted with an haloalkylthio group, for example 4-(chloromethylthio)-2-butenyl and the like.

The term "haloalkylthioalkynyl" refers to a straight chain or branched alkynyl as defined hereinbefore substituted with an haloalkylthio group, for example 4-(2-fluoroethylthio)-2-butynyl and the like.

The term "dialkoxyphosphorylalkyl" refers to two straight chain or branched alkoxy groups as defined hereinbefore attached to a pentavalent phosphorous atom, containing an oxo substituent, which is in turn attached to an alkyl, for example diethoxyphosphorylmethyl.

The term "oligomer" refers to a low-molecular weight polymer, whose number average molecular weight is typically less than about 5000 g/mol, and whose degree of polymerization (average number of monomer units per chain) is greater than one and typically equal to or less than about 50.

In a first preferred embodiment of this invention, the pesticidal compound is represented by formula (I)

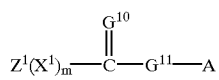

(I)

wherein

A is

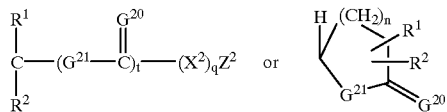

$G^{10}$, $G^{11}$ and $G^{20}$ are each independently an oxygen atom or a sulfur atom, $G^{21}$ is an oxygen atom, a sulfur atom or $NR^3$, $X^1$ is an oxygen atom, a sulfur atom or a nitrogen atom attached to $Z^1$, $X^2$ is an oxygen atom, a sulfur atom, a nitrogen atom or a carbon atom attached to $Z^2$, m, q and t are each independently 0 or 1, n is 1 or 2, $Z^1(X^1)_m$ is a pesticidal moiety when m is 1 wherein $Z^1(X^1)_m$—H represents the pesticide, $Z^2(X^2)_q(C(=G^{20})G^{21})_t$ is a pesticidal moiety when q is 1 wherein $Z^2(X^2)_q(C(=G^{20})G^{21})_t$ or $Z^2(X^2)_q(C(=G^{20})G^{21})_t$—H represents the pesticide, $Z^1(X^1)_m$, when m is 0, is a hydrogen atom, halo, $(C_1-C_{20})$alkyl, $(C_1-C_{10})$alkylcarbonyloxy$(C_1-C_{10})$alkyl, $(C_1-C_{20})$alkylcarbonyl, hydroxy$(C_1-C_{20})$alkyl, $(C_1-C_{10})$alkylsulfonyl$(C_1-C_{10})$alkyl, acetylamino$(C_1-C_{10})$alkyl, halo$(C_1-C_{20})$alkyl, $(C_2-C_{20})$alkenyl, halo$(C_2-C_{20})$alkenyl, acetylamino(C2–$C_{10}$)alkenyl, $(C_2-C_{20})$alkynyl, halo$(C_2-C_{20})$alkynyl, cyclo$(C_3-C_8)$alkyl, cyclo$(C_3-C_8)$alkenyl, carboxycyclo$(C_3-C_8)$alkyl, carboxycyclo$(C_3-C_8)$alkenyl, cyclo$(C_3-C_8)$alkyl$(C_1-C_{10})$alkyl, cyclo$(C_3-C_8)$alkyl$(C_2-C_{10})$alkenyl, cyclo$(C_3-C_8)$alkenyl$(C_1-C_{10})$alkyl, cyclo$(C_3-C_8)$alkenyl$(C_2-C_{10})$alkenyl, cyclo$(C_3-C_8)$alkyl$(C_2-C_{10})$alkynyl, cyclo$(C_3-C_8)$alkenyl$(C_2-C_{10})$alkynyl, carboxycyclo$(C_3-C_8)$alkyl$(C_1-C_{10})$alkyl, carboxy$(C_3-C_8)$cycloalkyl$(C_2-C_{10})$alkenyl, carboxycyclo$(C_3-C_8)$alkenyl$(C_1-C_{10})$alkyl, carboxycyclo$(C_3-C_8)$alkenyl$(C_2-C_{10})$alkenyl, carboxycyclo$(C_3-C_8)$alkyl$(C_2-C_{10})$alkynyl, carboxycyclo$(C_3-C_8)$alkenyl$(C_2-C_{10})$alkynyl, heterocyclyl, heterocyclyl$(C_1-C_{10})$alkyl, heterocyclyl$(C_2-C_{10})$alkenyl, heterocyclyl$(C_2-C_{10})$alkynyl, $(C_1-C_{10})$alkoxy$(C_1-C_{10})$alkyl, $(C_1-C_5)$alkoxy$(C_1-C_5)$alkoxy$(C_1-C_{10})$alkyl, $(C_1-C_{10})$alkoxy$(C_2-C_{10})$alkenyl, $(C_1-C_{10})$alkoxy$(C_2-C_{10})$alkynyl, $(C_1-C_{10})$alkoxycarbonyl$(C_1-C_{10})$alkyl, $(C_1-C_{10})$alkoxycarbonyl$(C_2-C_{10})$alkenyl, $(C_1-C_{10})$alkoxycarbonyl$(C_2-C_{10})$alkynyl, halo$(C_1-C_{10})$alkoxy$(C_1-C_{10})$alkyl, halo$(C_1-C_{10})$alkoxy$(C_2-C_{10})$alkenyl, halo$(C_1-C_{10})$alkoxy$(C_2-C_{10})$alkynyl, $(C_1-C_{10})$alkylthio$(C_1-C_{10})$alkyl, $(C_1-C_{10})$alkylthio$(C_2-C_{10})$alkenyl, $(C_1-C_{10})$alkylthio$(C_2-C_{10})$alkynyl, halo$(C_1-C_{10})$alkylthio $(C_1-C_{10})$alkyl, halo$(C_1-C_{10})$alkylthio$(C_2-C_{10})$alkenyl, halo$(C_1-C_{10})$alkylthio$(C_2-C_{10})$alkynyl, $SO_2NR^3R^4$, $NR^3R^4$, $OR^3$, $S(O)_jR^3$, carboxy$(C_1-C_{20})$alkyl, carboxy$(C_2-C_{20})$alkenyl, carboxy$(C_2-C_{20})$alkynyl, aryl, aryl substituted with one or more substituents independently selected from halo, nitro, cyano, hydroxy, $(C_1-C_{10})$alkyl, $(C_1-C_{10})$alkylsulfonyl$(C_1-C_{10})$alkyl, $(C_1-C_{10})$alkylsulfonyl, thiocyanato, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo$(C_1-C_{10})$alkoxy, $SO_2NR^3R^4$, and $NR^3R^4$, ar$(C_1-C_{10})$alkyl, ar$(C_2-C_{10})$alkenyl, ar$(C_2-C_{10})$alkynyl, arcyclo$(C_3-C_8)$alkyl, aroxy$(C_1-C_{10})$alkyl, or ar$(C_1-C_{10})$alkyl, ar$(C_2-C_{10})$alkenyl, ar$(C_2-C_{10})$alkynyl, arcyclo$(C_3-C_8)$alkyl, aroxy$(C_1-C_{10})$alkyl substituted with one or more substituents independently selected from halo, nitro, hydroxy, cyano, $(C_1-C_{10})$alkyl, cyclo$(C_3-C_8)$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo$(C_1-C_{10})$alkoxy, $SO_2NR^3R^4$ and $NR^3R^4$, heteroaryl, heteroaryl substituted with one or more substituents independently selected from halo, hydroxy, nitro, cyano, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo$(C_1-C_{10})$alkoxy and $NR^3R^4$, heteroar$(C_1-C_{10})$alkyl, heteroar$(C_2-C_{10})$alkenyl, heteroar$(C_2-C_{10})$alkynyl, or heteroar$(C_1-C_{10})$alkyl, heteroar$(C_2-C_{10})$alkenyl, heteroar$(C_2-C_{10})$alkynyl substituted with one or more substituents independently selected from halo, hydroxy, cyano, nitro, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo$(C_1-C_{10})$alkoxy, $SO_2NR^3R^4$ and $NR^3R^4$, wherein j is 0, 1 or 2, $Z^2(X^2)_q$ is a hydrogen atom, $(C_1-C_{20})$alkyl, $(C_1-C_{10})$alkylcarbonyloxy$(C_1-C_{10})$alkyl, $(C_1-C_{20})$alkylcarbonyl, hydroxy$(C_1-C_{20})$alkyl, $(C_1-C_{10})$alkylsulfonyl$(C_1-C_{10})$alkyl, acetylamino$(C_1-C_{10})$alkyl, halo$(C_1-C_{20})$alkyl, $(C_2-C_{20})$alkenyl, halo$(C_2-C_{20})$alkenyl, acetylamino$(C_2-C_{10})$alkenyl, $(C_2-C_{20})$alkynyl, halo$(C_2-C_{20})$alkynyl, cyclo$(C_3-C_8)$alkyl, cyclo$(C_3-C_8)$alkenyl, carboxycyclo$(C_3-C_8)$ alkyl, carboxycyclo($C_3$–$C_8$)alkenyl, cyclo($C_3$–$C_8$)alkyl($C_1$–$C_{10}$)alkyl, cyclo($C_3$–$C_8$)alkyl($C_2$–$C_{10}$)alkenyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$)alkyl($C_2$–$C_{10}$)alkynyl, cyclo($C_3$–$C_8$)alkenyl($C_2$–$C_{10}$)alkynyl, carboxycyclo($C_3$–$C_8$)alkyl($C_1$–$C_{10}$)alkyl, carboxy($C_3$–$C_8$)cycloalkyl($C_2$–$C_{10}$)alkenyl, carboxycyclo($C_3$–$C_8$)alkenyl($C_1$–$C_{10}$)alkyl, carboxycyclo($C_3$–$C_8$)alkenyl($C_2$–$C_{10}$)alkenyl, carboxycyclo($C_3$–$C_8$)alkyl($C_2$–$C_{10}$)alkynyl, carboxycyclo($C_3$–$C_8$)alkenyl($C_2$–$C_{10}$)alkynyl, heterocyclyl, heterocyclyl($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy($C_1$–$C_{10}$)alkyl, ($C_1$–$C_5$)alkoxy($C_1$–$C_5$)alkoxy($C_1$–$C_{10}$)alkyl, ($C_1$–$C_{10}$)alkoxy($C_2$–$C_{10}$)alkenyl, ($C_{10}$–$C_{10}$)alkoxy($C_2$–$C_{10}$)alkynyl, ($C_1$–$C_{10}$)alkoxycarbonyl($C_1$–$C_{10}$)alkyl, ($C_1$–$C_{10}$alkoxycarbonyl($C_2$–$C_{10}$)alkenyl, ($C_1$–$C_{10}$)alkoxycarbonyl($C_2$–$C_{10}$)alkynyl, halo($C_1$–$C_{10}$)alkoxy($C_1$–$C_{10}$)alkyl, halo($C_1$–$C_{10}$)alkoxy($C_2$–$C_{10}$)alkenyl, halo($C_1$–$C_{10}$)alkoxy($C_2$–$C_{10}$)alkynyl, ($C_1$–$C_{10}$)alkylthio($C_1$–$C_{10}$)alkyl, ($C_1$–$C_{10}$)alkylthio($C_2$–$C_{10}$)alkenyl, ($C_1$–$C_{10}$)alkylthio($C_2$–$C_{10}$)alkynyl, halo($C_1$–$C_{10}$)alkylthio($C_1$–$C_{10}$)alkyl, halo($C_1$–$C_{10}$)alkylthio($C_2$–$C_{10}$)alkenyl, halo($C_1$–$C_{10}$)alkylthio($C_2$–$C_{10}$)alkynyl, $SO_2NR^3R^4$, $NR^3R^4$, carboxy($C_1$–$C_{20}$)alkyl, carboxy($C_2$–$C_{20}$)alkenyl, carboxy($C_2$–$C_{20}$)alkynyl, di($C_1$–$C_{10}$)alkoxyphosphoryl($C_1$–$C_{10}$)alkyl, aryl, aryl substituted with one or more substituents independently selected from halo, nitro, cyano, hydroxy, ($C_1$–$C_{10}$)alkyl, ($C_1$–$C_{10}$)alkylsulfonyl($C_1$–$C_{10}$)alkyl, ($C_1$–$C_{10}$)alkylsulfonyl, thiocyanato, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$, and $NR^3R^4$, ar($C_1$–$C_{10}$)alkyl, ar($C_2$–$C_{10}$)alkenyl, ar($C_2$–$C_{10}$)alkynyl, arcyclo($C_3$–$C_8$)alkyl, aroxy($C_1$–$C_{10}$)alkyl, or ar($C_1$–$C_{10}$)alkyl, ar($C_2$–$C_{10}$)alkenyl, ar($C_2$–$C_{10}$)alkynyl, arcyclo($C_3$–$C_8$)alkyl, aroxy($C_1$–$C_{10}$)alkyl substituted with one or more substituents independently selected from halo, nitro, hydroxy, cyano, ($C_1$–$C_{10}$)alkyl, cyclo($C_3$–$C_8$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$ and $NR^3R^4$, heteroaryl, heteroaryl substituted with one or more substituents independently selected from halo, hydroxy, nitro, cyano, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy and $NR^3R^4$, heteroar($C_1$–$C_{10}$)alkyl, heteroar($C_2$–$C_{10}$)alkenyl, heteroar($C_2$–$C_{10}$)alkynyl, or heteroar($C_1$–$C_{10}$)alkyl, heteroar($C_2$–$C_{10}$)alkenyl, heteroar($C_2$–$C_{10}$)alkynyl substituted with one or more substituents independently selected from halo, hydroxy, cyano, nitro, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$ and $NR^3R^4$, when q is 0 and t is 1, $Z^2(X^2)_q$ is halo, $NR^3R^4$, {$(NR^3R^4R^5)^+M^-$}, $OR^3$, $S(O)_jR^3$ or $SO_2NR^3R^4$ when both q and t are 0 wherein $M^-$ is halo, hydroxy, ($C_1$–$C_8$)alkoxy or the anion of a carboxylic acid and j is 0, 1 or 2, $R^1$ and $R^2$ are each independently a hydrogen atom, ($C_1$–$C_{20}$)alkyl, ($C_2$–$C_{10}$)alkenyl, ($C_2$–$C_{10}$)alkynyl, ($C_1$–$C_{10}$)alkoxy($C_1$–$C_{10}$)alkyl, ($C_1$–$C_{10}$)alkoxy($C_2$–$C_{10}$)alkenyl, ($C_1$–$C_{10}$)alkoxy($C_2$–$C_{10}$)alkynyl, ($C_1$–$C_{10}$)alkylthio($C_1$–$C_{10}$)alkyl, ($C_1$–$C_{10}$)alkylthio($C_2$–$C_{10}$)alkenyl, ($C_1$–$C_{10}$)alkylthio($C_2$–$C_{10}$)alkynyl, carboxy, carboxy($C_1$–$C_{20}$)alkyl, carboxy($C_2$–$C_{20}$)alkenyl, carboxy($C_2$–$C_{20}$)alkynyl, ($C_1$–$C_{20}$)alkoxycarbonyl, ($C_1$–$C_{10}$)alkoxycarbonyl($C_1$–$C_{10}$)alkyl, ($C_1$–$C_{10}$)alkoxycarbonyl($C_2$–$C_{10}$)alkenyl, ($C_1$–$C_{10}$)alkoxycarbonyl($C_2$–$C_{10}$)alkynyl, ($C_1$–$C_{20}$)alkylcarbonyl, ($C_2$–$C_{20}$)alkenylcarbonyl, ($C_2$–$C_{20}$)alkynylcarbonyl, cyclo($C_3$–$C_8$)alkyl, cyclo($C_3$–$C_8$)alkenyl, cyclo($C_3$–$C_8$)alkyl($C_1$–$C_{10}$)alkyl, cyclo($C_3$–$C_8$)alkenyl($C_1$–$C_{10}$)alkyl, cyclo($C_3$–$C_8$)alkyl($C_2$–$C_{10}$)alkenyl, cyclo($C_3$–$C_8$)alkenyl($C_2$–$C_{10}$)alkenyl, cyclo($C_3$–$C_8$)alkyl($C_2$–$C_{10}$)alkynyl, cyclo($C_3$–$C_8$)alkenyl($C_2$–$C_{10}$)alkynyl, heterocyclyl, heterocyclyl($C_1$–$C_{10}$)alkyl, heterocyclyl($C_2$–$C_{10}$)alkenyl, heterocyclyl($C_2$–$C_{10}$)alkynyl, aryl, aryl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$ and $NR^3R^4$, ar($C_1$–$C_{10}$)alkyl, ar($C_2$–$C_{10}$)alkenyl, ar($C_2$–$C_{10}$)alkynyl, or ar($C_1$–$C_{10}$)alkyl, ar($C_2$–$C_{10}$)alkenyl, ar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$ and $NR^3R^4$, heteroaryl, heteroaryl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy and $NR^3R^4$, heteroar($C_1$–$C_{10}$)alkyl, heteroar($C_2$–$C_{10}$)alkenyl, heteroar($C_2$–$C_{10}$)alkynyl or heteroar($C_1$–$C_{10}$)alkyl, heteroar($C_2$–$C_{10}$)alkenyl, heteroar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$ and $NR^3R^4$, or $R^1$ and $R^2$ taken together with the carbon atom to which they are attached form a 5–7 membered saturated or unsaturated ring, or $R^1$ may be a pesticidal moiety if $R^2$ is a hydrogen atom, $R^3$, $R^4$ and $R^5$ are each independently a hydrogen atom, ($C_1$–$C_{20}$)alkyl, cyclo($C_3$–$C_8$)alkyl, cyclo($C_3$–$C_8$)alkenyl, cyclo($C_3$–$C_8$)alkyl($C_1$–$C_{10}$)alkyl, cyclo($C_3$–$C_8$)alkyl($C_2$–$C_{10}$)alkenyl, cyclo($C_3$–$C_8$)alkyl($C_2$–$C_{10}$)alkynyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$)alkenyl($C_2$–$C_{10}$)alkynyl, heterocyclyl, heterocyclyl($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy($C_1$–$C_{10}$)alkyl, ($C_2$–$C_{10}$)alkenyl, ($C_2$–$C_{10}$)alkynyl, or ($C_1$–$C_{10}$)alkyl, cyclo($C_3$–$C_8$)alkyl, cyclo($C_3$–$C_8$)alkenyl, cyclo($C_3$–$C_8$)alkyl($C_1$–$C_{10}$)alkyl, cyclo($C_3$–$C_8$)alkyl($C_2$–$C_{10}$)alkenyl, cyclo($C_3$–$C_8$)alkyl($C_2$–$C_{10}$)alkynyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$)alkenyl($C_2$–$C_{10}$)alkynyl heterocyclyl, heterocyclyl($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy($C_1$–$C_{10}$)alkyl, ($C_2$–$C_{10}$)alkenyl or ($C_2$–$C_{10}$)alkynyl substituted with one or more halo, aryl, ar($C_1$–$C_{10}$)alkyl, ar($C_2$–$C_{10}$)alkenyl, ar($C_2$–$C_{10}$)alkynyl or aryl, ar($C_1$–$C_{10}$)alkyl, ar($C_2$–$C_{10}$)alkenyl, ar($C_2$–$C_{10}$)alkynyl substituted with one or more substituents independently selected from halo, $(C_1-C_{10})$alkyl, $(C_2-C_{10})$ alkenyl, $(C_2-C_{10})$alkynyl, halo$(C_1-C_{10})$alkyl, halo $(C_2-C_{10})$alkenyl, halo$(C_2-C_{10})$alkynyl, $(C_1-C_{10})$ alkoxy and halo$(C_1-C_{10})$alkoxy, heteroaryl, heteroar $(C_1-C_{10})$alkyl, heteroar$(C_2-C_{10})$alkenyl, heteroar $(C_2-C_{10})$alkynyl or heteroaryl, heteroar$(C_1-C_{10})$alkyl, heteroar$(C_2-C_{10})$alkenyl, heteroar$(C_2-C_{10})$alkynyl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo $(C_2-C_{10})$alkenyl, halo$(C_2-C_{10})$alkynyl, $(C_1-C_{10})$ alkoxy and halo$(C_1-C_{10})$alkoxy, or $R^3$ and $R^4$ taken together with the nitrogen atom to which they are attached form a 5- or 6-membered saturated or unsaturated heterocyclic ring, provided that when both m and q are 0, A is

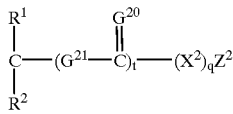

and $R^1$ is a pesticidal moiety, or the pesticidally acceptable salts, isomers and enantiomers thereof.

In a more preferred embodiment of this invention, the pesticidal compound is represented by formula (I)

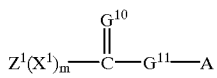 (I)

wherein

A is

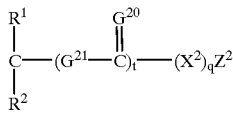

$G^{10}$, $G^{11}$ and $G^{20}$ are each independently an oxygen atom or a sulfur atom, $G^{21}$ is an oxygen atom, a sulfur atom or $NR^3$, $X^1$ is an oxygen atom, a sulfur atom or a nitrogen atom attached to $Z^1$, m is 1, q is 0, t is 0 or 1, $Z^1(X^1)_m$ is a pesticidal moiety wherein $Z^1(X^1)_m$—H represents the pesticide selected from the group consisting of cymoxanil, dodine, thifluzamide, flusulfamide, zarilamid, furametpyr, dicloran, flutolanil, fenhexamid, benomyl, carbendazim, fuberidazole, thiabendazole, diethofencarb, propamocarb, thiophante-methyl, iprovalicarb, methfuroxam, fenamidone, iprodione, carboxin, oxycarboxin, famoxadone, pencycuron, fluazinam, cyprodinil, ferimzone, pyrimethanil, metominostrobin, SSF-129, metsulfovax, zoxamide, capropamid, diclocymet, methasulfocarb, fenpiclonil, fludioxonil, 2-[5-(4-chlorophenyl)-4-methyl-2,7-dioxa-3,6-diazaocta-3,5-dien-1-yl]-α-(methoxyimino)-N-methyl-benzeneacetamide, 2-[5-(4-fluorophenyl)-4-methyl-2,7-dioxa-3,6-diazaocta-3,5-dien-1-yl]-α-(methoxyimino)-N-methyl-benzeneacetamide, pronamide, diflufenican, flumetsulam, propanil, asulam, chlorpropham, desmedipham, pendimethalin, aclonifen, fomesafen, atrazine, terbuthylazine, terbumeton, ametryn, metribuzin, amitrole, bentazon, bromacil, chlorotoluron, diuron, fluometuron, isoproturon, linuron, chlorsulfuron, nicosulfuron, rimsulfuron, chlorfluazuron, diflubenzuron, flucycloxuron, hexaflumuron, lufenuron, novaluron, teflubenzuron, triflumuron, fluazuron, aldicarb, bendiocarb, BPMC, carbaryl, carbofuran, cartap, ethiofencarb, fenoxycarb, formetanate, isoprocarb, methiocarb, methomyl, oxamyl, phosphocarb, promecarb, propoxur, tolfenpyrad, xylyl methylcarbamate, xylylcarb, clothianidin, imidacloprid, nidinotefuran, nitenpyram, NTN-32692, acephate, dimethoate, fenamiphos, isofenphos, methamidophos, monocrotophos, omethoate, vamidothion, cyromazine, diafenthiuron, fipronil, pymetrozine, pyrimidifen, tebufenpyrad, bifenazate, hexythiazox and fluvalinate when $X^1$ is a nitrogen atom, or the pesticide selected from the group consisting of fenhexamide, tebuconazole, cyproconazole, hexaconazole, triadimenol, fosetyl, fenarimol, 8-hydroxyquinoline sulfate, sulcotrione, sethoxydim, tralkoxydim, dinoseb, abamectin, enamectin benzoate, milbemectin, dicofol, bromopropylate and chlorobenzilate when $X^1$ is an oxygen atom, or the pesticide selected from the group consisting of mancozeb and maneb when $X^1$ is a sulfur atom, $Z^2(X^2)_q$ is a hydrogen atom, $(C_1-C_{20})$alkyl, $(C_1-C_{10})$alkylcarbonyloxy$(C_1-C_{10})$alkyl, $(C_1-C_{20})$alkylcarbonyl, hydroxy$(C_1-C_{20})$alkyl, $(C_1-C_{10})$alkylsulfonyl$(C_1-C_{10})$alkyl, acetylamino$(C_1-C_{10})$alkyl, halo$(C_1-C_{20})$alkyl, $(C_2-C_{20})$alkenyl, halo$(C_2-C_{20})$alkenyl, acetylamino$(C_2-C_{10})$alkenyl, $(C_2-C_{20})$alkynyl, halo$(C_2-C_{20})$alkynyl, cyclo$(C_3-C_8)$alkyl, cyclo$(C_3-C_8)$alkenyl, carboxycyclo$(C_3-C_8)$alkyl, carboxycyclo$(C_3-C_8)$alkenyl, cyclo$(C_3-C_8)$alkyl$(C_1-C_{10})$alkyl, cyclo$(C_3-C_8)$alkyl$(C_2-C_{10})$alkenyl, cyclo$(C_3-C_8)$alkenyl$(C_1-C_{10})$alkyl, cyclo$(C_3-C_8)$alkenyl$(C_2-C_{10})$alkenyl, cyclo$(C_3-C_8)$alkyl$(C_2-C_{10})$alkynyl, cyclo$(C_3-C_8)$alkenyl$(C_2-C_{10})$alkynyl, carboxycyclo$(C_3-C_8)$alkyl$(C_1-C_{10})$alkyl, carboxy $(C_3-C_8)$cycloalkyl$(C_2-C_{10})$alkenyl, carboxycyclo $(C_3-C_8)$alkenyl$(C_1-C_{10})$alkyl, carboxycyclo$(C_3-C_8)$alkenyl$(C_2-C_{10})$alkenyl, carboxycyclo$(C_3-C_8)$alkyl $(C_2-C_{10})$alkynyl, carboxycyclo$(C_3-C_8)$alkenyl $(C_2-C_{10})$alkynyl, heterocyclyl, heterocyclyl$(C_1-C_{10})$alkyl, heterocyclyl$(C_2-C_{10})$alkenyl, heterocyclyl $(C_2-C_{10})$alkynyl, $(C_1-C_{10})$alkoxy$(C_1-C_{10})$alkyl, $(C_1-C_5)$alkoxy$(C_1-C_5)$alkoxy$(C_1-C_{10})$alkyl, $(C_1-C_{10})$alkoxy$(C_2-C_{10})$alkenyl, $(C_1-C_{10})$alkoxy$(C_2-C_{10})$alkynyl, $(C_1-C_{10})$alkoxycarbonyl$(C_1-C_{10})$alkyl, $(C_1-C_{10})$alkoxycarbonyl$(C_2-C_{10})$alkenyl, $(C_1-C_{10})$alkoxycarbonyl$(C_2-C_{10})$alkynyl, halo$(C_1-C_{10})$alkoxy $(C_1-C_{10})$alkyl, halo$(C_1-C_{10})$alkoxy$(C_2-C_{10})$alkenyl, halo$(C_1-C_{10})$alkoxy$(C_2-C_{10})$alkynyl, $(C_1-C_{10})$alkylthio$(C_1-C_{10})$alkyl, $(C_1-C_{10})$alkylthio$(C_2-C_{10})$alkenyl, $(C_1-C_{10})$alkylthio$(C_2-C_{10})$alkynyl, halo $(C_1-C_{10})$alkylthio$(C_1-C_{10})$alkyl, halo$(C_1-C_{10})$alkylthio$(C_2-C_{10})$alkenyl, halo$(C_1-C_{10})$alkylthio $(C_2-C_{10})$alkynyl, $SO_2NR^3R^4$, $NR^3R^4$, carboxy $(C_1-C_{20})$alkyl, carboxy$(C_2-C_{20})$alkenyl, carboxy $(C_2-C_{20})$alkynyl, di$(C_1-C_{10})$alkoxyphosphoryl $(C_1-C_{10})$alkyl, aryl, aryl substituted with one or more substituents independently selected from halo, nitro, cyano, hydroxy, $(C_1-C_{10})$alkyl, $(C_1-C_{10})$alkylsulfonyl $(C_1-C_{10})$alkyl, $(C_1-C_{10})$alkylsulfonyl, thiocyanato, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$, and $NR^3R^4$, ar($C_1$–$C_{10}$)alkyl, ar($C_2$–$C_{10}$)alkenyl, ar($C_2$–$C_{10}$)alkynyl, arcyclo($C_3$–$C_8$)alkyl, aroxy($C_1$–$C_{10}$)alkyl, or ar($C_1$–$C_{10}$)alkyl, ar($C_2$–$C_{10}$)alkenyl, ar($C_2$–$C_{10}$)alkynyl, arcyclo($C_3$–$C_8$)alkyl, aroxy($C_1$–$C_{10}$)alkyl substituted with one or more substituents independently selected from halo, nitro, hydroxy, cyano, ($C_1$–$C_{10}$)alkyl, cyclo($C_3$–$C_8$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$ and $NR^3R^4$, heteroaryl, heteroaryl substituted with one or more substituents independently selected from halo, hydroxy, nitro, cyano, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy and $NR^3R^4$, heteroar($C_1$–$C_{10}$)alkyl, heteroar($C_2$–$C_{10}$)alkenyl, heteroar($C_2$–$C_{10}$)alkynyl, or heteroar($C_1$–$C_{10}$)alkyl, heteroar($C_2$–$C_{10}$)alkenyl, heteroar($C_2$–$C_{10}$)alkynyl substituted with one or more substituents independently selected from halo, hydroxy, cyano, nitro, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$ and $NR^3R^4$, when t is 1, $Z^2(X^2)_q$ is halo, $NR^3R^4$, {$(NR^3R^4R^5)^+M^-$}, $OR^3$, $S(O)_jR^3$ or $SO_2NR^3R^4$ when t is 0 wherein $M^-$ is halo, hydroxy, ($C_1$–$C_8$)alkoxy or the anion of a carboxylic acid and j is 0, 1 or 2, $R^1$ and $R^2$ are each independently a hydrogen atom, ($C_1$–$C_{20}$)alkyl, ($C_2$–$C_{10}$)alkenyl, ($C_2$–$C_{10}$)alkynyl, ($C_1$–$C_{10}$)alkoxy($C_1$–$C_{10}$)alkyl, ($C_1$–$C_{10}$)alkoxy($C_2$–$C_{10}$)alkenyl, ($C_1$–$C_{10}$)alkoxy($C_2$–$C_{10}$)alkynyl, ($C_1$–$C_{10}$)alkylthio($C_1$–$C_{10}$)alkyl, ($C_1$–$C_{10}$)alkylthio($C_2$–$C_{10}$)alkenyl, ($C_1$–$C_{10}$)alkylthio($C_2$–$C_{10}$)alkynyl, carboxy, carboxy($C_1$–$C_{20}$)alkyl, carboxy($C_2$–$C_{20}$)alkenyl, carboxy($C_2$–$C_{20}$)alkynyl, ($C_1$–$C_{20}$)alkoxycarbonyl, ($C_1$–$C_{10}$)alkoxycarbonyl($C_1$–$C_{10}$)alkyl, ($C_1$–$C_{10}$)alkoxycarbonyl($C_2$–$C_{10}$)alkenyl, ($C_1$–$C_{10}$)alkoxycarbonyl($C_2$–$C_{10}$)alkynyl, ($C_1$–$C_{20}$)alkylcarbonyl, ($C_2$–$C_{20}$)alkenylcarbonyl, ($C_2$–$C_{20}$)alkynylcarbonyl, cyclo($C_3$–$C_8$)alkyl, cyclo($C_3$–$C_8$)alkenyl, cyclo($C_3$–$C_8$)alkyl($C_1$–$C_{10}$)alkyl, cyclo($C_3$–$C_8$)alkyl($C_1$–$C_{10}$)alkyl, cyclo($C_3$–$C_8$)alkyl($C_2$–$C_{10}$)alkenyl, cyclo($C_3$–$C_8$)alkyl($C_2$–$C_{10}$)alkynyl, cyclo($C_3$–$C_8$)alkenyl($C_2$–$C_{10}$)alkynyl, heterocyclyl, heterocyclyl($C_1$–$C_{10}$)alkyl, heterocyclyl($C_2$–$C_{10}$)alkenyl, heterocyclyl($C_2$–$C_{10}$)alkynyl, aryl, aryl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$ and $NR^3R^4$, aryl, ar($C_1$–$C_{10}$)alkyl, ar($C_2$–$C_{10}$)alkenyl, ar($C_2$–$C_{10}$)alkynyl, or aryl, ar($C_1$–$C_{10}$)alkyl, ar($C_2$–$C_{10}$)alkenyl, ar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$ and $NR^3R^4$, heteroaryl, heteroar($C_1$–$C_{10}$)alkyl, heteroar($C_2$–$C_{10}$)alkenyl, heteroar($C_2$–$C_{10}$)alkynyl or heteroaryl, heteroar($C_1$–$C_{10}$)alkyl, heteroar($C_2$–$C_{10}$)alkenyl, heteroar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$ and $NR^3R^4$, or $R^1$ and $R^2$ taken together with the carbon atom to which they are attached form a 5–7 membered saturated or unsaturated ring, or $R^1$ may be a pesticidal moiety if $R^2$ is a hydrogen atom, $R^3$, $R^4$ and $R^5$ are each independently a hydrogen atom, ($C_1$–$C_{20}$)alkyl, cyclo($C_3$–$C_8$)alkyl, cyclo($C_3$–$C_8$)alkenyl, cyclo($C_3$–$C_8$)alkyl($C_1$–$C_{10}$)alkyl, cyclo($C_3$–$C_8$)alkyl($C_2$–$C_{10}$)alkenyl, cyclo($C_3$–$C_8$)alkyl($C_2$–$C_{10}$)alkynyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$)alkenyl($C_2$–$C_{10}$)alkynyl, heterocyclyl, heterocyclyl($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy ($C_1$–$C_{10}$)alkyl, ($C_2$–$C_{10}$)alkenyl, ($C_2$–$C_{10}$)alkynyl, or ($C_1$–$C_{10}$)alkyl, cyclo($C_3$–$C_8$)alkyl, cyclo($C_3$–$C_8$)alkenyl, cyclo($C_3$–$C_8$)alkyl($C_1$–$C_{10}$)alkyl, cyclo($C_3$–$C_8$)alkyl($C_2$–$C_{10}$)alkenyl, cyclo($C_3$–$C_8$)alkyl($C_2$–$C_{10}$)alkynyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$)alkenyl($C_2$–$C_{10}$)alkynyl, heterocyclyl, heterocyclyl($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy ($C_1$–$C_{10}$)alkyl, ($C_2$–$C_{10}$)alkenyl or ($C_2$–$C_{10}$)alkynyl substituted with one or more halo, aryl, ar($C_1$–$C_{10}$)alkyl, ar($C_2$–$C_{10}$)alkenyl, ar($C_2$–$C_{10}$)alkynyl or aryl, ar($C_1$–$C_{10}$)alkyl, ar($C_2$–$C_{10}$)alkenyl, ar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy and halo($C_1$–$C_{10}$)alkoxy, heteroaryl, heteroar($C_1$–$C_{10}$)alkyl, heteroar($C_2$–$C_{10}$)alkenyl, heteroar($C_2$–$C_{10}$)alkynyl or heteroaryl, heteroar($C_1$–$C_{10}$)alkyl, heteroar($C_2$–$C_{10}$)alkenyl, heteroar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy and halo($C_1$–$C_{10}$)alkoxy, or $R^3$ and $R^4$ taken together with the nitrogen atom to which they are attached form a 5- or 6-membered saturated or unsaturated heterocyclic ring, or the pesticidally acceptable salts, isomers and enantiomers thereof In another more preferred embodiment of this invention, the pesticidal compound is represented by formula (I)

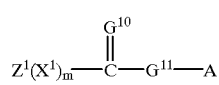

(I)

wherein

A is

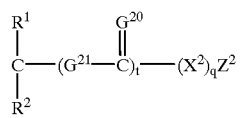

$G^{10}$, $G^{11}$ and $G^{20}$ are each independently an oxygen atom or a sulfur atom, $G^{21}$ is an oxygen atom, a sulfur atom or $NR^3$, $X^2$ is an oxygen atom, a sulfur atom or a nitrogen atom attached to $Z^2$, m is 0, q is 1, t is 0, $Z^2(X^2)_q$ is a pesticidal moiety wherein $Z^2(X^2)_q$—H or $Z^2(X^2)_q$ represents the pesticide selected from the group consisting of fenpropidin, spiroxamine, propamocarb, epoxiconazole, fluzilazole, propiconazole, penconazole, tebuconazole, fenbuconazole, myclobutanil, fenpropimorph, quinoxyfen, zoxamide, cymoxanil, trifluralin, hexazinone, pronamide, diflufenican, flumetsulam, propanil, asulam, chlorpropham, desmedipham, phenmedipham, pendimethalin, aclonifen, fomesafen, atrazine, terbuthylazine, terbumeton, ametryn, metribuzin, amitrole, bentazon, bromacil, chlorotoluron, diuron, fluometuron, isoproturon, linuron, chlorsulfuron, nicosulfuron, rimsulfuron, chlorfluazuron, diflubenzuron, flucycloxuron, hexaflumuron, lufenuron, novaluron, teflubenzuron, triflumuron, fluazuron, aldicarb, bendiocarb, BPMC, carbaryl, carbofuran, cartap, ethiofencarb, fenoxycarb, formetante, isoprocarb, methiocarb, methomyl, oxamyl, phosphocarb, promecarb, propoxur, tolfenpyrad, xylyl methylcarbamate, xylylcarb, clothianidin, imidacloprid, nidinotefuran, nitenpyram, NTN-32692, acephate, dimethoate, fenamiphos, isofenphos, methamidophos, monocrotophos, omethoate, vamidothion, cyromazine, diafenthiuron, fipronil, pymetrozine, pyrimidifen, tebufenpyrad, bifenazate, hexythiazox and fluvalinate when $X^2$ is a nitrogen atom, or the pesticide selected from the group consisting of fosetyl, tebuconazole, clopyralid, acifluorfen, imazaquin, imazethapyr, fenoxaprop, fluazifop, haloxyfop, sulcotrione, sethoxydim, tralkoxydim, dinoseb, abamectin, enamectin benzoate, milbemectin, dicofol, bromopropylate and chlorobenzilate when $X^2$ is an oxygen atom, or the pesticide selected from the group consisting of mancozeb, maneb and propineb when $X^2$ is a sulfur atom, $Z^1(X^1)_m$ is a hydrogen atom, halo, $(C_1-C_{20})$alkyl, $(C_1-C_{10})$alkylcarbonyloxy$(C_1-C_{10})$alkyl, $(C_1-C_{20})$alkylcarbonyl, hydroxy$(C_1-C_{20})$alkyl, $(C_1-C_{10})$alkylsulfonyl$(C_1-C_{10})$alkyl, acetylamino$(C_1-C_{10})$alkyl, halo$(C_1-C_{20})$alkyl, $(C_2-C_{20})$alkenyl, $(C_2-C_{20})$alkenyl, acetylamino $(C_2-C_{10})$alkenyl, $(C_2-C_{20})$alkynyl, halo$(C_2-C_{20})$alkynyl, cyclo$(C_3-C_8)$alkyl, cyclo$(C_3-C_8)$alkenyl, carboxycyclo$(C_3-C_8)$alkyl, carboxycyclo$(C_3-C_8)$alkenyl, cyclo$(C_3-C_8)$alkyl$(C_1-C_{10})$alkyl, cyclo$(C_3-C_8)$alkyl$(C_2-C_{10})$alkenyl, cyclo$(C_3-C_8)$alkenyl$(C_1-C_{10})$alkyl, cyclo$(C_3-C_8)$alkenyl$(C_2-C_{10})$alkenyl, cyclo$(C_3-C_8)$alkyl$(C_2-C_{10})$alkynyl, cyclo$(C_3-C_8)$alkenyl$(C_2-C_{10})$alkynyl, carboxycyclo$(C_3-C_8)$alkyl$(C_1-C_{10})$alkyl, carboxy$(C_3-C_8)$cycloalkyl$(C_2-C_{10})$alkenyl, carboxycyclo$(C_3-C_8)$alkenyl$(C_1-C_{10})$alkyl, carboxycyclo$(C_3-C_8)$alkenyl$(C_2-C_{10})$alkynyl, carboxycyclo$(C_3-C_8)$alkyl$(C_2-C_{10})$alkynyl, carboxycyclo$(C_3-C_8)$alkenyl$(C_2-C_{10})$alkynyl, heterocyclyl, heterocyclyl$(C_1-C_{10})$alkyl, heterocyclyl$(C_2-C_{10})$alkenyl, heterocyclyl$(C_2-C_{10})$alkynyl, $(C_1-C_{10})$alkoxy$(C_1-C_{10})$alkyl, $(C_1-C_5)$alkoxy$(C_1-C_5)$alkoxy$(C_1-C_{10})$alkyl, $(C_1-C_{10})$alkoxy$(C_2-C_{10})$alkenyl, $(C_1-C_{10})$alkoxy$(C_2-C_{10})$alkynyl, $(C_1-C_{10})$alkoxycarbonyl$(C_1-C_{10})$alkyl, $(C_1-C_{10})$alkoxycarbonyl$(C_2-C_{10})$alkenyl, $(C_1-C_{10})$alkoxycarbonyl$(C_2-C_{10})$alkynyl, halo$(C_1-C_{10})$alkoxy$(C_1-C_{10})$alkyl, halo$(C_1-C_{10})$alkoxy$(C_2-C_{10})$alkenyl, halo$(C_1-C_{10})$alkoxy$(C_2-C_{10})$alkynyl, $(C_1-C_{10})$alkylthio$(C_1-C_{10})$alkyl, $(C_1-C_{10})$alkylthio$(C_2-C_{10})$alkenyl, $(C_1-C_{10})$alkylthio$(C_2-C_{10})$alkynyl, halo $(C_1-C_{10})$alkylthio$(C_1-C_{10})$alkyl, halo$(C_1-C_{10})$alkylthio$(C_2-C_{10})$alkenyl, halo$(C_1-C_{10})$alkylthio $(C_2-C_{10})$alkynyl, $SO_2NR^3R^4$, $NR^3R^4$, $OR^3$, $S(O)_jR^3$, carboxy$(C_1-C_{20})$alkyl, carboxy$(C_2-C_{20})$alkenyl, carboxy$(C_2-C_{20})$alkynyl, aryl, aryl substituted with one or more substituents independently selected from halo, nitro, cyano, hydroxy, $(C_1-C_{10})$alkyl, $(C_1-C_{10})$alkylsulfonyl$(C_1-C_{10})$alkyl, $(C_1-C_{10})$alkylsulfonyl, thiocyanato, $(C_2-C_{10})$alkenyl, $(C_2-C_{10})$alkynyl, halo $(C_1-C_{10})$alkyl, halo$(C_2-C_{10})$alkenyl, halo$(C_2-C_{10})$alkynyl, $(C_1-C_{10})$alkoxy, halo$(C_1-C_{10})$alkoxy, $SO_2NR^3R^4$, and $NR^3R^4$, ar$(C_1-C_{10})$alkyl, ar$(C_2-C_{10})$alkenyl, ar$(C_2-C_{10})$alkynyl, arcyclo$(C_3-C_8)$alkyl, aroxy$(C_1-C_{10})$alkyl, or ar$(C_1-C_{10})$alkyl, ar$(C_2-C_{10})$alkenyl, ar$(C_2-C_{10})$alkynyl, arcyclo$(C_3-C_8)$alkyl, aroxy$(C_1-C_{10})$alkyl substituted with one or more substituents independently selected from halo, nitro, hydroxy, cyano, $(C_1-C_{10})$alkyl, cyclo$(C_3-C_8)$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo$(C_1-C_{10})$alkoxy, $SO_2NR^3R^4$ and $NR^3R^4$, heteroaryl, heteroaryl substituted with one or more substituents independently selected from halo, hydroxy, nitro, cyano, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo $(C_1-C_{10})$alkoxy and $NR^3R^4$, heteroar$(C_1-C_{10})$alkyl, heteroar$(C_2-C_{10})$alkenyl, heteroar$(C_2-C_{10})$alkynyl, or heteroar$(C_1-C_{10})$alkyl, heteroar$(C_2-C_{10})$alkenyl, heteroar$(C_2-C_{10})$alkynyl substituted with one or more substituents independently selected from halo, hydroxy, cyano, nitro, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo $(C_1-C_{10})$alkoxy, $SO_2NR^3R^4$ and $NR^3R^4$, wherein j is 0, 1 or 2, $R^1$ and $R^2$ are each independently a hydrogen atom, $(C_1-C_{20})$alkyl, $(C_2-C_{10})$alkenyl, $(C_2-C_{10})$alkynyl, $(C_1-C_{10})$alkoxy$(C_1-C_{10})$alkyl, $(C_1-C_{10})$alkoxy $(C_2-C_{10})$alkenyl, $(C_1-C_{10})$alkoxy$(C_2-C_{10})$alkynyl, $(C_1-C_{10})$alkylthio $(C_1-C_{10})$alkyl, $(C_1-C_{10})$alkylthio $(C_2-C_{10})$alkenyl, $(C_1-C_{10})$alkylthio$(C_2-C_{10})$alkynyl, carboxy, carboxy$(C_1-C_{20})$alkyl, carboxy$(C_2-C_{20})$alkenyl, carboxy$(C_2-C_{20})$alkynyl, $(C_1-C_{20})$alkoxycarbonyl, $(C_1-C_{10})$alkoxycarbonyl$(C_1-C_{10})$alkyl, $(C_1-C_{10})$alkoxycarbonyl$(C_2-C_{10})$alkenyl, $(C_1-C_{10})$alkoxycarbonyl$(C_2-C_{10})$alkynyl, $(C_1-C_{20})$alkylcarbonyl, $(C_2-C_{20})$alkenylcarbonyl, $(C_2-C_{20})$alkynylcarbonyl, cyclo$(C_3-C_8)$alkyl, cyclo$(C_3-C_8)$alkenyl, cyclo$(C_3-C_8)$alkyl$(C_1-C_{10})$alkyl, cyclo $(C_3-C_8)$alkenyl$(C_1-C_{10})$alkyl, cyclo$(C_3-C_8)$alkyl $(C_2-C_{10})$alkenyl, cyclo$(C_3-C_8)$alkenyl$(C_2-C_{10})$alkenyl, cyclo$(C_3-C_8)$alkyl$(C_2-C_{10})$alkynyl, cyclo $(C_3-C_8)$alkenyl$(C_2-C_{10})$alkynyl, heterocyclyl, heterocyclyl$(C_1-C_{10})$alkyl, heterocyclyl$(C_2-C_{10})$alkenyl, heterocyclyl$(C_2-C_{10})$alkynyl, aryl, aryl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo $(C_1-C_{10})$alkoxy, $SO_2NR^3R^4$ and $NR^3R^4$, aryl, ar$(C_1-C_{10})$alkyl, ar$(C_2-C_{10})$alkenyl, ar$(C_2-C_{10})$alkynyl, or aryl, ar$(C_1-C_{10})$alkyl, ar$(C_2-C_{10})$alkenyl, ar$(C_2-C_{10})$alkynyl substituted with one or more substituents independently selected from halo, $(C_1-C_{10})$alkyl, $(C_2-C_{10})$alkenyl, $(C_2-C_{10})$alkynyl, halo $(C_1-C_{10})$alkyl, halo$(C_2-C_{10})$alkenyl, halo$(C_2-C_{10})$alkynyl, $(C_1-C_{10})$alkoxy, halo$(C_1-C)$alkoxy, $SO_2NR^3R^4$ and $NR^3R^4$, heteroaryl, heteroar$(C_1-C_{10})$alkyl, heteroar$(C_2-C_{10})$alkenyl, heteroar$(C_2-C_{10})$alkynyl or heteroaryl, heteroar$(C_1-C_{10})$alkyl, heteroar ($C_2$–$C_{10}$)alkenyl, heteroar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$) alkynyl, halo($C_1$–$C_{10}$)alkyl, halo($C_2$–$C_{10}$)alkenyl, halo ($C_2$–$C_{10}$)alkynyl, ($C_1$–$C_{10}$)alkoxy, halo($C_1$–$C_{10}$) alkoxy, $SO_2NR^3R^4$ and $NR^3R^4$, or $R^1$ and $R^2$ taken together with the carbon atom to which they are attached form a 5–7 membered saturated or unsaturated ring, or $R^1$ may be a pesticidal moiety if $R^2$ is a hydrogen atom, $R^3$, $R^4$ and $R^5$ are each independently a hydrogen atom, ($C_1$–$C_{20}$)alkyl, cyclo($C_3$–$C_8$)alkyl, cyclo($C_3$–$C_8$) alkenyl, cyclo($C_3$–$C_8$)alkyl($C_1$–$C_{10}$)alkyl, cyclo ($C_3$–$C_8$)alkyl($C_2$–$C_{10}$)alkenyl, cyclo($C_3$–$C_8$)alkyl ($C_2$–$C_{10}$)alkynyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$) alkenyl($C_2$–$C_{10}$)alkynyl, heterocyclyl, heterocyclyl ($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy ($C_1$–$C_{10}$)alkyl, ($C_2$–$C_{10}$)alkenyl, ($C_2$–$C_{10}$)alkynyl, or ($C_1$–$C_{10}$)alkyl, cyclo($C_3$–$C_8$)alkyl, cyclo($C_3$–$C_8$) alkenyl, cyclo($C_3$–$C_8$)alkyl($C_1$–$C_{10}$)alkyl, cyclo ($C_3$–$C_8$)alkyl($C_2$–$C_{10}$)alkenyl, cyclo($C_3$–$C_8$)alkyl ($C_2$–$C_{10}$)alkynyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$) alkenyl($C_2$–$C_{10}$)alkynyl, heterocyclyl, heterocyclyl ($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy ($C_1$–$C_{10}$)alkyl, ($C_2$–$C_{10}$)alkenyl or ($C_2$–$C_{10}$)alkynyl, substituted with one or more halo, aryl, ar($C_1$–$C_{10}$) alkyl, ar($C_2$–$C_{10}$)alkenyl, ar($C_2$–$C_{10}$)alkynyl or aryl, ar($C_1$–$C_{10}$)alkyl, ar($C_2$–$C_{10}$)alkenyl, ar($C_2$–$C_{10}$) alkynyl substituted with one or more substituents independently selected from halo, ($C_1$–$C_{10}$)alkyl, ($C_2$–$C_{10}$) alkenyl, ($C_2$–$C_{10}$)alkynyl, halo($C_1$–$C_{10}$)alkyl, halo ($C_2$–$C_{10}$)alkenyl, halo($C_2$–$C_{10}$)alkynyl, ($C_1$–$C_{10}$) alkoxy and halo($C_1$–$C_{10}$)alkoxy, heteroaryl, heteroar ($C_1$–$C_{10}$)alkyl, heteroar($C_2$–$C_{10}$)alkenyl, heteroar ($C_2$–$C_{10}$)alkynyl or heteroaryl, heteroar($C_1$–$C_{10}$)alkyl, heteroar($C_2$–$C_{10}$)alkenyl, heteroar($C_2$–$C_{10}$)alkynyl substituted with one or more substituents independently selected from halo, ($C_1$–$C_{10}$)alkyl, ($C_2$–$C_{10}$) alkenyl, ($C_2$–$C_{10}$)alkynyl, halo($C_1$–$C_{10}$)alkyl, halo ($C_2$–$C_{10}$)alkenyl, halo($C_2$–$C_{10}$)alkynyl, ($C_1$–$C_{10}$) alkoxy and halo($C_1$–$C_{10}$)alkoxy, or $R^3$ and $R^4$ taken together with the nitrogen atom to which they are attached form a 5- or 6-membered saturated or unsaturated heterocyclic ring, or the pesticidally acceptable salts, isomers and enantiomers thereof In still another more preferred embodiment of this invention, the pesticidal compound is represented by formula (I)

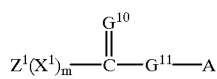

(I)

wherein
A is

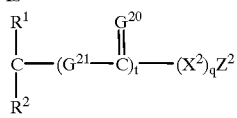

$G^{10}$ and $G^{11}$ are each independently an oxygen atom or a sulfur atom,
m is 1,
q is 1,
t is 0, $Z^1(X^1)_m$ and $Z^2(X^2)_q$—H or $Z^2(X^2)_q$, respectively, represent the pesticide combinations selected from the group consisting of cymoxanil and myclobutanil, cymoxanil and fenbuconazole, cymoxanil and epoxiconazole, cymoxanil and propiconazole, cymoxanil and tebuconazole, cymoxanil and zoxamide, cymoxanil and mancozeb, cymoxanil and famoxadone, cymoxanil and fenamidone, cymoxanil and propamocarb, cymoxanil and fluazinam, cymoxanil and fosetyl, thifluzamide and ferimzone, thifluzamide and capropamid, thifluzamide and myclobutanil, thifluzamide and fenbuconazole, thifluzamide and epoxiconazole, thifluzamide and tebuconazole, thifluzamide and propiconazole, thifluzamide and fenpiclonil, thifluzamide and fludioxonil, thifluzamide and metominostrobin, thifluzamide and SSF-129, thifluzamide and 2-[5-(4-chlorophenyl)-4-methyl-2,7-dioxa-3,6-diazaocta-3,5-dien-1-yl]-α-(methoxyimino)-N-methyl-benzeneacetamide, thifluzamide and fluazinam, flutolanil and capropamid, flutolanil and myclobutanil, flutolanil and fenbuconazole, flutolanil and epoxiconazole, flutolanil and propiconazole, flutolanil and tebuconazole, flutolanil and metominostrobin, flutolanil and SSF-129, flutolanil and 2-[5-(4-chlorophenyl)-4-methyl-2,7-dioxa-3,6-diazaocta-3,5-dien-1-yl]-α-(methoxyimino)-N-methyl-benzeneacetamide, flutolanil and ferimzone, propamocarb and myclobutanil, propamocarb and fenbuconazole, propamocarb and epoxiconazole, propamocarb and propiconazole, propamocarb and tebuconazole, propamocarb and zoxamide, propamocarb and mancozeb, propamocarb and famoxadone, propamocarb and fenamidone, propamocarb and fluazinam, propamocarb and metominostrobin, propamocarb and SSF-129, propamocarb and 2-[5-(4-chlorophenyl)-4-methyl-2,7-dioxa-3,6-diazaocta-3,5-dien-1-yl]-α-(methoxyimino)-N-methyl-benzeneacetamide, propamocarb and fosetyl, tebuconazole and zoxamide, tebuconazole and mancozeb, tebuconazole and famoxadone, tebuconazole and fenamidone, tebuconazole and ferimzone, tebuconazole and capropamid, tebuconazole and metominostrobin, tebuconazole and SSF-129, tebuconazole and 2-[5-(4-chlorophenyl)-4-methyl-2,7-dioxa-3,6-diazaocta-3,5-dien-1-yl]-α-(methoxyimino)-N-methyl-benzeneacetamide, tebuconazole and fluazinam, tebuconazole and cyprodinil, tebuconazole and pyrimethanil, tebuconazole and epoxiconazole, tebuconazole and propiconazole, tebuconazole and 2-[5-(4-fluorophenyl)-4-methyl-2,7-dioxa-3,6-diazaocta-3,5-dien-1-yl]-α-(methoxyimino)-N-methyl-benzeneacetamide, tebuconazole and myclobutanil, tebuconazole and fenbuconazole, tebuconazole and cyproconazole, tebuconazole and fenpropimorph, tebuconazole and fosetyl, cyproconazole and zoxamide, cyproconazole and mancozeb, cyproconazole and famoxadone, cyproconazole and fenamidone, cyproconazole and ferimzone, cyproconazole and capropamid, cyproconazole and metominostrobin, cyproconazole and SSF-129, cyproconazole and 2-[5-(4-chlorophenyl)-4-methyl-2,7-dioxa-3,6-diazaocta-3,5-dien-1-yl]-α-(methoxyimino)-N-methyl-benzeneacetamide, cyproconazole and fluazinam, cyproconazole and cyprodinil, cyproconazole and pyrimethanil, cyproconazole and epoxiconazole, cyproconazole and propiconazole, cyproconazole and myclobutanil, cyproconazole and fenbuconazole, cyproconazole and tebuconazole, cyproconazole and fenpropimorph, cyproconazole and fosetyl, fenamidone and myclobutanil, fenamidone and fenbuconazole, fenamidone and epoxiconazole, fenamidone and propiconazole, fenamidone and tebuconazole, fenamidone and zoxamide, fenamidone and mancozeb, fenamidone and famoxadone, fenamidone and cyprodinil, fenamidone and pyrimethanil, fenamidone and fluazinam, fenamidone and metominostrobin, fenamidone and SSF-129, fenamidone and 2-[5-(4-chlorophenyl)-4-methyl-2,7-dioxa-3,6-diazaocta-3,5-dien-1-yl]-α-(methoxyimino)-N-methyl-benzeneacetamide, fenamidone and fosetyl, iprodione and zoxamide, iprodione and fosetyl, iprodione and mancozeb, iprodione and famoxadone, iprodione and fenamidone, iprodione and ferimzone, iprodione and capropamid, iprodione and metominostrobin, iprodione and SSF-129, iprodione and 2-[5-(4-chlorophenyl)-4-methyl-2,7-dioxa-3,6-diazaocta-3,5-dien-1-yl]-α-(methoxyimino)-N-methyl-benzeneacetamide, iprodione and fluazinam, iprodione and cyprodinil, iprodione and pyrimethanil, iprodione and epoxiconazole, iprodione and propiconazole, iprodione and myclobutanil, iprodione and fenbuconazole, iprodione and cyproconazole, iprodione and tebuconazole, fosetyl and myclobutanil, fosetyl and fenbuconazole, fosetyl and epoxiconazole, fosetyl and propiconazole, fosetyl and tebuconazole, fosetyl and fenpropimorph, fosetyl and zoxamide, fosetyl and mancozeb, fosetyl and famoxadone, fosetyl and fenamidone, fosetyl and cyprodinil, fosetyl and pyrimethanil, fosetyl and fluazinam, fosetyl and metominostrobin, fosetyl and SSF-129, fosetyl and 2-[5-(4-chlorophenyl)-4-methyl-2,7-dioxa-3,6-diazaocta-3,5-dien-1-yl]-α-(methoxyimino)-N-methyl-benzeneacetamide, fosetyl and thifluzamide, carboxin and myclobutanil, carboxin and fenbuconazole, carboxin and epoxiconazole, carboxin and propiconazole, carboxin and tebuconazole, carboxin and zoxamide, carboxin and mancozeb, carboxin and famoxadone, carboxin and fenamidone, carboxin and cyprodinil, carboxin and pyrimethanil, carboxin and fluazinam, carboxin and metominostrobin, carboxin and SSF-129, carboxin and 2-[5-(4-chlorophenyl)-4-methyl-2,7-dioxa-3,6-diazaocta-3,5-dien-1-yl]-α-(methoxyimino)-N-methyl-benzeneacetamide, carboxin and thifluzamide, carboxin and fosetyl, famoxadone and myclobutanil, famoxadone and fenbuconazole, famoxadone and epoxiconazole, famoxadone and propiconazole, famoxadone and tebuconazole, famoxadone and zoxamide, famoxadone and mancozeb, famoxadone and cyprodinil, famoxadone and pyrimethanil, famoxadone and fluazinam, famoxadone and metominostrobin, famoxadone and SSF-129, famoxadone and 2-[5-(4-chlorophenyl)-4-methyl-2,7-dioxa-3,6-diazaocta-3,5-dien-1-yl]-α-(methoxyimino)-N-methyl-benzeneacetamide, famoxadone and thifluzamide, famoxadone and fosetyl, fluazinam and myclobutanil, fluazinam and fenbuconazole, fluazinam and epoxiconazole, fluazinam and propiconazole, fluazinam and tebuconazole, fluazinam and zoxamide, fluazinam and mancozeb, fluazinam and cyprodinil, fluazinam and pyrimethanil, fluazinam and fluazinam, fluazinam and metominostrobin, fluazinam and SSF-129, fluazinam and 2-[5-(4-chlorophenyl)-4-methyl-2,7-dioxa-3,6-diazaocta-3,5-dien-1-yl]-α-(methoxyimino)-N-methyl-benzeneacetamide, fluazinam and thifluzamide, fluazinam and fosetyl, cyprodinil and zoxamide, cyprodinil and mancozeb, cyprodinil and famoxadone, cyprodinil and fenamidone, cyprodinil and ferimzone, cyprodinil and capropamid, cyprodinil and metominostrobin, cyprodinil and SSF-129, cyprodinil and 2-[5-(4-chlorophenyl)-4-methyl-2,7-dioxa-3,6-diazaocta-3,5-dien-1-yl]-α-(methoxyimino)-N-methyl-benzeneacetamide, cyprodinil and fluazinam, cyprodinil and pyrimethanil, cyprodinil and epoxiconazole, cyprodinil and propiconazole, cyprodinil and tebuconazole, cyprodinil and cyproconazole, cyprodinil and myclobutanil, cyprodinil and fenbuconazole, cyprodinil and fenpropimorph, cyprodinil and fosetyl, fenarimol and zoxamide, fenarimol and mancozeb, fenarimol and famoxadone, fenarimol and fenamidone, fenarimol and SSF-129, fenarimol and 2-[5-(4-chlorophenyl)-4-methyl-2,7-dioxa-3,6-diazaocta-3,5-dien-1-yl]-α-(methoxyimino)-N-methyl-benzeneacetamide, fenarimol and fluazinam, fenarimol and pyrimethanil, ferimzone and capropamid, ferimzone and myclobutanil, ferimzone and fenbuconazole, ferimzone and epoxiconazole, ferimzone and propiconazole, ferimzone and metominostrobin, ferimzone and SSF-129, ferimzone and 2-[5-(4-chlorophenyl)-4-methyl-2,7-dioxa-3,6-diazaocta-3,5-dien-1-yl]-α-(methoxyimino)-N-methyl-benzeneacetamide, ferimzone and flutolanil, ferimzone and thifluzamide, ferimzone and pencycuron, pyrimethanil and zoxamide, pyrimethanil and mancozeb, pyrimethanil and famoxadone, pyrimethanil and fenamidone, pyrimethanil and SSF-129, pyrimethanil and 2-[5-(4-chlorophenyl)-4-methyl-2,7-dioxa-3,6-diazaocta-3,5-dien-1-yl]-α-(methoxyimino)-N-methyl-benzeneacetamide, pyrimethanil and fluazinam, pyrimethanil and cyprodinil, pyrimethanil and myclobutanil, pyrimethanil and fenbuconazole, pyrimethanil and epoxiconazole, ferimzone and tebuconazole, pyrimethanil and fosetyl, metominostrobin and mancozeb, metominostrobin and ferimzone, metominostrobin and capropamid, metominostrobin and myclobutanil, metominostrobin and fenbuconazole, metominostrobin and tebuconazole, metominostrobin and epoxiconazole, metominostrobin and SSF-129, metominostrobin and 2-[5-(4-chlorophenyl)-4-methyl-2,7-dioxa-3,6-diazaocta-3,5-dien-1-yl]-α-(methoxyimino)-N-methyl-benzeneacetamide, metominostrobin and flutolanil, metominostrobin and fosetyl, metominostrobin and pencycuron, zoxamide and myclobutanil, zoxamide and fenbuconazole, zoxamide and epoxiconazole, zoxamide and propiconazole, zoxamide and tebuconazole, zoxamide and cyproconazole, zoxamide and fenpropimorph, zoxamide and maneb, zoxamide and mancozeb, zoxamide and famoxadone, zoxamide and fenamidone, zoxamide and fosetyl, zoxamide and cyprodinil, zoxamide and pyrimethanil, zoxamide and fluazinam, zoxamide and metominostrobin, zoxamide and SSF-129, zoxamide and 2-[5-(4-chlorophenyl)-4-methyl-2,7-dioxa-3,6-diazaocta-3,5-dien-1-yl]-α-(methoxyimino)-N-methyl-benzeneacetamide, zoxamide and thifluzamide, capropamid and myclobutanil, capropamid and fenbuconazole, capropamid and epoxiconazole, capropamid and propiconazole, capropamid and tebuconazole, capropamid and metominostrobin, capropamid and SSF-129, capropamid and 2-[5-(4-chlorophenyl)-4-methyl-2,7-dioxa-3,6-diazaocta-3,5-dien-1-yl]-α-(methoxyimino)-N-methyl-benzeneacetamide, capropamid and flutolanil, capropamid and thifluzamide, capropamid and pencycuron, fenpiclonil and myclobutanil, fenpiclonil and tebuconazole, fenpiclonil and epoxiconazole, fenpiclonil and thifluzamide, fludioxonil and myclobutanil, fludioxonil and tebuconazole, fludioxonil and epoxiconazole, fludioxonil and thifluzamide, SSF-129 and zoxamide, SSF-129 and mancozeb, SSF-129 and famoxadone, SSF-129 and fenamidone, SSF-129 and ferimzone, SSF-129 and capropamid, SSF-129 and metominostrobin, SSF-129 and fluazinam, SSF- 129 and cyprodinil, SSF-129 and pyrimethanil, SSF-129 and propiconazole, SSF-129 and 2-[5-(4-chlorophenyl)-4-methyl-2,7-dioxa-3,6-diazaocta-3,5-dien-1-yl]-α-(methoxyimino)-N-methyl-benzeneacetamide, SSF-129 and epoxiconazole, SSF-129 and fenbuconazole, SSF-129 and tebuconazole, SSF-129 and cyproconazole, SSF-129 and fenpropimorph, SSF-129 and myclobutanil, SSF-129 and fosetyl, 2-[5-(4-chlorophenyl)-4-methyl-2,7-dioxa-3,6-diazaocta-3,5-dien-1-yl]-α-(methoxyimino)-N-methyl-benzeneacetamide and zoxamide, 2-[5-(4-chlorophenyl)-4-methyl-2,7-dioxa-3,6-diazaocta-3,5-dien-1-yl]-α-(methoxyimino)-N-methyl-benzeneacetamide and mancozeb, 2-[5-(4-chlorophenyl)-4-methyl-2,7-dioxa-3,6-diazaocta-3,5-dien-1-yl]-α-(methoxyimino)-N-methyl-benzeneacetamide and famoxadone, 2-[5-(4-chlorophenyl)-4-methyl-2,7-dioxa-3,6-diazaocta-3,5-dien-1-yl]-α-(methoxyimino)-N-methyl-benzeneacetamide and fenamidone, 2-[5-(4-chlorophenyl)-4-methyl-2,7-dioxa-3,6-diazaocta-3,5-dien-1-yl]-α-(methoxyimino)-N-methyl-benzeneacetamide and ferimzone, 2-[5-(4-chlorophenyl)-4-methyl-2,7-dioxa-3,6-diazaocta-3,5-dien-1-yl]-α-(methoxyimino)-N-methyl-benzeneacetamide and capropamid, 2-[5-(4-chlorophenyl)-4-methyl-2,7-dioxa-3,6-diazaocta-3,5-dien-1-yl]-α-(methoxyimino)-N-methyl-benzeneacetamide and metominostrobin, 2-[5-(4-chlorophenyl)-4-methyl-2,7-dioxa-3,6-diazaocta-3,5-dien-1-yl]-α-(methoxyimino)-N-methyl-benzeneacetamide and SSF-129, 2-[5-(4-chlorophenyl)-4-methyl-2,7-dioxa-3,6-diazaocta-3,5-dien-1-yl]-α-(methoxyimino)-N-methyl-benzeneacetamide and fluazinam, 2-[5-(4-chlorophenyl)-4-methyl-2,7-dioxa-3,6-diazaocta-3,5-dien-1-yl]-α-(methoxyimino)-N-methyl-benzeneacetamide and cyprodinil, 2-[5-(4-chlorophenyl)-4-methyl-2,7-dioxa-3,6-diazaocta-3,5-dien-1-yl]-α-(methoxyimino)-N-methyl-benzeneacetamide and pyrimethanil, 2-[5-(4-chlorophenyl)-4-methyl-2,7-dioxa-3,6-diazaocta-3,5-dien-1-yl]-α-(methoxyimino)-N-methyl-benzeneacetamide and epoxiconazole, 2-[5-(4-chlorophenyl)-4-methyl-2,7-dioxa-3,6-diazaocta-3,5-dien-1-yl]-α-(methoxyimino)-N-methyl-benzeneacetamide and propiconazole, 2-[5-(4-fluorophenyl)-4-methyl-2,7-dioxa-3,6-diazaocta-3,5-dien-1-yl]-α-(methoxyimino)-N-methyl-benzeneacetamide and metominostrobin, 2-[5-(4-fluorophenyl)-4-methyl-2,7-dioxa-3,6-diazaocta-3,5-dien-1-yl]-α-(methoxyimino)-N-methyl-benzeneacetamide and SSF-129, 2-[5-(4-fluorophenyl)-4-methyl-2,7-dioxa-3,6-diazaocta-3,5-dien-1-yl]-α-(methoxyimino)-N-methyl-benzeneacetamide and fluazinam, 2-[5-(4-fluorophenyl)-4-methyl-2,7-dioxa-3,6-diazaocta-3,5-dien-1-yl]-α-(methoxyimino)-N-methyl-benzeneacetamide and cyprodinil, 2-[5-(4-fluorophenyl)-4-methyl-2,7-dioxa-3,6-diazaocta-3,5-dien-1-yl]-α-(methoxyimino)-N-methyl-benzeneacetamide and pyrimethanil, 2-[5-(4-fluorophenyl)-4-methyl-2,7-dioxa-3,6-diazaocta-3,5-dien-1-yl]-α-(methoxyimino)-N-methyl-benzeneacetamide and epoxiconazole, 2-[5-(4-fluorophenyl)-4-methyl-2,7-dioxa-3,6-diazaocta-3,5-dien-1-yl]-α-(methoxyimino)-N-methyl-benzeneacetamide and propiconazole, 2-[5-(4-fluorophenyl)-4-methyl-2,7-dioxa-3,6-diazaocta-3,5-dien-1-yl]-α-(methoxyimino)-N-methyl-benzeneacetamide and tebuconazole, 2-[5-(4-fluorophenyl)-4-methyl-2,7-dioxa-3,6-diazaocta-3,5-dien-1-yl]-α-(methoxyimino)-N-methyl-benzeneacetamide and myclobutanil, 2-[5-(4-fluorophenyl)-4-methyl-2,7-dioxa-3,6-diazaocta-3,5-dien-1-yl]-α-(methoxyimino)-N-methyl-benzeneacetamide and fenbuconazole, 2-[5-(4-fluorophenyl)-4-methyl-2,7-dioxa-3,6-diazaocta-3,5-dien-1-yl]-α-(methoxyimino)-N-methyl-benzeneacetamide and cyproconazole, 2-[5-(4-fluorophenyl)-4-methyl-2,7-dioxa-3,6-diazaocta-3,5-dien-1-yl]-α-(methoxyimino)-N-methyl-benzeneacetamide and fenpropimorph, 2-[5-(4-fluorophenyl)-4-methyl-2,7-dioxa-3,6-diazaocta-3,5-dien-1-yl]-α-(methoxyimino)-N-methyl-benzeneacetamide and fosetyl, propamocarb and cymoxanil, tebuconazole and cymoxanil, fenamidone and cymoxanil, fosetyl and cymoxanil, famoxadone and cymoxanil, zoxamide and cymoxanil, SSF-129 and cymoxanil, 2-[5-(4-chlorophenyl)-4-methyl-2,7-dioxa-3,6-diazaocta-3,5-dien-1-yl]-α-(methoxyimino)-N-methyl-benzeneacetamide and cymoxanil, pronamide and clopyralid, diflufenican and clopyralid, flumetsulam and clopyralid, propanil and clopyralid, asulam and clopyralid, chlorpropham and clopyralid, desmedipham and clopyralid, phenmedipham and clopyralid, sulcotrione and clopyralid, sethoxydim and clopyralid, tralkoxydim and clopyralid, pendimethalin and clopyralid, dinoseb and clopyralid, aclonifen and clopyralid, fomesafen and clopyralid, atrazine and clopyralid, terbuthylazine and clopyralid, terbumeton and clopyralid, ametryn and clopyralid, metribuzin and clopyralid, amitrole and clopyralid, bentazon and clopyralid, bromacil and clopyralid, chlorotoluron and clopyralid, diuron and clopyralid, fluometuron and clopyralid, isoproturon and clopyralid, linuron and clopyralid, chlorsulfuron and clopyralid, nicosulfuron and clopyralid, rimsulfuron and clopyralid, pronamide and acifluorfen, diflufenican and acifluorfen, flumetsulam and acifluorfen, propanil and acifluorfen, asulam and acifluorfen, chlorpropham and acifluorfen, desmedipham and acifluorfen, phenmedipham and acifluorfen, sulcotrione and acifluorfen, sethoxydim and acifluorfen, tralkoxydim and acifluorfen, pendimethalin and acifluorfen, dinoseb and acifluorfen, aclonifen and acifluorfen, fomesafen and acifluorfen, atrazine and acifluorfen, terbuthylazine and acifluorfen, terbumeton and acifluorfen, ametryn and acifluorfen, metribuzin and acifluorfen, amitrole and acifluorfen, bentazon and acifluorfen, bromacil and acifluorfen, chlorotoluron and acifluorfen, diuron and acifluorfen, fluometuron and acifluorfen, isoproturon and acifluorfen, linuron and acifluorfen, chlorsulfuron and acifluorfen, nicosulfuron and acifluorfen, rimsulfuron and acifluorfen, pronamide and imazaquin, diflufenican and imazaquin, flumetsulam and imazaquin, propanil and imazaquin, asulam and imazaquin, chlorpropham and imazaquin, desmedipham and imazaquin, phenmedipham and imazaquin, sulcotrione and imazaquin, sethoxydim and imazaquin, tralkoxydim and imazaquin, pendimethalin and imazaquin, dinoseb and imazaquin, aclonifen and imazaquin, fomesafen and imazaquin, atrazine and imazaquin, terbuthylazine and imazaquin, terbumeton and imazaquin, ametryn and imazaquin, metribuzin and imazaquin, amitrole and imazaquin, bentazon and imazaquin, bromacil and imazaquin, chlorotoluron and imazaquin, diuron and imazaquin, fluometuron and imazaquin, isoproturon and imazaquin, linuron and imazaquin, chlorsulfuron and imazaquin, nicosulfuron and imazaquin, rimsulfuron and imazaquin, pronamide and imazethapyr, diflufenican and imazethapyr, flumetsulam and imazethapyr, propanil and imazethapyr, asulam and imazethapyr, chlorpropham and imazethapyr, desmedipham and imazethapyr, phenmedipham and imazethapyr, sulcotrione and imazethapyr, sethoxydim and imazethapyr, tralkoxydim and imazethapyr, pendimethalin and imazethapyr, dinoseb and imazethapyr, aclonifen and imazethapyr, fomesafen and imazethapyr, oisoxaben and imazethapyr, pyrazon and imazethapyr, atrazine and imazethapyr, terbuthylazine and imazethapyr, terbumeton and imazethapyr, ametryn and imazethapyr, metribuzin and imazethapyr, amitrole and imazethapyr, bentazon and imazethapyr, bromacil and imazethapyr, chlorotoluron and imazethapyr, diuron and imazethapyr, fluometuron and imazethapyr, isoproturon and imazethapyr, linuron and imazethapyr, chlorsulfuron and imazethapyr, nicosulfuron and imazethapyr, rimsulfuron and imazethapyr, tribenuron and fenoxaprop, thifensulfuron and fenoxaprop, pronamide and fenoxaprop, diflufenican and fenoxaprop, flumetsulam and fenoxaprop, propanil and fenoxaprop, asulam and fenoxaprop, chlorpropham and fenoxaprop, desmedipham and fenoxaprop, phenmedipham and fenoxaprop, sulcotrione and fenoxaprop, sethoxydim and fenoxaprop, tralkoxydim and fenoxaprop, pendimethalin and fenoxaprop, dinoseb and fenoxaprop, aclonifen and fenoxaprop, fomesafen and fenoxaprop, atrazine and fenoxaprop, terbuthylazine and fenoxaprop, terbumeton and fenoxaprop, ametryn and fenoxaprop, metribuzin and fenoxaprop, amitrole and fenoxaprop, bentazon and fenoxaprop, bromacil and fenoxaprop, chlorotoluron and fenoxaprop, diuron and fenoxaprop, fluometuron and fenoxaprop, isoproturon and fenoxaprop, linuron and fenoxaprop, chlorsulfuron and fenoxaprop, nicosulfuron and fenoxaprop, rimsulfuron and fenoxaprop, pronamide and fluazifop, diflufenican and fluazifop, flumetsulam and fluazifop, propanil and fluazifop, asulam and fluazifop, chlorpropham and fluazifop, desmedipham and fluazifop, phenmedipham and fluazifop, sulcotrione and fluazifop, sethoxydim and fluazifop, tralkoxydim and fluazifop, pendimethalin and fluazifop, dinoseb and fluazifop, aclonifen and fluazifop, fomesafen and fluazifop, atrazine and fluazifop, terbuthylazine and fluazifop, terbumeton and fluazifop, ametryn and fluazifop, metribuzin and fluazifop, amitrole and fluazifop, bentazon and fluazifop, bromacil and fluazifop, chlorotoluron and fluazifop, diuron and fluazifop, fluometuron and fluazifop, isoproturon and fluazifop, linuron and fluazifop, chlorsulfuron and fluazifop, nicosulfuron and fluazifop, rimsulfuron and fluazifop, pronamide and haloxyfop, diflufenican and haloxyfop, flumetsulam and haloxyfop, propanil and haloxyfop, asulam and haloxyfop, chlorpropham and haloxyfop, desmedipham and haloxyfop, phenmedipham and haloxyfop, sulcotrione and haloxyfop, sethoxydim and haloxyfop, tralkoxydim and haloxyfop, pendimethalin and haloxyfop, dinoseb and haloxyfop, aclonifen and haloxyfop, fomesafen and haloxyfop, oisoxaben and haloxyfop, pyrazon and haloxyfop, atrazine and haloxyfop, terbuthylazine and haloxyfop, terbumeton and haloxyfop, ametryn and haloxyfop, metribuzin and haloxyfop, amitrole and haloxyfop, bentazon and haloxyfop, bromacil and haloxyfop, chlorotoluron and haloxyfop, diuron and haloxyfop, fluometuron and haloxyfop, isoproturon and haloxyfop, linuron and haloxyfop, chlorsulfuron and haloxyfop, nicosulfuron and haloxyfop, rimsulfuron and haloxyfop, diflufenican and 2,4-D, pendimethalin and 2,4-D, nicosulfuron and 2,4-D, rimsulfuron and 2,4-D, diflufenican and 2,4-DB, pendimethalin and 2,4-DB, nicosulfuron and 2,4-DB, diflufenican and triclopyr, pendimethalin and triclopyr, nicosulfuron and triclopyr, diflufenican and dicamba, pendimethalin and dicamba, nicosulfuron and dicamba, clothianidin and chromafenozide, imidacloprid and chromafenozide, nidinotefuran and chromafenozide, nitenpyram and chromafenozide, NTN-32692 and chromafenozide, chromafenozide and clothianidin, chromafenozide and imidacloprid, chromafenozide and nidinotefuran, chromafenozide and nitenpyram, chromafenozide and NTN-32692, nitenpyram and halofenozide, NTN-32692 and halofenozide, clothianidin and halofenozide, imidacloprid and halofenozide, nidinotefuran and halofenozide, halofenozide and clothianidin, halofenozide and imidacloprid, halofenozide and nidinotefuran, halofenozide and nitenpyram, halofenozide and NTN-32692, nitenpyram and methoxyfenozide, NTN-32692 and methoxyfenozide, clothianidin and methoxyfenozide, imidacloprid and methoxyfenozide, nidinotefuran and methoxyfenozide, methoxyfenozide and clothianidin, methoxyfenozide and imidacloprid, methoxyfenozide and nidinotefuran, methoxyfenozide and nitenpyram, methoxyfenozide and NTN-32692, nidinotefuran and tebufenozide, nitenpyram and tebufenozide, NTN-32692 and tebufenozide, clothianidin and tebufenozide, imidacloprid and tebufenozide, tebufenozide and clothianidin, tebufenozide and imidacloprid, tebufenozide and nidinotefuran, tebufenozide and nitenpyram, tebufenozide and NTN-32692, chlorfluazuron and clothianidin, diflubenzuron and clothianidin, flucycloxuron and clothianidin, flufenoxuron and clothianidin, hexaflumuron and clothianidin, lufenuron and clothianidin, novaluron and clothianidin, teflubenzuron and clothianidin, triflumuron and clothianidin, clothianidin and chlorfluazuron, clothianidin and diflubenzuron, clothianidin and flucycloxuron, clothianidin and flufenoxuron, clothianidin and hexaflumuron, clothianidin and lufenuron, clothianidin and novaluron, clothianidin and teflubenzuron, clothianidin and triflumuron, chlorfluazuron and imidacloprid, diflubenzuron and imidacloprid, flucycloxuron and imidacloprid, flufenoxuron and imidacloprid, hexaflumuron and imidacloprid, lufenuron and imidacloprid, novaluron and imidacloprid, teflubenzuron and imidacloprid, triflumuron and imidacloprid, imidacloprid and chlorfluazuron, imidacloprid and diflubenzuron, imidacloprid and flucycloxuron, imidacloprid and flufenoxuron, imidacloprid and hexaflumuron, imidacloprid and lufenuron, imidacloprid and novaluron, imidacloprid and teflubenzuron, imidacloprid and triflumuron, chlorfluazuron and nidinotefuran, diflubenzuron and nidinotefuran, flucycloxuron and nidinotefuran, flufenoxuron and nidinotefuran, hexaflumuron and nidinotefuran, novaluron and nidinotefuran, teflubenzuron and nidinotefuran, triflumuron and nidinotefuran, nidinotefuran and chlorfluazuron, nidinotefuran and diflubenzuron, nidinotefuran and flucycloxuron, nidinotefuran and flufenoxuron, nidinotefuran and hexaflumuron, nidinotefuran and novaluron, nidinotefuran and teflubenzuron, nidinotefuran and triflumuron, diflubenzuron and nitenpyram, flucycloxuron and nitenpyram, flufenoxuron and nitenpyram, hexaflumuron and nitenpyram, lufenuron and nitenpyram, novaluron and nitenpyram, teflubenzuron and nitenpyram, triflumuron and nitenpyram, nitenpyram and diflubenzuron, nitenpyram and flucycloxuron, nitenpyram and flufenoxuron, nitenpyram and hexaflumuron, nitenpyram and lufenuron, nitenpyram and novaluron, nitenpyram and teflubenzuron, nitenpyram and triflumuron, chlorfluazuron and NTN- 32692, diflubenzuron and NTN-32692, flucycloxuron and NTN-32692, flufenoxuron and NTN-32692, hexaflumuron and NTN-32692, lufenuron and NTN-32692, novaluron and NTN-32692, teflubenzuron and NTN-32692, triflumuron and NTN-32692, NTN-32692 and chlorfluazuron, NTN-32692 and diflubenzuron, NTN-32692 and flucycloxuron, NTN-32692 and flufenoxuron, NTN-32692 and hexaflumuron, NTN-32692 and lufenuron, NTN-32692 and novaluron, NTN-32692 and teflubenzuron, NTN-32692 and triflumuron, chlorfluazuron and acephate, diflubenzuron and acephate, flucycloxuron and acephate, flufenoxuron and acephate, hexaflumuron and acephate, lufenuron and acephate, novaluron and acephate, teflubenzuron and acephate, triflumuron and acephate, chromafenozide and acephate, halofenozide and acephate, methoxyfenozide and acephate, tebufenozide and acephate and chlorfluazuron, acephate and diflubenzuron, acephate and flucycloxuron, acephate and flufenoxuron, acephate and hexaflumuron, acephate and lufenuron, acephate and novaluron, acephate and teflubenzuron, acephate and triflumuron, acephate and chromafenozide, acephate and halofenozide, acephate and methoxyfenozide, tebufenozide and tebufenozide, chromafenozide and fluvalinate, tebufenozide and fluvalinate, halofenozide and fluvalinate, methoxyfenozide and fluvalinate, chromafenozide and fluazuron, halofenozide and fluazuron, methoxyfenozide and fluazuron, tebufenozide and fluazuron, chromafenozide and fipronil, halofenozide and fipronil, methoxyfenozide and fipronil, tebufenozide and fipronil, fipronil and chromafenozide, fipronil and halofenozide, fipronil and methoxyfenozide, fipronil and tebufenozide, chromafenozide and pyrimidifen, halofenozide and pyrimidifen, methoxyfenozide and pyrimidifen, tebufenozide and pyrimidifen, chlorfluazuron and pyrimidifen, diflubenzuron and pyrimidifen, flucycloxuron and pyrimidifen, flufenoxuron and pyrimidifen, hexaflumuron and pyrimidifen, lufenuron and pyrimidifen, novaluron and pyrimidifen, teflubenzuron and pyrimidifen, triflumuron and pyrimidifen, chlorfluazuron and dicofol, diflubenzuron and dicofol, flucycloxuron and dicofol, flufenoxuron and dicofol, hexaflumuron and dicofol, lufenuron and dicofol, novaluron and dicofol, teflubenzuron and dicofol, triflumuron and dicofol, dicofol and chlorfluazuron, dicofol and diflubenzuron, dicofol and flucycloxuron, dicofol and flufenoxuron, dicofol and hexaflumuron, dicofol and lufenuron, dicofol and novaluron, dicofol and teflubenzuron, dicofol and triflumuron, chromafenozide and tebuconazole, methoxyfenozide and tebuconazole, tebufenozide and tebuconazole, bifenazate and tebuconazole, pyrimidifen and tebuconazole, tebuconazole and chromafenozide, tebuconazole and methoxyfenozide, tebuconazole and tebufenozide, tebuconazole and bifenazate, tebuconazole and pyrimidifen, chromafenozide and fenbuconazole, methoxyfenozide and fenbuconazole, tebufenozide and fenbuconazole, bifenazate and fenbuconazole, pyrimidifen and fenbuconazole, cyproconazole and chromafenozide, cyproconazole and methoxyfenozide, cyproconazole and tebufenozide, cyproconazole and bifenazate, cyproconazole and pyrimidifen, halofenozide and fenpiclonil, fenpiclonil and halofenozide, chromafenozide and fluazinam, halofenozide and fluazinam, methoxyfenozide and fluazinam, tebufenozide and fluazinam, chlorfluazuron and fluazinam, diflubenzuron and fluazinam, flucycloxuron and fluazinam, flufenoxuron and fluazinam, hexaflumuron and fluazinam, lufenuron and fluazinam, novaluron and fluazinam, teflubenzuron and fluazinam, triflumuron and fluazinam, fluazinam and chromafenozide, fluazinam and halofenozide, fluazinam and methoxyfenozide, fluazinam and tebufenozide, fluazinam and chlorfluazuron, fluazinam and diflubenzuron, fluazinam and flucycloxuron, fluazinam and flufenoxuron, fluazinam and hexaflumuron, fluazinam and lufenuron, fluazinam and novaluron, fluazinam and teflubenzuron, and fluazinam and triflumuron, $R^1$ and $R^2$ are each independently a hydrogen atom, $(C_1-C_{20})$alkyl, $(C_2-C_{10})$alkenyl, $(C_2-C_{10})$alkynyl, $(C_1-C_{10})$alkoxy$(C_1-C_{10})$alkyl, $(C_1-C_{10})$alkoxy$(C_2-C_{10})$alkenyl, $(C_1-C_{10})$alkoxy$(C_2-C_{10})$alkynyl, $(C_1-C_{10})$alkylthio$(C_1-C_{10})$alkyl, $(C_1-C_{10})$alkylthio$(C_2-C_{10})$alkenyl, $(C_1-C_{10})$alkylthio$(C_2-C_{10})$alkynyl, carboxy, carboxy$(C_1-C_{20})$alkyl, carboxy$(C_2-C_{20})$alkenyl, carboxy$(C_2-C_{20})$alkynyl, $(C_1-C_{20})$alkoxycarbonyl, $(C_1-C_{10})$alkoxycarbonyl$(C_1-C_{10})$alkyl, $(C_1-C_{10})$alkoxycarbonyl$(C_2-C_{10})$alkenyl, $(C_1-C_{10})$alkoxycarbonyl$(C_2-C_{10})$alkynyl, $(C_1-C_{20})$alkylcarbonyl, $(C_2-C_{20})$alkenylcarbonyl, $(C_2-C_{20})$alkynylcarbonyl, cyclo$(C_3-C_8)$alkyl, cyclo$(C_3-C_8)$alkenyl, cyclo$(C_3-C_8)$alkyl$(C_1-C_{10})$alkyl, cyclo$(C_3-C_8)$alkenyl$(C_1-C_{10})$alkyl, cyclo$(C_3-C_8)$alkyl$(C_2-C_{10})$alkenyl, cyclo$(C_3-C_8)$alkenyl$(C_2-C_{10})$alkenyl, cyclo$(C_3-C_8)$alkyl$(C_2-C_{10})$alkynyl, cyclo$(C_3-C_8)$alkenyl$(C_2-C_{10})$alkynyl, heterocyclyl, heterocyclyl$(C_1-C_{10})$alkyl, heterocyclyl$(C_2-C_{10})$alkenyl, heterocyclyl$(C_2-C_{10})$alkynyl, aryl, aryl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo$(C_1-C_{10})$alkoxy, $SO_2NR^3R^4$ and $NR^3R^4$, aryl, ar$(C_1-C_{10})$alkyl, ar$(C_2-C_{10})$alkenyl, ar$(C_2-C_{10})$alkynyl, or aryl, ar$(C_1-C_{10})$alkyl, ar$(C_2-C_{10})$alkenyl, ar$(C_2-C_{10})$alkynyl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo$(C_1-C_{10})$alkoxy, $SO_2NR^3R^4$ and $NR^3R^4$, heteroaryl, heteroar$(C_1-C_{10})$alkyl, heteroar$(C_2-C_{10})$alkenyl, heteroar$(C_2-C_{10})$alkynyl or heteroaryl, heteroar$(C_1-C_{10})$alkyl, heteroar$(C_2-C_{10})$alkenyl, heteroar$(C_2-C_{10})$alkynyl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo$(C_1-C_{10})$alkoxy, $SO_2NR^3R^4$ and $NR^3R^4$, or $R^1$ and $R^2$ taken together with the carbon atom to which they are attached form a 5–7 membered saturated or unsaturated ring, or $R^1$ may be a pesticidal moiety if $R^2$ is a hydrogen atom, $R^3$ and $R^4$ are each independently a hydrogen atom, $(C_1-C_{20})$alkyl, cyclo$(C_3-C_8)$alkyl, cyclo$(C_3-C_8)$alkenyl, cyclo$(C_3-C_8)$alkyl$(C_1-C_{10})$alkyl, cyclo$(C_3-C_8)$alkyl$(C_2-C_{10})$alkenyl, cyclo$(C_3-C_8)$alkyl$(C_2-C_{10})$alkynyl, cyclo$(C_3-C_8)$alkenyl$(C_1-C_{10})$alkyl, cyclo$(C_3-C_8)$alkenyl$(C_2-C_{10})$alkenyl, cyclo$(C_3-C_8)$alkenyl$(C_2-C_{10})$alkynyl, heterocyclyl, heterocyclyl$(C_1-C_{10})$alkyl, heterocyclyl$(C_2-C_{10})$alkenyl, heterocyclyl$(C_2-C_{10})$alkynyl, $(C_1-C_{10})$alkoxy$(C_1-C_{10})$alkyl, $(C_2-C_{10})$alkenyl, $(C_2-C_{10})$alkynyl, or $(C_1-C_{10})$alkyl, cyclo$(C_3-C_8)$alkyl, cyclo$(C_3-C_8)$alkenyl, cyclo$(C_3-C_8)$alkyl$(C_1-C_{10})$alkyl, cyclo$(C_3-C_8)$alkyl$(C_2-C_{10})$alkenyl, cyclo$(C_3-C_8)$alkyl$(C_2-C_{10})$alkynyl, cyclo$(C_3-C_8)$alkenyl$(C_1-C_{10})$alkyl, cyclo$(C_3-C_8)$alkenyl$(C_2-C_{10})$alkenyl, cyclo$(C_3-C_8)$alkenyl$(C_2-C_{10})$alkynyl, heterocyclyl, heterocyclyl ($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy($C_1$–$C_{10}$)alkyl, ($C_2$–$C_{10}$)alkenyl or ($C_2$–$C_{10}$)alkynyl substituted with one or more halo, aryl, ar($C_1$–$C_{10}$)alkyl, ar($C_2$–$C_{10}$)alkenyl, ar($C_2$–$C_{10}$)alkynyl or aryl, ar($C_1$–$C_{10}$)alkyl, ar($C_2$–$C_{10}$)alkenyl, ar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy and halo($C_1$–$C_{10}$)alkoxy, heteroaryl, heteroar($C_1$–$C_{10}$)alkyl, heteroar($C_2$–$C_{10}$)alkenyl, heteroar($C_2$–$C_{10}$)alkynyl or heteroaryl, heteroar($C_1$–$C_{10}$)alkyl, heteroar($C_2$–$C_{10}$)alkenyl, heteroar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy and halo($C_1$–$C_{10}$)alkoxy, or $R^3$ and $R^4$ taken together with the nitrogen atom to which they are attached form a 5- or 6-membered saturated or unsaturated heterocyclic ring, or the pesticidally acceptable salts, isomers and enantiomers thereof In a second preferred embodiment of this invention, the pesticidal compound is represented by formula (II)

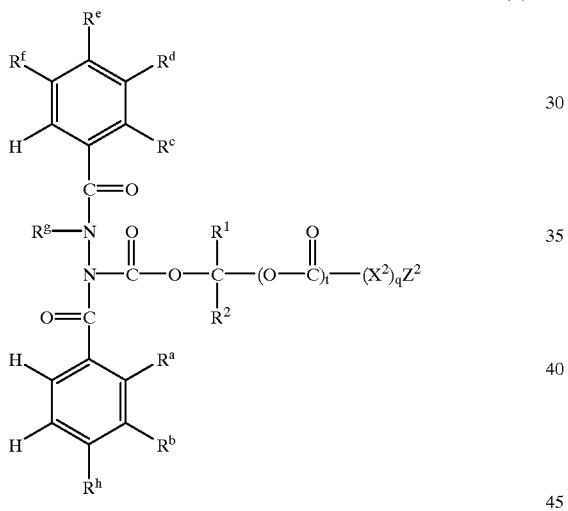

(II)

wherein $R^a$ is a hydrogen atom, halo or ($C_1$–$C_4$)alkyl, $R^b$ is a hydrogen atom or ($C_1$–$C_4$)alkoxy, optionally substituted with halo, $R^c$ is selected from a hydrogen atom, halo, ($C_1$–$C_4$)alkyl, ($C_1$–$C_4$)alkoxy, ($C_1$–$C_4$)alkoxy($C_1$–$C_4$)alkyl and nitro, $R^d$, $R^e$ and $R^f$ are each independently selected from a hydrogen atom, halo, ($C_1$–$C_4$)alkyl, ($C_1$–$C_4$)alkoxy, and ($C_1$–$C_4$)alkoxy($C_1$–$C_4$)alkyl, $R^g$ is a branched ($C_4$–$C_6$)alkyl, $R^h$ is a hydrogen atom, halo, ($C_1$–$C_4$)alkoxy, ($C_1$–$C_4$)alkyl, or when taken together with $R^b$ is methylenedioxy (—OCH$_2$O—), 1,2-ethylenedioxy (—OCH$_2$CH$_2$O—), or 1,2-ethyleneoxy (—CH$_2$CH$_2$O—) or 1,3-propyleneoxy (—CH$_2$CH$_2$CH$_2$O—) wherein the oxo atom is located at either the $R^b$ or $R^h$ position, the substituents $R^c$ and $R^d$, or $R^d$ and $R^e$, or $R^e$ and $R^f$ when taken together can be methylenedioxy or 1,2-ethylenedioxy, $R^1$ and $R^2$ are each independently a hydrogen atom, ($C_1$–$C_{20}$)alkyl, ($C_2$–$C_{10}$)alkenyl, ($C_2$–$C_{10}$)alkynyl, ($C_1$–$C_{10}$)alkoxy($C_{1-10}$)alkyl, ($C_1$–$C_{10}$)alkoxy($C_2$–$C_{10}$)alkenyl, ($C_1$–$C_{10}$)alkoxy($C_2$–$C_{10}$)alkynyl, ($C_1$–$C_{10}$)alkylthio($C_1$–$C_{10}$)alkyl, ($C_1$–$C_{10}$)alkylthio($C_2$–$C_{10}$)alkenyl, ($C_1$–$C_{10}$)alkylthio($C_2$–$C_{10}$)alkynyl, carboxy, carboxy($C_1$–$C_{20}$)alkyl, carboxy($C_2$–$C_{20}$)alkenyl, carboxy($C_2$–$C_{20}$)alkynyl, ($C_1$–$C_{20}$)alkoxycarbonyl, ($C_1$–$C_{10}$)alkoxycarbonyl($C_1$–$C_{10}$)alkyl, ($C_1$–$C_{10}$)alkoxycarbonyl($C_2$–$C_{10}$)alkenyl, ($C_1$–$C_{10}$)alkoxycarbonyl($C_2$–$C_{10}$)alkynyl, ($C_1$–$C_{20}$)alkylcarbonyl, ($C_2$–$C_{20}$)alkenylcarbonyl, ($C_2$–$C_{20}$)alkynylcarbonyl, cyclo($C_3$–$C_8$)alkyl, cyclo($C_3$–$C_8$)alkenyl, cyclo($C_3$–$C_8$)alkyl($C_1$–$C_{10}$)alkyl, cyclo($C_3$–$C_8$)alkenyl($C_1$–$C_{10}$)alkyl, cyclo($C_3$–$C_8$)alkyl($C_2$–$C_{10}$)alkenyl, cyclo($C_3$–$C_8$)alkenyl($C_2$–$C_{10}$)alkenyl, cyclo($C_3$–$C_8$)alkyl($C_2$–$C_{10}$)alkynyl, cyclo($C_3$–$C_8$)alkenyl($C_2$–$C_{10}$)alkynyl, heterocyclyl, heterocyclyl($C_1$–$C_{10}$)alkyl, heterocyclyl($C_2$–$C_{10}$)alkenyl, heterocyclyl($C_2$–$C_{10}$)alkynyl, aryl, aryl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, SO$_2$NR$^3$R$^4$, and NR$^3$R$^4$, ar($C_1$–$C_{10}$)alkyl, ar($C_2$–$C_{10}$)alkenyl, ar($C_2$–$C_{10}$)alkynyl, or ar($C_1$–$C_{10}$)alkyl, ar($C_2$–$C_{10}$)alkenyl, ar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, SO$_2$NR$^3$R$^4$ and NR$^3$R$^4$, heteroaryl, heteroaryl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy and NR$^3$R$^4$, heteroar($C_1$–$C_{10}$)alkyl, heteroar($C_2$–$C_{10}$)alkenyl, heteroar($C_2$–$C_{10}$)alkynyl or heteroar($C_1$–$C_{10}$)alkyl, heteroar($C_2$–$C_{10}$)alkenyl, heteroar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, SO$_2$NR$^3$R$^4$ and NR$^3$R$^4$, or $R^1$ and $R^2$ taken together with the carbon atom to which they are attached form a 5–7 membered saturated or unsaturated ring, or $R^1$ may be a pesticidal moiety if $R^2$ is a hydrogen atom, q and t are each independently 0 or 1, $Z^2(X^2)_q$ is halo, NR$^3$R$^4$, {(NR$^3$R$^4$R$^5$)$^+$M$^-$}, OR$^3$, S(O)$_j$R$^3$ or SO$_2$NR$^3$R$^4$ when both q and t are 0 wherein M$^-$ is halo, hydroxy, ($C_1$–$C_8$)alkoxy or the anion of a carboxylic acid and j is 0, 1 or 2, $R^3$, $R^4$ and $R^5$ are each independently a hydrogen atom, ($C_1$–$C_{20}$)alkyl, cyclo($C_3$–$C_8$)alkyl, cyclo($C_3$–$C_8$)alkenyl, cyclo($C_3$–$C_8$)alkyl($C_1$–$C_{10}$)alkyl, cyclo($C_3$–$C_8$)alkyl($C_2$–$C_{10}$)alkenyl, cyclo($C_3$–$C_8$)alkyl($C_2$–$C_{10}$)alkynyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$)alkenyl($C_2$–$C_{10}$)alkynyl, heterocyclyl, heterocyclyl($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy($C_1$–$C_{10}$)alkyl, ($C_2$–$C_{10}$)alkenyl, ($C_2$–$C_{10}$)alkynyl, or ($C_1$–$C_{10}$)alkyl, cyclo($C_3$–$C_8$)alkyl, cyclo($C_3$–$C_8$)alkenyl, cyclo($C_3$–$C_8$)alkyl($C_1$–$C_{10}$)alkyl, cyclo($C_3$–$C_8$)alkyl($C_2$–$C_{10}$)alkenyl, cyclo($C_3$–$C_8$)alkyl($C_2$–$C_{10}$)alkynyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$)alkenyl($C_2$–$C_{10}$)alkynyl, heterocyclyl, heterocyclyl($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy $(C_1-C_{10})$alkyl, $(C_2-C_{10})$alkenyl or $(C_2-C_{10})$alkynyl substituted with one or more halo, aryl, ar$(C_1-C_{10})$alkyl, ar$(C_2-C_{10})$alkenyl, ar$(C_2-C_{10})$alkynyl or aryl, ar$(C_1-C_{10})$alkyl, ar$(C_2-C_{10})$alkenyl, ar$(C_2-C_{10})$alkynyl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy and halo$(C_1-C_{10})$alkoxy, heteroaryl, heteroar$(C_1-C_{10})$alkyl, heteroar$(C_2-C_{10})$alkenyl, heteroar$(C_2-C_{10})$alkynyl or heteroaryl, heteroar$(C_1-C_{10})$alkyl, heteroar$(C_2-C_{10})$alkenyl, heteroar$(C_2-C_{10})$alkynyl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy and halo$(C_1-C_{10})$alkoxy, or $R^3$ and $R^4$ taken together with the nitrogen atom to which they are attached form a 5- or 6-membered saturated or unsaturated heterocyclic ring, and $M^-$ is halo, hydroxy, alkoxy or the anion of a carboxylic acid, $Z^2(X^2)_q$ is a hydrogen atom, methyl, tert-butyl, isobutyl, acetamidomethyl, α-carboxybenzyl, methoxycarbonylaminomethyl, diethylphosphorylmethyl, 2-hydroxy-2-propyl, 1-(isopropylideniminooxy)ethyl, 4,4,4-trifluoro-2-butyl, 2-(trifluoromethyl)propyl, 2,2,2-trifluoroethyl, ethynyl, 5-pyrrolidinyl-2-one, 1-(benzyloxycarbonylamino)-1-methylethyl, methylcarbonyl, 3-rhodaninylmethyl, 2-pyrazinyl, 4-pyrazolyl, 2-furylcarbonylaminomethyl, 2-(2,5-dihydropyrrolidion-1-yl)ethyl, 2-(methoxy)ethoxymethyl, mesylmethyl, 4-heptyloxyphenyl, 2,6-dichlorophenyl, 1-(3,5-diiodopyridin-4-one)ylmethyl, 3-pyridyl, 2,3-dichloro-5-pyridyl, 4-pyridyl, 2,6-dichloro-4-pyridyl, 4-mesylphenyl, 2-chloro-4-nitrophenyl, 2-nitro-4-chlorophenyl, 2-nitro-5-chlorophenyl, 2-ethoxyphenyl, cyclohexyl, cyclopropyl, 5-methyl-2-pyrazinyl, 2-tetrahydrofuryl, 3-(2-thienyl)propyl, 1-phenyl-1-cyclopentyl, α-cyclopentylbenzyl, 1-methylcyclohexyl, 2-chloro-3-pyridyl, cyclopentyl, 1-methyl-2-pyrrolyl, 2,6-dimethoxyphenyl, 2,6-dimethoxy-3-pyridyl, 2-(2-thienyl)vinyl, 2-nitro-5-thiocyanatophenyl, 2-(tert-butoxycarbonylamino)-2-propyl, 1-(tert-butoxycarbonyl)piperidin-4-yl, 2-methyl-3-pyridyl, 1-(acetylamino)-2-methylpropyl, 1-acetyl-4-hydroxypyrrolidin-2-yl, 1,3-dihydroxy-2-methyl-2-propyl, 3-methylthio-1-acetylaminopropyl, 2,6-dimethoxy-4-hydroxyphenyl, 4-nitro-3-pyrazolyl, 4-sulfamoylphenyl, 1-acetylaminovinyl, 2-(benzyloxycarbonyl)-1-(tert-butoxycarbonylamino)ethyl, 4-(1-hexyloxy)phenyl, 1-(2-chlorophenoxy)-1-methylethyl, 3-hydroxy-4-methoxyphenyl, 3,5-dinitro-4-hydroxyphenyl, 4-piperidinyl hydrochloride, 2-carboxy-1-(tert-butoxycarbonylamino)ethyl, 2-(benzyloxycarbonyl)-1-aminoethyl hydrochloride, 2-carboxy-1-aminoethyl hydrochloride, 2-methyl-3-pyridyl hydrochloride, 2,4-dinitrophenyl, 1-hydroxy-1-phenylethyl, 2-nitro-3-hydroxy-4-methylphenyl, 2-methylcyclopropyl, 1-phenylpropyl, 1,2,3,4-tetrahydronaphth-2-yl, 1-benzyl-2,2-dimethylpropyl, 2,2,3,3-tetramethylcyclopropyl, acetoxymethyl, 2,2,2-trifluoro-1-methoxy-1-phenylethyl, 2-hexyl, 1-heptynyl, 3-tetrahydrofuryl, 2-methyl-2-butyl, 2-methylcyclohexyl, 2-methyl-4-penten-2-yl, 4-heptyl, 2-pentyl, 1-phenylethyl, phenoxymethyl, 2,3,4,5,6-pentafluorophenoxymethyl, 1-(methoxyimino)-1-((2-formylamino)-4-thiazolyl)methyl, 3-hydroxy-3-pentyl, 2-methoxyphenoxymethyl, mesityl, 2-methyl-1,4-cyclohexadien-3-yl, 2-(4-chlorophenoxy)-2-propyl, 2-hydroxy-2-butyl, 3-heptyl, 1-phenyl-2-methylbutyl, sec-butyl, cyclobutyl, 3-pentyl, α-(3,5-dinitrobenzoylamino)benzyl, 2,2-dichloro-1-methylcyclopropyl, 1,1,1-trifluoro-2-hydroxy-2-butyl, 3-nitro-4-hydroxyphenyl, 4,8-dihydroxy-2-quinolinyl, 2-hydroxy-1-phenylethyl, 4-hydroxyphenyl, neopentyl, 1-(3,5-dinitrobenzoylamino)-3-methylbutyl, 2-hydroxybenzoylaminomethyl, 3,3,3-trifluoropropyl, 2-pyridyl-N-oxide, 6-hydroxy-2-pyridyl, 3-hydroxy-2-pyridyl, benzoylaminomethyl, 1-methyl-2-oxo-5-(3-pyridyl)pyrrolidin-4-yl, 1,3,4,5-tetrahydroxycyclohexyl, 1-acetamido-2-methylpropyl, 1-acetamido-3-methylthiopropyl, 1-(tert-butoxycarbonylamino)-2-methylpropyl, 2-(2-chlorophenyl)vinyl, benzofuran-2-yl, 3-thienyl, 3-methylinden-2-yl, 3,4,5-trihydroxy-1-cyclohexenyl, 2-(2-(trifluoromethyl)phenyl)vinyl, 2-(4-methylphenyl)vinyl, cyclohexenyl, 2-(4-(trifluoromethyl)phenyl)vinyl, cyclopentenyl, 2-penten-2-yl, 2-(trifluoromethyl)-1-propenyl, 2-(2-fluorophenyl)vinyl, vinyl, 2-(4-(dimethylamino)phenyl)vinyl, 2-(2-methoxyphenyl)vinyl, 2-(3-hydroxy-4-methoxyphenyl)vinyl, 2-(3-(trifluoromethyl)phenyl)vinyl, 1-fluoro-2-phenylvinyl, 3-methyl-2-thienyl, 1-cyano-2-(4-hydroxyphenyl)vinyl, 2-(4-fluorophenyl)vinyl, isobutylidene, 7-methyl-1-ethyl-3-naphthyridinyl-4-one, 2-(3-methoxy-4-hydroxyphenyl)vinyl, 2-(5-(1,3-benzodioxolanyl))vinyl, 1-methylcyclopropyl, 2-furyl, 2-phenylvinyl, 2-(4-bromophenyl)vinyl, 3-furyl, 2-(4-methoxyphenyl)vinyl, 1-methyl-2-indolyl, 2-(3-pyridyl)vinyl, 2-(3-fluorophenyl)vinyl, 5-methyl-2-thienyl, 3-isoquinolinyl-1-one, 2,6-dimethyl-1,5-heptadienyl, 1-pentenyl, 2-(2,3-dimethoxyphenyl)vinyl, 1,3-pentadienyl, 2-(3-nitrophenyl)vinyl, 2-(4-chlorophenyl)vinyl, 2-(4-nitrophenyl)vinyl, 2-(3,4-dimethoxyphenyl)vinyl, 2-pentafluorophenylvinyl, 1-methyl-2-phenylvinyl, 2-(4-hydroxyphenyl)vinyl, 2-(3-hydroxyphenyl)vinyl, 2-(2-furyl)vinyl, 2-(3,4-dichlorophenyl)vinyl, 2-(2,4-dichlorophenyl)vinyl, 2-(2-nitrophenyl)vinyl, 1,1,1,3,3,3-hexafluoro-2-methyl-2-propyl, 1-(tert-butoxycarbonyl)-2-pyrrolidinyl, 1-(di-n-propylamino)ethyl, 2-amino-2-propyl hydrochloride or 2-pyrrolidinyl hydrochloride, when q is 0 and t is 1, $Z^2(X^2)_q$ is 3,5,6-trichloro-2-pyridyloxymethyl, 3,6-dichloro-2-pyridyl, 3-(4,6-dimethoxy-2-pyrimidinyloxy)-2-pyridyl or

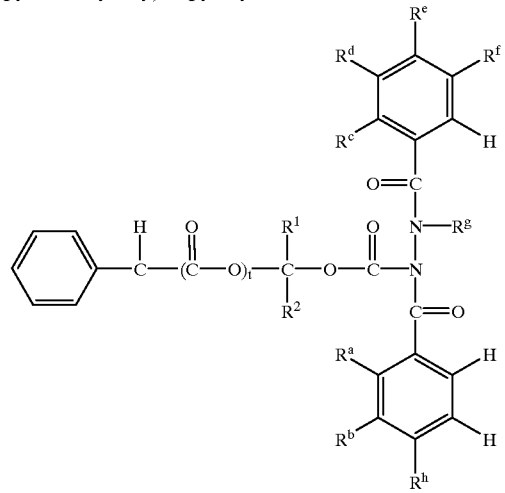

when both q and t are 1, or
the pesticidally acceptable salts, isomers and enantiomers thereof In a more preferred embodiment, $R^g$ is tert-butyl. In an even more preferred embodiment, $R^h$ is halo, preferably chloro, and $R^a$, $R^b$, $R^c$, $R^d$, $R^e$ and $R^f$ are hydrogen atoms. In another even more preferred embodiment, $R^h$ is methyl or ethyl, preferably ethyl, $R^a$, $R^b$, $R^c$ and $R^e$ are hydrogen atoms, and $R^d$ and $R^f$ are independently selected from methyl, ethyl, halo and cyano, preferably methyl. In yet another even more preferred embodiment, $R^a$ is halo, methyl or ethyl, preferably methyl, $R^b$ is methoxy or ethoxy, preferably methoxy, $R^c$, $R^e$ and $R^h$ are hydrogen atoms, and $R^d$ and $R^f$ are independently selected from methyl, ethyl, halo and cyano, preferably methyl. In still yet another even more preferred embodiment, $R^a$ is halo, methyl or ethyl, preferably methyl, $R^b$ and $R^h$ are taken together to form a methylenedioxy, a 1,2-ethylenedioxy, or a 1,2-ethyleneoxy or 1,3-propyleneoxy link wherein the oxo atom is located at either the $R^b$ or $R^h$ position, preferably 1,3-propyleneoxy, $R^c$ and $R^f$ are hydrogen atoms, and $R^d$ and $R^f$ are independently selected from methyl, ethyl, halo and cyano, preferably methyl.

In another more preferred embodiment, the pesticidal compound is represented by formula (II)

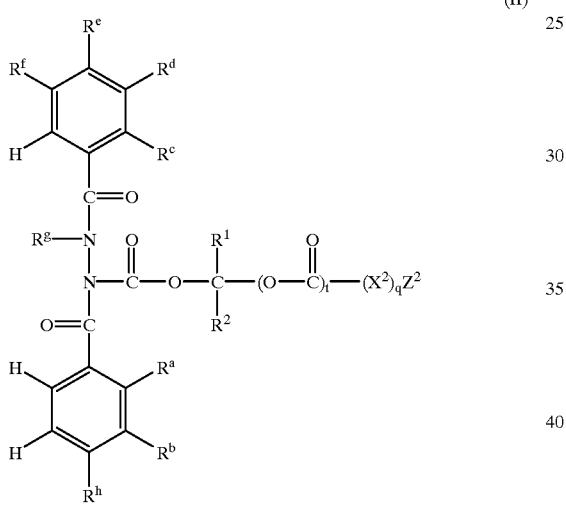

(II)

wherein
- $R^a$ is a hydrogen atom, halo or $(C_1-C_4)$alkyl,
- $R^b$ is a hydrogen atom or $(C_1-C_4)$alkoxy, optionally substituted with halo,
- $R^c$ is selected from a hydrogen atom, halo, $(C_1-C_4)$alkyl, $(C_1-C_4)$alkoxy, $(C_1-C_4)$alkoxy$(C_1-C_4)$alkyl and nitro,
- $R^d$, $R^e$ and $R^f$ are each independently selected from a hydrogen atom, halo, $(C_1-C_4)$alkyl, $(C_1-C_4)$alkoxy, and $(C_1-C_4)$alkoxy$(C_1-C_4)$alkyl,
- $R^g$ is a branched $(C_4-C_6)$alkyl,
- $R^h$ is a hydrogen atom, halo, $(C_1-C_4)$alkoxy, $(C_1-C_4)$alkyl, or when taken together with $R^b$ is methylenedioxy (—OCH$_2$O—), 1,2-ethylenedioxy (—OCH$_2$CH$_2$O—), or 1,2-ethyleneoxy (—CH$_2$CH$_2$O—) or 1,3-propyleneoxy (—CH$_2$CH$_2$CH$_2$O—) wherein the oxo atom is located at either the $R^b$ or $R^h$ position,
- the substituents $R^c$ and $R^d$, or $R^d$ and $R^e$, or $R^e$ and $R^f$ when taken together can be methylenedioxy or 1,2-ethylenedioxy,
- $R^1$ and $R^2$ are each independently a hydrogen atom, $(C_1-C_{20})$alkyl, $(C_2-C_{10})$alkenyl, $(C_2-C_{10})$alkynyl, $(C_1-C_{10})$alkoxy$(C_1-C_{10})$alkyl, $(C_1-C_{10})$alkoxy $(C_2-C_{10})$alkenyl, $(C_1-C_{10})$alkoxy$(C_2-C_{10})$alkynyl, $(C_1-C_{10})$alkylthio$(C_1-C_{10})$alkyl, $(C_1-C_{10})$alkylthio $(C_2-C_{10})$alkenyl, $(C_1-C_{10})$alkylthio$(C_2-C_{10})$alkynyl, carboxy, carboxy$(C_1-C_{20})$alkyl, carboxy$(C_2-C_{20})$ alkenyl, carboxy$(C_2-C_{10})$alkynyl, $(C_1-C_{20})$ alkoxycarbonyl, $(C_1-C_{10})$alkoxycarbonyl$(C_1-C_{10})$ alkyl, $(C_1-C_{10})$alkoxycarbonyl$(C_2-C_{10})$alkenyl, $(C_1-C_{10})$alkoxycarbonyl$(C_2-C_{10})$alkynyl, $(C_1-C_{20})$ alkylcarbonyl, $(C_2-C_{20})$alkenylcarbonyl, $(C_2-C_{20})$ alkynylcarbonyl, cyclo$(C_3-C_8)$alkyl, cyclo$(C_3-C_8)$ alkenyl, cyclo$(C_3-C_8)$alkyl$(C_1-C_{10})$alkyl, cyclo $(C_3-C_8)$alkenyl$(C_1-C_{10})$alkyl, cyclo$(C_3-C_8)$alkyl $(C_2-C_{10})$alkenyl, cyclo$(C_3-C_8)$alkenyl$(C_2-C_{10})$ alkenyl, cyclo$(C_3-C_8)$alkyl$(C_2-C_{10})$alkynyl, cyclo $(C_3-C_8)$alkenyl$(C_2-C_{10})$alkynyl, heterocyclyl, heterocyclyl$(C_1-C_{10})$alkyl, heterocyclyl$(C_2-C_{10})$ alkenyl, heterocyclyl$(C_2-C_{10})$alkynyl, aryl, aryl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$ alkenyl, halo$(C_2-C_{10})$alkynyl, $(C_1-C_{10})$alkoxy, halo $(C_1-C_{10})$alkoxy, $SO_2NR^3R^4$ and $NR^3R^4$, ar$(C_1-C_{10})$ alkyl, ar$(C_2-C_{10})$alkenyl, ar$(C_2-C_{10})$alkynyl, or ar$(C_1-C_{10})$alkyl, ar$(C_2-C_{10})$alkenyl, ar$(C_2-C_{10})$ alkynyl substituted with one or more substituents independently selected from halo, $(C_1-C_{10})$alkyl, $(C_2-C_{10})$ alkenyl, $(C_2-C_{10})$alkynyl, halo$(C_1-C_{10})$alkyl, halo $(C_2-C_{10})$alkenyl, halo$(C_2-C_{10})$alkynyl, $(C_1-C_{10})$ alkoxy, halo$(C_1-C_{10})$alkoxy, $SO_2NR^3R^4$ and $NR^3R^4$, heteroaryl, heteroaryl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo $(C_2-C_{10})$alkynyl, $(C_1-C_{10})$alkoxy, halo$(C_1-C_{10})$alkoxy and $NR^3R^4$, heteroar$(C_1-C_{10})$alkyl, heteroar$(C_2-C_{10})$ alkenyl, heteroar$(C_2-C_{10})$alkynyl or heteroar$(C_1-C_{10})$ alkyl, heteroar$(C_2-C_{10})$alkenyl, heteroar$(C_2-C_{10})$ alkynyl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$ alkoxy, halo$(C_1-C_{10})$alkoxy, $SO_2NR^3R^4$ and $NR^3R^4$, or $R^1$ and $R^2$ taken together with the carbon atom to which they are attached form a 5–7 membered saturated or unsaturated ring, or $R^1$ may be a pesticidal moiety if $R^2$ is a hydrogen atom,
- $Z^2(X^2)_q$ halo, $NR^3R^4$, $\{(NR^3R^4R^5)^+M^-\}$, $OR^3$, $S(O)_jR^3$ or $SO_2NR^3R^4$ when both q and t are 0 wherein $M^-$ is halo, hydroxy, $(C_1-C_8)$alkoxy or the anion of a carboxylic acid and j is 0, 1 or 2,
- $R^3$, $R^4$ and $R^5$ are each independently a hydrogen atom, $(C_1-C_{20})$alkyl, cyclo$(C_3-C_8)$alkyl, cyclo$(C_3-C_8)$ alkenyl, cyclo$(C_3-C_8)$alkyl$(C_1-C_{10})$alkyl, cyclo $(C_3-C_8)$alkyl$(C_2-C_{10})$alkenyl, cyclo$(C_3-C_8)$alkyl $(C_2-C_{10})$alkynyl, cyclo$(C_3-C_8)$alkenyl$(C_1-C_{10})$alkyl, cyclo$(C_3-C_8)$alkenyl$(C_2-C_{10})$alkenyl, cyclo$(C_3-C_8)$ alkenyl$(C_2-C_{10})$alkynyl, heterocyclyl, heterocyclyl $(C_1-C_{10})$alkyl, heterocyclyl$(C_2-C_{10})$alkenyl, heterocyclyl$(C_2-C_{10})$alkynyl, $(C_1-C_{10})$alkoxy $(C_1-C_{10})$alkyl, $(C_2-C_{10})$alkenyl, $(C_2-C_{10})$alkynyl, or $(C_1-C_{10})$alkyl, cyclo$(C_3-C_8)$alkyl, cyclo$(C_3-C_8)$ alkenyl, cyclo$(C_3-C_8)$alkyl$(C_1-C_{10})$alkyl, cyclo $(C_3-C_8)$alkyl$(C_2-C_{10})$alkenyl, cyclo$(C_3-C_8)$alkyl $(C_2-C_{10})$alkynyl, cyclo$(C_3-C_8)$alkenyl$(C_1-C_{10})$alkyl, cyclo$(C_3-C_8)$alkenyl$(C_2-C_{10})$alkenyl, cyclo$(C_3-C_8)$ alkenyl$(C_2-C_{10})$alkynyl, heterocyclyl, heterocyclyl ($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy($C_1$–$C_{10}$)alkyl, ($C_2$–$C_{10}$)alkenyl or ($C_2$–$C_{10}$)alkynyl substituted with one or more halo, aryl, ar($C_1$–$C_{10}$)alkyl, ar($C_2$–$C_{10}$)alkenyl, ar($C_2$–$C_{10}$)alkynyl or aryl, ar($C_1$–$C_{10}$)alkyl, ar($C_2$–$C_{10}$)alkenyl, ar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy and halo($C_1$–$C_{10}$)alkoxy, heteroaryl, heteroar($C_1$–$C_{10}$)alkyl, heteroar($C_2$–$C_{10}$)alkenyl, heteroar($C_2$–$C_{10}$)alkynyl or heteroaryl, heteroar($C_1$–$C_{10}$)alkyl, heteroar($C_2$–$C_{10}$)alkenyl, heteroar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy and halo($C_1$–$C_{10}$)alkoxy, or $R^3$ and $R^4$ taken together with the nitrogen atom to which they are attached form a 5- or 6-membered saturated or unsaturated heterocyclic ring, $Z^2(X^2)_q$ is a pesticidal moiety selected from the group consisting of (E,E)-8,10-dodecadienoxy, dodecane-1-oxy, (E)-11-tetradecen-1-oxy, (Z)-9-tetradecen-1-oxy, (Z)-11-hexadecene-1-oxy when q is 1 and t is 0, or the pesticidally acceptable salts, isomers and enantiomers thereof.

In yet another more preferred embodiment, the pesticidal compound is represented by formula (IIA)

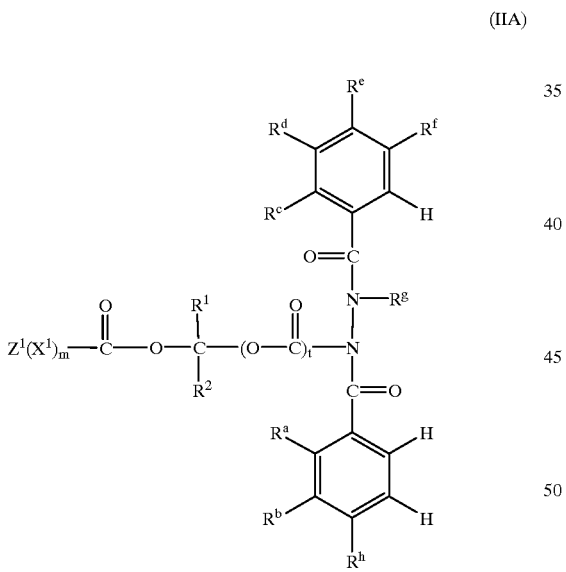

(IIA)

wherein $R^a$ is a hydrogen atom, halo or ($C_1$–$C_4$)alkyl, $R^b$ is a hydrogen atom or ($C_1$–$C_4$)alkoxy, optionally substituted with halo, $R^c$ is selected from a hydrogen atom, halo, ($C_1$–$C_4$)alkyl, ($C_1$–$C_4$)alkoxy, ($C_1$–$C_4$)alkoxy($C_1$–$C_4$)alkyl and nitro, $R^d$, $R^e$ and $R^f$ are each independently selected from a hydrogen atom, halo, ($C_1$–$C_4$)alkyl, ($C_1$–$C_4$)alkoxy, and ($C_1$–$C_4$)alkoxy($C_1$–$C_4$)alkyl, $R^g$ is a branched ($C_4$–$C_6$)alkyl, $R^h$ is a hydrogen atom, halo, ($C_1$–$C_4$)alkoxy, ($C_1$–$C_4$)alkyl, or when taken together with $R^b$ is methylenedioxy (—O$CH_2$O—), 1,2-ethylenedioxy (—O$CH_2CH_2$O—), or 1,2-ethyleneoxy (—$CH_2CH_2$O—) or 1,3-propyleneoxy (—$CH_2CH_2CH_2$O—) wherein the oxo atom is located at either the $R^b$ or $R^h$ position, the substituents $R^c$ and $R^d$, or $R^d$ and $R^e$, or $R^e$ and $R^f$ when taken together can be methylenedioxy or 1,2-ethylenedioxy, $R^1$ and $R^2$ are each independently a hydrogen atom, ($C_1$–$C_{20}$)alkyl, ($C_2$–$C_{10}$)alkenyl, ($C_2$–$C_{10}$)alkynyl, ($C_1$–$C_{10}$)alkoxy($C_1$–$C_{10}$)alkyl, ($C_1$–$C_{10}$)alkoxy($C_2$–$C_{10}$)alkenyl, ($C_1$–$C_{10}$)alkoxy($C_2$–$C_{10}$)alkynyl, ($C_1$–$C_{10}$)alkylthio ($C_1$–$C_{10}$)alkyl, ($C_1$–$C_{10}$)alkylthio($C_2$–$C_{10}$)alkenyl, ($C_1$–$C_{10}$)alkylthio($C_2$–$C_{10}$)alkynyl, carboxy, carboxy($C_1$–$C_{20}$)alkyl, carboxy($C_2$–$C_{20}$)alkenyl, carboxy($C_2$–$C_{20}$)alkynyl, ($C_1$–$C_{20}$)alkoxycarbonyl, ($C_1$–$C_{10}$)alkoxycarbonyl($C_1$–$C_{10}$)alkyl, ($C_1$–$C_{10}$)alkoxycarbonyl($C_2$–$C_{10}$)alkenyl, ($C_1$–$C_{10}$)alkoxycarbonyl($C_2$–$C_{10}$)alkynyl, ($C_1$–$C_{20}$)alkylcarbonyl, ($C_2$–$C_{20}$)alkenylcarbonyl, ($C_2$–$C_{20}$)alkynylcarbonyl, cyclo($C_3$–$C_8$)alkyl, cyclo($C_3$–$C_8$)alkenyl, cyclo($C_3$–$C_8$)alkyl($C_1$–$C_{10}$)alkyl, cyclo($C_3$–$C_8$)alkenyl($C_1$–$C_{10}$)alkyl, cyclo($C_3$–$C_8$)alkyl($C_2$–$C_{10}$)alkenyl, cyclo($C_3$–$C_8$)alkenyl($C_2$–$C_{10}$)alkenyl, cyclo($C_3$–$C_8$)alkyl($C_2$–$C_{10}$)alkynyl, cyclo($C_3$–$C_8$)alkenyl($C_2$–$C_{10}$)alkynyl, heterocyclyl, heterocyclyl($C_1$–$C_{10}$)alkyl, heterocyclyl($C_2$–$C_{10}$)alkenyl, heterocyclyl($C_2$–$C_{10}$)alkynyl, aryl, aryl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$ and $NR^3R^4$, ar($C_1$–$C_{10}$)alkyl, ar($C_2$–$C_{10}$)alkenyl, ar($C_2$–$C_{10}$)alkynyl, or ar($C_1$–$C_{10}$)alkyl, ar($C_2$–$C_{10}$)alkenyl, ar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO^2NR^3R^4$ and $NR^3R^4$, heteroaryl, heteroaryl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy and $NR^3R^4$, heteroar($C_1$–$C_{10}$)alkyl, heteroar($C_2$–$C_{10}$)alkenyl, heteroar($C_2$–$C_{10}$)alkynyl or heteroar($C_1$–$C_{10}$)alkyl, heteroar($C_2$–$C_{10}$)alkenyl, heteroar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$ and $NR^3R^4$, or $R^1$ and $R^2$ taken together with the carbon atom to which they are attached form a 5–7 membered saturated or unsaturated ring, or $R^1$ may be a pesticidal moiety if $R^2$ is a hydrogen atom, m is 0 or 1, t is 0, $Z^1(X^1)_m$ is $NR^3R^4$, $OR^3$, $S(O)_jR^3$ or $SO_2NR^3R^4$ when m is 0 and j is 0, 1 or 2, $R^3$, $R^4$ and $R^5$ are each independently a hydrogen atom, ($C_1$–$C_{20}$)alkyl, cyclo($C_3$–$C_8$)alkyl, cyclo($C_3$–$C_8$)alkenyl, cyclo($C_3$–$C_8$)alkyl($C_1$–$C_{10}$)alkyl, cyclo($C_3$–$C_8$)alkyl($C_2$–$C_{10}$)alkenyl, cyclo($C_3$–$C_8$)alkyl($C_2$–$C_{10}$)alkynyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$) alkenyl($C_2$–$C_{10}$)alkynyl, heterocyclyl, heterocyclyl ($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy ($C_1$–$C_{10}$)alkyl, ($C_2$–$C_{10}$)alkenyl, ($C_2$–$C_{10}$)alkynyl, or ($C_1$–$C_{10}$)alkyl, cyclo($C_3$–$C_8$)alkyl, cyclo($C_3$–$C_8$) alkenyl, cyclo($C_3$–$C_8$)alkyl($C_1$–$C_{10}$)alkyl, cyclo ($C_3$–$C_8$)alkyl($C_2$–$C_{10}$)alkenyl, cyclo($C_3$–$C_8$)alkyl ($C_2$–$C_{10}$)alkynyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$) alkenyl($C_2$–$C_{10}$)alkynyl, heterocyclyl, heterocyclyl ($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy ($C_1$–$C_{10}$)alkyl, ($C_2$–$C_{10}$)alkenyl or ($C_2$–$C_{10}$)alkynyl substituted with one or more halo, aryl, ar($C_1$–$C_{10}$) alkyl, ar($C_2$–$C_{10}$)alkenyl, ar($C_2$–$C_{10}$)alkynyl or aryl, ar($C_1$–$C_{10}$)alkyl, ar($C_2$–$C_{10}$)alkenyl, ar($C_2$–$C_{10}$) alkynyl substituted with one or more substituents independently selected from halo, ($C_1$–$C_{10}$)alkyl, ($C_2$–$C_{10}$) alkenyl, ($C_2$–$C_{10}$)alkynyl, halo($C_1$–$C_{10}$)alkyl, halo ($C_2$–$C_{10}$)alkenyl, halo($C_2$–$C_{10}$)alkynyl, ($C_1$–$C_{10}$) alkoxy and halo($C_1C_{10}$)alkoxy, heteroaryl, heteroar ($C_1$–$C_{10}$)alkyl, heteroar($C_2$–$C_{10}$)alkenyl, heteroar ($C_2$–$C_{10}$)alkynyl or heteroaryl, heteroar($C_1$–$C_{10}$)alkyl, heteroar($C_2$–$C_{10}$)alkenyl, heteroar($C_2$–$C_{10}$)alkynyl substituted with one or more substituents independently selected from halo, ($C_1$–$C_{10}$)alkyl, ($C_2$–$C_{10}$) alkenyl, ($C_2$–$C_{10}$)alkynyl, halo($C_1$–$C_{10}$)alkyl, halo ($C_2$–$C_{10}$)alkenyl, halo($C_2$–$C_{10}$)alkynyl, ($C_1$–$C_{10}$) alkoxy and halo($C_1$–$C_{10}$)alkoxy, or $R^3$ and $R^4$ taken together with the nitrogen atom to which they are attached form a 5- or 6-membered saturated or unsaturated heterocyclic ring, $Z^1(X^1)_m$ is a pesticidal moiety selected from the group consisting of (E,E)-8,10-dodecadienoxy, dodecane-1-oxy, (E)-11-tetradecen-1-oxy, (Z)-9-tetradecen-1-oxy, (Z)-11-hexadecene-1-oxy, when m is 1, or the pesticidally acceptable salts, isomers and enantiomers thereof.

In a third preferred embodiment of this invention, the pesticidal compound is of the formula

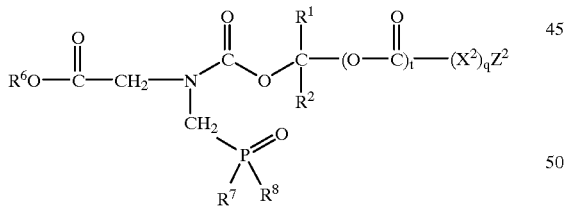

(III)

wherein
$R^1$ and $R^2$ are each independently a hydrogen atom, ($C_1$–$C_{20}$)alkyl, ($C_2$–$C_{10}$)alkenyl, ($C_2$–$C_{10}$)alkynyl, ($C_1$–$C_{10}$)alkoxy($C_1$–$C_{10}$)alkyl, ($C_1$–$C_{10}$)alkoxy ($C_2$–$C_{10}$)alkenyl, ($C_1$–$C_{10}$)alkoxy($C_2$–$C_{10}$)alkynyl, ($C_1$–$C_{10}$)alkylthio($C_1$–$C_{10}$)alkyl, ($C_1$–$C_{10}$)alkylthio ($C_2$–$C_{10}$)alkenyl, ($C_1$–$C_{10}$)alkylthio($C_2$–$C_{10}$)alkynyl, carboxy, carboxy($C_1$–$C_{20}$)alkyl, carboxy($C_2$–$C_{20}$) alkenyl, carboxy($C_2$–$C_{20}$)alkynyl, ($C_1$–$C_{20}$) alkoxycarbonyl, ($C_1$–$C_{10}$)alkoxycarbonyl($C_1$–$C_{20}$) alkyl, ($C_1$–$C_{10}$)alkoxycarbonyl($C_2$–$C_{10}$)alkenyl, ($C_1$–$C_{10}$)alkoxycarbonyl($C_2$–$C_{10}$)alkynyl, ($C_1$–$C_{20}$) alkylcarbonyl, ($C_2$–$C_{20}$)alkenylcarbonyl, ($C_2$–$C_{20}$) alkynylcarbonyl, cyclo($C_3$–$C_8$)alkyl, cyclo($C_3$–$C_8$) alkenyl, cyclo($C_3$–$C_8$)alkyl($C_1$–$C_{10}$)alkyl, cyclo ($C_3$–$C_8$)alkenyl($C_1$–$C_{10}$)alkyl, cyclo($C_3$–$C_8$)alkyl ($C_2$–$C_{10}$)alkenyl, cyclo($C_1$–$C_8$)alkenyl($C_2$–$C_{10}$) alkenyl, cyclo($C_3$–$C_8$)alkyl($C_2$–$C_{10}$)alkynyl, cyclo ($C_3$–$C_8$)alkenyl($C_2$–$C_{10}$)alkynyl, heterocyclyl, heterocyclyl($C_1$–$C_{10}$)alkyl, heterocyclyl($C_2$–$C_{10}$) alkenyl, heterocyclyl($C_2$–$C_{10}$)alkynyl, aryl, aryl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$) alkenyl, halo($C_2$–$C_{10}$)alkynyl, ($C_1$–$C_{10}$)alkoxy, halo ($C_1$–$C_{10}$)alkoxy, $SO_2NR^3R^4$ and $NR^3R^4$, ar($C_1$–$C_{10}$) alkyl, ar($C_2$–$C_{10}$)alkenyl, ar($C_2$–$C_{10}$)alkynyl, or ar($C_1$–$C_{10}$)alkyl, ar($C_2$–$C_{10}$)alkenyl, ar($C_2$–$C_{10}$) alkynyl substituted with one or more substituents independently selected from halo, ($C_1$–$C_{10}$)alkyl, ($C_2$–$C_{10}$) alkenyl, ($C_2$–$C_{10}$)alkynyl, halo($C_1$–$C_{10}$)alkyl, halo ($C_2$–$C_{10}$)alkenyl, halo($C_2$–$C_{10}$)alkynyl, ($C_1$–$C_{10}$) alkoxy, halo($C_1$–$C_{10}$)alkoxy, $SO_2NR^3R^4$ and $NR^3R^4$, heteroaryl, heteroaryl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo ($C_2$–$C_{10}$)alkynyl, ($C_1$–$C_{10}$)alkoxy, halo($C_1$–$C_{10}$)alkoxy and $NR^3R^4$, heteroar($C_1$–$C_{10}$)alkyl, heteroar($C_2$–$C_{10}$) alkenyl, heteroar($C_2$–$C_{10}$)alkynyl or heteroar($C_1$–$C_{10}$) alkyl, heteroar($C_2$–$C_{10}$)alkenyl, heteroar($C_2$–$C_{10}$) alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$) alkoxy, halo($C_1$–$C_{10}$)alkoxy, $SO_2NR^3R^4$ and $NR^3R^4$, or $R^1$ and $R^2$ taken together with the carbon atom to which they are attached form a 5–7 membered saturated or unsaturated ring, or $R^1$ may be a pesticidal moiety if $R^2$ is a hydrogen atom, $R^6$ is a hydrogen atom, ($C_1$–$C_4$)alkyl or $M^+$, $R^7$ and $R^8$ are each independently ($C_1$–$C_4$)alkyl, hydroxy, ($C_1$–$C_4$)alkoxy, phenoxy or phenoxy substituted with one or more substituents independently selected from halo, ($C_1$–$C_4$)alkyl, halo($C_1$–$C_4$)alkyl, cyano, nitro, ($C_1$–$C_4$)alkoxy, halo($C_1$–$C_4$)alkoxy, carboxy, hydroxy, amino, ($C_1$–$C_4$)alkylamino and {($C_1$–$C_4$)alkyl}$_2$amino, or $O^-M^+$, $M^+$ is an alkali metal cation, $(NHR^9R^{10}R^{11})^+$ or $(SR^9R^{10}R^{11})^+$, $R^9$, $R^{10}$ and $R^{11}$ are each independently hydrogen atom, ($C_1$–$C_{20}$)alkyl, cyclo($C_3$–$C_8$)alkyl, cyclo($C_3$–$C_8$) alkenyl, cyclo($C_3$–$C_8$)alkyl($C_1$–$C_{10}$)alkyl, cyclo ($C_3$–$C_8$)alkyl($C_2$–$C_{10}$)alkenyl, cyclo($C_3$–$C_8$)alkyl ($C_2$–$C_{10}$)alkynyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$) alkenyl($C_2$–$C_{10}$)alkynyl, heterocyclyl, heterocyclyl ($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy ($C_1$–$C_{10}$)alkyl, ($C_2$–$C_{10}$)alkenyl or ($C_2$–$C_{10}$)alkynyl substituted with one or more halo, aryl, ar($C_1$–$C_{10}$) alkyl, ar($C_2$–$C_{10}$)alkenyl, ar($C_2$–$C_{10}$)alkynyl or aryl, ar($C_1$–$C_{10}$)alkyl, ar($C_2$–$C_{10}$)alkenyl, ar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy and halo($C_1$–$C_{10}$)alkoxy, heteroaryl, heteroar($C_1$–$C_{10}$)alkyl, heteroar($C_2$–$C_{10}$)alkenyl, heteroar($C_2$–$C_{10}$)alkynyl or heteroaryl, heteroar($C_1$–$C_{10}$)alkyl, heteroar($C_2$–$C_{10}$)alkenyl, heteroar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy and halo($C_1$–$C_{10}$)alkoxy, or $R^3$ and $R^4$ taken together with the nitrogen atom to which they are attached form a 5- or 6-membered saturated or unsaturated heterocyclic ring, q and t are each independently 0 or 1, $Z^2(X^2)_q$ halo, $NR^3R^4$, $\{(NR^3R^4R^5)^+M^-\}$, $OR^3$, $S(O)_jR^3$ or $SO_2NR^3R^4$ when both q and t are 0 wherein $M^-$ is halo, hydroxy, ($C_1$–$C_8$)alkoxy or the anion of a carboxylic acid and j is 0, 1 or 2, $Z^2(X^2)_q$ is ($C_1$–$C_{20}$)alkyl, ($C_1$–$C_{10}$)alkylcarbonyloxy($C_1$–$C_{10}$)alkyl, ($C_1$–$C_{20}$)alkylcarbonyl, hydroxy($C_1$–$C_{20}$)alkyl, ($C_1$–$C_{10}$)alkylsulfonyl($C_1$–$C_{10}$)alkyl, acetylamino($C_1$–$C_{10}$)alkyl, halo($C_1$–$C_{20}$)alkyl, ($C_2$–$C_{20}$)alkenyl, halo($C_2$–$C_{20}$)alkenyl, acetylamino($C_2$–$C_{10}$)alkenyl, ($C_2$–$C_{20}$)alkynyl, halo($C_2$–$C_{20}$)alkynyl, cyclo($C_3$–$C_8$)alkyl, cyclo($C_3$–$C_8$)alkenyl, carboxycyclo($C_3$–$C_8$)alkyl, carboxycyclo($C_3$–$C_8$)alkenyl, cyclo($C_3$–$C_8$)alkyl($C_1$–$C_{10}$)alkyl, cyclo($C_3$–$C_8$)alkyl($C_2$–$C_{10}$)alkenyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$)alkyl($C_2$–$C_{10}$)alkynyl, cyclo($C_3$–$C_8$)alkenyl($C_2$–$C_{10}$)alkynyl, carboxycyclo($C_3$–$C_8$)alkyl($C_1$–$C_{10}$)alkyl, carboxy($C_3$–$C_8$)cycloalkyl($C_2$–$C_{10}$)alkenyl, carboxycyclo($C_3$–$C_8$)alkenyl($C_1$–$C_{10}$)alkyl, carboxycyclo($C_3$–$C_8$)alkenyl($C_2$–$C_{10}$)alkenyl, carboxycyclo($C_3$–$C_8$)alkyl($C_2$–$C_{10}$)alkynyl, carboxycyclo($C_3$–$C_8$)alkenyl($C_2$–$C_{10}$)alkynyl, heterocyclyl, heterocyclyl($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy($C_1$–$C_{10}$)alkyl, ($C_1$–$C_5$)alkoxy($C_1$–$C_5$)alkoxy($C_1$–$C_{10}$)alkyl, ($C_1$–$C_{10}$)alkoxy($C_2$–$C_{10}$)alkenyl, ($C_1$–$C_{10}$)alkoxy($C_2$–$C_{10}$)alkynyl, ($C_1$–$C_{10}$)alkoxycarbonyl($C_1$–$C_{10}$)alkyl, ($C_1$–$C_{10}$)alkoxycarbonyl($C_2$–$C_{10}$)alkenyl, ($C_1$–$C_{10}$)alkoxycarbonyl($C_2$–$C_{10}$)alkynyl, halo($C_1$–$C_{10}$)alkoxy($C_1$–$C_{10}$)alkyl, halo($C_1$–$C_{10}$)alkoxy($C_2$–$C_{10}$)alkenyl, halo($C_1$–$C_{10}$)alkoxy($C_2$–$C_{10}$)alkynyl, ($C_1$–$C_{10}$)alkylthio($C_1$–$C_{10}$)alkyl, ($C_1$–$C_{10}$)alkylthio($C_2$–$C_{10}$)alkenyl, ($C_1$–$C_{10}$)alkylthio($C_2$–$C_{10}$)alkynyl, halo($C_1$–$C_{10}$)alkylthio($C_1$–$C_{10}$)alkyl, halo($C_1$–$C_{10}$)alkylthio($C_2$–$C_{10}$)alkenyl, halo($C_1$–$C_{10}$)alkylthio($C_2$–$C_{10}$)alkynyl, $SO_2NR^3R^4$, $NR^3R^4$, carboxy($C_1$–$C_{20}$)alkyl, carboxy($C_2$–$C_{20}$)alkenyl, carboxy($C_2$–$C_{20}$)alkynyl, di($C_1$–$C_{10}$)alkoxyphosphoryl($C_1$–$C_{10}$)alkyl, aryl, aryl substituted with one or more substituents independently selected from halo, nitro, cyano, hydroxy, ($C_1$–$C_{10}$)alkyl, ($C_1$–$C_{10}$)alkylsulfonyl($C_1$–$C_{10}$)alkyl, ($C_1$–$C_{10}$)alkylsulfonyl, thiocyanato, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$ and $NR^3R^4$, ar($C_1$–$C_{10}$)alkyl, ar($C_2$–$C_{10}$)alkenyl, ar($C_2$–$C_{10}$)alkynyl, arcyclo($C_3$–$C_8$)alkyl, aroxy($C_1$–$C_{10}$)alkyl, or ar($C_1$–$C_{10}$)alkyl, ar($C_2$–$C_{10}$)alkenyl, ar($C_2$–$C_{10}$)alkynyl, arcyclo($C_3$–$C_8$)alkyl, aroxy($C_1$–$C_{10}$)alkyl substituted with one or more substituents independently selected from halo, nitro, hydroxy, cyano, ($C_1$–$C_{10}$)alkyl, cyclo($C_3$–$C_8$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$ and $NR^3R^4$, heteroaryl, heteroaryl substituted with one or more substituents independently selected from halo, hydroxy, nitro, cyano, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy and $NR^3R^4$, heteroar($C_1$–$C_{10}$)alkyl, heteroar($C_2$–$C_{10}$)alkenyl, heteroar($C_2$–$C_{10}$)alkynyl, or heteroar($C_1$–$C_{10}$)alkyl, heteroar($C_2$–$C_{10}$)alkenyl, heteroar($C_2$–$C_{10}$)alkynyl substituted with one or more substituents independently selected from halo, hydroxy, cyano, nitro, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy, halo($C_1$–$C_{10}$)alkoxy, $SO_2NR^3R^4$ and $NR^3R^4$, when q is 0 and t is 1, $R^3$, $R^4$ and $R^5$ are each independently a hydrogen atom, ($C_1$–$C_{20}$)alkyl, cyclo($C_3$–$C_8$)alkyl, cyclo($C_3$–$C_8$)alkenyl, cyclo($C_3$–$C_8$)alkyl($C_1$–$C_{10}$)alkyl, cyclo($C_3$–$C_8$)alkyl($C_2$–$C_{10}$)alkenyl, cyclo($C_3$–$C_8$)alkyl($C_2$–$C_{10}$)alkynyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$)alkenyl($C_2$–$C_{10}$)alkynyl, heterocyclyl, heterocyclyl($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy($C_1$–$C_{10}$)alkyl, ($C_2$–$C_{10}$)alkenyl, ($C_2$–$C_{10}$)alkynyl, or ($C_1$–$C_{10}$)alkyl, cyclo($C_3$–$C_8$)alkyl, cyclo($C_3$–$C_8$)alkenyl, cyclo($C_3$–$C_8$)alkyl($C_1$–$C_{10}$)alkyl, cyclo($C_3$–$C_8$)alkyl($C_2$–$C_{10}$)alkenyl, cyclo($C_3$–$C_8$)alkyl($C_2$–$C_{10}$)alkynyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$)alkenyl($C_2$–$C_{10}$)alkynyl, heterocyclyl, heterocyclyl($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy($C_1$–$C_{10}$)alkyl, ($C_2$–$C_{10}$)alkenyl or ($C_2$–$C_{10}$)alkynyl substituted with one or more halo, aryl, ar($C_1$–$C_{10}$)alkyl, ar($C_2$–$C_{10}$)alkenyl, ar($C_2$–$C_{10}$)alkynyl or aryl, ar($C_1$–$C_{10}$)alkyl, ar($C_2$–$C_{10}$)alkenyl, ar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy and halo($C_1$–$C_{10}$)alkoxy, heteroaryl, heteroar($C_1$–$C_{10}$)alkyl, heteroar($C_2$–$C_{10}$)alkenyl, heteroar($C_2$–$C_{10}$)alkynyl or heteroaryl, heteroar($C_1$–$C_{10}$)alkyl, heteroar($C_2$–$C_{10}$)alkenyl, heteroar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$)alkoxy and halo($C_1$–$C_{10}$)alkoxy, or $R^3$ and $R^4$ taken together with the nitrogen atom to which they are attached form a 5- or 6-membered saturated or unsaturated heterocyclic ring, $Z^2(X^2)_q$ is 3,6-dichloro-2-methoxyphenyl, 2,4-dichlorophenoxymethyl, 3-(2,4-dichlorophenoxy)-1-propyl, 3,5,6-trichloro-2-pyridyloxymethyl, 3,6-dichloro-2-pyridyl, 2-(4,6-dimethoxypyrimidin-2-yloxy)phenyl or 4-(2-chloro-4-trifluoromethylphenylphenoxy)-2-nitrophenyl, when q and t are each 1, or the pesticidally acceptable salts, isomers and enantiomers thereof.

In a more preferred embodiment, $R^1$ is a hydrogen atom, $(C_1-C_4)$alkyl, phenyl or phenyl substituted with one or more substituents independently selected from halo, $(C_1-C_4)$alkyl, halo$(C_1-C_4)$alkyl, cyano, nitro, $(C_1-C_4)$alkoxy, halo$(C_1-C_4)$alkoxy, carboxy, hydroxy, amino, $(C_1-C_4)$alkylamino or $\{(C_1-C_4)$alkyl$\}_2$amino, $R^2$ is a hydrogen atom, $R^6$ is a hydrogen atom or $(C_1-C_4)$alkyl, $R^7$ and $R^8$ are each independently $(C_1-C_4)$alkyl, hydroxy, $(C_1-C_4)$alkoxy or $O^-M^+$, $M^+$ is an alkali metal cation or $(NHR^9R^{10}R^{11})^+$, $R^9$, $R^{10}$ and $R^{11}$ are each independently hydrogen atom, $(C_1-C_{20})$alkyl, cyclo$(C_3-C_8)$alkyl, cyclo$(C_3-C_8)$alkenyl, cyclo$(C_3-C_8)$alkyl$(C_1-C_{10})$alkyl, cyclo$(C_3-C_8)$alkyl$(C_2-C_{10})$alkenyl, cyclo$(C_3-C_8)$alkyl$(C_2-C_{10})$alkynyl, cyclo$(C_3-C_8)$alkenyl$(C_1-C_{10})$alkyl, cyclo$(C_3-C_8)$alkenyl$(C_2-C_{10})$alkenyl, cyclo$(C_3-C_8)$alkenyl$(C_2-C_{10})$alkynyl, heterocyclyl, heterocyclyl$(C_1-C_{10})$alkyl, heterocyclyl$(C_2-C_{10})$alkenyl, heterocyclyl$(C_2-C_{10})$alkynyl, $(C_1-C_{10})$alkoxy$(C_1-C_{10})$alkyl, $(C_2-C_{10})$alkenyl, $(C_2-C_{10})$alkynyl, or $(C_1-C_{10})$alkyl, cyclo$(C_3-C_8)$alkyl, cyclo$(C_3-C_8)$alkenyl, cyclo$(C_3-C_8)$alkyl$(C_1-C_{10})$alkyl, cyclo$(C_3-C_8)$alkyl$(C_2-C_{10})$alkenyl, cyclo$(C_3-C_8)$alkyl$(C_2-C_{10})$alkynyl, cyclo$(C_3-C_8)$alkenyl$(C_1-C_{10})$alkyl, cyclo$(C_3-C_8)$alkenyl$(C_2-C_{10})$alkenyl, cyclo$(C_3-C_8)$alkenyl$(C_2-C_{10})$alkynyl, heterocyclyl, heterocyclyl$(C_1-C_{10})$alkyl, heterocyclyl$(C_2-C_{10})$alkenyl, heterocyclyl$(C_2-C_{10})$alkynyl, $(C_1-C_{10})$alkoxy$(C_1-C_{10})$alkyl, $(C_2-C_{10})$alkenyl or $(C_2-C_{10})$alkynyl substituted with one or more halo, aryl, ar$(C_1-C_{10})$alkyl, ar$(C_2-C_{10})$alkenyl, ar$(C_2-C_{10})$alkynyl or aryl, ar$(C_1-C_{10})$alkyl, ar$(C_2-C_{10})$alkenyl, ar$(C_2-C_{10})$alkynyl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy and halo$(C_1-C_{10})$alkoxy, heteroaryl, heteroar$(C_1-C_{10})$alkyl, heteroar$(C_2-C_{10})$alkenyl, heteroar$(C_2-C_{10})$alkynyl or heteroaryl, heteroar$(C_1-C_{10})$alkyl, heteroar$(C_2-C_{10})$alkenyl, heteroar$(C_2-C_{10})$alkynyl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy and halo$(C_1-C_{10})$alkoxy, or R3 and $R^4$ taken together with the nitrogen atom to which they are attached form a 5- or 6-membered saturated or unsaturated heterocyclic ring, q and t are each independently 0 or 1, $Z^2(X^2)_q$ is $(NR^3R^4R^5)^+$ $M^-$ when both q and t are 0 wherein $M^-$ is halo, hydroxy, $(C_1-C_8)$alkoxy or the anion of a carboxylic acid, $Z^2(X^2)_q$ is $(C_1-C_{20})$alkyl, cyclo$(C_3-C_8)$alkyl, halo$(C_1-C_{10})$alkyl, phenyl or phenyl substituted with one or more substituents selected from halo, nitro, cyano, hydroxy, $(C_1-C_4)$alkyl, halo$(C_1-C_4)$alkyl, $(C_1-C_4)$alkoxy and halo$(C_1-C_4)$alkoxy, phenoxy$(C_1-C_4)$alkyl or phenoxy$(C_1-C_4)$alkyl substituted on the phenyl ring with one or more substituents selected from halo, nitro, cyano, hydroxy, $(C_1-C_4)$alkyl, halo$(C_1-C_4)$alkyl, $(C_1-C_4)$alkoxy and halo$(C_1-C_4)$alkoxy, or di$(C_1-C_4)$alkoxyphosphoryl$(C_1-C_4)$alkyl when q is 0 and t is 1, $Z^2(X^2)_q$ is 3,6-dichloro-2-methoxyphenyl, 3-(2,4-dichlorophenoxy)-1-propyl or 3,5,6-trichloro-2-pyridyloxymethyl when q and t are each 1, $R^3$, $R^4$ and $R^5$ are each independently a hydrogen atom or a $(C_1-C_4)$alkyl, or the pesticidally acceptable salts, isomers and enantiomers thereof.

In an even more preferred embodiment, $R^1$ is a hydrogen atom, $(C_1-C_4)$alkyl, phenyl or phenyl substituted with one or more substituents independently selected from halo, $(C_1-C_4)$alkyl, halo$(C_1-C_4)$alkyl, cyano, nitro, $(C_1-C_4)$alkoxy, halo$(C_1-C_4)$alkoxy, carboxy, hydroxy, amino, $(C_1-C_4)$alkylamino or $\{(C_1-C_4)$alkyl$\}_2$amino, $R^2$ is a hydrogen atom, $R^6$ is a hydrogen atom or $(C_1-C_4)$alkyl, $R^7$ and $R^8$ are each independently hydroxy or $O^-M^+$, $M^+$ is $(NHR^9R^{10}R^{11})^+$, $R^9$, $R^{10}$ and $R^{11}$ are each a hydrogen atom or $(C_1-C_4)$alkyl, q is 0 or 1, t is 1, $Z^2(X^2)_q$ is $(C_1-C_6)$alkyl, cyclopropyl, methylcyclopropyl, cyclopentyl, cyclohexyl or halo$(C_1-C_4)$alkyl, when q is 0 or is 3,5,6-trichloropyridyloxymethyl or 2,4-dichlorophenoxymethyl when q is 1, or the pesticidally acceptable salts, isomers and enantiomers thereof.

In a fourth preferred embodiment of this invention, the pesticidal compound is represented by formula (IV)

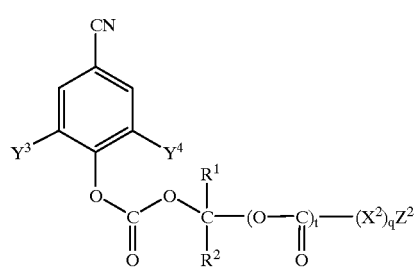

(IV)

wherein $R^1$ and $R^2$ are each independently a hydrogen atom, $(C_1-C_{20})$alkyl, $(C_2-C_{10})$alkenyl, $(C_2-C_{10})$alkynyl, $(C_1-C_{10})$alkoxy$(C_1-C_{10})$alkyl, $(C_1-C_{10})$alkoxy$(C_2-C_{10})$alkenyl, $(C_1-C_{10})$alkoxy$(C_2-C_{10})$alkynyl, $(C_1-C_{10})$alkylthio$(C_1-C_{10})$alkyl, $(C_1-C_{10})$alkylthio$(C_2-C_{10})$alkenyl, $(C_1-C_{10})$alkylthio$(C_2-C_{10})$alkynyl, carboxy, carboxy$(C_1-C_{20})$alkyl, carboxy$(C_2-C_{20})$alkenyl, carboxy$(C_2-C_{20})$alkynyl, $(C_1-C_{20})$alkoxycarbonyl, $(C_1-C_{10})$alkoxycarbonyl$(C_1-C_{10})$alkyl, $(C_1-C_{10})$alkoxycarbonyl$(C_2-C_{10})$alkenyl, $(C_1-C_{10})$alkoxycarbonyl$(C_2-C_{10})$alkynyl, $(C_1-C_{20})$alkylcarbonyl, $(C_2-C_{20})$alkenylcarbonyl, $(C_2-C_{20})$alkynylcarbonyl, cyclo$(C_3-C_8)$alkyl, cyclo$(C_3-C_8)$alkenyl, cyclo$(C_3-C_8)$alkyl$(C_1-C_{10})$alkyl, cyclo$(C_3-C_8)$alkenyl$(C_1-C_{10})$alkyl, cyclo$(C_3-C_8)$alkyl$(C_2-C_{10})$alkenyl, cyclo$(C_3-C_8)$alkenyl$(C_2-C_{10})$alkenyl, cyclo$(C_3-C_8)$alkyl$(C_2-C_{10})$alkynyl, cyclo$(C_3-C_8)$alkenyl$(C_2-C_{10})$alkynyl, heterocyclyl, heterocyclyl$(C_1-C_{10})$alkyl, heterocyclyl$(C_2-C_{10})$alkenyl, heterocyclyl$(C_2-C_{10})$alkynyl, aryl, aryl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo$(C_1-C_{10})$alkoxy, $SO_2NR^3R^4$ and $NR^3R^4$, ar$(C_1-C_{10})$alkyl, ar$(C_2-C_{10})$alkenyl, ar$(C_2-C_{10})$alkynyl, or ar$(C_1-C_{10})$alkyl, ar$(C_2-C_{10})$alkenyl, ar$(C_2-C_{10})$alkynyl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$ alkoxy, halo($C_1$–$C_{10}$)alkoxy, $SO_2NR^3R^4$ and $NR^3R^4$, heteroaryl, heteroaryl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo ($C_2$–$C_{10}$)alkynyl, ($C_1$–$C_{10}$)alkoxy, halo($C_1$–$C_{10}$)alkoxy and $NR^3R^4$, heteroar($C_1$–$C_{10}$)alkyl, heteroar($C_2$–$C_{10}$) alkenyl, heteroar($C_2$–$C_{10}$)alkynyl or heteroar($C_1$–$C_{10}$) alkyl, heteroar($C_2$–$C_{10}$)alkenyl, heteroar($C_2$–$C_{10}$) alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$) alkoxy, halo($C_1$–$C_{10}$)alkoxy, $SO_2NR^3R^4$ and $NR^3R^4$, or $R^1$ and $R^2$ taken together with the carbon atom to which they are attached form a 5–7 membered saturated or unsaturated ring, or $R^1$ may be a pesticidal moiety if $R^2$ is a hydrogen atom, $Y^3$ and $Y^4$ are each independently selected from halo, q and t are each independently 0 or 1, $Z^2(X^2)_q$ is halo, $NR^3R^4$, {$(NR^3R^4R^5)^+M^-$}, $OR^3$, $S(O)_jR^3$ or $SO_2NR^3R^4$ when both q and t are 0 wherein $M^{31}$ is halo, hydroxy, ($C_1$–$C_8$)alkoxy or the anion of a carboxylic acid and j is 0, 1 or 2, $Z^2(X^2)_q$ is ($C_1$–$C_{20}$)alkyl, ($C_1$–$C_{10}$)alkylcarbonyloxy ($C_1$–$C_{10}$)alkyl, ($C_1$–$C_{20}$)alkylcarbonyl, hydroxy ($C_1$–$C_{20}$)alkyl, ($C_1$–$C_{10}$)alkylsulfonyl($C_1$–$C_{10}$)alkyl, acetylamino($C_1$–$C_{10}$)alkyl, halo($C_1$–$C_{20}$)alkyl, ($C_2$–$C_{20}$)alkenyl, halo($C_2$–$C_{20}$)alkenyl, acetylamino ($C_2$–$C_{10}$)alkenyl, ($C_2$–$C_{20}$)alkynyl, halo($C_2$–$C_{20}$) alkynyl, cyclo($C_3$–$C_8$)alkyl, cyclo($C_3$–$C_8$)alkenyl, carboxycyclo($C_3$–$C_8$)alkyl, carboxycyclo($C_3$–$C_8$) alkenyl, cyclo($C_3$–$C_8$)alkyl($C_1$–$C_{10}$)alkyl, cyclo ($C_3$–$C_8$)alkyl($C_2$–$C_{10}$)alkenyl, cyclo($C_3$–$C_8$)alkenyl ($C_1$–$C_{10}$)alkyl, cyclo($C_3$–$C_8$)alkenyl($C_2$–$C_{10}$)alkenyl, cyclo($C_3$–$C_8$)alkyl($C_2$–$C_{10}$)alkynyl, cyclo($C_3$–$C_8$) alkenyl($C_2$–$C_{10}$)alkynyl, carboxycyclo($C_3$–$C_8$)alkyl ($C_1$–$C_{10}$)alkyl, carboxy($C_3$–$C_8$)cycloalkyl($C_2$–$C_{10}$) alkenyl, carboxycyclo($C_3$–$C_8$)alkenyl($C_1$–$C_{10}$)alkyl, carboxycyclo($C_3$–$C_8$)alkenyl($C_2$–$C_{10}$)alkenyl, carboxycyclo($C_3$–$C_8$)alkyl($C_2$–$C_{10}$)alkynyl, carboxycyclo($C_3$–$C_8$)alkenyl($C_2$–$C_{10}$)alkynyl, heterocyclyl, heterocyclyl($C_1$–$C_{10}$)alkyl, heterocyclyl ($C_2$–$C_{10}$)alkenyl, heterocyclyl($C_2$–$C_{10}$)alkynyl, ($C_1$–$C_{10}$)alkoxy($C_1$–$C_{10}$)alkyl, ($C_1$–$C_5$)alkoxy($C_1$–$C_5$) alkoxy($C_1$–$C_{10}$)alkyl, ($C_1$–$C_{10}$)alkoxy($C_2$–$C_{10}$) alkenyl, ($C_1$–$C_{10}$)alkoxy($C_2$–$C_{10}$)alkynyl, ($C_1$–$C_{10}$) alkoxycarbonyl($C_1$–$C_{10}$)alkyl, ($C_1$–$C_{10}$) alkoxycarbonyl($C_2$–$C_{10}$)alkenyl, ($C_1$–$C_{10}$) alkoxycarbonyl($C_2$–$C_{10}$)alkynyl, halo($C_1$–$C_{10}$)alkoxy ($C_1$–$C_{10}$)alkyl, halo($C_1$–$C_{10}$)alkoxy($C_2$–$C_{10}$)alkenyl, halo($C_1$–$C_{10}$)alkoxy($C_2$–$C_{10}$)alkynyl, ($C_1$–$C_{10}$) alkylthio($C_1$–$C_{10}$)alkyl, ($C_1$–$C_{10}$)alkylthio($C_2$–$C_{10}$) alkenyl, ($C_1$–$C_{10}$)alkylthio($C_2$–$C_{10}$)alkynyl, halo ($C_1$–$C_{10}$)alkylthio($C_1$–$C_{10}$)alkyl, halo($C_1$–$C_{10}$) alkylthio($C_2$–$C_{10}$)alkenyl, halo($C_1$–$C_{10}$)alkylthio ($C_2$–$C_{10}$)alkynyl, $SO_2NR^3R^4$, $NR^3R^4$, carboxy ($C_1$–$C_{20}$)alkyl, carboxy($C_2$–$C_{20}$)alkenyl, carboxy ($C_2$–$C_{20}$)alkynyl, aryl, aryl substituted with one or more substituents independently selected from halo, nitro, cyano, hydroxy, ($C_1$–$C_{10}$)alkyl, ($C_1$–$C_{10}$) alkylsulfonyl($C_1$–$C_{10}$)alkyl, ($C_1$–$C_{10}$)alkylsulfonyl, thiocyanato, ($C_2$–$C_{10}$)alkenyl, ($C_2$–$C_{10}$)alkynyl, halo ($C_1$–$C_{10}$)alkyl, halo($C_2$–$C_{10}$)alkenyl, halo($C_2$–$C_{10}$) alkynyl, ($C_1$–$C_{10}$)alkoxy, halo($C_1$–$C_{10}$)alkoxy, $SO_2NR^3R^4$ and $NR^3R^4$, ar($C_1$–$C_{10}$)alkyl, ar($C_2$–$C_{10}$) alkenyl, ar($C_2$–$C_{10}$)alkynyl, arcyclo($C_3$–$C_8$)alkyl, aroxy($C_1$–$C_{10}$)alkyl, or ar($C_1$–$C_{10}$)alkyl, ar($C_2$–$C_{10}$) alkenyl, ar($C_2$–$C_{10}$)alkynyl, arcyclo($C_3$–$C_8$)alkyl, aroxy($C_1$–$C_{10}$)alkyl substituted with one or more substituents independently selected from halo, nitro, hydroxy, cyano, ($C_1$–$C_{10}$)alkyl, cyclo($C_3$–$C_8$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$) alkoxy, halo($C_1$–$C_{10}$)alkoxy, $SO_2NR^3R^4$ and $NR^3R^4$, heteroaryl, heteroaryl substituted with one or more substituents independently selected from halo, hydroxy, nitro, cyano, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$) alkenyl, halo($C_2$–$C_{10}$)alkynyl, ($C_1$–$C_{10}$)alkoxy, halo ($C_1$–$C_{10}$)alkoxy and $NR^3R^4$, heteroar($C_1$–$C_{10}$)alkyl, heteroar($C_2$–$C_{10}$)alkenyl, heteroar($C_2$–$C_{10}$)alkynyl, or heteroar($C_1$–$C_{10}$)alkyl, heteroar($C_2$–$C_{10}$)alkenyl, heteroar($C_2$–$C_{10}$)alkynyl substituted with one or more substituents independently selected from halo, hydroxy, cyano, nitro, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$) alkenyl, halo($C_2$–$C_{10}$)alkynyl, ($C_1$–$C_{10}$)alkoxy, halo ($C_1$–$C_{10}$)alkoxy, $SO_2NR^3R^4$ and $NR^3R^4$, when q is 0 and t is 1, $R^3$, $R^4$ and $R^5$ are each independently a hydrogen atom, ($C_1$–$C_{20}$)alkyl, cyclo($C_3$–$C_8$)alkyl, cyclo($C_3$–$C_8$) alkenyl, cyclo($C_3$–$C_8$)alkyl, cyclo($C_3$–$C_8$)alkyl ($C_2$–$C_{10}$)alkenyl, cyclo($C_3$–$C_8$)alkyl($C_2$–$C_{10}$)alkynyl, cyclo($C_3$–$C_8$)alkenyl($C_1$–$C_{10}$)alkyl, cyclo($C_3$–$C_8$) alkenyl($C_2$–$C_{10}$)alkenyl, cyclo($C_3$–$C_8$)alkenyl ($C_2$–$C_{10}$)alkynyl, heterocyclyl, heterocyclyl($C_1$–$C_{10}$) alkyl, heterocyclyl($C_2$–$C_{10}$)alkenyl, heterocyclyl ($C_2$–$C_{10}$)alkynyl, ($C_1$–$C_{10}$)alkoxy($C_1$–$C_{10}$)alkyl, ($C_2$–$C_{10}$)alkenyl, ($C_2$–$C_{10}$)alkynyl, or ($C_1$–$C_{10}$)alkyl, cyclo($C_3$–$C_8$)alkyl, cyclo($C_3$–$C_8$)alkenyl, cyclo ($C_3$–$C_8$)alkyl($C_1$–$C_{10}$)alkyl, cyclo($C_3$–$C_8$)alkyl ($C_2$–$C_{10}$)alkenyl, cyclo($C_3$–$C_8$)alkyl($C_2$–$C_{10}$)alkynyl, cyclo($C_3$–$C_8$)alkenyl($C_1$–$C_{10}$)alkyl, cyclo($C_3$–$C_8$) alkenyl($C_2$–$C_{10}$)alkenyl, cyclo($C_3$–$C_8$)alkenyl ($C_2$–$C_{10}$)alkynyl, heterocyclyl, heterocyclyl($C_1$–$C_{10}$) alkyl, heterocyclyl($C_2$–$C_{10}$)alkenyl, heterocyclyl ($C_2$–$C_{10}$)alkynyl, ($C_1$–$C_{10}$)alkoxy($C_1$–$C_{10}$)alkyl, ($C_2$–$C_{10}$)alkenyl or ($C_2$–$C_{10}$)alkynyl substituted with one or more halo, ar($C_1$–$C_{10}$)alkyl, ar($C_2$–$C_{10}$)alkenyl, ar($C_2$–$C_{10}$)alkynyl or ar($C_1$–$C_{10}$)alkyl, ar($C_2$–$C_{10}$) alkenyl, ar($C_2$–$C_{10}$)alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo ($C_2$–$C_{10}$)alkynyl, ($C_1$–$C_{10}$)alkoxy and halo($C_1$–$C_{10}$) alkoxy, heteroar($C_1$–$C_{10}$)alkyl, heteroar($C_2$–$C_{10}$) alkenyl, heteroar($C_2$–$C_{10}$)alkynyl or heteroar($C_1$–$C_{10}$) alkyl, heteroar($C_2$–$C_{10}$)alkenyl, heteroar($C_2$–$C_{10}$) alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$) alkoxy and halo($C_1$–$C_{10}$)alkoxy, or $R^3$ and $R^4$ taken together with the nitrogen atom to which they are attached form a 5- or 6-membered saturated or unsaturated heterocyclic ring, $Z^2(X^2)_q$ is methoxycarbonylaminooxymethyl, 2,4-dichlorophenoxymethyl, 3,6-dichloro-2-pyridyl, 2-(4, 6-dimethoxypyrimidin-2-yloxy)phenyl, 2-chloro-6-(4, 6-dimethoxypyrimidin-2-ylsulfanyl)phenyl or 4-(2-chloro-4-trifluoromethylphenylphenoxy)-2-nitrophenyl, when q and t are each 1, or the pesticidally acceptable salts, isomers and enantiomers thereof.

In a more preferred embodiment, $R^1$ and $R^2$ are each independently a hydrogen atom, $(C_1-C_{20})$alkyl, $(C_2-C_{10})$alkenyl, $(C_2-C_{10})$alkynyl, $(C_1-C_{10})$alkoxy$(C_1-C_{10})$alkyl, $(C_1-C_{10})$alkoxy$(C_2-C_{10})$alkenyl, $(C_1-C_{10})$alkoxy$(C_2-C_{10})$alkynyl, $(C_1-C_{10})$alkylthio$(C_1-C_{10})$alkyl, $(C_1-C_{10})$alkylthio$(C_2-C_{10})$alkenyl, $(C_1-C_{10})$alkylthio$(C_2-C_{10})$alkynyl, carboxy, carboxy$(C_1-C_{20})$alkyl, carboxy$(C_2-C_{20})$alkenyl, carboxy$(C_2-C_{20})$alkynyl, $(C_1-C_{20})$alkoxycarbonyl, $(C_1-C_{10})$alkoxycarbonyl$(C_1-C_{10})$alkyl, $(C_1-C_{10})$alkoxycarbonyl$(C_2-C_{10})$alkenyl, $(C_1-C_{10})$alkoxycarbonyl$(C_2-C_{10})$alkynyl, $(C_1-C_{20})$alkylcarbonyl, $(C_2-C_{20})$alkenylcarbonyl, $(C_2-C_{20})$alkynylcarbonyl, cyclo$(C_3-C_8)$alkyl, cyclo$(C_3-C_8)$alkenyl, cyclo$(C_3-C_8)$alkyl$(C_1-C_{10})$alkyl, cyclo$(C_3-C_8)$alkyl$(C_2-C_{10})$alkenyl, cyclo$(C_3-C_8)$alkenyl$(C_1-C_{10})$alkyl, cyclo$(C_3-C_8)$alkyl$(C_2-C_{10})$alkynyl, cyclo$(C_3-C_8)$alkenyl$(C_2-C_{10})$alkynyl, cyclo$(C_3-C_8)$alkenyl$(C_2-C_{10})$alkynyl, cyclo$(C_3-C_8)$alkenyl$(C_2-C_{10})$alkynyl, heterocyclyl, heterocyclyl$(C_1-C_{10})$alkyl, heterocyclyl$(C_2-C_{10})$alkenyl, heterocyclyl$(C_2-C_{10})$alkynyl, aryl, aryl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo$(C_1-C_{10})$alkoxy, $SO_2NR^3R^4$ and $NR^3R^4$, ar$(C_1-C_{10})$alkyl, ar$(C_2-C_{10})$alkenyl, ar$(C_2-C_{10})$alkynyl, or ar$(C_1-C_{10})$alkyl, ar$(C_2-C_{10})$alkenyl, ar$(C_2-C_{10})$alkynyl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo$(C_1-C_{10})$alkoxy, $SO_2NR^3R^4$ and $NR^3R^4$, heteroaryl, heteroaryl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo$(C_1-C_{10})$alkoxy and $NR^3R^4$, heteroar$(C_1-C_{10})$alkyl, heteroar$(C_2-C_{10})$alkenyl, heteroar$(C_2-C_{10})$alkynyl or heteroar$(C_1-C_{10})$alkyl, heteroar$(C_2-C_{10})$alkenyl, heteroar$(C_2-C_{10})$alkynyl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo$(C_1-C_{10})$alkoxy, $SO_2NR^3R^4$ and $NR^3R^4$, or $R^1$ and $R^2$ taken together with the carbon atom to which they are attached form a 5–7 membered saturated or unsaturated ring, or $R^1$ may be a pesticidal moiety if $R^2$ is a hydrogen atom, $Y^3$ and $Y^4$ are each independently selected from halo, q and t are each independently 0 or 1, $Z^2(X^2)_q$ is halo or $\{(NR^3R^4R^5)^+M^-\}$ when both q and t are 0 wherein $M^-$ is halo, hydroxy, alkoxy or the anion of a carboxylic acid, $Z^2(X^2)_q$ is $(C_1-C_{20})$alkyl, cyclo$(C_3-C_8)$alkyl, halo$(C_1-C_{10})$alkyl, phenyl or phenyl substituted with one or more substituents selected from halo, nitro, cyano, hydroxy, $(C_1-C_4)$alkyl, halo$(C_1-C_4)$alkyl, $(C_1-C_4)$alkoxy and halo$(C_1-C_4)$alkoxy, phenoxy$(C_1-C_4)$alkyl or phenoxy$(C_1-C_4)$alkyl substituted on the phenyl ring with one or more substituents selected from halo, nitro, cyano, hydroxy, $(C_1-C_4)$alkyl, halo$(C_1-C_4)$alkyl, $(C_1-C_4)$alkoxy and halo$(C_1-C_4)$alkoxy, when q is 0 and t is 1, $Z^2(X^2)_q$ is methoxycarbonylaminooxymethyl, 2,4-dichlorophenoxymethyl, 3,6-dichloro-2-pyridyl, 2-(4,6-dimethoxypyrimidin-2-yloxy)phenyl, 2-chloro-6-(4,6-dimethoxypyrimidin-2-ylsulfanyl)phenyl or 4-(2-chloro-4-trifluoromethylphenylphenoxy)-2-nitrophenyl, when q and t are each 1, $R^3$, $R^4$ and $R^5$ are each independently a hydrogen atom or a $(C_1-C_4)$alkyl, or the pesticidally acceptable salts, isomers and enantiomers thereof.

In an even more preferred embodiment, $R^1$ is a hydrogen atom, phenyl or $(C_1-C_4)$alkyl, $R^2$ is a hydrogen atom, $Y^3$ and $Y^4$ are each bromo, chloro or iodo, q is 0 or 1, t is 1, $Z^2(X^2)_q$ is $(C_1-C_6)$alkyl, cyclopropyl, methylcyclopropyl, cyclopentyl, cyclohexyl or halo$(C_1-C_4)$alkyl when q is 0 or is methoxycarbonylaminooxymethyl, 2,4-dichlorophenoxymethyl, 3,6-dichloro-2-pyridyl, 2-(4,6-dimethoxypyrimidin-2-yloxy)phenyl, 2-chloro-6-(4,6-dimethoxypyrimidin-2-ylsulfanyl)phenyl or 4-(2-chloro-4-trifluoromethylphenylphenoxy)-2-nitrophenyl when q is 1, or the pesticidally acceptable salts, isomers and enantiomers thereof.

In Schemes 1–16 hereinafter showing how to synthesize compounds of this invention and Tables 1–9 hereinafter listing various representative compounds of this invention, the following abbreviations may be present: Me for methyl, Et for ethyl, $^i$Pr or $^i$Pr for isopropyl, n-Bu for n-butyl, t-Bu for tert-butyl, Ph for phenyl, 4Cl—Ph or (4Cl)Ph for 4-chlorophenyl, 4Me—Ph or (4Me)Ph for 4-methylphenyl, (p-CH$_3$O)Ph for p-methoxyphenyl, (p-NO$_2$)Ph for p-nitrophenyl, 4Br—Ph or (4Br)Ph for 4-bromophenyl, 2-CF$_3$—Ph or (2CF$_3$)Ph for 2-trifluoromethylphenyl, and the like.

The compounds of Formula I of this invention and the intermediates used in the synthesis of the compounds of this invention can be prepared according to the following methods. Method A can be used when preparing compounds of Formula I as shown below in Scheme 1.

Method A

Scheme 1

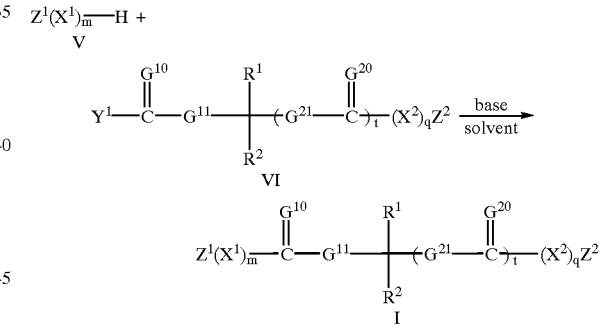

where $Z^1(X^1)_m$—H, $(X^2)_qZ^2$, $G^{10}$, $G^{11}$, $G^{20}$, $G^{21}$, $R^1$, $R^2$ are as defined above for compound of Formula I and m=0 or 1, t=0 or 1, q=0 or 1, $Y^1$=halogen such as chlorine.

A typical preparation, according to Method A, of the compound of Formula I is the reaction of the compound of Formula V with the compound of Formula VI in a suitable solvent in the presence of a suitable base. Suitable solvents for use in the above process include ethers such as tetrahydrofuran (THF), glyme, and the like; dimethylformamide (DMF); dimethylsulfoxide (DMSO); acetonitrile; chlorinated solvents such as methylene chloride (CH$_2$Cl$_2$) or chloroform (CHCl$_3$). If desired, mixtures of these solvents may be used, however, the preferred solvent is THF. Suitable bases for use in the above process include metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases may be used, however, the preferred base is pyridine. The above process may be carried out at temperatures between about −78° C. and about 100° C. Preferably, the reaction is carried out between 0° C. and about 50° C. The compounds of the present invention by the above process is preferably carried out at about atmospheric pressure although higher or lower pressures can be used if desired. Substantially equimolar amounts of reactants are preferably used although higher or lower amounts can be used if desired. Generally, one equivalent of base is used per equivalent of starting material of compound of Formula VI. The compounds of Formula V are generally commercially available or can be prepared according to known procedures.

The compounds of Formula VI of Scheme 1 are prepared as shown in Scheme 2. The compounds of Formula VI can also be prepared by similar methodology as cited in U.S. Pat. No. 5,401,868.

Scheme 2

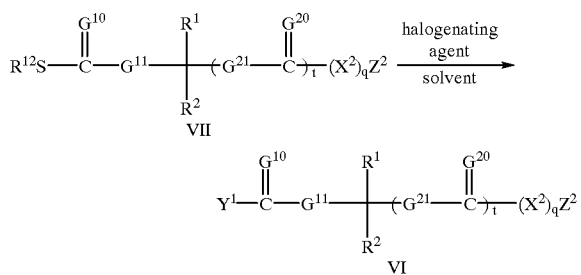

where $(X^2)_qZ^2$, $G^{10}$, $G^{11}$, $G^{20}$, $G^{21}$, $R^1$, $R^2$ are as defined previously for compound of Formula I and t=0 or 1, q=0 or 1, $R^{12}$ is an alkyl, aralkyl, or aryl group, and $Y^1$=halogen such as chlorine.

In a typical preparation of the compounds of Formula VI, the compound of Formula VII is treated with a suitable halogenating agent in a suitable solvent, where the suitable halogenating agents include chlorine gas, thionyl chloride, and sulfuryl chloride, however, the preferred halogenating agent is sulfuryl chloride. Suitable solvents for use in the above process include hexanes, chlorinated solvents such as methylene chloride, dichloroethane, chloroform, carbon tetrachloride, and the like, however, the reactions are normally run neat. The above process may be carried out at temperatures between about −78° C. and about 100° C. Preferably, the reaction is carried out between 0° C. and about 50° C. The compounds of the present invention by the above process is preferably carried out at about atmospheric pressure although higher or lower pressures can be used if desired. Substantially equimolar amounts of reactants are preferably used although higher or lower amounts can be used if desired.

The compounds of Formula VII of Scheme 2 are prepared as shown in Scheme 3.

Scheme 3

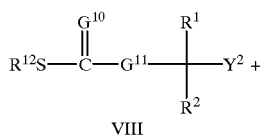

-continued

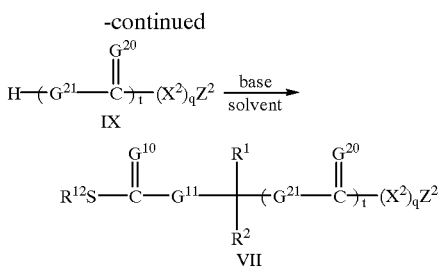

where $(X^2)_qZ^2$, $G^{10}$, $G^{11}$, $G^{20}$, $G^{21}$, $R^1$, $R^2$ are as defined previously for compound of Formula I and t=0 or 1, q=0 or 1, $R^{12}$=alkyl, aralkyl, or aryl, and $Y^2$=halogen such as chlorine, bromine, or iodine.

In a typical preparation of the compounds of Formula VII, compound of Formula VIII is reacted with compound of Formula IX in a suitable solvent in the presence of a suitable base. Suitable solvents for use in the above process include ethers such as tetrahydrofuran (THF), glyme, and the like; dimethylformamide (DMF); dimethylsulfoxide (DMSO); acetonitrile; chlorinated solvents such as methylene chloride ($CH_2Cl_2$) or chloroform ($CHCl_3$). If desired, mixtures of these solvents may be used, however, the preferred solvent is THF. Suitable bases for use in the above process include metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases may be used, however, the preferred base is diisopropylethylamine. The above process may be carried out at temperatures between about −78° C. and about 100° C. Preferably, the reaction is carried out between 0° C. and about 50° C. The compounds of the present invention by the above process is preferably carried out at about atmospheric pressure although higher or lower pressures can be used if desired. Substantially equimolar amounts of reactants are preferably used although higher or lower amounts can be used if desired. Generally, one equivalent of base is used per equivalent of starting material of compound of Formula VIII. The compounds of Formula IX are generally commercially available or can be prepared according to known procedures.

The compounds of Formula VIII of Scheme 3 are prepared as shown in Scheme 4.

Scheme 4

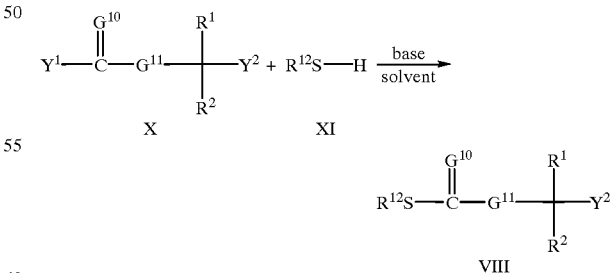

where $G^{10}$, $G^{11}$, $R^1$, $R^2$ are as defined previously for compound of Formula I and $R^{12}$=alkyl, aralkyl, or aryl, $Y^1$=halogen such as chlorine, and $Y^2$=halogen such as chlorine, bromine, or iodine.

In a typical preparation of the compounds of Formula VIII, compound of Formula X is reacted with compound of Formula XI in a suitable solvent in the presence of a suitable base. Suitable solvents for use in the above process include ethers such as tetrahydrofuran (THF), glyme, diethyl ether, and the like; dimethylformamide (DMF); dimethylsulfoxide (DMSO); acetonitrile; chlorinated solvents such as methylene chloride ($CH_2Cl_2$) or chloroform ($CHCl_3$). If desired, mixtures of these solvents may be used, however, the preferred solvent is diethyl ether. Suitable bases for use in the above process include metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases may be used, however, the preferred base is sodium hydride. The above process may be carried out at temperatures between about −78° C. and about 100° C. Preferably, the reaction is carried out between 0° C. and about 50° C. The compounds of the present invention by the above process is preferably carried out at about atmospheric pressure although higher or lower pressures can be used if desired. Substantially equimolar amounts of reactants are preferably used although higher or lower amounts can be used if desired. Generally, one equivalent of base is used per equivalent of starting material of compound of Formula X. The compounds of Formula XI are generally commercially available or can be prepared according to known procedures.

The compounds of Formula I can be prepared according to Method B as shown in Scheme 5.
Method B

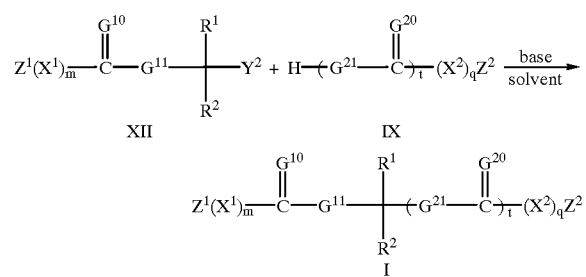

where $Z^1(X^1)_m$, $(X^2)_qZ^2$, $G^{10}$, $G^{11}$, $G^{20}$, $G^{21}$, $R^1$, $R^2$ are as defined previously for compound of Formula I and m=0 or 1, t=0 or 1, q=0 or 1, $Y^2$=halogen such as chlorine, bromine, or iodine.

In a typical preparation of the compounds of Formula I according to Method B, compound of Formula XII as shown in Scheme 5, is reacted with compound of Formula IX in a suitable solvent in the presence of a suitable base. Suitable solvents for use in the above process include ethers such as tetrahydrofuran (THF), glyme, diethyl ether, and the like; dimethylformamide (DMF); dimethylsulfoxide (DMSO); acetonitrile; chlorinated solvents such as methylene chloride ($CH_2Cl_2$) or chloroform ($CHCl_3$). If desired, mixtures of these solvents may be used, however, the preferred solvent is THF. Suitable bases for use in the above process include metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases may be used, however, the preferred base is diisopropylethylamine. The above process may be carried out at temperatures between about −78° C. and about 100° C. Preferably, the reaction is carried out between 0° C. and about 50° C. The compounds of the present invention by the above process is preferably carried out at about atmospheric pressure although higher or lower pressures can be used if desired. Substantially equimolar amounts of reactants are preferably used although higher or lower amounts can be used if desired. Generally, one equivalent of base is used per equivalent of starting material of compound of Formula IX. The compounds of Formula IX are generally commercially available or can be prepared according to known procedures.

The compounds of Formula XII of Scheme 5 are prepared as shown in Scheme 6.

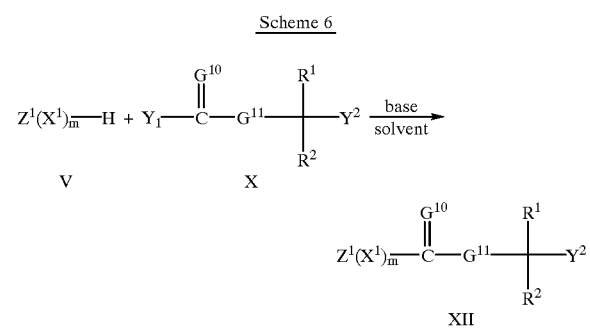

where $Z^1(X^1)_m$—H, $G^{10}$, $G^{11}$, $R^1$, $R^2$ are as defined previously for compound of Formula I and m=0 or 1, $Y^1$=halogen such as chlorine, and $Y^2$=halogen such as chlorine, bromine, or iodine.

In a typical preparation of the compounds of Formula XII, compound of Formula V is reacted with compound of Formula X in a suitable solvent in the presence of a suitable base. Suitable solvents for use in the above process include ethers such as tetrahydrofuran (THF), glyme, diethyl ether, and the like; dimethylformamide (DMF); dimethylsulfoxide (DMSO); acetonitrile; chlorinated solvents such as methylene chloride ($CH_2Cl_2$) or chloroform ($CHCl_3$). If desired, mixtures of these solvents may be used, however, the preferred solvent is THF. Suitable bases for use in the above process include metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases may be used, however, the preferred base is sodium hydride. The above process may be carried out at temperatures between about −78° C. and about 100° C. Preferably, the reaction is carried out between 0° C. and about 50° C. The compounds of the present invention by the above process is preferably carried out at about atmospheric pressure although higher or lower pressures can be used if desired. Substantially equimolar amounts of reactants are preferably used although higher or lower amounts can be used if desired. Generally, one equivalent of base is used per equivalent of starting material of compound of Formula V. The compounds of Formula V and X are generally commercially available or can be prepared according to known procedures. Additionally compounds of Formula XII, when m=0 and $Z^1$ is not a heteroatom bonded to C=$G^{20}$, can be prepared by known procedures or are generally commercially available.

The compounds of Formula I can be prepared according to Method C as shown in Scheme 7.

Method C

Scheme 7

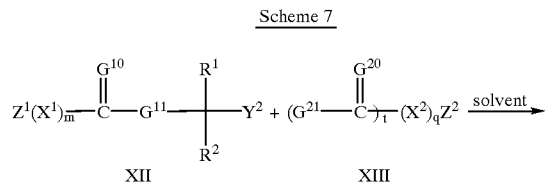

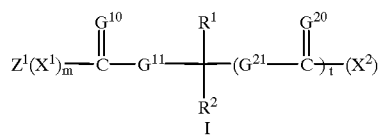

where $Y^2$=halogen such of as iodine, bromine, or chlorine, $Z^1(X^1)_m$, $G^{10}$, $G^{11}$, $R^1$, $R^2$ are as defined previously for compound of Formula I and m=0 or 1, t=0, q=0 or 1, where $(X^2)_qZ^2$=$NR^3R^4$, $NR^3R^4R^5$, or $\{(NR^3R^4R^5)M\}$ and when q=0, in compound of Formula XIII, $Z^2$ can be a tertiary amine where in compound of Formula I, $Z^2$ is a quaternary amine salt. When q=1, in compound of Formula XIII, $X^2Z^2$ can be a tertiary amine where in compound of Formula I, $X^2Z^2$ is a quaternary amine salt.

In a typical preparation of the compounds of Formula I, according to Method C, compound of Formula XII is reacted with compound of Formula XIII in a suitable solvent. Suitable solvents for use in the above process include ethers such as tetrahydrofuran (THF), glyme, diethyl ether, and the like; dimethylformamide (DMF); dimethylsulfoxide (DMSO); acetonitrile; chlorinated solvents such as methylene chloride ($CH_2Cl_2$) or chloroform ($CHCl_3$). If desired, mixtures of these solvents may be used, however, the preferred solvent is THF. The above process may be carried out at temperatures between about −78° C. and about 200° C. Preferably, the reaction is carried out between 0° C. and about 100° C. The compounds of the present invention by the above process is preferably carried out at about atmospheric pressure although higher or lower pressures can be used if desired. Substantially equimolar amounts of reactants are preferably used although higher or lower amounts can be used if desired. Generally, one equivalent of compound of Formula XIII is used per equivalent of starting material of compound of Formula XII. The compounds of Formula XIII are generally commercially available or can be prepared according to known procedures. The compounds of Formula XII can be prepared by the same process as that of Scheme 6.

Application of Method B (Scheme 6)as described previously for the synthesis of compound of Formula XII to the synthesis of compound of Formula XIV is described below in Scheme 8. Compound of Formula XV (compound of Formula V in which m=1 and $Z^1(X^1)_m$—H is a suitably substituted pesticidal hydrazine) is reacted with compound of Formula XVI in which $Y^2$=Cl (compound of Formula X in which $G^{10}$ and $G^{11}$=O and $Y^1$=Cl) to afford compound of Formula XIV in which $Y^2$=Cl (compound of Formula XII in which m=1, $Z^1(X^1)_m$ is a suitably substituted pesticidal hydrazine and $G^{10}$ and $G^{11}$=O):

Method B

Scheme 8

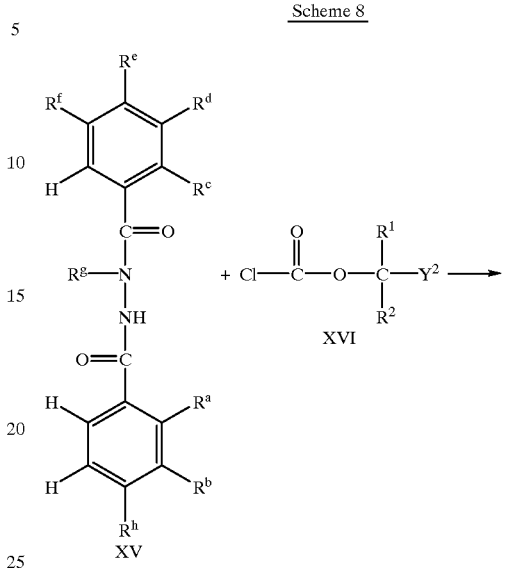

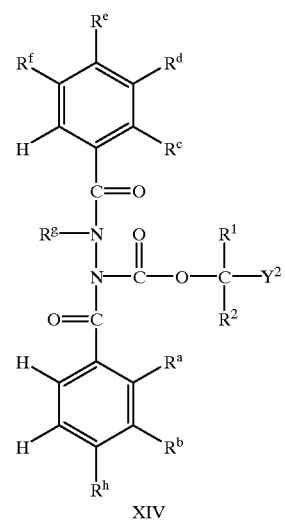

where $R_1$ and $R^2$ are as defined previously for compound of Formula I and $R^a$–$R^h$ are as defined above for compound of Formula II.

Suitable solvents for use in the above process include ethers such as tetrahydrofuran (THF), glyme, and the like; dimethylformamide (DMF); dimethylsulfoxide (DMSO); acetonitrile; chlorinated solvents such as methylene chloride ($CH_2Cl_2$) or chloroform ($CHCl_3$). If desired, mixtures of these solvents may be used, however, the preferred solvent is THF. Suitable bases for use in the above process include metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases may be used, however, the preferred base is sodium hydride. The above method may be carried out at temperatures between about −78° C. and about 100° C. Preferably, the reaction is carried out between 0° C. and about 100° C. Preparation of the compounds of the present invention by the above method is preferably carried out at about atmospheric pressure although higher or lower pressures can be used if desired. Substantially equimolar amounts of reactants are preferably used although higher or lower amounts can be used if desired. Generally, one equivalent of base is used per equivalent of starting material of compound of Formula XV. The compounds of Formula XVI are generally commercially available or can be prepared according to known procedures. The compounds of Formula XV can be prepared according to patented methods such as those found in U.S. Pat. Nos. 5,530,028 and 6,013,836.

Conversion of $Y^2$ from Cl to Br or Cl to I in compound of Formula XIV can be prepared according to literature procedures. A general description of the synthesis of halogen exchange (Finkelstein reaction) is described in March, Advanced Organic Chemistry, $4^{th}$ Ed, pp 430–431. Also, see synthesis Example 1–3 for conversion of $Y^2$ from Cl to I in compound of Formula XIV.

Application of Method B (Scheme 5)as described previously for the synthesis of compound of Formula I to the synthesis of compound of Formula II is described below in Scheme 9. Compound of Formula XVII in which t=1 (compound of Formula IX in which q=0 or 1 and $G^{20}$=O and $G^{21}$=O) is reacted with compound of Formula XIV [described in Method B (Scheme 8)] to afford compound of Formula II in which t=1 [compound of Formula I in which m=1, q=0 or 1, $Z^1(X^1)_m$ is a suitably substituted pesticidal hydrazine, and $G^{10}$, $G^{11}$, $G^{20}$, and $G^{21}$=O]:

Scheme 9

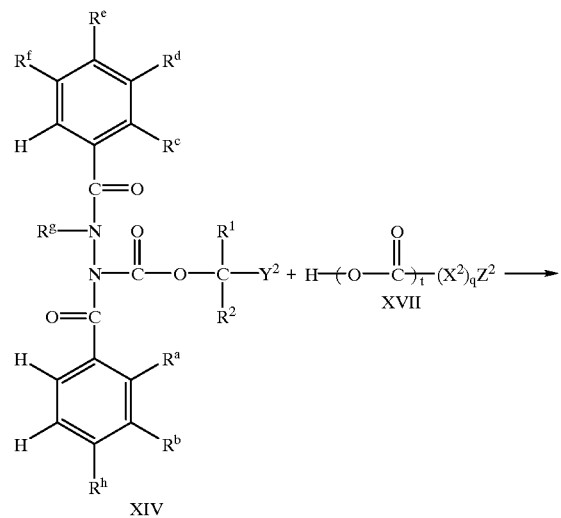

XIV

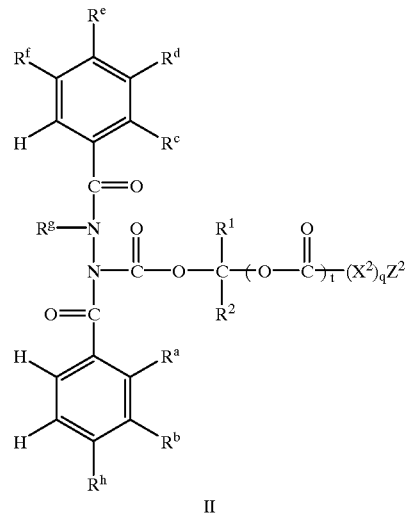

II where $(X^2)_qZ^2$, $R^1$ and $R^2$ are as defined previously for compound of Formula I, $R^a$–$R^h$ are as defined above for compound of Formula II, and $Y^2$=halogen such as iodine, bromine, or chlorine.

Suitable solvents for use in the above process include ethers such as tetrahydrofuran (THF), glyme, and the like; dimethylformamide (DMF); dimethylsulfoxide (DMSO); acetonitrile; chlorinated solvents such as methylene chloride ($CH_2Cl_2$) or chloroform ($CHCl_3$). If desired, mixtures of these solvents may be used, however, the preferred solvent is THF. Suitable bases for use in the above process include metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases may be used, however, the preferred base is diisopropylethylamine. The above method may be carried out at temperatures between about −78° C. and about 100° C. Preferably, the reaction is carried out between 0° C. and about 50° C. Preparation of the compounds of the present invention by the above method is preferably carried out at about atmospheric pressure although higher or lower pressures can be used if desired. Substantially equimolar amounts of reactants are preferably used although higher or lower amounts can be used if desired. Generally, one equivalent of base is used per equivalent of starting material of compound of Formula XVII. The compounds of Formula XVII are generally commercially available or can be prepared according to known procedures.

The compounds of Formula II in which $(X^2)_qZ^2$ contains a functional group which can be further manipulated are included as synthesis Examples 37–41 in which a tert-butoxycarbonyl group is removed by HCl/ether deprotection to afford amine-HCl salts. Synthesis Example 42 involves the deprotection of a benzyl ester under hydrogenation conditions to afford the free carboxylic acid.

Application of Method C (Scheme 7)as described previously for the synthesis of compound of Formula I (m=1, $Z^1(X^1)_m$ is a suitably substituted pesticidal hydrazine, t=0, q=0 or 1, and $G^{10}$ and $G^{11}$=O) to the synthesis of compound of Formula II is described below in Scheme 10. Compound of Formula XVIIA in which $X^2)_qZ^2$=$NR^3R^4R^5$ (compound of Formula XIII in which q=0 or 1 and t=0) is reacted with compound of Formula XIV [described in Method B (Scheme 8)] to afford compound of Formula II in which t=0 [compound of Formula I in which m=1, $Z^1(X^1)_m$ is a suitably substituted pesticidal hydrazine, q=0 or 1, $G^{10}$ and $G^{11}$=O, $Z^2$=$NR^3R^4$ or $\{(NR^3R^4R^5)^+M^-\}$ when q=0, and $(X^2)_qZ^2$=$NR^3R^4$ or $\{(NR^3R^4R^5)^+M^-\}$ when q=1, where $M=Y^2$]:

Scheme 10

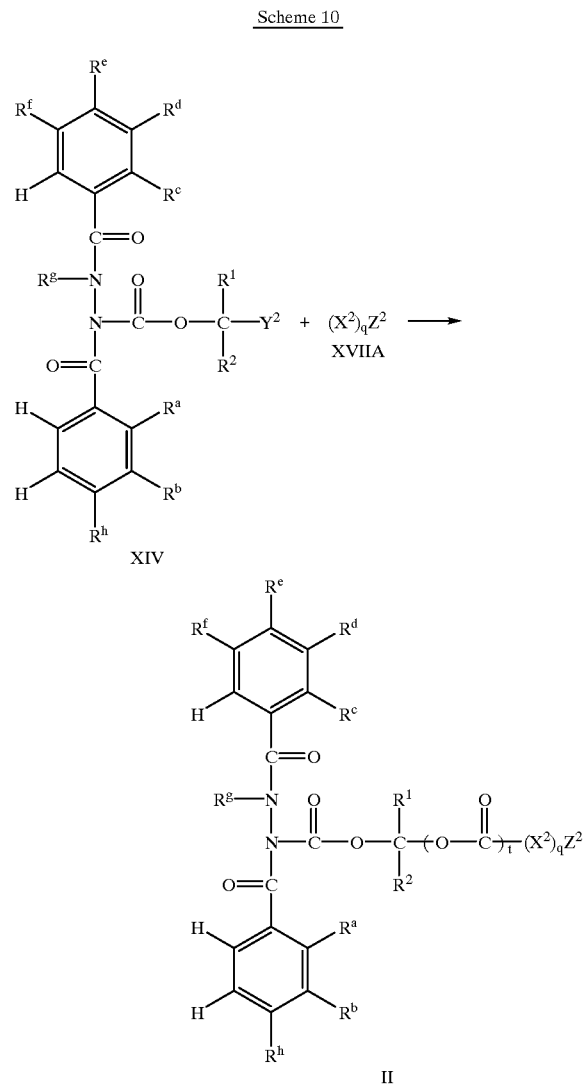

where $R^1$ and $R^2$ are as defined previously for compound of Formula I $R^a$–$R^h$ and M are as defined above for compound of Formula II, and $Y^2$=halogen such as iodine, bromine, or chlorine.

Suitable solvents for use in the above process include ethers such as tetrahydrofuran (THF), glyme, and the like; dimethylformamide (DMF); dimethylsulfoxide (DMSO); acetonitrile; chlorinated solvents such as methylene chloride ($CH_2Cl_2$) or chloroform ($CHCl_3$). If desired, mixtures of these solvents may be used, however, the preferred solvent is THF. The above method may be carried out at temperatures between about –78° C. and about 200° C. Preferably, the reaction is carried out between 0° C. and about 100° C.

Preparation of the compounds of the present invention by the above method is preferably carried out at about atmospheric pressure although higher or lower pressures can be used if desired. Substantially equimolar amounts of reactants are preferably used although higher or lower amounts can be used if desired. Generally, one equivalent of compound of Formula XVIIA is used per equivalent of starting material of compound of Formula XIV. The compounds of Formula XVIIA are generally commercially available or can be prepared according to known procedures. The compounds of Formula XIV can be prepared by the same method as that of Method B (Scheme 8).

Application of Method A (Scheme 4) as described previously for the synthesis of compound of Formula VIII to the synthesis of compound of Formula XVIII is described below in Scheme 11. Compound of Formula XIX (compound of Formula XI, $R^{12}$=Et) is reacted with compound of Formula XVI in which $Y^2$=Cl (compound of Formula X where $Y^1$=Cl) to afford compound of Formula XVIII in which $Y^2$=Cl (compound of Formula VIII where $G^{10}$ and $G^{11}$=O and $R^{12}$=Et).

Method A

Scheme 11

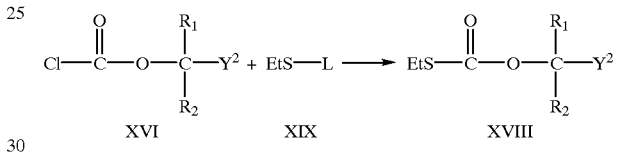

where $R^1$ and $R^2$ are as defined previously for compound of Formula I and L=metal salt such as Na or potassium.

Suitable solvents for use in the above process include ethers such as tetrahydrofuran (THF), glyme, diethyl ether and the like; dimethylformamide (DMF); dimethylsulfoxide (DMSO); acetonitrile; chlorinated solvents such as methylene chloride ($CH_2Cl_2$) or chloroform ($CHCl_3$). If desired, mixtures of these solvents may be used, however, the preferred solvent is diethyl ether. Suitable bases for use in the above process include metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases may be used, however, the preferred base is sodium hydride. The above process may be carried out at temperatures between about –78° C. and about 100° C. Preferably, the reaction is carried out between 0° C. and about 50° C. Preparation of the compounds of the present invention by the above process is preferably carried out at about atmospheric pressure although higher or lower pressures can be used if desired. Substantially equimolar amounts of reactants are preferably used although higher or lower amounts can be used if desired. Generally, one equivalent of base is used per equivalent of starting material of compound of Formula XIX. The compounds of Formula XIX are generally commercially available or can be prepared according to known procedures. For example, $R^{12}S$—L=EtS—Na, which is commercially available.

Conversion of $Y^2$ from Cl to Br or Cl to I can be prepared according to literature procedures. A general description of the synthesis of halogen exchange (Finkelstein reaction) is described in March, Advanced Organic Chemistry, $4^{th}$ Ed, pp 430–431. Also, see synthesis Example 199 for conversion of $Y^2$ from Cl to I in compound of Formula XVIII.

Application of Method A (Scheme 3) as described previously for the synthesis of compound of Formula VII to the synthesis of compound of Formula XX is described below in Scheme 12. Compound of Formula XVIII in which $Y^2$=Cl, Br, or I (compound of Formula VIII where $R^{12}$=Et and $G^{10}$ and $G^{11}$=O) is reacted with compound of Formula XVII in which t=1 (compound of Formula IX where $G^{20}$ and $G^{21}$=O and q=0 or 1) to afford compound of Formula XX in which t=1 (compound of Formula VII in which $G^{10}$, $G^{11}$, $G^{20}$, and $G^{21}$=O, $R^{12}$=Et and q=0 or 1):

Scheme 12

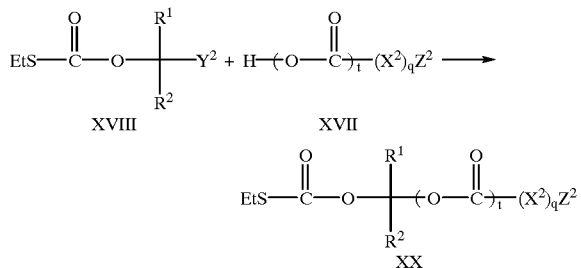

where $(X^2)_qZ^2$, $R^1$, and $R^2$ are as defined previously for compound of Formula I.

Suitable solvents for use in the above process include ethers such as tetrahydrofuran (THF), glyme, diethyl ether and the like; dimethylformamide (DMF); dimethylsulfoxide (DMSO); acetonitrile; chlorinated solvents such as methylene chloride ($CH_2Cl_2$) or chloroform ($CHCl_3$). If desired, mixtures of these solvents may be used, however, the preferred solvent is THF. Suitable bases for use in the above process include metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases may be used, however, the preferred base is diisopropylethylamine. The above process may be carried out at temperatures between about -78° C. and about 100° C. Preferably, the reaction is carried out between 0° C. and about 50° C. Preparation of the compounds of the present invention by the above process is preferably carried out at about atmospheric pressure although higher or lower pressures can be used if desired. Substantially equimolar amounts of reactants are preferably used although higher or lower amounts can be used if desired. Generally, one equivalent of base is used per equivalent of starting material of compound of Formula XVII. The compounds of Formula XVII are generally commercially available or can be prepared according to known procedures.

Application of Method A (Scheme 2) as described previously for the synthesis of compound of Formula VI to the synthesis of compound of Formula XXI is described below in Scheme 13. Compound of Formula XX in which t=1 (compound of Formula VII where $R^{12}$=Et, $G^{10}$, $G^{11}$, $G^{20}$, and $G^{21}$=O, and q=0 or 1) is reacted with sulfuryl chloride (halogenating agent) to afford compound of Formula XXI in which t=1 (compound of Formula VI where $G^{10}$, $G^{11}$, $G^{20}$, and $G^{21}$=O, $Y^1$=Cl and q=0 or 1):

Scheme 13

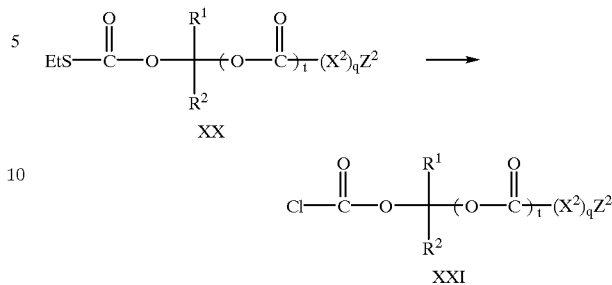

where $(X^2)_qZ^2$, $R^1$, and $R^2$ are as defined previously for compound of Formula I.

Suitable halogenating agents include chlorine gas, thionyl chloride, and sulfuryl chloride, however, the preferred halogenating agent is sulfuryl chloride. Suitable solvents for use in the above process include hexanes, chlorinated solvents such as methylene chloride, dichloroethane, chloroform, carbon tetrachloride and the like, however, the reactions are normally run neat. The above process may be carried out at temperatures between about -78° C. and about 100° C. Preferably, the reaction is carried out between 0° C. and about 50° C. Preparation of the compounds of the present invention by the above process is preferably carried out at about atmospheric pressure although higher or lower pressures can be used if desired. Substantially equimolar amounts of reactants are preferably used although higher or lower amounts can be used if desired.

Application of Method A (Scheme 1) as described previously for the synthesis of compound of Formula I to the synthesis of compound of Formula III is described below in Scheme 14. Compound of Formula XXII in which $R^6$=H, and $R^7$ and $R^8$=OH (compound of Formula V where m=1 and $Z^1(X^1)$m-H is a suitably substituted phosphonomethylglycine) is reacted with hexamethyldisilazane (HMDS) to afford compound of Formula XXIII where $R^6$=SiMe$_3$, and $R^7$ and $R^8$=OSiMe$_3$. Compound of Formula XXIII is then reacted with compound of Formula XXI in which t=1 and q=0 or 1 to afford compound of Formula III in which $R^6$=H, and $R^7$ and $R^8$=OH (compound of Formula I where m=1, t=1, q=0 or 1, $Z^1(X^1)_m$=phosphonomethylglycine, and $G^{10}$, $G^{11}$, $G^{20}$, and $G^{21}$=O):

Scheme 14

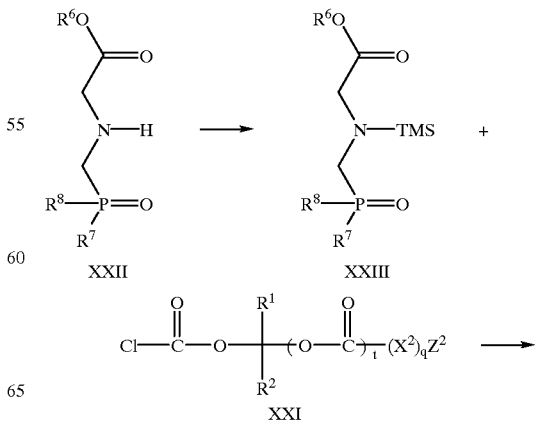

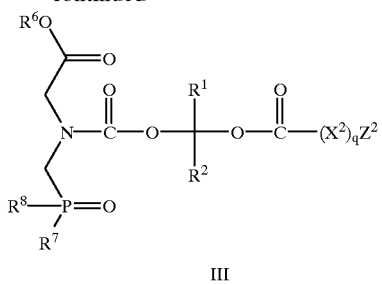

III where $(X^2)_qZ^2$, $R^1$, and $R^2$ are as defined previously for compound of Formula III.

In the reaction of compound of Formula XXII with HMDS to afford compound of Formula XXIII, the following conditions can be used: Suitable solvents include chlorinated solvents such as methylene chloride, dichloroethane, chloroform, carbon tetrachloride and the like; hexanes; tetrahydrofuran, diethyl ether, and the like. However, the reactions are normally run neat. The reaction can be carried out at temperatures between about −78° C. and about 200° C. Preferably, the reaction is carried out between 0° C. and about 150° C. Preparation of compound of Formula XXIII of the present invention by the above method is preferably carried out at about atmospheric pressure although higher or lower pressures can be used if desired. Substantially equimolar amounts of reactants are preferably used although higher or lower amounts can be used if desired. The preferred amount is a slight excess of HMDS. Compounds of the Formula XXII are generally commercially available or can be prepared according to known procedures.

In the reaction of compound of Formula XXIII with compound of Formula XXI to afford compound of Formula III, the following conditions can be used: Suitable solvents for use in the above method include ethers such as tetrahydrofuran (THF), glyme, and the like; dimethylformamide (DMF); dimethylsulfoxide (DMSO); acetonitrile; chlorinated solvents such as methylene chloride ($CH_2Cl_2$,)and chloroform ($CHCl_3$,). If desired, mixtures of these solvents may be used, however, the preferred solvent is methylene chloride. The above method may be carried out at temperatures between about −78° C. and about 100° C. Preferably, the reaction is carried out between 0° C. and about 50° C. Preparation of the compound of Formula III of the present invention by the above method is preferably carried out at about atmospheric pressure although higher or lower pressures can be used if desired. Substantially equimolar amounts of reactants are preferably used although higher or lower amounts can be used if desired.

Application of Method B (Scheme 6) as described previously for the synthesis of compound of Formula XII to the synthesis of compound of Formula XXIV is described below in Scheme 15. Compound of Formula XXV (compound of Formula V in which m=1 and $Z^1(X^1)_m$—H is a suitably substituted pesticidal phenol) is reacted with compound of Formula XVI in which $Y^2$=Cl (compound of Formula X in which $G^{10}$ and $G^{11}$=O and $Y^1$=Cl) to afford compound of Formula XXIV in which $Y^2$=Cl (compound of Formula XII where m=1, $Z^1(X^1)_m$ is a suitably substituted pesticidal phenol, and $G^{10}$ and $G^{11}$=O):

Scheme 15

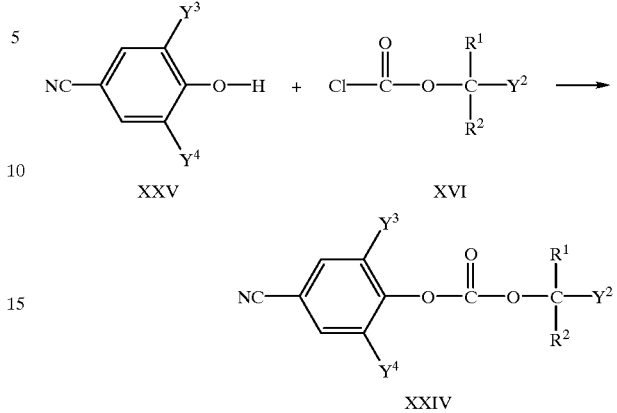

where $R^1$, $R^2$, and $Y^3$ and $Y^4$ are as defined previously for compound of Formula IV.

Suitable solvents for use in the above process include ethers such as tetrahydrofuran (THF), glyme, diethyl ether and the like; dimethylformamide (DMF); dimethylsulfoxide (DMSO); acetonitrile; chlorinated solvents such as methylene chloride ($CH_2Cl_2$) or chloroform ($CHCl_3$). If desired, mixtures of these solvents may be used, however, the preferred solvent is chloroform. Suitable bases for use in the above process include metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases may be used, however, the preferred base is pyridine. The above method may be carried out at temperatures between about −78° C. and about 100° C. Preferably, the reaction is carried out between 0° C. and about 50° C. Preparation of the compounds of the present invention by the above method is preferably carried out at about atmospheric pressure although higher or lower pressures can be used if desired. Substantially equimolar amounts of reactants are preferably used although higher or lower amounts can be used if desired. Generally, one equivalent of base is used per equivalent of starting material of compound of Formula XXV. The compounds of Formula XVI and XXV are generally commercially available or can be prepared according to known procedures.

Conversion of $Y^2$ from Cl to Br or Cl to I in compound of Formula XXIV can be prepared according to literature procedures. A general description of the synthesis of halogen exchange (Finkelstein reaction) is described in March, Advanced Organic Chemistry, $4^{th}$ Ed, pp 430–431. Also, see synthesis Example 297 for conversion of $Y^2$ from Cl to I in compound of Formula XXIV.

Application of Method B (Scheme 5) as described previously for the synthesis of compound of Formula I to the synthesis of compound of Formula IV is described below in Scheme 16. Compound of Formula XVII in which t=1 (compound of Formula IX in which q=0 or 1 and $G^{20}$ and $G^{21}$=O) is reacted with compound of Formula XXIV in which $Y^2$=I (described in Scheme 15) to afford compound of Formula IV in which t=1 (compound of Formula I where m=1, q=0 or 1, $Z^1(X^1)_m$ is a suitably substituted pesticidal phenol, and $G^{10}$, $G^{11}$, $G^{20}$, and $G^{21}$=O):

Scheme 16

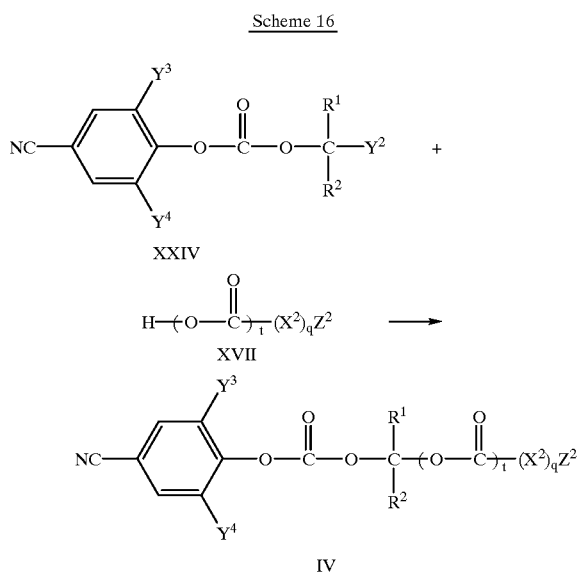

where $(X^2)_qZ^2$, $R^1$, $R^2$, and $Y^3$ and $Y^4$ are as defined previously for compound of Formula IV.

Suitable solvents for use in the above process include ethers such as tetrahydrofuran (THF), glyme, diethyl ether and the like; dimethylformamide (DMF); dimethylsulfoxide (DMSO); acetonitrile; chlorinated solvents such as methylene chloride ($CH_2Cl_2$) or chloroform ($CHCl_3$). If desired, mixtures of these solvents may be used, however, the preferred solvent is THF. Suitable bases for use in the above process include metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases may be used, however, the preferred base is diisopropylethylamine. The above method may be carried out at temperatures between about −78° C. Ado about 100° C. Preferably, the reaction is carried out between 0° C. Ado about 50° C. Preparation of the compounds of the present invention by the above method is preferably carried out at about atmospheric pressure although higher or lower pressures can be used if desired. Substantially equimolar amounts of reactants are preferably used although higher or lower amounts can be used if desired. Generally, one equivalent of base is used per equivalent of starting material of compound of Formula XVII. The compounds of Formula XVII are generally commercially available or can be prepared according to known procedures.

Following the general methods described hereinbefore, the following compounds of Formula (II) as listed in Table 1 were prepared.

TABLE 1

Listing of Compounds of Formula (II)

(II)

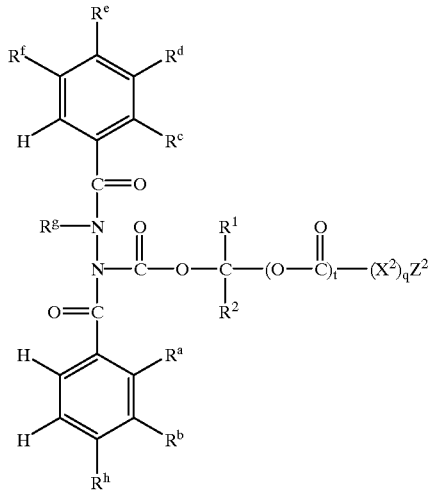

| Cmpd # | $R^a$ | $R^b$ | $R^c$ | $R^d$ | $R^e$ | $R^f$ | $R^g$ | $R^h$ | $R^1$ | $R^2$ | t | q | $(X^2)_qZ^2$ |
|---|---|---|---|---|---|---|---|---|---|---|---|---|---|
| 1-1 | Me | OMe | H | Me | H | Me | $C(CH_3)_3$ | H | H | H | 0 | 0 | Cl |
| 1-2 | Me | OMe | H | Me | H | Me | $C(CH_3)_3$ | H | H | H | 0 | 0 | I |
| 1-3 | Me | OMe | H | Me | H | Me | $C(CH_3)_3$ | H | H | H | 1 | 0 | Me |
| 1-4 | Me | OMe | H | Me | H | Me | $C(CH_3)_3$ | H | H | H | 1 | 1 | 3,5,6-trichloro-2-pyridyloxymethyl |
| 1-5 | Me | OMe | H | Me | H | Me | $C(CH_3)_3$ | H | H | H | 1 | 1 | 3,6-dichloro-2-pyridyl |
| 1-6 | Me | OMe | H | Me | H | Me | $C(CH_3)_3$ | H | H | H | 1 | 0 | $C(CH_3)_3$ |
| 1-7 | Me | OMe | H | Me | H | Me | $C(CH_3)_3$ | H | H | H | 1 | 0 | acetamidomethyl |
| 1-8 | Me | OMe | H | Me | H | Me | $C(CH_3)_3$ | H | H | H | 1 | 1 | methoxycarbonylaminooxymethyl |
| 1-9 | Me | OMe | H | Me | H | Me | $C(CH_3)_3$ | H | H | H | 1 | 0 | 2-nitro-5-thiocyanatophenyl |
| 1-10 | Me | OMe | H | Me | H | Me | $C(CH_3)_3$ | H | H | H | 1 | 0 | diethoxyphosphorylmethyl |
| 1-11 | Me | OMe | H | Me | H | Me | $C(CH_3)_3$ | H | H | H | 1 | 0 | 2-hydroxy-2-propyl |
| 1-12 | Me | OMe | H | Me | H | Me | $C(CH_3)_3$ | H | H | H | 1 | 0 | 1-(isopropylidineaminooxy)ethyl |
| 1-13 | Me | OMe | H | Me | H | Me | $C(CH_3)_3$ | H | H | H | 1 | 0 | 4,4,4-trifluoro-2-butyl |
| 1-14 | Me | OMe | H | Me | H | Me | $C(CH_3)_3$ | H | H | H | 1 | 0 | 2-(trifluoromethyl)propyl |
| 1-15 | Me | OMe | H | Me | H | Me | $C(CH_3)_3$ | H | H | H | 1 | 0 | 2,2,2-trifluoroethyl |

TABLE 1-continued

Listing of Compounds of Formula (II)

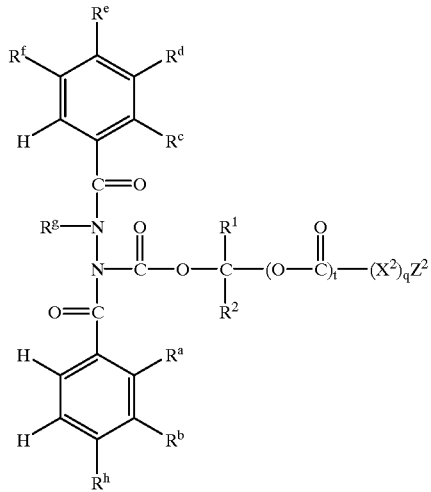

(II)

| Cmpd # | $R^a$ | $R^b$ | $R^c$ | $R^d$ | $R^e$ | $R^f$ | $R^g$ | $R^h$ | $R^1$ | $R^2$ | t | q | $(X^2)_q Z^2$ |
|---|---|---|---|---|---|---|---|---|---|---|---|---|---|
| 1-16 | Me | OMe | H | Me | H | Me | $C(CH_3)_3$ | H | H | H | 1 | 0 | 1-(benzyloxycarbonylamino)-1-methylethyl |
| 1-17 | Me | OMe | H | Me | H | Me | $C(CH_3)_3$ | H | H | H | 1 | 0 | 1-(tert)-butoxycarbonylamino)-1-methylethyl |
| 1-18 | Me | OMe | H | Me | H | Me | $C(CH_3)_3$ | H | H | H | 1 | 0 | 1-(tert)-butoxycarbonyl)-piperidin-4-yl |
| 1-19 | Me | OMe | H | Me | H | Me | $C(CH_3)_3$ | H | H | H | 1 | 0 | 1-acetyl-4-hydroxypyrrolidin-2-yl |
| 1-20 | Me | OMe | H | Me | H | Me | $C(CH_3)_3$ | H | H | H | 1 | 0 | 2-methyl-3-pyridyl |
| 1-21 | Me | OMe | H | Me | H | Me | $C(CH_3)_3$ | H | H | H | 1 | 0 | 1-(acetylamino)-2-methylpropyl |
| 1-22 | Me | OMe | H | Me | H | Me | $C(CH_3)_3$ | H | H | H | 1 | 0 | 2,6-dimethoxy-4-hydroxyphenyl |
| 1-23 | Me | OMe | H | Me | H | Me | $C(CH_3)_3$ | H | H | H | 1 | 0 | 3-methylthio-1-acetylaminopropyl |
| 1-24 | Me | OMe | H | Me | H | Me | $C(CH_3)_3$ | H | H | H | 1 | 0 | 1-acetylaminovinyl |
| 1-25 | Me | OMe | H | Me | H | Me | $C(CH_3)_3$ | H | H | H | 1 | 0 | 1-methyl-2-pyrrolyl |
| 1-26 | Me | OMe | H | Me | H | Me | $C(CH_3)_3$ | H | H | H | 1 | 0 | 2-benzyloxycarbonyl)-1-(tert-butoxycarbonylamino)ethyl |
| 1-27 | Me | OMe | H | Me | H | Me | $C(CH_3)_3$ | H | H | H | 1 | 0 | 4-hexyloxyphenyl |
| 1-28 | Me | OMe | H | Me | H | Me | $C(CH_3)_3$ | H | H | H | 1 | 0 | 1-(2-chlorophenoxy)-1-methylethyl |
| 1-29 | Me | OMe | H | Me | H | Me | $C(CH_3)_3$ | H | H | H | 1 | 0 | 3-hydroxy-4-methoxyphenyl |
| 1-30 | Me | OMe | H | Me | H | Me | $C(CH_3)_3$ | H | H | H | 1 | 0 | 3,5-dinitro-4-hydroxyphenyl |
| 1-31 | Me | OMe | H | Me | H | Me | $C(CH_3)_3$ | H | H | H | 1 | 0 | 1-(tert-butoxycarbonyl)-2-pyrrolidinyl |
| 1-32 | Me | OMe | H | Me | H | Me | $C(CH_3)_3$ | H | H | H | 1 | 0 | 1-(di-N-propylamino)ethyl |
| 1-33 | Me | OMe | H | Me | H | Me | $C(CH_3)_3$ | H | H | H | 1 | 0 | 1-(tert-butoxycarbonyl)-4-hydroxy-2-pyrrolidinyl |
| 1-34 | Me | OMe | H | Me | H | Me | $C(CH_3)_3$ | H | H | H | 1 | 0 | 5-acetylamino-1-(tert-butoxycarbonylamino)pentyl |
| 1-35 | Me | OMe | H | Me | H | Me | $C(CH_3)_3$ | H | H | H | 1 | 0 | 1-(tert-butoxycarbonylamino)-2,2-dimethyl-propyl |
| 1-36 | Me | OMe | H | Me | H | Me | $C(CH_3)_3$ | H | H | H | 1 | 0 | 1-(t-butoxycarbonylamino)-2-cyclohexyl-1-ethyl |
| 1-37 | Me | OMe | H | Me | H | Me | $C(CH_3)_3$ | H | H | H | 1 | 0 | 2-pyrrolidinylhydrochloride |
| 1-38 | Me | OMe | H | Me | H | Me | $C(CH_3)_3$ | H | H | H | 1 | 0 | 2-amino-2-propyl hydrochloride |
| 1-39 | Me | OMe | H | Me | H | Me | $C(CH_3)_3$ | H | H | H | 1 | 0 | 4-piperidinylhydrochloride |
| 1-40 | Me | OMe | H | Me | H | Me | $C(CH_3)_3$ | H | H | H | 1 | 0 | 2-(benzyloxycarbonyl)-1-aminoethyl hydrochloride |
| 1-41 | Me | OMe | H | Me | H | Me | $C(CH_3)_3$ | H | H | H | 1 | 0 | 2-carboxy-1-aminoethyl hydrochloride |
| 1-42 | Me | OMe | H | Me | H | Me | $C(CH_3)_3$ | H | H | H | 1 | 0 | 2-carboxy-1-(tert-butoxycarbonylamino)ethyl |
| 1-43 | Me | OMe | H | Me | H | Me | $C(CH_3)_3$ | H | H | H | 1 | 0 | [benzyl(diethoxyphosphorylmethyl)-amino]methyl |
| 1-44 | Me | OMe | H | Me | H | Me | $C(CH_3)_3$ | H | Me | H | 0 | 0 | Cl |
| 1-45 | Me | OMe | H | Me | H | Me | $C(CH_3)_3$ | H | Me | H | 1 | 0 | methyl |
| 1-46 | Me | OMe | H | Me | H | Me | $C(CH_3)_3$ | H | phenyl | H | 0 | 0 | Cl |
| 1-47 | Me | OMe | H | Me | H | Me | $C(CH_3)_3$ | H | phenyl | H | 1 | 0 | methyl |
| 1-48 | Me | OMe | H | Me | H | Me | $C(CH_3)_3$ | H | phenyl | H | 1 | 0 | 2-propyl |
| 1-49 | Me | OMe | H | Me | H | Me | $C(CH_3)_3$ | H | phenyl | H | 1 | 0 | 2-methylnicotinyl |
| 1-50 | Me | OMe | H | Me | H | Me | $C(CH_3)_3$ | H | phenyl | H | 1 | 0 | 1-(acetylamino)-2-methylpropyl |
| 1-51 | Me | OMe | H | Me | H | Me | $C(CH_3)_3$ | H | phenyl | H | 1 | 0 | 3-methylthio-1-acetylaminopropyl |

TABLE 1-continued

Listing of Compounds of Formula (II)

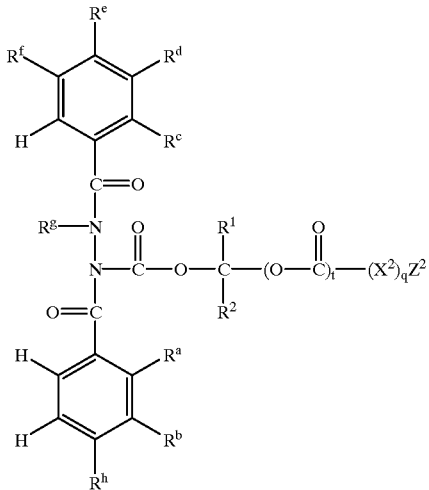

(II)

| Cmpd # | $R^a$ | $R^b$ | $R^c$ | $R^d$ | $R^e$ | $R^f$ | $R^g$ | $R^h$ | $R^1$ | $R^2$ | t | q | $(X^2)_qZ^2$ |
|---|---|---|---|---|---|---|---|---|---|---|---|---|---|
| 1-52 | Me | OMe | H | Me | H | Me | $C(CH_3)_3$ | H | phenyl | H | 1 | 0 | 1-tert-butoxycarbonyamino)-1-methylethyl |
| 1-53 | Me | OMe | H | Me | H | Me | $C(CH_3)_3$ | H | H | H | 0 | 0 | $^+N(Et)_3I^-$ |
| 1-54 | Me | OMe | H | Me | H | Me | $C(CH_3)_3$ | H | H | H | 1 | 0 | undecanyl |
| 1-55 | Me | OMe | H | Me | H | Me | $C(CH_3)_3$ | H | H | H | 1 | 0 | acetyl |
| 1-56 | Me | OMe | H | Me | H | Me | $C(CH_3)_3$ | H | H | H | 1 | 0 | 5-oxopyrrolin-2-yl |
| 1-57 | Me | OMe | H | Me | H | Me | $C(CH_3)_3$ | H | H | H | 1 | 0 | methoxymethyl |
| 1-58 | Me | OMe | H | Me | H | Me | $C(CH_3)_3$ | H | H | H | 1 | 0 | (4-oxo-2-thioxothiazolidin-3-yl)methyl |
| 1-59 | Me | OMe | H | Me | H | Me | $C(CH_3)_3$ | H | H | H | 1 | 0 | pyrazin-2-yl |
| 1-60 | Me | OMe | H | Me | H | Me | $C(CH_3)_3$ | H | H | H | 1 | 0 | 1H-pyrazol-4-yl |
| 1-61 | Me | OMe | H | Me | H | Me | $C(CH_3)_3$ | H | H | H | 1 | 0 | (furan-2-carbonyl)aminomethyl |
| 1-62 | Me | OMe | H | Me | H | Me | $C(CH_3)_3$ | H | H | H | 1 | 0 | 2-(2,5dioxo-2,5,dihydropyrrol-1-yl)ethyl |
| 1-63 | Me | OMe | H | Me | H | Me | $C(CH_3)_3$ | H | H | H | 1 | 0 | 2-methoxyethoxymethyl |
| 1-64 | Me | OMe | H | Me | H | Me | $C(CH_3)_3$ | H | H | H | 1 | 0 | methanesulfonylmethyl |
| 1-65 | Me | OMe | H | Me | H | Me | $C(CH_3)_3$ | H | H | H | 1 | 0 | 4-heptyloxyphenyl |
| 1-66 | Me | OMe | H | Me | H | Me | $C(CH_3)_3$ | H | H | H | 1 | 0 | 2,6-dichlorophenyl |
| 1-67 | Me | OMe | H | Me | H | Me | $C(CH_3)_3$ | H | H | H | 1 | 0 | (3,5-diiodo-4-oxo-4H-pyridin-1-yl)methyl |
| 1-68 | Me | OMe | H | Me | H | Me | $C(CH_3)_3$ | H | H | H | 1 | 0 | 3-pyridyl |
| 1-69 | Me | OMe | H | Me | H | Me | $C(CH_3)_3$ | H | H | H | 1 | 0 | 5,6-dichloro-3-pyridyl |
| 1-70 | Me | OMe | H | Me | H | Me | $C(CH_3)_3$ | H | H | H | 1 | 0 | 4-pyridyl |
| 1-71 | Me | OMe | H | Me | H | Me | $C(CH_3)_3$ | H | H | H | 1 | 0 | 2,6-dichloro-4-pyridyl |
| 1-72 | Me | OMe | H | Me | H | Me | $C(CH_3)_3$ | H | H | H | 1 | 0 | 4-methanesulphonylphenyl |
| 1-73 | Me | OMe | H | Me | H | Me | $C(CH_3)_3$ | H | H | H | 1 | 0 | 2-chloro-4-nitrophenyl |
| 1-74 | Me | OMe | H | Me | H | Me | $C(CH_3)_3$ | H | H | H | 1 | 0 | 4-chloro-2-nitrophenyl |
| 1-75 | Me | OMe | H | Me | H | Me | $C(CH_3)_3$ | H | H | H | 1 | 0 | 3-chloro-2-nitrophenyl |
| 1-76 | Me | OMe | H | Me | H | Me | $C(CH_3)_3$ | H | H | H | 1 | 0 | 2-ethoxyphenyl |
| 1-77 | Me | OMe | H | Me | H | Me | $C(CH_3)_3$ | H | H | H | 1 | 0 | cyclohexyl |
| 1-78 | Me | OMe | H | Me | H | Me | $C(CH_3)_3$ | H | H | H | 1 | 0 | cyclopropyl |
| 1-79 | Me | OMe | H | Me | H | Me | $C(CH_3)_3$ | H | H | H | 1 | 0 | 5-methylpyrazin-2-yl |
| 1-80 | Me | OMe | H | Me | H | Me | $C(CH_3)_3$ | H | H | H | 1 | 0 | tetrahydrofur-2-yl |
| 1-81 | Me | OMe | H | Me | H | Me | $C(CH_3)_3$ | H | H | H | 1 | 0 | 3-thiophen-2-ylpropyl |
| 1-82 | Me | OMe | H | Me | H | Me | $C(CH_3)_3$ | H | H | H | 1 | 0 | cyclopentylphenylmethyl |
| 1-83 | Me | OMe | H | Me | H | Me | $C(CH_3)_3$ | H | H | H | 1 | 0 | 1-phenylcyclopentyl |
| 1-84 | Me | OMe | H | Me | H | Me | $C(CH_3)_3$ | H | H | H | 1 | 0 | 1-methylcyclohexyl |
| 1-85 | Me | OMe | H | Me | H | Me | $C(CH_3)_3$ | H | H | H | 1 | 0 | 2-chloro-3-pyridyl |
| 1-86 | Me | OMe | H | Me | H | Me | $C(CH_3)_3$ | H | H | H | 1 | 0 | cyclopentyl |
| 1-87 | Me | OMe | H | Me | H | Me | $C(CH_3)_3$ | H | H | H | 1 | 0 | 1-methyl-1H-pyrrol-2-yl |
| 1-88 | Me | OMe | H | Me | H | Me | $C(CH_3)_3$ | H | H | H | 1 | 0 | 2,6-dimethoxyphenyl |
| 1-89 | Me | OMe | H | Me | H | Me | $C(CH_3)_3$ | H | H | H | 1 | 0 | 2,6-dimethoxy-3-pyridyl |
| 1-90 | Me | OMe | H | Me | H | Me | $C(CH_3)_3$ | H | H | H | 1 | 0 | 2-(thiophen-2-yl)ethenyl |
| 1-91 | Me | OMe | H | Me | H | Me | $C(CH_3)_3$ | H | H | H | 1 | 0 | 4-nitro-1H-pyrazol-3-yl |
| 1-92 | Me | OMe | H | Me | H | Me | $C(CH_3)_3$ | H | H | H | 1 | 0 | 4-sulfamoylphenyl |
| 1-93 | Me | OMe | H | Me | H | Me | $C(CH_3)_3$ | H | H | H | 1 | 0 | 2,4-dinitrophenyl |
| 1-94 | Me | OMe | H | Me | H | Me | $C(CH_3)_3$ | H | H | H | 1 | 0 | 1-hydroxy-1-phenylethyl |
| 1-95 | Me | OMe | H | Me | H | Me | $C(CH_3)_3$ | H | H | H | 1 | 0 | 3-hydroxy-4-methyl-2-nitrophenyl |
| 1-96 | Me | OMe | H | Me | H | Me | $C(CH_3)_3$ | H | H | H | 1 | 0 | 2-methylcyclopropyl |
| 1-97 | Me | OMe | H | Me | H | Me | $C(CH_3)_3$ | H | H | H | 1 | 0 | 1-phenylpropyl |

TABLE 1-continued

Listing of Compounds of Formula (II)

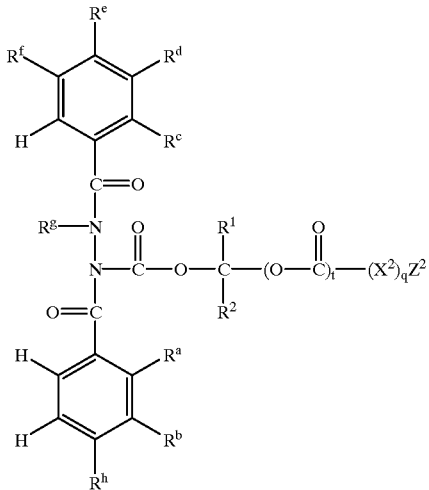

(II)

| Cmpd # | $R^a$ | $R^b$ | $R^c$ | $R^d$ | $R^e$ | $R^f$ | $R^g$ | $R^h$ | $R^1$ | $R^2$ | t | q | $(X^2)_q Z^2$ |
|---|---|---|---|---|---|---|---|---|---|---|---|---|---|
| 1-98 | Me | OMe | H | Me | H | Me | $C(CH_3)_3$ | H | H | H | 1 | 0 | 1,2,3,4-tetrahydronaphth-2-yl |
| 1-99 | Me | OMe | H | Me | H | Me | $C(CH_3)_3$ | H | H | H | 1 | 0 | 1-benzyl-2,2-dimethylpropyl |
| 1-100 | Me | OMe | H | Me | H | Me | $C(CH_3)_3$ | H | H | H | 1 | 0 | 2,2,3,3-tetramethylcyclopropyl |
| 1-101 | Me | OMe | H | Me | H | Me | $C(CH_3)_3$ | H | H | H | 1 | 0 | acetoxymethyl |
| 1-102 | Me | OMe | H | Me | H | Me | $C(CH_3)_3$ | H | H | H | 1 | 0 | 2,2,2-trifluoro-1-methoxy-1-phenylethyl |
| 1-103 | Me | OMe | H | Me | H | Me | $C(CH_3)_3$ | H | H | H | 1 | 0 | 1-methylpentyl |
| 1-104 | Me | O-Ie | H | Me | H | Me | $C(CH_3)_3$ | H | H | H | 1 | 0 | hept-1-ynyl |
| 1-105 | Me | OMe | H | Me | H | Me | $C(CH_3)_3$ | H | H | H | 1 | 0 | tetrahydrofur-3-yl |
| 1-106 | Me | OMe | H | Me | H | Me | $C(CH_3)_3$ | H | H | H | 1 | 0 | 1,1-methylpropyl |
| 1-107 | Me | OMe | H | Me | H | Me | $C(CH_3)_3$ | H | H | H | 1 | 0 | 2-methylcyclohexyl |
| 1-108 | Me | OMe | H | Me | H | Me | $C(CH_3)_3$ | H | H | H | 1 | 0 | 1,1-dimethylbut-3-enyl |
| 1-109 | Me | OMe | H | Me | H | Me | $C(CH_3)_3$ | H | H | H | 1 | 0 | 1-propylbutyl |
| 1-110 | Me | OMe | H | Me | H | Me | $C(CH_3)_3$ | H | H | H | 1 | 0 | 1-methylbutyl |
| 1-111 | Me | OMe | H | Me | H | Me | $C(CH_3)_3$ | H | H | H | 1 | 0 | 1-phenylethyl |
| 1-112 | Me | OMe | H | Me | H | Me | $C(CH_3)_3$ | H | H | H | 1 | 0 | phenyloxymethyl |
| 1-113 | Me | OMe | H | Me | H | Me | $C(CH_3)_3$ | H | H | H | 1 | 0 | pentafluorophenyloxymethyl |
| 1-114 | Me | OMe | H | Me | H | Me | $C(CH_3)_3$ | H | H | H | 1 | 0 | (2-formylaminothiazol-4-yl)methoxyiminomethyl |
| 1-115 | Me | OMe | H | Me | H | Me | $C(CH_3)_3$ | H | H | H | 1 | 0 | 1-hydroxy-1-ethylpropyl |
| 1-116 | Me | OMe | H | Me | H | Me | $C(CH_3)_3$ | H | H | H | 1 | 0 | 2-methoxyphenyloxymethyl |
| 1-117 | Me | OMe | H | Me | H | Me | $C(CH_3)_3$ | H | H | H | 1 | 0 | 2,4,6-trimethylphenyl |
| 1-118 | Me | OMe | H | Me | H | Me | $C(CH_3)_3$ | H | H | H | 1 | 0 | 2-methylphenyl |
| 1-119 | Me | OMe | H | Me | H | Me | $C(CH_3)_3$ | H | H | H | 1 | 0 | 1-methyl-1-(4-chlorophenyloxy)ethyl |
| 1-120 | Me | OMe | H | Me | H | Me | $C(CH_3)_3$ | H | H | H | 1 | 0 | 1-hydroxy-1-methylpropyl |
| 1-121 | Me | OMe | H | Me | H | Me | $C(CH_3)_3$ | H | H | H | 1 | 0 | 1-ethylpentyl |
| 1-122 | Me | OMe | H | Me | H | Me | $C(CH_3)_3$ | H | H | H | 1 | 0 | 2-methyl-1-phenylbutyl |
| 1-123 | Me | OMe | H | Me | H | Me | $C(CH_3)_3$ | H | H | H | 1 | 0 | 1-methylpropyl |
| 1-124 | Me | OMe | H | Me | H | Me | $C(CH_3)_3$ | H | H | H | 1 | 0 | cyclobutyl |
| 1-125 | Me | OMe | H | Me | H | Me | $C(CH_3)_3$ | H | H | H | 1 | 0 | 1-ethylpropyl |
| 1-126 | Me | OMe | H | Me | H | Me | $C(CH_3)_3$ | H | H | H | 1 | 0 | (3,5-dinitrobenzoylamino)phenylmethyl |
| 1-127 | Me | OMe | H | Me | H | Me | $C(CH_3)_3$ | H | H | H | 1 | 0 | 2,2-dichloro-1-methylcyclopropyl |
| 1-128 | Me | OMe | H | Me | H | Me | $C(CH_3)_3$ | H | H | H | 1 | 0 | 2,2,2-trifluoro-1-hydroxy-1-methylethyl |
| 1-129 | Me | OMe | H | Me | H | Me | $C(CH_3)_3$ | H | H | H | 1 | 0 | 1-hydroxy-2-trifluoromethylpropyl |
| 1-130 | Me | OMe | H | Me | H | Me | $C(CH_3)_3$ | H | H | H | 1 | 0 | 4-hydroxy-3-nitrophenyl |
| 1-131 | Me | OMe | H | Me | H | Me | $C(CH_3)_3$ | H | H | H | 1 | 0 | 4,8-dihydroxyquinol-2-yl |
| 1-132 | Me | OMe | H | Me | H | Me | $C(CH_3)_3$ | H | H, | H | 1 | 0 | 2-hydroxy-1-phenylethyl |
| 1-133 | Me | OMe | H | Me | H | Me | $C(CH_3)_3$ | H | H | H | 1 | 0 | 4-hydroxyphenyl |
| 1-134 | Me | OMe | H | Me | H | Me | $C(CH_3)_3$ | H | H | H | 1 | 0 | 2,2-dimethylpropyl |
| 1-135 | Me | OMe | H | Me | H | Me | $C(CH_3)_3$ | H | H | H | 1 | 0 | 1-(3,5-dinitrobenzoylamino)-3-methylbutyl |
| 1-136 | Me | OMe | H | Me | H | Me | $C(CH_3)_3$ | H | H | H | 1 | 0 | (2-hydroxybenzoylamino)methyl |
| 1-137 | Me | OMe | H | Me | H | Me | $C(CH_3)_3$ | H | H | H | 1 | 0 | 3,3,3-trifluoropropyl |
| 1-138 | Me | OMe | H | Me | H | Me | $C(CH_3)_3$ | H | H | H | 1 | 0 | 1-oxypyrid-2-yl |
| 1-139 | Me | OMe | H | Me | H | Me | $C(CH_3)_3$ | H | H | H | 1 | 0 | 6-hydroxypyrid-2-yl |
| 1-140 | Me | OMe | H | Me | H | Me | $C(CH_3)_3$ | H | H | H | 1 | 0 | 3-hydroxypyrid-2-yl |

TABLE 1-continued

Listing of Compounds of Formula (II)

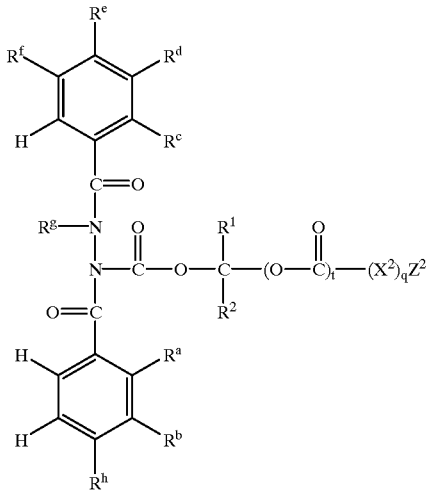

(II)

| Cmpd # | R$^a$ | R$^b$ | R$^c$ | R$^d$ | R$^e$ | R$^f$ | R$^g$ | R$^h$ | R$^1$ | R$^2$ | t | q | (X$^2$)$_q$Z$^2$ |
|---|---|---|---|---|---|---|---|---|---|---|---|---|---|
| 1-141 | Me | OMe | H | Me | H | Me | C(CH$_3$)$_3$ | H | H | H | 1 | 0 | benzoylaminomethyl |
| 1-142 | Me | OMe | H | Me | H | Me | C(CH$_3$)$_3$ | H | H | H | 1 | 0 | 1-methyl-5-oxo-2-pyrid-3-ylpyrrolin-3-yl |
| 1-143 | Me | OMe | H | Me | H | Me | C(CH$_3$)$_3$ | H | H | H | 1 | 0 | 1R,3R,4R,5R-tetrahydroxy cyclohexyl |
| 1-144 | Me | OMe | H | Me | H | Me | C(CH$_3$)$_3$ | H | H | H | 1 | 0 | 2-(2-chlorphenyl)ethenyl |
| 1-145 | Me | OMe | H | Me | H | Me | C(CH$_3$)$_3$ | H | H | H | 1 | 0 | benzofur-2-yl |
| 1-146 | Me | OMe | H | Me | H | Me | C(CH$_3$)$_3$ | H | H | H | 1 | 0 | 3-thienyl |
| 1-147 | Me | OMe | H | Me | H | Me | C(CH$_3$)$_3$ | H | H | H | 1 | 0 | 3-methyl-1H-inden-2-yl |
| 1-148 | Me | OMe | H | Me | H | Me | C(CH$_3$)$_3$ | H | H | H | 1 | 0 | 3R,4S,5R-trihydroxy-1-cyclohexenyl |
| 1-149 | Me | OMe | H | Me | H | Me | C(CH$_3$)$_3$ | H | H | H | 1 | 0 | 2-(2-trifluoromethylphenyl)ethenyl |
| 1-150 | Me | OMe | H | Me | H | Me | C(CH$_3$)$_3$ | H | H | H | 1 | 0 | 2-(4-methylphenyl)ethenyl |
| 1-151 | Me | OMe | H | Me | H | Me | C(CH$_3$)$_3$ | H | H | H | 1 | 0 | 1-cyclohexenyl |
| 1-152 | Me | OMe | H | Me | H | Me | C(CH$_3$)$_3$ | H | H | H | 1 | 0 | 2-(4-trifluoromethylphenyl)ethenyl |
| 1-153 | Me | OMe | H | Me | H | Me | C(CH$_3$)$_3$ | H | H | H | 1 | 0 | 1-cyclopentenyl |
| 1-154 | Me | OMe | H | Me | H | Me | C(CH$_3$)$_3$ | H | H | H | 1 | 0 | 1-methyl-1-butenyl |
| 1-155 | Me | OMe | H | Me | H | Me | C(CH$_3$)$_3$ | H | H | H | 1 | 0 | 3,3,3-trifluoro-2-methyl-1-propenyl |
| 1-156 | Me | OMe | H | Me | H | Me | C(CH$_3$)$_3$ | H | H | H | 1 | 0 | 2-(2-fluorophenyl)ethenyl |
| 1-157 | Me | OMe | H | Me | H | Me | C(CH$_3$)$_3$ | H | H | H | 1 | 0 | vinyl |
| 1-158 | Me | OMe | H | Me | H | Me | C(CH$_3$)$_3$ | H | H | H | 1 | 0 | 2-(4-dimethylaminophenyl)ethenyl |
| 1-159 | Me | OMe | H | Me | H | Me | C(CH$_3$)$_3$ | H | H | H | 1 | 0 | 2-(2-methoxyphenyl)ethenyl |
| 1-160 | Me | OMe | H | Me | H | Me | C(CH$_3$)$_3$ | H | H | H | 1 | 0 | 2-(3-hydroxy-4-methoxyphenyl)ethenyl |
| 1-161 | Me | OMe | H | Me | H | Me | C(CH$_3$)$_3$ | H | H | H | 1 | 0 | 2-(3-trifluoromethylphenyl)ethenyl |
| 1-162 | Me | OMe | H | Me | H | Me | C(CH$_3$)$_3$ | H | H | H | 1 | 0 | 1-fluoro-2-phenylethenyl |
| 1-163 | Me | OMe | H | Me | H | Me | C(CH$_3$)$_3$ | H | H | H | 1 | 0 | 3-methyl-2-thienyl |
| 1-164 | Me | OMe | H | Me | H | Me | C(CH$_3$)$_3$ | H | H | H | 1 | 0 | 1-cyano-2-(4-hydroxyphenyl)ethenyl |
| 1-165 | Me | OMe | H | Me | H | Me | C(CH$_3$)$_3$ | H | H | H | 1 | 0 | 2-(4-fluorophenyl)ethenyl |
| 1-166 | Me | OMe | H | Me | H | Me | C(CH$_3$)$_3$ | H | H | H | 1 | 0 | 2-methyl-1-propenyl |
| 1-167 | Me | OMe | H | Me | H | Me | C(CH$_3$)$_3$ | H | H | H | 1 | 0 | 1-ethyl-7-methyl-4-oxo-[1,8]naphthyridin-3-yl |
| 1-168 | Me | OMe | H | Me | H | Me | C(CH$_3$)$_3$ | H | H | H | 1 | 0 | 2-(4-hydroxy-3-methoxyphenyl)ethenyl |
| 1-169 | Me | OMe | H | Me | H | Me | C(CH$_3$)$_3$ | H | H | H | 1 | 0 | 2-(benzo[1,3]dioxol-5-yl)ethenyl |
| 1-170 | Me | OMe | H | Me | H | Me | C(CH$_3$)$_3$ | H | H | H | 1 | 0 | 1-methylcyclopropyl |
| 1-171 | Me | OMe | H | Me | H | Me | C(CH$_3$)$_3$ | H | H | H | 1 | 0 | 2-furyl |
| 1-172 | Me | OMe | H | Me | H | Me | C(CH$_3$)$_3$ | H | H | H | 1 | 0 | 2-phenylethenyl |
| 1-173 | Me | OMe | H | Me | H | Me | C(CH$_3$)$_3$ | H | H | H | 1 | 0 | 2-(4-bromophenyl)ethenyl |
| 1-174 | Me | OMe | H | Me | H | Me | C(CH$_3$)$_3$ | H | H | H | 1 | 0 | 3-furyl |
| 1-175 | Me | OMe | H | Me | H | Me | C(CH$_3$)$_3$ | H | H | H | 1 | 0 | 2-(4-methoxyphenyl)ethenyl |
| 1-176 | Me | OMe | H | Me | H | Me | C(CH$_3$)$_3$ | H | H | H | 1 | 0 | 1-methyl-1H-indol-2-yl |
| 1-177 | Me | OMe | H | Me | H | Me | C(CH$_3$)$_3$ | H | H | H | 1 | 0 | 2-(3-pyridyl)ethenyl |
| 1-178 | Me | OMe | H | Me | H | Me | C(CH$_3$)$_3$ | H | H | H | 1 | 0 | 2-(3-fluorophenyl)ethenyl |

TABLE 1-continued

Listing of Compounds of Formula (II)

(II)

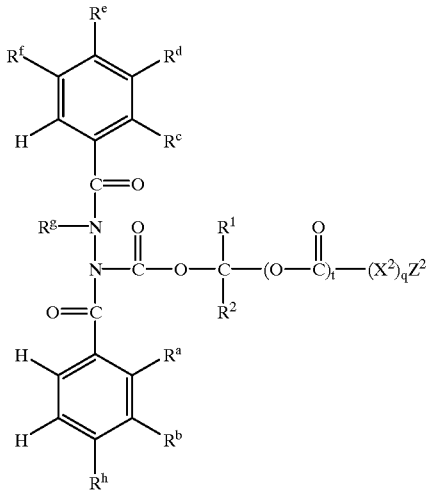

| Cmpd # | $R^a$ | $R^b$ | $R^c$ | $R^d$ | $R^e$ | $R^f$ | $R^g$ | $R^h$ | $R^1$ | $R^2$ | t | q | $(X^2)_qZ^2$ |
|---|---|---|---|---|---|---|---|---|---|---|---|---|---|
| 1-179 | Me | OMe | H | Me | H | Me | $C(CH_3)_3$ | H | H | H | 1 | 0 | 5-methyl-2-thienyl |
| 1-180 | Me | OMe | H | Me | H | Me | $C(CH_3)_3$ | H | H | H | 1 | 0 | 1-acetylamino-2-phenylethenyl |
| 1-181 | Me | OMe | H | Me | H | Me | $C(CH_3)_3$ | H | H | H | 1 | 0 | 2,6-dimethyl-1,5-heptadienyl |
| 1-182 | Me | OMe | H | Me | H | Me | $C(CH_3)_3$ | H | H | H | 1 | 0 | 1-pentenyl |
| 1-183 | Me | OMe | H | Me | H | Me | $C(CH_3)_3$ | H | H | H | 1 | 0 | 2-(2,3-dimethoxyphenyl)ethenyl |
| 1-184 | Me | OMe | H | Me | H | Me | $C(CH_3)_3$ | H | H | H | 1 | 0 | 1,3-pentadienyl |
| 1-185 | Me | OMe | H | Me | H | Me | $C(CH_3)_3$ | H | H | H | 1 | 0 | 2-(3-nitrophenyl)ethenyl |
| 1-186 | Me | OMe | H | Me | H | Me | $C(CH_3)_3$ | H | H | H | 1 | 0 | 2-(4-chlorophenyl)ethenyl |
| 1-187 | Me | OMe | H | Me | H | Me | $C(CH_3)_3$ | H | H | H | 1 | 0 | 2-(4-nitrophenyl)ethenyl |
| 1-188 | Me | OMe | H | Me | H | Me | $C(CH_3)_3$ | H | H | H | 1 | 0 | 2-(3,4-dimethoxyphenyl)ethenyl |
| 1-189 | Me | OMe | H | Me | H | Me | $C(CH_3)_3$ | H | H | H | 1 | 0 | 2-pentafluorophenylethenyl |
| 1-190 | Me | OMe | H | Me | H | Me | $C(CH_3)_3$ | H | H | H | 1 | 0 | 1-methyl-2-phenylethenyl |
| 1-191 | Me | OMe | H | Me | H | Me | $C(CH_3)_3$ | H | H | H | 1 | 0 | 2-(4-hydroxyphenyl)ethenyl |
| 1-192 | Me | OMe | H | Me | H | Me | $C(CH_3)_3$ | H | H | H | 1 | 0 | 2-(3-hydroxyphenyl)ethenyl |
| 1-193 | Me | OMe | H | Me | H | Me | $C(CH_3)_3$ | H | H | H | 1 | 0 | 2-(2-furyl)ethenyl |
| 1-194 | Me | OMe | H | Me | H | Me | $C(CH_3)_3$ | H | H | H | 1 | 0 | 2-(3,4-dichlorophenyl)ethenyl |
| 1-195 | Me | OMe | H | Me | H | Me | $C(CH_3)_3$ | H | H | H | 1 | 0 | 2-(2,4-dichlorophenyl)ethenyl |
| 1-196 | Me | OMe | H | Me | H | Me | $C(CH_3)_3$ | H | H | H | 1 | 0 | 2-(2-nitrophenyl)ethenyl |
| 1-197 | Me | OMe | H | Me | H | Me | $C(CH_3)_3$ | H | H | H | 1 | 0 | 2,2,2-trifluoro-1-trifluoromethyl-1-methylethyl |
| 1-198 | Me | OMe | H | Me | H | Me | $C(CH_3)_3$ | H | $2CF_3$—Ph | H | 0 | 0 | Cl |

The following Examples are provided for guidance to the practitioner in order to practice the invention.

EXAMPLE 1

(Method B)

N'-tert-Butyl-N'-(3,5-dimethylbenzoyl)-N-(3-methoxy-2-methylbenzoyl)hydrazine carboxylic acid chloromethyl ester (Compound 1-1 of Table 1)

To a suspension of sodium hydride (2.4 g, 60 mmol, 60% by wt in oil) in 400 mL of tetrahydrofuran (THF) was added N'-tert-butyl-N'-3,5-dimethylbenzoyl-N-(3-methoxy-2-methylbenzoyl)hydrazide portionwise (20.0 g, 54 mmol) over 5 min. The mixture was then heated to reflux for 30 min. then allowed to cool to room temperature and stir for an additional 2 h. Chloromethyl chloroformate (5.2 mL 60 mmol) was then added dropwise to the yellow homogeneous mixture slowly over 5 min. The mixture was stirred at room temperature for 10 h. THF was then removed under vacuum and the resulting slurry was taken up into 300 mL of ether and washed with water (2×) followed by brine. The ether layer was then dried over sodium sulfate, filtered, and evaporated to afford a white solid. Silica gel chromatography (5:1 hexanes:EtOAc)afforded a white solid (21.0 g) in 85% yield. 1H-NMR (300 MHz, CDCl$_3$) δ (ppm): 1.65 (s, 9H), 1.95 (bs, 3H), 2.24 (s, 6H), 3.79 (s, 3H), 5.60 (s, 2H), 6.75–7.0 (m, 6H). Mp=117–119° C.

EXAMPLE 2

N'-tert-Butyl-N'-(3,5-dimethylbenzoyl)-N-(3-methoxy-2-methylbenzoyl)hydrazine carboxylic acid iodomethyl ester (Compound 1-2 of Table 1)

A solution of N'-tert-butyl-N'-(3,5-dimethylbenzoyl)-N-(3-methoxy-2-methylbenzoyl)hydrazine carboxylic acid chloromethyl ester (15.0 g, 32.5 mmol) in 40 mL of acetone was added sodium iodide (9.8 g, 65.1 mmol)and heated to 30° C. for 3 h. The acetone was removed and the resulting slurry was treated with ether. The resulting white precipitated solids were filtered off, and the ether was then concentrated to afford yellow solids. Recrystallization from ether/hexanes afforded tannish crystals (20 g, 96%). 1H-NMR (300 MHz, CDCl$_3$) δ (ppm): 1.64 (s, 9H), 1.97 (bs, 3H), 2.25 (s, 6H), 3.79 (s, 3H), 5.76 (s, 2H), 6,78–7.1 (m, 6H). Mp=70–72° C.

EXAMPLE 3

Acetic acid N'-tert-butyl-N'-(3,5-dimethylbenzoyl)-N-(3-methoxy-2-methylbenzoyl)hydrazinocarbonyloxymethyl ester (Compound 1-3 of Table 1)

A solution of N'-tert-butyl-N'-(3,5-dimethylbenzoyl)-N-(3-methoxy-2-methylbenzoyl)hydrazine carboxylic acid iodomethyl ester (0.5 g, 0.91 mmol) in THF was added glacial acetic acid (0.1 mL, 1.82 mmol) and diisopropylethylamine (0.17 mL, 1.0 mmol). The mixture was stirred for 16 h. The white precipitate which had formed was filtered off and the THF solution was concentrated to an oil. Silica gel chromatography (4:1 hexanes:EtOAc) afforded 400 mg of pure acetic acid N'-tert-butyl-N'-(3,5-dimethylbenzoyl)-N-(3-methoxy-2-methylbenzoyl)hydrazinocarbonyloxymethyl ester as a white solid in 91% yield. 1H-NMR (300 MHz, CDCl$_3$) δ (ppm): 1.63 (s, 9H), 1.90 (bs, 3H), 2.05 (s, 3H), 2.25 (s, 6H), 3.78 (s, 3H), 5.60 (s, 2H), 6.75–7.02 (m, 6H). Mp=123–125° C.

EXAMPLE 4

(3,5,6-Trichloropyridin-2-yloxy)-acetic acid N'-tert-butyl-N'-(3,5-dimethylbenzoyl)-N-(3-methoxy-2-methylbenzoyl)hydrazinocarbonyloxymethyl ester (Compound 1-4 of Table 1)

The title compound was prepared according to the procedure described in Example 3 above except for the substitution of (3,5,6-trichloropyridin-2-yloxy)-acetic acid for acetic acid. 1H-NMR (300 MHz, CDCl$_3$) δ (ppm): 1.63 (s, 9H), 1.92 (bs, 3H), 2.25 (s, 6H), 3.79 (s, 3H), 4.89 (s, 2H), 5.65 (s, 2H), 6.75–7.02 (m, 6H), 7.78 (s, 1H).

EXAMPLE 5

3,6-Dichloropyridine-2-carboxylic acid N'-tert-butyl-N'-(3;5-dimethylbenzoyl)-N-(3-methoxy-2-methylbenzoyl)hydrazinocarbonyloxymethyl ester (Compound 1-5 of Table 1)

The title compound was prepared according to the procedure described in Example 3 above except for the substitution of 3,6-dichloropyridine-2-carboxylic acid for acetic acid. 1H-NMR (300 MHz, CDCl$_3$) δ (ppm): 1.65 (s, 9H), 1.92 (bs, 3H), 2.22 (s, 6H), 3.75 (s, 3H), 5.85–5.92 (m, 2H), 6.67–7.00 (m, 6H), 7.45 (d,1H), 7.75 (d, 1H).

EXAMPLE 6

2,2-Dimethylpropionic acid N'-tert-butyl-N'-(3,5-dimethylbenzoyl)-N-(3-methoxy-2-methylbenzoyl)hydrazinocarbonyloxymethyl ester (Compound 1-6 of Table 1)

The title compound was prepared according to the procedure described in Example 3 above except for the substitution of 2,2-dimethylpropionic acid for acetic acid. 1H-NMR (300 MHz, CDCl$_3$) δ (ppm): 1.19 (s, 9H), 1.63 (s, 9H), 1.90 (bs, 3H), 2.25 (s, 6H), 3.78 (s, 3H), 5.63 (d, 1H), 5.67 (d, 1H), 5.85–5.92 (m, 2H), 6.75–7.01 (m, 6H). Mp=82–83° C.

EXAMPLE 7

Acetylaminoacetic acid N'-tert-butyl-N'-(3,5-dimethylbenzoyl)-N-(3-methoxy-2-methylbenzoyl)hydrazinocarbonyloxymethyl ester (Compound 1-7 of Table 1)

The title compound was prepared according to the procedure described in Example 3 above except for the substitution of acetylaminoacetic acid for acetic acid. 1H-NMR (300 MHz, CDCl$_3$) δ (ppm): 1.63 (s, 9H), 1.90 (bs, 3H), 2.20 (s, 3H), 2.25 (s, 6H), 3.78 (s, 3H), 3.97 (d, 2H), 5.65 (m, 2H), 6.02 (bs, 1H), 6.75–7.01 (m, 6H). Mp=69–70° C.

EXAMPLE 8

Methoxycarbonylaminooxyacetic acid N'-tert-butyl-N'-(3,5-dimethylbenzoyl)-N-(3-methoxy-2-methylbenzoyl)hydrazinocarbonyloxymethyl ester (Compound 1-8 of Table 1)

The title compound was prepared according to the procedure described in Example 3 above except for the substitution of methoxycarbonylaminoxyacetic acid for acetic acid. 1H-NMR (300 MHz, CDCl$_3$) δ (ppm): 1.63 (s, 9H), 1.90 (bs, 3H), 2.25 (s, 6H), 3.79 (s, 3H), 4.38 (s, 2H), 5.65 (s, 2H), 6.75–7.00 (m, 6H), 7.90 (s, 1H).

EXAMPLE 9

2-Nitro-5-thiocyanatobenzoic acid N'-tert-butyl-N'-(3,5-dimethylbenzoyl)-N-(3-methoxy-2-methylbenzoyl)hydrazinocarbonyloxymethyl ester (Compound 1-9 of Table 1)

The title compound was prepared according to the procedure described in Example 3 above except for the substitution of 2-nitro-5-thiocyanatobenzoic acid for acetic acid. 1H-NMR (300 MHz, CDCl$_3$) δ (ppm): 1.66 (s, 9H), 1.92 (bs, 3H), 2.20 (s, 6H), 3.77 (s, 3H), 5.72 (d, 1H), 5.85 (d, 1H), 6.75–6.97 (m, 6H), 7.70 (s, 1H), 7.80 (d, 1H), 8.05 (d, 1H).

EXAMPLE 10

(Diethoxyphosphoryl)-acetic acid N'-tert-butyl-N'-(3,5-dimethylbenzoyl)-N-(3-methoxy-2-methylbenzoyl)hydrazinocarbonyloxymethyl ester (Compound 1-10 of Table 1)

The title compound was prepared according to the procedure described in Example 3 above except for the substitution of (diethoxyphosphoryl)-acetic acid for acetic acid. 1H-NMR (300 MHz, CDCl$_3$) δ (ppm): 1.33 (t, 6H), 1.63 (s, 9H), 1.90 (bs, 3H), 2.25 (s, 6H), 2.93 (d, 2H), 3.78 (s, 3H), 4.158 (m, 4H), 5.58 (d, 1H), 5.65 (d, 1H), 6.75–7.00 (m, 6H).

EXAMPLE 11

2-Hydroxy-2-methylpropionic acid N'-tert-butyl-N'-(3,5-dimethylbenzoyl)-N-(3-methoxy-2-methylbenzoyl)hydrazinocarbonyloxymethyl ester (Compound 1-11 of Table 1)

The title compound was prepared according to the procedure described in Example 3 above except for the substitution of 2-hydroxy-2-methylpropionic acid for acetic acid. 1H-NMR (300 MHz, CDCl$_3$) δ (ppm): 1.39 (s, 6H), 1.63 (s, 9H), 1.90 (bs, 3H), 2.25 (s, 6H), 3.79 (s, 3H), 5.65 (d, 1H), 5.70 (d, 1H), 6.75–7.00 (m, 6H).

EXAMPLE 12

2-Isopropylideneaminooxypropionic acid N'-tert-butyl-N'-(3,5-dimethylbenzoyl)-N-(3-methoxy-2-methylbenzoyl)hydrazinocarbonyloxymethyl ester (Compound 1-12 of Table 1)

The title compound was prepared according to the procedure described in Example 3 above except for the substitution of 2-isopropylideneaminooxypropionic acid for acetic acid. 1H-NMR (300 MHz, CDCl₃) δ (ppm): 1.42 (d, 3H), 1.63 (s, 9H), 1.83 (s, 3H), 1.89 (s, 3H), 1.90 (bs, 3H), 2.25 (s, 6H), 3.78 (s, 3H), 4.63 (q, 1H), 5.70 (m, 2H), 6.75–6.97 (m, 6H).

EXAMPLE 13

4,4,4-Trifluoro-2-methylbutyric acid N'-tert-butyl-N'-(3,5-dimethylbenzoyl)-N-(3-methoxy-2-methylbenzoyl)hydrazinocarbonyloxymethyl ester (Compound 1-13 of Table 1)

The title compound was prepared according to the procedure described in Example 3 above except for the substitution of 4,4,4-trifluoro-2-methylbutyric acid for acetic acid. 1H-NMR (300 MHz, CDCl₃) δ (ppm): 1.25 (d, 3H), 1.63 (s, 9H), 1.90 (bs, 3H), 2.10 (m, 2H), 2.25 (s, 6H), 2.75 (m, 1H), 3.78 (s, 3H), 5.65 (m, 2H), 6.75–6.97 (m, 6H).

EXAMPLE 14

4,4,4-Trifluoro-3-methylbutyric acid N'-tert-butyl-N'-(3,5-dimethylbenzoyl)-N-(3-methoxy-2-methylbenzoyl)hydrazinocarbonyloxymethyl ester (Compound 1-14 of Table 1)

The title compound was prepared according to the procedure described in Example 3 above except for the substitution of 4,4,4-trifluoro-3-methylbutyric acid for acetic acid. 1H-NMR (300 MHz, CDCl₃) δ (ppm): 1.15 (d, 3H), 1.63 (s, 9H), 1.90 (bs, 3H), 2.25 (s, 6H), 2.30 (m, 1H), 2.65 (m, 2H), 3.78 (s, 3H), 5.65 (m, 2H), 6.75–6.97 (m, 6H).

EXAMPLE 15

3,3,3-Trifluoropropionic acid N'-tert-butyl-N'-(3,5-dimethylbenzoyl)-N-(3-methoxy-2-methylbenzoyl)hydrazinocarbonyloxymethyl ester (Compound 1-15 of Table 1)

The title compound was prepared according to the procedure described in Example 3 above except for the substitution of 3,3,3-trifluoropropionic acid for acetic acid. 1H-NMR (300 MHz, CDCl₃) δ (ppm): 1.63 (s, 9H), 1.90 (bs, 3H), 2.25 (s, 6H), 3.17 (q, 2H), 3.79 (s, 3H), 5.65 (bs, 2H), 6.75–6.97 (m, 6H).

EXAMPLE 16

2-Benzyloxycarbonylamino-2-methylpropionic acid N'-tert-butyl-N'-(3,5-dimethylbenzoyl)-N-(3-methoxy-2-methylbenzoyl)hydrazinocarbonyloxymethyl ester (Compound 1-16 of Table 1)

The title compound was prepared according to the procedure described in Example 3 above except for the substitution of 2-benzyloxycarbonylamino-2-methylpropionic acid for acetic acid. 1H-NMR (300 MHz, CDCl₃) δ (ppm): 1.50 (s, 6H), 1.62 (s, 9H), 1.90 (bs, 3H), 2.25 (s, 6H), 3.76 (s, 3H), 5.05 (s, 2H), 5.21 (bs, 1H), 5.65 (m, 2H), 6.75–6.97 (m, 6H), 7.34 (m, 5H).

EXAMPLE 17

2-tert-Butoxycarbonylamino-2-methylpropionic acid N'-tert-butyl-N'-(3,5-dimethylbenzoyl)-N-(3-methoxy-2-methylbenzoyl)hydrazinocarbonyloxymethyl ester (Compound 1-17 of Table 1)

The title compound was prepared according to the procedure described in Example 3 above except for the substitution of 2-tert-butoxycarbonylamino-2-methylpropionic acid for acetic acid. 1H-NMR (300 MHz, CDCl₃) δ (ppm): 1.41 (s, 9H), 1.45 (s, 3H), 1.46 (s, 3H), 1.63 (s, 9H), 1.90 (bs, 5H), 2.25 (s, 6H), 3.78 (s, 3H), 4.91 (bs, 1H), 5.63 (d, 1H), 5.71 (d, 1H), 6.75–7.01 (m, 6H). Mp=74–76° C.

EXAMPLE 18

Piperidine-1,4-dicarboxylic acid 1-tert-butyl ester 4-[N'-tert-butyl-N'-(3,5-dimethylbenzoyl)-N-(3-methoxy-2-methylbenzoyl)hydrazinocarbonyloxymethyl] ester (Compound 1-18 of Table 1)

The title compound was prepared according to the procedure described in Example 3 above except for the substitution of piperidine-1,4-dicarboxylic acid 1-tert-butyl Ester for acetic acid. 1H-NMR (300 MHz, CDCl₃) δ (ppm): 1.47 (s, 9H), 1.58 (bs, 2H), 1.62 (s, 9H), 1.90 (bs, 5H), 2.25 (s, 6H), 2.42 (m, 1H), 2.80 (t, 2H), 3.78 (s, 3H), 4.02 (bs, 2H), 5.60 (d, 1H), 5.65 (d, 1H), 6.75–6.97 (m, 6H).

EXAMPLE 19

1-Acetyl-4-hydroxypyrrolidine-2-carboxylic acid N'-tert-butyl-N'-(3,5-dimethylbenzoyl)-N-(3-methoxy-2-methylbenzoyl)hydrazinocarbonyloxymethyl ester (Compound 1-19 of Table 1)

The title compound was prepared according to the procedure described in Example 3 above except for the substitution of 1-acetyl-4-hydroxypyrrolidine-2-carboxylic acid for acetic acid. Mp=82–83° C.

EXAMPLE 20

2-Methylnicotinic acid N'-tert-butyl-N'-(3,5-dimethylbenzoyl)-N-(3-methoxy-2-methylbenzoyl)hydrazinocarbonyloxymethyl ester (Compound 1-20 of Table 1)

The title compound was prepared according to the procedure described in Example 3 above except for the substitution of 2-methylnicotinic acid for acetic acid. 1H-NMR (300 MHz, CDCl₃) δ (ppm): 1.63 (s, 9H), 1.90 (bs, 3H), 2.20 (s, 6H), 2.80 (s, 3H), 3.70 (s, 3H), 5.85 (s, 2H), 6.60–7.00 (m, 6H), 7.25 (d, 1H), 8.11 (d, 1H), 8.70 (d, 1H).

EXAMPLE 21

2-Acetylamino-3-methylbutyric acid N'-tert-butyl-N'-(3,5-dimethylbenzoyl)-N-(3-methoxy-2-methylbenzoyl)hydrazinocarbonyloxymethyl ester (Compound 1-21 of Table 1)

The title compound was prepared according to the procedure described in Example 3 above except for the substitution of 2-acetylamino-3-methylbutyric acid for acetic acid. 1H-NMR (300 MHz, CDCl₃) δ (ppm): 0.86 (d, 3H), 0.94 (d, 3H), 1.62 (s, 9H), 1.90 (bs, 3H), 2.04 (s, 3H), 2.25 (s, 6H), 3.78 (s, 3H), 4.55 (m, 1H), 5.50–5.80 (m, 2H), 5.86 (d,1H), 6.75–7.00 (m, 6H). Mp=58–60° C.

EXAMPLE 22

4-Hydroxy-2,6-dimethoxybenzoic acid N'-tert-butyl-N'-(3,5-dimethylbenzoyl)-N-(3-methoxy-2-methylbenzoyl)hydrazinocarbonyloxymethyl ester (Compound 1-22 of Table 1)

The title compound was prepared according to the procedure described in Example 3 above except for the substi-

EXAMPLE 23

2-Acetylamino-4-methylsulfanylbutyric acid N'-tert-butyl-N'-(3,5-dimethylbenzoyl)-N-(3-methoxy-2-methylbenzoyl)hydrazinocarbonyloxymethyl ester (Compound 1-23 of Table 1)

The title compound was prepared according to the procedure described in Example 3 above except for the substitution of 2-acetylamino-4-methylsulfanylbutyric acid for acetic acid. 1H-NMR (300 MHz, CDCl$_3$) δ (ppm): 1.63 (s, 9H), 1.90 (bs, 5H), 2.03 (s, 3H), 2.07 (s, 3H), 2.25 (s, 6H), 2.50 (t, 2H), 3.79 (s, 3H), 4.69 (m, 1H), 5.60–5.73 (m, 2H), 6.12 (d, 1H), 6.76–6.97 (m, 6H). Mp=58–59° C.

EXAMPLE 24

2-Acetylaminoacrylic acid N'-tert-butyl-N'-(3,5-dimethylbenzoyl)-N-(3-methoxy-2-methylbenzoyl)hydrazinocarbonyloxymethyl ester (Compound 1-24 of Table 1)

The title compound was prepared according to the procedure described in Example 3 above except for the substitution of N-acetamido acrylic acid for acetic acid. 1H-NMR (300 MHz, CDCl$_3$) δ (ppm): 1.63 (s, 9H), 1.90 (bs, 5H), 2.15 (s, 3H), 2.24 (s, 6H), 3.77 (s, 3H), 5.75 (bs, 2H), 5.85 (s, 2H), 6.70–7.00 (m, 6H), 7.55 (bs, 1H).

EXAMPLE 25

1-Methyl-1H-pyrrole-2-carboxylic acid N'-tert-butyl-N'-(3,5-dimethylbenzoyl)-N-(3-methoxy-2-methylbenzoyl)hydrazinocarbonyloxymethyl ester (Compound 1-25 of Table 1)

The title compound was prepared according to the procedure described in Example 3 above except for the substitution of 1-methyl-1H-pyrrole-2-carboxylic acid for acetic acid. 1H-NMR (300 MHz, CDCl$_3$) δ (ppm): 1.62 (s, 9H), 1.90 (bs, 5H), 2.21 (s, 6H), 3.72 (s, 3H), 3.90 (s, 3H), 5.80 (bs, 2H), 6.14 (m, 1H), 6.65–7.00 (m, 8H).

EXAMPLE 26

2-tert-Butoxycarbonylaminosuccinic acid 4-benzyl ester N'-tert-butyl-N'-(3,5-dimethylbenzoyl)-N-(3-methoxy-2-methylbenzoyl)hydrazinocarbonyloxymethyl ester (Compound 1-26 of Table 1)

The title compound was prepared according to the procedure described in Example 3 above except for the substitution of 2-tert-butoxycarbonylaminosuccinic acid 4-benzyl ester for acetic acid. 1H-NMR (300 MHz, CDCl$_3$) δ (ppm): 1.45 (s, 9H), 1.63 (s, 9H), 1.90 (bs, 5H), 2.24 (s, 6H), 2.85 (m, 2H), 3.77 (s, 3H), 4.55 (m, 1H), 5.10 (m, 2H), 5.50 (m, 2H), 5.65 (d, 1H), 6.70–7.00 (m, 6H), 7.35 (m, 5H). Mp=64–65° C.

EXAMPLE 27

4-Hexyloxybenzoic acid 4-benzyl ester N'-tert-butyl-N'-(3,5-dimethylbenzoyl)-N-(3-methoxy-2-methylbenzoyl)hydrazinocarbonyloxymethyl ester (Compound 1-27 of Table 1)

The title compound was prepared according to the procedure described in Example 3 above except for the substitution of 4-hexyloxybenzoic acid for acetic acid. 1H-NMR (300 MHz, CDCl$_3$) δ (ppm): 0.92 (t, 3H), 1.35–1.50 (m, 6H), 1.62 (s, 9H), 1.82 (m, 2H), 1.90 (bs, 3H), 2.21 (s, 6H), 3.71 (s, 3H), 4.02 (t, 2H), 5.84 (s, 2H), 6.62–7.00 (m, 8H), 7.93 (d, 2H).

EXAMPLE 28

2-(2-Chlorophenoxy)-2-methylpropionic acid N'-tert-butyl-N'-(3,5-dimethylbenzoyl)-N-(3-methoxy-2-methylbenzoyl)hydrazinocarbonyloxymethyl ester (Compound 1-28 of Table 1)

The title compound was prepared according to the procedure described in Example 3 above except for the substitution of 2-(2-chlorophexoxy)-2-methylpropionic acid for acetic acid. 1H-NMR (300 MHz, CDCl$_3$) δ (ppm): 1.57 (s, 3H), 1.58 (s, 3H), 1.61 (s, 9H), 1.90 (bs, 3H), 2.24 (s, 6H), 3.78 (s, 3H), 5.69 (d, 1H), 5.79 (d, 1H), 6.75–7.38 (m, 10H).

EXAMPLE 29

3-Hydroxy-4-methoxybenzoic acid N'-tert-butyl-N'-(3,5-dimethylbenzoyl)-N-(3-methoxy-2-methylbenzoyl)hydrazinocarbonyloxymethyl ester (Compound 1-29 of Table 1)

The title compound was prepared according to the procedure described in Example 3 above except for the substitution of 3-hydroxy-4-methoxybenzoic acid for acetic acid. 1H-NMR (300 MHz, CDCl$_3$) δ (ppm): 1.62 (s, 9H), 1.90 (bs, 3H), 2.21 (s, 6H), 3.72 (s, 3H), 3.98 (s, 3H), 5.74 (s, 1H), 5.82 (s, 2H), 6.65–6.98 (m, 7H), 7.48 (s, 1H), 7.57 (d, 1H). Mp=59–61° C.

EXAMPLE 30

4-Hydroxy-3,5-dinitrobenzoic acid N'-tert-butyl-N'-(3,5-dimethylbenzoyl)-N-(3-methoxy-2-methylbenzoyl)hydrazinocarbonyloxymethyl ester (Compound 1-30 of Table 1)

The title compound was prepared according to the procedure described in Example 3 above except for the substitution of 4-hydroxy-3,5-dinitrobenzoic acid for acetic acid. 1H-NMR (300 MHz, CDCl$_3$) δ (ppm): 1.55 (s, 9H), 1.76 (bs, 3H), 2.14 (s, 6H), 3.72 (s, 3H), 5.80 (s, 2H), 6.67–6.91 (m, 6H), 8.59 (s, 2H).

EXAMPLE 31

Pyrrolidine-1,2-dicarboxylic acid 1-tert-butyl ester 2-[N'-tert-butyl-N'-(3,5-dimethylbenzoyl)-N-(3-methoxy-2-methylbenzoyl)hydrazinocarbonyloxymethyl]ester (Compound 1-31 of Table 1)

The title compound was prepared according to the procedure described in Example 3 above except for the substitution of pyrrolidine-1,2-dicarboxylic acid 1-tert-butyl ester for acetic acid. 1H-NMR (300 MHz, CDCl$_3$) δ (ppm): 1.40 (d, 9H), 1.63 (s, 9H), 1.90 (bs, 7H), 2.26 (s, 6H), 3.45 (m, 2H), 3.78 (s, 3H), 4.30 (m, 1H), 5.50–5.90 (m, 2H), 6.80–7.00 (m, 6H). Mp=62–63° C.

EXAMPLE 32

2-Diisopropylaminopropionic acid N'-tert-butyl-N'-(3,5-dimethylbenzoyl)-N-(3-methoxy-2-methylbenzoyl)hydrazinocarbonyloxymethyl ester (Compound 1-32 of Table 1)

The title compound was prepared according to the procedure described in Example 3 above except for the substitution of 2-diisopropylaminopropionic acid for acetic acid. 1H-NMR (300 MHz, CDCl$_3$) δ (ppm): 0.85 (t, 6H), 1.25 (d, 3H), 1.40 (m, 4H), 1.63 (s, 9H), 1.90 (bs, 3H), 2.26 (s, 6H), 2.45 (m, 4H), 3.52 (m, 1H), 3.78 (s, 3H), 5.60–5.75 (m, 2H), 6.78–7.00 (m, 6H).

EXAMPLE 33

4-Hydroxypyrrolidine-1,2-dicarboxylic acid 1-tert-butyl ester 2-[N'-tert-butyl-N'-(3,5-dimethylbenzoyl)-N-(3-methoxy-2-methylbenzoyl) hydrazinocarbonyloxymethyl ester] (Compound 1-33 of Table 1)

The title compound was prepared according to the procedure described in Example 3 above except for the substitution of 4-hydroxypyrrolidine-1,2-dicarboxylic acid 1-tert-butyl ester for acetic acid. Mp=87–88° C.

EXAMPLE 34

6-Acetylamino-2-tert-butoxycarbonylaminohexanoic acid N'-tert-butyl-N'-(3,5-dimethylbenzoyl)-N-(3-methoxy-2-methylbenzoyl) hydrazinocarbonyloxymethyl ester (Compound 1-34 of Table 1)

The title compound was prepared according to the procedure described in Example 3 above except for the substitution of 6-acetylamino-2-tert-butoxycarbonylaminohexanoic acid for acetic acid. Mp=82–83° C.

EXAMPLE 35

2-tert-Butoxycarbonylamino-3,3-dimethylbutyric acid N'-tert-butyl-N'-(3,5-dimethylbenzoyl)-N-(3-methoxy-2-methylbenzoyl) hydrazinocarbonyloxymethyl ester (Compound 1-35 of Table 1)

The title compound was prepared according to the procedure described in Example 3 above except for the substitution of 2-tert-butoxycarbonylamino-3,3-dimethylbutyric acid for acetic acid. Mp=82–83° C.

EXAMPLE 36

2-tert-Butoxycarbonylamino-3-cyclohexyl-propionic acid N'-tert-butyl-N'-(3,5-dimethylbenzoyl)-N-(3-methoxy-2-methylbenzoyl) hydrazinocarbonyloxymethyl ester (Compound 1-36 of Table 1)

The title compound was prepared according to the procedure described in Example 3 above except for the substitution of 2-tert-butoxycarbonylamino-3-cyclohexyl-propionic acid for acetic acid. Mp=81–82° C.

EXAMPLE 37

2-Pyrrolidine carboxylic acid N'-tert-butyl-N'-(3,5-dimethylbenzoyl)-N-(3-methoxy-2-methylbenzoyl) hydrazinocarbonyloxymethyl ester-hydrochloride salt (Compound 1-37 of Table 1)

A solution of pyrrolidine-1,2-dicarboxylic acid 1-tert-butyl ester 2-[N'-tert-butyl-N'-(3,5-dimethylbenzoyl)-N-(3-methoxy-2-methylbenzoyl)hydrazinocarbonyloxymethyl] ester (500 mg, 0.78 mmol) in diethyl ether (1 mL) was cooled to 0° C. HCl gas was then bubbled through the solution and the reaction capped and allowed to stir for 1 h. The solvent was removed and the white solid was triturated with ether and isolated in 100% yield (450 mg). 1H-NMR (300 MHz, CDCl$_3$) δ (ppm): 1.62 (s, 9H), 1.85–2.10 (bm, 7H), 2.25 (s, 6H), 3.47 (m, 2H), 3.79 (s, 3H), 4.42 (bs, 1H), 5.55 (dd, 1H), 5.85 (dd, 1H), 6.80–7.00 (m, 6H), 9.20 (bs, 1H), 11.05 (bs, 1H). Mp=107–108° C.

EXAMPLE 38

2-Amino-2-methylpropionic acid N'-tert-butyl-N'-(3,5-dimethylbenzoyl)-N-(3-methoxy-2-methylbenzoyl)hydrazinocarbonyloxymethyl ester-hydrochloride salt (Compound 1-38 of Table 1)

A solution of 2-tert-butoxycarbonylamino-2-methylpropionic acid N'-tert-butyl-N'-(3,5-dimethylbenzoyl)-N-(3-methoxy-2-methylbenzoyl) hydrazinocarbonyloxymethyl ester (500 mg, 0.80 mmol) in diethyl ether (1 mL) was cooled to 0° C. HCl gas was then bubbled through the solution and the reaction capped and allowed to stir for 1 h. The solvent was removed and the white solid was triturated with ether and isolated in 100% yield (450 mg). 1H-NMR (300 MHz, CDCl$_3$) δ (ppm): 1.61 (s, 9H), 1.66 (bs, 6H), 2.24 (s, 6H), 3.77 (s, 3H), 5.65 (bs, 1H), 5.75 (bs, 1H), 6.78–7.01 (m, 6H), 9.05 (bs, 3H). Mp=153–154° C.

EXAMPLE 39

Piperidine-4-carboxylic acid N'-tert-butyl-N'-(3,5-dimethylbenzoyl)-N-(3-methoxy-2-methylbenzoyl) hydrazinocarbonyloxymethyl ester-hydrochloride salt (Compound 1-39 of Table 1)

A solution of piperidine-1,4-dicarboxylic acid 1-tert-butyl ester 4-[N'-tert-butyl-N'-(3,5-dimethylbenzoyl)-N-(3-methoxy-2-methylbenzoyl)hydrazinocarbonyloxymethyl] ester (500 mg, 0.92 mmol) in diethyl ether (1 mL) was cooled to 0° C. HCl gas was then bubbled through the solution and the reaction capped and allowed to stir for 1 h. The solvent was removed and the white solid was triturated with ether and isolated in 100% yield (542 mg). 1H-NMR (300 MHz, CDCl$_3$) δ (ppm): 1.62 (s, 9H), 1.70–2.20 (m, 9H), 2.25 (s, 6H), 3.79 (s, 3H), 5.60 (bs, 1H), 5.68 (bs, 1H), 6.78–7.02 (m, 6H), 9.70 (bs, 2H). Mp=138–139° C.

EXAMPLE 40

2-Aminosuccinic acid 4-benzyl ester 4-[N'-tert-butyl-N'-(3,5-(dimethylbenzoyl)-N-(3-methoxy-2-methylbenzoyl)hydrazinocarbonyloxymethyl]ester-hydrochloride salt (Compound 1-40 of Table 1)

A solution of 2-aminosuccinic acid 4-benzyl ester 4-[N'-tert-butyl-N'-(3,5-dimethylbenzoyl)-N-(3-methoxy-2-methylbenzoyl)hydrazinocarbonyloxymethyl]ester (500 mg, 0.67 mmol) in diethyl ether (1 mL) was cooled to 0° C. HCl gas was then bubbled through the solution and the reaction capped and allowed to stir for 1 h. The solvent was removed and the white solid was triturated with ether and isolated in 100% yield (460 mg). 1H-NMR (300 MHz, CDCl$_3$) δ (ppm): 1.58 (s, 9H), 1.90 (bs, 3H), 2.21 (s, 6H), 3.20 (m, 2H), 3.72 (s, 3H), 4.45 (bs, 1H), 5.08 (m, 2H), 5.45 (bs, 1H), 5.60 (m, 1H), 6.77–6.95 (m, 6H), 9.01 (bs, 3H). Mp=127–128° C.

EXAMPLE 41

2-Aminosuccinic acid 4-[N'-tert-butyl-N'-(3,5-dimethylbenzoyl)-N-(3-methoxy-2-methylbenzoyl) hydrazinocarbonyloxymethyl]ester-hydrochloride salt (Compound 1-41 of Table 1)

A solution of 2-aminosuccinic acid 4-[N'-tert-butyl-N'-(3,5-dimethylbenzoyl)-N-(3-methoxy-2-methylbenzoyl)

hydrazinocarbonyloxymethyl]ester (100 mg, 0.13 mmol) in diethyl ether (1 mL) was cooled to 0° C. HCl gas was then bubbled through the solution and the reaction capped and allowed to stir for 1 h. The solvent was removed and the white solid was triturated with ether and isolated in 100% yield (77 mg). 1H-NMR (300 MHz, CDCl$_3$) δ (ppm): 1.58 (s, 9H), 1.90 (bs, 3H), 2.22 (s, 6H), 3.15 (m, 2H), 3.75 (s, 3H), 4.45 (bs, 1H), 5.55–5.61 (m, 1H). 5.78–5.88 (m, 1H), 5.60 (m, 1H), 6.80–7.00 (m, 6H), 8.40 (bs, 3H). Mp=154–155° C.

EXAMPLE 42

2-tert-Butoxycarbonylaminosuccinic acid 4-[N'-tert-butyl-N'-(3,5-dimethylbenzoyl)-N-(3-methoxy-2-methylbenzoyl)hydrazinocarbonyloxymethyl]ester (Compound 1-42 of Table 1)

A solution of 2-tert-butoxycarbonylaminosuccinic acid 4-benzyl ester 4-[N'-tert-butyl-N'-(3,5-dimethylbenzoyl)-N-(3-methoxy-2-methylbenzoyl) hydrazinocarbonyloxymethyl]ester (500 mg, 0.67 mmol) in ethyl acetate (3 mL) was purged with nitrogen. 10% Pd/C was then added and the reaction placed under a hydrogen atmosphere. After 1 h, the reaction was complete. The Pd/C was filtered off and washed with ethyl acetate. The ethyl acetate was then removed to afford a white solid in 100% yield. 1H-NMR (300 MHz, CDCl$_3$) δ (ppm): 1.46 (s, 9H), 1.62 (s, 9H), 1.90 (bs, 3H), 2.25 (s, 6H), 2.90 (m, 2H), 3.78 (s, 3H), 4.55 (bs, 1H), 5.55–5.80 (m, 4H), 6.78–7.00 (m, 6H). M=88–89° C.

EXAMPLE 43

[Benzyl-(diethoxyphosphorylmethyl)-amino]-acetic acid N'-tert-butyl-N'-(3,5-dimethylbenzoyl)-N-(3-methoxy-2-methylbenzoyl) hydrazinocarbonyloxymethyl ester (Compound 1-43 of Table 1)

The title compound was prepared according to the procedure described in Example 3 above except for the substitution of [benzyl-(diethoxyphosphorylmethyl)-amino]-acetic acid for acetic acid. 1H-NMR (300 MHz, CDCl$_3$) δ (ppm): 1.30 (t, 6H), 1.62 (s, 9H), 1.90 (bs, 3H), 2.24 (s, 6H), 3.10 (d, 2H), 3.64 (s, 2H), 3.76 (s, 3H), 3.89 (s, 2H), 4.08 (m, 4H), 5.67 (dd, 2H), 6.78–7.00 (m, 6H), 7.31–7.33 (m, 5H).

EXAMPLE 44

N'-tert-butyl-N'-(3,5-methylbenzoyl)-N-(3-methoxy-2-methylbenzoyl)hydrazinecarboxylic acid 1-chloroethyl ester (Compound 1-44 of Table 1)

The title compound was prepared according to the procedure described in Example 1 above except for the substitution of 1-chloroethylchloroformate for chloromethylchloroformate. 1H-NMR (300 MHz, CDCl$_3$) δ (ppm): 1.58 (d, 3H), 1.67 (s, 9H), 1.90 (bs, 3H), 2.24 (s, 6H), 3.79 (s, 3H), 6.25 (q, 2H), 6.78–7.00 (m, 6H).

EXAMPLE 45

Acetic acid 1-[N'-tert-butyl-N'-(3,5-dimethylbenzoyl)-N-(3-methoxy-2-methylbenzoyl) hydrazinocarbonyloxy]-ethyl ester (Compound 1-45 of Table 1)

A solution of N'-tert-butyl-N'-(3,5-methylbenzoyl)-N-(3-methoxy-2-methylbenzoyl)hydrazinecarboxylic acid 1-chloroethyl ester (0.5 g, 1.05 mmol) in DMF was added potassium acetate (0.16 g, 1.20 mmol). The mixture was stirred for 48 h. Ether was added and washed with water (3×) followed by brine. The ether layer was dried over sodium sulfate, filtered, and concentrated. Silica gel chromatography with 4:1 hexanes:EtOAc afforded the desired product as an oil. 1H-NMR (300 MHz, CDCl$_3$) δ (ppm): 1.41 (bs, 3H), 1.62 (s, 9H), 2.01 (s, 6H), 2.25 (s, 6H), 3.77 (s, 3H), 6.65–7.10 (m, 7H).

EXAMPLE 46

N'-tert-butyl-N'-(3,5-methylbenzoyl)-N-(3-methoxy-2-methylbenzoyl)hydrazinecarboxylic acid chlorophenylmethyl ester (Compound 1-46 of Table 1)

The title compound was prepared according to the procedure described in Example 1 above except for the substitution of chlorobenzylchloroformate for chloromethylchloroformate. 1H-NMR (300 MHz, CDCl$_3$) δ (ppm): 1.60 (s, 9H), 2.20 (s, 6H), 3.75 (s, 3H), 6.60–7.40 (m, 13H). Mp 65–68° C.

EXAMPLE 47

Acetic acid [N'-tert-butyl-N'-(3,5-dimethylbenzoyl)-N-(3-methoxy-2-methylbenzoyl) hydrazinocarbonyloxy]phenylmethyl ester (Compound 1-47 of Table 1)

A solution of N'-tert-butyl-N'-(3,5-dimethylbenzoyl)-N-(3-methoxy-2-methylbenzoyl)hydrazinecarboxylic acid chlorophenylmethyl ester (1.5 g, 2.90 mmol) in DMF was added potassium acetate (0.30 g, 3.20 mmol). The mixture was stirred for 48 h. Ether was added and washed with water (3×) followed by brine. The ether layer was dried over sodium sulfate, filtered, and concentrated. Silica gel chromatography with 4:1 hexanes:EtOAc afforded the desired product as a white solid. 1H-NMR (300 MHz, CDCl$_3$) δ (ppm): 1.64 (s, 9H), 2.06 (s, 12H), 3.77 (s, 3H), 6.75–7.47 (m, 12H). Mp=65–68° C.

EXAMPLE 48

2-Methylpropionic acid [N'-tert-butyl-N'-(3,5-dimethylbenzoyl)-N-(3-methoxy-2-methylbenzoyl) hydrazinocarbonyloxy]phenylmethyl ester (Compound 1-48 of Table 1)

The title compound was prepared according to the procedure described in Example 47 above except for the substitution of potassium isobutyrate for potassium acetate. 1H-NMR (300 MHz, CDCl$_3$) δ (ppm): 1.16 ( (m, 6H), 1.63 (s, 9H), 1.90 (bs, 31), 2.03 (s, 6H), 2.55 (m, 1H), 3.78 (s, 3H), 6.60–7.40 (m, 13H).

EXAMPLE 49

2-Methylnicotinic acid N'-tert-butyl-N'-(3,5-dimethylbenzoyl)-N-(3-methoxy-2-methylbenzoyl) hydrazinocarbonyloxy]phenylmethyl ester (Compound 1-49 of Table 1)

The title compound was prepared according to the procedure described in Example 47 above except for the substitution of potassium 2-methylnicotinate for potassium acetate. Mp 66–70° C.

EXAMPLE 50

2-Acetylamino-3-methylbutyric acid N'-tert-butyl-N'-(3,5-dimethylbenzoyl)-N-(3-methoxy-2-methylbenzoyl)hydrazinocarbonyloxy]-phenylmethyl ester (Compound 1-50 of Table 1)

The title compound was prepared according to the procedure described in Example 47 above except for the substitution of potassium 2-acetylamino-3-methylbutyrate for potassium acetate. 1H-NMR (300 MHz, CDCl$_3$) δ (ppm): 0.69–0.98 (m, 6H), 1.65 (d, 9H), 1.99 (s, 3H), 2.05 (m, 9H), 3.82 (d, 3H), 4.61 (m, 1H), 5.95 (bs, 1H), 6.68–7.00 (m, 6H), 7.27–7.54 (m, 6H). Mp=81–86° C.

EXAMPLE 51

2-Acetylamino-4-methylsulfanylbutyric acid N'-tert-butyl-N'-(3,5-dimethylbenzoyl)-N-(3-methoxy-2-methylbenzoyl)hydrazinocarbonyloxy]-phenylmethyl ester (Compound 1-51 of Table 1)

The title compound was prepared according to the procedure described in Example 47 above except for the substitution of potassium 2-acetylamino-4-methylsulfanylbutyrate for potassium acetate. 1H-NMR (300 MHz, CDCl$_3$) δ (ppm): 1.57–2.19 (m, 28H), 3.78 (m, 3H), 4.71 (m, 1H), 6.09 (m, 1H), 6.68–7.00 (m, 6H), 7.27–7.54 (m, 6H). Mp=75–80° C.

EXAMPLE 52

2-tert-Butoxycarbonylamino-2-methylpropionic acid N'-tert-butyl-N'-(3,5-dimethylbenzoyl)-N-(3-methoxy-2-methylbenzoyl)hydrazinocarbonyloxy]-phenylmethyl ester (Compound 1-52 of Table 1)

The title compound was prepared according to the procedure described in Example 47 above except for the substitution of potassium 2-tert-butoxycarbonylamino-2-methylpropionate for potassium acetate. 1H-NMR (300 MHz, CDCl$_3$) δ (ppm): 1.26 (s, 9H), 1.43 (s, 3H), 1.51 (s, 3H), 1.68 (s, 9H), 1.90 (bs, 3H), 2.01 (s, 6H), 3.78 (s, 3H), 4.93 (bs, 1H), 6.65–6.91 (m, 6H), 7.42–7.50 (m, 6H). Mp=80–85° C.

EXAMPLE 53

[N'-tert-Butyl-N'-(3,5-dimethylbenzoyl)-N-(3-methoxy-2-methylbenzoyl)hydrazinocarbonyloxymethyl]-triethylammonium iodide (Compound 1-53 of Table 1)

A solution of N'-tert-butyl-N'-3,5-dimethylbenzoyl-N-(iodomethoxy carbonyl)-N-(2-methyl-3-methoxy-carbono) hydrazide (0.3 g, 0.54 mmol) in THF was added triethylamine (0.054 g, 0.54 mmol). The mixture was stirred for 16 h. The desired product precipitated from the solution and was filtered and washed with ether. 1H-NMR (300 MHz, CDCl$_3$) δ (ppm): 1.43 (bs, 9H), 1.65 (s, 9H), 2.13 (s, 3H), 2.27 (s, 6H), 2.90 (m, 6H), 3.86 (s, 3H), 5.15 (bs, 2H), 6.98–7.15 (m, 6H). Mp=202–203° C.

EXAMPLE 54

Dodecanoic acid N'-tert-butyl-N'-(3,5-dimethylbenzoyl)-N-(3-methoxy-2methylbenzoyl)hydrazinocarbonyloxymethyl ester (Compound 1-54)

Compounds (1-54) through (1-197) were synthesized by the following method:

Dodecanoic acid (38 mg, 0.19 mmol, 1.5 eq.) was weighed into a reaction vial. A solution of DIEA (1.4 eq., 31 mL, 0.178 mmol in 0.35 mL THF) was delivered via pipette and the contents of the vial were mechanically stirred at room temperature for 30 min at which time a solution of N'-tert-Butyl-N'-(3,5-dimethylbenzoyl)-N-(3-methoxy-2-methylbenzoyl)hydrazinecarboxylic acid iodomethyl ester (70 mg, 0.127 mmol in 0.35 mL THF) was delivered to the vial via pipette. The vial was capped and stirring was continued at room temperature for 48 h.

The reaction was monitored by TLC (3:1 Hexanes/EtOAc). The solvent was evaporated and the residue was taken up in a minimal quantity of methylene chloride and placed on a preconditioned (Hexanes) 2 gm pre-packed silica solid phase extraction cartridge (Extrac-Clean Silica, Alltech). The less polar starting material was removed with 5 mL Hexanes and the product was removed with 5 mL 1:1 Hexanes/EtOAc using a SPE vacuum manifold. The solvent was stripped and the product was dried 17 vacuo, yielding 78 mg of dodecanoic acid N'-tert-butyl-N'-(3,5-dimethylbenzoyl)-N-(3-methoxy-2-methylbenzoyl)hydrazinocarbonyloxymethyl ester. 1H-NMR (300 MHz, CDCl$_3$) δ ppm): 0.88 (t, 3H), 1.26 (s, 16H), 1.63 (s, 11H), 1.90 (bs, 3H), 2.25 (s, 8H), 3.78 (s, 3H), 5.67 (m, 2H), 6.78–7.03 (m, 6H).

EXAMPLES 55–197

$Z^2$ acid N'-tert-butyl-N'-(3,5-dimethylbenzoyl)-N-(3-methoxy-2methylbenzoyl)hydrazinocarbonyloxymethyl ester (Compounds (1-55) though (1-197))

Compounds (1-55)–(1-197) were prepared according to the procedure described in Example 54 above except for the substitution of $Z^2$COOH for dodecanoic acid. LC/MS and was conducted for confirmation of structure and purity.

EXAMPLE 198

N'-tert-butyl-N'-(3,5-methylbenzoyl)-N-(3-methoxy-2-methylbenzoyl)hydrazinecarboxylic acid chloro-(2-trifluoromethylphenyl)methyl ester (Compound 1-198 of Table 1)

The title compound was prepared according to the procedure described in Example 1 above except for the substitution of chloro-(2-trifluorophenyl)methylchloroformate for chloromethylchloroformate. 1H-NMR (300 MHz, CDCl$_3$) δ (ppm) (mixture of rotational isomers): 1.65 (d, 9H), 1.90 (bs, 3H), 2.18 (d, 6H), 3.74 (d, 3H), 6.78–7.02 (m, 5H), 7.45–7.65 (m, 6H).

For liquid chromatography (LC)/ultraviolet (UV) mass spectrometry (MS) analysis, the samples were dissolved in acetonitrile:water (1:1). Concentrations were 100 ug/mL to 1000 ug/mL. Analysis was performed using LC/UV MS system HPLC 1100-VG Platform. UV and MS were connected in sequence and carried out in one injection where UV afforded purity (%) and MS confirmed molecular weight. UV was carried out using diode array detector (DAD) scanning 200–300 nm. MS was carried out in positive mode scanning 100–1000 daltons. A short C18 HPLC column (3 mm ID, 5 cm length) was used with a flow rate of 1 mL/min where the flow was split after UV detection from 1 to 25 in which 1 part went to the MS. Typically, the HPLC gradient began at 25% water: 75% acetonitrile and went to 100% acetonitrile in 5 min in which the mobile phases contained 0.1% formic acid. Injection volume varied between 1 and 25 uL. Similar results should be reproduced with slight variations of HPLC parameters including mobile phase percentages which are allowed to optimize any HPLC system. Variations of UV/MS parameters including ion mode (positive or negative), UV wavelengths, and solvent buffers (no buffer, formic acid, acetic acid, or ammonia acetate) are allowed to optimize the MS system. Any other variations of C-8 and C-18 columns and instrumentation brand could be used if 0.5 ug/mL (or lower) standard can be analyzed. The data is presented in Table 1A.

TABLE 1A

LC/UV MS data for compounds (1-55) through (1-197).

| Compound # | Mass found | % UV purity |
|---|---|---|
| 1-55 | 512 | 96 |
| 1-56 | 553 | 99 |
| 1-57 | 514 | 100 |
| 1-58 | 615 | 92 |
| 1-59 | 548 | 99 |
| 1-60 | 536 | 98 |
| 1-61 | 593 | 99 |
| 1-62 | 593 | 89 |
| 1-63 | 558 | 96 |
| 1-64 | 562 | 99 |
| 1-65 | 660 | 96 |
| 1-66 | 614 | 99 |
| 1-67 | 829 | 98 |
| 1-68 | 547 | 100 |
| 1-69 | 615 | 90 |
| 1-70 | 547 | 99 |
| 1-71 | 615 | 90 |
| 1-72 | 624 | 99 |
| 1-73 | 625 | 90 |
| 1-74 | 625 | 93 |
| 1-75 | 625 | 89 |
| 1-76 | 590 | 99 |
| 1-77 | 552 | 98 |
| 1-78 | 510 | 99 |
| 1-79 | 562 | 98 |
| 1-80 | 540 | 98 |
| 1-81 | 594 | 99 |
| 1-82 | 628 | 99 |
| 1-83 | 614 | 92 |
| 1-84 | 566 | 97 |
| 1-85 | 581 | 99 |
| 1-86 | 538 | 87 |
| 1-87 | 549 | 99 |
| 1-88 | 606 | 99 |
| 1-89 | 607 | 98 |
| 1-90 | 578 | 98 |
| 1-91 | 581 | 97 |
| 1-92 | 625 | 100 |
| 1-93 | 636 | 96 |
| 1-94 | 590 | 100 |
| 1-95 | 621 | 100 |
| 1-96 | 524 | 100 |
| 1-97 | 588 | 100 |
| 1-98 | 600 | 100 |
| 1-99 | 630 | 96 |
| 1-100 | 566 | 100 |
| 1-101 | 542 | 100 |
| 1-102 | 658 | 100 |
| 1-103 | 554 | 100 |
| 1-104 | 564 | 100 |
| 1-105 | 540 | 100 |
| 1-106 | 540 | 100 |
| 1-107 | 566 | 100 |
| 1-108 | 552 | 100 |
| 1-109 | 568 | 100 |
| 1-110 | 540 | 100 |
| 1-111 | 574 | 100 |
| 1-112 | 576 | 100 |
| 1-113 | 666 | 96 |
| 1-114 | 653 | 92 |
| 1-115 | 556 | 100 |
| 1-116 | 606 | 100 |
| 1-117 | 588 | 100 |
| 1-118 | 562 | 100 |
| 1-119 | 638 | 100 |
| 1-120 | 542 | 100 |
| 1-121 | 568 | 100 |
| 1-122 | 616 | 100 |
| 1-123 | 526 | 100 |
| 1-124 | 524 | 100 |
| 1-125 | 540 | 100 |
| 1-126 | 769 | 88 |
| 1-127 | 592 | 100 |
| 1-128 | 582 | 93 |
| 1-129 | 596 | 100 |
| 1-130 | 607 | 100 |
| 1-131 | 629 | 100 |
| 1-132 | 590 | 100 |
| 1-133 | 562 | 100 |
| 1-134 | 540 | 100 |
| 1-135 | 749 | 96 |
| 1-136 | 619 | 100 |
| 1-137 | 566 | 100 |
| 1-138 | 563 | 100 |
| 1-139 | 563 | 100 |
| 1-140 | 563 | 100 |
| 1-141 | 603 | 100 |
| 1-142 | 644 | 100 |
| 1-143 | 616 | 100 |
| 1-144 | 606 | 100 |
| 1-145 | 586 | 100 |
| 1-146 | 552 | 100 |
| 1-147 | 598 | 100 |
| 1-148 | 598 | 100 |
| 1-149 | 640 | 100 |
| 1-150 | 586 | 100 |
| 1-151 | 550 | 100 |
| 1-152 | 640 | 100 |
| 1-153 | 536 | 100 |
| 1-154 | 538 | 100 |
| 1-155 | 578 | 91 |
| 1-156 | 590 | 100 |
| 1-157 | 496 | 100 |
| 1-158 | 615 | 100 |
| 1-159 | 602 | 100 |
| 1-160 | 618 | 100 |
| 1-161 | 640 | 94 |
| 1-162 | 590 | 96 |
| 1-163 | 566 | 100 |
| 1-164 | 613 | 100 |
| 1-165 | 590 | 100 |
| 1-166 | 524 | 100 |
| 1-167 | 656 | 100 |
| 1-168 | 618 | 100 |
| 1-169 | 616 | 100 |
| 1-170 | 524 | 100 |
| 1-171 | 536 | 100 |
| 1-172 | 572 | 100 |
| 1-173 | 650 | 100 |
| 1-174 | 536 | 100 |
| 1-175 | 602 | 100 |
| 1-176 | 599 | 100 |
| 1-177 | 573 | 100 |
| 1-178 | 590 | 100 |
| 1-179 | 566 | 100 |
| 1-180 | 629 | 100 |
| 1-181 | 592 | 100 |
| 1-182 | 538 | 100 |
| 1-183 | 632 | 100 |
| 1-184 | 536 | 100 |
| 1-185 | 617 | 100 |
| 1-186 | 606 | 100 |
| 1-187 | 617 | 100 |
| 1-188 | 632 | 100 |
| 1-189 | 662 | 100 |
| 1-190 | 586 | 95 |
| 1-191 | 588 | 100 |
| 1-192 | 588 | 100 |
| 1-193 | 562 | 100 |
| 1-194 | 640 | 100 |
| 1-195 | 640 | 100 |
| 1-196 | 617 | 100 |
| 1-197 | 634 | 100 |

Following the general methods described hereinbefore, the following compounds of Formula (II) as listed in Tables 1B and 1C can be prepared.

TABLE 1B

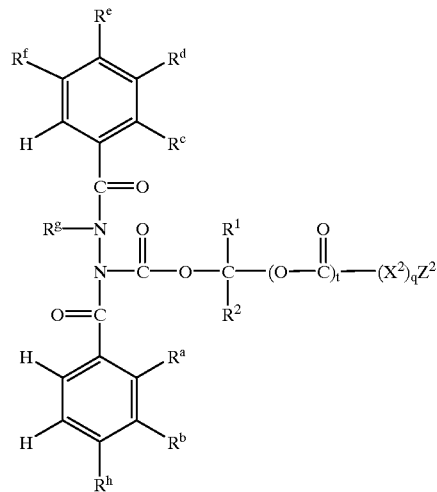

(II)

| Cmpd# | $R^a$ | $R^b$ | $R^c$ | $R^d$ | $R^e$ | $R^f$ | $R^g$ | $R^h$ | $R^1$ | $R^2$ | t | q | $(X^2)_qZ^2$ |
|---|---|---|---|---|---|---|---|---|---|---|---|---|---|
| 1-199 | Me | OMe | H | Me | H | Me | $C(CH_3)_3$ | H | H | H | 0 | 0 | methoxy |
| 1-200 | Me | OMe | H | Me | H | Me | $C(CH_3)_3$ | H | H | H | 0 | 0 | ethoxy |
| 1-201 | Me | OMe | H | Me | H | Me | $C(CH_3)_3$ | H | H | H | 0 | 0 | 2,2,2-trifluoroethoxy |
| 1-202 | Me | OMe | H | Me | H | Me | $C(CH_3)_3$ | H | H | H | 0 | 0 | n-propoxy |
| 1-203 | Me | OMe | H | Me | H | Me | $C(CH_3)_3$ | H | H | H | 0 | 0 | isopropoxy |
| 1-204 | Me | OMe | H | Me | H | Me | $C(CH_3)_3$ | H | H | H | 0 | 0 | n-butoxy |
| 1-205 | Me | OMe | H | Me | H | Me | $C(CH_3)_3$ | H | H | H | 0 | 0 | isobutoxy |
| 1-206 | Me | OMe | H | Me | H | Me | $C(CH_3)_3$ | H | H | H | 0 | 0 | tert-butoxy |
| 1-207 | Me | OMe | H | Me | H | Me | $C(CH_3)_3$ | H | H | H | 0 | 0 | n-pentoxy |
| 1-208 | Me | OMe | H | Me | H | Me | $C(CH_3)_3$ | H | H | H | 0 | 0 | isopentoxy |
| 1-209 | Me | OMe | H | Me | H | Me | $C(CH_3)_3$ | H | H | H | 0 | 0 | tert-pentoxy |
| 1-210 | Me | OMe | H | Me | H | Me | $C(CH_3)_3$ | H | H | H | 0 | 0 | neopentoxy |
| 1-211 | Me | OMe | H | Me | H | Me | $C(CH_3)_3$ | H | H | H | 0 | 0 | n-hexyloxy |
| 1-212 | Me | OMe | H | Me | H | Me | $C(CH_3)_3$ | H | H | H | 0 | 0 | n-decyloxy |
| 1-213 | Me | OMe | H | Me | H | Me | $C(CH_3)_3$ | H | H | H | 0 | 0 | n-undecyloxy |
| 1-214 | Me | OMe | H | Me | H | Me | $C(CH_3)_3$ | H | H | H | 0 | 0 | n-dodecyloxy |
| 1-215 | Me | OMe | H | Me | H | Me | $C(CH_3)_3$ | H | H | H | 0 | 0 | methoxyethoxy |
| 1-216 | Me | OMe | H | Me | H | Me | $C(CH_3)_3$ | H | H | H | 0 | 0 | ethoxymethoxy |
| 1-217 | Me | OMe | H | Me | H | Me | $C(CH_3)_3$ | H | H | H | 0 | 0 | methoxyethoxy |
| 1-218 | Me | OMe | H | Me | H | Me | $C(CH_3)_3$ | H | H | H | 0 | 0 | ethoxyethoxy |
| 1-219 | Me | OMe | H | Me | H | Me | $C(CH_3)_3$ | H | H | H | 0 | 0 | cyclohexyloxy |
| 1-220 | Me | OMe | H | Me | H | Me | $C(CH_3)_3$ | H | H | H | 0 | 0 | phenoxy |
| 1-221 | Me | OMe | H | Me | H | Me | $C(CH_3)_3$ | H | H | H | 0 | 0 | 2,6-dichlorophenoxy |
| 1-222 | Me | OMe | H | Me | H | Me | $C(CH_3)_3$ | H | H | H | 0 | 0 | 2,4,6-trimethylphenoxy |
| 1-223 | Me | OMe | H | Me | H | Me | $C(CH_3)_3$ | H | H | H | 0 | 0 | 2-carboxyphenoxy |
| 1-224 | Me | OMe | H | Me | H | Me | $C(CH_3)_3$ | H | H | H | 0 | 0 | benzyloxy |
| 1-225 | Me | OMe | H | Me | H | Me | $C(CH_3)_3$ | H | H | H | 0 | 0 | 2-phenylethoxy |
| 1-226 | Me | OMe | H | Me | H | Me | $C(CH_3)_3$ | H | H | H | 0 | 0 | 3-phenylpropoxy |
| 1-227 | Me | OMe | H | Me | H | Me | $C(CH_3)_3$ | H | H | H | 0 | 0 | 2-phenoxyethoxy |
| 1-228 | Me | OMe | H | Me | H | Me | $C(CH_3)_3$ | H | H | H | 0 | 0 | 1-naphthoxy |
| 1-229 | Me | OMe | H | Me | H | Me | $C(CH_3)_3$ | H | H | H | 0 | 0 | methylthio |
| 1-230 | Me | OMe | H | Me | H | Me | $C(CH_3)_3$ | H | H | H | 0 | 0 | tert-butylthio |
| 1-231 | Me | OMe | H | Me | H | Me | $C(CH_3)_3$ | H | H | H | 0 | 0 | phenylthio |
| 1-232 | Me | OMe | H | Me | H | Me | $C(CH_3)_3$ | H | H | H | 0 | 1 | (E,E)-8,10-dodecadienoxy |
| 1-233 | Me | OMe | H | Me | H | Me | $C(CH_3)_3$ | H | H | H | 6 | 1 | dodecane-1-oxy |
| 1-234 | Me | OMe | H | Me | H | Me | $C(CH_3)_3$ | H | H | H | 0 | 1 | (E)-11-tetradecen-1-oxy |
| 1-235 | Me | OMe | H | Me | H | Me | $C(CH_3)_3$ | H | H | H | 0 | 1 | (Z)-9-tetradecen-1-oxy |
| 1-236 | Me | OMe | H | Me | H | Me | $C(CH_3)_3$ | H | H | H | 0 | 1 | (Z)-11-hexadecene-1-oxy |
| 1-237 | Me | OMe | H | Me | H | Me | $C(CH_3)_3$ | H | H | H | 0 | 0 | pyrazin-2-yloxy |
| 1-238 | Me | OMe | H | Me | H | Me | $C(CH_3)_3$ | H | H | H | 0 | 0 | 1H-pyrazol-4-yloxy |
| 1-239 | Me | OMe | H | Me | H | Me | $C(CH_3)_3$ | H | H | H | 0 | 0 | 4-pyridyloxy |
| 1-240 | Me | OMe | H | Me | H | Me | $C(CH_3)_3$ | H | H | H | 0 | 0 | 2,6-dichloro-4-pyridyloxy |
| 1-241 | Me | OMe | H | Me | H | Me | $C(CH_3)_3$ | H | H | H | 0 | 0 | EtNH |
| 1-242 | Me | OMe | H | Me | H | Me | $C(CH_3)_3$ | H | H | H | 0 | 0 | n-BuNH |
| 1-243 | Me | OMe | H | Me | H | Me | $C(CH_3)_3$ | H | H | H | 0 | 0 | PhNH |
| 1-244 | Me | OMe | H | Me | H | Me | $C(CH_3)_3$ | H | H | H | 0 | 0 | $PhCH_2NH$ |
| 1-245 | Me | OMe | H | Me | H | Me | $C(CH_3)_3$ | H | H | H | 0 | 0 | $Et_2N$ |
| 1-246 | Me | OMe | H | Me | H | Me | $C(CH_3)_3$ | H | H | H | 0 | 0 | $^+N(ethyl)_3I^-$ |
| 1-247 | Me | OMe | H | Me | H | Me | $C(CH_3)_3$ | H | H | H | 0 | 0 | $^+N(n-butyl)_3I^-$ |
| 1-248 | Me | OMe | H | Me | H | Me | $C(CH_3)_3$ | H | H | H | 0 | 0 | $^+N((ethyl)_2Ph)I^-$ |
| 1-249 | Me | OMe | H | Me | H | Me | $C(CH_3)_3$ | H | H | H | 0 | 0 | $^+N(methyl)_2PhCH_2I^-$ |

TABLE 1B-continued

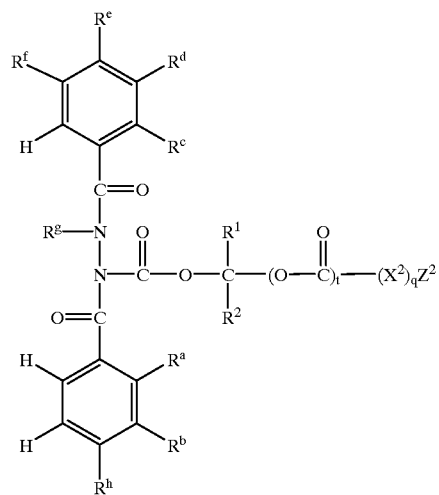

(II)

| Cmpd# | R$^a$ | R$^b$ | R$^c$ | R$^d$ | R$^e$ | R$^f$ | R$^g$ | R$^h$ | R$^1$ | R$^2$ | t | q | (X$^2$)$_q$Z$^2$ |
|---|---|---|---|---|---|---|---|---|---|---|---|---|---|
| 1-250 | Me | OMe | H | Me | H | Me | C(CH$_3$)$_3$ | H | H | H | 0 | 0 | $^+$N(ethyl)$_2$PhCH$_2$I$^-$ |
| 1-251 | Me | OMe | H | Me | H | Me | C(CH$_3$)$_3$ | H | H | H | 0 | 0 | $^+$N(butyl)$_2$PhCH$_2$I$^-$ |
| 1-252 | Me | OMe | H | Me | H | Me | C(CH$_3$)$_3$ | H | methyl | H | 0 | 0 | methoxy |
| 1-253 | Me | OMe | H | Me | H | Me | C(CH$_3$)$_3$ | H | methyl | H | 0 | 0 | ethoxy |
| 1-254 | Me | OMe | H | Me | H | Me | C(CH$_3$)$_3$ | H | methyl | H | 0 | 0 | 2,2,2-trifluoroethoxy |
| 1-255 | Me | OMe | H | Me | H | Me | C(CH$_3$)$_3$ | H | methyl | H | 0 | 0 | n-propoxy |
| 1-256 | Me | OMe | H | Me | H | Me | C(CH$_3$)$_3$ | H | methyl | H | 0 | 0 | tert-butoxy |
| 1-257 | Me | OMe | H | Me | H | Me | C(CH$_3$)$_3$ | H | methyl | H | 0 | 0 | phenoxy |
| 1-258 | Me | OMe | H | Me | H | Me | C(CH$_3$)$_3$ | H | methyl | H | 0 | 0 | 2,6-dichlorophenoxy |
| 1-259 | Me | OMe | H | Me | H | Me | C(CH$_3$)$_3$ | H | methyl | H | 0 | 0 | 2-carboxyphenoxy |
| 1-260 | Me | OMe | H | Me | H | Me | C(CH$_3$)$_3$ | H | methyl | H | 0 | 0 | benzyloxy |
| 1-261 | Me | OMe | H | Me | H | Me | C(CH$_3$)$_3$ | H | methyl | H | 0 | 0 | 1-naphthoxy |
| 1-262 | Me | OMe | H | Me | H | Me | C(CH$_3$)$_3$ | H | methyl | H | 0 | 0 | methylthio |
| 1-263 | Me | OMe | H | Me | H | Me | C(CH$_3$)$_3$ | H | methyl | H | 0 | 0 | tert-butylthio |
| 1-264 | Me | OMe | H | Me | H | Me | C(CH$_3$)$_3$ | H | methyl | H | 0 | 0 | phenylthio |
| 1-265 | Me | OMe | H | Me | H | Me | C(CH$_3$)$_3$ | H | methyl | H | 0 | 1 | (E,E)-8,10-dodecadienoxy |
| 1-266 | Me | OMe | H | Me | H | Me | C(CH$_3$)$_3$ | H | methyl | H | 0 | 1 | dodecane-1-oxy |
| 1-267 | Me | OMe | H | Me | H | Me | C(CH$_3$)$_3$ | H | methyl | H | 0 | 1 | (E)-11-tetradecen-1-oxy |
| 1-268 | Me | OMe | H | Me | H | Me | C(CH$_3$)$_3$ | H | methyl | H | 0 | 1 | (Z)-9-tetradecen-1-oxy |
| 1-269 | Me | OMe | H | Me | H | Me | C(CH$_3$)$_3$ | H | methyl | H | 0 | 1 | (Z)-11-hexadecene-1-oxy |
| 1-270 | Me | OMe | H | Me | H | Me | C(CH$_3$)$_3$ | H | methyl | H | 0 | 0 | pyrazin-2-yloxy |
| 1-271 | Me | OMe | H | Me | H | Me | C(CH$_3$)$_3$ | H | methyl | H | 0 | 0 | 1H-pyrazol-4-yloxy |
| 1-272 | Me | OMe | H | Me | H | Me | C(CH$_3$)$_3$ | H | methyl | H | 0 | 0 | 4-pyridyloxy |
| 1-273 | Me | OMe | H | Me | H | Me | C(CH$_3$)$_3$ | H | methyl | H | 0 | 0 | 2,6-dichloro-4-pyridyloxy |
| 1-274 | Me | OMe | H | Me | H | Me | C(CH$_3$)$_3$ | H | methyl | H | 0 | 0 | EtNH |
| 1-275 | Me | OMe | H | Me | H | Me | C(CH$_3$)$_3$ | H | methyl | H | 0 | 0 | n-BuNH |
| 1-276 | Me | OMe | H | Me | H | Me | C(CH$_3$)$_3$ | H | methyl | H | 0 | 0 | $^+$N(ethyl)$_3$I$^-$ |
| 1-277 | Me | OMe | H | Me | H | Me | C(CH$_3$)$_3$ | H | methyl | H | 0 | 0 | $^+$N(n-butyl)$_3$I$^-$ |
| 1-278 | Me | OMe | H | Me | H | Me | C(CH$_3$)$_3$ | H | methyl | H | 0 | 0 | $^+$N((ethyl)$_2$Ph)I$^-$ |
| 1-279 | Me | OMe | H | Me | H | Me | C(CH$_3$)$_3$ | H | methyl | H | 0 | 0 | $^+$N(methyl)$_2$PhCH$_2$I$^-$ |
| 1-280 | Me | OMe | H | Me | H | Me | C(CH$_3$)$_3$ | H | methyl | H | 0 | 0 | $^+$N(ethyl)$_2$PhCH$_2$I$^-$ |
| 1-281 | Me | OMe | H | Me | H | Me | C(CH$_3$)$_3$ | H | methyl | H | 0 | 0 | $^+$N(butyl)$_2$PhCH$_2$I$^-$ |
| 1-282 | Me | OMe | H | Me | H | Me | C(CH$_3$)$_3$ | H | phenyl | H | 0 | 0 | methoxy |
| 1-283 | Me | OMe | H | Me | H | Me | C(CH$_3$)$_3$ | H | phenyl | H | 0 | 0 | ethoxy |
| 1-284 | Me | OMe | H | Me | H | Me | C(CH$_3$)$_3$ | H | phenyl | H | 0 | 0 | 2,2,2-trifluoroethoxy |
| 1-285 | Me | OMe | H | Me | H | Me | C(CH$_3$)$_3$ | H | phenyl | H | 0 | 0 | n-propoxy |
| 1-286 | Me | OMe | H | Me | H | Me | C(CH$_3$)$_3$ | H | phenyl | H | 0 | 0 | tert-butoxy |
| 1-287 | Me | OMe | H | Me | H | Me | C(CH$_3$)$_3$ | H | phenyl | H | 0 | 0 | n-decyloxy |
| 1-288 | Me | OMe | H | Me | H | Me | C(CH$_3$)$_3$ | H | phenyl | H | 0 | 0 | n-undecyloxy |
| 1-289 | Me | OMe | H | Me | H | Me | C(CH$_3$)$_3$ | H | phenyl | H | 0 | 0 | methoxyethoxy |
| 1-290 | Me | OMe | H | Me | H | Me | C(CH$_3$)$_3$ | H | phenyl | H | 0 | 0 | ethoxymethoxy |
| 1-291 | Me | OMe | H | Me | H | Me | C(CH$_3$)$_3$ | H | phenyl | H | 0 | 0 | ethoxyethoxy |
| 1-292 | Me | OMe | H | Me | H | Me | C(CH$_3$)$_3$ | H | phenyl | H | 0 | 0 | cyclohexyloxy |
| 1-293 | Me | OMe | H | Me | H | Me | C(CH$_3$)$_3$ | H | phenyl | H | 0 | 0 | phenoxy |
| 1-294 | Me | OMe | H | Me | H | Me | C(CH$_3$)$_3$ | H | phenyl | H | 0 | 0 | 2,6-dichlorophenoxy |
| 1-295 | Me | OMe | H | Me | H | Me | C(CH$_3$)$_3$ | H | phenyl | H | 0 | 0 | 2-carboxyphenoxy |
| 1-296 | Me | OMe | H | Me | H | Me | C(CH$_3$)$_3$ | H | phenyl | H | 0 | 0 | benzyloxy |
| 1-297 | Me | OMe | H | Me | H | Me | C(CH$_3$)$_3$ | H | phenyl | H | 0 | 0 | 1-naphthoxy |
| 1-298 | Me | OMe | H | Me | H | Me | C(CH$_3$)$_3$ | H | phenyl | H | 0 | 0 | methylthio |
| 1-299 | Me | OMe | H | Me | H | Me | C(CH$_3$)$_3$ | H | phenyl | H | 0 | 0 | tert-butylthio |
| 1-300 | Me | OMe | H | Me | H | Me | C(CH$_3$)$_3$ | H | phenyl | H | 0 | 0 | phenylthio |

TABLE 1B-continued

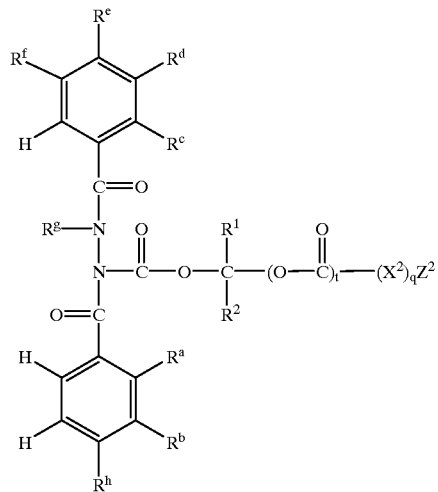

(II)

| Cmpd# | $R^a$ | $R^b$ | $R^c$ | $R^d$ | $R^e$ | $R^f$ | $R^g$ | $R^h$ | $R^1$ | $R^2$ | t | q | $(X^2)_qZ^2$ |
|---|---|---|---|---|---|---|---|---|---|---|---|---|---|
| 1-301 | Me | OMe | H | Me | H | Me | $C(CH_3)_3$ | H | phenyl | H | 0 | 1 | (E,E)-8,10-dodecadienoxy |
| 1-302 | Me | OMe | H | Me | H | Me | $C(CH_3)_3$ | H | phenyl | H | 0 | 1 | dodecane-1-oxy |
| 1-303 | Me | OMe | H | Me | H | Me | $C(CH_3)_3$ | H | phenyl | H | 0 | 1 | (E)-11-tetradecen-1-oxy |
| 1-304 | Me | OMe | H | Me | H | Me | $C(CH_3)_3$ | H | phenyl | H | 0 | 1 | (Z)-9-tetradecen-1-oxy |
| 1-305 | Me | OMe | H | Me | H | Me | $C(CH_3)_3$ | H | phenyl | H | 0 | 1 | (Z)-11-hexadecene-1-oxy |
| 1-306 | Me | OMe | H | Me | H | Me | $C(CH_3)_3$ | H | phenyl | H | 0 | 0 | 2,6-dichloro-4-pyridyloxy |
| 1-307 | Me | OMe | H | Me | H | Me | $C(CH_3)_3$ | H | phenyl | H | 0 | 0 | pyrazin-2-yloxy |
| 1-308 | Me | OMe | H | Me | H | Me | $C(CH_3)_3$ | H | phenyl | H | 0 | 0 | 1H-pyrazol-4-yloxy |
| 1-309 | Me | OMe | H | Me | H | Me | $C(CH_3)_3$ | H | phenyl | H | 0 | 0 | $^+N(ethyl)_3I^-$ |
| 1-310 | Me | OMe | H | Me | H | Me | $C(CH_3)_3$ | H | phenyl | H | 0 | 0 | $^+N(n\text{-}butyl)_3I^-$ |
| 1-311 | Me | OMe | H | Me | H | Me | $C(CH_3)_3$ | H | phenyl | H | 0 | 0 | $^+N((ethyl)_2Ph)I^-$ |
| 1-312 | Me | OMe | H | Me | H | Me | $C(CH_3)_3$ | H | phenyl | H | 0 | 0 | $^+N(methyl)_2PhCH_2I^-$ |
| 1-313 | Me | OMe | H | Me | H | Me | $C(CH_3)_3$ | H | phenyl | H | 0 | 0 | $^+N(ethyl)_2PhCH_2I^-$ |
| 1-314 | Me | OMe | H | Me | H | Me | $C(CH_3)_3$ | H | phenyl | H | 0 | 0 | $^+N(butyl)_2PhCH_2I^-$ |
| 1-315 | H | H | H | Me | H | Me | $C(CH_3)_3$ | Et | H | H | 0 | 0 | methoxy |
| 1-316 | H | H | H | Me | H | Me | $C(CH_3)_3$ | Et | H | H | 0 | 0 | ethoxy |
| 1-317 | H | H | H | Me | H | Me | $C(CH_3)_3$ | Et | H | H | 0 | 0 | 2,2,2-trifluoroethoxy |
| 1-318 | H | H | H | Me | H | Me | $C(CH_3)_3$ | Et | H | H | 0 | 0 | n-propoxy |
| 1-319 | H | H | H | Me | H | Me | $C(CH_3)_3$ | Et | H | H | 0 | 0 | isopropoxy |
| 1-320 | H | H | H | Me | H | Me | $C(CH_3)_3$ | Et | H | H | 0 | 0 | n-butoxy |
| 1-321 | H | H | H | Me | H | Me | $C(CH_3)_3$ | Et | H | H | 0 | 0 | isobutoxy |
| 1-322 | H | H | H | Me | H | Me | $C(CH_3)_3$ | Et | H | H | 0 | 0 | tert-butoxy |
| 1-323 | H | H | H | Me | H | Me | $C(CH_3)_3$ | Et | H | H | 0 | 0 | n-pentoxy |
| 1-324 | H | H | H | Me | H | Me | $C(CH_3)_3$ | Et | H | H | 0 | 0 | isopentoxy |
| 1-325 | H | H | H | Me | H | Me | $C(CH_3)_3$ | Et | H | H | 0 | 0 | tert-pentoxy |
| 1-326 | H | H | H | Me | H | Me | $C(CH_3)_3$ | Et | H | H | 0 | 0 | neopentoxy |
| 1-327 | H | H | H | Me | H | Me | $C(CH_3)_3$ | Et | H | H | 0 | 0 | n-hexyloxy |
| 1-328 | H | H | H | Me | H | Me | $C(CH_3)_3$ | Et | H | H | 0 | 0 | n-decyloxy |
| 1-329 | H | H | H | Me | H | Me | $C(CH_3)_3$ | Et | H | H | 0 | 0 | n-undecyloxy |
| 1-330 | H | H | H | Me | H | Me | $C(CH_3)_3$ | Et | H | H | 0 | 0 | n-dodecyloxy |
| 1-331 | H | H | H | Me | H | Me | $C(CH_3)_3$ | Et | H | H | 0 | 0 | methoxyethoxy |
| 1-332 | H | H | H | Me | H | Me | $C(CH_3)_3$ | Et | H | H | 0 | 0 | ethoxymethoxy |
| 1-333 | H | H | H | Me | H | Me | $C(CH_3)_3$ | Et | H | H | 0 | 0 | methoxyethoxy |
| 1-334 | H | H | H | Me | H | Me | $C(CH_3)_3$ | Et | H | H | 0 | 0 | ethoxyethoxy |
| 1-335 | H | H | H | Me | H | Me | $C(CH_3)_3$ | Et | H | H | 0 | 0 | cyclohexyloxy |
| 1-336 | H | H | H | Me | H | Me | $C(CH_3)_3$ | Et | H | H | 0 | 0 | phenoxy |
| 1-337 | H | H | H | Me | H | Me | $C(CH_3)_3$ | Et | H | H | 0 | 0 | 2,6-dichlorophenoxy |
| 1-338 | H | H | H | Me | H | Me | $C(CH_3)_3$ | Et | H | H | 0 | 0 | 2,4,6-trimethylphenoxy |
| 1-339 | H | H | H | Me | H | Me | $C(CH_3)_3$ | Et | H | H | 0 | 0 | 2-carboxyphenoxy |
| 1-340 | H | H | H | Me | H | Me | $C(CH_3)_3$ | Et | H | H | 0 | 0 | benzyloxy |
| 1-341 | H | H | H | Me | H | Me | $C(CH_3)_3$ | Et | H | H | 0 | 0 | 2-phenylethoxy |
| 1-342 | H | H | H | Me | H | Me | $C(CH_3)_3$ | Et | H | H | 0 | 0 | 3-phenylpropoxy |
| 1-343 | H | H | H | Me | H | Me | $C(CH_3)_3$ | Et | H | H | 0 | 0 | 2-phenoxyethoxy |
| 1-344 | H | H | H | Me | H | Me | $C(CH_3)_3$ | Et | H | H | 0 | 0 | 1-naphthoxy |
| 1-345 | H | H | H | Me | H | Me | $C(CH_3)_3$ | Et | H | H | 0 | 0 | methylthio |
| 1-346 | H | H | H | Me | H | Me | $C(CH_3)_3$ | Et | H | H | 0 | 0 | tert-butylthio |
| 1-347 | H | H | H | Me | H | Me | $C(CH_3)_3$ | Et | H | H | 0 | 0 | phenylthio |
| 1-348 | H | H | H | Me | H | Me | $C(CH_3)_3$ | Et | H | H | 0 | 1 | (E,E)-8,10-dodecadienoxy |
| 1-349 | H | H | H | Me | H | Me | $C(CH_3)_3$ | Et | H | H | 0 | 1 | dodecane-1-oxy |
| 1-350 | H | H | H | Me | H | Me | $C(CH_3)_3$ | Et | H | H | 0 | 1 | (E)-11-tetradecen-1-oxy |
| 1-351 | H | H | H | Me | H | Me | $C(CH_3)_3$ | Et | H | H | 0 | 1 | (Z)-9-tetradecen-1-oxy |

TABLE 1B-continued

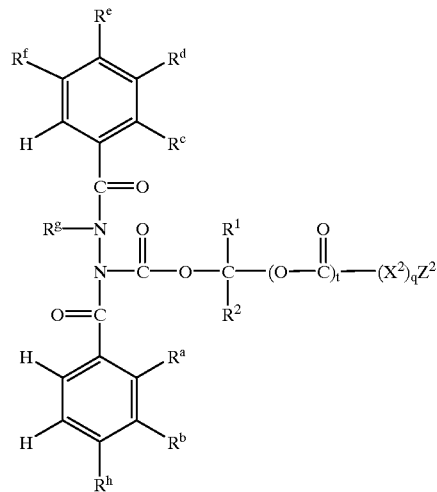

(II)

| Cmpd# | $R^a$ | $R^b$ | $R^c$ | $R^d$ | $R^e$ | $R^f$ | $R^g$ | $R^h$ | $R^1$ | $R^2$ | t | q | $(X^2)_qZ^2$ |
|---|---|---|---|---|---|---|---|---|---|---|---|---|---|
| 1-352 | H | H | H | Me | H | Me | C(CH$_3$)$_3$ | Et | H | H | 0 | 1 | (Z)-11-hexadecene-1-oxy |
| 1-353 | H | H | H | Me | H | Me | C(CH$_3$)$_3$ | Et | H | H | 0 | 1 | pyrazin-2-yloxy |
| 1-354 | H | H | H | Me | H | Me | C(CH$_3$)$_3$ | Et | H | H | 0 | 0 | 1H-pyrazol-4-yloxy |
| 1-355 | H | H | H | Me | H | Me | C(CH$_3$)$_3$ | Et | H | H | 0 | 0 | 4-pyridyloxy |
| 1-356 | H | H | H | Me | H | Me | C(CH$_3$)$_3$ | Et | H | H | 0 | 0 | 2,6-dichloro-4-pyridyloxy |
| 1-357 | H | H | H | Me | H | Me | C(CH$_3$)$_3$ | Et | H | H | 0 | 0 | EtNH |
| 1-358 | H | H | H | Me | H | Me | C(CH$_3$)$_3$ | Et | H | H | 0 | 0 | n-BuNH |
| 1-359 | H | H | H | Me | H | Me | C(CH$_3$)$_3$ | Et | H | H | 0 | 0 | PhNH |
| 1-360 | H | H | H | Me | H | Me | C(CH$_3$)$_3$ | Et | H | H | 0 | 0 | PhCH$_2$NH |
| 1-361 | H | H | H | Me | H | Me | C(CH$_3$)$_3$ | Et | H | H | 0 | 0 | Et$_2$N |
| 1-362 | H | H | H | Me | H | Me | C(CH$_3$)$_3$ | Et | H | H | 0 | 0 | $^+$N(ethyl)$_3$I$^-$ |
| 1-363 | H | H | H | Me | H | Me | C(CH$_3$)$_3$ | Et | H | H | 0 | 0 | $^+$N(n-butyl)$_3$I$^-$ |
| 1-364 | H | H | H | Me | H | Me | C(CH$_3$)$_3$ | Et | H | H | 0 | 0 | $^+$N((ethyl)$_2$Ph)I$^-$ |
| 1-365 | H | H | H | Me | H | Me | C(CH$_3$)$_3$ | Et | H | H | 0 | 0 | $^+$N(methyl)$_2$PhCH$_2$I$^-$ |
| 1-366 | H | H | H | Me | H | Me | C(CH$_3$)$_3$ | Et | H | H | 0 | 0 | $^+$N(ethyl)$_2$PhCH$_2$I$^-$ |
| 1-367 | H | H | H | Me | H | Me | C(CH$_3$)$_3$ | Et | H | H | 0 | 0 | $^+$N(butyl)$_2$PhCH$_2$I$^-$ |
| 1-368 | H | H | H | Me | H | Me | C(CH$_3$)$_3$ | Et | methyl | H | 0 | 0 | methoxy |
| 1-369 | H | H | H | Me | H | Me | C(CH$_3$)$_3$ | Et | methyl | H | 0 | 0 | ethoxy |
| 1-370 | H | H | H | Me | H | Me | C(CH$_3$)$_3$ | Et | methyl | H | 0 | 0 | 2,2,2-trifluoroethoxy |
| 1-371 | H | H | H | Me | H | Me | C(CH$_3$)$_3$ | Et | methyl | H | 0 | 0 | n-propoxy |
| 1-372 | H | H | H | Me | H | Me | C(CH$_3$)$_3$ | Et | methyl | H | 0 | 0 | tert-butoxy |
| 1-373 | H | H | H | Me | H | Me | C(CH$_3$)$_3$ | Et | methyl | H | 0 | 0 | phenoxy |
| 1-374 | H | H | H | Me | H | Me | C(CH$_3$)$_3$ | Et | methyl | H | 0 | 0 | 2,6-dichlorophenoxy |
| 1-375 | H | H | H | Me | H | Me | C(CH$_3$)$_3$ | Et | methyl | H | 0 | 0 | 2-carboxyphenoxy |
| 1-376 | H | H | H | Me | H | Me | C(CH$_3$)$_3$ | Et | methyl | H | 0 | 0 | benzyloxy |
| 1-377 | H | H | H | Me | H | Me | C(CH$_3$)$_3$ | Et | methyl | H | 0 | 0 | 1-naphthoxy |
| 1-378 | H | H | H | Me | H | Me | C(CH$_3$)$_3$ | Et | methyl | H | 0 | 0 | methylthio |
| 1-379 | H | H | H | Me | H | Me | C(CH$_3$)$_3$ | Et | methyl | H | 0 | 0 | tert-butylthio |
| 1-380 | H | H | H | Me | H | Me | C(CH$_3$)$_3$ | Et | methyl | H | 0 | 0 | phenylthio |
| 1-381 | H | H | H | Me | H | Me | C(CH$_3$)$_3$ | Et | methyl | H | 0 | 1 | (E,E)-8,10-dodecadienoxy |
| 1-382 | H | H | H | Me | H | Me | C(CH$_3$)$_3$ | Et | methyl | H | 0 | 1 | dodecane-1-oxy |
| 1-383 | H | H | H | Me | H | Me | C(CH$_3$)$_3$ | Et | methyl | H | 0 | 1 | (E)-11-tetradecen-1-oxy |
| 1-384 | H | H | H | Me | H | Me | C(CH$_3$)$_3$ | Et | methyl | H | 0 | 1 | (Z)-9-tetradecen-1-oxy |
| 1-385 | H | H | H | Me | H | Me | C(CH$_3$)$_3$ | Et | methyl | H | 0 | 1 | (Z)-11-hexadecene-1-oxy |
| 1-386 | H | H | H | Me | H | Me | C(CH$_3$)$_3$ | Et | methyl | H | 0 | 0 | pyrazin-2-yloxy |
| 1-387 | H | H | H | Me | H | Me | C(CH$_3$)$_3$ | Et | methyl | H | 0 | 0 | 1H-pyrazol-4-yloxy |
| 1-388 | H | H | H | Me | H | Me | C(CH$_3$)$_3$ | Et | methyl | H | 0 | 0 | 4-pyridyloxy |
| 1-389 | H | H | H | Me | H | Me | C(CH$_3$)$_3$ | Et | methyl | H | 0 | 0 | 2,6-dichloro-4-pyridyloxy |
| 1-390 | H | H | H | Me | H | Me | C(CH$_3$)$_3$ | Et | methyl | H | 0 | 0 | EtNH |
| 1-391 | H | H | H | Me | H | Me | C(CH$_3$)$_3$ | Et | methyl | H | 0 | 0 | n-BuNH |
| 1-392 | H | H | H | Me | H | Me | C(CH$_3$)$_3$ | Et | methyl | H | 0 | 0 | $^+$N(ethyl)$_3$I$^-$ |
| 1-393 | H | H | H | Me | H | Me | C(CH$_3$)$_3$ | Et | methyl | H | 0 | 0 | $^+$N(n-butyl)$_3$I$^-$ |
| 1-394 | H | H | H | Me | H | Me | C(CH$_3$)$_3$ | Et | methyl | H | 0 | 0 | $^+$N((ethyl)$_2$Ph)I$^-$ |
| 1-395 | H | H | H | Me | H | Me | C(CH$_3$)$_3$ | Et | methyl | H | 0 | 0 | $^+$N(methyl)$_2$PhCH$_2$I$^-$ |
| 1-396 | H | H | H | Me | H | Me | C(CH$_3$)$_3$ | Et | methyl | H | 0 | 0 | $^+$N(ethyl)$_2$PhCH$_2$I$^-$ |
| 1-397 | H | H | H | Me | H | Me | C(CH$_3$)$_3$ | Et | methyl | H | 0 | 0 | $^+$N(butyl)$_2$PhCH$_2$I$^-$ |
| 1-398 | H | H | H | Me | H | Me | C(CH$_3$)$_3$ | Et | phenyl | H | 0 | 0 | methoxy |
| 1-399 | H | H | H | Me | H | Me | C(CH$_3$)$_3$ | Et | phenyl | H | 0 | 0 | ethoxy |
| 1-400 | H | H | H | Me | H | Me | C(CH$_3$)$_3$ | Et | phenyl | H | 0 | 0 | 2,2,2-trifluoroethoxy |
| 1-401 | H | H | H | Me | H | Me | C(CH$_3$)$_3$ | Et | phenyl | H | 0 | 0 | n-propoxy |
| 1-402 | H | H | H | Me | H | Me | C(CH$_3$)$_3$ | Et | phenyl | H | 0 | 0 | tert-butoxy |

TABLE 1B-continued

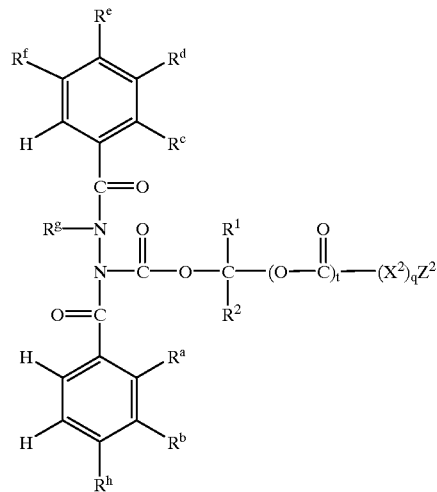

(II)

| Cmpd# | $R^a$ | $R^b$ | $R^c$ | $R^d$ | $R^e$ | $R^f$ | $R^g$ | $R^h$ | $R^1$ | $R^2$ | t | q | $(X^2)_qZ^2$ |
|---|---|---|---|---|---|---|---|---|---|---|---|---|---|
| 1-403 | H | H | H | Me | H | Me | $C(CH_3)_3$ | Et | phenyl | H | 0 | 0 | n-decyloxy |
| 1-404 | H | H | H | Me | H | Me | $C(CH_3)_3$ | Et | phenyl | H | 0 | 0 | n-undecyloxy |
| 1-405 | H | H | H | Me | H | Me | $C(CH_3)_3$ | Et | phenyl | H | 0 | 0 | methoxyethoxy |
| 1-406 | H | H | H | Me | H | Me | $C(CH_3)_3$ | Et | phenyl | H | 0 | 0 | ethoxymethoxy |
| 1-407 | H | H | H | Me | H | Me | $C(CH_3)_3$ | Et | phenyl | H | 0 | 0 | ethoxyethoxy |
| 1-408 | H | H | H | Me | H | Me | $C(CH_3)_3$ | Et | phenyl | H | 0 | 0 | cyclohexyloxy |
| 1-409 | H | H | H | Me | H | Me | $C(CH_3)_3$ | Et | phenyl | H | 0 | 0 | phenoxy |
| 1-410 | H | H | H | Me | H | Me | $C(CH_3)_3$ | Et | phenyl | H | 0 | 0 | 2,6-dichlorophenoxy |
| 1-411 | H | H | H | Me | H | Me | $C(CH_3)_3$ | Et | phenyl | H | 0 | 0 | 2-carboxyphenoxy |
| 1-412 | H | H | H | Me | H | Me | $C(CH_3)_3$ | Et | phenyl | H | 0 | 0 | benzyloxy |
| 1-413 | H | H | H | Me | H | Me | $C(CH_3)_3$ | Et | phenyl | H | 0 | 0 | 1-naphthoxy |
| 1-414 | H | H | H | Me | H | Me | $C(CH_3)_3$ | Et | phenyl | H | 0 | 0 | methylthio |
| 1-415 | H | H | H | Me | H | Me | $C(CH_3)_3$ | Et | phenyl | H | 0 | 0 | tert-butylthio |
| 1-416 | H | H | H | Me | H | Me | $C(CH_3)_3$ | Et | phenyl | H | 0 | 0 | phenylthio |
| 1-417 | H | H | H | Me | H | Me | $C(CH_3)_3$ | Et | phenyl | H | 0 | 1 | (E,E)-8,10-dodecadienoxy |
| 1-418 | H | H | H | Me | H | Me | $C(CH_3)_3$ | Et | phenyl | H | 0 | 1 | dodecane-1-oxy |
| 1-419 | H | H | H | Me | H | Me | $C(CH_3)_3$ | Et | phenyl | H | 0 | 1 | (E)-11-tetradecen-1-oxy |
| 1-420 | H | H | H | Me | H | Me | $C(CH_3)_3$ | Et | phenyl | H | 0 | 1 | (Z)-9-tetradecen-1-oxy |
| 1-421 | H | H | H | Me | H | Me | $C(CH_3)_3$ | Et | phenyl | H | 0 | 1 | (Z)-11-hexadecene-1-oxy |
| 1-422 | H | H | H | Me | H | Me | $C(CH_3)_3$ | Et | phenyl | H | 0 | 0 | 2,6-dichloro-4-pyridyloxy |
| 1-423 | H | H | H | Me | H | Me | $C(CH_3)_3$ | Et | phenyl | H | 0 | 0 | pyrazin-2-yloxy |
| 1-424 | H | H | H | Me | H | Me | $C(CH_3)_3$ | Et | phenyl | H | 0 | 0 | 1H-pyrazol-4-yloxy |
| 1-425 | H | H | H | Me | H | Me | $C(CH_3)_3$ | Et | phenyl | H | 0 | 0 | $^+N(ethyl)_3I^-$ |
| 1-426 | H | H | H | Me | H | Me | $C(CH_3)_3$ | Et | phenyl | H | 0 | 0 | $^+N(n-butyl)_3I^-$ |
| 1-427 | H | H | H | Me | H | Me | $C(CH_3)_3$ | Et | phenyl | H | 0 | 0 | $^+N((ethyl)_2Ph)I^-$ |
| 1-428 | H | H | H | Me | H | Me | $C(CH_3)_3$ | Et | phenyl | H | 0 | 0 | $^+N(methyl)_2PhCH_2I^-$ |
| 1-429 | H | H | H | Me | H | Me | $C(CH_3)_3$ | Et | phenyl | H | 0 | 0 | $^+N(ethyl)_2PhCH_2I^-$ |
| 1-430 | H | H | H | Me | H | Me | $C(CH_3)_3$ | Et | phenyl | H | 0 | 0 | $^+N(butyl)_2PhCH_2I^-$ |
| 1-431 | H | H | H | H | H | H | $C(CH_3)_3$ | Cl | H | H | 0 | 0 | methoxy |
| 1-432 | H | H | H | H | H | H | $C(CH_3)_3$ | Cl | H | H | 0 | 0 | ethoxy |
| 1-433 | H | H | H | H | H | H | $C(CH_3)_3$ | Cl | H | H | 0 | 0 | 2,2,2-trifluoroethoxy |
| 1-434 | H | H | H | H | H | H | $C(CH_3)_3$ | Cl | H | H | 0 | 0 | n-propoxy |
| 1-435 | H | H | H | H | H | H | $C(CH_3)_3$ | Cl | H | H | 0 | 0 | isopropoxy |
| 1-436 | H | H | H | H | H | H | $C(CH_3)_3$ | Cl | H | H | 0 | 0 | n-butoxy |
| 1-437 | H | H | H | H | H | H | $C(CH_3)_3$ | Cl | H | H | 0 | 0 | isobutoxy |
| 1-438 | H | H | H | H | H | H | $C(CH_3)_3$ | Cl | H | H | 0 | 0 | tert-butoxy |
| 1-439 | H | H | H | H | H | H | $C(CH_3)_3$ | Cl | H | H | 0 | 0 | n-pentoxy |
| 1-440 | H | H | H | H | H | H | $C(CH_3)_3$ | Cl | H | H | 0 | 0 | isopentoxy |
| 1-441 | H | H | H | H | H | H | $C(CH_3)_3$ | Cl | H | H | 0 | 0 | tert-pentoxy |
| 1-442 | H | H | H | H | H | H | $C(CH_3)_3$ | Cl | H | H | 0 | 0 | neopentoxy |
| 1-443 | H | H | H | H | H | H | $C(CH_3)_3$ | Cl | H | H | 0 | 0 | n-hexyloxy |
| 1-444 | H | H | H | H | H | H | $C(CH_3)_3$ | Cl | H | H | 0 | 0 | n-decyloxy |
| 1-445 | H | H | H | H | H | H | $C(CH_3)_3$ | Cl | H | H | 0 | 0 | n-undecyloxy |
| 1-446 | H | H | H | H | H | H | $C(CH_3)_3$ | Cl | H | H | 0 | 0 | n-dodecyloxy |
| 1-447 | H | H | H | H | H | H | $C(CH_3)_3$ | Cl | H | H | 0 | 0 | methoxyethoxy |
| 1-448 | H | H | H | H | H | H | $C(CH_3)_3$ | Cl | H | H | 0 | 0 | ethoxymethoxy |
| 1-449 | H | H | H | H | H | H | $C(CH_3)_3$ | Cl | H | H | 0 | 0 | methoxyethoxy |
| 1-450 | H | H | H | H | H | H | $C(CH_3)_3$ | Cl | H | H | 0 | 0 | ethoxyethoxy |
| 1-451 | H | H | H | H | H | H | $C(CH_3)_3$ | Cl | H | H | 0 | 0 | cyclohexyloxy |
| 1-452 | H | H | H | H | H | H | $C(CH_3)_3$ | Cl | H | H | 0 | 0 | phenoxy |
| 1-453 | H | H | H | H | H | H | $C(CH_3)_3$ | Cl | H | H | 0 | 0 | 2,6-dichlorophenoxy |

TABLE 1B-continued

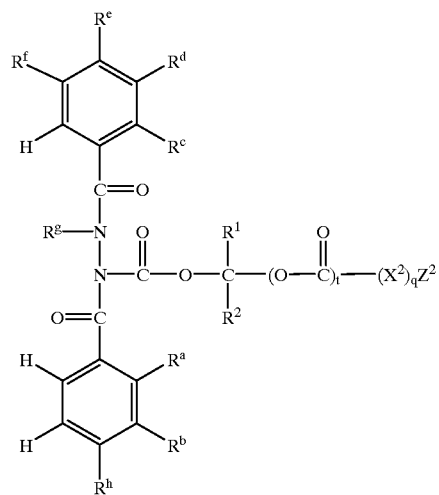

(II)

| Cmpd# | $R^a$ | $R^b$ | $R^c$ | $R^d$ | $R^e$ | $R^f$ | $R^g$ | $R^h$ | $R^1$ | $R^2$ | t | q | $(X^2)_qZ^2$ |
|---|---|---|---|---|---|---|---|---|---|---|---|---|---|
| 1-454 | H | H | H | H | H | H | $C(CH_3)_3$ | Cl | H | H | 0 | 0 | 2,4,6-trimethylphenoxy |
| 1-455 | H | H | H | H | H | H | $C(CH_3)_3$ | Cl | H | H | 0 | 0 | 2-carboxyphenoxy |
| 1-456 | H | H | H | H | H | H | $C(CH_3)_3$ | Cl | H | H | 0 | 0 | benzyloxy |
| 1-457 | H | H | H | H | H | H | $C(CH_3)_3$ | Cl | H | H | 0 | 0 | 2-phenylethoxy |
| 1-458 | H | H | H | H | H | H | $C(CH_3)_3$ | Cl | H | H | 0 | 0 | 3-phenylpropoxy |
| 1-459 | H | H | H | H | H | H | $C(CH_3)_3$ | Cl | H | H | 0 | 0 | 2-phenoxyethoxy |
| 1-460 | H | H | H | H | H | H | $C(CH_3)_3$ | Cl | H | H | 0 | 0 | 1-naphthoxy |
| 1-461 | H | H | H | H | H | H | $C(CH_3)_3$ | Cl | H | H | 0 | 0 | methylthio |
| 1-462 | H | H | H | H | H | H | $C(CH_3)_3$ | Cl | H | H | 0 | 0 | tert-butylthio |
| 1-463 | H | H | H | H | H | H | $C(CH_3)_3$ | Cl | H | H | 0 | 0 | phenylthio |
| 1-464 | H | H | H | H | H | H | $C(CH_3)_3$ | Cl | H | H | 0 | 1 | (E,E)-8,10-dodecadienoxy |
| 1-465 | H | H | H | H | H | H | $C(CH_3)_3$ | Cl | H | H | 0 | 1 | dodecane-1-oxy |
| 1-466 | H | H | H | H | H | H | $C(CH_3)_3$ | Cl | H | H | 0 | 1 | (E)-11-tetradecen-1-oxy |
| 1-467 | H | H | H | H | H | H | $C(CH_3)_3$ | Cl | H | H | 0 | 1 | (Z)-9-tetradecen-1-oxy |
| 1-468 | H | H | H | H | H | H | $C(CH_3)_3$ | Cl | H | H | 0 | 1 | (Z)-11-hexadecene-1-oxy |
| 1-469 | H | H | H | H | H | H | $C(CH_3)_3$ | Cl | H | H | 0 | 0 | pyrazin-2-yloxy |
| 1-470 | H | H | H | H | H | H | $C(CH_3)_3$ | Cl | H | H | 0 | 0 | 1H-pyrazol-4-yloxy |
| 1-471 | H | H | H | H | H | H | $C(CH_3)_3$ | Cl | .H | H | 0 | 0 | 4-pyridyloxy |
| 1-472 | H | H | H | H | H | H | $C(CH_3)_3$ | Cl | H | H | 0 | 0 | 2,6-dichloro-4-pyridyloxy |
| 1-473 | H | H | H | H | H | H | $C(CH_3)_3$ | Cl | H | H | 0 | 0 | EtNH |
| 1-474 | H | H | H | H | H | H | $C(CH_3)_3$ | Cl | H | H | 0 | 0 | n-BuNH |
| 1-475 | H | H | H | H | H | H | $C(CH_3)_3$ | Cl | H | H | 0 | 0 | PhNH |
| 1-476 | H | H | H | H | H | H | $C(CH_3)_3$ | Cl | H | H | 0 | 0 | $PhCH_2NH$ |
| 1-477 | H | H | H | H | H | H | $C(CH_3)_3$ | Cl | H | H | 0 | 0 | $Et_2N$ |
| 1-478 | H | H | H | H | H | H | $C(CH_3)_3$ | Cl | H | H | 0 | 0 | $^+N(ethyl)_3I^-$ |
| 1-479 | H | H | H | H | H | H | $C(CH_3)_3$ | Cl | H | H | 0 | 0 | $^+N(n-butyl)_3I^-$ |
| 1-480 | H | H | H | H | H | H | $C(CH_3)_3$ | Cl | H | H | 0 | 0 | $^+N((ethyl)_2Ph)I^-$ |
| 1-481 | H | H | H | H | H | H | $C(CH_3)_3$ | Cl | H | H | 0 | 0 | $^+N(methyl)_2PhCH_2I^-$ |
| 1-482 | H | H | H | H | H | H | $C(CH_3)_3$ | Cl | H | H | 0 | 0 | $^+N(ethyl)_2PhCH_2I^-$ |
| 1-483 | H | H | H | H | H | H | $C(CH_3)_3$ | Cl | H | H | 0 | 0 | $^+N(butyl)_2PhCH_2I^-$ |
| 1-484 | H | H | H | H | H | H | $C(CH_3)_3$ | Cl | methyl | H | 0 | 0 | methoxy |
| 1-485 | H | H | H | H | H | H | $C(CH_3)_3$ | Cl | methyl | H | 0 | 0 | ethoxy |
| 1-486 | H | H | H | H | H | H | $C(CH_3)_3$ | Cl | methyl | H | 0 | 0 | 2,2,2-trifluoroethoxy |
| 1-487 | H | H | H | H | H | H | $C(CH_3)_3$ | Cl | methyl | H | 0 | 0 | n-propoxy |
| 1-488 | H | H | H | H | H | H | $C(CH_3)_3$ | Cl | methyl | H | 0 | 0 | tert-butoxy |
| 1-489 | H | H | H | H | H | H | $C(CH_3)_3$ | Cl | methyl | H | 0 | 0 | phenoxy |
| 1-490 | H | H | H | H | H | H | $C(CH_3)_3$ | Cl | methyl | H | 0 | 0 | 2,6-dichlorophenoxy |
| 1-491 | H | H | H | H | H | H | $C(CH_3)_3$ | Cl | methyl | H | 0 | 0 | 2-carboxyphenoxy |
| 1-492 | H | H | H | H | H | H | $C(CH_3)_3$ | Cl | methyl | H | 0 | 0 | benzyloxy |
| 1-493 | H | H | H | H | H | H | $C(CH_3)_3$ | Cl | methyl | H | 0 | 0 | 1-naphthoxy |
| 1-494 | H | H | H | H | H | H | $C(CH_3)_3$ | Cl | methyl | H | 0 | 0 | methylthio |
| 1-495 | H | H | H | H | H | H | $C(CH_3)_3$ | Cl | methyl | H | 0 | 0 | tert-butylthio |
| 1-496 | H | H | H | H | H | H | $C(CH_3)_3$ | Cl | methyl | H | 0 | 0 | phenylthio |
| 1-497 | H | H | H | H | H | H | $C(CH_3)_3$ | Cl | methyl | H | 0 | 1 | (E,E)-8,10-dodecadienoxy |
| 1-498 | H | H | H | H | H | H | $C(CH_3)_3$ | Cl | methyl | H | 0 | 1 | dodecane-1-oxy |
| 1-499 | H | H | H | H | H | H | $C(CH_3)_3$ | Cl | methyl | H | 0 | 1 | (E)-11-tetradecen-1-oxy |
| 1-500 | H | H | H | H | H | H | $C(CH_3)_3$ | Cl | methyl | H | 0 | 1 | (Z)-9-tetradecen-1-oxy |
| 1-501 | H | H | H | H | H | H | $C(CH_3)_3$ | Cl | methyl | H | 0 | 1 | (Z)-11-hexadecene-1-oxy |
| 1-502 | H | H | H | H | H | H | $C(CH_3)_3$ | Cl | methyl | H | 0 | 0 | pyrazin-2-yloxy |
| 1-503 | H | H | H | H | H | H | $C(CH_3)_3$ | Cl | methyl | H | 0 | 0 | 1H-pyrazol-4-yloxy |
| 1-504 | H | H | H | H | H | H | $C(CH_3)_3$ | Cl | methyl | H | 0 | 0 | 4-pyridyloxy |

TABLE 1B-continued (II)

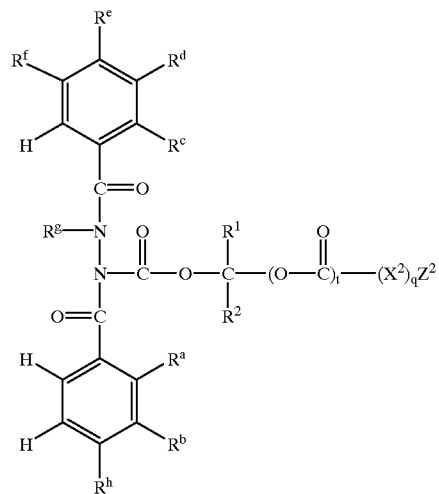

| Cmpd# | R$^a$ | R$^b$ | R$^c$ | R$^d$ | R$^e$ | R$^f$ | R$^g$ | R$^h$ | R$^1$ | R$^2$ | t | q | (X$^2$)$_q$Z$^2$ |
|---|---|---|---|---|---|---|---|---|---|---|---|---|---|
| 1-505 | H | H | H | H | H | H | C(CH$_3$)$_3$ | Cl | methyl | H | 0 | 0 | 2,6-dichloro-4-pyridyloxy |
| 1-506 | H | H | H | H | H | H | C(CH$_3$)$_3$ | Cl | methyl | H | 0 | 0 | EtNH |
| 1-507 | H | H | H | H | H | H | C(CH$_3$)$_3$ | Cl | methyl | H | 0 | 0 | n-BuNH |
| 1-508 | H | H | H | H | H | H | C(CH$_3$)$_3$ | Cl | methyl | H | 0 | 0 | $^+$N(ethyl)$_3$I$^-$ |
| 1-509 | H | H | H | H | H | H | C(CH$_3$)$_3$ | Cl | methyl | H | 0 | 0 | $^+$N(n-butyl)$_3$I$^-$ |
| 1-510 | H | H | H | H | H | H | C(CH$_3$)$_3$ | Cl | methyl | H | 0 | 0 | $^+$N((ethyl)$_2$Ph)I$^-$ |
| 1-511 | H | H | H | H | H | H | C(CH$_3$)$_3$ | Cl | methyl | H | 0 | 0 | $^+$N(methyl)$_2$PhCH$_2$I$^-$ |
| 1-512 | H | H | H | H | H | H | C(CH$_3$)$_3$ | Cl | methyl | H | 0 | 0 | $^+$N(ethyl)$_2$PhCH$_2$I$^-$ |
| 1-513 | H | H | H | H | H | H | C(CH$_3$)$_3$ | Cl | methyl | H | 0 | 0 | $^+$N(butyl)$_2$PhCH$_2$I$^-$ |
| 1-514 | H | H | H | H | H | H | C(CH$_3$)$_3$ | Cl | phenyl | H | 0 | 0 | methoxy |
| 1-515 | H | H | H | H | H | H | C(CH$_3$)$_3$ | Cl | phenyl | H | 0 | 0 | ethoxy |
| 1-516 | H | H | H | H | H | H | C(CH$_3$)$_3$ | Cl | phenyl | H | 0 | 0 | 2,2,2-trifluoroethoxy |
| 1-517 | H | H | H | H | H | H | C(CH$_3$)$_3$ | Cl | phenyl | H | 0 | 0 | n-propoxy |
| 1-518 | H | H | H | H | H | H | C(CH$_3$)$_3$ | Cl | phenyl | H | 0 | 0 | tert-butoxy |
| 1-519 | H | H | H | H | H | H | C(CH$_3$)$_3$ | Cl | phenyl | H | 0 | 0 | n-decyloxy |
| 1-520 | H | H | H | H | H | H | C(CH$_3$)$_3$ | Cl | phenyl | H | 0 | 0 | n-undecyloxy |
| 1-521 | H | H | H | H | H | H | C(CH$_3$)$_3$ | Cl | phenyl | H | 0 | 0 | methoxyethoxy |
| 1-522 | H | H | H | H | H | H | C(CH$_3$)$_3$ | Cl | phenyl | H | 0 | 0 | ethoxymethoxy |
| 1-523 | H | H | H | H | H | H | C(CH$_3$)$_3$ | Cl | phenyl | H | 0 | 0 | ethoxyethoxy |
| 1-524 | H | H | H | H | H | H | C(CH$_3$)$_3$ | Cl | phenyl | H | 0 | 0 | cyclohexyloxy |
| 1-525 | H | H | H | H | H | H | C(CH$_3$)$_3$ | Cl | phenyl | H | 0 | 0 | phenoxy |
| 1-526 | H | H | H | H | H | H | C(CH$_3$)$_3$ | Cl | phenyl | H | 0 | 0 | 2,6-dichlorophenoxy |
| 1-527 | H | H | H | H | H | H | C(CH$_3$)$_3$ | Cl | phenyl | H | 0 | 0 | 2-carboxyphenoxy |
| 1-528 | H | H | H | H | H | H | C(CH$_3$)$_3$ | Cl | phenyl | H | 0 | 0 | benzyloxy |
| 1-529 | H | H | H | H | H | H | C(CH$_3$)$_3$ | Cl | phenyl | H | 0 | 0 | 1-naphthoxy |
| 1-530 | H | H | H | H | H | H | C(CH$_3$)$_3$ | Cl | phenyl | H | 0 | 0 | methylthio |
| 1-531 | H | H | H | H | H | H | C(CH$_3$)$_3$ | Cl | phenyl | H | 0 | 0 | tert-butylthio |
| 1-532 | H | H | H | H | H | H | C(CH$_3$)$_3$ | Cl | phenyl | H | 0 | 0 | phenylthio |
| 1-533 | H | H | H | H | H | H | C(CH$_3$)$_3$ | Cl | phenyl | H | 0 | 1 | (E,E)-8,10-dodecadienoxy |
| 1-534 | H | H | H | H | H | H | C(CH$_3$)$_3$ | Cl | phenyl | H | 0 | 1 | dodecane-1-oxy |
| 1-535 | H | H | H | H | H | H | C(CH$_3$)$_3$ | Cl | phenyl | H | 0 | 1 | (E)-11-tetradecen-1-oxy |
| 1-536 | H | H | H | H | H | H | C(CH$_3$)$_3$ | Cl | phenyl | H | 0 | 1 | (Z)-9-tetradecen-1-oxy |
| 1-537 | H | H | H | H | H | H | C(CH$_3$)$_3$ | Cl | phenyl | H | 0 | 1 | (Z)-11-hexadecene-1-oxy |
| 1-538 | H | H | H | H | H | H | C(CH$_3$)$_3$ | Cl | phenyl | H | 0 | 0 | 2,6-dichloro-4-pyridyloxy |
| 1-539 | H | H | H | H | H | H | C(CH$_3$)$_3$ | Cl | phenyl | H | 0 | 0 | pyrazin-2-yloxy |
| 1-540 | H | H | H | H | H | H | C(CH$_3$)$_3$ | Cl | phenyl | H | 0 | 0 | 1H-pyrazol-4-yloxy |
| 1-541 | H | H | H | H | H | H | C(CH$_3$)$_3$ | Cl | phenyl | H | 0 | 0 | $^+$N(ethyl)$_3$I$^-$ |
| 1-542 | H | H | H | H | H | H | C(CH$_3$)$_3$ | Cl | phenyl | H | 0 | 0 | $^+$N(n-butyl)$_3$I$^-$ |
| 1-543 | H | H | H | H | H | H | C(CH$_3$)$_3$ | Cl | phenyl | H | 0 | 0 | $^+$N((ethyl)$_2$Ph)I$^-$ |
| 1-544 | H | H | H | H | H | H | C(CH$_3$)$_3$ | Cl | phenyl | H | 0 | 0 | $^+$N(methyl)$_2$PhCH$_2$I$^-$ |
| 1-545 | H | H | H | H | H | H | C(CH$_3$)$_3$ | Cl | phenyl | H | 0 | 0 | $^+$N(ethyl)$_2$PhCH$_2$I$^-$ |
| 1-546 | H | H | H | H | H | H | C(CH$_3$)$_3$ | Cl | phenyl | H | 0 | 0 | $^+$N(butyl)$_2$PhCH$_2$I$^-$ |

TABLE 1C

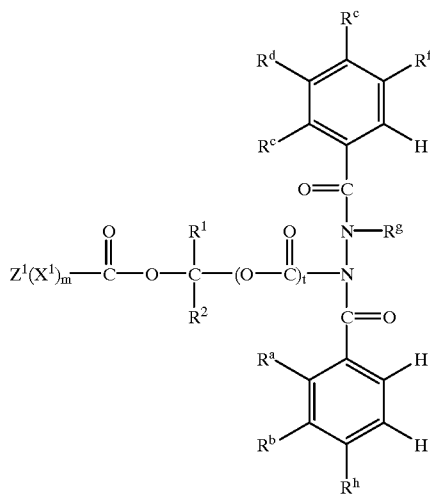

(IIA)

| Cmpd# | R$^a$ | R$^b$ | R$^c$ | R$^d$ | R$^e$ | R$^f$ | R$^g$ | R$^h$ | R$^1$ | R$^2$ | t | m | Z$^1$(X$^1$)$_m$ |
|---|---|---|---|---|---|---|---|---|---|---|---|---|---|
| 1-547 | Me | OMe | H | Me | H | Me | C(CH$_3$)$_3$ | H | H | H | 0 | 0 | methoxy |
| 1-548 | Me | OMe | H | Me | H | Me | C(CH$_3$)$_3$ | H | H | H | 0 | 0 | ethoxy |
| 1-549 | Me | OMe | H | Me | H | Me | C(CH$_3$)$_3$ | H | H | H | 0 | 0 | 2,2,2-trifluoroethoxy |
| 1-550 | Me | OMe | H | Me | H | Me | C(CH$_3$)$_3$ | H | H | H | 0 | 0 | n-propoxy |
| 1-551 | Me | OMe | H | Me | H | Me | C(CH$_3$)$_3$ | H | H | H | 0 | 0 | isopropoxy |
| 1-552 | Me | OMe | H | Me | H | Me | C(CH$_3$)$_3$ | H | H | H | 0 | 0 | n-butoxy |
| 1-553 | Me | OMe | H | Me | H | Me | C(CH$_3$)$_3$ | H | H | H | 0 | 0 | isobutoxy |
| 1-554 | Me | OMe | H | Me | H | Me | C(CH$_3$)$_3$ | H | H | H | 0 | 0 | tert-butoxy |
| 1-555 | Me | OMe | H | Me | H | Me | C(CH$_3$)$_3$ | H | H | H | 0 | 0 | n-pentoxy |
| 1-556 | Me | OMe | H | Me | H | Me | C(CH$_3$)$_3$ | H | H | H | 0 | 0 | isopentoxy |
| 1-557 | Me | OMe | H | Me | H | Me | C(CH$_3$)$_3$ | H | H | H | 0 | 0 | tert-pentoxy |
| 1-558 | Me | OMe | H | Me | H | Me | C(CH$_3$)$_3$ | H | H | H | 0 | 0 | neopentoxy |
| 1-559 | Me | OMe | H | Me | H | Me | C(CH$_3$)$_3$ | H | H | H | 0 | 0 | n-hexyloxy |
| 1-560 | Me | OMe | H | Me | H | Me | C(CH$_3$)$_3$ | H | H | H | 0 | 0 | n-decyloxy |
| 1-561 | Me | OMe | H | Me | H | Me | C(CH$_3$)$_3$ | H | H | H | 0 | 0 | n-undecyloxy |
| 1-562 | Me | OMe | H | Me | H | Me | C(CH$_3$)$_3$ | H | H | H | 0 | 0 | n-dodecyloxy |
| 1-563 | Me | OMe | H | Me | H | Me | C(CH$_3$)$_3$ | H | H | H | 0 | 0 | methoxyethoxy |
| 1-564 | Me | OMe | H | Me | H | Me | C(CH$_3$)$_3$ | H | H | H | 0 | 0 | ethoxymethoxy |
| 1-565 | Me | OMe | H | Me | H | Me | C(CH$_3$)$_3$ | H | H | H | 0 | 0 | methoxyethoxy |
| 1-566 | Me | OMe | H | Me | H | Me | C(CH$_3$)$_3$ | H | H | H | 0 | 0 | ethoxyethoxy |
| 1-567 | Me | OMe | H | Me | H | Me | C(CH$_3$)$_3$ | H | H | H | 0 | 0 | cyclohexyloxy |
| 1-568 | Me | OMe | H | Me | H | Me | C(CH$_3$)$_3$ | H | H | H | 0 | 0 | phenoxy |
| 1-569 | Me | OMe | H | Me | H | Me | C(CH$_3$)$_3$ | H | H | H | 0 | 0 | 2,6-dichlorophenoxy |
| 1-570 | Me | OMe | H | Me | H | Me | C(CH$_3$)$_3$ | H | H | H | 0 | 0 | 2,4,6-trimethylphenoxy |
| 1-571 | Me | OMe | H | Me | H | Me | C(CH$_3$)$_3$ | H | H | H | 0 | 0 | 2-carboxyphenoxy |
| 1-572 | Me | OMe | H | Me | H | Me | C(CH$_3$)$_3$ | H | H | H | 0 | 0 | benzyloxy |
| 1-573 | Me | OMe | H | Me | H | Me | C(CH$_3$)$_3$ | H | H | H | 0 | 0 | 2-phenylethoxy |
| 1-574 | Me | OMe | H | Me | H | Me | C(CH$_3$)$_3$ | H | H | H | 0 | 0 | 3-phenylpropoxy |
| 1-575 | Me | OMe | H | Me | H | Me | C(CH$_3$)$_3$ | H | H | H | 0 | 0 | 2-phenoxyethoxy |
| 1-576 | Me | OMe | H | Me | H | Me | C(CH$_3$)$_3$ | H | H | H | 0 | 0 | 1-naphthoxy |
| 1-577 | Me | OMe | H | Me | H | Me | C(CH$_3$)$_3$ | H | H | H | 0 | 0 | methylthio |
| 1-578 | Me | OMe | H | Me | H | Me | C(CH$_3$)$_3$ | H | H | H | 0 | 0 | tert-butylthio |
| 1-579 | Me | OMe | H | Me | H | Me | C(CH$_3$)$_3$ | H | H | H | 0 | 0 | phenylthio |
| 1-580 | Me | OMe | H | Me | H | Me | C(CH$_3$)$_3$ | H | H | H | 0 | 1 | (E,E)-8,10-dodecadienoxy |
| 1-581 | Me | OMe | H | Me | H | Me | C(CH$_3$)$_3$ | H | H | H | 0 | 1 | dodecane-1-oxy |
| 1-582 | Me | OMe | H | Me | H | Me | C(CH$_3$)$_3$ | H | H | H | 0 | 1 | (E)-11-tetradecen-1-oxy |
| 1-583 | Me | OMe | H | Me | H | Me | C(CH$_3$)$_3$ | H | H | H | 0 | 1 | (Z)-9-tetradecen-1-oxy |
| 1-584 | Me | OMe | H | Me | H | Me | C(CH$_3$)$_3$ | H | H | H | 0 | 1 | (Z)-11-hexadecene-1-oxy |
| 1-585 | Me | OMe | H | Me | H | Me | C(CH$_3$)$_3$ | H | H | H | 0 | 0 | pyrazin-2-yloxy |
| 1-586 | Me | OMe | H | Me | H | Me | C(CH$_3$)$_3$ | H | H | H | 0 | 0 | 1H-pyrazol-4-yloxy |
| 1-587 | Me | OMe | H | Me | H | Me | C(CH$_3$)$_3$ | H | H | H | 0 | 0 | 4-pyridyloxy |
| 1-588 | Me | OMe | H | Me | H | Me | C(CH$_3$)$_3$ | H | H | H | 0 | 0 | 2,6-dichloro-4-pyridyloxy |
| 1-589 | Me | OMe | H | Me | H | Me | C(CH$_3$)$_3$ | H | H | H | 0 | 0 | EtNH |
| 1-590 | Me | OMe | H | Me | H | Me | C(CH$_3$)$_3$ | H | H | H | 0 | 0 | (Et)$_2$N |
| 1-591 | Me | OMe | H | Me | H | Me | C(CH$_3$)$_3$ | H | H | H | 0 | 0 | n-BuNH |
| 1-592 | Me | OMe | H | Me | H | Me | C(CH$_3$)$_3$ | H | H | H | 0 | 0 | (CH$_3$)$_3$CNH |
| 1-593 | Me | OMe | H | Me | H | Me | C(CH$_3$)$_3$ | H | H | H | 0 | 0 | PhNH |
| 1-594 | Me | OMe | H | Me | H | Me | C(CH$_3$)$_3$ | H | H | H | 0 | 0 | (4Cl)PhNH |
| 1-595 | Me | OMe | H | Me | H | Me | C(CH$_3$)$_3$ | H | H | H | 0 | 0 | PhCH$_2$NH |
| 1-596 | Me | OMe | H | Me | H | Me | C(CH$_3$)$_3$ | H | H | H | 0 | 0 | PhCH$_2$CH$_2$NH |
| 1-597 | Me | OMe | H | Me | H | Me | C(CH$_3$)$_3$ | H | H | H | 0 | 0 | Ph$_2$N |

TABLE 1C-continued

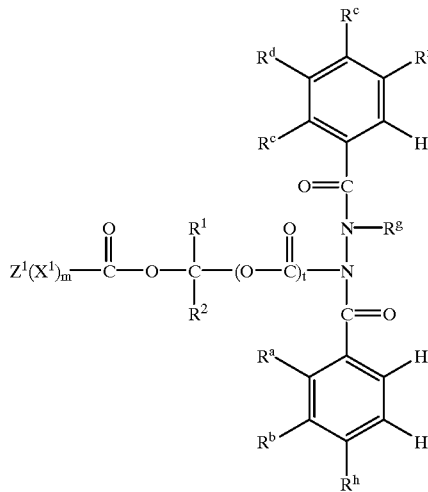

(IIA)

| Cmpd# | $R^a$ | $R^b$ | $R^c$ | $R^d$ | $R^e$ | $R^f$ | $R^g$ | $R^h$ | $R^1$ | $R^2$ | t | m | $Z^1(X^1)_m$ |
|---|---|---|---|---|---|---|---|---|---|---|---|---|---|
| 1-598 | Me | OMe | H | Me | H | Me | C(CH$_3$)$_3$ | H | H | H | 0 | 0 | 4-pyridylNH |
| 1-599 | Me | OMe | H | Me | H | Me | C(CH$_3$)$_3$ | H | H | H | 0 | 0 | Ph(Me)N |
| 1-600 | Me | OMe | H | Me | H | Me | C(CH$_3$)$_3$ | H | methyl | H | 0 | 0 | methoxy |
| 1-601 | Me | OMe | H | Me | H | Me | C(CH$_3$)$_3$ | H | methyl | H | 0 | 0 | ethoxy |
| 1-602 | Me | OMe | H | Me | H | Me | C(CH$_3$)$_3$ | H | methyl | H | 0 | 0 | 2,2,2-trifluoroethoxy |
| 1-603 | Me | OMe | H | Me | H | Me | C(CH$_3$)$_3$ | H | methyl | H | 0 | 0 | n-propoxy |
| 1-604 | Me | OMe | H | Me | H | Me | C(CH$_3$)$_3$ | H | methyl | H | 0 | 0 | tert-butoxy |
| 1-605 | Me | OMe | H | Me | H | Me | C(CH$_3$)$_3$ | H | methyl | H | 0 | 0 | phenoxy |
| 1-606 | Me | OMe | H | Me | H | Me | C(CH$_3$)$_3$ | H | methyl | H | 0 | 0 | 2,6-dichlorophenoxy |
| 1-607 | Me | OMe | H | Me | H | Me | C(CH$_3$)$_3$ | H | methyl | H | 0 | 0 | 2-carboxyphenoxy |
| 1-608 | Me | OMe | H | Me | H | Me | C(CH$_3$)$_3$ | H | methyl | H | 0 | 0 | benzyloxy |
| 1-609 | Me | OMe | H | Me | H | Me | C(CH$_3$)$_3$ | H | methyl | H | 0 | 0 | 1-naphthoxy |
| 1-610 | Me | OMe | H | Me | H | Me | C(CH$_3$)$_3$ | H | methyl | H | 0 | 0 | methylthio |
| 1-611 | Me | OMe | H | Me | H | Me | C(CH$_3$)$_3$ | H | methyl | H | 0 | 0 | tert-butylthio |
| 1-612 | Me | OMe | H | Me | H | Me | C(CH$_3$)$_3$ | H | methyl | H | 0 | 0 | phenylthio |
| 1-613 | Me | OMe | H | Me | H | Me | C(CH$_3$)$_3$ | H | methyl | H | 0 | 1 | (E,E)-8,10-dodecadienoxy |
| 1-614 | Me | OMe | H | Me | H | Me | C(CH$_3$)$_3$ | H | methyl | H | 0 | 1 | dodecane-1-oxy |
| 1-615 | Me | OMe | H | Me | H | Me | C(CH$_3$)$_3$ | H | methyl | H | 0 | 1 | (E)-11-tetradecen-1-oxy |
| 1-616 | Me | OMe | H | Me | H | Me | C(CH$_3$)$_3$ | H | methyl | H | 0 | 1 | (Z)-9-tetradecen-1-oxy |
| 1-617 | Me | OMe | H | Me | H | Me | C(CH$_3$)$_3$ | H | methyl | H | 0 | 1 | (Z)-11-hexadecene-1-oxy |
| 1-618 | Me | OMe | H | Me | H | Me | C(CH$_3$)$_3$ | H | methyl | H | 0 | 0 | pyrazin-2-yloxy |
| 1-619 | Me | OMe | H | Me | H | Me | C(CH$_3$)$_3$ | H | methyl | H | 0 | 0 | 1H-pyrazol-4-yloxy |
| 1-620 | Me | OMe | H | Me | H | Me | C(CH$_3$)$_3$ | H | methyl | H | 0 | 0 | 4-pyridyloxy |
| 1-621 | Me | OMe | H | Me | H | Me | C(CH$_3$)$_3$ | H | methyl | H | 0 | 0 | 1H-pyrazol-4-yloxy |
| 1-622 | Me | OMe | H | Me | H | Me | C(CH$_3$)$_3$ | H | methyl | H | 0 | 0 | 4-pyridyloxy |
| 1-623 | Me | OMe | H | Me | H | Me | C(CH$_3$)$_3$ | H | methyl | H | 0 | 0 | 2,6-dichloro-4-pyridyloxy |
| 1-624 | Me | OMe | H | Me | H | Me | C(CH$_3$)$_3$ | H | methyl | H | 0 | 0 | EtNH |
| 1-625 | Me | OMe | H | Me | H | Me | C(CH$_3$)$_3$ | H | methyl | H | 0 | 0 | (Et)$_2$N |
| 1-626 | Me | OMe | H | Me | H | Me | C(CH$_3$)$_3$ | H | methyl | H | 0 | 0 | n-BuNH |
| 1-627 | Me | OMe | H | Me | H | Me | C(CH$_3$)$_3$ | H | methyl | H | 0 | 0 | PhNH |
| 1-628 | Me | OMe | H | Me | H | Me | C(CH$_3$)$_3$ | H | methyl | H | 0 | 0 | PhCH$_2$NH |
| 1-629 | Me | OMe | H | Me | H | Me | C(CH$_3$)$_3$ | H | methyl | H | 0 | 0 | PhCH$_2$CH$_2$NH |
| 1-630 | Me | OMe | H | Me | H | Me | C(CH$_3$)$_3$ | H | phenyl | H | 0 | 0 | methoxy |
| 1-631 | Me | OMe | H | Me | H | Me | C(CH$_3$)$_3$ | H | phenyl | H | 0 | 0 | ethoxy |
| 1-632 | Me | OMe | H | Me | H | Me | C(CH$_3$)$_3$ | H | phenyl | H | 0 | 0 | 2,2,2-trifluoroethoxy |
| 1-633 | Me | OMe | H | Me | H | Me | C(CH$_3$)$_3$ | H | phenyl | H | 0 | 0 | n-propoxy |
| 1-634 | Me | OMe | H | Me | H | Me | C(CH$_3$)$_3$ | H | phenyl | H | 0 | 0 | tert-butoxy |
| 1-635 | Me | OMe | H | Me | H | Me | C(CH$_3$)$_3$ | H | phenyl | H | 0 | 0 | n-decyloxy |
| 1-636 | Me | OMe | H | Me | H | Me | C(CH$_3$)$_3$ | H | phenyl | H | 0 | 0 | n-undecyloxy |
| 1-637 | Me | OMe | H | Me | H | Me | C(CH$_3$)$_3$ | H | phenyl | H | 0 | 0 | methoxyethoxy |
| 1-638 | Me | OMe | H | Me | H | Me | C(CH$_3$)$_3$ | H | phenyl | H | 0 | 0 | ethoxymethoxy |
| 1-639 | Me | OMe | H | Me | H | Me | C(CH$_3$)$_3$ | H | phenyl | H | 0 | 0 | ethoxyethoxy |
| 1-640 | Me | OMe | H | Me | H | Me | C(CH$_3$)$_3$ | H | phenyl | H | 0 | 0 | cyclohexyloxy |
| 1-641 | Me | OMe | H | Me | H | Me | C(CH$_3$)$_3$ | H | phenyl | H | 0 | 0 | phenoxy |
| 1-642 | Me | OMe | H | Me | H | Me | C(CH$_3$)$_3$ | H | phenyl | H | 0 | 0 | 2,6-dichlorophenoxy |
| 1-643 | Me | OMe | H | Me | H | Me | C(CH$_3$)$_3$ | H | phenyl | H | 0 | 0 | 2-carboxyphenoxy |
| 1-644 | Me | OMe | H | Me | H | Me | C(CH$_3$)$_3$ | H | phenyl | H | 0 | 0 | benzyloxy |
| 1-645 | Me | OMe | H | Me | H | Me | C(CH$_3$)$_3$ | H | phenyl | H | 0 | 0 | 1-naphthoxy |
| 1-646 | Me | OMe | H | Me | H | Me | C(CH$_3$)$_3$ | H | phenyl | H | 0 | 0 | methylthio |
| 1-647 | Me | OMe | H | Me | H | Me | C(CH$_3$)$_3$ | H | phenyl | H | 0 | 0 | tert-butylthio |
| 1-648 | Me | OMe | H | Me | H | Me | C(CH$_3$)$_3$ | H | phenyl | H | 0 | 0 | phenylthio |

TABLE 1C-continued

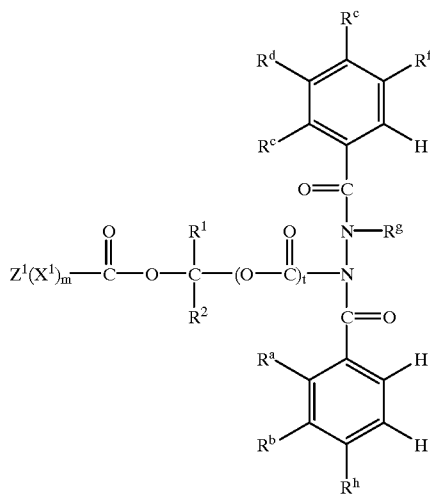

(IIA)

| Cmpd# | $R^a$ | $R^b$ | $R^c$ | $R^d$ | $R^e$ | $R^f$ | $R^g$ | $R^h$ | $R^1$ | $R^2$ | t | m | $Z^1(X^1)_m$ |
|---|---|---|---|---|---|---|---|---|---|---|---|---|---|
| 1-649 | Me | OMe | H | Me | H | Me | C(CH$_3$)$_3$ | H | phenyl | H | 0 | 1 | (E,E)-8,10-dodecadienoxy |
| 1-650 | Me | OMe | H | Me | H | Me | C(CH$_3$)$_3$ | H | phenyl | H | 0 | 1 | dodecane-1-oxy |
| 1-651 | Me | OMe | H | Me | H | Me | C(CH$_3$)$_3$ | H | phenyl | H | 0 | 1 | (E)-11-tetradecen-1-oxy |
| 1-652 | Me | OMe | H | Me | H | Me | C(CH$_3$)$_3$ | H | phenyl | H | 0 | 1 | (Z)-9-tetradecen-1-oxy |
| 1-653 | Me | OMe | H | Me | H | Me | C(CH$_3$)$_3$ | H | phenyl | H | 0 | 1 | (Z)-11-hexadecene-1-oxy |
| 1-654 | Me | OMe | H | Me | H | Me | C(CH$_3$)$_3$ | H | phenyl | H | 0 | 0 | 2,6-dichloro-4-pyridyloxy |
| 1-655 | Me | OMe | H | Me | H | Me | C(CH$_3$)$_3$ | H | phenyl | H | 0 | 0 | pyrazin-2-yloxy |
| 1-656 | Me | OMe | H | Me | H | Me | C(CH$_3$)$_3$ | H | phenyl | H | 0 | 0 | 1H-pyrazol-4-yloxy |
| 1-657 | Me | OMe | H | Me | H | Me | C(CH$_3$)$_3$ | H | phenyl | H | 0 | 0 | EtNH |
| 1-658 | Me | OMe | H | Me | H | Me | C(CH$_3$)$_3$ | H | phenyl | H | 0 | 0 | (Et)$_2$N |
| 1-659 | Me | OMe | H | Me | H | Me | C(CH$_3$)$_3$ | H | phenyl | H | 0 | 0 | (CH$_3$)$_3$CNH |
| 1-660 | Me | OMe | H | Me | H | Me | C(CH$_3$)$_3$ | H | phenyl | H | 0 | 0 | PhNH |
| 1-661 | Me | OMe | H | Me | H | Me | C(CH$_3$)$_3$ | H | phenyl | H | 0 | 0 | PhCH$_2$NH |
| 1-662 | Me | OMe | H | Me | H | Me | C(CH$_3$)$_3$ | H | phenyl | H | 0 | 0 | PhCH$_2$CH$_2$NH |
| 1-663 | H | H | H | Me | H | Me | C(CH$_3$)$_3$ | Et | H | H | 0 | 0 | methoxy |
| 1-664 | H | H | H | Me | H | Me | C(CH$_3$)$_3$ | Et | H | H | 0 | 0 | ethoxy |
| 1-665 | H | H | H | Me | H | Me | C(CH$_3$)$_3$ | Et | H | H | 0 | 0 | 2,2,2-trifluoroethoxy |
| 1-666 | H | H | H | Me | H | Me | C(CH$_3$)$_3$ | Et | H | H | 0 | 0 | n-propoxy |
| 1-667 | H | H | H | Me | H | Me | C(CH$_3$)$_3$ | Et | H | H | 0 | 0 | isopropoxy |
| 1-668 | H | H | H | Me | H | Me | C(CH$_3$)$_3$ | Et | H | H | 0 | 0 | n-butoxy |
| 1-669 | H | H | H | Me | H | Me | C(CH$_3$)$_3$ | Et | H | H | 0 | 0 | isobutoxy |
| 1-670 | H | H | H | Me | H | Me | C(CH$_3$)$_3$ | Et | H | H | 0 | 0 | tert-butoxy |
| 1-671 | H | H | H | Me | H | Me | C(CH$_3$)$_3$ | Et | H | H | 0 | 0 | n-pentoxy |
| 1-672 | H | H | H | Me | H | Me | C(CH$_3$)$_3$ | Et | H | H | 0 | 0 | isopentoxy |
| 1-673 | H | H | H | Me | H | Me | C(CH$_3$)$_3$ | Et | H | H | 0 | 0 | tert-pentoxy |
| 1-674 | H | H | H | Me | H | Me | C(CH$_3$)$_3$ | Et | H | H | 0 | 0 | neopentoxy |
| 1-675 | H | H | H | Me | H | Me | C(CH$_3$)$_3$ | Et | H | H | 0 | 0 | n-hexyloxy |
| 1-676 | H | H | H | Me | H | Me | C(CH$_3$)$_3$ | Et | H | H | 0 | 0 | n-decyloxy |
| 1-677 | H | H | H | Me | H | Me | C(CH$_3$)$_3$ | Et | H | H | 0 | 0 | n-undecyloxy |
| 1-678 | H | H | H | Me | H | Me | C(CH$_3$)$_3$ | Et | H | H | 0 | 0 | n-dodecyloxy |
| 1-679 | H | H | H | Me | H | Me | C(CH$_3$)$_3$ | Et | H | H | 0 | 0 | methoxyethoxy |
| 1-680 | H | H | H | Me | H | Me | C(CH$_3$)$_3$ | Et | H | H | 0 | 0 | ethoxymethoxy |
| 1-681 | H | H | H | Me | H | Me | C(CH$_3$)$_3$ | Et | H | H | 0 | 0 | methoxyethoxy |
| 1-682 | H | H | H | Me | H | Me | C(CH$_3$)$_3$ | Et | H | H | 0 | 0 | ethoxyethoxy |
| 1-683 | H | H | H | Me | H | Me | C(CH$_3$)$_3$ | Et | H | H | 0 | 0 | cyclohexyloxy |
| 1-684 | H | H | H | Me | H | Me | C(CH$_3$)$_3$ | Et | H | H | 0 | 0 | phenoxy |
| 1-685 | H | H | H | Me | H | Me | C(CH$_3$)$_3$ | Et | H | H | 0 | 0 | 2,6-dichlorophenoxy |
| 1-686 | H | H | H | Me | H | Me | C(CH$_3$)$_3$ | Et | H | H | 0 | 0 | 2,4,6-trimethylphenoxy |
| 1-687 | H | H | H | Me | H | Me | C(CH$_3$)$_3$ | Et | H | H | 0 | 0 | 2-carboxyphenoxy |
| 1-688 | H | H | H | Me | H | Me | C(CH$_3$)$_3$ | Et | H | H | 0 | 0 | benzyloxy |
| 1-689 | H | H | H | Me | H | Me | C(CH$_3$)$_3$ | Et | H | H | 0 | 0 | 2-phenylethoxy |
| 1-690 | H | H | H | Me | H | Me | C(CH$_3$)$_3$ | Et | H | H | 0 | 0 | 3-phenylpropoxy |
| 1-691 | H | H | H | Me | H | Me | C(CH$_3$)$_3$ | Et | H | H | 0 | 0 | 2-phenoxyethoxy |
| 1-692 | H | H | H | Me | H | Me | C(CH$_3$)$_3$ | Et | H | H | 0 | 0 | 1-naphthoxy |
| 1-693 | H | H | H | Me | H | Me | C(CH$_3$)$_3$ | Et | H | H | 0 | 0 | methylthio |
| 1-694 | H | H | H | Me | H | Me | C(CH$_3$)$_3$ | Et | H | H | 0 | 0 | tert-butylthio |
| 1-695 | H | H | H | Me | H | Me | C(CH$_3$)$_3$ | Et | H | H | 0 | 0 | phenylthio |
| 1-696 | H | H | H | Me | H | Me | C(CH$_3$)$_3$ | Et | H | H | 0 | 1 | (E,E)-8,10-dodecadienoxy |
| 1-697 | H | H | H | Me | H | Me | C(CH$_3$)$_3$ | Et | H | H | 0 | 1 | dodecane-1-oxy |
| 1-698 | H | H | H | Me | H | Me | C(CH$_3$)$_3$ | Et | H | H | 0 | 1 | (E)-11-tetradecen-1-oxy |
| 1-699 | H | H | H | Me | H | Me | C(CH$_3$)$_3$ | Et | H | H | 0 | 1 | (Z)-9-tetradecen-1-oxy |

TABLE 1C-continued

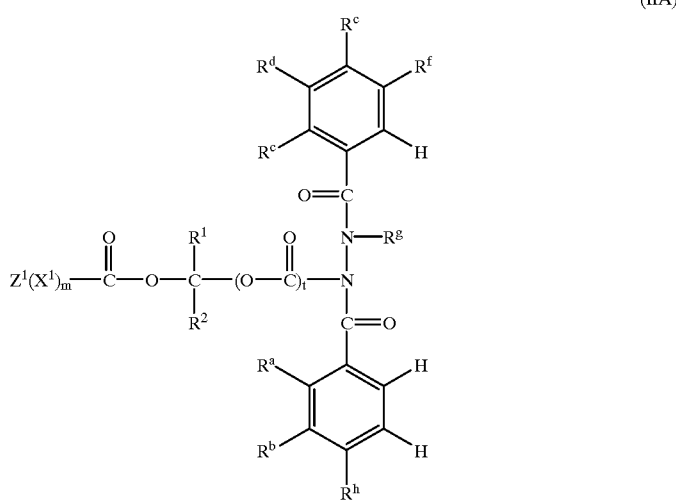

(IIA)

| Cmpd# | R$^a$ | R$^b$ | R$^c$ | R$^d$ | R$^e$ | R$^f$ | R$^g$ | R$^h$ | R$^1$ | R$^2$ | t | m | Z$^1$(X$^1$)$_m$ |
|---|---|---|---|---|---|---|---|---|---|---|---|---|---|
| 1-700 | H | H | H | Me | H | Me | C(CH$_3$)$_3$ | Et | H | H | 0 | 1 | (Z)-11-hexadecene-1-oxy |
| 1-701 | H | H | H | Me | H | Me | C(CH$_3$)$_3$ | Et | H | H | 0 | 0 | pyrazin-2-yloxy |
| 1-702 | H | H | H | Me | H | Me | C(CH$_3$)$_3$ | Et | H | H | 0 | 0 | 1H-pyrazol-4-yloxy |
| 1-703 | H | H | H | Me | H | Me | C(CH$_3$)$_3$ | Et | H | H | 0 | 0 | 4-pyridyloxy |
| 1-704 | H | H | H | Me | H | Me | C(CH$_3$)$_3$ | Et | H | H | 0 | 0 | 1H-pyrazol-4-yloxy |
| 1-705 | H | H | H | Me | H | Me | C(CH$_3$)$_3$ | Et | H | H | 0 | 0 | 4-pyridyloxy |
| 1-706 | H | H | H | Me | H | Me | C(CH$_3$)$_3$ | Et | H | H | 0 | 0 | 2,6-dichloro-4-pyridyloxy |
| 1-707 | H | H | H | Me | H | Me | C(CH$_3$)$_3$ | Et | H | H | 0 | 0 | EtNH |
| 1-708 | H | H | H | Me | H | Me | C(CH$_3$)$_3$ | Et | H | H | 0 | 0 | (Et)$_2$NH |
| 1-709 | H | H | H | Me | H | Me | C(CH$_3$)$_3$ | Et | H | H | 0 | 0 | n-BuNH |
| 1-710 | H | H | H | Me | H | Me | C(CH$_3$)$_3$ | Et | H | H | 0 | 0 | PhNH |
| 1-711 | H | H | H | Me | H | Me | C(CH$_3$)$_3$ | Et | H | H | 0 | 0 | (4Cl)PhNH |
| 1-712 | H | H | H | Me | H | Me | C(CH$_3$)$_3$ | Et | H | H | 0 | 0 | PhCH$_2$NH |
| 1-713 | H | H | H | Me | H | Me | C(CH$_3$)$_3$ | Et | H | H | 0 | 0 | PhCH$_2$CH$_2$NH |
| 1-714 | H | H | H | Me | H | Me | C(CH$_3$)$_3$ | Et | H | H | 0 | 0 | Ph$_2$N |
| 1-715 | H | H | H | Me | H | Me | C(CH$_3$)$_3$ | Et | H | H | 0 | 0 | 4-pyridyl |
| 1-716 | H | H | H | Me | H | Me | C(CH$_3$)$_3$ | Et | methyl | H | 0 | 0 | methoxy |
| 1-717 | H | H | H | Me | H | Me | C(CH$_3$)$_3$ | Et | methyl | H | 0 | 0 | ethoxy |
| 1-718 | H | H | H | Me | H | Me | C(CH$_3$)$_3$ | Et | methyl | H | 0 | 0 | 2,2,2-trifluoroethoxy |
| 1-719 | H | H | H | Me | H | Me | C(CH$_3$)$_3$ | Et | methyl | H | 0 | 0 | n-propoxy |
| 1-720 | H | H | H | Me | H | Me | C(CH$_3$)$_3$ | Et | methyl | H | 0 | 0 | tert-butoxy |
| 1-721 | H | H | H | Me | H | Me | C(CH$_3$)$_3$ | Et | methyl | H | 0 | 0 | phenoxy |
| 1-722 | H | H | H | Me | H | Me | C(CH$_3$)$_3$ | Et | methyl | H | 0 | 0 | 2,6-dichlorophenoxy |
| 1-723 | H | H | H | Me | H | Me | C(CH$_3$)$_3$ | Et | methyl | H | 0 | 0 | 2-carboxyphenoxy |
| 1-724 | H | H | H | Me | H | Me | C(CH$_3$)$_3$ | Et | methyl | H | 0 | 0 | benzyloxy |
| 1-725 | H | H | H | Me | H | Me | C(CH$_3$)$_3$ | Et | methyl | H | 0 | 0 | 1-naphthoxy |
| 1-726 | H | H | H | Me | H | Me | C(CH$_3$)$_3$ | Et | methyl | H | 0 | 0 | methylthio |
| 1-727 | H | H | H | Me | H | Me | C(CH$_3$)$_3$ | Et | methyl | H | 0 | 0 | tert-butylthio |
| 1-728 | H | H | H | Me | H | Me | C(CH$_3$)$_3$ | Et | methyl | H | 0 | 0 | phenylthio |
| 1-729 | H | H | H | Me | H | Me | C(CH$_3$)$_3$ | Et | methyl | H | 0 | 1 | (E,E)-8,10-dodecadienoxy |
| 1-730 | H | H | H | Me | H | Me | C(CH$_3$)$_3$ | Et | methyl | H | 0 | 1 | dodecane-1-oxy |
| 1-731 | H | H | H | Me | H | Me | C(CH$_3$)$_3$ | Et | methyl | H | 0 | 1 | (E)-11-tetradecen-1-oxy |
| 1-732 | H | H | H | Me | H | Me | C(CH$_3$)$_3$ | Et | methyl | H | 0 | 1 | (Z)-9-tetradecen-1-oxy |
| 1-733 | H | H | H | Me | H | Me | C(CH$_3$)$_3$ | Et | methyl | H | 0 | 1 | (Z)-11-hexadecene-1-oxy |
| 1-734 | H | H | H | Me | H | Me | C(CH$_3$)$_3$ | Et | methyl | H | 0 | 0 | pyrazin-2-yloxy |
| 1-735 | H | H | H | Me | H | Me | C(CH$_3$)$_3$ | Et | methyl | H | 0 | 0 | 1H-pyrazol-4-yloxy |
| 1-736 | H | H | H | Me | H | Me | C(CH$_3$)$_3$ | Et | methyl | H | 0 | 0 | 4-pyridyloxy |
| 1-737 | H | H | H | Me | H | Me | C(CH$_3$)$_3$ | Et | methyl | H | 0 | 0 | EtNH |
| 1-738 | H | H | H | Me | H | Me | C(CH$_3$)$_3$ | Et | methyl | H | 0 | 0 | (Et)$_2$N |
| 1-739 | H | H | H | Me | H | Me | C(CH$_3$)$_3$ | Et | methyl | H | 0 | 0 | (CH$_3$)$_3$CNH |
| 1-740 | H | H | H | Me | H | Me | C(CH$_3$)$_3$ | Et | methyl | H | 0 | 0 | PhNH |
| 1-741 | H | H | H | Me | H | Me | C(CH$_3$)$_3$ | Et | methyl | H | 0 | 0 | PhCH$_2$NH |
| 1-742 | H | H | H | Me | H | Me | C(CH$_3$)$_3$ | Et | methyl | H | 0 | 0 | PhCH$_2$CH$_2$NH |
| 1-743 | H | H | H | Me | H | Me | C(CH$_3$)$_3$ | Et | methyl | H | 0 | 0 | Ph$_2$N |
| 1-744 | H | H | H | Me | H | Me | C(CH$_3$)$_3$ | Et | methyl | H | 0 | 0 | 4-pyridylNH |
| 1-745 | H | H | H | Me | H | Me | C(CH$_3$)$_3$ | Et | methyl | H | 0 | 0 | Ph(Me)N |
| 1-746 | H | H | H | Me | H | Me | C(CH$_3$)$_3$ | Et | phenyl | H | 0 | 0 | methoxy |
| 1-747 | H | H | H | Me | H | Me | C(CH$_3$)$_3$ | Et | phenyl | H | 0 | 0 | ethoxy |
| 1-748 | H | H | H | Me | H | Me | C(CH$_3$)$_3$ | Et | phenyl | H | 0 | 0 | 2,2,2-trifluoroethoxy |
| 1-749 | H | H | H | Me | H | Me | C(CH$_3$)$_3$ | Et | phenyl | H | 0 | 0 | n-propoxy |
| 1-750 | H | H | H | Me | H | Me | C(CH$_3$)$_3$ | Et | phenyl | H | 0 | 0 | tert-butoxy |

TABLE 1C-continued

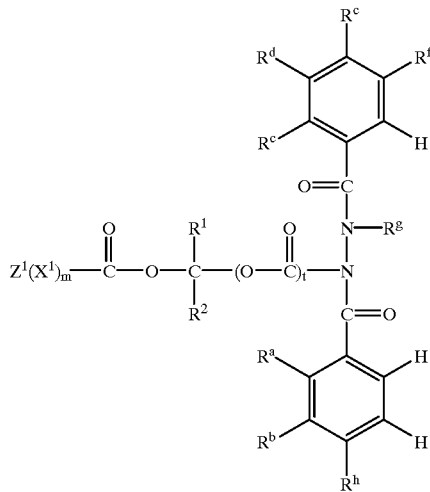

(IIA)

| Cmpd# | $R^a$ | $R^b$ | $R^c$ | $R^d$ | $R^e$ | $R^f$ | $R^g$ | $R^h$ | $R^1$ | $R^2$ | t | m | $Z^1(X^1)_m$ |
|---|---|---|---|---|---|---|---|---|---|---|---|---|---|
| 1-751 | H | H | H | Me | H | Me | C(CH₃)₃ | Et | phenyl | H | 0 | 0 | n-decyloxy |
| 1-752 | H | H | H | Me | H | Me | C(CH₃)₃ | Et | phenyl | H | 0 | 0 | n-undecyloxy |
| 1-753 | H | H | H | Me | H | Me | C(CH₃)₃ | Et | phenyl | H | 0 | 0 | methoxyethoxy |
| 1-754 | H | H | H | Me | H | Me | C(CH₃)₃ | Et | phenyl | H | 0 | 0 | ethoxymethoxy |
| 1-755 | H | H | H | Me | H | Me | C(CH₃)₃ | Et | phenyl | H | 0 | 0 | ethoxyethoxy |
| 1-756 | H | H | H | Me | H | Me | C(CH₃)₃ | Et | phenyl | H | 0 | 0 | cyclohexyloxy |
| 1-757 | H | H | H | Me | H | Me | C(CH₃)₃ | Et | phenyl | H | 0 | 0 | phenoxy |
| 1-758 | H | H | H | Me | H | Me | C(CH₃)₃ | Et | phenyl | H | 0 | 0 | 2,6-dichlorophenoxy |
| 1-759 | H | H | H | Me | H | Me | C(CH₃)₃ | Et | phenyl | H | 0 | 0 | 2-carboxyphenoxy |
| 1-760 | H | H | H | Me | H | Me | C(CH₃)₃ | Et | phenyl | H | 0 | 0 | benzyloxy |
| 1-761 | H | H | H | Me | H | Me | C(CH₃)₃ | Et | phenyl | H | 0 | 0 | 1-naphthoxy |
| 1-762 | H | H | H | Me | H | Me | C(CH₃)₃ | Et | phenyl | H | 0 | 0 | methylthio |
| 1-763 | H | H | H | Me | H | Me | C(CH₃)₃ | Et | phenyl | H | 0 | 0 | tert-butylthio |
| 1-764 | H | H | H | Me | H | Me | C(CH₃)₃ | Et | phenyl | H | 0 | 0 | phenylthio |
| 1-765 | H | H | H | Me | H | Me | C(CH₃)₃ | Et | phenyl | H | 0 | 1 | (E,E)-8,10-dodecadienoxy |
| 1-766 | H | H | H | Me | H | Me | C(CH₃)₃ | Et | phenyl | H | 0 | 1 | dodecane-1-oxy |
| 1-767 | H | H | H | Me | H | Me | C(CH₃)₃ | Et | phenyl | H | 0 | 1 | (E)-11-tetradecen-1-oxy |
| 1-768 | H | H | H | Me | H | Me | C(CH₃)₃ | Et | phenyl | H | 0 | 1 | (Z)-9-tetradecen-1-oxy |
| 1-769 | H | H | H | Me | H | Me | C(CH₃)₃ | Et | phenyl | H | 0 | 1 | (Z)-11-hexadecene-1-oxy |
| 1-770 | H | H | H | Me | H | Me | C(CH₃)₃ | Et | phenyl | H | 0 | 0 | 2,6-dichloro-4-pyridyloxy |
| 1-771 | H | H | H | Me | H | Me | C(CH₃)₃ | Et | phenyl | H | 0 | 0 | pyrazin-2-yloxy |
| 1-772 | H | H | H | Me | H | Me | C(CH₃)₃ | Et | phenyl | H | 0 | 0 | 1H-pyrazol-4-yloxy |
| 1-773 | H | H | H | Me | H | Me | C(CH₃)₃ | Et | phenyl | H | 0 | 0 | EtNH |
| 1-774 | H | H | H | Me | H | Me | C(CH₃)₃ | Et | phenyl | H | 0 | 0 | (Et)₂N |
| 1-775 | H | H | H | Me | H | Me | C(CH₃)₃ | Et | phenyl | H | 0 | 0 | (CH₃)₃CNH |
| 1-776 | H | H | H | Me | H | Me | C(CH:3)3 | Et | phenyl | H | 0 | 0 | PhNH |
| 1-777 | H | H | H | Me | H | Me | C(CH₃)₃ | Et | phenyl | H | 0 | 0 | PhCH₂NH |
| 1-778 | H | H | H | Me | H | Me | C(CH₃)₃ | Et | phenyl | H | 0 | 0 | PhCH₂CH₂NH |
| 1-779 | H | H | H | H | H | H | C(CH₃)₃ | Cl | H | H | 0 | 0 | methoxy |
| 1-780 | H | H | H | H | H | H | C(CH₃)₃ | Cl | H | H | 0 | 0 | ethoxy |
| 1-781 | H | H | H | H | H | H | C(CH₃)₃ | Cl | H | H | 0 | 0 | 2,2,2-trifluoroethoxy |
| 1-782 | H | H | H | H | H | H | C(CH₃)₃ | Cl | H | H | 0 | 0 | n-propoxy |
| 1-783 | H | H | H | H | H | H | C(CH₃)₃ | Cl | H | H | 0 | 0 | isopropoxy |
| 1-784 | H | H | H | H | H | H | C(CH₃)₃ | Cl | H | H | 0 | 0 | n-butoxy |
| 1-785 | H | H | H | H | H | H | C(CH₃)₃ | Cl | H | H | 0 | 0 | isobutoxy |
| 1-786 | H | H | H | H | H | H | C(CH₃)₃ | Cl | H | H | 0 | 0 | tert-butoxy |
| 1-787 | H | H | H | H | H | H | C(CH₃)₃ | Cl | H | H | 0 | 0 | n-pentoxy |
| 1-788 | H | H | H | H | H | H | C(CH₃)₃ | Cl | H | H | 0 | 0 | isopentoxy |
| 1-789 | H | H | H | H | H | H | C(CH:3)3 | Cl | H | H | 0 | 0 | tert-pentoxy |
| 1-790 | H | H | H | H | H | H | C(CH₃)₃ | Cl | H | H | 0 | 0 | neopentoxy |
| 1-791 | H | H | H | H | H | H | C(CH₃)₃ | Cl | H | H | 0 | 0 | n-hexyloxy |
| 1-792 | H | H | H | H | H | H | C(CH₃)₃ | Cl | H | H | 0 | 0 | n-decyloxy |
| 1-793 | H | H | H | H | H | H | C(CH₃)₃ | Cl | H | H | 0 | 0 | n-undecyloxy |
| 1-794 | H | H | H | H | H | H | C(CH₃)₃ | Cl | H | H | 0 | 0 | n-dodecyloxy |
| 1-795 | H | H | H | H | H | H | C(CH₃)₃ | Cl | H | H | 0 | 0 | methoxyethoxy |
| 1-796 | H | H | H | H | H | H | C(CH₃)₃ | Cl | H | H | 0 | 0 | ethoxymethoxy |
| 1-797 | H | H | H | H | H | H | C(CH₃)₃ | Cl | H | H | 0 | 0 | methoxyethoxy |
| 1-798 | H | H | H | H | H | H | C(CH₃)₃ | Cl | H | H | 0 | 0 | ethoxyethoxy |
| 1-799 | H | H | H | H | H | H | C(CH₃)₃ | Cl | H | H | 0 | 0 | cyclohexyloxy |
| 1-800 | H | H | H | H | H | H | C(CH₃)₃ | Cl | H | H | 0 | 0 | phenoxy |
| 1-801 | H | H | H | H | H | H | C(CH₃)₃ | Cl | H | H | 0 | 0 | 2,6-dichlorophenoxy |

TABLE 1C-continued (IIA)

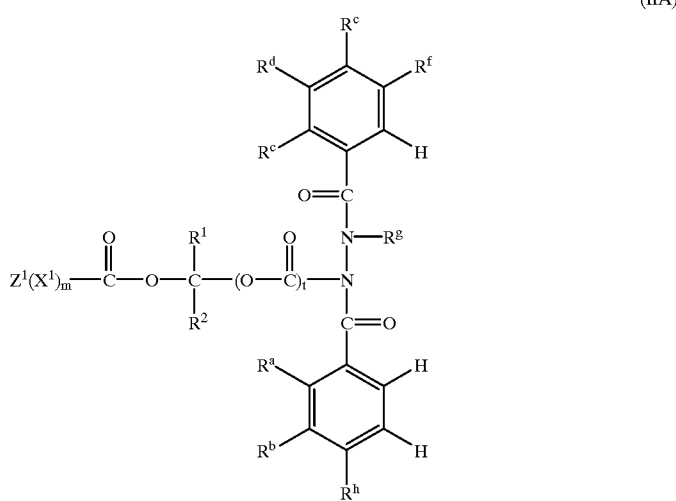

| Cmpd# | R$^a$ | R$^b$ | R$^c$ | R$^d$ | R$^e$ | R$^f$ | R$^g$ | R$^h$ | R$^1$ | R$^2$ | t | m | Z$^1$(X$^1$)$_m$ |
|---|---|---|---|---|---|---|---|---|---|---|---|---|---|
| 1-802 | H | H | H | H | H | H | C(CH$_3$)$_3$ | Cl | H | H | 0 | 0 | 2,4,6-trimethylphenoxy |
| 1-803 | H | H | H | H | H | H | C(CH$_3$)$_3$ | Cl | H | H | 0 | 0 | 2-carboxyphenoxy |
| 1-804 | H | H | H | H | H | H | C(CH$_3$)$_3$ | Cl | H | H | 0 | 0 | benzyloxy |
| 1-805 | H | H | H | H | H | H | C(CH$_3$)$_3$ | Cl | H | H | 0 | 0 | 2-phenylethoxy |
| 1-806 | H | H | H | H | H | H | C(CH$_3$)$_3$ | Cl | H | H | 0 | 0 | 3-phenylpropoxy |
| 1-807 | H | H | H | H | H | H | C(CH$_3$)$_3$ | Cl | H | H | 0 | 0 | 2-phenoxyethoxy |
| 1-808 | H | H | H | H | H | H | C(CH$_3$)$_3$ | Cl | H | H | 0 | 0 | 1-naphthoxy |
| 1-809 | H | H | H | H | H | H | C(CH$_3$)$_3$ | Cl | H | H | 0 | 0 | methylthio |
| 1-810 | H | H | H | H | H | H | C(CH$_3$)$_3$ | Cl | H | H | 0 | 0 | tert-butylthio |
| 1-811 | H | H | H | H | H | H | C(CH$_3$)$_3$ | Cl | H | H | 0 | 0 | phenylthio |
| 1-812 | H | H | H | H | H | H | C(CH$_3$)$_3$ | Cl | H | H | 0 | 1 | (E,E)-8,10-dodecadienoxy |
| 1-813 | H | H | H | H | H | H | C(CH$_3$)$_3$ | Cl | H | H | 0 | 1 | dodecane-1-oxy |
| 1-814 | H | H | H | H | H | H | C(CH$_3$)$_3$ | Cl | H | H | 0 | 1 | (E)-11-tetradecen-1-oxy |
| 1-815 | H | H | H | H | H | H | C(CH$_3$)$_3$ | Cl | H | H | 0 | 1 | (Z)-9-tetradecen-1-oxy |
| 1-816 | H | H | H | H | H | H | C(CH$_3$)$_3$ | Cl | H | H | 0 | 1 | (Z)-11-hexadecene-1-oxy |
| 1-817 | H | H | H | H | H | H | C(CH$_3$)$_3$ | Cl | H | H | 0 | 0 | pyrazin-2-yloxy |
| 1-818 | H | H | H | H | H | H | C(CH$_3$)$_3$ | Cl | H | H | 0 | 0 | 1H-pyrazol-4-yloxy |
| 1-819 | H | H | H | H | H | H | C(CH$_3$)$_3$ | Cl | H | H | 0 | 0 | 4-pyridyloxy |
| 1-820 | H | H | H | H | H | H | C(CH$_3$)$_3$ | Cl | H | H | 0 | 0 | 2,6-dichloro-4-pyridyloxy |
| 1-821 | H | H | H | H | H | H | C(CH$_3$)$_3$ | Cl | H | H | 0 | 0 | EtNH |
| 1-822 | H | H | H | H | H | H | C(CH$_3$)$_3$ | Cl | H | H | 0 | 0 | (Et)$_2$N |
| 1-823 | H | H | H | H | H | H | C(CH$_3$)$_3$ | Cl | H | H | 0 | 0 | n-BuNH |
| 1-824 | H | H | H | H | H | H | C(CH$_3$)$_3$ | Cl | H | H | 0 | 0 | (CH$_3$)$_3$CNH |
| 1-825 | H | H | H | H | H | H | C(CH$_3$)$_3$ | Cl | H | H | 0 | 0 | PhNH |
| 1-826 | H | H | H | H | H | H | C(CH$_3$)$_3$ | Cl | H | H | 0 | 0 | (4Cl)PhNH |
| 1-827 | H | H | H | H | H | H | C(CH$_3$)$_3$ | Cl | H | H | 0 | 0 | PhCH$_2$NH |
| 1-828 | H | H | H | H | H | H | C(CH$_3$)$_3$ | Cl | H | H | 0 | 0 | PhCH$_2$CH$_2$NH |
| 1-829 | H | H | H | H | H | H | C(CH$_3$)$_3$ | Cl | H | H | 0 | 0 | Ph$_2$N |
| 1-830 | H | H | H | H | H | H | C(CH$_3$)$_3$ | Cl | H | H | 0 | 0 | 4-pyridylNH |
| 1-831 | H | H | H | H | H | H | C(CH$_3$)$_3$ | Cl | H | H | 0 | 0 | Ph(Me)N |
| 1-832 | H | H | H | H | H | H | C(CH$_3$)$_3$ | Cl | methyl | H | 0 | 0 | methoxy |
| 1-833 | H | H | H | H | H | H | C(CH$_3$)$_3$ | Cl | methyl | H | 0 | 0 | ethoxy |
| 1-834 | H | H | H | H | H | H | C(CH$_3$)$_3$ | Cl | methyl | H | 0 | 0 | 2,2,2-trifluoroethoxy |
| 1-835 | H | H | H | H | H | H | C(CH$_3$)$_3$ | Cl | methyl | H | 0 | 0 | n-propoxy |
| 1-836 | H | H | H | H | H | H | C(CH$_3$)$_3$ | Cl | methyl | H | 0 | 0 | tert-butoxy |
| 1-837 | H | H | H | H | H | H | C(CH$_3$)$_3$ | Cl | methyl | H | 0 | 0 | phenoxy |
| 1-838 | H | H | H | H | H | H | C(CH$_3$)$_3$ | Cl | methyl | H | 0 | 0 | 2,6-dichlorophenoxy |
| 1-839 | H | H | H | H | H | H | C(CH$_3$)$_3$ | Cl | methyl | H | 0 | 0 | 2-carboxyphenoxy |
| 1-840 | H | H | H | H | H | H | C(CH$_3$)$_3$ | Cl | methyl | H | 0 | 0 | benzyloxy |
| 1-841 | H | H | H | H | H | H | C(CH$_3$)$_3$ | Cl | methyl | H | 0 | 0 | 1-naphthoxy |
| 1-842 | H | H | H | H | H | H | C(CH$_3$)$_3$ | Cl | methyl | H | 0 | 0 | methylthio |
| 1-843 | H | H | H | H | H | H | C(CH$_3$)$_3$ | Cl | methyl | H | 0 | 0 | tert-butylthio |
| 1-844 | H | H | H | H | H | H | C(CH$_3$)$_3$ | Cl | methyl | H | 0 | 0 | phenylthio |
| 1-845 | H | H | H | H | H | H | C(CH$_3$)$_3$ | Cl | methyl | H | 0 | 1 | (E,E)-8,10-dodecadienoxy |
| 1-846 | H | H | H | H | H | H | C(CH$_3$)$_3$ | Cl | methyl | H | 0 | 1 | dodecane-1-oxy |
| 1-847 | H | H | H | H | H | H | C(CH$_3$)$_3$ | Cl | methyl | H | 0 | 1 | (E)-11-tetradecen-1-oxy |
| 1-848 | H | H | H | H | H | H | C(CH$_3$)$_3$ | Cl | methyl | H | 0 | 1 | (Z)-9-tetradecen-1-oxy |
| 1-849 | H | H | H | H | H | H | C(CH$_3$)$_3$ | Cl | methyl | H | 0 | 1 | (Z)-11-hexadecene-1-oxy |
| 1-850 | H | H | H | H | H | H | C(CH$_3$)$_3$ | Cl | methyl | H | 0 | 0 | pyrazin-2-yloxy |
| 1-851 | H | H | H | H | H | H | C(CH$_3$)$_3$ | Cl | methyl | H | 0 | 0 | 1H-pyrazol-4-yloxy |
| 1-852 | H | H | H | H | H | H | C(CH$_3$)$_3$ | Cl | methyl | H | 0 | 0 | 4-pyridyloxy |

TABLE 1C-continued

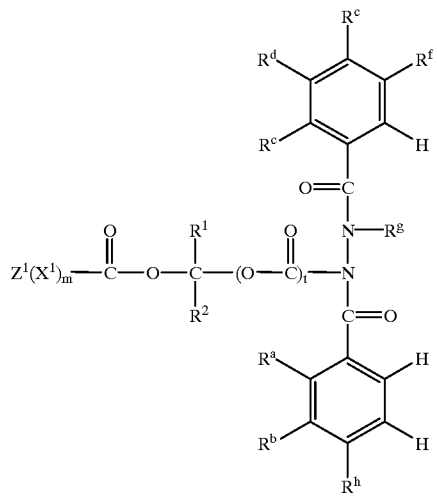

(IIA)

| Cmpd# | $R^a$ | $R^b$ | $R^c$ | $R^d$ | $R^e$ | $R^f$ | $R^g$ | $R^h$ | $R^1$ | $R^2$ | t | m | $Z^1(X^1)_m$ |
|---|---|---|---|---|---|---|---|---|---|---|---|---|---|
| 1-853 | H | H | H | H | H | H | C(CH₃)₃ | Cl | methyl | H | 0 | 0 | 2,6-dichloro-4-pyridyloxy |
| 1-854 | H | H | H | H | H | H | C(CH₃)₃ | Cl | methyl | H | 0 | 0 | EtNH |
| 1-855 | H | H | H | H | H | H | C(CH₃)₃ | Cl | methyl | H | 0 | 0 | (Et)₂N |
| 1-856 | H | H | H | H | H | H | C(CH₃)₃ | Cl | methyl | H | 0 | 0 | n-BuNH |
| 1-857 | H | H | H | H | H | H | C(CH₃)₃ | Cl | methyl | H | 0 | 0 | (CH₃)₃CNH |
| 1-858 | H | H | H | H | H | H | C(CH₃)₃ | Cl | methyl | H | 0 | 0 | PhNH |
| 1-859 | H | H | H | H | H | H | C(CH₃)₃ | Cl | methyl | H | 0 | 0 | (4Cl)PhNH |
| 1-860 | H | H | H | H | H | H | C(CH₃)₃ | Cl | methyl | H | 0 | 0 | PhCH₂NH |
| 1-861 | H | H | H | H | H | H | C(CH₃)₃ | Cl | methyl | H | 0 | 0 | PhCH₂CH₂NH |
| 1-862 | H | H | H | H | H | H | C(CH₃)₃ | Cl | phenyl | H | 0 | 0 | methoxy |
| 1-863 | H | H | H | H | H | H | C(CH₃)₃ | Cl | phenyl | H | 0 | 0 | ethoxy |
| 1-864 | H | H | H | H | H | H | C(CH₃)₃ | Cl | phenyl | H | 0 | 0 | 2,2,2-trifluoroethoxy |
| 1-865 | H | H | H | H | H | H | C(CH₃)₃ | Cl | phenyl | H | 0 | 0 | n-propoxy |
| 1-866 | H | H | H | H | H | H | C(CH₃)₃ | Cl | phenyl | H | 0 | 0 | tert-butoxy |
| 1-867 | H | H | H | H | H | H | C(CH₃)₃ | Cl | phenyl | H | 0 | 0 | n-decyloxy |
| 1-868 | H | H | H | H | H | H | C(CH₃)₃ | Cl | phenyl | H | 0 | 0 | n-undecyloxy |
| 1-869 | H | H | H | H | H | H | C(CH₃)₃ | Cl | phenyl | H | 0 | 0 | methoxyethoxy |
| 1-870 | H | H | H | H | H | H | C(CH₃)₃ | Cl | phenyl | H | 0 | 0 | ethoxymethoxy |
| 1-871 | H | H | H | H | H | H | C(CH₃)₃ | Cl | phenyl | H | 0 | 0 | ethoxyethoxy |
| 1-872 | H | H | H | H | H | H | C(CH₃)₃ | Cl | phenyl | H | 0 | 0 | cyclohexyloxy |
| 1-873 | H | H | H | H | H | H | C(CH₃)₃ | Cl | phenyl | H | 0 | 0 | phenoxy |
| 1-874 | H | H | H | H | H | H | C(CH₃)₃ | Cl | phenyl | H | 0 | 0 | 2,6-dichlorophenoxy |
| 1-875 | H | H | H | H | H | H | C(CH₃)₃ | Cl | phenyl | H | 0 | 0 | 2-carboxyphenoxy |
| 1-876 | H | H | H | H | H | H | C(CH₃)₃ | Cl | phenyl | H | 0 | 0 | benzyloxy |
| 1-877 | H | H | H | H | H | H | C(CH₃)₃ | Cl | phenyl | H | 0 | 0 | 1-naphthoxy |
| 1-878 | H | H | H | H | H | H | C(CH₃)₃ | Cl | phenyl | H | 0 | 0 | methylthio |
| 1-879 | H | H | H | H | H | H | C(CH₃)₃ | Cl | phenyl | H | 0 | 0 | tert-butylthio |
| 1-880 | H | H | H | H | H | H | C(CH₃)₃ | Cl | phenyl | H | 0 | 0 | phenylthio |
| 1-881 | H | H | H | H | H | H | C(CH₃)₃ | Cl | phenyl | H | 0 | 1 | (E,E)-8,10-dodecadienoxy |
| 1-882 | H | H | H | H | H | H | C(CH₃)₃ | Cl | phenyl | H | 0 | 1 | dodecane-1-oxy |
| 1-883 | H | H | H | H | H | H | C(CH₃)₃ | Cl | phenyl | H | 0 | 1 | (E)-11-tetradecen-1-oxy |
| 1-884 | H | H | H | H | H | H | C(CH₃)₃ | Cl | phenyl | H | 0 | 1 | (Z)-9-tetradecen-1-oxy |
| 1-885 | H | H | H | H | H | H | C(CH₃)₃ | Cl | phenyl | H | 0 | 1 | (Z)-11-hexadecene-1-oxy |
| 1-886 | H | H | H | H | H | H | C(CH₃)₃ | Cl | phenyl | H | 0 | 0 | 2,6-dichloro-4-pyridyloxy |
| 1-887 | H | H | H | H | H | H | C(CH₃)₃ | Cl | phenyl | H | 0 | 0 | pyrazin-2-yloxy |
| 1-888 | H | H | H | H | H | H | C(CH₃)₃ | Cl | phenyl | H | 0 | 0 | 1H-pyrazol-4-yloxy |
| 1-889 | H | H | H | H | H | H | C(CH₃)₃ | Cl | phenyl | H | 0 | 0 | EtNH |
| 1-890 | H | H | H | H | H | H | C(CH₃)₃ | Cl | phenyl | H | 0 | 0 | (Et)₂N |
| 1-891 | H | H | H | H | H | H | C(CH₃)₃ | Cl | phenyl | H | 0 | 0 | (CH₃)₃CNH |
| 1-892 | H | H | H | H | H | H | C(CH₃)₃ | Cl | phenyl | H | 0 | 0 | PhNH |
| 1-893 | H | H | H | H | H | H | C(CH₃)₃ | Cl | phenyl | H | 0 | 0 | PhCH₂NH |
| 1-894 | H | H | H | H | H | H | C(CH₃)₃ | Cl | phenyl | H | 0 | 0 | PhCH₂CH₂NH |

Following the general methods described hereinbefore, the following compounds of Formula (III) as listed in Table 2 were prepared.

TABLE 2

Listing of Compounds of Formula (III)

(III)

$$R^6O-\overset{O}{\overset{\|}{C}}-CH_2-\underset{\underset{\underset{R^7\ R^8}{\overset{\|}{P}=O}}{\overset{|}{CH_2}}}{N}-\overset{O}{\overset{\|}{\underset{|}{C}}}-O-\overset{R^1}{\underset{R^2}{\overset{|}{C}}}-(O-\overset{O}{\overset{\|}{C}})_t-(X^2)_qZ^2$$

| Cmpd# | $R^1$ | $R^2$ | $R^6$ | $R^7$ | $R^8$ | t | q | $(X^2)_qZ^2$ |
|---|---|---|---|---|---|---|---|---|
| 2-1 | H | H | H | OH | OH | 1 | 0 | 2-propyl |
| 2-2 | H | H | H | OH | O—NH$_3^i$Pr | 1 | 0 | 2-propyl |
| 2-3 | H | H | H | OH | OH | 1 | 1 | 3,6-dichloro-2-methoxyphenyl |
| 2-4 | H | H | H | OH | OH | 1 | 1 | 3,5,6-trichloropyridyl-oxymethyl |
| 2-5 | H | H | H | OH | OH | 1 | 1 | 3-(2,4-dichloro phenoxy)-1-propyl |
| 2-6 | H | H | H | OH | OH | 1 | 0 | ethyl |
| 2-7 | H | H | H | OH | O—NH$_3^i$Pr | 1 | 0 | ethyl |
| 2-8 | H | H | H | OH | OH | 1 | 0 | cyclohexyl |
| 2-9 | H | H | H | OH | O—NH$_3^i$Pr | 1 | 0 | cyclohexyl |
| 2-10 | H | H | H | OH | OH | 1 | 0 | cyclopentyl |
| 2-11 | H | H | H | OH | O—NH$_3^i$Pr | 1 | 0 | cyclopentyl |
| 2-12 | H | H | H | OH | OH | 1 | 0 | pentyl |
| 2-13 | H | H | H | OH | O—NH$_3^i$Pr | 1 | 0 | pentyl |
| 2-14 | H | H | H | OH | OH | 1 | 0 | heptyl |
| 2-15 | H | H | H | OH | O—NH$_3^i$Pr | 1 | 0 | heptyl |
| 2-16 | H | H | H | OH | OH | 1 | 0 | 2-hexyl |
| 2-17 | H | H | H | OH | O—NH$_3^i$Pr | 1 | 0 | 2-hexyl |
| 2-18 | H | H | H | OH | OH | 1 | 0 | pentadecyl |
| 2-19 | H | H | H | OH | O—NH$_3^i$Pr | 1 | 0 | pentadecyl |
| 2-20 | H | H | H | OH | OH | 1 | 0 | decyl |
| 2-21 | H | H | H | OH | O—NH$_3^i$Pr | 1 | 0 | decyl |
| 2-22 | H | H | H | OH | OH | 1 | 0 | 2-methyl-2-propyl |
| 2-23 | H | H | H | OH | O—NH$_3^i$Pr | 1 | 0 | 2-methyl-2-propyl |
| 2-24 | H | H | H | OH | OH | 1 | 0 | 2-ethoxyphenyl |
| 2-25 | H | H | H | OH | O—NH$_3^i$Pr | 1 | 0 | 2-ethoxyphenyl |
| 2-26 | H | H | H | OH | OH | 1 | 1 | 2,4-dichlorophenoxy methyl |
| 2-27 | H | H | H | OH | OH | 1 | 0 | cyclopropyl |
| 2-28 | H | H | H | OH | O—NH$_3^i$Pr | 1 | 0 | cyclopropyl |
| 2-29 | H | H | H | OH | OH | 1 | 0 | 2,2,2-trifluoroethyl |
| 2-30 | H | H | H | OH | O—NH$_3^i$Pr | 1 | 0 | 2,2,2-trifluoroethyl |
| 2-31 | H | H | H | OH | OH | 1 | 0 | (diethoxyphosphoryl)-methyl |
| 2-32 | H | H | H | OH | O—NH$_3^i$Pr | 1 | 0 | (diethoxyphosphoryl)-methyl |
| 2-33 | H | H | H | OH | OH | 1 | 0 | 2,2-dimethyl-1-propyl |
| 2-34 | H | H | H | OH | O—NH$_3^i$Pr | 1 | 0 | 2,2-dimethyl-1-propyl |
| 2-35 | H | H | H | OH | OH | 1 | 0 | 4-heptyl |
| 2-36 | H | H | H | OH | O—NH$_3^i$Pr | 1 | 0 | 4-heptyl |
| 2-37 | H | H | H | O—NH$_3^i$Pr | O—NH$_3^i$Pr | 1 | 0 | 4-heptyl |
| 2-38 | H | H | H | OH | O—K | 1 | 0 | 2-propyl |
| 2-39 | H | H | H | OH | OH | 1 | 0 | 2,2,2-trifluoropropyl |
| 2-40 | H | H | H | OH | O—NH$_3^i$Pr | 1 | 0 | 2,2,2-trifluoropropyl |
| 2-41 | H | H | H | OH | OH | 1 | 0 | 2-methyl-2-butyl |
| 2-42 | H | H | H | OH | O—NH$_3^i$Pr | 1 | 0 | 2-methyl-2-butyl |
| 2-43 | H | H | H | OH | OH | 1 | 0 | 2-methylcyclopropyl |
| 2-44 | H | H | H | OH | OH | 1 | 0 | dodecyl |

EXAMPLE 199

O-Iodomethyl S-ethyl carbonothioate

A 500 mL roundbottom flask was charged with sodium ethylthiolate (10.0 g, 119 mmol) and 250 mL of dry diethyl ether. The mixture was cooled to −70° C. in an acetone dry ice bath. Chloromethyl chloroformate (13.0 g, 115 mmol) was added as a solution in 50 mL of diethyl ether over 1.25 h at such a rate that the reaction temperature did not exceed −65° C. The reaction was allowed to slowly warm to room temperature and stir for 16 h. The reaction was vacuum filtered and the filtrate dried (MgSO$_4$), gravity filtered, and concentrated under reduced pressure to yield a clear liquid. 1H-NMR (300 MHz, CDCl$_3$) δ (ppm): 1.35 (t, 3H), 2.93 (q, 2H), 5.77 (s, 2H). The material was then taken on without further purification. To a stirred solution of S-ethyl carbonothiolate (14.1 g, 91.0 mmol) in 100 mL of dry acetone was added NaI (27.3 g, 182 mmol) and sodium bicarbonate (0.76 g, 9.1 mmol). The mixture was stirred at room temperature for 6 h. The acetone was removed and remaining slurry was diluted with 200 mL of diethyl ether. The reaction was then filtered through Celite and concentrated under reduced pressure to yield a brown liquid. The oil was redissolved in 100 mL of diethyl ether and gravity filtered to afford 19.1 g of a brown liquid. 1H-NMR (300 MHz, CDCl$_3$) δ (ppm): 1.34 (t, 3H), 2.93 (q, 2H), 5.99 (s, 2H).

EXAMPLE 200

2-Methylpropanoic acid ethylsulfanylcarbonyloxymethyl ester

To a stirred ice cold solution of O-iodomethyl S-ethyl carbothiolate (19.1 g, 77.6 mmol) in 200 mL of dry THF was added 2-methylpropanoic acid (8.89 g, 101 mmol) followed by diisopropylethylamine (13.0 g, 101 mmol). The reaction was allowed to stir at room temperature for 16 h. The reaction was diluted with 250 mL of diethyl ether, gravity filtered, and concentrated under reduced pressure. The liquid was suction filtered through a pad of flash grade silica gel and eluted with 20% methylene chloride/hexanes. 1H-NMR (300 MHz, CDCl$_3$) δ (ppm): 1.9 (d, 6H), 1.33 (t, 3H), 2.63 (q, 1H), 2.90 (q, 2H), 5.81 (s, 2H).

EXAMPLE 201

3,6-Dichloro-2-methoxybenzoic acid ethylsulfanylcarbonyloxymethyl ester

The title compound was prepared according to the procedure described in Example 200 above except for the substitution of 3,6-dichloro-2-methoxybenzoic acid for 2-methylpropanoic acid. 1H-NMR (300 MHz, CDCl$_3$) δ (ppm): 1.34 (t, 3H), 2.92 (q, 2H), 3.92 (s, 3H), 6.05 (s, 2H), 7.13 (d, 1H), 7.37 (d, 1H).

EXAMPLE 202

(3,5,6-Trichloro-2-pyridyloxy)acetic acid ethylsulfanylcarbonyloxymethyl ester

The title compound was prepared according to the procedure described in Example 200 above except for the substitution of (3,5,6-trichloro-2-pyridyloxy)acetic acid for 2-methylpropanoic acid. Mp=70–71° C. 1H-NMR (300 MHz, CDCl$_3$) δ (ppm): 1.33 (t, 3H), 2.90 (q, 2H), 5.00 (s, 2H), 5.88 (s, 2H), 7.77 (s, 1H).

EXAMPLE 203

4-(2,4-Dichlorophenoxy)butyric acid ethylsulfanylcarbonyloxymethyl ester

The title compound was prepared according to the procedure described in Example 200 above except for the substitution of 4-(2,4-dichlorophenoxy)butyric acid for 2-methylpropanoic acid. 1H-NMR (300 MHz, CDCl$_3$) δ (ppm): 1.32 (t, 3H), 2.17 (m, 2H), 2.66 (t, 2H), 2.90 (q, 2H), 4.05(t, 2H), 5.83 (s, 2H), 6.83 (d, 1H), 7.18 (dd, 1H), 7.35 (d, 1H).

EXAMPLE 204

Propionic acid ethylsulfanylcarbonyloxymethyl ester

The title compound was prepared according to the procedure described in Example 200 above except for the substitution of propionic acid for 2-methylpropanoic acid. 1H-NMR (300 MHz, CDCl$_3$) δ (ppm): 1.16 (t, 3H), 1.33 (t, 3H), 2.41 (q, 2H), 2.90 (q, 2H), 5.81 (s, 2H).

EXAMPLE 205

Cyclohexanecarboxylic acid ethylsulfanylcarbonyloxymethyl ester

The title compound was prepared according to the procedure described in Example 200 above except for the substitution of cyclohexanecarboxylic acid for 2-methylpropanoic acid. 1H-NMR (300 MHz, CDCl$_3$) δ (ppm): 1.25–1.50 (m, 8H), 1.65–1.95 (m, 5H), 2.40 (m, 1H), 2.89 (q, 2H), 5.81 (s, 2H).

EXAMPLE 206

Cyclopentanecarboxylic acid ethylsulfanylcarbonyloxymethyl ester

The title compound was prepared according to the procedure described in Example 200 above except for the substitution of cyclopentanecarboxylic acid for 2-methylpropanoic acid. 1H-NMR (300 MHz, CDCl$_3$) δ (ppm): 1.33 (t, 3H), 1.60–1.95 (m, 8H), 2.80 (m, 1H), 2.90 (q, 2H), 5.81 (s, 2H).

EXAMPLE 207

Hexanoic acid ethylsulfanylcarbonyloxymethyl ester

The title compound was prepared according to the procedure described in Example 200 above except for the substitution of hexanoic acid for 2-methylpropanoic acid. 1H-NMR (300 MHz, CDCl$_3$) δ (ppm): 0.90 (m, 3H), 1.33 (m, 7H), 1.65 (m, 2H), 2.37 (m, 2H), 2.90 (q, 2H), 5.81 (s, 2H).

EXAMPLE 208

Octanoic acid ethylsulfanylcarbonyloxymethyl ester

The title compound was prepared according to the procedure described in Example 200 above except for the substitution of octanoic acid for 2-methylpropanoic acid. 1H-NMR (300 MHz, CDCl$_3$) δ (ppm): 0.90 (t, 3H), 1.33 (m, 11H), 1.65 (m, 2H), 2.37 (m, 2H), 2.90 (q, 2H), 5.81 (s, 2H).

EXAMPLE 209

2-Methylhexanoic acid ethylsulfanylcarbonyloxymethyl ester

The title compound was prepared according to the procedure described in Example 200 above except for the substitution of 2-methylhexanoic acid for 2-methylpropanoic acid. 1H-NMR (300 MHz, CDCl$_3$) δ (ppm): 0.90 (t, 3H), 1.16 (d, 3H), 1.33 (m, 7H), 1.65 (m, 2H), 2.50 (m, 1H), 2.90 (q, 2H), 5.81 (s, 2H).

EXAMPLE 210

Hexadecanoic acid ethylsulfanylcarbonyloxymethyl ester

The title compound was prepared according to the procedure described in Example 200 above except for the substitution of hexadecanoic acid for 2-methylpropanoic acid. 1H-NMR (300 MHz, CDCl$_3$) δ (ppm): 0.88 (t, 3H), 1.25–1.33 (m, 27H), 1.65 (m, 2H), 2.39 (m, 2H), 2.90 (q, 2H), 5.81 (s, 2H).

EXAMPLE 211

Undecanoic acid ethylsulfanylcarbonyloxymethyl ester

The title compound was prepared according to the procedure described in Example 200 above except for the substitution of undecanoic acid for 2-methylpropanoic acid 1H-NMR (300 MHz, CDCl$_3$) δ (ppm): 0.88 (t, 3H), 1.26–1.36 (m, 17H), 1.63 (m, 2H), 2.35 (t, 2H), 2.90 (q, 2H), 5.81 (s, 2H).

EXAMPLE 212

2,2-Dimethylpropionic acid ethylsulfanylcarbonyloxymethyl ester

The title compound was prepared according to the procedure described in Example 200 above except for the substitution of 2,2-dimethylpropionic acid for 2-methylpropanoic acid. 1H-NMR (300 MHz, CDCl$_3$) δ (ppm): 1.22 (s, 9H), 1.33 (t, 3H), 2.90 (q, 2H), 5.81 (s, 2H).

EXAMPLE 213

4-Chlorobenzoic acid ethylsulfanylcarbonyloxymethyl ester

The title compound was prepared according to the procedure described in Example 200 above except for the substitution of 4-chlorobenzoic acid for 2-methylpropanoic acid. 1H-NMR (300 MHz, CDCl$_3$) δ (ppm): 1.33 (t, 3H), 2.90 (q, 2H), 6.05(s, 2H), 7.43 (d, 2H), 8.01 (d, 2H).

EXAMPLE 214

2-Ethoxybenzoic acid ethylsulfanylcarbonyloxymethyl ester

The title compound was prepared according to the procedure described in Example 200 above except for the substitution of 2-ethoxybenzoic acid for 2-methylpropanoic acid. 1H-NMR (300 MHz, CDCl$_3$) δ (ppm): 1.33 (t, 3H), 1.46 (t, 3H), 2.90 (q, 2H), 4.11 (d, 2H), 6.03 (s, 2H), 6.94–6.97 (m, 2H), 7.48 (t, 1H), 7.85 (d, 1H).

EXAMPLE 215

(2,4-Dichlorophenoxy)acetic acid Ethylsulfanylcarbonyloxymethyl ester

The title compound was prepared according to the procedure described in Example 200 above except for the substitution of (2,4-dichlorophenoxy)acetic acid for 2-methylpropanoic acid. 1H-NMR (300 MHz, CDCl$_3$) δ (ppm): 1.33 (t, 3H), 2.89 (q, 2H), 4.75 (s, 2H), 5.89 (s, 2H), 6.78 (d, 1H), 7.18 (dd, 1H), 7.38 (d, 1H).

EXAMPLE 216

2,2-Dimethylmalonic acid diethylsulfanylcarbonyloxymethyl ester

The title compound was prepared according to the procedure described in Example 200 above except for the substitution of 2,2-dimethylmalonic acid for 2-methylpropanoic acid. 1H-NMR (300 MHz, CDCl$_3$) δ (ppm): 1.33 (t, 6H), 1.48 (s, 6H), 2.90 (q, 4H), 5.82 (s, 4H).

EXAMPLE 217

3-Methyl-2-phenylpentanoic acid ethylsulfanylcarbonyloxymethyl ester

The title compound was prepared according to the procedure described in Example 200 above except for the substitution of 3-methyl-2-phenylpentanoic acid for 2-methylpropanoic acid. 1H-NMR (300 MHz, CDCl$_3$) δ (ppm): 0.67–1.03 (m, 8H), 1.29 (t, 3H), 2.18 (bs, 1H), 2.85 (q, 2H), 3.32 (dd, 1H), 5.77 (dd, 2H), 7.28 (m, 5H).

EXAMPLE 218

2-Ethylbutyric acid ethylsulfanylcarbonyloxymethyl ester

The title compound was prepared according to the procedure described in Example 200 above except for the substitution of 2-ethylbutyric acid for 2-methylpropanoic acid. 1H-NMR (300 MHz, CDCl$_3$) δ (ppm): 0.90 (t, 6H), 1.33 (t, 3H), 1.51–1.72 (m, 4H), 2.28 (m, 1H), 2.90 (q, 2H), 5.83 (s, 2H).

EXAMPLE 219

Tetrahydrofuran-2-carboxylic acid ethylsulfanylcarbonyloxymethyl ester

The title compound was prepared according to the procedure described in Example 200 above except for the substitution of tetrahydrofuran-2-carboxylic acid for 2-methylpropanoic acid. 1H-NMR (300 MHz, CDCl$_3$) δ (ppm): 1.33 (t, 3H), 1.93–2.07 (m, 3H), 2.28 (m, 1H), 2.89 (q, 2H), 3.90–4.08 (m, 2H), 4.54 (m, 1H), 5.85 (dd, 2H).

EXAMPLE 220

2-Methylcyclopropanecarboxylic acid ethylsulfanylcarbonyloxymethyl ester

The title compound was prepared according to the procedure described in Example 200 above except for the substitution of 2-methylcyclopropanecarboxylic acid for 2-methylpropanoic acid. 1H-NMR (300 MHz, CDCl$_3$) δ (ppm): 0.78 (m, 1H), 1.12 (d, 3H), 1.25–1.50 (m, 3H), 1.34 (t, 3H), 2.90 (q, 2H), 5.79 (s, 2H).

EXAMPLE 221

2,2,3,3-Tetramethylcyclopropylcarboxylic acid ethylsulfanylcarbonyloxymethyl ester The title compound was prepared according to the procedure described in Example 200 above except for the substitution of 2,2,3,3-tetramethylcyclopropylcarboxylic acid for 2-methylpropanoic acid. 1H-NMR (300 MHz, CDCl$_3$) δ (ppm): 1.20 (s, 6H), 1.25 (s, 6H), 1.33 (t, 3H), 2.90 (q, 2H), 5.79 (s, 2H).

EXAMPLE 222

2,2-Dimethylbutyric acid ethylsulfanylcarbonyloxymethyl ester

The title compound was prepared according to the procedure described in Example 200 above except for the substitution of 2,2-dimethylbutyric acid for 2-methylpropanoic acid. 1H-NMR (300 MHz, CDCl$_3$) δ (ppm): 0.84 (t, 3H), 1.17 (s, 6H), 1.33 (t, 3H), 1.58 (q, 2H), 2.89 (q, 2H), 5.81 (s, 2H).

EXAMPLE 223

2-Phenylpropionic acid
ethylsulfanylcarbonyloxymethyl ester

The title compound was prepared according to the procedure described in Example 200 above except for the substitution of 2-phenylpropionic acid for 2-methylpropanoic acid. 1H-NMR (300 MHz, CDCl$_3$) δ (ppm): 1.29 (t, 3H), 1.52 (d, 3H), 2.85 (q, 2H), 3.77 (q, 2H), 5.77 (dd, 2H), 7.29 (m, 5H).

EXAMPLE 224

2-Ethylhexanoic acid
ethylsulfanylcarbonyloxymethyl ester

The title compound was prepared according to the procedure described in Example 200 above except for the substitution of 2-ethylhexanoic acid for 2-methylpropanoic acid. 1H-NMR (300 MHz, CDCl$_3$) δ (ppm): 0.86–0.92 (m, 6H), 1.28–1.35 (m, 5H), 1.50–1.67 (m, 5H), 2.32 (m, 1H), 2.89 (q, 2H), 5.82 (s, 2H).

EXAMPLE 225

2-Methylbutyric acid
ethylsulfanylcarbonyloxymethyl ester

The title compound was prepared according to the procedure described in Example 200 above except for the substitution of 2-methylbutyric acid for 2-methylpropanoic acid. 1H-NMR (300 MHz, CDCl$_3$) δ (ppm): 0.91 (t, 3H), 1.16 (d, 3H), 1.33 (d, 3H), 1.48–1.75 (m, 5H), 2.45 (m, 1H), 2.89 (q, 2H), 5.82 (s, 2H).

EXAMPLE 226

2,2-Dichloro-1-methylcyclopropanecarboxylic acid
ethylsulfanylcarbonyloxymethyl ester The title compound was prepared according to the procedure described in Example 200 above except for the substitution of 2,2-dichloro-1-methylcyclopropanecarboxylic acid for 2-methylpropanoic acid. 1H-NMR (300 MHz, CDCl$_3$) δ (ppm): 1.33 (t, 3H), 1.48 (d, 1H), 1.60 (s, 3H), 2.31 (d, 1H), 2.90 (q, 2H), 5.87 (dd, 2H).

EXAMPLE 227

2-Methylpentanoic acid
ethylsulfanylcarbonyloxymethyl ester

The title compound was prepared according to the procedure described in Example 200 above except for the substitution of 2-methylpentanoic acid for 2-methylpropanoic acid. 1H-NMR (300 MHz, CDCl$_3$) δ (ppm): 0.90 (t, 3H), 1.16 (d, 3H), 1.31–1.36 (m, 7H), 2.51 (m, 1H), 2.89 (q, 2H), 5.81 (s, 2H).

EXAMPLE 228

2-Ethylhexanoic acid
ethylsulfanylcarbonyloxymethyl ester

The title compound was prepared according to the procedure described in Example 200 above except for the substitution of 2-ethylhexanoic acid for 2-methylpropanoic acid. 1H-NMR (300 MHz, CDCl$_3$) δ (ppm): 0.89 (m, 6H), 1.26–1.35 (m, 7H), 1.48–1.70 (m, 4H), 2.35 (m, 1H), 2.89 (q, 2H), 5.83 (s, 2H).

EXAMPLE 229

Cyclopropanecarboxylic acid
ethylsulfanylcarbonyloxymethyl ester

The title compound was prepared according to the procedure described in Example 200 above except for the substitution of cyclopropanecarboxylic acid for 2-methylpropanoic acid. 1H-NMR (300 MHz, CDCl$_3$) δ (ppm): 0.96 (m, 2H), 1.07 (m, 2H), 1.36 (t, 3H), 1.65 (m, 1H), 2.90 (q, 2H), 5.81 (s, 2H).

EXAMPLE 230

3,3,3-Trifluoropropanoic acid
ethylsulfanylcarbonyloxymethyl ester

The title compound was prepared according to the procedure described in Example 200 above except for the substitution of 3,3,3-trifluoropropanoic acid for 2-methylpropanoic acid. 1H-NMR (300 MHz, CDCl$_3$) δ (ppm): 1.34 (t, 3H), 2.93 (q, 2H), 3.27 (q, 2H), 5.88 (s, 2H).

EXAMPLE 231

(Diethoxyphosphoryl)acetic acid
ethylsulfanylcarbonyloxymethyl ester

The title compound was prepared according to the procedure described in Example 200 above except for the substitution of (diethoxyphosphoryl)acetic acid for 2-methylpropanoic acid. 1H-NMR (300 MHz, CDCl$_3$) δ (ppm): 1.34 (m, 9H), 2.90 (q, 2H), 3.04 (d, 2H), 4.18 (q, 4H), 5.85 (s, 2H).

EXAMPLE 232

2-Propylpentanoic acid
ethylsulfanylcarbonyloxymethyl ester

The title compound was prepared according to the procedure described in Example 200 above except for the substitution of 2-propylpentanoic acid for 2-methylpropanoic acid. 1H-NMR (300 MHz, CDCl$_3$) δ (ppm): 0.89 (t, 6H), 1.26–1.69 (m, 11H), 2.44 (m, 1H), 2.89 (q, 2H), 5.82 (s, 1H).

EXAMPLE 233

2-Methylpropanoic acid chlorocarbonyloxymethyl ester

A 100 mL roundbottom flask was charged with the 2-methylpropanoic acid ethylsulfanylcarbonyloxymethyl ester (2.91 g, 14.1 mmol) and cooled to −40° C. in an acetone dry ice bath. Sulfuryl chloride (1.90 g, 14.1 mmol) was added over one minute. After 10 minutes the acetone/dry ice cooling bath was removed and replaced with an ice/water bath. After 30 minutes of stirring, the cooling bath was removed and the reaction was allowed to stir for one hour at room temperature and then placed under vacuum for 90 minutes. The material was used without purification. 1H-NMR (300 MHz, CDCl$_3$) δ (ppm): 1.22 (d, 6H), 2.65 (m, 1H), 5.83 (s, 2H).

EXAMPLE 234

3,6-Dichloro-2-methoxybenzoic acid
chlorocarbonyloxymethyl ester

The title compound was prepared according to the procedure described in Example 233 above except for the substitution of 3,6-dichloro-2-methoxybenzoic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 3.93 (s, 3H), 6.06 (s, 2H), 7.15 (d, 1H), 7.41 (d, 1H).

EXAMPLE 235

(3,5,6-Trichloro-2-pyridyloxy)acetic acid chlorocarbonyloxymethyl ester

The title compound was prepared according to the procedure described in Example 233 above except for the substitution of (3,5,6-triichloro-2-pyridyloxy)acetic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 5.03 (s, 2H), 5.90 (s, 2H), 7.79 (s, 1H).

EXAMPLE 236

4-(2,4-Dichlorophenoxy)butyric acid Chlorocarbonyloxymethyl ester

The title compound was prepared according to the procedure described in Example 233 above except for the substitution of 4-(2,4-dichlorophenoxy)butyric acid ethylsulfanylcarbonyloxymethyl ester for 2-methylpropanoic acid ethylsulfanylcarbonyloxymethyl ester. 1H-NMR (300 MHz, CDCl$_3$) δ (ppm): 2.19 (m, 2H), 2.70 (t, 2H), 4.06 (t, 2H), 5.84 (s, 2H), 6.83 (d, 1H), 7.18 (dd, 1H), 7.35 (d, 1H).

EXAMPLE 237

Propionic acid chlorocarbonyloxymethyl ester

The title compound was prepared according to the procedure described in Example 233 above except for the substitution of propionic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 1.19 (t, 3H), 2.45 (q, 2H), 5.83 (s, 2H).

EXAMPLE 238

Cyclohexanecarboxylic acid chlorocarbonyloxymethyl ester

The title compound was prepared according to the procedure described in Example 233 above except for the substitution of cyclohexanecarboxylic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 1.20–1.50 (m, 5H), 1.60–1.95 (m, 5H), 2.42 (m, 1H), 5.83 (s, 2H).

EXAMPLE 239

Cyclopentanecarboxylic acid chlorocarbonyloxymethyl ester

The title compound was prepared according to the procedure described in Example 233 above except for the substitution of cyclopentanecarboxylic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 1.60–1.92 (m, 8H), 2.85 (m, 1H), 5.83 (s, 2H).

EXAMPLE 240

Hexanoic acid chlorocarbonyloxymethyl ester

The title compound was prepared according to the procedure described in Example 233 above except for the substitution of hexanoic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 0.91 (m, 3H), 1.31–1.35 (m, 4H), 1.67 (m, 2H), 2.41 (m, 2H), 5.83 (s, 2H).

EXAMPLE 241

Octanoic acid chlorocarbonyloxymethyl ester

The title compound was prepared according to the procedure described in Example 233 above except for the substitution of octanoic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 0.89 (t, 3H), 1.30 (m, 8H), 1.65 (m, 2H), 2.41 (t, 2H), 5.83 (s, 2H).

EXAMPLE 242

2-Methylhexanoic acid chlorocarbonyloxymethyl ester

The title compound was prepared according to the procedure described in Example 233 above except for the substitution of 2-methylhexanoic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 0.90 (t, 3H), 1.19 (d, 3H), 1.28–1.55 (m, 4H), 1.70 (m, 2H), 2.55 (m, 1H), 5.84 (s, 2H).

EXAMPLE 243

Hexadecanoic acid chlorocarbonyloxymethyl ester

The title compound was prepared according to the procedure described in Example 233 above except for the substitution of hexadecanoic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 0.88 (t, 3H), 1.26 (m, 24H), 1.68 (m, 2H), 2.41 (t, 2H), 5.83 (s, 2H).

EXAMPLE 244

Undecanoic acid chlorocarbonyloxymethyl ester

The title compound was prepared according to the procedure described in Example 233 above except for the substitution of undecanoic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 0.88 (t, 3H), 1.25 (m, 14H), 1.65 (m, 2H), 2.41 (t, 2H), 5.83 (s, 2H).

EXAMPLE 245

4-Chlorobenzoic acid chlorocarbonyloxymethyl ester

The title compound was prepared according to the procedure described in Example 233 above except for the substitution of 4-chlorobenzoic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 6.07 (s, 2H), 7.46 (d, 2H), 8.02 (d, 2H).

EXAMPLE 246

2-Ethoxybenzoic acid chlorocarbonyloxymethyl ester

The title compound was prepared according to the procedure described in Example 233 above except for the substitution of 2-ethoxybenzoic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 1.46 (t, 3H), 4.11 (d, 2H), 6.03 (s, 2H), 6.94–6.97 (m, 2H), 7.55 (t, 1H), 7.89 (d, 1H).

EXAMPLE 247

(2,4-Dichlorophenoxy)acetic acid chlorocarbonyloxymethyl ester

The title compound was prepared according to the procedure described in Example 233 above except for the substitution of (2,4-dichlorophenoxy)acetic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 4.79 (s, 2H), 5.90 (s, 2H), 6.79 (d, 1H), 7.18 (dd, 1H), 7.39 (d, 1H).

EXAMPLE 248

Cyclopropanecarboxylic acid chlorocarbonyloxymethyl ester

The title compound was prepared according to the procedure described in Example 233 above except for the substitution of cyclopropanecarboxylic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 1.01 (m, 4H), 1.12 (m, 2H), 1.71 (m, 1H), 5.83 (s, 2H).

EXAMPLE 249

3,3,3-Trifluoropropanoic acid chlorocarbonyloxymethyl ester

The title compound was prepared according to the procedure described in Example 233 above except for the substitution of 3,3,3-trifluoropropanoic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 3.31 (q, 2H), 5.88 (s, 2H).

EXAMPLE 250

(Diethoxyphosphoryl)acetic acid chlorocarbonyloxymethyl ester

The title compound was prepared according to the procedure described in Example 233 above except for the substitution of (diethoxyphosphoryl)acetic acid ethylsulfanylcarbonyloxymethyl ester for 2-methylpropanoic acid ethylsulfanylcarbonyloxymethyl ester. 1H-NMR (300 MHz, CDCl$_3$) δ (ppm): 1.36 (t, 6H), 3.06 (d, 2H), 4.19 (q, 4H), 5.86 (s, 2H).

EXAMPLE 251

2,2-Dimethylmalonic acid dichlorocarbonyloxymethyl ester

The title compound was prepared according to the procedure described in Example 233 above except for the substitution of 2,2-dimethylmalonic acid diethylsulfanylcarbonyloxymethyl ester for 2-methylpropanoic acid ethylsulfanylcarbonyloxymethyl ester. 1H-NMR (300 MHz, CDCl$_3$) δ (ppm): 1.53 (s, 6H), 5.85 (s, 4H).

EXAMPLE 252

(Method A, Procedure A)

2-Methylpropanoic acid (carboxymethyl phosphonomethylcarbamoyloxy)-methyl ester (Compound 2-1 of Table 2)

A stirred solution of phosphonomethyl glycine (9.49 g, 56.2 mmol) in hexamethyldisilazane (25.5 mL, 121 mmol) was slowly heated to 90° C. (at this temperature it was noted out gassing of ammonia occurred). The reaction temperature was increased to 125° C. for 150 min at which time the reaction became homogeneous. The solution was allowed to cool to room temperature at which time, dry methylene chloride (60 mL) was added. The material (34.0 g, 74.5 mmol) was syringed into a flask and placed under a N$_2$ atm. Methylene chloride (120 mL) was added and the solution cooled in a dry ice acetone bath. A solution of 2-methylpropanoic acid chlorocarbonyloxymethyl ester (10.7 g, 59.1 mmol) in 5 mL of methylene chloride was added dropwise over two minutes through a 3 mL syringe. After 10 minutes the cooling bath was removed and the reaction was allowed to warm to room temperature and stir for 12 h. The reaction solution was concentrated under reduced pressure and dissolved in 200 mL of methanol and allowed to stand for 4 h. The reaction was vacuum filtered and concentrated under reduced pressure. The oil was dissolved with 120 mL of dry acetone and allowed to stand for one hour, vacuum filtered, and concentrated under vacuum. The solid was triterated with 60 mL of warm hexanes and then placed under vacuum. Yield 14.0 grams. 1H-NMR (300 MHz, D$_2$O) δ (ppm): 1.01 (dd, 6H), 2.51 (m, 1H), 3.47 (d, 2H), 4.09 (d, 2H), 5.63 (d, 2H).

EXAMPLE 253

3,6-Dichloro-2-methoxybenzoic acid (carboxymethyl phosphonomethylcarbamoyloxy)-methyl ester (Compound 2-3 of Table 2)

The title compound was prepared according to the procedure described in Example 252 above except for the substitution of 3,6-dichloro-2-methoxybenzoic acid chlorocarbonyloxymethyl ester for 2-methylpropanoic acid chlorocarbonyloxymethyl ester. 1H-NMR (300 MHz, CD$_3$OD) δ (ppm): 3.66 (dd, 2H), 3.78 (s, 3H), 4.14 (d, 2H), 5.90 (d, 2H), 7.13 (d, 1H), 7.41 (d, 1H).

EXAMPLE 254

(3,5,6-Trichloro-2-pyridyloxy)acetic acid (carboxymethyl phosphonomethylcarbamoyloxy)-methyl ester (Compound 2-4 of Table 2)

The title compound was prepared according to the procedure described in Example 252 above except for the substitution of (3,5,6-trichloro-2-pyridyloxy)acetic acid chlorocarbonyloxymethyl ester for 2-methylpropanoic acid chlorocarbonyloxymethyl ester. 1H-NMR (300 MHz, CD$_3$OD) δ (ppm): 3.71 (m, 2H), 4.24 (d, 2H), 5.04 (d, 2H), 5.86 (d, 2H), 8.09 (s, 1H).

EXAMPLE 255

4-(2,4-Dichlorophenoxy)butyric acid (carboxymethyl phosphonomethylcarbamoyloxy)-methyl ester (Compound 2-5 of Table 2)

The title compound was prepared according to the procedure described in Example 252 above except for the substitution of 4-(2,4-dichlorophenoxy)butyric acid chlorocarbonyloxymethyl ester for 2-methylpropanoic acid chlorocarbonyloxymethyl ester. 1H-NMR (300 MHz, CD$_3$OD) δ (ppm): 2.05 (m, 2H), 2.49 (m, 2H), 3.60 (m, 2H), 3.97 (m, 2H), 4.09 (d, 2H), 5.66 (d, 2H), 6.94 (d, 1H), 7.13 (dd, 1H), 7.27 (d, 1H).

EXAMPLE 256

Propionic acid (carboxymethylphosphonomethyl carbamoyloxy)-methyl ester (Compound 2-6 of Table 2)

The title compound was prepared according to the procedure described in Example 252 above except for the substitution of propionic acid chlorocarbonyloxymethyl ester for 2-methylpropanoic acid chlorocarbonyloxymethyl ester. 1H-NMR (300 MHz, CD$_3$OD) δ (ppm): 0.98 (t, 3H), 2.25 (q, 2H), 3.61 (dd, 2H), 4.09 (d, 2H), 5.64 (d, 2H).

EXAMPLE 257

Cyclohexanecarboxylic acid (carboxymethyl phosphonomethylcarbamoyloxy)-methyl ester (Compound 2-8 of Table 2)

The title compound was prepared according to the procedure described in Example 252 above except for the substitution of cyclohexanecarboxylic acid chlorocarbonyloxymethyl ester for 2-methylpropanoic acid chlorocarbonyloxymethyl ester. 1H-NMR (300 MHz, CD$_3$OD) δ (ppm): 1.19–1.35 (m, 5H), 1.50–1.80 (m, 5H), 2.23 (m, 1H), 3.61 (m, 2H), 4.08 (d, 2H), 5.64 (d, 2H).

EXAMPLE 258

Cyclopentanecarboxylic acid (carboxymethyl phosphonomethylcarbamoyloxy)-methyl ester (Compound 2-10 of Table 2)

The title compound was prepared according to the procedure described in Example 252 above except for the substitution of cyclopentanecarboxylic acid chlorocarbonyloxymethyl ester for 2-methylpropanoic acid chlorocarbonyloxymethyl ester. 1H-NMR (300 MHz, CD$_3$OD) δ (ppm): 1.70–2.05 (m, 8H), 2.90 (m, 1H), 4.84 (m, 2H), 4.29 (d, 2H), 5.86 (d, 2H).

EXAMPLE 259

Hexanoic acid (carboxymethylphosphonomethyl carbamoyloxy)-methyl ester (Compound 2-12 of Table 2)

The title compound was prepared according to the procedure described in Example 252 above except for the substitution of hexanoic acid chlorocarbonyloxymethyl ester for 2-methylpropanoic acid chlorocarbonyloxymethyl ester. 1H-NMR (300 MHz, CD$_3$OD) δ (ppm): 0.81 (m, 3H), 1.19–1.21 (m, 4H), 1.51 (m, 2H), 2.23 (m, 2H), 3.61 (m, 2H), 4.08 (d, 2H), 5.64 (d, 2H).

EXAMPLE 260

Octanoic acid (carboxymethylphosphonomethyl carbamoyloxy)-methyl ester (Compound 2-14 of Table 2)

The title compound was prepared according to the procedure described in Example 252 above except for the substitution of octanoic acid chlorocarbonyloxymethyl ester for 2-methylpropanoic acid chlorocarbonyloxymethyl ester. 1H-NMR (300 MHz, CD$_3$OD) δ (ppm): 0.79 (t, 3H), 1.19 (m, 8H), 1.49 (bs, 2H), 2.23 (m, 2H), 3.62 (m, 2H), 4.08 (d, 2H), 5.64 (d, 2H).

EXAMPLE 261

2-Methylhexanoic acid (carboxymethylphosphonomethyl carbamoyloxy)-methyl ester (Compound 2-16 of Table 2)

The title compound was prepared according to the procedure described in Example 252 above except for the substitution of 2-methylhexanoic acid chlorocarbonyloxymethyl ester for 2-methylpropanoic acid chlorocarbonyloxymethyl ester. 1H-NMR (300 MHz, CD$_3$OD) δ (ppm): 0.81 (t, 3H), 1.03 (d, 3H), 1.15–1.55 (m, 6H), 2.38 (m, 1H), 3.63 (m, 2H), 4.09 (d, 2H), 5.66 (d, 2H).

EXAMPLE 262

Hexadecanoic acid (carboxymethylphosphonomethyl carbamoyloxy)-methyl ester (Compound 2-18 of Table 2)

The title compound was prepared according to the procedure described in Example 252 above except for the substitution of hexadecanoic acid chlorocarbonyloxymethyl ester for 2-methylpropanoic acid chlorocarbonyloxymethyl ester. 1H-NMR (300 MHz, CD$_3$OD) δ (ppm): 0.79 (t, 3H), 1.18 (m, 24H), 1.51 (bs, 2H), 2.22 (bs, 2H), 3.60 (bs, 2H), 4.08 (m, 2H), 5.63 (d, 2H).

EXAMPLE 263

Undecanoic acid (carboxymethylphosphonomethyl carbamoyloxy)-methyl ester (Compound 2-20 of Table 2)

The title compound was prepared according to the procedure described in Example 252 above except for the substitution of undecanoic acid chlorocarbonyloxymethyl ester for 2-methylpropanoic acid chlorocarbonyloxymethyl ester. 1H-NMR (300 MHz, CD$_3$OD) δ (ppm): 0.71 (t, 3H), 1.10 (m, 14H), 1.41 (bs, 2H), 2.16 (m, 2H), 3.52 (m, 2H), 4.02 (m, 2H), 5.58 (d, 2H).

EXAMPLE 264

2,2-Dimethylpropionic acid (carboxymethylphosphonomethyl carbamoyloxy)-methyl ester (Compound 2-22 of Table 2)

The title compound was prepared according to the procedure described in Example 252 above except for the substitution of 2,2-dimethylpropionic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, CD$_3$OD) δ (ppm): 0.82 (s, 9H), 3.22 (d, 2H), 3.83 (m, 2H), 5.38 (d, 2H).

EXAMPLE 265

2-Ethoxybenzoic acid (carboxymethylphosphonomethyl carbamoyloxy)-methyl ester (Compound 2-24 of Table 2)

The title compound was prepared according to the procedure described in Example 252 above except for the substitution of 2-ethoxybenzoic acid chlorocarbonyloxymethyl ester for 2-methylpropanoic acid chlorocarbonyloxymethyl ester. 1H-NMR (300 MHz, $CD_3OD$) δ (ppm): 1.43 (t, 3H), 3.78 (m, 2H), 4.13 (m, 2H), 4.25 (s, 2H), 5.96 (d, 2H), 7.00 (dd, 1H), 7.11 (d, 1H), 7.53 (dd, 1H), 7.81 (m, 1H).

EXAMPLE 266

(2,4-Dichlorophenoxy)acetic acid (carboxymethyl phosphonomethylcarbamoyloxy)-methyl ester (Compound 2-26 of Table 2)

The title compound was prepared according to the procedure described in Example 252 above except for the substitution of (2,4-dichlorophenoxy)acetic acid chlorocarbonyloxymethyl ester for 2-methylpropanoic acid chlorocarbonyloxymethyl ester. 1H-NMR (300 MHz, $CD_3OD$) δ (ppm): 3.60 (dd, 2H), 4.11 (d, 2H), 4.75 (d, 2H), 5.75 (d, 2H), 6.89 (m, 1H), 7.16 (dd, 1H), 7.31 (d, 1H).

EXAMPLE 267

Cyclopropanecarboxylic acid (carboxymethyl phosphonomethylcarbamoyloxy)-methyl ester (Compound 2-27 of Table 2)

The title compound was prepared according to the procedure described in Example 252 above except for the substitution of cyclopropanecarboxylic acid chlorocarbonyloxymethyl ester for 2-methylpropanoic acid chlorocarbonyloxymethyl ester. 1H-NMR (300 MHz, $CD_3OD$) δ (ppm): 0.86 (m, 4H), 1.53 (m, 1H), 3.61 (m, 2H), 4.08 (d, 2H), 5.63 (d, 2H).

EXAMPLE 268

3,3,3-Trifluoropropanoic acid (carboxymethyl phosphonomethylcarbamoyloxy)-methyl ester (Compound 2-29 of Table 2)

The title compound was prepared according to the procedure described in Example 252 above except for the substitution of 3,3,3-trifluoropropanoic acid chlorocarbonyloxymethyl ester for 2-methylpropanoic acid chlorocarbonyloxymethyl ester. 1H-NMR (300 MHz, $CD_3OD$) δ (ppm): 3.34 (m, 2H), 3.61 (dd, 2H), 4.09 (d, 2H), 5.71 (d, 2H).

EXAMPLE 269

(Diethoxyphosphoryl)acetic acid (carboxymethyl phosphonomethylcarbamoyloxy)-methyl ester (Compound 2-31 of Table 2)

The title compound was prepared according to the procedure described in Example 252 above except for the substitution of (diethoxyphosphoryl)acetic acid chlorocarbonyloxymethyl ester for 2-methylpropanoic acid chlorocarbonyloxymethyl ester. 1H-NMR (300 MHz, $CD_3OD$) δ (ppm): 1.26 (t, 6H), 3.08 (dd, 2H), 3.68 (dd, 2H), 4.13 (m, 6H), 5.73 (d, 2H).

EXAMPLE 270
(Method A, Procedure B)

3,3-Dimethylbutyric acid (carboxymethyl phosphonomethylcarbamoyloxy)-methyl ester (Compound 2-33 of Table 2)

To a stirred ice cold solution of O-iodomethyl S-ethyl carbothioate (5.80 g, 23.6 mmol) in 60 mL of dry THF was added 3,3-dimethylbutyric acid (3.56 g, 30.7 mmol) followed by diisopropylethylamine (3.90 g, 30.2 mmol). The reaction was allowed to stir at room temperature for 16 h. The reaction was concentrated under reduced pressure. The soft solid was dissolved with 25 mL of methylene chloride and suction filtered through a pad of flash grade silica gel and eluted with 20% methylene chloride/hexanes. The material was carried on directly to the next step. A 100 mL roundbottom flask was charged with the 3,3-dimethylbutyric acid ethylsulfanylcarbonyloxymethyl ester (4.4 g1, 8.8 mmol) and cooled to 10° C. in an ice bath. Sulfuryl chloride (3.04 g, 22.6 mmol) was added over one minute. After 10 min, the cooling bath was removed. After 30 minutes of stirring, the cooling bath was removed, and the reaction was allowed to stir for 1 h at room temperature and then placed under vacuum for 15 min. The material was used without purification. In a separate flask, a stirred solution of phosphonomethyl glycine (1.69 g, 10 mmol) in hexamethyldisilazane (4.4 mL, 3.4 g, 21 mmol) was slowly heated to 90° C. (at this temperature it was noted out gassing of ammonia occurred). The reaction temperature was increased to 125° C. for 150 min at which time the reaction became homogeneous. The solution was allowed to cool to room temperature at which time, dry methylene chloride (10 mL) was added. This material (4.57 g,, 10.0 mmol) was cooled in an acetone/dry ice bath. The generated chloroformate (1.95 g, 9.33 mmol) was added by syringe to the silylated phosphonomethylglycine solution. After 10 min the cooling bath was removed and the reaction was allowed to warm to room temperature and stir for 16 h. The reaction solution was concentrated under reduced pressure and dissolved in 25 mL of a 9:1 mixture of acetone/water and allowed to stand for 4 h. The reaction was dried with $MgSO_4$, vacuum filtered, and concentrated under reduced pressure. The solid was triterated twice with 60 mL of warm hexanes and then placed under vacuum to afford the desired product (3.04 g) in 96% yield. 1H-NMR (300 MHz, $D_2O$) δ (ppm): 1H-NMR 0.86 (s, 9H), 2.16 (d, 2H), 3.52 (dd, 2H), 4.10 (d, 2H), 5.61 (d, 2H).

EXAMPLE 271

2-Propylpentanoic acid (carboxymethyl phosphonomethylcarbamoyloxy)-methyl ester (Compound 2-35 of Table 2)

The title compound was prepared according to the procedure described in Example 270 above except for the substitution of 2-propylpentanoic acid for 3,3-dimethylbutyric acid. 1H-NMR (300 MHz, $CD_3OD$) δ (ppm): 0.80 (t, 6H), 1.19–1.51 (m, 8H), 2.31 (m, 1H), 3.62 (t, 2H), 4.09 (bs, 2H), 5.65 (d, 2H).

EXAMPLE 272

3,3,3-Trifluorobutanoic acid (carboxymethyl phosphonomethylcarbamoyloxy)-methyl ester (Compound 2-39 of Table 2)

The title compound was prepared according to the procedure described in Example 270 above except for the substitution of 3,3,3-trifluorobutanoic acid for 3,3-dimethylbutyric acid. 1H-NMR (300 MHz, $D_2O$) δ (ppm): 2.41 (m, 2H), 2.61 (m, 2H), 3.54 (dd, 2H), 4.09 (d, 2H), 5,65 (d, 2H).

EXAMPLE 273

2,2-Dimethylbutanoic acid (carboxymethylphosphonomethyl carbamoyloxy)-methyl ester (Compound 2-41 of Table 2)

The title compound was prepared according to the procedure described in Example 270 above except for the substitution of 2,2-dimethylbutanoic acid for 3,3-dimethylbutyric acid. 1H-NMR (300 MHz, CD$_3$OD) δ (ppm): 0.73 (t, 3H), 1.04 (s, 3H), 1.05 (s, 3H), 1.48 (q, 2H), 3.59 (dd, 2H), 4.10 (d, 2H), 5.65 (d, 2H).

EXAMPLE 274

2-Methylcyclopropanecarboxylic acid (carboxymethyl phosphonomethylcarbamoyloxy)-methyl ester (Compound 2-43 of Table 2)

The title compound was prepared according to the procedure described in Example 270 above except for the substitution of 2-methylcyclopropanecarboxylic acid for 3,3-dimethylbutyric acid. 1H-NMR (300 MHz, CD$_3$OD) δ (ppm): 1.00–1.31 (m, 7H), 3.62 (m, 2H), 4.08 (d, 2H), 5.62 (d, 2H).

EXAMPLE 275

Tridecanoic acid (carboxymethyl phosphonomethyl carbamoyloxy)-methyl ester (Compound 2-44 of Table 2)

The title compound was prepared according to the procedure described in Example 270 above except for the substitution of tridecanoic acid for 3,3-dimethylbutyric acid. 1H-NMR (300 MHz, CD$_3$OD) δ (ppm): 0.79 (m, 3H), 1.18 (s, 20H), 1.51 (bs, 2H), 2.27 (m, 2H), 3.60 (dd, 2H), 4.10 (d, 2H), 5.65 (d, 2H).

EXAMPLE 276

2-Methylpropanoic acid (carboxymethylphosphonomethyl carbamoyloxy)-methyl ester-isopropylamine salt (Compound 2-2 of Table 2)

To a stirred ice cold solution of 2-methylpropanoic acid (carboxymethylphosphonomethylcarbamoyloxy)-methyl ester (14.1 g, 43.8 mmol) in 80 mL of acetone was added isopropylamine (3.71 mL, 43.8 mmol). After 15 min of stirring the solvent was removed was removed under vacuum. The solid was washed with diethyl ether and subsequently dried under vacuum to afford 14.8 g of a tannish solid. 1H-NMR (300 MHz, D$_2$O) δ (ppm): 1.01 (dd, 6H), 1.16 (d, 6H), 2.51 (m, 1H), 3.35 (m, 1H), 3.47 (d, 2H), 4.09 (d, 2H), 5.63 (d, 2H).

EXAMPLE 277

Propionic acid (carboxymethylphosphonomethyl carbamoyloxy)-methyl ester-isopropylamine salt (Compound 2-7 of Table 2)

The title compound was prepared according to the procedure described in Example 276 above except for the substitution of propionic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, D$_2$O) δ (ppm): 0.69 (t, 3H), 0.88 (d, 6H), 2.01 (m, 2H), 3.08 (m, 1H), 3.18 (d, 2H), 3.78 (d, 2H), 5.35 (d, 2H).

EXAMPLE 278

Cyclohexanecarboxylic acid (carboxymethylphosphonomethyl carbamoyloxy)-methyl ester-isopropylamine salt (Compound 2-9 of Table 2)

The title compound was prepared according to the procedure described in Example 276 above except for the substitution of cyclohexanecarboxylic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, D$_2$O) δ (ppm): 1.19 (d, 6H), 1.19–1.35 (m, 5H), 1.50–1.80 (m, 5H), 2.23 (m, 1H), 3.30 (m, 1H), 3.49 (m, 2H), 4.09 (d, 2H), 5.63 (d, 2H).

EXAMPLE 279

Cyclopentanecarboxylic acid (carboxymethyl phosphonomethylcarbamoyloxy)-methyl ester-isopropylamine salt (Compound 2-11 of Table 2)

The title compound was prepared according to the procedure described in Example 276 above except for the substitution of cyclopentanecarboxylic acid (carboxymethylphosphonomethylcarbamoyloxy)-methyl ester for 2-methylprop anoic acid (carboxymethylphosphonomethylcarbamoyloxy)-methyl ester. 1H-NMR (300 MHz, D$_2$O) δ (ppm): 1.15 (d, 6H), 1.48–1.80 (m, 8H), 2.71 (m, 1H), 3.37 (m, 1H), 3.44 (d, 2H), 4.02 (d, 2H), 5.61 (d, 2H).

EXAMPLE 280

Hexanoic acid (carboxymethylphosphonomethyl carbamoyloxy)-methyl ester-isopropylamine salt (Compound 2-13 of Table 2)

The title compound was prepared according to the procedure described in Example 276 above except for the substitution of hexanoic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, D$_2$O) δ (ppm): 0.71 (m, 3H), 1.12–1.15 (m, 10H), 1.45 (m, 2H), 2.26 (m, 2H), 3.33 (m, 1H), 3.45 (dd, 2H), 4.07 (d, 2H), 5.59 (d, 2H).

EXAMPLE 281

Octanoic acid (carboxymethylphosphonomethyl carbamoyloxy)-methyl ester-isopropylamine salt (Compound 2-15 of Table 2)

The title compound was prepared according to the procedure described in Example 276 above except for the substitution of octanoic acid -methylpropanoic acid (carboxymethylphosphonomethylcarbamoyloxy)-methyl ester. 1H-NMR (300 MHz, D$_2$O) δ (ppm): 0.73 (t, 3H), 1.18 (m, 14H), 1.48 (bs, 2H), 2.30 (m, 2H), 3.35 (m, 1H), 3.47 (dd, 2H), 4.09 (s, 2H), 5.63 (d, 2H).

EXAMPLE 282

2-Methylhexanoic acid (carboxymethylphosphonomethyl carbamoyloxy)-methyl ester-isopropylamine salt (Compound 2-17 of Table 2)

The title compound was prepared according to the procedure described in Example 276 above except for the substitution of 2-methylhexanoic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, D$_2$O) δ (ppm): 0.61 (t, 3H), 0.90 (d, 3H), 1.06 (m, 10H), 1.20–1.40 (m, 2H), 2.32 (m, 1H), 3.25 (m, 1H), 3.35 (d, 2H), 3.96 (d, 2H), 5.52 (d, 2H).

EXAMPLE 283

Hexadecanoic acid (carboxymethylphosphonomethyl carbamoyloxy)-methyl ester-isopropylamine salt (Compound 2-19 of Table 2)

The title compound was prepared according to the procedure described in Example 276 above except for the substitution of hexadecanoic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, $D_2O$) δ (ppm): 0.79 (t, 3H), 1.18 (m, 24H), 1.51 (bs, 2H), 2.22 (bs, 2H), 3.60 (bs, 2H), 4.08 (m, 2H), 5.63 (d, 2H).

EXAMPLE 284

Undecanoic acid (carboxymethylphosphonomethyl carbamoyloxy)-methyl ester-isopropylamine salt (Compound 2-21 of Table 2)

The title compound was prepared according to the procedure described in Example 276 above except for the substitution of undecanoic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, $D_2O$) δ (ppm): 0.71 (t, 3H), 1.10 (m, 14H), 1.41 (bs, 2H), 2.16 (m, 2H), 3.52 (m, 2H), 4.02 (m, 2H), 5.58 (d, 2H).

EXAMPLE 285

2,2-Dimethylpropionic acid (carboxymethylphosphonomethyl carbamoyloxy)-methyl ester-isopropylamine salt (Compound 2-23 of Table 2)

The title compound was prepared according to the procedure described in Example 276 above except for the substitution of 2,2-dimethylpropionic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, $D_2O$) δ (ppm): 0.82 (s, 9H), 0.92 (d, 6H), 3.11 (m, 1H), 3.22 (d, 2H), 3.83 (m, 2H), 5.38 (d, 21).

EXAMPLE 286

2-Ethoxybenzoic acid (carboxymethylphosphonomethyl carbamoyloxy)-methyl ester-isopropylamine salt (Compound 2-25 of Table 2)

The title compound was prepared according to the procedure described in Example 276 above except for the substitution of 2-ethoxybenzoic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, $D_2O$) δ (ppm): 1.14 (d, 6H), 1.27 (t, 3H), 3.35 (m, 1H), 3.45 (d, 2H), 4.09 (m, 4H), 5.82 (d, 2H), 6.95–7.07 (m, 2H), 7.48 (m, 1H), 7.74 (m, 1H).

EXAMPLE 287

Cyclopropanecarboxylic acid (carboxymethyl phosphonomethylcarbamoyloxy)-methyl ester-isopropylamine salt (Compound 2-28 of Table 2)

The title compound was prepared according to the procedure described in Example 276 above except for the substitution of cyclopropanecarboxylic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, $D_2O$) δ (ppm): 0.89 (m, 4H), 1.16 (d, 6H), 1.53 (m, 1H), 3.36 (m, 1H), 3.45 (m, 2H), 4.07 (d, 2H), 5.61 (d, 2H).

EXAMPLE 288

3,3,3-Trifluoropropanoic acid (carboxymethyl phosphonomethylcarbamoyloxy)-methyl ester-isopropylamine salt (Compound 2-30 of Table 2)

The title compound was prepared according to the procedure described in Example 276 above except for the substitution of 3,3,3-trifluoropropanoic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, $D_2O$) δ (ppm): 1.16 (d, 6H), 3.44 (m, 4H), 4.04 (d, 2H), 5.69 (d, 2H).

EXAMPLE 289

(Diethoxyphosphoryl)acetic acid (carboxymethyl phosphonomethylcarbamoyloxy)-methyl ester-isopropylamine salt (Compound 2-32 of Table 2)

The title compound was prepared according to the procedure described in Example 276 above except for the substitution of (diethoxyphosphoryl)acetic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, $D_2O$) δ (ppm): 1.18 (m, 12H), 3.19 (dd, 2H), 3.35 (m, 1H), 3.45 (m, 2H), 4.00 (d, 2H), 4.06 (m, 4H), 5.78 (d, 2H).

EXAMPLE 290

2-Propylpentanoic acid (carboxymethylphosphonomethyl carbamoyloxy)-methyl ester-isopropylamine salt (Compound 2-36 of Table 2)

The title compound was prepared according to the procedure described in Example 276 above except for the substitution of 2-propylpentanoic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, $D_2O$) δ (ppm): 0.73 (t, 6H), 1.11–1.45 (m, 14H), 2.41 (m, 1H), 3.37 (m, 1H), 3.47 (d, 2H), 4.05 (d, 2H), 5.63 (d, 2H).

EXAMPLE 291

2-Propylpentanoic acid (carboxymethylphosphonomethyl carbamoyloxy)-methyl ester-bis-(isopropylamine) salt (Compound 2-37 of Table 2)

The title compound was prepared according to the procedure described in Example 276 above except for the substitution of 2-propylpentanoic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, $D_2O$) δ (ppm): 0.74 (t, 6H), 1.11–1.45 (m, 20H), 2.41 (m, 1H), 3.37 (m, 1H), 3.45 (d, 2H), 3.88 (s, 2H), 5.66 (d, 2H).

EXAMPLE 292

3,3-Dimethylbutyric acid (carboxymethylphosphonomethyl carbamoyloxy)-methyl ester-isopropylamine salt (Compound 2-39 of Table 2)

The title compound was prepared according to the procedure described in Example 276 above except for the substitution of 3,3-dimethylbutyric acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, $D_2O$) δ (ppm): 0.86 (s, 9H), 1.16 (d, 2H), 2.16 (d, 2H), 3.36 (m, 1H), 3.45 (dd, 2H), 4.01 (d, 2H), 5.61 (d, 2H).

EXAMPLE 293

3,3,3-Trifluorobutanoic acid (carboxymethyl phosphonomethylcarbamoyloxy)-methyl ester-isopropylamine salt (Compound 2-40 of Table 2)

The title compound was prepared according to the procedure described in Example 276 above except for the substitution of 3,3,3-trifluorobutanoic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, $D_2O$) δ (ppm): 1.16 (d, 6H), 2.45 (m, 2H), 2.61 (m, 2H), 3.36 m(1H), 3.48 (dd, 2H), 4.02 (d, 2H), 5,65 (d, 2H).

EXAMPLE 294

2,2-Dimethylbutanoic acid (carboxymethylphosphonomethyl carbamoyloxy)-methyl ester-isopropylamine salt (Compound 2-42 of Table 2)

The title compound was prepared according to the procedure described in Example 276 above except for the substitution of 2,2-dimethylbutanoic acid (carboxymethylphosphonomethylcarbamoyloxy)-methyl ester for 2-methylpropanoic acid (carboxymethylphosphonomethylcarbamoyloxy)-methyl ester. 1H-NMR (300 MHz, $D_2O$) δ (ppm): 0.53 (m, 3H), 0.87 (s, 3H), 0.88 (s, 3H), 1.00 (d, 12H), 1.30 (m, 2H), 3.20 (m, 3H), 3.71 (s, 2H), 5.46 (d, 2H).

EXAMPLE 295

2-Methylpropanoic acid (carboxymethylphosphonomethyl carbamoyloxy)-methyl ester-potassium salt (Compound 2-36 of Table 2)

To a stirred ice cold solution of 2-methylpropanoic acid (carboxymethylphosphonomethylcarbamoyloxy)-methyl ester (0.57 g, 1.82 mmol) in 8 mL of acetone was added a 1M THF solution of potassium tert-butoxide (1.82 mL, 1.82 mmol). After 15 minutes of stirring the solvent was removed under vacuum. The solid was washed with diethyl ether and subsequently dried under vacuum. 1H-NMR (300 MHz, $D_2O$) δ (ppm): 1.01 (d, 6H), 2.51 (m, 1H), 3.44 (d, 2H), 4.03 (d, 2H), 5.62 (d, 2H).

Following the general methods described hereinbefore, the following compounds of Formula (III) as listed in Tables 3A–3U can be prepared.

TABLE 3A (III)

$$R^6O-\overset{O}{\underset{}{C}}-CH_2-N(\overset{CH_2}{\underset{\overset{P}{R^7\ R^8}=O}{}})-\overset{O}{\underset{}{C}}-O-\overset{R^1}{\underset{R^2}{C}}-(O-\overset{O}{\underset{}{C}})_t-(X^2)_qZ^2$$

| Cmpd # | $R^1$ | $R^2$ | $R^6$ | $R^7$ | $R^8$ | t | q | $(X^2)_qZ^2$ |
|---|---|---|---|---|---|---|---|---|
| 3-1 | H | H | H | OH | OH | 1 | 1 | 3,6-dichloro-2-pyridyl |
| 3-2 | H | H | H | OH | OH | 1 | 0 | $C(CH_3)_3$ |
| 3-3 | H | H | H | OH | OH | 1 | 0 | acetamidomethyl |
| 3-4 | H | H | H | OH | OH | 1 | 0 | 2-nitro-5-thiocyanatophenyl |
| 3-5 | H | H | H | OH | OH | 1 | 0 | cycloheptyl |
| 3-6 | H | H | H | OH | OH | 1 | 0 | 2-hydroxy-2-propyl |
| 3-7 | H | H | H | OH | OH | 1 | 0 | 1-(isopropyldineaminooxy)ethyl |
| 3-8 | H | H | H | OH | OH | 1 | 0 | 4,4,4-trifluoro-2-butyl |
| 3-9 | H | H | H | OH | OH | 1 | 0 | 2-(trifluoromethyl)propyl |
| 3-10 | H | H | H | OH | OH | 1 | 0 | 2,2,2-trifluoroethyl |
| 3-11 | H | H | H | OH | OH | 1 | 0 | 1-(benzyloxycarbonylamino)-1-methylethyl |
| 3-12 | H | H | H | OH | OH | 1 | 0 | 1-(tert-butoxycarbonylamino)-1-methylethyl |
| 3-13 | H | H | H | OH | OH | 1 | 0 | 1-(tert-butoxycarbonyl)-piperidin-4-yl |
| 3-14 | H | H | H | OH | OH | 1 | 0 | 1-acetyl-4-hydroxypyrrolidin-2-yl |
| 3-15 | H | H | H | OH | OH | 1 | 0 | 2-methyl-3-pyridyl |
| 3-16 | H | H | H | OH | OH | 1 | 0 | 1-(acetylamino)-2-methylpropyl |
| 3-17 | H | H | H | OH | OH | 1 | 0 | 2,6-dimethoxy-4-hydroxyphenyl |
| 3-18 | H | H | H | OH | OH | 1 | 0 | 3-methylthio-1-acetylaminopropyl |
| 3-19 | H | H | H | OH | OH | 1 | 0 | 1-acetylaminovinyl |
| 3-20 | H | H | H | OH | OH | 1 | 0 | 1-methyl-2-pyrrolyl |

TABLE 3A-continued (III)

$$R^6O-\overset{O}{\underset{}{C}}-CH_2-\underset{\underset{\underset{R^7\ R^8}{P=O}}{CH_2}}{N}-\overset{O}{\underset{}{C}}-O-\underset{R^2}{\overset{R^1}{C}}-(O-\overset{O}{C})_t-(X^2)_qZ^2$$

| Cmpd # | R¹ | R² | R⁶ | R⁷ | R⁸ | t | q | (X²)qZ² |
|---|---|---|---|---|---|---|---|---|
| 3-21 | H | H | H | OH | OH | 1 | 0 | 2-benzyloxycarbonyl)-1-(tert-butoxy carbonylamino)ethyl |
| 3-22 | H | H | H | OH | OH | 1 | 0 | 4-hexyloxyphenyl |
| 3-23 | H | H | H | OH | OH | 1 | 0 | 1-(2-chlorophenoxy)-1-methylethyl |
| 3-24 | H | H | H | OH | OH | 1 | 0 | 3-hydroxy-4-methoxyphenyl |
| 3-25 | H | H | H | OH | OH | 1 | 0 | 3,5-dinitro-4-hydroxyphenyl |
| 3-26 | H | H | H | OH | OH | 1 | 0 | 1-(tert-butoxycarbonyl)-2-pyrrolidinyl |
| 3-27 | H | H | H | OH | OH | 1 | 0 | 1-(di-N-propylamino)ethyl |
| 3-28 | H | H | H | OH | OH | 1 | 0 | 1-(tert-butoxycarbonyl)-4-hydroxy-2-pyrrolidinyl |
| 3-29 | H | H | H | OH | OH | 1 | 0 | 5-acetylamino-1-(tert-butoxycarbonylamino)pentyl |
| 3-30 | H | H | H | OH | OH | 1 | 0 | 1-(tert-butoxycarbonylamino)-2,2-dimethylpropyl |
| 3-31 | H | H | H | OH | OH | 1 | 0 | 2-pyrrolidinyl hydrochloride |
| 3-32 | H | H | H | OH | OH | 1 | 0 | 2-amino-2-propyl hydrochloride |
| 3-33 | H | H | H | OH | OH | 1 | 0 | 4-piperidinyl hydrochloride |
| 3-34 | H | H | H | OH | OH | 1 | 0 | 2-(benzyloxycarbonyl)-1-aminoethyl hydrochloride |
| 3-35 | H | H | H | OH | OH | 1 | 0 | 2-carboxy-1-aminoethyl hydrochloride |
| 3-36 | H | H | H | OH | OH | 1 | 0 | 2-carboxy-1-(tert-butoxycarbonylamino)ethyl |
| 3-37 | H | H | H | OH | OH | 1 | 0 | [benzyl-(diethoxyphosphorylmethyl)-amino]methyl |
| 3-38 | H | H | H | OH | OH | 1 | 0 | 2-methylnicotinyl |
| 3-39 | H | H | H | OH | OH | 1 | 0 | 1-(acetylamino)-2-methylpropyl |
| 3-40 | H | H | H | OH | OH | 1 | 0 | 3-methylthio-1-acetylaminopropyl |
| 3-41 | H | H | H | OH | OH | 1 | 0 | 1-tert-butoxycarbonyamino)-1-methylethyl |
| 3-42 | H | H | H | OH | OH | 0 | 0 | ⁺N(Et)₃Cl⁻ |
| 3-43 | H | H | H | OH | OH | 1 | 0 | undecyl |
| 3-44 | H | H | H | OH | OH | 1 | 0 | acetyl |
| 3-45 | H | H | H | OH | OH | 1 | 0 | 5-oxopyrrolidin-2-yl |
| 3-46 | H | H | H | OH | OH | 1 | 0 | methoxymethyl |
| 3-47 | H | H | H | OH | OH | 1 | 0 | (4-oxo-2-thioxothiazolidin-3-yl)methyl |
| 3-48 | H | H | H | OH | OH | 1 | 0 | pyrazin-2-yl |
| 3-49 | H | H | H | OH | OH | 1 | 0 | 1H-pyrazol-4-yl |
| 3-50 | H | H | H | OH | OH | 1 | 0 | (furan-2-carbonyl)aminomethyl |
| 3-51 | H | H | H | OH | OH | 1 | 0 | 2-(2,5-dioxo-2,5-dihydropyrrol-1-yl) ethyl |
| 3-52 | H | H | H | OH | OH | 1 | 0 | 2-methoxyethoxymethyl |
| 3-53 | H | H | H | OH | OH | 1 | 0 | methanesulfonylmethyl |
| 3-54 | H | H | H | OH | OH | 1 | 0 | 4-heptyloxyphenyl |
| 3-55 | H | H | H | OH | OH | 1 | 0 | 2,6-dichlorophenyl |
| 3-56 | H | H | H | OH | OH | 1 | 0 | (3,5-diiodo-4-oxo-4H-pyridin-1-yl)methyl |
| 3-57 | H | H | H | OH | OH | 1 | 0 | 3-pyridyl |
| 3-58 | H | H | H | OH | OH | 1 | 0 | 5,6-dich1oro-3-pyridyl |
| 3-59 | H | H | H | OH | OH | 1 | 0 | 4-pyridyl |
| 3-60 | H | H | H | OH | OH | 1 | 0 | 2,6-dichloro-4-pyridyl |
| 3-61 | H | H | H | OH | OH | 1 | 0 | 4-methanesulphonylphenyl |
| 3-62 | H | H | H | OH | OH | 1 | 0 | 2-chloro-4-nitrophenyl |
| 3-63 | H | H | H | OH | OH | 1 | 0 | 4-chloro-2-nitrophenyl |
| 3-64 | H | H | H | OH | OH | 1 | 0 | 3-chloro-2-nitrophenyl |
| 3-65 | H | H | H | OH | OH | 1 | 0 | 5-methylpyrazin-2-yl |
| 3-66 | H | H | H | OH | OH | 1 | 0 | tetrahydrofur-2-yl |
| 3-67 | H | H | H | OH | OH | 1 | 0 | 3-thiophen-2-ylpropyl |
| 3-68 | H | H | H | OH | OH | 1 | 0 | cyclopentylphenylmethyl |
| 3-69 | H | H | H | OH | OH | 1 | 0 | 1-phenylcyclopentyl |
| 3-70 | H | H | H | OH | OH | 1 | 0 | 1-methylcyclohexyl |
| 3-71 | H | H | H | OH | OH | 1 | 0 | 2-chloro-3-pyridyl |
| 3-72 | H | H | H | OH | OH | 1 | 0 | 1-methyl-1H-pyrrol-2-yl |
| 3-73 | H | H | H | OH | OH | 1 | 0 | 2,6-dimethoxyphenyl |
| 3-74 | H | H | H | OH | OH | 1 | 0 | 2,6-dimethoxy-3-pyridyl |
| 3-75 | H | H | H | OH | OH | 1 | 0 | 2-(thiophen-2-yl)ethenyl |

TABLE 3A-continued (III)

$$R^6O-\underset{O}{\overset{O}{C}}-CH_2-\underset{\underset{\underset{R^7\ R^8}{P=O}}{CH_2}}{N}-\underset{O}{\overset{O}{C}}-O-\underset{R^2}{\overset{R^1}{C}}-(O-C)_t-(X^2)_qZ^2$$

| Cmpd # | R¹ | R² | R⁶ | R⁷ | R⁸ | t | q | (X²)qZ² |
|---|---|---|---|---|---|---|---|---|
| 3-76 | H | H | H | OH | OH | 1 | 0 | 4-nitro-1H-pyrazol-3-yl |
| 3-77 | H | H | H | OH | OH | 1 | 0 | 4-sulfamoylphenyl |
| 3-78 | H | H | H | OH | OH | 1 | 0 | 2,4-dinitrophenyl |
| 3-79 | H | H | H | OH | OH | 1 | 0 | 1-hydroxy-1-phenylethyl |
| 3-80 | H | H | H | OH | OH | 1 | 0 | 3-hydroxy-4-methyl-2-nitrophenyl |
| 3-81 | H | H | H | OH | OH | 1 | 0 | 2-methylcyclopropyl |
| 3-82 | H | H | H | OH | OH | 1 | 0 | 1-phenylpropyl |
| 3-83 | H | H | H | OH | OH | 1 | 0 | 1,2,3,4-tetrahydronaphth-2-yl |
| 3-84 | H | H | H | OH | OH | 1 | 0 | 1-benzyl-2,2-dimethylpropyl |
| 3-85 | H | H | H | OH | OH | 1 | 0 | 2,2,3,3-tetramethylcyclopropyl |
| 3-86 | H | H | H | OH | OH | 1 | 0 | acetoxymethyl |
| 3-87 | H | H | H | OH | OH | 1 | 0 | 2,2,2-trifluoro-1-methoxy-1-phenylethyl |
| 3-88 | H | H | H | OH | OH | 1 | 0 | 1-methylpentyl |
| 3-89 | H | H | H | OH | OH | 1 | 0 | hept-1-ynyl |
| 3-90 | H | H | H | OH | OH | 1 | 0 | tetrahydrofur-3-yl |
| 3-91 | H | H | H | OH | OH | 1 | 0 | 1,1-methylpropyl |
| 3-92 | H | H | H | OH | OH | 1 | 0 | 2-methylcyclohexyl |
| 3-93 | H | H | H | OH | OH | 1 | 0 | 1,1-dimethylbut-3-enyl |
| 3-94 | H | H | H | OH | OH | 1 | 0 | 1-propylbutyl |
| 3-95 | H | H | H | OH | OH | 1 | 0 | 1-methylbutyl |
| 3-96 | H | H | H | OH | OH | 1 | 0 | 1-phenylethyl |
| 3-97 | H | H | H | OH | OH | 1 | 0 | phenyloxymethyl |
| 3-98 | H | H | H | OH | OH | 1 | 0 | pentafluorophenyloxymethyl |
| 3-99 | H | H | H | OH | OH | 1 | 0 | (2-formylaminothiazol-4-yl)methoxyiminomethyl |
| 3-100 | H | H | H | OH | OH | 1 | 0 | 1-hydroxy-1-ethylpropyl |
| 3-101 | H | H | H | OH | OH | 1 | 0 | 2-methoxyphenyloxymethyl |
| 3-102 | H | H | H | OH | OH | 1 | 0 | 2,4,6-trimethylphenyl |
| 3-103 | H | H | H | OH | OH | 1 | 0 | 2-methylphenyl |
| 3-104 | H | H | H | OH | OH | 1 | 0 | 1-methyl-1-(4-chlorophenyloxy)ethyl |
| 3-105 | H | H | H | OH | OH | 1 | 0 | 1-hydroxy-1-methylpropyl |
| 3-106 | H | H | H | OH | OH | 1 | 0 | 1-ethylpentyl |
| 3-107 | H | H | H | OH | OH | 1 | 0 | 2-methyl-1-phenylbutyl |
| 3-108 | H | H | H | OH | OH | 1 | 0 | 1-methylpropyl |
| 3-109 | H | H | H | OH | OH | 1 | 0 | cyclobutyl |
| 3-110 | H | H | H | OH | OH | 1 | 0 | 1-ethylpropyl |
| 3-111 | H | H | H | OH | OH | 1 | 0 | (3,5-dinitrobenzoylamino)phenylmethyl |
| 3-112 | H | H | H | OH | OH | 1 | 0 | 2,2-dichloro-1-methylcyclopropyl |
| 3-113 | H | H | H | OH | OH | 1 | 0 | 2,2,2-trifluoro-1-hydroxy-1-methylethyl |
| 3-114 | H | H | H | OH | OH | 1 | 0 | 1-hydroxy-2-trifluoromethylpropyl |
| 3-115 | H | H | H | OH | OH | 1 | 0 | 4-hydroxy-3-nitrophenyl |
| 3-116 | H | H | H | OH | OH | 1 | 0 | 4,8-dihydroxyquinol-2-yl |
| 3-117 | H | H | H | OH | OH | 1 | 0 | 2-hydroxy-1-phenylethyl |
| 3-118 | H | H | H | OH | OH | 1 | 0 | 4-hydroxyphenyl |
| 3-119 | H | H | H | OH | OH | 1 | 0 | 2,2-dimethylpropyl |
| 3-120 | H | H | H | OH | OH | 1 | 0 | 1-(3,5-dinitrobenzoylamino)-3-methylbutyl |
| 3-121 | H | H | H | OH | OH | 1 | 0 | (2-hydroxybenzoylamino)methyl |
| 3-122 | H | H | H | OH | OH | 1 | 0 | 3,3,3-trifluoropropyl |
| 3-123 | H | H | H | OH | OH | 1 | 0 | 1-oxypyrid-2-yl |
| 3-124 | H | H | H | OH | OH | 1 | 0 | 6-hydroxypyrid-2-yl |
| 3-125 | H | H | H | OH | OH | 1 | 0 | 3-hydroxypyrid-2-yl |
| 3-126 | H | H | H | OH | OH | 1 | 0 | benzoylaminomethyl |
| 3-127 | H | H | H | OH | OH | 1 | 0 | 1-methyl-5-oxo-2-pyrid-3-ylpyrrolin-3-yl |
| 3-128 | H | H | H | OH | OH | 1 | 0 | 1R,3R,4R,5R-tetrahydroxycyclohexyl |
| 3-129 | H | H | H | OH | OH | 1 | 0 | 2-(2-chlorphenyl)ethenyl |
| 3-130 | H | H | H | OH | OH | 1 | 0 | benzofur-2-yl |
| 3-131 | H | H | H | OH | OH | 1 | 0 | 3-thienyl |
| 3-132 | H | H | H | OH | OH | 1 | 0 | 3-methyl-1H-inden-2-yl |
| 3-133 | H | H | H | OH | OH | 1 | 0 | 3R,4S,5R-trihydroxy-1-cyclohexenyl |
| 3-134 | H | H | H | OH | OH | 1 | 0 | 2-(2-trifluoromethylphenyl)ethenyl |

TABLE 3A-continued (III)

$$R^6O-\overset{O}{\underset{}{C}}-CH_2-\underset{\underset{\underset{R^7}{\overset{|}{P}}{R^8}}{\underset{\overset{||}{O}}{\overset{|}{CH_2}}}}{N}-\overset{O}{\underset{}{C}}-O-\overset{R^1}{\underset{R^2}{\overset{|}{C}}}-(O-\overset{O}{\underset{}{C}})_t-(X^2)_qZ^2$$

| Cmpd # | R¹ | R² | R⁶ | R⁷ | R⁸ | t | q | (X²)qZ² |
|---|---|---|---|---|---|---|---|---|
| 3-135 | H | H | H | OH | OH | 1 | 0 | 2-(4-methylphenyl)ethenyl |
| 3-136 | H | H | H | OH | OH | 1 | 0 | 1-cyclohexenyl |
| 3-137 | H | H | H | OH | OH | 1 | 0 | 2-(4-trifluoromethylphenyl)ethenyl |
| 3-138 | H | H | H | OH | OH | 1 | 0 | 1-cyclopentenyl |
| 3-139 | H | H | H | OH | OH | 1 | 0 | 1-methyl-1-butenyl |
| 3-140 | H | H | H | OH | OH | 1 | 0 | 3,3,3-trifluoro-2-methyl-1-propenyl |
| 3-141 | H | H | H | OH | OH | 1 | 0 | 2-(2-fluorophenyl)ethenyl |
| 3-142 | H | H | H | OH | OH | 1 | 0 | vinyl |
| 3-143 | H | H | H | OH | OH | 1 | 0 | 2-(4-dimethylaminophenyl)ethenyl |
| 3-144 | H | H | H | OH | OH | 1 | 0 | 2-(2-methoxyphenyl)ethenyl |
| 3-145 | H | H | H | OH | OH | 1 | 0 | 2-(3-hydroxy-4-methoxyphenyl)ethenyl |
| 3-146 | H | H | H | OH | OH | 1 | 0 | 2-(3-trifluoromethylphenyl)ethenyl |
| 3-147 | H | H | H | OH | OH | 1 | 0 | 1-fluoro-2-phenylethenyl |
| 3-148 | H | H | H | OH | OH | 1 | 0 | 3-methyl-2-thienyl |
| 3-149 | H | H | H | OH | OH | 1 | 0 | l-cyano-2-(4-hydroxyphenyl)ethenyl |
| 3-150 | H | H | H | OH | OH | 1 | 0 | 2-(4-fluorophenyl)ethenyl |
| 3-151 | H | H | H | OH | OH | 1 | 0 | 2-methyl-1-propenyl |
| 3-152 | H | H | H | OH | OH | 1 | 0 | 1-ethyl-7-methyl-4-oxo-[1,8]naphthyridin-3-yl |
| 3-153 | H | H | H | OH | OH | 1 | 0 | 2-(4-hydroxy-3-methoxyphenyl)ethenyl |
| 3-154 | H | H | H | OH | OH | 1 | 0 | 2-(benzo[1,3]dioxol-5-yl)ethenyl |
| 3-155 | H | H | H | OH | OH | 1 | 0 | 1-methylcyclopropyl |
| 3-156 | H | H | H | OH | OH | 1 | 0 | 2-furyl |
| 3-157 | H | H | H | OH | OH | 1 | 0 | 2-phenylethenyl |
| 3-158 | H | H | H | OH | OH | 1 | 0 | 2-(4-bromophenyl)ethenyl |
| 3-159 | H | H | H | OH | OH | 1 | 0 | 3-furyl |
| 3-160 | H | H | H | OH | OH | 1 | 0 | 2-(4-methoxyphenyl)ethenyl |
| 3-161 | H | H | H | OH | OH | 1 | 0 | 1-methyl-1H-indol-2-yl |
| 3-162 | H | H | H | OH | OH | 1 | 0 | 2-(3-pyridyl)ethenyl |
| 3-163 | H | H | H | OH | OH | 1 | 0 | 2-(3-fluorophenyl)ethenyl |
| 3-164 | H | H | H | OH | OH | 1 | 0 | 5-methyl-2-thienyl |
| 3-165 | H | H | H | OH | OH | 1 | 0 | 1-acetylamino-2-phenylethenyl |
| 3-166 | H | H | H | OH | OH | 1 | 0 | 2,6-dimethyl-1,5-heptadienyl |
| 3-167 | H | H | H | OH | OH | 1 | 0 | 1-pentenyl |
| 3-168 | H | H | H | OH | OH | 1 | 0 | 2-(2,3-dimethoxyphenyl)ethenyl |
| 3-169 | H | H | H | OH | OH | 1 | 0 | 1,3-pentadienyl |
| 3-170 | H | H | H | OH | OH | 1 | 0 | 2-(3-nitrophenyl)ethenyl |
| 3-171 | H | H | H | OH | OH | 1 | 0 | 2-(4-chlorophenyl)ethenyl |
| 3-172 | H | H | H | OH | OH | 1 | 0 | 2-(4-nitrophenyl)ethenyl |
| 3-173 | H | H | H | OH | OH | 1 | 0 | 2-(3,4-dimethoxyphenyl)ethenyl |
| 3-174 | H | H | H | OH | OH | 1 | 0 | 2-pentafluorophenylethenyl |
| 3-175 | H | H | H | OH | OH | 1 | 0 | 1-methyl-2-phenylethenyl |
| 3-176 | H | H | H | OH | OH | 1 | 0 | 2-(4-hydroxyphenyl)ethenyl |
| 3-177 | H | H | H | OH | OH | 1 | 0 | 2-(3-hydroxyphenyl)ethenyl |
| 3-178 | H | H | H | OH | OH | 1 | 0 | 2-(2-furyl)ethenyl |
| 3-179 | H | H | H | OH | OH | 1 | 0 | 2-(3,4-dichlorophenyl)ethenyl |
| 3-180 | H | H | H | OH | OH | 1 | 0 | 2-(2,4-dichlorophenyl)ethenyl |
| 3-181 | H | H | H | OH | OH | 1 | 0 | 2-(2-nitrophenyl)ethenyl |
| 3-182 | H | H | H | OH | OH | 1 | 0 | 2,2,2-trifluoro-1-trifluoromethyl-1-methylethyl |

TABLE 3B

Compounds (3-183)–(3-364) are compounds of Formula III where $R^1$, $R^2$, $R^6$, $R^7$, q, and t are identical to those in Table 3A except for $R^8$ which equals O—NH₃$^i$Pr.

TABLE 3C

Compounds (3-365)–(3-546) are compounds of Formula III where $R^1$, $R^2$, $R^6$, $R^7$, q, and t are identical to those in Table 3A except for $R^8$ which equals O—K.

TABLE 3D

| Cmpd # | R$^1$ | R$^2$ | R$^6$ | R$^7$ | R$^8$ | t | q | (X$^2$)$_q$Z$^2$ |
|---|---|---|---|---|---|---|---|---|
| 3-547 | CH$_3$ | H | H | OH | OH | 1 | 0 | 2-propyl |
| 3-548 | CH$_3$ | H | H | OH | OH | 1 | 1 | 3,6-dichloro-2-methoxyphenyl |
| 3-549 | CH$_3$ | H | H | OH | OH | 1 | 1 | 3,5,6-trichloropyridyloxymethyl |
| 3-550 | CH$_3$ | H | H | OH | OH | 1 | 1 | 3-(2,4-dichlorophenoxy)-1-propyl |
| 3-551 | CH$_3$ | H | H | OH | OH | 1 | 0 | 1-propyl |
| 3-552 | CH$_3$ | H | H | OH | OH | 1 | 0 | ethyl |
| 3-553 | CH$_3$ | H | H | OH | OH | 1 | 0 | cyclohexyl |
| 3-554 | CH$_3$ | H | H | OH | OH | 1 | 0 | cyclopentyl |
| 3-555 | CH$_3$ | H | H | OH | OH | 1 | 0 | pentyl |
| 3-556 | CH$_3$ | H | H | OH | OH | 1 | 0 | heptyl |
| 3-557 | CH$_3$ | H | H | OH | OH | 1 | 0 | 2-hexyl |
| 3-558 | CH$_3$ | H | H | OH | OH | 1 | 0 | pentadecyl |
| 3-559 | CH$_3$ | H | H | OH | OH | 1 | 0 | decyl |
| 3-560 | CH$_3$ | H | H | OH | OH | 1 | 0 | 2-methyl-2-propyl |
| 3-561 | CH$_3$ | H | H | OH | OH | 1 | 0 | 4-chlorophenyl |
| 3-562 | CH$_3$ | H | H | OH | OH | 1 | 0 | 2-ethoxyphenyl |
| 3-563 | CH$_3$ | H | H | OH | OH | 1 | 1 | 2,4-dichlorophenoxymethyl |
| 3-564 | CH$_3$ | H | H | OH | OH | 1 | 0 | cyclopropyl |
| 3-565 | CH$_3$ | H | H | OH | OH | 1 | 0 | 2,2,2-trifluoropropyl |
| 3-566 | CH$_3$ | H | H | OH | OH | 1 | 0 | diethoxyphosphorylmethyl |
| 3-567 | CH$_3$ | H | H | OH | OH | 1 | 0 | 4-heptyl |
| 3-568 | CH$_3$ | H | H | OH | OH | 1 | 1 | 2-(4,6-dimethoxypyrimidin-2-yloxy)phenyl |
| 3-569 | CH$_3$ | H | H | OH | OH | 1 | 1 | 4-(2-chloro-4-trifluoromethylphenoxy)-2-nitrophenyl |
| 3-570 | CH$_3$ | H | H | OH | OH | 1 | 1 | 3,6-dichloro-2-pyridyl |
| 3-571 | CH$_3$ | H | H | OH | OH | 1 | 0 | C(CH$_3$)$_3$ |
| 3-572 | CH$_3$ | H | H | OH | OH | 1 | 0 | acetamidomethyl |
| 3-573 | CH$_3$ | H | H | OH | OH | 1 | 0 | 2-nitro-5-thiocyanatophenyl |
| 3-574 | CH$_3$ | H | H | OH | OH | 1 | 0 | cycloheptyl |
| 3-575 | CH$_3$ | H | H | OH | OH | 1 | 0 | 2-hydroxy-2-propyl |
| 3-576 | CH$_3$ | H | H | OH | OH | 1 | 0 | 1-(isopropylidineaminooxy)ethyl |
| 3-577 | CH$_3$ | H | H | OH | OH | 1 | 0 | 4,4,4-trifluoro-2-butyl |
| 3-578 | CH$_3$ | H | H | OH | OH | 1 | 0 | 2-(trifluoromethyl)propyl |
| 3-579 | CH$_3$ | H | H | OH | OH | 1 | 0 | 2,2,2-trifluoroethyl |
| 3-580 | CH$_3$ | H | H | OH | OH | 1 | 0 | 1-benzyloxycarbonylamino)-1-methylethyl |
| 3-581 | CH$_3$ | H | H | OH | OH | 1 | 0 | 1-(tert-butoxycarbonylamino)-1-methylethyl |
| 3-582 | CH$_3$ | H | H | OH | OH | 1 | 0 | 1-(tert-butoxycarbonyl)-piperidin-4-yl |
| 3-583 | CH$_3$ | H | H | OH | OH | 1 | 0 | 1-acetyl-4-hydroxypyrrolidin-2-yl |
| 3-584 | CH$_3$ | H | H | OH | OH | 1 | 0 | 2-methyl-3-pyridyl |
| 3-585 | CH$_3$ | H | H | OH | OH | 1 | 0 | 1-(acetylamino)-2-methylpropyl |
| 3-586 | CH$_3$ | H | H | OH | OH | 1 | 0 | 2,6-dimethoxy-4-hydroxyphenyl |
| 3-587 | CH$_3$ | H | H | OH | OH | 1 | 0 | 3-methylthio-1-acetylaminopropyl |
| 3-588 | CH$_3$ | H | H | OH | OH | 1 | 0 | 1-acetylaminovinyl |
| 3-589 | CH$_3$ | H | H | OH | OH | 1 | 0 | 1-methyl-2-pyrrolyl |
| 3-590 | CH$_3$ | H | H | OH | OH | 1 | 0 | 2-benzyloxycarbonyl)-1-(tert-butoxycarbonylamino)ethyl |
| 3-591 | CH$_3$ | H | H | OH | OH | 1 | 0 | 4-hexyloxyphenyl |
| 3-592 | CH$_3$ | H | H | OH | OH | 1 | 0 | 1-(2-chlorophenoxy)-1-methylethyl |
| 3-593 | CH$_3$ | H | H | OH | OH | 1 | 0 | 3-hydroxy-4-methoxyphenyl |
| 3-594 | CH$_3$ | H | H | OH | OH | 1 | 0 | 3,5-dinitro-4-hydroxyphenyl |
| 3-595 | CH$_3$ | H | H | OH | OH | 1 | 0 | 1-(tert-butoxycarbonyl)-2-pyrrolidinyl |
| 3-596 | CH$_3$ | H | H | OH | OH | 1 | 0 | 1-(di-N-propylamino)ethyl |
| 3-597 | CH$_3$ | H | H | OH | OH | 1 | 0 | 1-(tert-butoxycarbonyl)-4-hydroxy-2-pyrrolidinyl |
| 3-598 | CH$_3$ | H | H | OH | OH | 1 | 0 | 5-acetylamino-1-(tert-butoxycarbonylamino)pentyl |
| 3-599 | CH$_3$ | H | H | OH | OH | 1 | 0 | 1-(tert-butoxycarbonylamino)-2,2-dimethyl-propyl |
| 3-600 | CH$_3$ | H | H | OH | OH | 1 | 0 | 2-pyrrolidinyl hydrochloride |
| 3-601 | CH$_3$ | H | H | OH | OH | 1 | 0 | 2-amino-2-propyl hydrochloride |
| 3-602 | CH$_3$ | H | H | OH | OH | 1 | 0 | 4-piperidinyl hydrochloride |
| 3-603 | CH$_3$ | H | H | OH | OH | 1 | 0 | 2-benzyloxycarbonyl)-1-aminoethyl hydrochloride |
| 3-604 | CH$_3$ | H | H | OH | OH | 1 | 0 | 2-carboxy-1-aminoethyl hydrochloride |
| 3-605 | CH$_3$ | H | H | OH | OH | 1 | 0 | 2-carboxy-1-(tert-butoxycarbonylamino)ethyl |
| 3-606 | CH$_3$ | H | H | OH | OH | 1 | 0 | [benzyl-(diethoxyphosphorylmethyl)-amino]methyl |
| 3-607 | CH$_3$ | H | H | OH | OH | 1 | 0 | 2-methylnicotinyl |
| 3-608 | CH$_3$ | H | H | OH | OH | 1 | 0 | 1-(acetylamino)-2-methylpropyl |
| 3-609 | CH$_3$ | H | H | OH | OH | 1 | 0 | 3-methylthio-1-acetylaminopropyl |
| 3-610 | CH$_3$ | H | H | OH | OH | 1 | 0 | 1-tert-butoxycarbonyamino)-1-methylethyl |
| 3-611 | CH$_3$ | H | H | OH | OH | 0 | 0 | $^+$N(Et)$_3$Cl$^-$ |
| 3-612 | CH$_3$ | H | H | OH | OH | 1 | 0 | undecyl |
| 3-613 | CH$_3$ | H | H | OH | OH | 1 | 0 | acetyl |
| 3-614 | CH$_3$ | H | H | OH | OH | 1 | 0 | 5-oxopyrrolin-2-yl |
| 3-615 | CH$_3$ | H | H | OH | OH | 1 | 0 | methoxymethyl |
| 3-616 | CH$_3$ | H | H | OH | OH | 1 | 0 | (4-oxo-2-thioxothiazolidin-3-yl)methyl |
| 3-617 | CH$_3$ | H | H | OH | OH | 1 | 0 | pyrazin-2-yl |
| 3-618 | CH$_3$ | H | H | OH | OH | 1 | 0 | 1H-pyrazol-4-yl |
| 3-619 | CH$_3$ | H | H | OH | OH | 1 | 0 | (furan-2-carbonyl)aminomethyl |
| 3-620 | CH$_3$ | H | H | OH | OH | 1 | 0 | 2-(2,5-dioxo-2,5-dihydropyrrol-1-yl)ethyl |
| 3-621 | CH$_3$ | H | H | OH | OH | 1 | 0 | 2-methoxyethoxymethyl |
| 3-622 | CH$_3$ | H | H | OH | OH | 1 | 0 | methanesulfonylmethyl |
| 3-623 | CH$_3$ | H | H | OH | OH | 1 | 0 | 4-heptyloxyphenyl |

TABLE 3D-continued

| Cmpd # | R¹ | R² | R⁶ | R⁷ | R⁸ | t | q | (X²)qZ² |
|---|---|---|---|---|---|---|---|---|
| 3-624 | CH₃ | H | H | OH | OH | 1 | 0 | 2,6-dichlorophenyl |
| 3-625 | CH₃ | H | H | OH | OH | 1 | 0 | (3,5-diiodo-4-oxo-4H-pyridin-1-yl)methyl |
| 3-626 | CH₃ | H | H | OH | OH | 1 | 0 | 3-pyridyl |
| 3-627 | CH₃ | H | H | OH | OH | 1 | 0 | 5,6-dichloro-3-pyridyl |
| 3-628 | CH₃ | H | H | OH | OH | 1 | 0 | 4-pyridyl |
| 3-629 | CH₃ | H | H | OH | OH | 1 | 0 | 2,6-dichloro-4-pyridyl |
| 3-630 | CH₃ | H | H | OH | OH | 1 | 0 | 4-methanesulphonylphenyl |
| 3-631 | CH₃ | H | H | OH | OH | 1 | 0 | 2-chloro-4-nitrophenyl |
| 3-632 | CH₃ | H | H | OH | OH | 1 | 0 | 4-chloro-2-nitrophenyl |
| 3-633 | CH₃ | H | H | OH | OH | 1 | 0 | 3-chloro-2-nitrophenyl |
| 3-634 | CH₃ | H | H | OH | OH | 1 | 0 | 5-methylpyrazin-2-yl |
| 3-635 | CH₃ | H | H | OH | OH | 1 | 0 | tetrahydrofur-2-yl |
| 3-636 | CH₃ | H | H | OH | OH | 1 | 0 | 3-thiophen-2-ylpropyl |
| 3-637 | CH₃ | H | H | OH | OH | 1 | 0 | cyclopentylphenylmethyl |
| 3-638 | CH₃ | H | H | OH | OH | 1 | 0 | 1-phenylcyclopentyl |
| 3-639 | CH₃ | H | H | OH | OH | 1 | 0 | 1-methylcyclohexyl |
| 3-640 | CH₃ | H | H | OH | OH | 1 | 0 | 2-chloro-3-pyridyl |
| 3-641 | CH₃ | H | H | OH | OH | 1 | 0 | 1-methyl-1H-pyrrol-2-yl |
| 3-642 | CH₃ | H | H | OH | OH | 1 | 0 | 2,6-dimethoxyphenyl |
| 3-643 | CH₃ | H | H | OH | OH | 1 | 0 | 2,6-dimethoxy-3-pyridyl |
| 3-644 | CH₃ | H | H | OH | OH | 1 | 0 | 2-(thiophen-2-yl)ethenyl |
| 3-645 | CH₃ | H | H | OH | OH | 1 | 0 | 4-nitro-1H-pyrazol-3-yl |
| 3-646 | CH₃ | H | H | OH | OH | 1 | 0 | 4-sulfamoylphenyl |
| 3-647 | CH₃ | H | H | OH | OH | 1 | 0 | 2,4-dinitrophenyl |
| 3-648 | CH₃ | H | H | OH | OH | 1 | 0 | 1-hydroxy-1-phenylethyl |
| 3-649 | CH₃ | H | H | OH | OH | 1 | 0 | 3-hydroxy-4-methyl-2-nitrophenyl |
| 3-650 | CH₃ | H | H | OH | OH | 1 | 0 | 2-methylcyclopropyl |
| 3-651 | CH₃ | H | H | OH | OH | 1 | 0 | 1-phenylpropyl |
| 3-652 | CH₃ | H | H | OH | OH | 1 | 0 | 1,2,3,4-tetrahydronaphth-2-yl |
| 3-653 | CH₃ | H | H | OH | OH | 1 | 0 | 1-benzyl-2,2-dimethylpropyl |
| 3-654 | CH₃ | H | H | OH | OH | 1 | 0 | 2,2,3,3-tetramethylcyclopropyl |
| 3-655 | CH₃ | H | H | OH | OH | 1 | 0 | acetoxymethyl |
| 3-656 | CH₃ | H | H | OH | OH | 1 | 0 | 2,2,2-trifluoro-1-methoxy-1-phenylethyl |
| 3-657 | CH₃ | H | H | OH | OH | 1 | 0 | 1-methylpentyl |
| 3-658 | CH₃ | H | H | OH | OH | 1 | 0 | hept-1-ynyl |
| 3-659 | CH₃ | H | H | OH | OH | 1 | 0 | tetrahydrofur-3-yl |
| 3-660 | CH₃ | H | H | OH | OH | 1 | 0 | 1,1-methylpropyl |
| 3-661 | CH₃ | H | H | OH | OH | 1 | 0 | 2-methylcyclohexyl |
| 3-662 | CH₃ | H | H | OH | OH | 1 | 0 | 1,1-dimethylbut-3-enyl |
| 3-663 | CH₃ | H | H | OH | OH | 1 | 0 | 1-propylbutyl |
| 3-664 | CH₃ | H | H | OH | OH | 1 | 0 | 1-methylbutyl |
| 3-665 | CH₃ | H | H | OH | OH | 1 | 0 | 1-phenylethyl |
| 3-666 | CH₃ | H | H | OH | OH | 1 | 0 | phenyloxymethyl |
| 3-667 | CH₃ | H | H | OH | OH | 1 | 0 | pentafluorophenyloxymethyl |
| 3-668 | CH₃ | H | H | OH | OH | 1 | 0 | (2-formylaminothiazol-4-yl)methoxyiminomethyl |
| 3-669 | CH₃ | H | H | OH | OH | 1 | 0 | 1-hydroxy-1-ethylpropyl |
| 3-670 | CH₃ | H | H | OH | OH | 1 | 0 | 2-methoxyphenyloxymethyl |
| 3-671 | CH₃ | H | H | OH | OH | 1 | 0 | 2,4,6-trimethylphenyl |
| 3-672 | CH₃ | H | H | OH | OH | 1 | 0 | 2-methylphenyl |
| 3-673 | CH₃ | H | H | OH | OH | 1 | 0 | 1-methyl-1-(4-chlorophenyloxy)ethyl |
| 3-674 | CH₃ | H | H | OH | OH | 1 | 0 | 1-hydroxy-1-methylpropyl |
| 3-675 | CH₃ | H | H | OH | OH | 1 | 0 | 1-ethylpentyl |
| 3-676 | CH₃ | H | H | OH | OH | 1 | 0 | 2-methyl-1-phenylbutyl |
| 3-677 | CH₃ | H | H | OH | OH | 1 | 0 | 1-methylpropyl |
| 3-678 | CH₃ | H | H | OH | OH | 1 | 0 | cyclobutyl |
| 3-679 | CH₃ | H | H | OH | OH | 1 | 0 | 1-ethylpropyl |
| 3-680 | CH₃ | H | H | OH | OH | 1 | 0 | (3,5-dinitrobenzoylamino)phenylmethyl |
| 3-681 | CH₃ | H | H | OH | OH | 1 | 0 | 2,2-dichloro-1-methylcyclopropyl |
| 3-682 | CH₃ | H | H | OH | OH | 1 | 0 | 2,2,2-trifluoro-1-hydroxy-1-methylethyl |
| 3-683 | CH₃ | H | H | OH | OH | 1 | 0 | 1-hydroxy-2-trifluoromethylpropyl |
| 3-684 | CH₃ | H | H | OH | OH | 1 | 0 | 4-hydroxy-3-nitrophenyl |
| 3-685 | CH₃ | H | H | OH | OH | 1 | 0 | 4,8-dihydroxyquinol-2-yl |
| 3-686 | CH₃ | H | H | OH | OH | 1 | 0 | 2-hydroxy-1-phenylethyl |
| 3-687 | CH₃ | H | H | OH | OH | 1 | 0 | 4-hydroxyphenyl |
| 3-688 | CH₃ | H | H | OH | OH | 1 | 0 | 2,2-dimethylpropyl |
| 3-689 | CH₃ | H | H | OH | OH | 1 | 0 | 1-(3,5-dinitrobenzoylamino)-3-methylbutyl |
| 3-690 | CH₃ | H | H | OH | OH | 1 | 0 | (2-hydroxybenzoylamino)methyl |
| 3-691 | CH₃ | H | H | OH | OH | 1 | 0 | 3,3,3-trifluoropropyl |
| 3-692 | CH₃ | H | H | OH | OH | 1 | 0 | 1-oxypyrid-2-yl |
| 3-693 | CH₃ | H | H | OH | OH | 1 | 0 | 6-hydroxypyrid-2-yl |
| 3-694 | CH₃ | H | H | OH | OH | 1 | 0 | 3-hydroxypyrid-2-yl |
| 3-695 | CH₃ | H | H | OH | OH | 1 | 0 | benzoylaminomethyl |
| 3-696 | CH₃ | H | H | OH | OH | 1 | 0 | 1-methyl-5-oxo-2-pyrid-3-ylpyrrolin-3-yl |
| 3-697 | CH₃ | H | H | OH | OH | 1 | 0 | 1R,3R,4R,5R-tetrahydroxycyclohexyl |
| 3-698 | CH₃ | H | H | OH | OH | 1 | 0 | 2-(2-chlorphenyl)ethenyl |
| 3-699 | CH₃ | H | H | OH | OH | 1 | 0 | benzofur-2-yl |
| 3-700 | CH₃ | H | H | OH | OH | 1 | 0 | 3-thienyl |

TABLE 3D-continued

| Cmpd # | $R^1$ | $R^2$ | $R^6$ | $R^7$ | $R^8$ | t | q | $(X^2)_qZ^2$ |
|---|---|---|---|---|---|---|---|---|
| 3-701 | $CH_3$ | H | H | OH | OH | 1 | 0 | 3-methyl-1H-inden-2-yl |
| 3-702 | $CH_3$ | H | H | OH | OH | 1 | 0 | 3R,4S,5R-trihydroxy-1-cyclohexenyl |
| 3-703 | $CH_3$ | H | H | OH | OH | 1 | 0 | 2-(2-trifluoromethylphenyl)ethenyl |
| 3-704 | $CH_3$ | H | H | OH | OH | 1 | 0 | 2-(4-methylphenyl)ethenyl |
| 3-705 | $CH_3$ | H | H | OH | OH | 1 | 0 | 1-cyclohexenyl |
| 3-706 | $CH_3$ | H | H | OH | OH | 1 | 0 | 2-(4-trifluoromethylphenyl)ethenyl |
| 3-707 | $CH_3$ | H | H | OH | OH | 1 | 0 | 1-cyclopentenyl |
| 3-708 | $CH_3$ | H | H | OH | OH | 1 | 0 | 1-methyl-1-butenyl |
| 3-709 | $CH_3$ | H | H | OH | OH | 1 | 0 | 3,3,3-trifluoro-2-methyl-1-propenyl |
| 3-710 | $CH_3$ | H | H | OH | OH | 1 | 0 | 2-(2-fluorophenyl)ethenyl |
| 3-711 | $CH_3$ | H | H | OH | OH | 1 | 0 | vinyl |
| 3-712 | $CH_3$ | H | H | OH | OH | 1 | 0 | 2-(4-dimethylaminophenyl)ethenyl |
| 3-713 | $CH_3$ | H | H | OH | OH | 1 | 0 | 2-(2-methoxyphenyl)ethenyl |
| 3-714 | $CH_3$ | H | H | OH | OH | 1 | 0 | 2-(3-hydroxy-4-methoxyphenyl)ethenyl |
| 3-715 | $CH_3$ | H | H | OH | OH | 1 | 0 | 2-(3-trifluoromethylphenyl)ethenyl |
| 3-716 | $CH_3$ | H | H | OH | OH | 1 | 0 | 1-fluoro-2-phenylethenyl |
| 3-717 | $CH_3$ | H | H | OH | OH | 1 | 0 | 3-methyl-2-thienyl |
| 3-718 | $CH_3$ | H | H | OH | OH | 1 | 0 | 1-cyano-2-(4-hydroxyphenyl)ethenyl |
| 3-719 | $CH_3$ | H | H | OH | OH | 1 | 0 | 2-(4-fluorophenyl)ethenyl |
| 3-720 | $CH_3$ | H | H | OH | OH | 1 | 0 | 2-methyl-1-propenyl |
| 3-721 | $CH_3$ | H | H | OH | OH | 1 | 0 | 1-ethyl-7-methyl-4-oxo-[1,8]naphthyridin-3-yl |
| 3-722 | $CH_3$ | H | H | OH | OH | 1 | 0 | 2-(4-hydroxy-3-methoxyphenyl)ethenyl |
| 3-723 | $CH_3$ | H | H | OH | OH | 1 | 0 | 2-(benzo[1,3]dioxol-5-yl)ethenyl |
| 3-724 | $CH_3$ | H | H | OH | OH | 1 | 0 | 1-methylcyclopropyl |
| 3-725 | $CH_3$ | H | H | OH | OH | 1 | 0 | 2-furyl |
| 3-726 | $CH_3$ | H | H | OH | OH | 1 | 0 | 2-phenylethenyl |
| 3-727 | $CH_3$ | H | H | OH | OH | 1 | 0 | 2-(4-bromophenyl)ethenyl |
| 3-728 | $CH_3$ | H | H | OH | OH | 1 | 0 | 3-furyl |
| 3-729 | $CH_3$ | H | H | OH | OH | 1 | 0 | 2-(4-methoxyphenyl)ethenyl |
| 3-730 | $CH_3$ | H | H | OH | OH | 1 | 0 | 1-methyl-1H-indol-2-yl |
| 3-731 | $CH_3$ | H | H | OH | OH | 1 | 0 | 2-(3-pyridyl)ethenyl |
| 3-732 | $CH_3$ | H | H | OH | OH | 1 | 0 | 2-(3-fluorophenyl)ethenyl |
| 3-733 | $CH_3$ | H | H | OH | OH | 1 | 0 | 5-methyl-2-thienyl |
| 3-734 | $CH_3$ | H | H | OH | OH | 1 | 0 | 1-acetylamino-2-phenylethenyl |
| 3-735 | $CH_3$ | H | H | OH | OH | 1 | 0 | 2,6-dimethyl-1,5-heptadienyl |
| 3-736 | $CH_3$ | H | H | OH | OH | 1 | 0 | 1-pentenyl |
| 3-737 | $CH_3$ | H | H | OH | OH | 1 | 0 | 2-(2,3-dimethoxyphenyl)ethenyl |
| 3-738 | $CH_3$ | H | H | OH | OH | 1 | 0 | 1,3-pentadienyl |
| 3-739 | $CH_3$ | H | H | OH | OH | 1 | 0 | 2-(3-nitrophenyl)ethenyl |
| 3-740 | $CH_3$ | H | H | OH | OH | 1 | 0 | 2-(4-chlorophenyl)ethenyl |
| 3-741 | $CH_3$ | H | H | OH | OH | 1 | 0 | 2-(4-nitrophenyl)ethenyl |
| 3-742 | $CH_3$ | H | H | OH | OH | 1 | 0 | 2-(3,4-dimethoxyphenyl)ethenyl |
| 3-743 | $CH_3$ | H | H | OH | OH | 1 | 0 | 2-pentafluorophenylethenyl |
| 3-744 | $CH_3$ | H | H | OH | OH | 1 | 0 | 1-methyl-2-phenylethenyl |
| 3-745 | $CH_3$ | H | H | OH | OH | 1 | 0 | 2-(4-hydroxyphenyl)ethenyl |
| 3-746 | $CH_3$ | H | H | OH | OH | 1 | 0 | 2-(3-hydroxyphenyl)ethenyl |
| 3-747 | $CH_3$ | H | H | OH | OH | 1 | 0 | 2-(2-furyl)ethenyl |
| 3-748 | $CH_3$ | H | H | OH | OH | 1 | 0 | 2-(3,4-dichlorophenyl)ethenyl |
| 3-749 | $CH_3$ | H | H | OH | OH | 1 | 0 | 2-(2,4-dichlorophenyl)ethenyl |
| 3-750 | $CH_3$ | H | H | OH | OH | 1 | 0 | 2-(2-nitrophenyl)ethenyl |
| 3-751 | $CH_3$ | H | H | OH | OH | 1 | 0 | 2,2,2-trifluoro-1-trifluoromethyl-1-methylethyl |
| 3-752 | $CH_3$ | H | H | OH | OH | 1 | 0 | cyclooctyl |

TABLE 3E

Compounds (3-753)–(3-958) are compounds of Formula III where $R^1$, $R^2$, $R^6$, $R^7$, q, and t are identical to those in Table 3D except for $R^8$ which equals O—$NH_3^i$Pr.

TABLE 3F

Compounds (3-959)–(3-1164) are compounds of Formula III where $R^1$, $R^2$, $R^6$, $R^7$, q, and t are identical to those in Table 3D except for $R^8$ which equals O—K.

TABLE 3G

Compounds (3-1165)–(3-1370) are compounds of Formula III where $R^2$, $R^6$, $R^7$, $R^8$, q, and t are identical to those in Table 3D except for $R^1$ which equals Ph.

TABLE 3H

Compounds (3-1371)–(3-1576) are compounds of Formula III where $R^2$, $R^6$, $R^7$, q, and t are identical to those in Table 3D except for $R^1$ which equals Ph and $R^8$ which equals O—$NH_3^i$Pr.

TABLE 3I

Compounds (3-1577)–(3-1782) are compounds of Formula III where $R^2$, $R^6$, $R^7$, q, and t are identical to those in Table 3D except for $R^1$ which equals Ph and $R^8$ which equals O—K.

TABLE 3J

| Cmpd # | R$^1$ | R$^2$ | R$^6$ | R$^7$ | R$^8$ | t | q | (X$^2$)$_q$Z$^2$ |
|---|---|---|---|---|---|---|---|---|
| 3-1783 | Ph | H | CH$_3$ | OH | OH | 1 | 0 | 2-propyl |
| 3-1784 | Ph | H | CH$_3$ | OH | OH | 1 | 1 | 3,6-dichloro-2-methoxyphenyl |
| 3-1785 | Ph | H | CH$_3$ | OH | OH | 1 | 1 | 3,5,6-trichloropyridyloxymethyl |
| 3-1786 | Ph | H | CH$_3$ | OH | OH | 1 | 1 | 3-(2,4-dichlorophenoxy)-1-propyl |
| 3-1787 | Ph | H | CH$_3$ | OH | OH | 1 | 0 | 1-propyl |
| 3-1788 | Ph | H | CH$_3$ | OH | OH | 1 | 0 | ethyl |
| 3-1789 | Ph | H | CH$_3$ | OH | OH | 1 | 0 | cyclohexyl |
| 3-1790 | Ph | H | CH$_3$ | OH | OH | 1 | 0 | cyclopentyl |
| 3-1791 | Ph | H | CH$_3$ | OH | OH | 1 | 0 | pentyl |
| 3-1792 | Ph | H | CH$_3$ | OH | OH | 1 | 0 | heptyl |
| 3-1793 | Ph | H | CH$_3$ | OH | OH | 1 | 0 | 2-hexyl |
| 3-1794 | Ph | H | CH$_3$ | OH | OH | 1 | 0 | pentadecyl |
| 3-1795 | Ph | H | CH$_3$ | OH | OH | 1 | 0 | decyl |
| 3-1796 | Ph | H | CH$_3$ | OH | OH | 1 | 0 | 2-methyl-2-propyl |
| 3-1797 | Ph | H | CH$_3$ | OH | OH | 1 | 0 | 4-chlorophenyl |
| 3-1798 | Ph | H | CH$_3$ | OH | OH | 1 | 0 | 2-ethoxyphenyl |
| 3-1799 | Ph | H | CH$_3$ | OH | OH | 1 | 1 | 2,4-dichlorophenoxymethyl |
| 3-1800 | Ph | H | CH$_3$ | OH | OH | 1 | 0 | cyclopropyl |
| 3-1801 | Ph | H | CH$_3$ | OH | OH | 1 | 0 | 2,2,2-trifluoropropyl |
| 3-1802 | Ph | H | CH$_3$ | OH | OH | 1 | 0 | diethoxyphosphorylmethyl |
| 3-1803 | Ph | H | CH$_3$ | OH | OH | 1 | 0 | 4-heptyl |
| 3-1804 | Ph | H | CH$_3$ | OH | OH | 1 | 1 | 2-(4,6-dimethoxypyrimidin-2-yloxy)phenyl |
| 3-1805 | Ph | H | CH$_3$ | OH | OH | 1 | 1 | 4-(2-chloro-4-trifluoromethyl phenoxy)-2-nitrophenyl |
| 3-1806 | Ph | H | CH$_3$ | OH | OH | 1 | 1 | 3,6-dichloro-2-pyridyl |
| 3-1807 | Ph | H | CH$_3$ | OH | OH | 1 | 0 | C(CH$_3$)$_3$ |
| 3-1808 | Ph | H | CH$_3$ | OH | OH | 1 | 0 | acetamidomethyl |
| 3-1809 | Ph | H | CH$_3$ | OH | OH | 1 | 0 | 2-nitro-5-thiocyanatophenyl |
| 3-1810 | Ph | H | CH$_3$ | OH | OH | 1 | 0 | cycloheptyl |
| 3-1811 | Ph | H | CH$_3$ | OH | OH | 1 | 0 | 2-hydroxy-2-propyl |
| 3-1812 | Ph | H | CH$_3$ | OH | OH | 1 | 0 | 1-(isopropylideneaminooxy)ethyl |
| 3-1813 | Ph | H | CH$_3$ | OH | OH | 1 | 0 | 4,4,4-trifluoro-2-butyl |
| 3-1814 | Ph | H | CH$_3$ | OH | OH | 1 | 0 | 2-(trifluoromethyl)propyl |
| 3-1815 | Ph | H | CH$_3$ | OH | OH | 1 | 0 | 2,2,2-trifluoroethyl |
| 3-1816 | Ph | H | CH$_3$ | OH | OH | 1 | 0 | 1-(benzyloxycarbonylamino)-1-methylethyl |
| 3-1817 | Ph | H | CH$_3$ | OH | OH | 1 | 0 | 1-(tert-butoxycarbonylamino)-1-methylethyl |
| 3-1818 | Ph | H | CH$_3$ | OH | OH | 1 | 0 | 1-(tert-butoxycarbonyl)-piperidin-4-yl |
| 3-1819 | Ph | H | CH$_3$ | OH | OH | 1 | 0 | 1-acetyl-4-hydroxypyrrolidin-2-yl |
| 3-1820 | Ph | H | CH$_3$ | OH | OH | 1 | 0 | 2-methyl-3-pyridyl |
| 3-1821 | Ph | H | CH$_3$ | OH | OH | 1 | 0 | 1-(acetylamino)-2-methylpropyl |
| 3-1822 | Ph | H | CH$_3$ | OH | OH | 1 | 0 | 2,6-dimethoxy-4-hydroxyphenyl |
| 3-1823 | Ph | H | CH$_3$ | OH | OH | 1 | 0 | 3-methylthio-1-acetylaminopropyl |
| 3-1824 | Ph | H | CH$_3$ | OH | OH | 1 | 0 | 1-acetylaminovinyl |
| 3-1825 | Ph | H | CH$_3$ | OH | OH | 1 | 0 | 1-methyl-2-pyrrolyl |
| 3-1826 | Ph | H | CH$_3$ | OH | OH | 1 | 0 | 2-benzyloxycarbonyl-1-(tert-butoxy carbonylamino)ethyl |
| 3-1827 | Ph | H | CH$_3$ | OH | OH | 1 | 0 | 4-hexyloxyphenyl |
| 3-1828 | Ph | H | CH$_3$ | OH | OH | 1 | 0 | 1-(2-chlorophenoxy)-1-methylethyl |
| 3-1829 | Ph | H | CH$_3$ | OH | OH | 1 | 0 | 3-hydroxy-4-methoxyphenyl |
| 3-1830 | Ph | H | CH$_3$ | OH | OH | 1 | 0 | 3,5-dinitro-4-hydroxyphenyl |
| 3-1831 | Ph | H | CH$_3$ | OH | OH | 1 | 0 | 1-(tert-butoxycarbonyl)-2-pyrrolidinyl |
| 3-1832 | Ph | H | CH$_3$ | OH | OH | 1 | 0 | 1-(di-N-propylamino)ethyl |
| 3-1833 | Ph | H | CH$_3$ | OH | OH | 1 | 0 | 1-(tert-butoxycarbonyl)-4-hydroxy-2-pyrrolidinyl |
| 3-1834 | Ph | H | CH$_3$ | OH | OH | 1 | 0 | 5-acetylamino-1-(tert-butoxycarbonylamino)pentyl |
| 3-1835 | Ph | H | CH$_3$ | OH | OH | 1 | 0 | 1-(tert-butoxycarbonylamino)-2,2-dimethyl-propyl |
| 3-1836 | Ph | H | CH$_3$ | OH | OH | 1 | 0 | 2-pyrrolidinyl hydrochloride |
| 3-1837 | Ph | H | CH$_3$ | OH | OH | 1 | 0 | 2-amino-2-propyl hydrochloride |
| 3-1838 | Ph | H | CH$_3$ | OH | OH | 1 | 0 | 4-piperidinyl hydrochloride |
| 3-1839 | Ph | H | CH$_3$ | OH | OH | 1 | 0 | 2-(benzyloxycarbonyl)-1-aminoethyl hydrochloride |
| 3-1840 | Ph | H | CH$_3$ | OH | OH | 1 | 0 | 2-carboxy-1-aminoethyl hydrochloride |
| 3-1841 | Ph | H | CH$_3$ | OH | OH | 1 | 0 | 2-carboxy-1-(tert-butoxycarbonylamino)ethyl |
| 3-1842 | Ph | H | CH$_3$ | OH | OH | 1 | 0 | [benzyl-(diethoxyphosphoryl methyl)-amino]methyl |
| 3-1843 | Ph | H | CH$_3$ | OH | OH | 1 | 0 | 2-methylnicotinyl |
| 3-1844 | Ph | H | CH$_3$ | OH | OH | 1 | 0 | 1-(acetylamino)-2-methylpropyl |
| 3-1845 | Ph | H | CH$_3$ | OH | OH | 1 | 0 | 3-methylthio-1-acetylaminopropyl |

TABLE 3J-continued

| Cmpd # | R¹ | R² | R⁶ | R⁷ | R⁸ | t | q | (X²)qZ² |
|---|---|---|---|---|---|---|---|---|
| 3-1846 | Ph | H | CH₃ | OH | OH | 1 | 0 | 1-tert-butoxycarbonyamino)-1-methylethyl |
| 3-1847 | Ph | H | CH₃ | OH | OH | 0 | 0 | ⁺N(Et)₃Cl⁻ |
| 3-1848 | Ph | H | CH₃ | OH | OH | 1 | 0 | undecyl |
| 3-1849 | Ph | H | CH₃ | OH | OH | 1 | 0 | acetyl |
| 3-1850 | Ph | H | CH₃ | OH | OH | 1 | 0 | 5-oxopyrrolin-2-yl |
| 3-1851 | Ph | H | CH₃ | OH | OH | 1 | 0 | methoxymethyl |
| 3-1852 | Ph | H | CH₃ | OH | OH | 1 | 0 | (4-oxo-2-thioxothiazolidin-3-yl)methyl |
| 3-1853 | Ph | H | CH₃ | OH | OH | 1 | 0 | pyrazin-2-yl |
| 3-1854 | Ph | H | CH₃ | OH | OH | 1 | 0 | 1H-pyrazol-4-yl |
| 3-1855 | Ph | H | CH₃ | OH | OH | 1 | 0 | (furan-2-carbonyl)aminomethyl |
| 3-1856 | Ph | H | CH₃ | OH | OH | 1 | 0 | 2-(2,5-dioxo-2,5-dihydropyrrol-1-yl)ethyl |
| 3-1857 | Ph | H | CH₃ | OH | OH | 1 | 0 | 2-methoxyethoxymethyl |
| 3-1858 | Ph | H | CH₃ | OH | OH | 1 | 0 | methanesulfonylmethyl |
| 3-1859 | Ph | H | CH₃ | OH | OH | 1 | 0 | 4-heptyloxyphenyl |
| 3-1860 | Ph | H | CH₃ | OH | OH | 1 | 0 | 2,6-dichlorophenyl |
| 3-1861 | Ph | H | CH₃ | OH | OH | 1 | 0 | (3,5-diiodo-4-oxo-4H-pyridin-1-yl)methyl |
| 3-1862 | Ph | H | CH₃ | OH | OH | 1 | 0 | 3-pyridyl |
| 3-1863 | Ph | H | CH₃ | OH | OH | 1 | 0 | 5,6-dichloro-3-pyridyl |
| 3-1864 | Ph | H | CH₃ | OH | OH | 1 | 0 | 4-pyridyl |
| 3-1865 | Ph | H | CH₃ | OH | OH | 1 | 0 | 2,6-dichloro-4-pyridyl |
| 3-1866 | Ph | H | CH₃ | OH | OH | 1 | 0 | 4-methanesulphonylphenyl |
| 3-1867 | Ph | H | CH₃ | OH | OH | 1 | 0 | 2-chloro-4-nitrophenyl |
| 3-1868 | Ph | H | CH₃ | OH | OH | 1 | 0 | 4-chloro-2-nitrophenyl |
| 3-1869 | Ph | H | CH₃ | OH | OH | 1 | 0 | 3-chloro-2-nitrophenyl |
| 3-1870 | Ph | H | CH₃ | OH | OH | 1 | 0 | 5-methylpyrazin-2-yl |
| 3-1871 | Ph | H | CH₃ | OH | OH | 1 | 0 | tetrahydrofur-2-yl |
| 3-1872 | Ph | H | CH₃ | OH | OH | 1 | 0 | 3-thiophen-2-ylpropyl |
| 3-1873 | Ph | H | CH₃ | OH | OH | 1 | 0 | cyclopentylphenylmethyl |
| 3-1874 | Ph | H | CH₃ | OH | OH | 1 | 0 | 1-phenylcyclopentyl |
| 3-1875 | Ph | H | CH₃ | OH | OH | 1 | 0 | 1-methylcyclohexyl |
| 3-1876 | Ph | H | CH₃ | OH | OH | 1 | 0 | 2-chloro-3-pyridyl |
| 3-1877 | Ph | H | CH₃ | OH | OH | 1 | 0 | 1-methyl-1H-pyrrol-2-yl |
| 3-1878 | Ph | H | CH₃ | OH | OH | 1 | 0 | 2,6-dimethoxyphenyl |
| 3-1879 | Ph | H | CH₃ | OH | OH | 1 | 0 | 2,6-dimethoxy-3-pyridyl |
| 3-1880 | Ph | H | CH₃ | OH | OH | 1 | 0 | 2-(thiophen-2-yl)ethenyl |
| 3-1881 | Ph | H | CH₃ | OH | OH | 1 | 0 | 4-nitro-1H-pyrazol-3-yl |
| 3-1882 | Ph | H | CH₃ | OH | OH | 1 | 0 | 4-sulfamoylphenyl |
| 3-1883 | Ph | H | CH₃ | OH | OH | 1 | 0 | 2,4-dinitrophenyl |
| 3-1884 | Ph | H | CH₃ | OH | OH | 1 | 0 | 1-hydroxy-1-phenylethyl |
| 3-1885 | Ph | H | CH₃ | OH | OH | 1 | 0 | 3-hydroxy-4-methyl-2-nitrophenyl |
| 3-1886 | Ph | H | CH₃ | OH | OH | 1 | 0 | 2-methylcyclopropyl |
| 3-1887 | Ph | H | CH₃ | OH | OH | 1 | 0 | 1-phenylpropyl |
| 3-1888 | Ph | H | CH₃ | OH | OH | 1 | 0 | 1,2,3,4-tetrahydronaphth-2-yl |
| 3-1889 | Ph | H | CH₃ | OH | OH | 1 | 0 | 1-benzyl-2,2-dimethylpropyl |
| 3-1890 | Ph | H | CH₃ | OH | OH | 1 | 0 | 2,2,3,3-tetramethylcyclopropyl |
| 3-1891 | Ph | H | CH₃ | OH | OH | 1 | 0 | acetoxymethyl |
| 3-1892 | Ph | H | CH₃ | OH | OH | 1 | 0 | 2,2,2-trifluoro-1-methoxy-1-phenylethyl |
| 3-1893 | Ph | H | CH₃ | OH | OH | 1 | 0 | 1-methylpentyl |
| 3-1894 | Ph | H | CH₃ | OH | OH | 1 | 0 | hept-1-ynyl |
| 3-1895 | Ph | H | CH₃ | OH | OH | 1 | 0 | tetrahydrofur-3-yl |
| 3-1896 | Ph | H | CH₃ | OH | OH | 1 | 0 | 1,1-methylpropyl |
| 3-1897 | Ph | H | CH₃ | OH | OH | 1 | 0 | 2-methylcyclohexyl |
| 3-1898 | Ph | H | CH₃ | OH | OH | 1 | 0 | 1,1-dimethylbut-3-enyl |
| 3-1899 | Ph | H | CH₃ | OH | OH | 1 | 0 | 1-propylbutyl |
| 3-1900 | Ph | H | CH₃ | OH | OH | 1 | 0 | 1-methylbutyl |
| 3-1901 | Ph | H | CH₃ | OH | OH | 1 | 0 | 1-phenylethyl |
| 3-1902 | Ph | H | CH₃ | OH | OH | 1 | 0 | phenyloxymethyl |
| 3-1903 | Ph | H | CH₃ | OH | OH | 1 | 0 | pentafluorophenyloxymethyl |
| 3-1904 | Ph | H | CH₃ | OH | OH | 1 | 0 | (2-formylaminothiazol-4-yl)methoxyiminomethyl |
| 3-1905 | Ph | H | CH₃ | OH | OH | 1 | 0 | 1-hydroxy-1-ethylpropyl |
| 3-1906 | Ph | H | CH₃ | OH | OH | 1 | 0 | 2-methoxyphenyloxymethyl |
| 3-1907 | Ph | H | CH₃ | OH | OH | 1 | 0 | 2,4,6-trimethylphenyl |
| 3-1908 | Ph | H | CH₃ | OH | OH | 1 | 0 | 2-methylphenyl |
| 3-1909 | Ph | H | CH₃ | OH | OH | 1 | 0 | 1-methyl-1-(4-chlorophenyloxy)ethyl |
| 3-1910 | Ph | H | CH₃ | OH | OH | 1 | 0 | 1-hydroxy-1-methylpropyl |
| 3-1911 | Ph | H | CH₃ | OH | OH | 1 | 0 | 1-ethylpentyl |
| 3-1912 | Ph | H | CH₃ | OH | OH | 1 | 0 | 2-methyl-1-phenylbutyl |
| 3-1913 | Ph | H | CH₃ | OH | OH | 1 | 0 | 1-methylpropyl |
| 3-1914 | Ph | H | CH₃ | OH | OH | 1 | 0 | cyclobutyl |
| 3-1915 | Ph | H | CH₃ | OH | OH | 1 | 0 | 1-ethylpropyl |

TABLE 3J-continued

| Cmpd # | R¹ | R² | R⁶ | R⁷ | R⁸ | t | q | (X²)qZ² |
|---|---|---|---|---|---|---|---|---|
| 3-1916 | Ph | H | CH₃ | OH | OH | 1 | 0 | (3,5-dinitrobenzoylamino)phenylmethyl |
| 3-1917 | Ph | H | CH₃ | OH | OH | 1 | 0 | 2,2-dichloro-1-methylcyclopropyl |
| 3-1918 | Ph | H | CH₃ | OH | OH | 1 | 0 | 2,2,2-trifluoro-1-hydroxy-1-methylethyl |
| 3-1919 | Ph | H | CH₃ | OH | OH | 1 | 0 | 1-hydroxy-2-trifluoromethylpropyl |
| 3-1920 | Ph | H | CH₃ | OH | OH | 1 | 0 | 4-hydroxy-3-nitrophenyl |
| 3-1921 | Ph | H | CH₃ | OH | OH | 1 | 0 | 4,8-dihydroxyquinol-2-yl |
| 3-1922 | Ph | H | CH₃ | OH | OH | 1 | 0 | 2-hydroxy-1-phenylethyl |
| 3-1923 | Ph | H | CH₃ | OH | OH | 1 | 0 | 4-hydroxyphenyl |
| 3-1924 | Ph | H | CH₃ | OH | OH | 1 | 0 | 2,2-dimethylpropyl |
| 3-1925 | Ph | H | CH₃ | OH | OH | 1 | 0 | 1-(3,5-dinitrobenzoylamino)-3-methylbutyl |
| 3-1926 | Ph | H | CH₃ | OH | OH | 1 | 0 | (2-hydroxybenzoylamino)methyl |
| 3-1927 | Ph | H | CH₃ | OH | OH | 1 | 0 | 3,3,3-trifluoropropyl |
| 3-1928 | Ph | H | CH₃ | OH | OH | 1 | 0 | 1-oxypyrid-2-yl |
| 3-1929 | Ph | H | CH₃ | OH | OH | 1 | 0 | 6-hydroxypyrid-2-yl |
| 3-1930 | Ph | H | CH₃ | OH | OH | 1 | 0 | 3-hydroxypyrid-2-yl |
| 3-1931 | Ph | H | CH₃ | OH | OH | 1 | 0 | benzoylaminomethyl |
| 3-1932 | Ph | H | CH₃ | OH | OH | 1 | 0 | 1-methyl-5-oxo-2-pyrid-3-ylpyrrolin-3-yl |
| 3-1933 | Ph | H | CH₃ | OH | OH | 1 | 0 | 1R,3R,4R,5R-tetrahydroxycyclohexyl |
| 3-1934 | Ph | H | CH₃ | OH | OH | 1 | 0 | 2-(2-chlorphenyl)ethenyl |
| 3-1935 | Ph | H | CH₃ | OH | OH | 1 | 0 | benzofur-2-yl |
| 3-1936 | Ph | H | CH₃ | OH | OH | 1 | 0 | 3-thienyl |
| 3-1937 | Ph | H | CH₃ | OH | OH | 1 | 0 | 3-methyl-1H-inden-2-yl |
| 3-1938 | Ph | H | CH₃ | OH | OH | 1 | 0 | 3R,4S,5R-trihydroxy-1-cyclohexenyl |
| 3-1939 | Ph | H | CH₃ | OH | OH | 1 | 0 | 2-(2-trifluoromethylphenyl)ethenyl |
| 3-1940 | Ph | H | CH₃ | OH | OH | 1 | 0 | 2-(4-methylphenyl)ethenyl |
| 3-1941 | Ph | H | CH₃ | OH | OH | 1 | 0 | 1-cyclohexenyl |
| 3-1942 | Ph | H | CH₃ | OH | OH | 1 | 0 | 2-(4-trifluoromethylphenyl)ethenyl |
| 3-1943 | Ph | H | CH₃ | OH | OH | 1 | 0 | 1-cyclopentenyl |
| 3-1944 | Ph | H | CH₃ | OH | OH | 1 | 0 | 1-methyl-1-butenyl |
| 3-1945 | Ph | H | CH₃ | OH | OH | 1 | 0 | 3,3,3-trifluoro-2-methyl-1-propenyl |
| 3-1946 | Ph | H | CH₃ | OH | OH | 1 | 0 | 2-(2-fluorophenyl)ethenyl |
| 3-1947 | Ph | H | CH₃ | OH | OH | 1 | 0 | vinyl |
| 3-1948 | Ph | H | CH₃ | OH | OH | 1 | 0 | 2-(4-dimethylaminophenyl)ethenyl |
| 3-1949 | Ph | H | CH₃ | OH | OH | 1 | 0 | 2-(2-methoxyphenyl)ethenyl |
| 3-1950 | Ph | H | CH₃ | OH | OH | 1 | 0 | 2-(3-hydroxy-4-methoxyphenyl)ethenyl |
| 3-1951 | Ph | H | CH₃ | OH | OH | 1 | 0 | 2-(3-trifluoromethylphenyl)ethenyl |
| 3-1952 | Ph | H | CH₃ | OH | OH | 1 | 0 | 1-fluoro-2-phenylethenyl |
| 3-1953 | Ph | H | CH₃ | OH | OH | 1 | 0 | 3-methyl-2-thienyl |
| 3-1954 | Ph | H | CH₃ | OH | OH | 1 | 0 | 1-cyano-2-(4-hydroxyphenyl)ethenyl |
| 3-1955 | Ph | H | CH₃ | OH | OH | 1 | 0 | 2-(4-fluorophenyl)ethenyl |
| 3-1956 | Ph | H | CH₃ | OH | OH | 1 | 0 | 2-methyl-1-propenyl |
| 3-1957 | Ph | H | CH₃ | OH | OH | 1 | 0 | 1-ethyl-7-methyl-4-oxo-[1,8]naphthyridin-3-yl |
| 3-1958 | Ph | H | CH₃ | OH | OH | 1 | 0 | 2-(4-hydroxy-3-methoxyphenyl)ethenyl |
| 3-1959 | Ph | H | CH₃ | OH | OH | 1 | 0 | 2-(benzo[1,3]dioxol-5-yl)ethenyl |
| 3-1960 | Ph | H | CH₃ | OH | OH | 1 | 0 | 1-methylcyclopropyl |
| 3-1961 | Ph | H | CH₃ | OH | OH | 1 | 0 | 2-furyl |
| 3-1962 | Ph | H | CH₃ | OH | OH | 1 | 0 | 2-phenylethenyl |
| 3-1963 | Ph | H | CH₃ | OH | OH | 1 | 0 | 2-(4-bromophenyl)ethenyl |
| 3-1964 | Ph | H | CH₃ | OH | OH | 1 | 0 | 3-furyl |
| 3-1965 | Ph | H | CH₃ | OH | OH | 1 | 0 | 2-(4-methoxyphenyl)ethenyl |
| 3-1966 | Ph | H | CH₃ | OH | OH | 1 | 0 | 1-methyl-1H-indol-2-yl |
| 3-1967 | Ph | H | CH₃ | OH | OH | 1 | 0 | 2-(3-pyridyl)ethenyl |
| 3-1968 | Ph | H | CH₃ | OH | OH | 1 | 0 | 2-(3-fluorophenyl)ethenyl |
| 3-1969 | Ph | H | CH₃ | OH | OH | 1 | 0 | 5-methyl-2-thienyl |
| 3-1970 | Ph | H | CH₃ | OH | OH | 1 | 0 | 1-acetylamino-2-phenylethenyl |
| 3-1971 | Ph | H | CH₃ | OH | OH | 1 | 0 | 2,6-dimethyl-1,5-heptadienyl |
| 3-1972 | Ph | H | CH₃ | OH | OH | 1 | 0 | 1-pentenyl |
| 3-1973 | Ph | H | CH₃ | OH | OH | 1 | 0 | 2-(2,3-dimethoxyphenyl)ethenyl |
| 3-1974 | Ph | H | CH₃ | OH | OH | 1 | 0 | 1,3-pentadienyl |
| 3-1975 | Ph | H | CH₃ | OH | OH | 1 | 0 | 2-(3-nitrophenyl)ethenyl |
| 3-1976 | Ph | H | CH₃ | OH | OH | 1 | 0 | 2-(4-chlorophenyl)ethenyl |
| 3-1977 | Ph | H | CH₃ | OH | OH | 1 | 0 | 2-(4-nitrophenyl)ethenyl |
| 3-1978 | Ph | H | CH₃ | OH | OH | 1 | 0 | 2-(3,4-dimethoxyphenyl)ethenyl |
| 3-1979 | Ph | H | CH₃ | OH | OH | 1 | 0 | 2-pentafluorophenylethenyl |
| 3-1980 | Ph | H | CH₃ | OH | OH | 1 | 0 | 1-methyl-2-phenylethenyl |
| 3-1981 | Ph | H | CH₃ | OH | OH | 1 | 0 | 2-(4-hydroxyphenyl)ethenyl |
| 3-1982 | Ph | H | CH₃ | OH | OH | 1 | 0 | 2-(3-hydroxyphenyl)ethenyl |

TABLE 3J-continued

| Cmpd # | R¹ | R² | R⁶ | R⁷ | R⁸ | t | q | (X²)qZ² |
|---|---|---|---|---|---|---|---|---|
| 3-1983 | Ph | H | CH₃ | OH | OH | 1 | 0 | 2-(2-furyl)ethenyl |
| 3-1984 | Ph | H | CH₃ | OH | OH | 1 | 0 | 2-(3,4-dichlorophenyl)ethenyl |
| 3-1985 | Ph | H | CH₃ | OH | OH | 1 | 0 | 2-(2,4-dichlorophenyl)ethenyl |
| 3-1986 | Ph | H | CH₃ | OH | OH | 1 | 0 | 2-(2-nitrophenyl)ethenyl |
| 3-1987 | Ph | H | CH₃ | OH | OH | 1 | 0 | 2,2,2-trifluoro-1-trifluoromethyl-1-methylethyl |
| 3-1988 | Ph | H | CH₃ | OH | OH | 1 | 0 | cyclooctyl |

TABLE 3K

Compounds (3-1989)–(3-2194) are compounds of Formula III where R¹, R², R⁶, R⁷, q, and t are identical to those in Table 3J except for R⁸ which equals O—NH₃ⁱPr.

TABLE 3L

Compounds (3-2195)–(3-2400) are compounds of Formula III where R¹, R², R⁶, R⁷, q, and t are identical to those in Table 3J except for R⁸ which equals O—K.

TABLE 3M

Compounds (3-2401)–(3-2606) are compounds of Formula III where R², R⁶, R⁷, R⁸, q, and t are identical to those in Table 3J except for R¹ which equals H.

TABLE 3N

Compounds (3-2607)–(3-2812) are compounds of Formula III where R², R⁶, R⁷, q, and t are identical to those in Table 3J except for R¹ which equals H and R⁸ which equals O—NH₃ⁱPr.

TABLE 3O

Compounds (3-2813)–(3-3018) are compounds of Formula III where R², R⁶, R⁷, q, and t are identical to those in Table 3J except for R¹ which equals H and R⁸ which equals O—K.

TABLE 3P

Compounds (3-3019)–(3-3224) are compounds of Formula III where R², R⁶, R⁷, R⁸, q and t are identical to those in Table 3J except for R¹ which equals Me.

TABLE 3Q

Compounds (3-3225)–(3-3430) are compounds of Formula III where R², R⁶, R⁷, q, and t are identical to those in Table 3J except for R¹ which equals Me and R⁸ which equals O—NH₃ⁱPr.

TABLE 3R

Compounds (3-3431)–(3-3636) are compounds of Formula III where R², R⁶, R⁷, q, and t are identical to those in Table 3J except for R¹ which equals Me and R⁸ which equals O—K.

TABLE 3S

| Cmpd # | R¹ | R² | R⁶ | R⁷ | R⁸ | t | q | (X²)qZ² |
|---|---|---|---|---|---|---|---|---|
| 3-3637 | H | H | Et | OEt | OEt | 1 | 0 | 2-propyl |
| 3-3638 | H | H | Et | OEt | OEt | 1 | 1 | 3,6-dichloro-2-methoxyphenyl |
| 3-3639 | H | H | Et | OEt | OEt | 1 | 1 | 3,5,6-trichloropyridyloxymethyl |
| 3-3640 | H | H | Et | OEt | OEt | 1 | 1 | 3-(2,4-dichlorophenoxy)-1-propyl |
| 3-3641 | H | H | Et | OEt | OEt | 1 | 0 | 1-propyl |
| 3-3642 | H | H | Et | OEt | OEt | 1 | 0 | ethyl |
| 3-3643 | H | H | Et | OEt | OEt | 1 | 0 | cyclohexyl |
| 3-3644 | H | H | Et | OEt | OEt | 1 | 0 | cyclopentyl |
| 3-3645 | H | H | Et | OEt | OEt | 1 | 0 | pentyl |
| 3-3646 | H | H | Et | OEt | OEt | 1 | 0 | heptyl |
| 3-3647 | H | H | Et | OEt | OEt | 1 | 0 | 2-hexyl |
| 3-3648 | H | H | Et | OEt | OEt | 1 | 0 | pentadecyl |
| 3-3649 | H | H | Et | OEt | OEt | 1 | 0 | decyl |
| 3-3650 | H | H | Et | OEt | OEt | 1 | 0 | 2-methyl-2-propyl |
| 3-3651 | H | H | Et | OEt | OEt | 1 | 0 | 4-chlorophenyl |
| 3-3652 | H | H | Et | OEt | OEt | 1 | 0 | 2-ethoxyphenyl |
| 3-3653 | H | H | Et | OEt | OEt | 1 | 1 | 2,4-dichlorophenoxymethyl |
| 3-3654 | H | H | Et | OEt | OEt | 1 | 0 | cyclopropyl |
| 3-3655 | H | H | Et | OEt | OEt | 1 | 0 | 2,2,2-trifluoropropyl |
| 3-3656 | H | H | Et | OEt | OEt | 1 | 0 | diethoxyphosphorylmethyl |
| 3-3657 | H | H | Et | OEt | OEt | 1 | 0 | 4-heptyl |
| 3-3658 | H | H | Et | OEt | OEt | 1 | 1 | 2-(4,6-dimethoxypyrimidin-2-yloxy)phenyl |
| 3-3659 | H | H | Et | OEt | OEt | 1 | 1 | 4-(2-chloro-4-trifluoromethylphenoxy)-2-nitrophenyl |

TABLE 3S-continued

| Cmpd # | R¹ | R² | R⁶ | R⁷ | R⁸ | t | q | (X²)qZ² |
|---|---|---|---|---|---|---|---|---|
| 3-3660 | H | H | Et | OEt | OEt | 1 | 1 | 3,6-dichloro-2-pyridyl |
| 3-3661 | H | H | Et | OEt | OEt | 1 | 0 | C(CH₃)₃ |
| 3-3662 | H | H | Et | OEt | OEt | 1 | 0 | acetamidomethyl |
| 3-3663 | H | H | Et | OEt | OEt | 1 | 0 | 2-nitro-5-thiocyanatophenyl |
| 3-3664 | H | H | Et | OEt | OEt | 1 | 0 | cycloheptyl |
| 3-3665 | H | H | Et | OEt | OEt | 1 | 0 | 2-hydroxy-2-propyl |
| 3-3666 | H | H | Et | OEt | OEt | 1 | 0 | 1-(isopropylidineaminooxy)ethyl |
| 3-3667 | H | H | Et | OEt | OEt | 1 | 0 | 4,4,4-trifluoro-2-butyl |
| 3-3668 | H | H | Et | OEt | OEt | 1 | 0 | 2-(trifluoromethyl)propyl |
| 3-3669 | H | H | Et | OEt | OEt | 1 | 0 | 2,2,2-trifluoroethyl |
| 3-3670 | H | H | Et | OEt | OEt | 1 | 0 | 1-(benzyloxycarbonylamino)-1-methylethyl |
| 3-3671 | H | H | Et | OEt | OEt | 1 | 0 | 1-(tert-butoxycarbonylamino)-1-methylethyl |
| 3-3672 | H | H | Et | OEt | OEt | 1 | 0 | 1-(tert-butoxycarbonyl)-piperidin-4-yl |
| 3-3673 | H | H | Et | OEt | OEt | 1 | 0 | 1-acetyl-4-hydroxypyrrolidin-2-yl |
| 3-3674 | H | H | Et | OEt | OEt | 1 | 0 | 2-methyl-3-pyridyl |
| 3-3675 | H | H | Et | OEt | OEt | 1 | 0 | 1-(acetylamino)-2-methylpropyl |
| 3-3676 | H | H | Et | OEt | OEt | 1 | 0 | 2,6-dimethoxy-4-hydroxyphenyl |
| 3-3677 | H | H | Et | OEt | OEt | 1 | 0 | 3-methylthio-1-acetylaminopropyl |
| 3-3678 | H | H | Et | OEt | OEt | 1 | 0 | 1-acetylaminovinyl |
| 3-3679 | H | H | Et | OEt | OEt | 1 | 0 | 1-methyl-2-pyrrolyl |
| 3-3680 | H | H | Et | OEt | OEt | 1 | 0 | 2-(benzyloxycarbonyl)-1-(tert-butoxy carbonylamino)ethyl |
| 3-3681 | H | H | Et | OEt | OEt | 1 | 0 | 4-hexyloxyphenyl |
| 3-3682 | H | H | Et | OEt | OEt | 1 | 0 | 1-(2-chlorophenoxy)-1-methylethyl |
| 3-3683 | H | H | Et | OEt | OEt | 1 | 0 | 3-hydroxy-4-methoxyphenyl |
| 3-3684 | H | H | Et | OEt | OEt | 1 | 0 | 3,5-dinitro-4-hydroxyphenyl |
| 3-3685 | H | H | Et | OEt | OEt | 1 | 0 | 1-(tert-butoxycarbonyl)-2-pyrrolidinyl |
| 3-3686 | H | H | Et | OEt | OEt | 1 | 0 | 1-(di-N-propylamino)ethyl |
| 3-3687 | H | H | Et | OEt | OEt | 1 | 0 | 1-(tert-butoxycarbonyl)-4-hydroxy-2-pyrrolidinyl |
| 3-3688 | H | H | Et | OEt | OEt | 1 | 0 | 5-acetylamino-1-(tert-butoxycarbonylamino)pentyl |
| 3-3689 | H | H | Et | OEt | OEt | 1 | 0 | 1-(tert-butoxycarbonylamino)-2,2-dimethyl-propyl |
| 3-3690 | H | H | Et | OEt | OEt | 1 | 0 | 2-pyrrolidinyl hydrochloride |
| 3-3691 | H | H | Et | OEt | OEt | 1 | 0 | 2-amino-2-propyl hydrochloride |
| 3-3692 | H | H | Et | OEt | OEt | 1 | 0 | 4-piperidinyl hydrochloride |
| 3-3693 | H | H | Et | OEt | OEt | 1 | 0 | 2-(benzyloxycarbonyl)-1-aminoethyl hydrochloride |
| 3-3694 | H | H | Et | OEt | OEt | 1 | 0 | 2-carboxy-1-aminoethyl hydrochloride |
| 3-3695 | H | H | Et | OEt | OEt | 1 | 0 | 2-carboxy-1-(tert-butoxycarbonylamino)ethyl |
| 3-3696 | H | H | Et | OEt | OEt | 1 | 0 | [benzyl-(diethoxyphosphoryl methyl)-amino]methyl |
| 3-3697 | H | H | Et | OEt | OEt | 1 | 0 | 2-methylnicotinyl |
| 3-3698 | H | H | Et | OEt | OEt | 1 | 0 | 1-(acetylamino)-2-methylpropyl |
| 3-3699 | H | H | Et | OEt | OEt | 1 | 0 | 3-methylthio-1-acetylaminopropyl |
| 3-3700 | H | H | Et | OEt | OEt | 1 | 0 | 1-tert-butoxycarbonyamino-1-methylethyl |
| 3-3701 | H | H | Et | OEt | OEt | 0 | 0 | ⁺N(Et)₃Cl⁻ |
| 3-3702 | H | H | Et | OEt | OEt | 1 | 0 | undecyl |
| 3-3703 | H | H | Et | OEt | OEt | 1 | 0 | acetyl |
| 3-3704 | H | H | Et | OEt | OEt | 1 | 0 | 5-oxopyrrolin-2-yl |
| 3-3705 | H | H | Et | OEt | OEt | 1 | 0 | methoxymethyl |
| 3-3706 | H | H | Et | OEt | OEt | 1 | 0 | (4-oxo-2-thioxothiazolidin-3-yl)methyl |
| 3-3707 | H | H | Et | OEt | OEt | 1 | 0 | pyrazin-2-yl |
| 3-3708 | H | H | Et | OEt | OEt | 1 | 0 | 1H-pyrazol-4-yl |
| 3-3709 | H | H | Et | OEt | OEt | 1 | 0 | (furan-2-carbonyl)aminomethyl |
| 3-3710 | H | H | Et | OEt | OEt | 1 | 0 | 2-(2,5-dioxo-2,5-dihydropyrrol-1-yl)ethyl |
| 3-3711 | H | H | Et | OEt | OEt | 1 | 0 | 2-methoxyethoxymethyl |
| 3-3712 | H | H | Et | OEt | OEt | 1 | 0 | methanesulfonylmethyl |
| 3-3713 | H | H | Et | OEt | OEt | 1 | 0 | 4-heptyloxyphenyl |
| 3-3714 | H | H | Et | OEt | OEt | 1 | 0 | 2,6-dichlorophenyl |
| 3-3715 | H | H | Et | OEt | OEt | 1 | 0 | (3,5-diiodo-4-oxo-4H-pyridin-1-yl)methyl |
| 3-3716 | H | H | Et | OEt | OEt | 1 | 0 | 3-pyridyl |
| 3-3717 | H | H | Et | OEt | OEt | 1 | 0 | 5,6-dichloro-3-pyridyl |
| 3-3718 | H | H | Et | OEt | OEt | 1 | 0 | 4-pyridyl |
| 3-3719 | H | H | Et | OEt | OEt | 1 | 0 | 2,6-dichloro-4-pyridyl |
| 3-3720 | H | H | Et | OEt | OEt | 1 | 0 | 4-methanesulphonylphenyl |

TABLE 3S-continued

| Cmpd # | R¹ | R² | R⁶ | R⁷ | R⁸ | t | q | (X²)qZ² |
|---|---|---|---|---|---|---|---|---|
| 3-3721 | H | H | Et | OEt | OEt | 1 | 0 | 2-chloro-4-nitrophenyl |
| 3-3722 | H | H | Et | OEt | OEt | 1 | 0 | 4-chloro-2-nitrophenyl |
| 3-3723 | H | H | Et | OEt | OEt | 1 | 0 | 3-chloro-2-nitrophenyl |
| 3-3724 | H | H | Et | OEt | OEt | 1 | 0 | 5-methylpyrazin-2-yl |
| 3-3725 | H | H | Et | OEt | OEt | 1 | 0 | tetrahydrofur-2-yl |
| 3-3726 | H | H | Et | OEt | OEt | 1 | 0 | 3-thiophen-2-ylpropyl |
| 3-3727 | H | H | Et | OEt | OEt | 1 | 0 | cyclopentylphenylmethyl |
| 3-3728 | H | H | Et | OEt | OEt | 1 | 0 | 1-phenylcyclopentyl |
| 3-3729 | H | H | Et | OEt | OEt | 1 | 0 | 1-methylcyclohexyl |
| 3-3730 | H | H | Et | OEt | OEt | 1 | 0 | 2-chloro-3-pyridyl |
| 3-3731 | H | H | Et | OEt | OEt | 1 | 0 | 1-methyl-1H-pyrrol-2-yl |
| 3-3732 | H | H | Et | OEt | OEt | 1 | 0 | 2,6-dimethoxyphenyl |
| 3-3733 | H | H | Et | OEt | OEt | 1 | 0 | 2,6-dimethoxy-3-pyridyl |
| 3-3734 | H | H | Et | OEt | OEt | 1 | 0 | 2-(thiophen-2-yl)ethenyl |
| 3-3735 | H | H | Et | OEt | OEt | 1 | 0 | 4-nitro-1H-pyrazol-3-yl |
| 3-3736 | H | H | Et | OEt | OEt | 1 | 0 | 4-sulfamoylphenyl |
| 3-3737 | H | H | Et | OEt | OEt | 1 | 0 | 2,4-dinitrophenyl |
| 3-3738 | H | H | Et | OEt | OEt | 1 | 0 | 1-hydroxy-1-phenylethyl |
| 3-3739 | H | H | Et | OEt | OEt | 1 | 0 | 3-hydroxy-4-methyl-2-nitrophenyl |
| 3-3740 | H | H | Et | OEt | OEt | 1 | 0 | 2-methylcyclopropyl |
| 3-3741 | H | H | Et | OEt | OEt | 1 | 0 | 1-phenylpropyl |
| 3-3742 | H | H | Et | OEt | OEt | 1 | 0 | 1,2,3,4-tetrahydronaphth-2-yl |
| 3-3743 | H | H | Et | OEt | OEt | 1 | 0 | 1-benzyl-2,2-dimethylpropyl |
| 3-3744 | H | H | Et | OEt | OEt | 1 | 0 | 2,2,3,3-tetramethylcyclopropyl |
| 3-3745 | H | H | Et | OEt | OEt | 1 | 0 | acetoxymethyl |
| 3-3746 | H | H | Et | OEt | OEt | 1 | 0 | 2,2,2-trifluoro-1-methoxy-1-phenylethyl |
| 3-3747 | H | H | Et | OEt | OEt | 1 | 0 | 1-methylpentyl |
| 3-3748 | H | H | Et | OEt | OEt | 1 | 0 | hept-1-ynyl |
| 3-3749 | H | H | Et | OEt | OEt | 1 | 0 | tetrahydrofur-3-yl |
| 3-3750 | H | H | Et | OEt | OEt | 1 | 0 | 1,1-methylpropyl |
| 3-3751 | H | H | Et | OEt | OEt | 1 | 0 | 2-methylcyclohexyl |
| 3-3752 | H | H | Et | OEt | OEt | 1 | 0 | 1,1-dimethylbut-3-enyl |
| 3-3753 | H | H | Et | OEt | OEt | 1 | 0 | 1-propylbutyl |
| 3-3754 | H | H | Et | OEt | OEt | 1 | 0 | 1-methylbutyl |
| 3-3755 | H | H | Et | OEt | OEt | 1 | 0 | 1-phenylethyl |
| 3-3756 | H | H | Et | OEt | OEt | 1 | 0 | phenyloxymethyl |
| 3-3757 | H | H | Et | OEt | OEt | 1 | 0 | pentafluorophenyloxymethyl |
| 3-3758 | H | H | Et | OEt | OEt | 1 | 0 | (2-formylaminothiazol-4-yl)methoxyiminomethyl |
| 3-3759 | H | H | Et | OEt | OEt | 1 | 0 | 1-hydroxy-1-ethylpropyl |
| 3-3760 | H | H | Et | OEt | OEt | 1 | 0 | 2-methoxyphenyloxymethyl |
| 3-3761 | H | H | Et | OEt | OEt | 1 | 0 | 2,4,6-trimethylphenyl |
| 3-3762 | H | H | Et | OEt | OEt | 1 | 0 | 2-methylphenyl |
| 3-3763 | H | H | Et | OEt | OEt | 1 | 0 | 1-methyl-1-(4-chlorophenyloxy)ethyl |
| 3-3764 | H | H | Et | OEt | OEt | 1 | 0 | 1-hydroxy-1-methylpropyl |
| 3-3765 | H | H | Et | OEt | OEt | 1 | 0 | 1-ethylpentyl |
| 3-3766 | H | H | Et | OEt | OEt | 1 | 0 | 2-methyl-1-phenylbutyl |
| 3-3767 | H | H | Et | OEt | OEt | 1 | 0 | 1-methylpropyl |
| 3-3768 | H | H | Et | OEt | OEt | 1 | 0 | cyclobutyl |
| 3-3769 | H | H | Et | OEt | OEt | 1 | 0 | 1-ethylpropyl |
| 3-3770 | H | H | Et | OEt | OEt | 1 | 0 | (3,5-dinitrobenzoylamino)phenylmethyl |
| 3-3771 | H | H | Et | OEt | OEt | 1 | 0 | 2,2-dichloro-1-methylcyclopropyl |
| 3-3772 | H | H | Et | OEt | OEt | 1 | 0 | 2,2,2-trifluoro-1-hydroxy-1-methylethyl |
| 3-3773 | H | H | Et | OEt | OEt | 1 | 0 | 1-hydroxy-2-trifluoromethylpropyl |
| 3-3774 | H | H | Et | OEt | OEt | 1 | 0 | 4-hydroxy-3-nitrophenyl |
| 3-3775 | H | H | Et | OEt | OEt | 1 | 0 | 4,8-dihydroxyquinol-2-yl |
| 3-3776 | H | H | Et | OEt | OEt | 1 | 0 | 2-hydroxy-1-phenylethyl |
| 3-3777 | H | H | Et | OEt | OEt | 1 | 0 | 4-hydroxyphenyl |
| 3-3778 | H | H | Et | OEt | OEt | 1 | 0 | 2,2-dimethylpropyl |
| 3-3779 | H | H | Et | OEt | OEt | 1 | 0 | 1-(3,5-dinitrobenzoylamino)-3-methylbutyl |
| 3-3780 | H | H | Et | OEt | OEt | 1 | 0 | (2-hydroxybenzoylamino)methyl |
| 3-3781 | H | H | Et | OEt | OEt | 1 | 0 | 3,3,3-trifluoropropyl |
| 3-3782 | H | H | Et | OEt | OEt | 1 | 0 | 1-oxypyrid-2-yl |
| 3-3783 | H | H | Et | OEt | OEt | 1 | 0 | 6-hydroxypyrid-2-yl |
| 3-3784 | H | H | Et | OEt | OEt | 1 | 0 | 3-hydroxypyrid-2-yl |
| 3-3785 | H | H | Et | OEt | OEt | 1 | 0 | benzoylaminomethyl |
| 3-3786 | H | H | Et | OEt | OEt | 1 | 0 | 1-methyl-5-oxo-2-pyrid-3-ylpyrrolin-3-yl |
| 3-3787 | H | H | Et | OEt | OEt | 1 | 0 | 1R,3R,4R,5R-tetrahydroxycyclohexyl |
| 3-3788 | H | H | Et | OEt | OEt | 1 | 0 | 2-(2-chlorphenyl)ethenyl |
| 3-3789 | H | H | Et | OEt | OEt | 1 | 0 | benzofur-2-yl |
| 3-3790 | H | H | Et | OEt | OEt | 1 | 0 | 3-thienyl |

TABLE 3S-continued

| Cmpd # | $R^1$ | $R^2$ | $R^6$ | $R^7$ | $R^8$ | t | q | $(X^2)_q Z^2$ |
|---|---|---|---|---|---|---|---|---|
| 3-3791 | H | H | Et | OEt | OEt | 1 | 0 | 3-methyl-1H-inden-2-yl |
| 3-3792 | H | H | Et | OEt | OEt | 1 | 0 | 3R,4S,5R-trihydroxy-1-cyclohexenyl |
| 3-3793 | H | H | Et | OEt | OEt | 1 | 0 | 2-(2-trifluoromethylphenyl)ethenyl |
| 3-3794 | H | H | Et | OEt | OEt | 1 | 0 | 2-(4-methylphenyl)ethenyl |
| 3-3795 | H | H | Et | OEt | OEt | 1 | 0 | 1-cyclohexenyl |
| 3-3796 | H | H | Et | OEt | OEt | 1 | 0 | 2-(4-trifluoromethylphenyl)ethenyl |
| 3-3797 | H | H | Et | OEt | OEt | 1 | 0 | 1-cyclopentenyl |
| 3-3798 | H | H | Et | OEt | OEt | 1 | 0 | 1-methyl-1-butenyl |
| 3-3799 | H | H | Et | OEt | OEt | 1 | 0 | 3,3,3-trifluoro-2-methyl-1-propenyl |
| 3-3800 | H | H | Et | OEt | OEt | 1 | 0 | 2-(2-fluorophenyl)ethenyl |
| 3-3801 | H | H | Et | OEt | OEt | 1 | 0 | vinyl |
| 3-3802 | H | H | Et | OEt | OEt | 1 | 0 | 2-(4-dimethylaminophenyl)ethenyl |
| 3-3803 | H | H | Et | OEt | OEt | 1 | 0 | 2-(2-methoxyphenyl)ethenyl |
| 3-3804 | H | H | Et | OEt | OEt | 1 | 0 | 2-(3-hydroxy-4-methoxyphenyl)ethenyl |
| 3-3805 | H | H | Et | OEt | OEt | 1 | 0 | 2-(3-trifluoromethylphenyl)ethenyl |
| 3-3806 | H | H | Et | OEt | OEt | 1 | 0 | 1-fluoro-2-phenylethenyl |
| 3-3807 | H | H | Et | OEt | OEt | 1 | 0 | 3-methyl-2-thienyl |
| 3-3808 | H | H | Et | OEt | OEt | 1 | 0 | 1-cyano-2-(4-hydroxyphenyl)ethenyl |
| 3-3809 | H | H | Et | OEt | OEt | 1 | 0 | 2-(4-fluorophenyl)ethenyl |
| 3-3810 | H | H | Et | OEt | OEt | 1 | 0 | 2-methyl-1-propenyl |
| 3-3811 | H | H | Et | OEt | OEt | 1 | 0 | 1-ethyl-7-methyl-4-oxo-[1,8]naphthyridin-3-yl |
| 3-3812 | H | H | Et | OEt | OEt | 1 | 0 | 2-(4-hydroxy-3-methoxyphenyl)ethenyl |
| 3-3813 | H | H | Et | OEt | OEt | 1 | 0 | 2-(benzo[1,3]dioxol-5-yl)ethenyl |
| 3-3814 | H | H | Et | OEt | OEt | 1 | 0 | 1-methylcyclopropyl |
| 3-3815 | H | H | Et | OEt | OEt | 1 | 0 | 2-furyl |
| 3-3816 | H | H | Et | OEt | OEt | 1 | 0 | 2-phenylethenyl |
| 3-3817 | H | H | Et | OEt | OEt | 1 | 0 | 2-(4-bromophenyl)ethenyl |
| 3-3818 | H | H | Et | OEt | OEt | 1 | 0 | 3-furyl |
| 3-3819 | H | H | Et | OEt | OEt | 1 | 0 | 2-(4-methoxyphenyl)ethenyl |
| 3-3820 | H | H | Et | OEt | OEt | 1 | 0 | 1-methyl-1H-indol-2-yl |
| 3-3821 | H | H | Et | OEt | OEt | 1 | 0 | 2-(3-pyridyl)ethenyl |
| 3-3822 | H | H | Et | OEt | OEt | 1 | 0 | 2-(3-fluorophenyl)ethenyl |
| 3-3823 | H | H | Et | OEt | OEt | 1 | 0 | 5-methyl-2-thienyl |
| 3-3824 | H | H | Et | OEt | OEt | 1 | 0 | 1-acetylamino-2-phenylethenyl |
| 3-3825 | H | H | Et | OEt | OEt | 1 | 0 | 2,6-dimethyl-1,5-heptadienyl |
| 3-3826 | H | H | Et | OEt | OEt | 1 | 0 | 1-pentenyl |
| 3-3827 | H | H | Et | OEt | OEt | 1 | 0 | 2-(2,3-dimethoxyphenyl)ethenyl |
| 3-3828 | H | H | Et | OEt | OEt | 1 | 0 | 1,3-pentadienyl |
| 3-3829 | H | H | Et | OEt | OEt | 1 | 0 | 2-(3-nitrophenyl)ethenyl |
| 3-3830 | H | H | Et | OEt | OEt | 1 | 0 | 2-(4-chlorophenyl)ethenyl |
| 3-3831 | H | H | Et | OEt | OEt | 1 | 0 | 2-(4-nitrophenyl)ethenyl |
| 3-3832 | H | H | Et | OEt | OEt | 1 | 0 | 2-(3,4-dimethoxyphenyl)ethenyl |
| 3-3833 | H | H | Et | OEt | OEt | 1 | 0 | 2-pentafluorophenylethenyl |
| 3-3834 | H | H | Et | OEt | OEt | 1 | 0 | 1-methyl-2-phenylethenyl |
| 3-3835 | H | H | Et | OEt | OEt | 1 | 0 | 2-(4-hydroxyphenyl)ethenyl |
| 3-3836 | H | H | Et | OEt | OEt | 1 | 0 | 2-(3-hydroxyphenyl)ethenyl |
| 3-3837 | H | H | Et | OEt | OEt | 1 | 0 | 2-(2-furyl)ethenyl |
| 3-3838 | H | H | Et | OEt | OEt | 1 | 0 | 2-(3,4-dichlorophenyl)ethenyl |
| 3-3839 | H | H | Et | OEt | OEt | 1 | 0 | 2-(2,4-dichlorophenyl)ethenyl |
| 3-3840 | H | H | Et | OEt | OEt | 1 | 0 | 2-(2-nitrophenyl)ethenyl |
| 3-3841 | H | H | Et | OEt | OEt | 1 | 0 | 2,2,2-trifluoro-1-trifluoromethyl-1-methylethyl |
| 3-3842 | H | H | Et | OEt | OEt | 1 | 0 | cyclooctyl |

TABLE 3T

Compounds (3-3843)–(3-4048) are compounds of Formula III where $R^2$, $R^6$, $R^7$, $R^8$, q, and t are identical to those in Table 3S except for $R^1$ which equals Me.

TABLE 3U

Compounds (3-4049)–(3-4254) are compounds of Formula III where $R^2$, $R^6$, $R^7$, $R^8$, q, and t are identical to those in Table 3S except for $R^1$ which equals Ph.

Following the general methods described hereinbefore, the following compounds of Formula (IV) as listed in Table 4 were prepared.

TABLE 4

Listing of Compounds of Formula (IV)

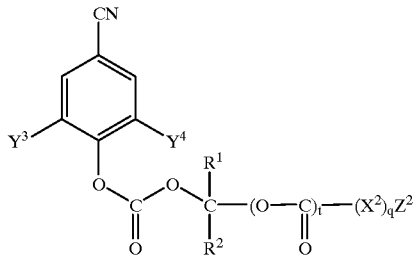

(IV)

| Cmpd # | $Y^3$ | $Y^4$ | $R^1$ | $R^2$ | q | t | $(X^2)_qZ^2$ |
|---|---|---|---|---|---|---|---|
| 4-1 | Br | Br | H | H | 0 | 0 | Cl |
| 4-2 | Br | Br | H | H | 0 | 0 | I |
| 4-3 | Br | Br | H | H | 0 | 1 | methyl |
| 4-4 | Br | Br | H | H | 1 | 1 | methoxycarbonylaininooxymethyl |
| 4-5 | Br | Br | H | H | 1 | 1 | 2-(4,6-dimethoxypyrimidin-2-yloxy)-phenyl |
| 4-6 | Br | Br | H | H | 1 | 1 | 2,4-dichlorophenoxymethyl |
| 4-7 | Br | Br | H | H | 1 | 1 | 4-(2-chloro-4-trifluoromethyl phenoxy)-2-nitrophenyl |
| 4-8 | Br | Br | H | H | 1 | 1 | 2-Chloro-6-(4,6dimethoxy pyrimidin-2-ylsulfanyl)-phenyl |
| 4-9 | Br | Br | $CH_3$ | H | 0 | 0 | Cl |

The following Examples are provided for guidance to the practitioner in order to practice the invention.

EXAMPLE 296

(Method B)

Carbonic acid chloromethyl ester 2,6-dibromo-4-cyanophenyl ester (Compound 4-1 of Table 4)

To a suspension of 3,5-dibromo-4-hydroxybenzonitrile (10.0 g, 36.1 mmol) in 180 mL of chloroform was added pyridine (2.92 ml, 36.1 mmol). Chloromethylchloroformate (5.2 mL 60 mmol) was then added over 5 min. The mixture was allowed to stir at room temperature for 12 h. The reaction was then washed with 1% HCl aq, water, and brine. The organic layer was then dried over sodium sulfate, filtered, and evaporated to afford a white solid (12.5 g) in 94% yield. 1H-NMR (300 MHz, $CDCl_3$) δ (ppm): 5.87 (d, 2H), 7.90 (s, 2H). 13C-NMR (300 MHz, $CDCl_3$) δ (ppm): 73.58, 113.87, 115.68, 119.01, 136.40, 149.53, 149.71. Mp=83–85° C.

EXAMPLE 297

Carbonic acid iodomethyl ester 2,6-dibromo-4-cyanophenyl ester (Compound 4-2 of Table 4)

A solution of carbonic acid chloromethyl ester 2,6-dibromo-4-cyanophenyl ester (10.0 g, 27.1 mmol) in 30 mL of acetone was added sodium iodide (8.12 g, 54.1 mmol) and heated to 30° C. for 3 h. The acetone was removed, and the resulting slurry was treated with ether. The resulting white precipitated solids were filtered off, and the filtrate was then concentrated to afford tannish solids which was recrystallized from ether/hexanes to afford white solids (20 g, 96%). 1H-NMR (300 MHz, $CDCl_3$) δ (ppm): 6.09 (s, 2H), 7.90 (s, 2H). Mp=103–105° C.

EXAMPLE 298

Acetic acid 2,6-dibromo-4-cyano-phenoxycarbonyloxymethyl ester (Compound 4-3 of Table 4)

A solution of carbonic acid iodomethyl ester 2,6-dibromo-4-cyanophenyl ester (0.30 g, 0.65 mmol) in acetic acid (6.5 mL) was added silver acetate (0.33 g, 1.95 mmol). The mixture was stirred for 3 h. The slurry was concentrated to solids and washed with ether. The ether was concentrated to afford the desired product as white solids (240 mg). 1H-NMR (300 MHz, $CDCl_3$) δ (ppm): 2.19 (s, 3H), 5.90 (s, 2H), 7.89 (s, 2H).). 13C-NMR (300 MHz, $CDCl_3$) δ (ppm): 21.0, 83.3, 113.7, 115.7, 119.1, 136.4, 149.9, 169.4, 183.7. Mp=84–86° C.

EXAMPLE 299

Methoxycarbonylaminooxyacetic acid 2,6-dibromo-4-cyano-phenoxycarbonyloxymethyl ester (Compound 4-4 of Table 4)

A solution of carbonic acid iodomethyl ester 2,6-dibromo-4-cyanophenyl ester (0.20 g, 0.43 mmol) in DMF (2 mL) was added sodium methoxycarbonylaminooxyacetate (0.89 g, 0.52 mmol). The mixture was stirred for 16 h. Ether was added to the reaction and washed with water then brine then dried over sodium sulfate, filtered, and concentrated to an oil. Silica gel chromatography (2:1 EtOAc:hexanes) afforded the desired product as a clear oil. 1H-NMR (300 MHz, $CDCl_3$) δ (ppm): 3.80 (s, 3H), 4.57 (s, 2H), 5.99 (s, 2H), 7.90 (s, 2H), 8.02 (bs, 1H). Mp=110–111° C.

EXAMPLE 300

2-(4,6-Dimethoxypyrimidin-2-yloxy)benozoic acid 2,6-dibromo-4-cyanophenoxycarbonyloxymethyl ester (Compound 4-5 of Table 4)

A solution of carbonic acid iodomethyl ester 2,6-dibromo-4-cyanophenyl ester (0.50 g, 1.08 mmol) in THF was added 2-(4,6-dimethoxypyrimidin-2-yloxy)benozoic acid (0.60 g, 2.17 mmol) and diusopropylethylamine (0.21 mL, 1.2 mmol). The mixture was stirred for 10 h. The white precipicate which had formed was filtered off, and the filtrate was concentrated to an oil. Silica gel chromatography (2:1 hexanes:EtOAc) afforded 450 mg (69%) of the desired product as a white solid. 1H-NMR (300 MHz, $CDCl_3$) δ (ppm): 3.80 (s, 6H), 5.76 (s, 1H), 5.98 (s, 2H), 7.27–7.39 (m, 2H), 7.67 (t, 1H), 7.87 (s, 2H), 8.09 (d, 1H). Mp=121–122° C.

EXAMPLE 301

2,4-Dichlorophenoxy acetic acid 2,6-dibromo-4-cyanophenoxycarbonyloxymethyl ester (Compound 4-6 of Table 4)

The title compound was prepared according to the procedure described in Example 300 above except for the substitution of 2,4-dichlorophenoxy acetic acid for 2-(4,6-dimethoxypyrimidine-2-yloxy)benozoic acid. 1H-NMR (300 MHz, CDCl$_3$) δ (ppm): 4.80 (s, 2H), 6.00 (s, 2H), 6.82 (d, 1H), 7.21 (1H), 7.41 (d, 1H), 7.89 (s, 2H). Mp=88–89° C.

EXAMPLE 302

4-(2-Chloro-4-trifluoromethylphenoxy)-2-nitrobenzoic acid 2,6-dibromo-4-cyanophenoxycarbonyloxymethyl ester (Compound 4-7 of Table 4)

The title compound was prepared according to the procedure described in Example 300 above except for the substitution of 4-(2-chloro-4-trifluoromethylphenoxy)-2-nitrobenzoic acid for 2-(4,6-dimethoxypyrimidine-2-yloxy)benozoic acid. 1H-NMR (300 MHz, CDCl$_3$) δ (ppm): 6.10 (s, 2H), 7.12–7.20 (m, 2H), 7.31 (s, 1H), 7.65 (d, 1H), 7.84 (s, 1H), 7.88 (s, 2H), 8.12 (d, 1H). Mp=122–123° C.

EXAMPLE 303

2-Chloro-6-(4,6-dimethoxypyrimidin-2-ylsulfanyl)benzoic acid 2,6-dibromo-4-cyanophenoxycarbonyloxymethyl ester (Compound 4-8 of Table 4)

The title compound was prepared according to the procedure described in Example 300 above except for the substitution of 2-chloro-6-(4,6-dimethoxypyrimidin-2-ylsulfanyl)benzoic acid for 2-(4,6-dimethoxypyrimidine-2-yloxy)benozoic acid. 1H-NMR (300 MHz, CDCl$_3$) δ (ppm): 3.72 (s, 6H), 5.73 (s, 1H), 6.07 (s, 2H), 7.42–7.52 (m, 2H), 7.66 (d, 1H), 7.88 (s, 2H). Mp=100–101° C.

EXAMPLE 304

Carbonic acid 1-chloroethyl ester 2,6-dibromo-4-cyanophenyl ester (Compound 4-9 of Table 4)

The title compound was prepared according to the procedure described in Example 296 above except for the substitution of 1-chloroethylchloroformate for chloromethylchloroformate. 1H-NMR (300 MHz, CDCl$_3$) δ (ppm): 1.95 (d, 3H), 6.49 m(q, 1H), 7.90 (m, 2H). Mp=91–93° C.

Tables 5A through 5L show additional examples of compounds of Formula (IV) which can be made using the procedures described hereinbefore.

TABLE 5A

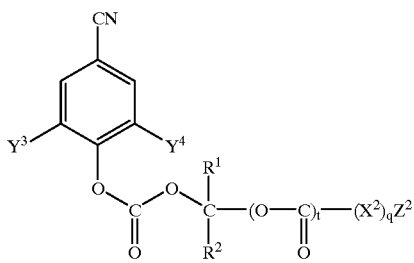

(IV)

| Cmpd # | Y$^3$ | Y$^4$ | R$^1$ | R$^2$ | q | t | (X$^2$)$_q$Z$^2$ |
|---|---|---|---|---|---|---|---|
| 5-1 | Cl | Cl | H | H | 0 | 0 | Br |
| 5-2 | Cl | Cl | H | H | 0 | 0 | Cl |
| 5-3 | Cl | Cl | H | H | 0 | 0 | I |
| 5-4 | Cl | Cl | H | H | 0 | 1 | methyl |
| 5-5 | Cl | Cl | H | H | 1 | 1 | methoxycarbonylaminooxymethyl |
| 5-6 | Cl | Cl | H | H | 1 | 1 | 2-(4,6-dimethoxypyrimidin-2-yloxy)-phenyl |
| 5-7 | Cl | Cl | H | H | 1 | 1 | 2,4-dichlorophenoxymethyl |
| 5-8 | Cl | Cl | H | H | 1 | 1 | 4-(2-chloro-4-trifluoromethylphenoxy)-2-nitrophenyl |
| 5-9 | Cl | Cl | H | H | 1 | 1 | 2-chloro-6-(4,6-dimethoxypyrimidin-2-ylsulfanyl)-phenyl |
| 5-10 | I | I | H | H | 0 | 0 | Br |
| 5-11 | I | I | H | H | 0 | 0 | Cl |
| 5-12 | Br | Br | Ph | H | 0 | 0 | Cl |
| 5-13 | I | I | H | H | 0 | 1 | methyl |
| 5-14 | I | I | H | H | 1 | 1 | methoxycarbonylaminooxymethyl |
| 5-15 | I | I | H | H | 1 | 1 | 2-(4,6-dimethoxypyrimidin-2-yl oxy)-phenyl |
| 5-16 | I | I | H | H | 1 | 1 | 2,4-dichlorophenoxymethyl |
| 5-17 | I | I | H | H | 1 | 1 | 4-2-chloro-4-trifluoromethylphenoxy)-2-nitrophenyl |
| 5-18 | I | I | H | H | 1 | 1 | 2-Chloro-6-(4,6-dimethoxypyrimidin-2-ylsulfanyl)-phenyl |
| 5-19 | Cl | Cl | H | H | 1 | 1 | 3,6-dichloro-2-pyridyl |
| 5-20 | Cl | Cl | H | H | 0 | 1 | C(CH$_3$)$_3$ |
| 5-21 | Cl | Cl | H | H | 0 | 1 | acetamidomethyl |
| 5-22 | Cl | Cl | H | H | 0 | 1 | 2-nitro-5-thiocyanatophenyl |
| 5-23 | Cl | Cl | H | H | 0 | 1 | cycloheptyl |
| 5-24 | Cl | Cl | H | H | 0 | 1 | 2-hydroxy-2-propyl |
| 5-25 | Cl | Cl | H | H | 0 | 1 | 1-(isopropylidineaminooxy)ethyl |
| 5-26 | Cl | Cl | H | H | 0 | 1 | 4,4,4-trifluoro-2-butyl |
| 5-27 | Cl | Cl | H | H | 0 | 1 | 2-(trifluoromethyl)propyl |
| 5-28 | Cl | Cl | H | H | 0 | 1 | 2,2,2-trifluoroethyl |
| 5-29 | Cl | Cl | H | H | 0 | 1 | 1-(benzyloxycarbonylamino)-1-methylethyl |
| 5-30 | Cl | Cl | H | H | 0 | 1 | 1-(tert-butoxycarbonylamino)-1-methylethyl |
| 5-31 | Cl | Cl | H | H | 0 | 1 | 1-(tert-butoxycarbonyl)-piperidin-4-yl |
| 5-32 | Cl | Cl | H | H | 0 | 1 | 1-acetyl-4-hydroxypyrrolidin-2-yl |
| 5-33 | Cl | Cl | H | H | 0 | 1 | 2-methyl-3-pyridyl |
| 5-34 | Cl | Cl | H | H | 0 | 1 | 1-(acetylamino)-2-methylpropyl |
| 5-35 | Cl | Cl | H | H | 0 | 1 | 2,6-dimethoxy-4-hydroxyphenyl |
| 5-36 | Cl | Cl | H | H | 0 | 1 | 3-methylthio-1-acetylaminopropyl |
| 5-37 | Cl | Cl | H | H | 0 | 1 | 1-acetylaminovinyl |
| 5-38 | Cl | Cl | H | H | 0 | 1 | 1-methyl-2-pyrrolyl |
| 5-39 | Cl | Cl | H | H | 0 | 1 | 2-benzyloxycarbonyl)-1-(tert-butoxycarbonylamino)ethyl |
| 5-40 | Cl | Cl | H | H | 0 | 1 | 4-hexyloxyphenyl |
| 5-41 | Cl | Cl | H | H | 0 | 1 | 1-(2-chlorophenoxy)-1-methylethyl |
| 5-42 | Cl | Cl | H | H | 0 | 1 | 3-hydroxy-4-methoxyphenyl |
| 5-43 | Cl | Cl | H | H | 0 | 1 | 3,5-dinitro-4-hydroxyphenyl |
| 5-44 | Cl | Cl | H | H | 0 | 1 | 1-(tert-butoxycarbonyl)-2-pyrrolidinyl |
| 5-45 | Cl | Cl | H | H | 0 | 1 | 1-(di-N-propylamino)ethyl |
| 5-46 | Cl | Cl | H | H | 0 | 1 | 1-(tert-butoxycarbonyl)-4-hydroxy-2-pyrrolidinyl |
| 5-47 | Cl | Cl | H | H | 0 | 1 | 5-acetylamino-1-(tert-butoxycarbonylamino)pentyl |
| 5-48 | Cl | Cl | H | H | 0 | 1 | 1-(tert-butoxycarbonylamino)-2,2-dimethyl-propyl |
| 5-49 | Cl | Cl | H | H | 0 | 1 | 2-pyrrolidinyl hydrochloride |
| 5-5o | Cl | Cl | H | H | 0 | 1 | 2-amino-2-propyl hydrochloride |
| 5-51 | Cl | Cl | H | H | 0 | 1 | 4-piperidinyl hydrochloride |

TABLE 5A-continued (IV)

| Cmpd # | Y³ | Y⁴ | R¹ | R² | q | t | $(X^2)_qZ^2$ |
|---|---|---|---|---|---|---|---|
| 5-52 | Cl | Cl | H | H | 0 | 1 | 2-(benzyloxycarbonyl)-1-aminoethyl hydrochloride |
| 5-53 | Cl | Cl | H | H | 0 | 1 | 2-carboxy-1-aminoethyl hydrochloride |
| 5-54 | Cl | Cl | H | H | 0 | 1 | 2-carboxy-1-(tert-butoxycarbonylaminoethyl |
| 5-55 | Cl | Cl | H | H | 0 | 1 | [benzyl-(diethoxyphosphorylmethyl)-amino]methyl |
| 5-56 | Cl | Cl | H | H | 0 | 1 | 2-methylnicotinyl |
| 5-57 | Cl | Cl | H | H | 0 | 1 | 1-(acetylamino)-2-methylpropyl |
| 5-58 | Cl | Cl | H | H | 0 | 1 | 3-methylthio-1-acetylaminopropyl |
| 5-59 | Cl | Cl | H | H | 0 | 1 | 1-tert-(butoxycarbonylamino)-1-methylethyl |
| 5-60 | Cl | Cl | H | H | 0 | 0 | ⁺N(Et)₃Cl⁻ |
| 5-61 | Cl | Cl | H | H | 0 | 1 | undecyl |
| 5-62 | Cl | Cl | H | H | 0 | 1 | acetyl |
| 5-63 | Cl | Cl | H | H | 0 | 1 | 5-oxopyrrolin-2-yl |
| 5-64 | Cl | Cl | H | H | 0 | 1 | methoxymethyl |
| 5-65 | Cl | Cl | H | H | 0 | 1 | (4-oxo-2-thioxothiazolidin-3-yl)methyl |
| 5-66 | Cl | Cl | H | H | 0 | 1 | pyrazin-2-yl |
| 5-67 | Cl | Cl | H | H | 0 | 1 | 1H-pyrazol-4-yl |
| 5-68 | Cl | Cl | H | H | 0 | 1 | (furan-2-carbonyl)aminomethyl |
| 5-69 | Cl | Cl | H | H | 0 | 1 | 2-(2,5-dioxo-2,5-dihyropyrrol-1-yl)ethyl |
| 5-70 | Cl | Cl | H | H | 0 | 1 | 2-methoxyethoxymethyl |
| 5-71 | Cl | Cl | H | H | 0 | 1 | methanesulfonylmethyl |
| 5-72 | Cl | Cl | H | H | 0 | 1 | 4-heptyloxyphenyl |
| 5-73 | Cl | Cl | H | H | 0 | 1 | 2-6-dichlorophenyl |
| 5-74 | Cl | Cl | H | H | 0 | 1 | (3,5-diiodo-4-oxo-4H-pyridin-1-yl)methyl |
| 5-75 | Cl | Cl | H | H | 0 | 1 | 3-pyridyl |
| 5-76 | Cl | Cl | H | H | 0 | 1 | 5,6-dichloro-3-pyridyl |
| 5-77 | Cl | Cl | H | H | 0 | 1 | 4-pyridyl |
| 5-78 | Cl | Cl | H | H | 0 | 1 | 2,6-dichloro-4-pyridyl |
| 5-79 | Cl | Cl | H | H | 0 | 1 | 4-methanesulphonylphenyl |
| 5-80 | Cl | Cl | H | H | 0 | 1 | 2-chloro-4-nitrophenyl |
| 5-81 | Cl | Cl | H | H | 0 | 1 | 4-chloro-2-nitrophenyl |
| 5-82 | Cl | Cl | H | H | 0 | 1 | 3-chloro-2-nitrophenyl |
| 5-83 | Cl | Cl | H | H | 0 | 1 | 5-methylpyrazin-2-yl |
| 5-84 | Cl | Cl | H | H | 0 | 1 | tetrahydrofur-2-yl |
| 5-85 | Cl | Cl | H | H | 0 | 1 | 3-thiophen-2-ylpropyl |
| 5-86 | Cl | Cl | H | H | 0 | 1 | cyclopentylphenylmethyl |
| 5-87 | Cl | Cl | H | H | 0 | 1 | 1-phenylcyclopentyl |
| 5-88 | Cl | Cl | H | H | 0 | 1 | 1-methylcyclohexyl |
| 5-89 | Cl | Cl | H | H | 0 | 1 | 2-chloro-3-pyridyl |
| 5-90 | Cl | Cl | H | H | 0 | 1 | 1-methyl-1H-pyrrol-2-yl |
| 5-91 | Cl | Cl | H | H | 0 | 1 | 2,6-dimethoxyphenyl |
| 5-92 | Cl | Cl | H | H | 0 | 1 | 2,6-dimethoxy-3-pyridyl |
| 5-93 | Cl | Cl | H | H | 0 | 1 | 2-(thiophen-2-yl)ethenyl |
| 5-94 | Cl | Cl | H | H | 0 | 1 | 4-nitro-1H-pyrazol-3-yl |
| 5-95 | Cl | Cl | H | H | 0 | 1 | 4-sulfamoylphenyl |
| 5-96 | Cl | Cl | H | H | 0 | 1 | 2-4-dinitrophenyl |
| 5-97 | Cl | Cl | H | H | 0 | 1 | 1-hydroxy-1-phenylethyl |
| 5-98 | Cl | Cl | H | H | 0 | 1 | 3-hydroxy-4-methyl-2-nitrophenyl |
| 5-99 | Cl | Cl | H | H | 0 | 1 | 2-methylcyclopropyl |
| 5-100 | Cl | Cl | H | H | 0 | 1 | 1-phenylpropyl |
| 5-101 | Cl | Cl | H | H | 0 | 1 | 1,2,3,4-tetrahydronaphth-2-yl |
| 5-102 | Cl | Cl | H | H | 0 | 1 | 1-benzyl-2,2-dimethylpropyl |
| 5-103 | Cl | Cl | H | H | 0 | 1 | 2,2,3,3-tetramethylcyclopropyl |
| 5-104 | Cl | Cl | H | H | 0 | 1 | acetoxymethyl |
| 5-105 | Cl | Cl | H | H | 0 | 1 | 2,2,2-trifluoro-1-methoxy-1-phenylethyl |
| 5-106 | Cl | Cl | H | H | 0 | 1 | 1-methylpentyl |
| 5-107 | Cl | Cl | H | H | 0 | 1 | hept-1-ynyl |
| 5-108 | Cl | Cl | H | H | 0 | 1 | tetrahydrofur-3-yl |
| 5-109 | Cl | Cl | H | H | 0 | 1 | 1,1-methylpropyl |
| 5-110 | Cl | Cl | H | H | 0 | 1 | 2-methylcyclohexyl |
| 5-111 | Cl | Cl | H | H | 0 | 1 | 1,1-dimethylbut-3-enyl |
| 5-112 | Cl | Cl | H | H | 0 | 1 | 1-propylbutyl |
| 5-113 | Cl | Cl | H | H | 0 | 1 | 1-methylbutyl |
| 5-114 | Cl | Cl | H | H | 0 | 1 | 1-phenylethyl |
| 5-115 | Cl | Cl | H | H | 0 | 1 | phenyloxymethyl |
| 5-116 | Cl | Cl | H | H | 0 | 1 | pentafluorophenyloxymethyl |
| 5-117 | Cl | Cl | H | H | 0 | 1 | (2-formylaminothiazol-4-yl)methoxyiminomethyl |
| 5-118 | Cl | Cl | H | H | 0 | 1 | 1-hydroxy-1-ethylpropyl |
| 5-119 | Cl | Cl | H | H | 0 | 1 | 2-methoxyphenyloxymethyl |
| 5-120 | Cl | Cl | H | H | 0 | 1 | 2,4,6-trimethylphenyl |
| 5-121 | Cl | Cl | H | H | 0 | 1 | 2-methylphenyl |
| 5-122 | Cl | Cl | H | H | 0 | 1 | 1-methyl-1-(4-chlorophenyloxy)ethyl |
| 5-123 | Cl | Cl | H | H | 0 | 1 | 1-hydroxy-1-methylpropyl |
| 5-124 | Cl | Cl | H | H | 0 | 1 | 1-ethylpentyl |
| 5-125 | Cl | Cl | H | H | 0 | 1 | 2-methyl-1-phenylbutyl |
| 5-126 | Cl | Cl | H | H | 0 | 1 | 1-methylpropyl |
| 5-127 | Cl | Cl | H | H | 0 | 1 | cyclobutyl |
| 5-128 | Cl | Cl | H | H | 0 | 1 | 1-ethylpropyl |
| 5-129 | Cl | Cl | H | H | 0 | 1 | (3,5-dinitrobenzoylamino)-phenylmethyl |
| 5-130 | Cl | Cl | H | H | 0 | 1 | 2,2-dichloro-1-methylcyclopropyl |
| 5-131 | Cl | Cl | H | H | 0 | 1 | 2,2,2-trifluoro-1-hydroxy-1-methylethyl |
| 5-132 | Cl | Cl | H | H | 0 | 1 | 1-hydroxy-2-trifluoromethylpropyl |
| 5-133 | Cl | Cl | H | H | 0 | 1 | 4-hydroxy-3-nitrophenyl |
| 5-134 | Cl | Cl | H | H | 0 | 1 | 4,8-dihydroxyquinol-2-yl |
| 5-135 | Cl | Cl | H | H | 0 | 1 | 2-hydroxy-1-phenylethyl |
| 5-136 | Cl | Cl | H | H | 0 | 1 | 4-hydroxyphenyl |
| 5-137 | Cl | Cl | H | H | 0 | 1 | 2,2-dimethylpropyl |
| 5-138 | Cl | Cl | H | H | 0 | 1 | 1-(3,5-dinitrobenzoylamino)-3-methylbutyl |
| 5-139 | Cl | Cl | H | H | 0 | 1 | (2-hydroxybenzoylamino)methyl |
| 5-140 | Cl | Cl | H | H | 0 | 1 | 3,3,3-trifluoropropyl |
| 5-141 | Cl | Cl | H | H | 0 | 1 | 1-oxypyrid-2-yl |
| 5-142 | Cl | Cl | H | H | 0 | 1 | 6-hydroxypyrid-2-yl |
| 5-143 | Cl | Cl | H | H | 0 | 1 | 3-hydroxypyrid-2-yl |
| 5-144 | Cl | Cl | H | H | 0 | 1 | benzoylaminomethyl |
| 5-145 | Cl | Cl | H | H | 0 | 1 | 1-methyl-5-oxo-2-pyrid-3-yl-pyrrolin-3-yl |
| 5-146 | Cl | Cl | H | H | 0 | 1 | 1R,3R,4R,5R-tetrahydroxycyclohexyl |
| 5-147 | Cl | Cl | H | H | 0 | 1 | 2-(2-chlorpenyl)ethenyl |
| 5-148 | Cl | Cl | H | H | 0 | 1 | benzofur-2-yl |
| 5-149 | Cl | Cl | H | H | 0 | 1 | 3-thienyl |
| 5-150 | Cl | Cl | H | H | 0 | 1 | 3-methyl-1H-inden-2-yl |
| 5-151 | Cl | Cl | H | H | 0 | 1 | 3R,4S,5R-trihydroxy-1-cyclohexenyl |
| 5-152 | Cl | Cl | H | H | 0 | 1 | 2-(2-trifluoromethylphenyl)ethenyl |
| 5-153 | Cl | Cl | H | H | 0 | 1 | 2-(4-methylphenyl)ethenyl |
| 5-154 | Cl | Cl | H | H | 0 | 1 | 1-cyclohexenyl |
| 5-155 | Cl | Cl | H | H | 0 | 1 | 2-(4-trifluoromethylphenyl)ethenyl |
| 5-156 | Cl | Cl | H | H | 0 | 1 | 1-cyclopentenyl |
| 5-157 | Cl | Cl | H | H | 0 | 1 | 1-methyl-1-butenyl |
| 5-158 | Cl | Cl | H | H | 0 | 1 | 3,3,3-trifluoro-2-methyl-1-propenyl |
| 5-159 | Cl | Cl | H | H | 0 | 1 | 2-(2-fluorophenyl)ethenyl |

TABLE 5A-continued (IV)

A structural formula is shown: a benzene ring with a CN group at the para position, Y³ and Y⁴ substituents at the meta positions, and at the ipso position an -O-C(=O)-O-C(R¹)(R²)-(O)_t-C(=O)-(X²)_qZ² group.

| Cmpd # | Y³ | Y⁴ | R¹ | R² | q | t | (X²)_qZ² |
|---|---|---|---|---|---|---|---|
| 5-160 | Cl | Cl | H | H | 0 | 1 | vinyl |
| 5-161 | Cl | Cl | H | H | 0 | 1 | 2-(4-dimethylaminophenyl)ethenyl |
| 5-162 | Cl | Cl | H | H | 0 | 1 | 2-(2-methoxyphenyl)ethenyl |
| 5-163 | Cl | Cl | H | H | 0 | 1 | 2-(3-hydroxy-4-methoxy-phenyl)ethenyl |
| 5-164 | Cl | Cl | H | H | 0 | 1 | 2-(3-trifluoromethylphenyl)ethenyl |
| 5-165 | Cl | Cl | H | H | 0 | 1 | 1-fluoro-2-phenylethenyl |
| 5-166 | Cl | Cl | H | H | 0 | 1 | 3-methyl-2-thienyl |
| 5-167 | Cl | Cl | H | H | 0 | 1 | 1-cyano-2-(4-hydroxyphenyl)ethenyl |
| 5-168 | Cl | Cl | H | H | 0 | 1 | 2-(4-fluorophenyl)ethenyl |
| 5-169 | Cl | Cl | H | H | 0 | 1 | 2-methyl-1-propenyl |
| 5-170 | Cl | Cl | H | H | 0 | 1 | 1-ethyl-7-methyl-4-oxo-[1,8]naphthyridin-3-yl |
| 5-171 | Cl | Cl | H | H | 0 | 1 | 2-(4-hydroxy-3-methoxy-phenyl)ethenyl |
| 5-172 | Cl | Cl | H | H | 0 | 1 | 2-(benzo[1,3]dioxol-5-yl)ethenyl |
| 5-173 | Cl | Cl | H | H | 0 | 1 | 1-methylcyclopropyl |
| 5-174 | Cl | Cl | H | H | 0 | 1 | 2-furyl |
| 5-175 | Cl | Cl | H | H | 0 | 1 | 2-phenylethenyl |
| 5-176 | Cl | Cl | H | H | 0 | 1 | 2-(4-bromophenyl)ethenyl |
| 5-177 | Cl | Cl | H | H | 0 | 1 | 3-furyl |
| 5-178 | Cl | Cl | H | H | 0 | 1 | 2-(4-methoxyphenyl)ethenyl |
| 5-179 | Cl | Cl | H | H | 0 | 1 | 1-methyl-1H-indol-2-yl |
| 5-180 | Cl | Cl | H | H | 0 | 1 | 2-(3-pyridyl)ethenyl |
| 5-181 | Cl | Cl | H | H | 0 | 1 | 2-(3-fluorophenyl)ethenyl |
| 5-182 | Cl | Cl | H | H | 0 | 1 | 5-methyl-2-thienyl |
| 5-183 | Cl | Cl | H | H | 0 | 1 | 1-acetylamino-2-phenylethenyl |
| 5-184 | Cl | Cl | H | H | 0 | 1 | 2,6-dimethyl-1,5-heptadienyl |
| 5-185 | Cl | Cl | H | H | 0 | 1 | 1-pentenyl |
| 5-186 | Cl | Cl | H | H | 0 | 1 | 2-(2,3-dimethoxyphenyl)ethenyl |
| 5-187 | Cl | Cl | H | H | 0 | 1 | 1,3-pentadienyl |
| 5-188 | Cl | Cl | H | H | 0 | 1 | 2-(3-nitrophenyl)ethenyl |
| 5-189 | Cl | Cl | H | H | 0 | 1 | 2-(4-chlorophenyl)ethenyl |
| 5-190 | Cl | Cl | H | H | 0 | 1 | 2-(4-nitrophenyl)ethenyl |
| 5-191 | Cl | Cl | H | H | 0 | 1 | 2-(3,4-dimethoxyphen-)ethenyl |
| 5-192 | Cl | Cl | H | H | 0 | 1 | 2-pentafluorophenylethenyl |
| 5-193 | Cl | Cl | H | H | 0 | 1 | 1-methyl-2-phenylethenyl |
| 5-194 | Cl | Cl | H | H | 0 | 1 | 2-(4-hydroxyphenyl)ethenyl |
| 5-195 | Cl | Cl | H | H | 0 | 1 | 2-(3-hydroxyphenyl)ethenyl |
| 5-196 | Cl | Cl | H | H | 0 | 1 | 2-(2-furyl)ethenyl |
| 5-197 | Cl | Cl | H | H | 0 | 1 | 2-(3,4-dichlorophenyl)ethenyl |
| 5-198 | Cl | Cl | H | H | 0 | 1 | 2-(2,4-dichlorophenyl)ethenyl |
| 5-199 | Cl | Cl | H | H | 0 | 1 | 2-(2-nitrophenyl)ethenyl |
| 5-200 | Cl | Cl | H | H | 0 | 1 | 2,2,2-trifluoro-1-trifluoromethyl-1-methylethyl |

TABLE 5B

| Cmpd # | Y³ | Y⁴ | R¹ | R² | q | t | (X²)_qZ² |
|---|---|---|---|---|---|---|---|
| 5-201 | Br | Br | H | H | 1 | 1 | 3,6-dichloro-2-pyridyl |
| 5-202 | Br | Br | H | H | 0 | 1 | C(CH₃)₃ |
| 5-203 | Br | Br | H | H | 0 | 1 | acetamidomethyl |
| 5-204 | Br | Br | H | H | 0 | 1 | 2-nitro-5-thiocyanatophenyl |
| 5-205 | Br | Br | H | H | 0 | 1 | cycloheptyl |
| 5-206 | Br | Br | H | H | 0 | 1 | 2-hydroxy-2-propyl |
| 5-207 | Br | Br | H | H | 0 | 1 | 1-(isopropylideneaminooxy)ethyl |
| 5-208 | Br | Br | H | H | 0 | 1 | 4,4,4-trifluoro-2-butyl |
| 5-209 | Br | Br | H | H | 0 | 1 | 2-(trifluoromethyl)propyl |

TABLE 5B-continued

| Cmpd # | Y³ | Y⁴ | R¹ | R² | q | t | (X²)_qZ² |
|---|---|---|---|---|---|---|---|
| 5-210 | Br | Br | H | H | 0 | 1 | 2,2,2-trifluoroethyl |
| 5-211 | Br | Br | H | H | 0 | 1 | 1-(benzyloxycarbonylamino)-1-methylethyl |
| 5-212 | Br | Br | H | H | 0 | 1 | 1-(tert-butoxycarbonylamino)-1-methylethyl |
| 5-213 | Br | Br | H | H | 0 | 1 | 1-(tert-butoxycarbonyl)-piperidin-4-yl |
| 5-214 | Br | Br | H | H | 0 | 1 | 1-acetyl-4-hydroxypyrrolidin-2-yl |
| 5-215 | Br | Br | H | H | 0 | 1 | 2-methyl-3-pyridyl |
| 5-216 | Br | Br | H | H | 0 | 1 | 1-(acetylamino)-2-methylpropyl |
| 5-217 | Br | Br | H | H | 0 | 1 | 2,6-dimethoxy-4-hydroxyphenyl |
| 5-218 | Br | Br | H | H | 0 | 1 | 3-methylthio-1-acetylaminopropyl |
| 5-219 | Br | Br | H | H | 0 | 1 | 1-acetylaminovinyl |
| 5-220 | Br | Br | H | H | 0 | 1 | 1-methyl-2-pyrrolyl |
| 5-221 | Br | Br | H | H | 0 | 1 | 2-benzyloxycarbonyl-1-(tert-butoxycarbonylamino)ethyl |
| 5-222 | Br | Br | H | H | 0 | 1 | 4-hexyloxyphenyl |
| 5-223 | Br | Br | H | H | 0 | 1 | 1-(2-chlorophenoxy)-1-methylethyl |
| 5-224 | Br | Br | H | H | 0 | 1 | 3-hydroxy-4-methoxyphenyl |
| 5-225 | Br | Br | H | H | 0 | 1 | 3,5-dinitro-4-hydroxyphenyl |
| 5-226 | Br | Br | H | H | 0 | 1 | 1-(tert-butoxycarbonyl)-2-pyrrolidinyl |
| 5-227 | Br | Br | H | H | 0 | 1 | 1-(di-N-propylamino)ethyl |
| 5-228 | Br | Br | H | H | 0 | 1 | 1-(tert-butoxycarbonyl)-4-hydroxy-2-pyrrolidinyl |
| 5-229 | Br | Br | H | H | 0 | 1 | 5-acetylamino-1-(tert-butoxycarbonylamino)pentyl |
| 5-230 | Br | Br | H | H | 0 | 1 | 1-(tert-butoxycarbonylamino)-2,2-dimethyl-propyl |
| 5-231 | Br | Br | H | H | 0 | 1 | 2-pyrrolidinyl hydrochloride |
| 5-232 | Br | Br | H | H | 0 | 1 | 2-amino-2-propyl hydrochloride |
| 5-233 | Br | Br | H | H | 0 | 1 | 4-piperidinyl hydrochloride |
| 5-234 | Br | Br | H | H | 0 | 1 | 2-(benzyloxycarbonyl)-1-aminoethyl hydrochloride |
| 5-235 | Br | Br | H | H | 0 | 1 | 2-carboxy-1-aminoethyl hydrochloride |
| 5-236 | Br | Br | H | H | 0 | 1 | 2-carboxy-1-(tert-butoxycarbonylaminoethyl |
| 5-237 | Br | Br | H | H | 0 | 1 | [benzyl-(diethoxyphosphoryl-methyl)amino]methyl |
| 5-238 | Br | Br | H | H | 0 | 1 | 2-methylnicotinyl |
| 5-239 | Br | Br | H | H | 0 | 1 | 1-(acetylamino)-2-methylpropyl |
| 5-240 | Br | Br | H | H | 0 | 1 | 3-methylthio-1-acetylaminopropyl |
| 5-241 | Br | Br | H | H | 0 | 1 | 1-tert-(butoxycarbonylamino)-1-methylethyl |
| 5-242 | Br | Br | H | H | 0 | 0 | ⁺N(Et)₃Cl⁻ |
| 5-243 | Br | Br | H | H | 0 | 1 | undecyl |
| 5-244 | Br | Br | H | H | 0 | 1 | acetyl |
| 5-245 | Br | Br | H | H | 0 | 1 | 5-oxopyrrolin-2-yl |
| 5-246 | Br | Br | H | H | 0 | 1 | methoxymethyl |
| 5-247 | Br | Br | H | H | 0 | 1 | (4-oxo-2-thioxothiazolidin-3-yl)methyl |
| 5-248 | Br | Br | H | H | 0 | 1 | pyrazin-2-yl |
| 5-249 | Br | Br | H | H | 0 | 1 | 1H-pyrazol-4-yl |
| 5-250 | Br | Br | H | H | 0 | 1 | (furan-2-carbonyl)aminomethyl |
| 5-251 | Br | Br | H | H | 0 | 1 | 2-(2,5-dioxo-2,5-dihydropyrrol-1-yl)ethyl |
| 5-252 | Br | Br | H | H | 0 | 1 | 2-methoxyethoxymethyl |
| 5-253 | Br | Br | H | H | 0 | 1 | methanesulfonylmethyl |
| 5-254 | Br | Br | H | H | 0 | 1 | 4-heptyloxyphenyl |
| 5-255 | Br | Br | H | H | 0 | 1 | 2,6-dichlorophenyl |
| 5-256 | Br | Br | H | H | 0 | 1 | (3,5-diiodo-4-oxo-4H-pyridin-1-yl)methyl |
| 5-257 | Br | Br | H | H | 0 | 1 | 3-pyridyl |
| 5-258 | Br | Br | H | H | 0 | 1 | 5,6-dichloro-3-pyridyl |
| 5-259 | Br | Br | H | H | 0 | 1 | 4-pyridyl |
| 5-260 | Br | Br | H | H | 0 | 1 | 2,6-dichloro-4-pyridyl |
| 5-261 | Br | Br | H | H | 0 | 1 | 4-methanesulphonylphenyl |
| 5-262 | Br | Br | H | H | 0 | 1 | 2-chloro-4-nitrophenyl |
| 5-263 | Br | Br | H | H | 0 | 1 | 4-chloro-2-nitrophenyl |
| 5-264 | Br | Br | H | H | 0 | 1 | 3-chloro-2-nitrophenyl |
| 5-265 | Br | Br | H | H | 0 | 1 | 5-methylpyrazin-2-yl |
| 5-266 | Br | Br | H | H | 0 | 1 | tetrahydrofur-2-yl |
| 5-267 | Br | Br | H | H | 0 | 1 | 3-thiophen-2-ylpropyl |
| 5-268 | Br | Br | H | H | 0 | 1 | cyclopentylphenylmethyl |
| 5-269 | Br | Br | H | H | 0 | 1 | 1-phenylcyclopentyl |
| 5-270 | Br | Br | H | H | 0 | 1 | 1-methylcyclohexyl |

TABLE 5B-continued

| Cmpd # | Y³ | Y⁴ | R¹ | R² | q | t | (X²)$_q$Z² |
|---|---|---|---|---|---|---|---|
| 5-271 | Br | Br | H | H | 0 | 1 | 2-chloro-3-pyridyl |
| 5-272 | Br | Br | H | H | 0 | 1 | 1-methyl-1H-pyrrol-2-yl |
| 5-273 | Br | Br | H | H | 0 | 1 | 2,6-dimethoxyphenyl |
| 5-274 | Br | Br | H | H | 0 | 1 | 2,6-dimethoxy-3-pyridyl |
| 5-275 | Br | Br | H | H | 0 | 1 | 2-(thiophen-2-yl)ethenyl |
| 5-276 | Br | Br | H | H | 0 | 1 | 4-nitro-1H-pyrazol-3-yl |
| 5-277 | Br | Br | H | H | 0 | 1 | 4-sulfamoylphenyl |
| 5-278 | Br | Br | H | H | 0 | 1 | 2,4-dinitrophenyl |
| 5-279 | Br | Br | H | H | 0 | 1 | 1-hydroxy-1-phenylethyl |
| 5-280 | Br | Br | H | H | 0 | 1 | 3-hydroxy-4-methyl-2-nitrophenyl |
| 5-281 | Br | Br | H | H | 0 | 1 | 2-methylcyclopropyl |
| 5-282 | Br | Br | H | H | 0 | 1 | 1-phenylpropyl |
| 5-283 | Br | Br | H | H | 0 | 1 | 1,2,3,4-tetrahydronaphth-2-yl |
| 5-284 | Br | Br | H | H | 0 | 1 | 1-benzyl-2,2-dimethylpropyl |
| 5-285 | Br | Br | H | H | 0 | 1 | 2,2,3,3-tetramethylcyclopropyl |
| 5-286 | Br | Br | H | H | 0 | 1 | acetoxymethyl |
| 5-287 | Br | Br | H | H | 0 | 1 | 2,2,2-trifluoro-1-methoxy-1-phenylethyl |
| 5-288 | Br | Br | H | H | 0 | 1 | 1-methylpentyl |
| 5-289 | Br | Br | H | H | 0 | 1 | hept-1-ynyl |
| 5-290 | Br | Br | H | H | 0 | 1 | tetrahydrofur-3-yl |
| 5-291 | Br | Br | H | H | 0 | 1 | 1,1-methylpropyl |
| 5-292 | Br | Br | H | H | 0 | 1 | 2-methylcyclohexyl |
| 5-293 | Br | Br | H | H | 0 | 1 | 1,1-dimethylbut-3-enyl |
| 5-294 | Br | Br | H | H | 0 | 1 | 1-propylbutyl |
| 5-295 | Br | Br | H | H | 0 | 1 | 1-methylbutyl |
| 5-296 | Br | Br | H | H | 0 | 1 | 1-phenylethyl |
| 5-297 | Br | Br | H | H | 0 | 1 | phenyloxymethyl |
| 5-298 | Br | Br | H | H | 0 | 1 | pentafluorophenyloxymethyl |
| 5-299 | Br | Br | H | H | 0 | 1 | (2-formylaminothiazol-4-yl)methoxyiminomethyl |
| 5-300 | Br | Br | H | H | 0 | 1 | 1-hydroxy-1-ethylpropyl |
| 5-301 | Br | Br | H | H | 0 | 1 | 2-methoxyphenyloxymethyl |
| 5-302 | Br | Br | H | H | 0 | 1 | 2,4,6-trimethylphenyl |
| 5-303 | Br | Br | H | H | 0 | 1 | 2-methylphenyl |
| 5-304 | Br | Br | H | H | 0 | 1 | 1-methyl-1-(4-chlorophenyloxy)-ethyl |
| 5-305 | Br | Br | H | H | 0 | 1 | 1-hydroxy-1-methylpropyl |
| 5-306 | Br | Br | H | H | 0 | 1 | 1-ethylpentyl |
| 5-307 | Br | Br | H | H | 0 | 1 | 2-methyl-1-phenylbutyl |
| 5-308 | Br | Br | H | H | 0 | 1 | 1-methylpropyl |
| 5-309 | Br | Br | H | H | 0 | 1 | cyclobutyl |
| 5-310 | Br | Br | H | H | 0 | 1 | 1-ethylpropyl |
| 5-311 | Br | Br | H | H | 0 | 1 | (3,5-dinitrobenzoylamino)-phenylmethyl |
| 5-312 | Br | Br | H | H | 0 | 1 | 2,2-dichloro-1-methylcyclopropyl |
| 5-313 | Br | Br | H | H | 0 | 1 | 2,2,2-trifluoro-1-hydroxy-1-methylethyl |
| 5-314 | Br | Br | H | H | 0 | 1 | 1-hydroxy-2-trifluoromethylpropyl |
| 5-315 | Br | Br | H | H | 0 | 1 | 4-hydroxy-3-nitrophenyl |
| 5-316 | Br | Br | H | H | 0 | 1 | 4,8-dihydroxyquinol-2-yl |
| 5-317 | Br | Br | H | H | 0 | 1 | 2-hydroxy-1-phenylethyl |
| 5-318 | Br | Br | H | H | 0 | 1 | 4-hydroxyphenyl |
| 5-319 | Br | Br | H | H | 0 | 1 | 2,2-dimethylpropyl |
| 5-320 | Br | Br | H | H | 0 | 1 | 1-(3,5-dinitrobenzoylamino)-3-methylbutyl |
| 5-321 | Br | Br | H | H | 0 | 1 | (2-hydroxybenzoylamino)methyl |
| 5-322 | Br | Br | H | H | 0 | 1 | 3,3,3-trifluoropropyl |
| 5-323 | Br | Br | H | H | 0 | 1 | 1-oxypyrid-2-yl |
| 5-324 | Br | Br | H | H | 0 | 1 | 6-hydroxypyrid-2-yl |
| 5-325 | Br | Br | H | H | 0 | 1 | 3-hydroxypyrid-2-yl |
| 5-326 | Br | Br | H | H | 0 | 1 | benzoylaminomethyl |
| 5-327 | Br | Br | H | H | 0 | 1 | 1-methyl-5-oxo-2-pyrid-3-ylpyrrolin-3-yl |
| 5-328 | Br | Br | H | H | 0 | 1 | 1R,3R,4R,5R-tetrahydroxy-cyclohexyl |
| 5-329 | Br | Br | H | H | 0 | 1 | 2-(2-chlorophenyl)ethenyl |
| 5-330 | Br | Br | H | H | 0 | 1 | benzofur-2-yl |
| 5-331 | Br | Br | H | H | 0 | 1 | 3-thienyl |
| 5-332 | Br | Br | H | H | 0 | 1 | 3-methyl-1H-inden-2-yl |
| 5-333 | Br | Br | H | H | 0 | 1 | 3R,4S,5R-trihydroxy-1-cyclohexenyl |
| 5-334 | Br | Br | H | H | 0 | 1 | 2-(2-trifluoromethylphenyl)-ethenyl |
| 5-335 | Br | Br | H | H | 0 | 1 | 2-(4-methylphenyl)ethenyl |
| 5-336 | Br | Br | H | H | 0 | 1 | 1-cyclohexenyl |
| 5-337 | Br | Br | H | H | 0 | 1 | 2-(4-trifluoromethylphenyl)ethenyl |
| 5-338 | Br | Br | H | H | 0 | 1 | 1-cyclopentenyl |
| 5-339 | Br | Br | H | H | 0 | 1 | 1-methyl-1-butenyl |
| 5-340 | Br | Br | H | H | 0 | 1 | 3,3,3-trifluoro-2-methyl-1-propenyl |
| 5-341 | Br | Br | H | H | 0 | 1 | 2-(2-fluorophenyl)ethenyl |
| 5-342 | Br | Br | H | H | 0 | 1 | vinyl |
| 5-343 | Br | Br | H | H | 0 | 1 | 2-(4-dimethylaminophenyl)ethenyl |
| 5-344 | Br | Br | H | H | 0 | 1 | 2-(2-methoxyphenyl)ethenyl |
| 5-345 | Br | Br | H | H | 0 | 1 | 2-(3-hydroxy-4-methoxyphenyl)-ethenyl |
| 5-346 | Br | Br | H | H | 0 | 1 | 2-(3-trifluoromethylphenyl)ethenyl |
| 5-347 | Br | Br | H | H | 0 | 1 | 1-fluoro-2-phenylethenyl |
| 5-348 | Br | Br | H | H | 0 | 1 | 3-methyl-2-thienyl |
| 5-349 | Br | Br | H | H | 0 | 1 | 1-cyano-2-(4-hydroxyphenyl)-ethenyl |
| 5-350 | Br | Br | H | H | 0 | 1 | 2-(4-fluorophenyl)ethenyl |
| 5-351 | Br | Br | H | H | 0 | 1 | 2-methyl-1-propenyl |
| 5-352 | Br | Br | H | H | 0 | 1 | 1-ethyl-7-methyl-4-oxo-[1,8]naphthyridin-3-yl |
| 5-353 | Br | Br | H | H | 0 | 1 | 2-(4-hydroxy-3-methoxyphenyl)-ethenyl |
| 5-354 | Br | Br | H | H | 0 | 1 | 2-(benzo[1,3]dioxol-5-yl)ethenyl |
| 5-355 | Br | Br | H | H | 0 | 1 | 1-methylcyclopropyl |
| 5-356 | Br | Br | H | H | 0 | 1 | 2-furyl |
| 5-357 | Br | Br | H | H | 0 | 1 | 2-phenylethenyl |
| 5-358 | Br | Br | H | H | 0 | 1 | 2-(4-bromophenyl)ethenyl |
| 5-359 | Br | Br | H | H | 0 | 1 | 3-furyl |
| 5-360 | Br | Br | H | H | 0 | 1 | 2-(4-methoxyphenyl)ethenyl |
| 5-361 | Br | Br | H | H | 0 | 1 | 1-methyl-1H-indol-2-yl |
| 5-362 | Br | Br | H | H | 0 | 1 | 2-(3-pyridyl)ethenyl |
| 5-363 | Br | Br | H | H | 0 | 1 | 2-(3-fluorophenyl)ethenyl |
| 5-364 | Br | Br | H | H | 0 | 1 | 5-methyl-2-thienyl |
| 5-365 | Br | Br | H | H | 0 | 1 | 1-acetylamino-2-phenylethenyl |
| 5-366 | Br | Br | H | H | 0 | 1 | 2,6-dimethyl-1,5-heptadienyl |
| 5-367 | Br | Br | H | H | 0 | 1 | 1-pentenyl |
| 5-368 | Br | Br | H | H | 0 | 1 | 2-(2,3-dimethoxyphenyl)ethenyl |
| 5-369 | Br | Br | H | H | 0 | 1 | 1,3-pentadienyl |
| 5-370 | Br | Br | H | H | 0 | 1 | 2-(3-nitrophenyl)ethenyl |
| 5-371 | Br | Br | H | H | 0 | 1 | 2-(4-chlorophenyl)ethenyl |
| 5-372 | Br | Br | H | H | 0 | 1 | 2-(4-nitrophenyl)ethenyl |
| 5-373 | Br | Br | H | H | 0 | 1 | 2-(3,4-dimethoxyphenyl)ethenyl |
| 5-374 | Br | Br | H | H | 0 | 1 | 2-pentafluorophenylethenyl |
| 5-375 | Br | Br | H | H | 0 | 1 | 1-methyl-2-phenylethenyl |
| 5-376 | Br | Br | H | H | 0 | 1 | 2-(4-hydroxyphenyl)ethenyl |
| 5-377 | Br | Br | H | H | 0 | 1 | 2-(3-hydroxyphenyl)ethenyl |
| 5-378 | Br | Br | H | H | 0 | 1 | 2-(2-furyl)ethenyl |
| 5-379 | Br | Br | H | H | 0 | 1 | 2-(3,4-dichlorophenyl)ethenyl |
| 5-380 | Br | Br | H | H | 0 | 1 | 2-(2,4-dichlorophenyl)ethenyl |
| 5-381 | Br | Br | H | H | 0 | 1 | 2-(2-nitrophenyl)ethenyl |
| 5-382 | Br | Br | H | H | 0 | 1 | 2,2,2-trifluoro-1-trifluoromethyl-1-methylethyl |

TABLE 5C

Compounds (5-383)–(5-564) are compounds of Formula IV where R¹, R², q, and t are identical to those in Table 5B except for Y³ and Y⁴ which both equal I.

TABLE 5D

| Cmpd # | Y³ | Y⁴ | R¹ | R² | q | t | (X²)$_q$Z² |
|---|---|---|---|---|---|---|---|
| 5-565 | Cl | Cl | CH₃ | H | 0 | 1 | 3,6-dichloro-2-pyridyl |
| 5-566 | Cl | Cl | CH₃ | H | 0 | 1 | C(CH₃)₃ |
| 5-567 | Cl | Cl | CH₃ | H | 0 | 1 | acetamidomethyl |
| 5-568 | Cl | Cl | CH₃ | H | 0 | 1 | 2-nitro-5-thiocyanatophenyl |
| 5-569 | Cl | Cl | CH₃ | H | 0 | 1 | cycloheptyl |
| 5-570 | Cl | Cl | CH₃ | H | 0 | 1 | 2-hydroxy-2-propyl |
| 5-571 | Cl | Cl | CH₃ | H | 0 | 1 | 1-(isopropylidineaminooxy)ethyl |
| 5-572 | Cl | Cl | CH₃ | H | 0 | 1 | 4,4,4-trifluoro-2-butyl |
| 5-573 | Cl | Cl | CH₃ | H | 0 | 1 | 2-(trifluoromethyl)propyl |
| 5-574 | Cl | Cl | CH₃ | H | 0 | 1 | 2,2,2-trifluoroethyl |
| 5-575 | Cl | Cl | CH₃ | H | 0 | 1 | 1-(benzyloxycarbonylamino)-1-methylethyl |

TABLE 5D-continued

| Cmpd # | Y³ | Y⁴ | R¹ | R² | q | t | (X²)qZ² |
|---|---|---|---|---|---|---|---|
| 5-576 | Cl | Cl | CH₃ | H | 0 | 1 | 1-(tert-butoxycarbonylamino)-1-methylethyl |
| 5-577 | Cl | Cl | CH₃ | H | 0 | 1 | 1-(tert-butoxycarbonyl)-piperidin-4-yl |
| 5-578 | Cl | Cl | CH₃ | H | 0 | 1 | 1-acetyl-4-hydroxy-pyrrolidin-2-yl |
| 5-579 | Cl | Cl | CH₃ | H | 0 | 1 | 2-methyl-3-pyridyl |
| 5-580 | Cl | Cl | CH₃ | H | 0 | 1 | 1-(acetylamino)-2-methylpropyl |
| 5-581 | Cl | Cl | CH₃ | H | 0 | 1 | 2,6-dimethoxy-4-hydroxyphenyl |
| 5-582 | Cl | Cl | CH₃ | H | 0 | 1 | 3-methylthio-1-acetylamino-propyl |
| 5-583 | Cl | Cl | CH₃ | H | 0 | 1 | 1-acetylaminovinyl |
| 5-584 | Cl | Cl | CH₃ | H | 0 | 1 | 1-methyl-2-pyrrolyl |
| 5-585 | Cl | Cl | CH₃ | H | 0 | 1 | 2-(benzyloxycarbonyl)-1-(tert-butoxycarbonylamino)ethyl |
| 5-586 | Cl | Cl | CH₃ | H | 0 | 1 | 4-hexyloxyphenyl |
| 5-587 | Cl | Cl | CH₃ | H | 0 | 1 | 1-(2-chlorophenoxy)-1-methylethyl |
| 5-588 | Cl | Cl | CH₃ | H | 0 | 1 | 3-hydroxy-4-methoxyphenyl |
| 5-589 | Cl | Cl | CH₃ | H | 0 | 1 | 3,5-dinitro-4-hydroxyphenyl |
| 5-590 | Cl | Cl | CH₃ | H | 0 | 1 | 1-(tert-butoxycarbonyl)-2-pyrrolidinyl |
| 5-591 | Cl | Cl | CH₃ | H | 0 | 1 | 1-(di-N-propylamino)ethyl |
| 5-592 | Cl | Cl | CH₃ | H | 0 | 1 | 1-(tert-butoxycarbonyl)-4-hydroxy-2-pyrrolidinyl |
| 5-593 | Cl | Cl | CH₃ | H | 0 | 1 | 5-acetylamino-1-(tert-butoxycarbonylamino)pentyl |
| 5-594 | Cl | Cl | CH₃ | H | 0 | 1 | 1-(tert-butoxycarbonylamino)-2,2-dimethyl-propyl |
| 5-595 | Cl | Cl | CH₃ | H | 0 | 1 | 2-pyrrolidinyl hydrochloride |
| 5-596 | Cl | Cl | CH₃ | H | 0 | 1 | 2-amino-2-propyl hydrochloride |
| 5-597 | Cl | Cl | CH₃ | H | 0 | 1 | 4-piperidinyl hydrochloride |
| 5-598 | Cl | Cl | CH₃ | H | 0 | 1 | 2-(benzyloxycarbonyl)-1-aminoethyl hydrochloride |
| 5-599 | Cl | Cl | CH₃ | H | 0 | 1 | 2-carboxy-1-aminoethyl hydrochloride |
| 5-600 | Cl | Cl | CH₃ | H | 0 | 1 | 2-carboxy-1-(tert-butoxycarbonylaminoethyl |
| 5-601 | Cl | Cl | CH₃ | H | 0 | 1 | [benzyl-(diethoxyphosphoryl-methyl)amino]methyl |
| 5-602 | Cl | Cl | CH₃ | H | 0 | 1 | 2-methylnicotinyl |
| 5-603 | Cl | Cl | CH₃ | H | 0 | 1 | 1-(acetylamino)-2-methylpropyl |
| 5-604 | Cl | Cl | CH₃ | H | 0 | 1 | 3-methylthio-1-acetylamino-propyl |
| 5-605 | Cl | Cl | CH₃ | H | 0 | 1 | 1-tert-(butoxycarbonylamino)-1-methylethyl |
| 5-606 | Cl | Cl | CH₃ | H | 0 | 0 | ⁺N(Et)₃Cl⁻ |
| 5-607 | Cl | Cl | CH₃ | H | 0 | 1 | undecyl |
| 5-608 | Cl | Cl | CH₃ | H | 0 | 1 | acetyl |
| 5-609 | Cl | Cl | CH₃ | H | 0 | 1 | 5-oxopyrrolin-2-yl |
| 5-610 | Cl | Cl | CH₃ | H | 0 | 1 | methoxymethyl |
| 5-611 | Cl | Cl | CH₃ | H | 0 | 1 | (4-oxo-2-thioxothiazolidin-3-yl)-methyl |
| 5-612 | Cl | Cl | CH₃ | H | 0 | 1 | pyrazin-2-yl |
| 5-613 | Cl | Cl | CH₃ | H | 0 | 1 | 1H-pyrazol-4-yl |
| 5-614 | Cl | Cl | CH₃ | H | 0 | 1 | (furan-2-carbonyl)aminomethyl |
| 5-615 | Cl | Cl | CH₃ | H | 0 | 1 | 2-(2,5-dioxo-2,5-dihydropyrrol-1-yl)ethyl |
| 5-616 | Cl | Cl | CH₃ | H | 0 | 1 | 2-methoxyethoxymethyl |
| 5-617 | Cl | Cl | CH₃ | H | 0 | 1 | methanesulfonylmethyl |
| 5-618 | Cl | Cl | CH₃ | H | 0 | 1 | 4-heptyloxyphenyl |
| 5-619 | Cl | Cl | CH₃ | H | 0 | 1 | 2,6-dichlorophenyl |
| 5-620 | Cl | Cl | CH₃ | H | 0 | 1 | (3,5-diiodo-4-oxo-4H-pyridin-1-yl)methyl |
| 5-621 | Cl | Cl | CH₃ | H | 0 | 1 | 3-pyridyl |
| 5-622 | Cl | Cl | CH₃ | H | 0 | 1 | 5,6-dichloro-3-pyridyl |
| 5-623 | Cl | Cl | CH₃ | H | 0 | 1 | 4-pyridyl |
| 5-624 | Cl | Cl | CH₃ | H | 0 | 1 | 2,6-dichloro-4-pyridyl |
| 5-625 | Cl | Cl | CH₃ | H | 0 | 1 | 4-methanesulphonylphenyl |
| 5-626 | Cl | Cl | CH₃ | H | 0 | 1 | 2-chloro-4-nitrophenyl |
| 5-627 | Cl | Cl | CH₃ | H | 0 | 1 | 4-chloro-2-nitrophenyl |
| 5-628 | Cl | Cl | CH₃ | H | 0 | 1 | 3-chloro-2-nitrophenyl |
| 5-629 | Cl | Cl | CH₃ | H | 0 | 1 | 5-methylpyrazin-2-yl |
| 5-630 | Cl | Cl | CH₃ | H | 0 | 1 | tetrahydrofur-2-yl |
| 5-631 | Cl | Cl | CH₃ | H | 0 | 1 | 3-thiophen-2-ylpropyl |
| 5-632 | Cl | Cl | CH₃ | H | 0 | 1 | cyclopentylphenylmethyl |
| 5-633 | Cl | Cl | CH₃ | H | 0 | 1 | 1-phenylcyclopentyl |
| 5-634 | Cl | Cl | CH₃ | H | 0 | 1 | 1-methylcyclohexyl |
| 5-635 | Cl | Cl | CH₃ | H | 0 | 1 | 2-chloro-3-pyridyl |
| 5-636 | Cl | Cl | CH₃ | H | 0 | 1 | 1-methyl-1H-pyrrol-2-yl |
| 5-637 | Cl | Cl | CH₃ | H | 0 | 1 | 2,6-dimethoxyphenyl |
| 5-638 | Cl | Cl | CH₃ | H | 0 | 1 | 2,6-dimethoxy-3-pyridyl |
| 5-639 | Cl | Cl | CH₃ | H | 0 | 1 | 2-(thiophen-2-yl)ethenyl |
| 5-640 | Cl | Cl | CH₃ | H | 0 | 1 | 4-nitro-1H-pyrazol-3-yl |
| 5-641 | Cl | Cl | CH₃ | H | 0 | 1 | 4-sulfamoylphenyl |
| 5-642 | Cl | Cl | CH₃ | H | 0 | 1 | 2,4-dinitrophenyl |
| 5-643 | Cl | Cl | CH₃ | H | 0 | 1 | 1-hydroxy-1-phenylethyl |
| 5-644 | Cl | Cl | CH₃ | H | 0 | 1 | 3-hydroxy-4-methyl-2-nitrophenyl |
| 5-645 | Cl | Cl | CH₃ | H | 0 | 1 | 2-methylcyclopropyl |
| 5-646 | Cl | Cl | CH₃ | H | 0 | 1 | 1-phenylpropyl |
| 5-647 | Cl | Cl | CH₃ | H | 0 | 1 | 1,2,3,4-tetrahydronaphth-2-yl |
| 5-648 | Cl | Cl | CH₃ | H | 0 | 1 | 1-benzyl-2,2-dimethylpropyl |
| 5-649 | Cl | Cl | CH₃ | H | 0 | 1 | 2,2,3,3-tetramethylcyclopropyl |
| 5-650 | Cl | Cl | CH₃ | H | 0 | 1 | acetoxymethyl |
| 5-651 | Cl | Cl | CH₃ | H | 0 | 1 | 2,2,2-trifluoro-1-methoxy-1-phenylethyl |
| 5-652 | Cl | Cl | CH₃ | H | 0 | 1 | 1-methylpentyl |
| 5-653 | Cl | Cl | CH₃ | H | 0 | 1 | hept-1-ynyl |
| 5-654 | Cl | Cl | CH₃ | H | 0 | 1 | tetrahydrofur-3-yl |
| 5-655 | Cl | Cl | CH₃ | H | 0 | 1 | 1,1-methylpropyl |
| 5-656 | Cl | Cl | CH₃ | H | 0 | 1 | 2-methylcyclohexyl |
| 5-657 | Cl | Cl | CH₃ | H | 0 | 1 | 1,1-dimethylbut-3-enyl |
| 5-658 | Cl | Cl | CH₃ | H | 0 | 1 | 1-propylbutyl |
| 5-659 | Cl | Cl | CH₃ | H | 0 | 1 | 1-methylbutyl |
| 5-660 | Cl | Cl | CH₃ | H | 0 | 1 | 1-phenylethyl |
| 5-661 | Cl | Cl | CH₃ | H | 0 | 1 | phenyloxymethyl |
| 5-662 | Cl | Cl | CH₃ | H | 0 | 1 | pentafluorophenyloxymethyl |
| 5-663 | Cl | Cl | CH₃ | H | 0 | 1 | (2-formylaminothiazol-4-yl)methoxyiminomethyl |
| 5-664 | Cl | Cl | CH₃ | H | 0 | 1 | 1-hydroxy-1-ethylpropyl |
| 5-665 | Cl | Cl | CH₃ | H | 0 | 1 | 2-methoxyphenyloxymethyl |
| 5-666 | Cl | Cl | CH₃ | H | 0 | 1 | 2,4,6-trimethylphenyl |
| 5-667 | Cl | Cl | CH₃ | H | 0 | 1 | 2-methylphenyl |
| 5-668 | Cl | Cl | CH₃ | H | 0 | 1 | 1-methyl-1-(4-chlorophenyloxy)-ethyl |
| 5-669 | Cl | Cl | CH₃ | H | 0 | 1 | 1-hydroxy-1-methylpropyl |
| 5-670 | Cl | Cl | CH₃ | H | 0 | 1 | 1-ethylpentyl |
| 5-671 | Cl | Cl | CH₃ | H | 0 | 1 | 2-methyl-1-phenylbutyl |
| 5-672 | Cl | Cl | CH₃ | H | 0 | 1 | 1-methylpropyl |
| 5-673 | Cl | Cl | CH₃ | H | 0 | 1 | cyclobutyl |
| 5-674 | Cl | Cl | CH₃ | H | 0 | 1 | 1-ethylpropyl |
| 5-675 | Cl | Cl | CH₃ | H | 0 | 1 | (3,5-dinitrobenzoylamino)-phenylmethyl |
| 5-676 | Cl | Cl | CH₃ | H | 0 | 1 | 2,2-dichloro-1-methyl-cyclopropyl |
| 5-677 | Cl | Cl | CH₃ | H | 0 | 1 | 2,2,2-trifluoro-1-hydroxy-1-methylethyl |
| 5-678 | Cl | Cl | CH₃ | H | 0 | 1 | 1-hydroxy-2-trifluoromethyl-propyl |
| 5-679 | Cl | Cl | CH₃ | H | 0 | 1 | 4-hydroxy-3-nitrophenyl |
| 5-680 | Cl | Cl | CH₃ | H | 0 | 1 | 4,8-dihydroxyquinol-2-yl |
| 5-681 | Cl | Cl | CH₃ | H | 0 | 1 | 2-hydroxy-1-phenylethyl |
| 5-682 | Cl | Cl | CH₃ | H | 0 | 1 | 4-hydroxyphenyl |
| 5-683 | Cl | Cl | CH₃ | H | 0 | 1 | 2,2-dimethylpropyl |
| 5-684 | Cl | Cl | CH₃ | H | 0 | 1 | 1-(3,5-dinitrobenzoylamino)-3-methylbutyl |
| 5-685 | Cl | Cl | CH₃ | H | 0 | 1 | (2-hydroxybenzoylamino)methyl |
| 5-686 | Cl | Cl | CH₃ | H | 0 | 1 | 3,3,3-trifluoropropyl |
| 5-687 | Cl | Cl | CH₃ | H | 0 | 1 | 1-oxypyrid-2-yl |
| 5-688 | Cl | Cl | CH₃ | H | 0 | 1 | 6-hydroxypyrid-2-yl |
| 5-689 | Cl | Cl | CH₃ | H | 0 | 1 | 3-hydroxypyrid-2-yl |
| 5-690 | Cl | Cl | CH₃ | H | 0 | 1 | benzoylaminomethyl |
| 5-691 | Cl | Cl | CH₃ | H | 0 | 1 | 1-methyl-5-oxo-2-pyrid-3-ylpyrrolin-3-yl |
| 5-692 | Cl | Cl | CH₃ | H | 0 | 1 | 1R,3R,4R,5R-tetrahydroxy-cyclohexyl |
| 5-693 | Cl | Cl | CH₃ | H | 0 | 1 | 2-(2-chlorphenyl)ethenyl |
| 5-694 | Cl | Cl | CH₃ | H | 0 | 1 | benzofur-2-yl |
| 5-695 | Cl | Cl | CH₃ | H | 0 | 1 | 3-thienyl |
| 5-696 | Cl | Cl | CH₃ | H | 0 | 1 | 3-methyl-1H-inden-2-yl |
| 5-697 | Cl | Cl | CH₃ | H | 0 | 1 | 3R,4S,5R-trihydroxy-1-cyclohexenyl |

TABLE 5D-continued

| Cmpd # | Y³ | Y⁴ | R¹ | R² | q | t | (X²)qZ² |
|---|---|---|---|---|---|---|---|
| 5-698 | Cl | Cl | CH₃ | H | 0 | 1 | 2-(2-trifluoromethylphenyl)-ethenyl |
| 5-699 | Cl | Cl | CH₃ | H | 0 | 1 | 2-(4-methylphenyl)ethenyl |
| 5-700 | Cl | Cl | CH₃ | H | 0 | 1 | 1-cyclohexenyl |
| 5-701 | Cl | Cl | CH₃ | H | 0 | 1 | 2-(4-trifluoromethylphenyl)-ethenyl |
| 5-702 | Cl | Cl | CH₃ | H | 0 | 1 | 1-cyclopentenyl |
| 5-703 | Cl | Cl | CH₃ | H | 0 | 1 | 1-methyl-1-butenyl |
| 5-704 | Cl | Cl | CH₃ | H | 0 | 1 | 3,3,3-trifluoro-2-methyl-1-propenyl |
| 5-705 | Cl | Cl | CH₃ | H | 0 | 1 | 2-(2-fluorophenyl)ethenyl |
| 5-706 | Cl | Cl | CH₃ | H | 0 | 1 | vinyl |
| 5-707 | Cl | Cl | CH₃ | H | 0 | 1 | 2-(4-dimethylaminophenyl)-ethenyl |
| 5-708 | Cl | Cl | CH₃ | H | 0 | 1 | 2-(2-methoxyphenyl)ethenyl |
| 5-709 | Cl | Cl | CH₃ | H | 0 | 1 | 2-(3-hydroxy-4-methoxyphenyl)-ethenyl |
| 5-710 | Cl | Cl | CH₃ | H | 0 | 1 | 2-(3-trifluoromethylphenyl)-ethenyl |
| 5-711 | Cl | Cl | CH₃ | H | 0 | 1 | 1-fluoro-2-phenylethenyl |
| 5-712 | Cl | Cl | CH₃ | H | 0 | 1 | 3-methyl-2-thienyl |
| 5-713 | Cl | Cl | CH₃ | H | 0 | 1 | 1-cyano-2-(4-hydroxyphenyl)-ethenyl |
| 5-714 | Cl | Cl | CH₃ | H | 0 | 1 | 2-(4-fluorophenyl)ethenyl |
| 5-715 | Cl | Cl | CH₃ | H | 0 | 1 | 2-methyl-1-propenyl |
| 5-716 | Cl | Cl | CH₃ | H | 0 | 1 | 1-ethyl-7-methyl-4-oxo-[1,8]naphthyridin-3-yl |
| 5-717 | Cl | Cl | CH₃ | H | 0 | 1 | 2-(4-hydroxy-3-methoxyphenyl)-ethenyl |
| 5-718 | Cl | Cl | CH₃ | H | 0 | 1 | 2-(benzo[1,3]dioxol-5-yl)ethenyl |
| 5-719 | Cl | Cl | CH₃ | H | 0 | 1 | 1-methylcyclopropyl |
| 5-720 | Cl | Cl | CH₃ | H | 0 | 1 | 2-furyl |
| 5-721 | Cl | Cl | CH₃ | H | 0 | 1 | 2-phenylethenyl |
| 5-722 | Cl | Cl | CH₃ | H | 0 | 1 | 2-(4-bromophenyl)ethenyl |
| 5-723 | Cl | Cl | CH₃ | H | 0 | 1 | 3-furyl |
| 5-724 | Cl | Cl | CH₃ | H | 0 | 1 | 2-(4-methoxyphenyl)ethenyl |
| 5-725 | Cl | Cl | CH₃ | H | 0 | 1 | 1-methyl-1H-indol-2-yl |
| 5-726 | Cl | Cl | CH₃ | H | 0 | 1 | 2-(3-pyridyl)ethenyl |
| 5-727 | Cl | Cl | CH₃ | H | 0 | 1 | 2-(3-fluorophenyl)ethenyl |
| 5-728 | Cl | Cl | CH₃ | H | 0 | 1 | 5-methyl-2-thienyl |
| 5-729 | Cl | Cl | CH₃ | H | 0 | 1 | 1-acetylamino-2-phenylethenyl |
| 5-730 | Cl | Cl | CH₃ | H | 0 | 1 | 2,6-dimethyl-1,5-heptadienyl |
| 5-731 | Cl | Cl | CH₃ | H | 0 | 1 | 1-pentenyl |
| 5-732 | Cl | Cl | CH₃ | H | 0 | 1 | 2-(2,3-dimethoxyphenyl)ethenyl |
| 5-733 | Cl | Cl | CH₃ | H | 0 | 1 | 1,3-pentadienyl |
| 5-734 | Cl | Cl | CH₃ | H | 0 | 1 | 2-(3-nitrophenyl)ethenyl |
| 5-735 | Cl | Cl | CH₃ | H | 0 | 1 | 2-(4-chlorophenyl)ethenyl |
| 5-736 | Cl | Cl | CH₃ | H | 0 | 1 | 2-(4-nitrophenyl)ethenyl |
| 5-737 | Cl | Cl | CH₃ | H | 0 | 1 | 2-(3,4-dimethoxyphenyl)ethenyl |
| 5-738 | Cl | Cl | CH₃ | H | 0 | 1 | 2-pentafluorophenylethenyl |
| 5-739 | Cl | Cl | CH₃ | H | 0 | 1 | 1-methyl-2-phenylethenyl |
| 5-740 | Cl | Cl | CH₃ | H | 0 | 1 | 2-(4-hydroxyphenyl)ethenyl |
| 5-741 | Cl | Cl | CH₃ | H | 0 | 1 | 2-(3-hydroxyphenyl)ethenyl |
| 5-742 | Cl | Cl | CH₃ | H | 0 | 1 | 2-(2-furyl)ethenyl |
| 5-743 | Cl | Cl | CH₃ | H | 0 | 1 | 2-(3,4-dichlorophenyl)ethenyl |
| 5-744 | Cl | Cl | CH₃ | H | 0 | 1 | 2-(2,4-dichlorophenyl)ethenyl |
| 5-745 | Cl | Cl | CH₃ | H | 0 | 1 | 2-(2-nitrophenyl)ethenyl |
| 5-746 | Cl | Cl | CH₃ | H | 0 | 1 | 2,2,2-trifluoro-1-trifluoromethyl-1-methylethyl |

TABLE 5E

Compounds (5-747)–(5-928) are compounds of Formula IV where R¹, R², q, and t are identical to those in Table 5D except for Y³ and Y⁴ which both equal Br.

TABLE 5F

Compounds (5-929)–(5-1110) are compounds of Formula IV where R¹, R², q, and t are identical to those in Table 5D except for Y³ and Y⁴ which both equal I.

TABLE 5G

| Cmpd # | Y³ | Y⁴ | R¹ | R² | q | t | (X²)qZ² |
|---|---|---|---|---|---|---|---|
| 5-1111 | Cl | Cl | Ph | H | 1 | 1 | 3,6-dichloro-2-pyridyl |
| 5-1112 | Cl | Cl | Ph | H | 0 | 1 | C(CH₃)₃ |
| 5-1113 | Cl | Cl | Ph | H | 0 | 1 | acetamidomethyl |
| 5-1114 | Cl | Cl | Ph | H | 0 | 1 | 2-nitro-5-thiocyanatophenyl |
| 5-1115 | Cl | Cl | Ph | H | 0 | 1 | cycloheptyl |
| 5-1116 | Cl | Cl | Ph | H | 0 | 1 | 2-hydroxy-2-propyl |
| 5-1117 | Cl | Cl | Ph | H | 0 | 1 | 1-(isopropylidineaminooxy)ethyl |
| 5-1118 | Cl | Cl | Ph | H | 0 | 1 | 4,4,4-trifluoro-2-butyl |
| 5-1119 | Cl | Cl | Ph | H | 0 | 1 | 2-(trifluoromethyl)propyl |
| 5-1120 | Cl | Cl | Ph | H | 0 | 1 | 2,2,2-trifluoroethyl |
| 5-1121 | Cl | Cl | Ph | H | 0 | 1 | 1-(benzyloxycarbonylamino)-1-methylethyl |
| 5-1122 | Cl | Cl | Ph | H | 0 | 1 | 1-(tert-butoxycarbonylamino)-1-methylethyl |
| 5-1123 | Cl | Cl | Ph | H | 0 | 1 | 1-(tert-butoxycarbonyl)-piperidin-4-yl |
| 5-1124 | Cl | Cl | Ph | H | 0 | 1 | 1-acetyl-4-hydroxypyrrolidin-2-yl |
| 5-1125 | Cl | Cl | Ph | H | 0 | 1 | 2-methyl-3-pyridyl |
| 5-1126 | Cl | Cl | Ph | H | 0 | 1 | 1-(acetylamino)-2-methylpropyl |
| 5-1127 | Cl | Cl | Ph | H | 0 | 1 | 2,6-dimethoxy-4-hydroxyphenyl |
| 5-1128 | Cl | Cl | Ph | H | 0 | 1 | 3-methylthio-1-acetylaminopropyl |
| 5-1129 | Cl | Cl | Ph | H | 0 | 1 | 1-acetylaminovinyl |
| 5-1130 | Cl | Cl | Ph | H | 0 | 1 | 1-methyl-2-pyrrolyl |
| 5-1131 | Cl | Cl | Ph | H | 0 | 1 | 2-benzyloxycarbonyl)-1-(tert-butoxycarbonylamino)ethyl |
| 5-1132 | Cl | Cl | Ph | H | 0 | 1 | 4-hexyloxyphenyl |
| 5-1133 | Cl | Cl | Ph | H | 0 | 1 | 1-(2-chlorophenoxy)-1-methylethyl |
| 5-1134 | Cl | Cl | Ph | H | 0 | 1 | 3-hydroxy-4-methoxyphenyl |
| 5-1135 | Cl | Cl | Ph | H | 0 | 1 | 3,5-dinitro-4-hydroxyphenyl |
| 5-1136 | Cl | Cl | Ph | H | 0 | 1 | 1-(tert-butoxycarbonyl)-2-pyrrolidinyl |
| 5-1137 | Cl | Cl | Ph | H | 0 | 1 | 1-(di-N-propylamino)ethyl |
| 5-1138 | Cl | Cl | Ph | H | 0 | 1 | 1-(tert-butoxycarbonyl)-4-hydroxy-2-pyrrolidinyl |
| 5-1139 | Cl | Cl | Ph | H | 0 | 1 | 5-acetylamino-1-(tert-butoxycarbonylamino)pentyl |
| 5-1140 | Cl | Cl | Ph | H | 0 | 1 | 1-(tert-butoxycarbonylamino)-2,2-dimethyl-propyl |
| 5-1141 | Cl | Cl | Ph | H | 0 | 1 | 2-pyrrolidinyl hydrochloride |
| 5-1142 | Cl | Cl | Ph | H | 0 | 1 | 2-amino-2-propyl hydrochloride |
| 5-1143 | Cl | Cl | Ph | H | 0 | 1 | 4-piperidinyl hydrochloride |
| 5-1144 | Cl | Cl | Ph | H | 0 | 1 | 2-(benzyloxycarbonyl)-1-aminoethyl hydrochloride |
| 5-1145 | Cl | Cl | Ph | H | 0 | 1 | 2-carboxy-1-aminoethyl hydrochloride |
| 5-1146 | Cl | Cl | Ph | H | 0 | 1 | 2-carboxy-1-(tert-butoxycarbonylaminoethyl |
| 5-1147 | Cl | Cl | Ph | H | 0 | 1 | [benzyl-(diethoxyphosphoryl-methyl)amino]methyl |
| 5-1148 | Cl | Cl | Ph | H | 0 | 1 | 2-methylnicotinyl |
| 5-1149 | Cl | Cl | Ph | H | 0 | 1 | 1-(acetylamino)-2-methylpropyl |
| 5-1150 | Cl | Cl | Ph | H | 0 | 1 | 3-methylthio-1-acetylamino-propyl |
| 5-1151 | Cl | Cl | Ph | H | 0 | 1 | 1-tert-(butoxycarbonyamino)-1-methylethyl |
| 5-1152 | Cl | Cl | Ph | H | 0 | 0 | ⁺N(Et)₃Cl⁻ |
| 5-1153 | Cl | Cl | Ph | H | 0 | 1 | undecyl |
| 5-1154 | Cl | Cl | Ph | H | 0 | 1 | acetyl |
| 5-1155 | Cl | Cl | Ph | H | 0 | 1 | 5-oxopyrrolin-2-yl |
| 5-1156 | Cl | Cl | Ph | H | 0 | 1 | methoxymethyl |
| 5-1157 | Cl | Cl | Ph | H | 0 | 1 | (4-oxo-2-thioxothiazolidin-3-yl)methyl |
| 5-1158 | Cl | Cl | Ph | H | 0 | 1 | pyrazin-2-yl |
| 5-1159 | Cl | Cl | Ph | H | 0 | 1 | 1H-pyrazol-4-yl |
| 5-1160 | Cl | Cl | Ph | H | 0 | 1 | (furan-2-carbonyl)aminomethyl |
| 5-1161 | Cl | Cl | Ph | H | 0 | 1 | 2-(2,5-dioxo-2,5-dihydropyrrol-1-yl)ethyl |
| 5-1162 | Cl | Cl | Ph | H | 0 | 1 | 2-methoxyethoxymethyl |
| 5-1163 | Cl | Cl | Ph | H | 0 | 1 | methanesulfonylmethyl |
| 5-1164 | Cl | Cl | Ph | H | 0 | 1 | 4-heptyloxyphenyl |
| 5-1165 | Cl | Cl | Ph | H | 0 | 1 | 2,6-dichlorophenyl |
| 5-1166 | Cl | Cl | Ph | H | 0 | 1 | (3,5-diiodo-4-oxo-4H-pyridin-1-yl)methyl |
| 5-1167 | Cl | Cl | Ph | H | 0 | 1 | 3-pyridyl |
| 5-1168 | Cl | Cl | Ph | H | 0 | 1 | 5,6-dichloro-3-pyridyl |
| 5-1169 | Cl | Cl | Ph | H | 0 | 1 | 4-pyridyl |
| 5-1170 | Cl | Cl | Ph | H | 0 | 1 | 2,6-dichloro-4-pyridyl |

TABLE 5G-continued

| Cmpd # | Y³ | Y⁴ | R¹ | R² | q | t | (X²)qZ² |
|---|---|---|---|---|---|---|---|
| 5-1171 | Cl | Cl | Ph | H | 0 | 1 | 4-methanesulphonylphenyl |
| 5-1172 | Cl | Cl | Ph | H | 0 | 1 | 2-chloro-4-nitrophenyl |
| 5-1173 | Cl | Cl | Ph | H | 0 | 1 | 4-chloro-2-nitrophenyl |
| 5-1174 | Cl | Cl | Ph | H | 0 | 1 | 3-chloro-2-nitrophenyl |
| 5-1175 | Cl | Cl | Ph | H | 0 | 1 | 5-methylpyrazin-2-yl |
| 5-1176 | Cl | Cl | Ph | H | 0 | 1 | tetrahydrofur-2-yl |
| 5-1177 | Cl | Cl | Ph | H | 0 | 1 | 3-thiophen-2-ylpropyl |
| 5-1178 | Cl | Cl | Ph | H | 0 | 1 | cyclopentylphenylmethyl |
| 5-1179 | Cl | Cl | Ph | H | 0 | 1 | 1-phenylcyclopentyl |
| 5-1180 | Cl | Cl | Ph | H | 0 | 1 | 1-methylcyclohexyl |
| 5-1181 | Cl | Cl | Ph | H | 0 | 1 | 2-chloro-3-pyridyl |
| 5-1182 | Cl | Cl | Ph | H | 0 | 1 | 1-methyl-1H-pyrrol-2-yl |
| 5-1183 | Cl | Cl | Ph | H | 0 | 1 | 2,6-dimethoxyphenyl |
| 5-1184 | Cl | Cl | Ph | H | 0 | 1 | 2,6-dimethoxy-3-pyridyl |
| 5-1185 | Cl | Cl | Ph | H | 0 | 1 | 2-(thiophen-2-yl)ethenyl |
| 5-1186 | Cl | Cl | Ph | H | 0 | 1 | 4-nitro-1H-pyrazol-3-yl |
| 5-1187 | Cl | Cl | Ph | H | 0 | 1 | 4-sulfamoylphenyl |
| 5-1188 | Cl | Cl | Ph | H | 0 | 1 | 2,4-dinitrophenyl |
| 5-1189 | Cl | Cl | Ph | H | 0 | 1 | 1-hydroxy-1-phenylethyl |
| 5-1190 | Cl | Cl | Ph | H | 0 | 1 | 3-hydroxy-4-methyl-2-nitrophenyl |
| 5-1191 | Cl | Cl | Ph | H | 0 | 1 | 2-methylcyclopropyl |
| 5-1192 | Cl | Cl | Ph | H | 0 | 1 | 1-phenylpropyl |
| 5-1193 | Cl | Cl | Ph | H | 0 | 1 | 1,2,3,4-tetrahydronaphth-2-yl |
| 5-1194 | Cl | Cl | Ph | H | 0 | 1 | 1-benzyl-2,2-dimethylpropyl |
| 5-1195 | Cl | Cl | Ph | H | 0 | 1 | 2,2,3,3-tetramethylcyclopropyl |
| 5-1196 | Cl | Cl | Ph | H | 0 | 1 | acetoxymethyl |
| 5-1197 | Cl | Cl | Ph | H | 0 | 1 | 2,2,2-trifluoro-1-methoxy-1-phenylethyl |
| 5-1198 | Cl | Cl | Ph | H | 0 | 1 | 1-methylpentyl |
| 5-1199 | Cl | Cl | Ph | H | 0 | 1 | hept-1-ynyl |
| 5-1200 | Cl | Cl | Ph | H | 0 | 1 | tetrahydrofur-3-yl |
| 5-1201 | Cl | Cl | Ph | H | 0 | 1 | 1,1-methylpropyl |
| 5-1202 | Cl | Cl | Ph | H | 0 | 1 | 2-methylcyclohexyl |
| 5-1203 | Cl | Cl | Ph | H | 0 | 1 | 1,1-dimethylbut-3-enyl |
| 5-1204 | Cl | Cl | Ph | H | 0 | 1 | 1-propylbutyl |
| 5-1205 | Cl | Cl | Ph | H | 0 | 1 | 1-methylbutyl |
| 5-1206 | Cl | Cl | Ph | H | 0 | 1 | 1-phenylethyl |
| 5-1207 | Cl | Cl | Ph | H | 0 | 1 | phenyloxymethyl |
| 5-1208 | Cl | Cl | Ph | H | 0 | 1 | pentafluorophenyloxymethyl |
| 5-1209 | Cl | Cl | Ph | H | 0 | 1 | (2-formylaminothiazol-4-yl)methoxyiminomethyl |
| 5-1210 | Cl | Cl | Ph | H | 0 | 1 | 1-hydroxy-1-ethylpropyl |
| 5-1211 | Cl | Cl | Ph | H | 0 | 1 | 2-methoxyphenyloxymethyl |
| 5-1212 | Cl | Cl | Ph | H | 0 | 1 | 2,4,6-trimethylphenyl |
| 5-1213 | Cl | Cl | Ph | H | 0 | 1 | 2-methylphenyl |
| 5-1214 | Cl | Cl | Ph | H | 0 | 1 | 1-methyl-1-(4-chlorophenyloxy)-ethyl |
| 5-1215 | Cl | Cl | Ph | H | 0 | 1 | 1-hydroxy-1-methylpropyl |
| 5-1216 | Cl | Cl | Ph | H | 0 | 1 | 1-ethylpentyl |
| 5-1217 | Cl | Cl | Ph | H | 0 | 1 | 2-methyl-1-phenylbutyl |
| 5-1218 | Cl | Cl | Ph | H | 0 | 1 | 1-methylpropyl |
| 5-1219 | Cl | Cl | Ph | H | 0 | 1 | cyclobutyl |
| 5-1220 | Cl | Cl | Ph | H | 0 | 1 | 1-ethylpropyl |
| 5-1221 | Cl | Cl | Ph | H | 0 | 1 | (3,5-dinitrobenzoylamino)-phenylmethyl |
| 5-1222 | Cl | Cl | Ph | H | 0 | 1 | 2,2-dichloro-1-methyl-cyclopropyl |
| 5-1223 | Cl | Cl | Ph | H | 0 | 1 | 2,2,2-trifluoro-1-hydroxy-1-methylethyl |
| 5-1224 | Cl | Cl | Ph | H | 0 | 1 | 1-hydroxy-2-trifluoromethyl-propyl |
| 5-1225 | Cl | Cl | Ph | H | 0 | 1 | 4-hydroxy-3-nitrophenyl |
| 5-1226 | Cl | Cl | Ph | H | 0 | 1 | 4,8-dihydroxyquinol-2-yl |
| 5-1227 | Cl | Cl | Ph | H | 0 | 1 | 2-hydroxy-1-phenylethyl |
| 5-1228 | Cl | Cl | Ph | H | 0 | 1 | 4-hydroxyphenyl |
| 5-1229 | Cl | Cl | Ph | H | 0 | 1 | 2,2-dimethylpropyl |
| 5-1230 | Cl | Cl | Ph | H | 0 | 1 | 1-(3,5-dinitrobenzoylamino)-3-methylbutyl |
| 5-1231 | Cl | Cl | Ph | H | 0 | 1 | (2-hydroxybenzoylamino)methyl |
| 5-1232 | Cl | Cl | Ph | H | 0 | 1 | 3,3,3-trifluoropropyl |
| 5-1233 | Cl | Cl | Ph | H | 0 | 1 | 1-oxypyrid-2-yl |
| 5-1234 | Cl | Cl | Ph | H | 0 | 1 | 6-hydroxypyrid-2-yl |
| 5-1235 | Cl | Cl | Ph | H | 0 | 1 | 3-hydroxypyrid-2-yl |
| 5-1236 | Cl | Cl | Ph | H | 0 | 1 | benzoylaminomethyl |
| 5-1237 | Cl | Cl | Ph | H | 0 | 1 | 1-methyl-5-oxo-2-pyrid-3-yl-pyrrolin-3-yl |
| 5-1238 | Cl | Cl | Ph | H | 0 | 1 | 1R,3R,4R,5R-tetrahydroxy-cyclohexyl |
| 5-1239 | Cl | Cl | Ph | H | 0 | 1 | 2-(2-chlorphenyl)ethenyl |
| 5-1240 | Cl | Cl | Ph | H | 0 | 1 | benzofur-2-yl |
| 5-1241 | Cl | Cl | Ph | H | 0 | 1 | 3-thienyl |
| 5-1242 | Cl | Cl | Ph | H | 0 | 1 | 3-methyl-1H-inden-2-yl |
| 5-1243 | Cl | Cl | Ph | H | 0 | 1 | 3R,4S,5R-trihydroxy-1-cyclohexenyl |
| 5-1244 | Cl | Cl | Ph | H | 0 | 1 | 2-(2-trifluoromethylphenyl)-ethenyl |
| 5-1245 | Cl | Cl | Ph | H | 0 | 1 | 2-(4-methylphenyl)ethenyl |
| 5-1246 | Cl | Cl | Ph | H | 0 | 1 | 1-cyclohexenyl |
| 5-1247 | Cl | Cl | Ph | H | 0 | 1 | 2-(4-trifluoromethylphenyl)-ethenyl |
| 5-1248 | Cl | Cl | Ph | H | 0 | 1 | 1-cyclopentenyl |
| 5-1249 | Cl | Cl | Ph | H | 0 | 1 | 1-methyl-1-butenyl |
| 5-1250 | Cl | Cl | Ph | H | 0 | 1 | 3,3,3-trifluoro-2-methyl-1-propenyl |
| 5-1251 | Cl | Cl | Ph | H | 0 | 1 | 2-(2-fluorophenyl)ethenyl |
| 5-1252 | Cl | Cl | Ph | H | 0 | 1 | vinyl |
| 5-1253 | Cl | Cl | Ph | H | 0 | 1 | 2-(4-dimethylaminophenyl)-ethenyl |
| 5-1254 | Cl | Cl | Ph | H | 0 | 1 | 2-(2-methoxyphenyl)ethenyl |
| 5-1255 | Cl | Cl | Ph | H | 0 | 1 | 2-(3-hydroxy-4-methoxyphenyl)-ethenyl |
| 5-1256 | Cl | Cl | Ph | H | 0 | 1 | 2-(3-trifluoromethylphenyl)-ethenyl |
| 5-1257 | Cl | Cl | Ph | H | 0 | 1 | 1-fluoro-2-phenylethenyl |
| 5-1258 | Cl | Cl | Ph | H | 0 | 1 | 3-methyl-2-thienyl |
| 5-1259 | Cl | Cl | Ph | H | 0 | 1 | 1-cyano-2-(4-hydroxyphenyl)-ethenyl |
| 5-1260 | Cl | Cl | Ph | H | 0 | 1 | 2-(4-fluorophenyl)ethenyl |
| 5-1261 | Cl | Cl | Ph | H | 0 | 1 | 2-methyl-1-propenyl |
| 5-1262 | Cl | Cl | Ph | H | 0 | 1 | 1-ethyl-7-methyl-4-oxo-[1,8]naphthyridin-3-yl |
| 5-1263 | Cl | Cl | Ph | H | 0 | 1 | 2-(4-hydroxy-3-methoxyphenyl)-ethenyl |
| 5-1264 | Cl | Cl | Ph | H | 0 | 1 | 2-(benzo[1,3]dioxol-5-yl)ethenyl |
| 5-1265 | Cl | Cl | Ph | H | 0 | 1 | 1-methylcyclopropyl |
| 5-1266 | Cl | Cl | Ph | H | 0 | 1 | 2-furyl |
| 5-1267 | Cl | Cl | Ph | H | 0 | 1 | 2-phenylethenyl |
| 5-1268 | Cl | Cl | Ph | H | 0 | 1 | 2-(4-bromophenyl)ethenyl |
| 5-1269 | Cl | Cl | Ph | H | 0 | 1 | 3-furyl |
| 5-1270 | Cl | Cl | Ph | H | 0 | 1 | 2-(4-methoxyphenyl)ethenyl |
| 5-1271 | Cl | Cl | Ph | H | 0 | 1 | 1-methyl-1H-indol-2-yl |
| 5-1272 | Cl | Cl | Ph | H | 0 | 1 | 2-(3-pyridyl)ethenyl |
| 5-1273 | Cl | Cl | Ph | H | 0 | 1 | 2-(3-fluorophenyl)ethenyl |
| 5-1274 | Cl | Cl | Ph | H | 0 | 1 | 5-methyl-2-thienyl |
| 5-1275 | Cl | Cl | Ph | H | 0 | 1 | 1-acetylamino-2-phenylethenyl |
| 5-1276 | Cl | Cl | Ph | H | 0 | 1 | 2,6-dimethyl-1,5-heptadienyl |
| 5-1277 | Cl | Cl | Ph | H | 0 | 1 | 1-pentenyl |
| 5-1278 | Cl | Cl | Ph | H | 0 | 1 | 2-(2,3-dimethoxyphenyl)ethenyl |
| 5-1279 | Cl | Cl | Ph | H | 0 | 1 | 1,3-pentadienyl |
| 5-1280 | Cl | Cl | Ph | H | 0 | 1 | 2-(3-nitrophenyl)ethenyl |
| 5-1281 | Cl | Cl | Ph | H | 0 | 1 | 2-(4-chlorophenyl)ethenyl |
| 5-1282 | Cl | Cl | Ph | H | 0 | 1 | 2-(4-nitrophenyl)ethenyl |
| 5-1283 | Cl | Cl | Ph | H | 0 | 1 | 2-(3,4-dimethoxyphenyl)ethenyl |
| 5-1284 | Cl | Cl | Ph | H | 0 | 1 | 2-pentafluorophenylethenyl |
| 5-1285 | Cl | Cl | Ph | H | 0 | 1 | 1-methyl-2-phenylethenyl |
| 5-1286 | Cl | Cl | Ph | H | 0 | 1 | 2-(4-hydroxyphenyl)ethenyl |
| 5-1287 | Cl | Cl | Ph | H | 0 | 1 | 2-(3-hydroxyphenyl)ethenyl |
| 5-1288 | Cl | Cl | Ph | H | 0 | 1 | 2-(2-furyl)ethenyl |
| 5-1289 | Cl | Cl | Ph | H | 0 | 1 | 2-(3,4-dichlorophenyl)ethenyl |
| 5-1290 | Cl | Cl | Ph | H | 0 | 1 | 2-(2,4-dichlorophenyl)ethenyl |
| 5-1291 | Cl | Cl | Ph | H | 0 | 1 | 2-(2-nitrophenyl)ethenyl |
| 5-1292 | Cl | Cl | Ph | H | 0 | 1 | 2,2,2-trifluoro-1-trifluoromethyl-1-methylethyl |

TABLE 5H

Compounds (5-1293)–(5-1474) are compounds of Formula IV where $R^1$, $R^2$, q, and t are identical to those in Table 5G except for $Y^3$ and $Y^4$ which both equal Br.

TABLE 5I

Compounds (5-1475)–(5-1656) are compounds of Formula IV where $R^1$, $R^2$, q, and t are identical to those in Table 5G except for $Y^3$ and $Y^4$ which both equal I.

TABLE 5J

| Cmpd # | $Y^3$ | $Y^4$ | $R^1$ | $R^2$ | q | t | $(X^2)_q Z^2$ |
|---|---|---|---|---|---|---|---|
| 5-1657 | Cl | Cl | 2-propyl | H | 1 | 1 | 3,6-dichloro-2-pyridyl |
| 5-1658 | Cl | Cl | 2-propyl | H | 0 | 1 | $C(CH_3)_3$ |
| 5-1659 | Cl | Cl | 2-propyl | H | 0 | 1 | acetamidomethyl |
| 5-1660 | Cl | Cl | 2-propyl | H | 0 | 1 | 2-nitro-5-thiocyanatophenyl |
| 5-1661 | Cl | Cl | 2-propyl | H | 0 | 1 | cycloheptyl |
| 5-1662 | Cl | Cl | 2-propyl | H | 0 | 1 | 2-hydroxy-2-propyl |
| 5-1663 | Cl | Cl | 2-propyl | H | 0 | 1 | 1-(isopropylidineaminooxy)ethyl |
| 5-1664 | Cl | Cl | 2-propyl | H | 0 | 1 | 4,4,4-trifluoro-2-butyl |
| 5-1665 | Cl | Cl | 2-propyl | H | 0 | 1 | 2-(trifluoromethyl)propyl |
| 5-1666 | Cl | Cl | 2-propyl | H | 0 | 1 | 2,2,2-trifluoroethyl |
| 5-1667 | Cl | Cl | 2-propyl | H | 0 | 1 | 1-(benzyloxycarbonylamino)-1-methylethyl |
| 5-1668 | Cl | Cl | 2-propyl | H | 0 | 1 | 1-(tert-butoxycarbonylamino)-1-methylethyl |
| 5-1669 | Cl | Cl | 2-propyl | H | 0 | 1 | 1-(tert-butoxycarbonyl)-piperidin-4-yl |
| 5-1670 | Cl | Cl | 2-propyl | H | 0 | 1 | 1-acetyl-4-hydroxypyrrolidin-2-yl |
| 5-1671 | Cl | Cl | 2-propyl | H | 0 | 1 | 2-methyl-3-pyridyl |
| 5-1672 | Cl | Cl | 2-propyl | H | 0 | 1 | 1-(acetylamino)-2-methylpropyl |
| 5-1673 | Cl | Cl | 2-propyl | H | 0 | 1 | 2,6-dimethoxy-4-hydroxyphenyl |
| 5-1674 | Cl | Cl | 2-propyl | H | 0 | 1 | 3-methylthio-1-acetylaminopropyl |
| 5-1675 | Cl | Cl | 2-propyl | H | 0 | 1 | 1-acetylaminovinyl |
| 5-1676 | Cl | Cl | 2-propyl | H | 0 | 1 | 1-methyl-2-pyrrolyl |
| 5-1677 | Cl | Cl | 2-propyl | H | 0 | 1 | 2-benzyloxycarbonyl)-1-(tert-butoxycarbonylamino)ethyl |
| 5-1678 | Cl | Cl | 2-propyl | H | 0 | 1 | 4-hexyloxyphenyl |
| 5-1679 | Cl | Cl | 2-propyl | H | 0 | 1 | 1-(2-chlorophenoxy)-1-methylethyl |
| 5-1680 | Cl | Cl | 2-propyl | H | 0 | 1 | 3-hydroxy-4-methoxyphenyl |
| 5-1681 | Cl | Cl | 2-propyl | H | 0 | 1 | 3,5-dinitro-4-hydroxyphenyl |
| 5-1682 | Cl | Cl | 2-propyl | H | 0 | 1 | 1-(tert-butoxycarbonyl)-2-pyrrolidinyl |
| 5-1683 | Cl | Cl | 2-propyl | H | 0 | 1 | 1-(di-N-propylamino)ethyl |
| 5-1684 | Cl | Cl | 2-propyl | H | 0 | 1 | 1-(tert-butoxycarbonyl)-4-hydroxy-2-pyrrolidinyl |
| 5-1685 | Cl | Cl | 2-propyl | H | 0 | 1 | 5-acetylamino-1-(tert-butoxycarbonylamino)pentyl |
| 5-1686 | Cl | Cl | 2-propyl | H | 0 | 1 | 1-(tert-butoxycarbonylamino)-2,2-dimethyl-propyl |
| 5-1687 | Cl | Cl | 2-propyl | H | 0 | 1 | 2-pyrrolidinyl hydrochloride |
| 5-1688 | Cl | Cl | 2-propyl | H | 0 | 1 | 2-amino-2-propyl hydrochloride |
| 5-1689 | Cl | Cl | 2-propyl | H | 0 | 1 | 4-piperidinyl hydrochloride |
| 5-1690 | Cl | Cl | 2-propyl | H | 0 | 1 | 2-(benzyloxycarbonyl)-1-aminoethyl hydrochloride |
| 5-1691 | Cl | Cl | 2-propyl | H | 0 | 1 | 2-carboxy-1-aminoethyl hydrochloride |
| 5-1692 | Cl | Cl | 2-propyl | H | 0 | 1 | 2-carboxy-1-(tert-butoxycarbonylaminoethyl |
| 5-1693 | Cl | Cl | 2-propyl | H | 0 | 1 | [benzyl-(diethoxyphosphorylmethyl)-amino]methyl |
| 5-1694 | Cl | Cl | 2-propyl | H | 0 | 1 | 2-methylnicotinyl |
| 5-1695 | Cl | Cl | 2-propyl | H | 0 | 1 | 1-(acetylamino)-2-methylpropyl |
| 5-1696 | Cl | Cl | 2-propyl | H | 0 | 1 | 3-methylthio-1-acetylaminopropyl |
| 5-1697 | Cl | Cl | 2-propyl | H | 0 | 1 | 1-tert-(butoxycarbonyamino)-1-methylethyl |
| 5-1698 | Cl | Cl | 2-propyl | H | 0 | 0 | $^+N(Et)_3Cl^-$ |
| 5-1699 | Cl | Cl | 2-propyl | H | 0 | 1 | undecyl |
| 5-1700 | Cl | Cl | 2-propyl | H | 0 | 1 | acetyl |
| 5-1701 | Cl | Cl | 2-propyl | H | 0 | 1 | 5-oxopyrrolin-2-yl |
| 5-1702 | Cl | Cl | 2-propyl | H | 0 | 1 | methoxymethyl |
| 5-1703 | Cl | Cl | 2-propyl | H | 0 | 1 | (4-oxo-2-thioxothiazolidin-3-yl)methyl |
| 5-1704 | Cl | Cl | 2-propyl | H | 0 | 1 | pyrazin-2-yl |
| 5-1705 | Cl | Cl | 2-propyl | H | 0 | 1 | 1H-pyrazol-4-yl |
| 5-1706 | Cl | Cl | 2-propyl | H | 0 | 1 | (furan-2-carbonyl)aminomethyl |
| 5-1707 | Cl | Cl | 2-propyl | H | 0 | 1 | 2-(2,5-dioxo-2,5-dihydropyrrol-1-yl)ethyl |

TABLE 5J-continued

| Cmpd # | Y³ | Y⁴ | R¹ | R² | q | t | (X²)qZ² |
|---|---|---|---|---|---|---|---|
| 5-1708 | Cl | Cl | 2-propyl | H | 0 | 1 | 2-methoxyethoxymethyl |
| 5-1709 | Cl | Cl | 2-propyl | H | 0 | 1 | methanesulfonylmethyl |
| 5-1710 | Cl | Cl | 2-propyl | H | 0 | 1 | 4-heptyloxyphenyl |
| 5-1711 | Cl | Cl | 2-propyl | H | 0 | 1 | 2,6-dichlorophenyl |
| 5-1712 | Cl | Cl | 2-propyl | H | 0 | 1 | (3,5-diiodo-4-oxo-4H-pyridin-1-yl)methyl |
| 5-1713 | Cl | Cl | 2-propyl | H | 0 | 1 | 3-pyridyl |
| 5-1714 | Cl | Cl | 2-propyl | H | 0 | 1 | 5,6-dichloro-3-pyridyl |
| 5-1715 | Cl | Cl | 2-propyl | H | 0 | 1 | 4-pyridyl |
| 5-1716 | Cl | Cl | 2-propyl | H | 0 | 1 | 2,6-dichloro-4-pyridyl |
| 5-1717 | Cl | Cl | 2-propyl | H | 0 | 1 | 4-methanesulphonylphenyl |
| 5-1718 | Cl | Cl | 2-propyl | H | 0 | 1 | 2-chloro-4-nitrophenyl |
| 5-1719 | Cl | Cl | 2-propyl | H | 0 | 1 | 4-chloro-2-nitrophenyl |
| 5-1720 | Cl | Cl | 2-propyl | H | 0 | 1 | 3-chloro-2-nitrophenyl |
| 5-1721 | Cl | Cl | 2-propyl | H | 0 | 1 | 5-methylpyrazin-2-yl |
| 5-1722 | Cl | Cl | 2-propyl | H | 0 | 1 | tetrahydrofur-2-yl |
| 5-1723 | Cl | Cl | 2-propyl | H | 0 | 1 | 3-thiophen-2-ylpropyl |
| 5-1724 | Cl | Cl | 2-propyl | H | 0 | 1 | cyclopentylphenylmethyl |
| 5-1725 | Cl | Cl | 2-propyl | H | 0 | 1 | 1-phenylcyclopentyl |
| 5-1726 | Cl | Cl | 2-propyl | H | 0 | 1 | 1-methylcyclohexyl |
| 5-1727 | Cl | Cl | 2-propyl | H | 0 | 1 | 2-chloro-3-pyridyl |
| 5-1728 | Cl | Cl | 2-propyl | H | 0 | 1 | 1-methyl-1H-pyrrol-2-yl |
| 5-1729 | Cl | Cl | 2-propyl | H | 0 | 1 | 2,6-dimethoxyphenyl |
| 5-1730 | Cl | Cl | 2-propyl | H | 0 | 1 | 2,6-dimethoxy-3-pyridyl |
| 5-1731 | Cl | Cl | 2-propyl | H | 0 | 1 | 2-(thiophen-2-yl)ethenyl |
| 5-1732 | Cl | Cl | 2-propyl | H | 0 | 1 | 4-nitro-1H-pyrazol-3-yl |
| 5-1733 | Cl | Cl | 2-propyl | H | 0 | 1 | 4-sulfamoylphenyl |
| 5-1734 | Cl | Cl | 2-propyl | H | 0 | 1 | 2,4-dinitrophenyl |
| 5-1735 | Cl | Cl | 2-propyl | H | 0 | 1 | 1-hydroxy-1-phenylethyl |
| 5-1736 | Cl | Cl | 2-propyl | H | 0 | 1 | 3-hydroxy-4-methyl-2-nitrophenyl |
| 5-1737 | Cl | Cl | 2-propyl | H | 0 | 1 | 2-methylcyclopropyl |
| 5-1738 | Cl | Cl | 2-propyl | H | 0 | 1 | 1-phenylpropyl |
| 5-1739 | Cl | Cl | 2-propyl | H | 0 | 1 | 1,2,3,4-tetrahydronaphth-2-yl |
| 5-1740 | Cl | Cl | 2-propyl | H | 0 | 1 | 1-benzyl-2,2-dimethylpropyl |
| 5-1741 | Cl | Cl | 2-propyl | H | 0 | 1 | 2,2,3,3-tetramethylcyclopropyl |
| 5-1742 | Cl | Cl | 2-propyl | H | 0 | 1 | acetoxymethyl |
| 5-1743 | Cl | Cl | 2-propyl | H | 0 | 1 | 2,2,2-trifluoro-1-methoxy-1-phenylethyl |
| 5-1744 | Cl | Cl | 2-propyl | H | 0 | 1 | 1-methylpentyl |
| 5-1745 | Cl | Cl | 2-propyl | H | 0 | 1 | hept-1-ynyl |
| 5-1746 | Cl | Cl | 2-propyl | H | 0 | 1 | tetrahydrofur-3-yl |
| 5-1747 | Cl | Cl | 2-propyl | H | 0 | 1 | 1,1-methylpropyl |
| 5-1748 | Cl | Cl | 2-propyl | H | 0 | 1 | 2-methylcyclohexyl |
| 5-1749 | Cl | Cl | 2-propyl | H | 0 | 1 | 1,1-dimethylbut-3-enyl |
| 5-1750 | Cl | Cl | 2-propyl | H | 0 | 1 | 1-propylbutyl |
| 5-1751 | Cl | Cl | 2-propyl | H | 0 | 1 | 1-methylbutyl |
| 5-1752 | Cl | Cl | 2-propyl | H | 0 | 1 | 1-phenylethyl |
| 5-1753 | Cl | Cl | 2-propyl | H | 0 | 1 | phenyloxymethyl |
| 5-1754 | Cl | Cl | 2-propyl | H | 0 | 1 | pentafluorophenyloxymethyl |
| 5-1755 | Cl | Cl | 2-propyl | H | 0 | 1 | (2-formylaminothiazol-4-yl)methoxyiminomethyl |
| 5-1756 | Cl | Cl | 2-propyl | H | 0 | 1 | 1-hydroxy-1-ethylpropyl |
| 5-1757 | Cl | Cl | 2-propyl | H | 0 | 1 | 2-methoxyphenyloxymethyl |
| 5-1758 | Cl | Cl | 2-propyl | H | 0 | 1 | 2,4,6-trimethylphenyl |
| 5-1759 | Cl | Cl | 2-propyl | H | 0 | 1 | 2-methylphenyl |
| 5-1760 | Cl | Cl | 2-propyl | H | 0 | 1 | 1-methyl-1-(4-chlorophenyloxy)ethyl |
| 5-1761 | Cl | Cl | 2-propyl | H | 0 | 1 | 1-hydroxy-1-methylpropyl |
| 5-1762 | Cl | Cl | 2-propyl | H | 0 | 1 | 1-ethylpentyl |
| 5-1763 | Cl | Cl | 2-propyl | H | 0 | 1 | 2-methyl-1-phenylbutyl |
| 5-1764 | Cl | Cl | 2-propyl | H | 0 | 1 | 1-methylpropyl |
| 5-1765 | Cl | Cl | 2-propyl | H | 0 | 1 | cyclobutyl |
| 5-1766 | Cl | Cl | 2-propyl | H | 0 | 1 | 1-ethylpropyl |
| 5-1767 | Cl | Cl | 2-propyl | H | 0 | 1 | (3,5-dinitrobenzoylamino)phenylmethyl |
| 5-1768 | Cl | Cl | 2-propyl | H | 0 | 1 | 2,2-dichloro-1-methylcyclopropyl |
| 5-1769 | Cl | Cl | 2-propyl | H | 0 | 1 | 2,2,2-trifluoro-1-hydroxy-1-methylethyl |
| 5-1770 | Cl | Cl | 2-propyl | H | 0 | 1 | 1-hydroxy-2-trifluoromethylpropyl |
| 5-1771 | Cl | Cl | 2-propyl | H | 0 | 1 | 4-hydroxy-3-nitrophenyl |
| 5-1772 | Cl | Cl | 2-propyl | H | 0 | 1 | 4,8-dihydroxyquinol-2-yl |
| 5-1773 | Cl | Cl | 2-propyl | H | 0 | 1 | 2-hydroxy-1-phenylethyl |
| 5-1774 | Cl | Cl | 2-propyl | H | 0 | 1 | 4-hydroxyphenyl |
| 5-1775 | Cl | Cl | 2-propyl | H | 0 | 1 | 2,2-dimethylpropyl |
| 5-1776 | Cl | Cl | 2-propyl | H | 0 | 1 | 1-(3,5-dinitrobenzoylamino)-3-methylbutyl |
| 5-1777 | Cl | Cl | 2-propyl | H | 0 | 1 | (2-hydroxybenzoylamino)methyl |
| 5-1778 | Cl | Cl | 2-propyl | H | 0 | 1 | 3,3,3-trifluoropropyl |

TABLE 5J-continued

| Cmpd # | Y³ | Y⁴ | R¹ | R² | q | t | (X²)qZ² |
|---|---|---|---|---|---|---|---|
| 5-1779 | Cl | Cl | 2-propyl | H | 0 | 1 | 1-oxypyrid-2-yl |
| 5-1780 | Cl | Cl | 2-propyl | H | 0 | 1 | 6-hydroxypyrid-2-yl |
| 5-1781 | Cl | Cl | 2-propyl | H | 0 | 1 | 3-hydroxypyrid-2-yl |
| 5-1782 | Cl | Cl | 2-propyl | H | 0 | 1 | benzoylaminomethyl |
| 5-1783 | Cl | Cl | 2-propyl | H | 0 | 1 | 1-methyl-5-oxo-2-pyrid-3-ylpyrrolin-3-yl |
| 5-1784 | Cl | Cl | 2-propyl | H | 0 | 1 | 1R,3R,4R,5R-tetrahydroxycyclohexyl |
| 5-1785 | Cl | Cl | 2-propyl | H | 0 | 1 | 2-(2-chlorphenyl)ethenyl |
| 5-1786 | Cl | Cl | 2-propyl | H | 0 | 1 | benzofur-2-yl |
| 5-1787 | Cl | Cl | 2-propyl | H | 0 | 1 | 3-thienyl |
| 5-1788 | Cl | Cl | 2-propyl | H | 0 | 1 | 3-methyl-1H-inden-2-yl |
| 5-1789 | Cl | Cl | 2-propyl | H | 0 | 1 | 3R,4S,5R-trihydroxy-1-cyclohexenyl |
| 5-1790 | Cl | Cl | 2-propyl | H | 0 | 1 | 2-(2-trifluoromethylphenyl)ethenyl |
| 5-1791 | Cl | Cl | 2-propyl | H | 0 | 1 | 2-(4-methylphenyl)ethenyl |
| 5-1792 | Cl | Cl | 2-propyl | H | 0 | 1 | 1-cyclohexenyl |
| 5-1793 | Cl | Cl | 2-propyl | H | 0 | 1 | 2-(4-trifluoromethylphenyl)ethenyl |
| 5-1794 | Cl | Cl | 2-propyl | H | 0 | 1 | 1-cyclopentenyl |
| 5-1795 | Cl | Cl | 2-propyl | H | 0 | 1 | 1-methyl-1-butenyl |
| 5-1796 | Cl | Cl | 2-propyl | H | 0 | 1 | 3,3,3-trifluoro-2-methyl-1-propenyl |
| 5-1797 | Cl | Cl | 2-propyl | H | 0 | 1 | 2-(2-fluorophenyl)ethenyl |
| 5-1798 | Cl | Cl | 2-propyl | H | 0 | 1 | vinyl |
| 5-1799 | Cl | Cl | 2-propyl | H | 0 | 1 | 2-(4-dimethylaminophenyl)ethenyl |
| 5-1800 | Cl | Cl | 2-propyl | H | 0 | 1 | 2-(2-methoxyphenyl)ethenyl |
| 5-1801 | Cl | Cl | 2-propyl | H | 0 | 1 | 2-(3-hydroxy-4-methoxyphenyl)ethenyl |
| 5-1802 | Cl | Cl | 2-propyl | H | 0 | 1 | 2-(3-trifluoromethylphenyl)ethenyl |
| 5-1803 | Cl | Cl | 2-propyl | H | 0 | 1 | 1-fluoro-2-phenylethenyl |
| 5-1804 | Cl | Cl | 2-propyl | H | 0 | 1 | 3-methyl-2-thienyl |
| 5-1805 | Cl | Cl | 2-propyl | H | 0 | 1 | 1-cyano-2-(4-hydroxyphenyl)ethenyl |
| 5-1806 | Cl | Cl | 2-propyl | H | 0 | 1 | 2-(4-fluorophenyl)ethenyl |
| 5-1807 | Cl | Cl | 2-propyl | H | 0 | 1 | 2-methyl-1-propenyl |
| 5-1808 | Cl | Cl | 2-propyl | H | 0 | 1 | 1-ethyl-7-methyl-4-oxo-[1,8]naphthyridin-3-yl |
| 5-1809 | Cl | Cl | 2-propyl | H | 0 | 1 | 2-(4-hydroxy-3-methoxyphenyl)ethenyl |
| 5-1810 | Cl | Cl | 2-propyl | H | 0 | 1 | 2-(benzo[1,3]dioxol-5-yl)ethenyl |
| 5-1811 | Cl | Cl | 2-propyl | H | 0 | 1 | 1-methylcyclopropyl |
| 5-1812 | Cl | Cl | 2-propyl | H | 0 | 1 | 2-furyl |
| 5-1813 | Cl | Cl | 2-propyl | H | 0 | 1 | 2-phenylethenyl |
| 5-1814 | Cl | Cl | 2-propyl | H | 0 | 1 | 2-(4-bromophenyl)ethenyl |
| 5-1815 | Cl | Cl | 2-propyl | H | 0 | 1 | 3-furyl |
| 5-1816 | Cl | Cl | 2-propyl | H | 0 | 1 | 2-(4-methoxyphenyl)ethenyl |
| 5-1817 | Cl | Cl | 2-propyl | H | 0 | 1 | 1-methyl-1H-indol-2-yl |
| 5-1818 | Cl | Cl | 2-propyl | H | 0 | 1 | 2-(3-pyridyl)ethenyl |
| 5-1819 | Cl | Cl | 2-propyl | H | 0 | 1 | 2-(3-fluorophenyl)ethenyl |
| 5-1820 | Cl | Cl | 2-propyl | H | 0 | 1 | 5-methyl-2-thienyl |
| 5-1821 | Cl | Cl | 2-propyl | H | 0 | 1 | 1-acetylamino-2-phenylethenyl |
| 5-1822 | Cl | Cl | 2-propyl | H | 0 | 1 | 2,6-dimethyl-1,5-heptadienyl |
| 5-1823 | Cl | Cl | 2-propyl | H | 0 | 1 | 1-pentenyl |
| 5-1824 | Cl | Cl | 2-propyl | H | 0 | 1 | 2-(2,3-dimethoxyphenyl)ethenyl |
| 5-1825 | Cl | Cl | 2-propyl | H | 0 | 1 | 1,3-pentadienyl |
| 5-1826 | Cl | Cl | 2-propyl | H | 0 | 1 | 2-(3-nitrophenyl)ethenyl |
| 5-1827 | Cl | Cl | 2-propyl | H | 0 | 1 | 2-(4-chlorophenyl)ethenyl |
| 5-1828 | Cl | Cl | 2-propyl | H | 0 | 1 | 2-(4-nitrophenyl)ethenyl |
| 5-1829 | Cl | Cl | 2-propyl | H | 0 | 1 | 2-(3,4-dimethoxyphenyl)ethenyl |
| 5-1830 | Cl | Cl | 2-propyl | H | 0 | 1 | 2-pentafluorophenylethenyl |
| 5-1831 | Cl | Cl | 2-propyl | H | 0 | 1 | 1-methyl-2-phenylethenyl |
| 5-1832 | Cl | Cl | 2-propyl | H | 0 | 1 | 2-(4-hydroxyphenyl)ethenyl |
| 5-1833 | Cl | Cl | 2-propyl | H | 0 | 1 | 2-(3-hydroxyphenyl)ethenyl |
| 5-1834 | Cl | Cl | 2-propyl | H | 0 | 1 | 2-(2-furyl)ethenyl |
| 5-1835 | Cl | Cl | 2-propyl | H | 0 | 1 | 2-(3,4-dichlorophenyl)ethenyl |
| 5-1836 | Cl | Cl | 2-propyl | H | 0 | 1 | 2-(2,4-dichlorophenyl)ethenyl |
| 5-1837 | Cl | Cl | 2-propyl | H | 0 | 1 | 2-(2-nitrophenyl)ethenyl |
| 5-1838 | Cl | Cl | 2-propyl | H | 0 | 1 | 2,2,2-trifluoro-1-trifluoromethyl-1-methylethyl |

TABLE 5K

Compounds (5-1839)–(5-2020) are compounds of Formula IV where R¹, R², q, and t are identical to those in Table 5J except for Y³ and Y⁴ which both equal Br.

TABLE 5L

Compounds (5-2021)–(5-2202) are compounds of Formula IV where R¹, R², q, and t are identical to those in Table 5J except for Y³ and Y⁴ which both are equal I.

Table 6 describes additional examples of compounds of Formula I, when m=1, q=0 and the pesticides which define the pesticidal moiety of these examples is $Z^1(X^1)$—H, which can be made using the procedures described hereinbefore.

TABLE 6

$$Z^1(X^1)_m\!\!-\!\!\overset{\overset{G^{10}}{\|}}{C}\!\!-\!\!G^{11}\!\!-\!\!A \quad \text{where A is} \quad \overset{R^1}{\underset{R^2}{C}}\!\!-\!\!(G^{21}\!\!-\!\!\overset{\overset{G^{20}}{\|}}{C})_t\!\!-\!\!(X^2)_qZ^2$$

(I)

| Cmpd# | $Z^1(X^1)_m$—H | $X^1$ | $G^{10}$ | $G^{11}$ | $R^1$ | $R^2$ | $G^{20}$ | $G^{21}$ | t | $Z^2$ |
|---|---|---|---|---|---|---|---|---|---|---|
| 6-1 | cymoxanil(A) | N | O | O | H | H | — | — | 0 | Cl |
| 6-2 | cymoxanil(A) | N | O | O | H | H | O | O | 1 | methyl |
| 6-3 | cymoxanil(A) | N | O | O | H | H | O | O | 1 | $C(CH_3)_3$ |
| 6-4 | cymoxanil(A) | N | O | O | H | H | O | O | 1 | Ph |
| 6-5 | cymoxanil(A) | N | O | O | H | H | O | O | 1 | 4 Me—Ph |
| 6-6 | cymoxanil(A) | N | O | O | H | H | O | O | 1 | 2,2,2-trifluoroethyl |
| 6-7 | cymoxanil(A) | N | O | O | H | H | O | O | 1 | Ph—$CH_2$ |
| 6-8 | cymoxanil(A) | N | O | O | H | H | O | O | 1 | Ph—$CH_2CH_2$ |
| 6-9 | cymoxanil(B) | N | O | O | H | H | O | O | 1 | $C(CH_3)_3$ |
| 6-10 | cymoxanil(B) | N | O | O | H | H | O | O | 1 | Ph |
| 6-11 | cymoxanil(B) | N | O | O | H | H | O | O | 1 | 2,2,2-trifluoroethyl |
| 6-12 | dodine(A) | N | O | O | H | H | O | O | 1 | $C(CH_3)_3$ |
| 6-13 | dodine(A) | N | O | O | H | H | O | O | 1 | Ph |
| 6-14 | dodine(B) | N | O | O | H | H | O | O | 1 | $C(CH_3)_3$ |
| 6-15 | dodine(B) | N | O | O | H | H | O | O | 1 | Ph |
| 6-16 | thifluzamide | N | O | O | H | H | — | — | 0 | Cl |
| 6-17 | thifluzamide | N | O | O | H | H | O | O | 1 | methyl |
| 6-18 | thifluzamide | N | O | O | H | H | O | O | 1 | 2-methoxyethoxymethyl |
| 6-19 | thifluzamide | N | O | O | H | H | O | O | 1 | $C(CH_3)_3$ |
| 6-20 | thifluzamide | N | O | O | H | H | O | O | 1 | Ph |
| 6-21 | thifluzamide | N | O | O | H | H | O | O | 1 | pyrid-2-yl |
| 6-22 | thifluzamide | N | O | O | H | H | O | O | 1 | 2-methyl-pyrid-3-yl |
| 6-23 | thifluzamide | N | O | O | H | H | O | O | 1 | 1H-pyrazol-4-yl |
| 6-24 | thifluzamide | N | O | O | Me | H | O | O | 1 | methyl |
| 6-25 | thifluzamide | N | O | O | Me | H | O | O | 1 | 2-methoxyethoxymethyl |
| 6-26 | thifluzamide | N | O | O | Me | H | O | O | 1 | t-butyl |
| 6-27 | thifluzamide | N | O | S | H | H | O | O | 1 | methyl |
| 6-28 | thifluzamide | N | O | S | H | H | O | O | 1 | 2-methoxyethoxymethyl |
| 6-29 | thifluzamide | N | O | S | H | H | O | O | 1 | $C(CH_3)_3$ |
| 6-30 | thifluzamide | N | O | S | Me | H | O | O | 1 | methyl |
| 6-31 | thifluzamide | N | O | S | Me | H | O | O | 1 | 2-methoxyethoxymethyl |
| 6-32 | thifluzamide | N | O | S | Me | H | O | O | 1 | $C(CH_3)_3$ |
| 6-33 | flusulfamide | N | O | O | H | H | O | O | 1 | methyl |
| 6-34 | flusulfamide | N | O | O | H | H | O | O | 1 | $C(CH_3)_3$ |
| 6-35 | zarilamid | N | O | O | H | H | — | — | 0 | Cl |
| 6-36 | zarilamid | N | O | O | H | H | O | O | 1 | methyl |
| 6-37 | zarilamid | N | O | O | H | H | O | O | 1 | $C(CH_3)_3$ |
| 6-38 | zarilamid | N | O | O | H | H | O | O | 1 | Ph |
| 6-39 | furametpyr | N | O | O | H | H | O | O | 1 | methyl |
| 6-40 | furametpyr | N | O | O | H | H | O | O | 1 | $C(CH_3)_3$ |
| 6-41 | furametpyr | N | O | O | H | H | O | O | 1 | Ph |
| 6-42 | dicloran | N | O | O | H | H | O | O | 1 | methyl |
| 6-43 | dicloran | N | O | O | H | H | O | O | 1 | $C(CH_3)_3$ |
| 6-44 | dicloran | N | O | O | H | H | O | O | 1 | Ph |
| 6-45 | flutolanil | N | O | O | H | H | O | O | 1 | methyl |
| 6-46 | flutolanil | N | O | O | H | H | O | O | 1 | Ph |
| 6-47 | flutolanil | N | O | O | H | H | O | O | 1 | pyrid-2-yl |
| 6-48 | flutolanil | N | O | O | H | H | O | O | 1 | pyrid-3-yl |
| 6-49 | flutolanil | N | O | O | H | H | O | O | 1 | 2-methyl-pyrid-3-yl |
| 6-50 | flutolanil | N | O | O | H | H | O | O | 1 | 1H-pyrazol-4-yl |
| 6-51 | fenhexamid | N | O | O | H | H | O | O | 1 | methyl |
| 6-52 | fenhexamid | N | O | O | H | H | O | O | 1 | $C(CH_3)_3$ |
| 6-53 | fenhexamid | N | O | O | H | H | O | O | 1 | Ph |
| 6-54 | fenhexamid | O | O | O | H | H | O | O | 1 | methyl |
| 6-55 | fenhexamid | O | O | O | H | H | O | O | 1 | $C(CH_3)_3$ |
| 6-56 | benomyl(A) | N | O | O | H | H | O | O | 1 | methyl |
| 6-57 | benomyl(A) | N | O | O | H | H | O | O | 1 | $C(CH_3)_3$ |
| 6-58 | benomyl(B) | N | O | O | H | H | O | O | 1 | methyl |
| 6-59 | benomyl(B) | N | O | O | H | H | O | O | 1 | $C(CH_3)_3$ |
| 6-60 | carbendazim(A) | N | O | O | H | H | O | O | 1 | $C(CH_3)_3$ |
| 6-61 | carbendazim(B) | N | O | O | H | H | O | O | 1 | $C(CH_3)_3$ |
| 6-62 | fuberidazole | N | O | O | H | H | O | O | 1 | methyl |
| 6-63 | fuberidazole | N | O | O | H | H | O | O | 1 | $C(CH_3)_3$ |
| 6-64 | fuberidazole | N | O | O | H | H | O | O | 1 | Ph |
| 6-65 | thiabendazole | N | O | O | H | H | O | O | 1 | methyl |
| 6-66 | thiabendazole | N | O | O | H | H | O | O | 1 | $C(CH_3)_3$ |
| 6-67 | thiabendazole | N | O | O | H | H | O | O | 1 | Ph |

TABLE 6-continued $$Z^1(X^1)_m\!-\!\overset{\overset{G^{10}}{\|}}{C}\!-\!G^{11}\!-\!A \text{ where A is } \overset{\overset{R^1}{|}}{\underset{R^2}{C}}\!-\!(G^{21}\!-\!\overset{\overset{G^{20}}{\|}}{C})_t\!-\!(X^2)_q Z^2$$

(I)

| Cmpd# | Z¹(X¹)ₘ—H | X¹ | G¹⁰ | G¹¹ | R¹ | R² | G²⁰ | G²¹ | t | Z² |
|---|---|---|---|---|---|---|---|---|---|---|
| 6-68 | diethofencarb | N | O | O | H | H | O | O | 1 | methyl |
| 6-69 | diethofencarb | N | O | O | H | H | O | O | 1 | 2-methoxyethoxymethyl |
| 6-70 | diethofencarb | N | O | O | H | H | O | O | 1 | C(CH₃)₃ |
| 6-71 | diethofencarb | N | O | O | H | H | O | O | 1 | Ph |
| 6-72 | diethofencarb | N | O | O | H | H | O | O | 1 | pyrid-2-yl |
| 6-73 | diethofencarb | N | O | O | H | H | O | O | 1 | pyrid-3-yl |
| 6-74 | diethofencarb | N | O | O | H | H | O | O | 1 | 2-methyl-pyrid-3-yl |
| 6-75 | diethofencarb | N | O | O | H | H | O | O | 1 | 1H-pyrazol-4-yl |
| 6-76 | propamocarb | N | O | O | H | H | O | O | 1 | methyl |
| 6-77 | propamocarb | N | O | O | H | H | O | O | 1 | C(CH₃)₃ |
| 6-78 | propamocarb | N | O | O | H | H | O | O | 1 | Ph |
| 6-79 | propamocarb | N | O | O | H | H | O | O | 1 | pyrid-2-yl |
| 6-80 | propamocarb | N | O | O | H | H | O | O | 1 | pyrid-3-yl |
| 6-81 | propamocarb | N | O | O | H | H | O | O | 1 | 2-methyl-pyrid-3-yl |
| 6-82 | propamocarb | N | O | O | H | H | O | O | 1 | 1H-pyrazol-4-yl |
| 6-83 | thiophanate-methyl(A) | N | O | O | H | H | O | O | 1 | methyl |
| 6-84 | thiophanate-methyl(A) | N | O | O | H | H | O | O | 1 | C(CH₃)₃ |
| 6-85 | thiophanate-methyl(B) | N | O | O | H | H | O | O | 1 | C(CH₃)₃ |
| 6-86 | iprovalicarb | N | O | O | H | H | O | O | 1 | methyl |
| 6-87 | iprovalicarb | N | O | O | H | H | O | O | 1 | t-butyl |
| 6-88 | iprovalicarb | N | O | O | H | H | O | O | 1 | pyrid-3-yl |
| 6-89 | tebuconazole | O | O | O | H | H | O | O | 1 | methyl |
| 6-90 | tebuconazole | O | O | O | H | H | O | O | 1 | ethyl |
| 6-91 | tebuconazole | O | O | O | H | H | O | O | 1 | n-propyl |
| 6-92 | tebuconazole | O | O | O | H | H | O | O | 1 | 2-methoxyethoxymethyl |
| 6-93 | tebuconazole | O | O | O | H | H | O | O | 1 | C(CH₃)₃ |
| 6-94 | tebuconazole | O | O | O | H | H | O | O | 1 | Ph |
| 6-95 | tebuconazole | O | O | O | H | H | O | O | 1 | pyrid-2-yl |
| 6-96 | tebuconazole | O | O | O | H | H | O | O | 1 | pyrid-3-yl |
| 6-97 | tebuconazole | O | O | O | H | H | O | O | 1 | 2-methyl-pyrid-3-yl |
| 6-98 | tebuconazole | O | O | O | H | H | O | O | 1 | 1H-pyrazol-4-yl |
| 6-99 | cyproconazole | O | O | O | H | H | O | O | 1 | n-propyl |
| 6-100 | cyproconazole | O | O | O | H | H | O | O | 1 | C(CH₃)₃ |
| 6-101 | cyproconazole | O | O | O | H | H | O | O | 1 | Ph |
| 6-102 | cyproconazole | O | O | O | H | H | O | O | 1 | pyrid-2-yl |
| 6-103 | cyproconazole | O | O | O | H | H | O | O | 1 | pyrid-3-yl |
| 6-104 | hexaconazole | O | O | O | H | H | O | O | 1 | C(CH₃)₃ |
| 6-105 | hexaconazole | O | O | O | H | H | O | O | 1 | pyrid-3-yl |
| 6-106 | triadimenol | O | O | O | H | H | O | O | 1 | C(CH₃)₃ |
| 6-107 | triadimenol | O | O | O | H | H | O | O | 1 | Ph |
| 6-108 | mancozeb | S | O | O | H | H | O | O | 1 | propyl |
| 6-109 | mancozeb | S | O | O | H | H | O | O | 1 | 2-methoxyethoxymethyl |
| 6-110 | mancozeb | S | O | O | H | H | O | O | 1 | C(CH₃)₃ |
| 6-111 | mancozeb | S | O | O | H | H | O | O | 1 | Ph |
| 6-112 | mancozeb | S | O | O | H | H | O | O | 1 | pyrid-2-yl |
| 6-113 | mancozeb | S | O | O | H | H | O | O | 1 | pyrid-3-yl |
| 6-114 | mancozeb | S | O | O | Me | H | O | O | 1 | C(CH₃)₃ |
| 6-115 | mancozeb | S | O | O | Me | H | O | O | 1 | Ph |
| 6-116 | maneb | S | O | O | H | H | O | O | 1 | propyl |
| 6-117 | maneb | S | O | O | H | H | O | O | 1 | 2-methoxyethoxymethyl |
| 6-118 | maneb | S | O | O | H | H | O | O | 1 | C(CH₃)₃ |
| 6-119 | maneb | S | O | O | H | H | O | O | 1 | Ph |
| 6-120 | maneb | S | O | O | H | H | O | O | 1 | pyrid-2-yl |
| 6-121 | maneb | S | O | O | H | H | O | O | 1 | pyrid-3-yl |
| G-122 | maneb | S | O | O | Me | H | O | O | 1 | C(CH₃)₃ |
| 6-123 | methfuroxam | N | O | O | H | H | O | O | 1 | t-butyl |
| 6-124 | methfuroxam | N | O | O | H | H | O | O | 1 | Ph |
| 6-125 | methfuroxam | N | O | O | H | H | O | O | 1 | 2,6-dimethoxy-3-pyridyl |
| 6-126 | fenamidone | N | O | O | H | H | O | O | 1 | C(CH₃)₃ |
| 6-127 | fenamidone | N | O | O | H | H | O | O | 1 | 3,3,3-trifluoropropyl |
| 6-128 | fenamidone | N | O | O | H | H | O | O | 1 | Ph |
| 6-129 | fenamidone | N | O | S | H | H | O | O | 1 | C(CH₃)₃ |
| 6-130 | fenamidone | N | O | S | H | H | O | O | 1 | 3,3,3-trifluoropropyl |
| 6-131 | fenamidone | N | O | S | H | H | O | O | 1 | Ph |
| 6-132 | iprodione | N | O | O | H | H | O | O | 1 | methoxymethyl |
| 6-133 | iprodione | N | O | O | H | H | O | O | 1 | 3,3,3-trifluoropropyl |
| 6-134 | iprodione | N | O | O | H | H | O | O | 1 | C(CH₃)₃ |

TABLE 6-continued $$Z^1(X^1)_{\overline{m}}\overset{\overset{G^{10}}{\|}}{C}-G^{11}-A \text{ where A is } \overset{\overset{R^1}{|}}{\underset{\underset{R^2}{|}}{C}}-(G^{21}-\overset{\overset{G^{20}}{\|}}{C})_t-(X^2)_qZ^2$$

(I)

| Cmpd# | $Z^1(X^1)_m$—H | $X^1$ | $G^{10}$ | $G^{11}$ | $R^1$ | $R^2$ | $G^{20}$ | $G^{21}$ | t | $Z^2$ |
|---|---|---|---|---|---|---|---|---|---|---|
| 6-135 | iprodione | N | O | O | Ph | H | O | O | 1 | methoxymethyl |
| 6-136 | iprodione | N | O | O | Ph | H | O | O | 1 | 3,3,3-trifluoropropyl |
| 6-137 | iprodione | N | O | O | Ph | H | O | O | 1 | C(CH$_3$)$_3$ |
| 6-138 | iprodione | N | O | S | H | H | O | O | 1 | methoxymethyl |
| 6-139 | iprodione | N | O | S | H | H | O | O | 1 | 3,3,3-trifluoropropyl |
| 6-140 | iprodione | N | O | S | H | H | O | O | 1 | C(CH$_3$)$_3$ |
| 6-141 | iprodione | N | O | S | Ph | H | O | O | 1 | methoxymethyl |
| 6-142 | iprodione | N | O | S | Ph | H | O | O | 1 | 3,3,3-trifluoropropyl |
| 6-143 | iprodione | N | O | S | Ph | H | O | O | 1 | C(CH$_3$)$_3$ |
| 6-144 | fosetyl | O | O | O | H | H | O | O | 1 | methoxymethyl |
| 6-145 | fosetyl | O | O | O | H | H | O | O | 1 | 3,3,3-trifluoropropyl |
| 6-146 | fosetyl | O | O | O | H | H | O | O | 1 | C(CH$_3$)$_3$ |
| 6-147 | fosetyl | O | O | O | H | H | O | O | 1 | Ph |
| 6-148 | fosetyl | O | O | O | H | H | O | O | 1 | Ph—CH=CH |
| 6-149 | fosetyl | O | O | O | H | H | O | O | 1 | (4-Br)PhCH=CH |
| 6-150 | carboxin | N | O | O | H | H | O | O | 1 | methoxymethyl |
| 6-151 | carboxin | N | O | O | H | H | O | O | 1 | C(CH$_3$)$_3$ |
| 6-152 | carboxin | N | O | O | H | H | O | O | 1 | Ph |
| 6-153 | carboxin | N | O | O | H | H | O | O | 1 | Ph—CH=CH |
| 6-154 | carboxin | N | O | O | H | H | O | O | 1 | (4-Br)PhCH=CH |
| 6-155 | oxycarboxin | N | O | O | H | H | O | O | 1 | methoxymethyl |
| 6-156 | oxycarboxin | N | O | O | H | H | O | O | 1 | C(CH$_3$)$_3$ |
| 6-157 | oxycarboxin | N | O | O | H | H | O | O | 1 | Ph |
| 6-158 | oxycarboxin | N | O | O | H | H | O | O | 1 | Ph—CH=CH |
| 6-159 | oxycarboxin | N | O | O | H | H | O | O | 1 | (4-Br)PhCH=CH |
| 6-160 | famoxadone | N | O | O | H | H | O | O | 1 | methyl |
| 6-161 | famoxadone | N | O | O | H | H | O | O | 1 | methoxymethyl |
| 6-162 | famoxadone | N | O | O | H | H | O | O | 1 | 3,3,3-trifluoropropyl |
| 6-163 | famoxadone | N | O | O | H | H | O | O | 1 | t-butyl |
| 6-164 | famoxadone | N | O | O | H | H | O | O | 1 | Ph |
| 6-165 | famoxadone | N | O | S | H | H | O | O | 1 | methyl |
| 6-166 | famoxadone | N | O | S | H | H | O | O | 1 | methoxymethyl |
| 6-167 | famoxadone | N | O | S | H | H | O | O | 1 | 3,3,3-trifluoropropyl |
| 6-168 | famoxadone | N | O | S | H | H | O | O | 1 | C(CH$_3$)$_3$ |
| 6-169 | famoxadone | N | O | S | Me | H | O | O | 1 | C(CH$_3$)$_3$ |
| 6-170 | famoxadone | N | O | S | Me | H | O | O | 1 | Ph |
| 6-171 | pencycuron | N | O | O | H | H | O | O | 1 | C(CH$_3$)$_3$ |
| 6-172 | pencycuron | N | O | O | H | H | O | O | 1 | Ph |
| 6-173 | pencycuron | N | O | O | H | H | O | O | 1 | Ph—CH=CH |
| 6-174 | fluazinam | N | O | O | H | H | O | O | 1 | methyl |
| 6-175 | fluazinam | N | O | O | H | H | O | O | 1 | methoxymethyl |
| 6-176 | fluazinam | N | O | O | H | H | O | O | 1 | 3,3,3-trifluoropropyl |
| 6-177 | fluazinam | N | O | O | H | H | O | O | 1 | C(CH$_3$)$_3$ |
| 6-178 | fluazinam | N | O | O | H | H | O | O | 1 | Ph |
| 6-179 | fluazinam | N | O | O | H | H | O | O | 1 | Ph—CH=CH |
| 6-180 | fluazinam | N | O | O | Me | H | O | O | 1 | 3,3,3-trifluoropropyl |
| 6-181 | fluazinam | N | O | O | Me | H | O | O | 1 | C(CH$_3$)$_3$ |
| 6-182 | fluazinam | N | O | O | Me | H | O | O | 1 | Ph |
| 6-183 | fluazinam | N | O | S | H | H | O | O | 1 | 3,3,3-trifluoropropyl |
| 6-184 | fluazinam | N | O | S | H | H | O | O | 1 | C(CH$_3$)$_3$ |
| 6-185 | fluazinam | N | O | S | H | H | O | O | 1 | Ph |
| 6-186 | fluazinam | N | O | S | Me | H | O | O | 1 | 3,3,3-trifluoropropyl |
| 6-187 | fluazinam | N | O | S | Me | H | O | O | 1 | C(CH$_3$)$_3$ |
| 6-188 | fluazinam | N | O | S | Me | H | O | O | 1 | Ph |
| 6-189 | cyprodinil | N | O | O | H | H | O | O | 1 | methoxymethyl |
| 6-190 | cyprodinil | N | O | O | H | H | O | O | 1 | 3,3,3-trifluoropropyl |
| 6-191 | cyprodinil | N | O | O | H | H | O | O | 1 | C(CH$_3$)$_3$ |
| 6-192 | cyprodinil | N | O | O | H | H | O | O | 1 | Ph |
| 6-193 | cyprodinil | N | O | O | H | H | O | O | 1 | 2-(4-(Me)$_2$NPh)CH=CH |
| 6-194 | cyprodinil | N | O | O | H | H | O | O | 1 | 2-(2-methoxyPh)CH=CH |
| 6-195 | cyprodinil | N | O | O | Me | H | O | O | 1 | C(CH$_3$)$_3$ |
| 6-196 | cyprodinil | N | O | O | Me | H | O | O | 1 | Ph |
| 6-197 | cyprodinil | N | O | S | H | H | O | O | 1 | Ph—CH=CH |
| 6-198 | cyprodinil | N | O | S | H | H | O | O | 1 | (4-Br)PhCH=CH |
| 6-199 | cyprodinil | N | O | S | Me | H | O | O | 1 | C(CH$_3$)$_3$ |
| 6-200 | cyprodinil | N | O | S | Me | H | O | O | 1 | Ph |
| 6-201 | fenarimol | O | O | O | H | H | O | O | 1 | methoxymethyl |
| 6-202 | fenarimol | O | O | O | H | H | O | O | 1 | n-propyl |
| 6-203 | fenarimol | O | O | O | H | H | O | O | 1 | C(CH$_3$)$_3$ |
| 6-204 | fenarimol | O | O | O | H | H | O | O | 1 | Ph |

TABLE 6-continued $$Z^1(X^1)_{\overline{m}}\overset{G^{10}}{\underset{(I)}{\overset{\|}{C}}}-G^{11}-A \text{ where A is } \overset{R^1}{\underset{R^2}{\overset{|}{C}}}-(G^{21}-\overset{G^{20}}{\overset{\|}{C}})_t-(X^2)_qZ^2$$

| Cmpd# | $Z^1(X^1)_m$—H | $X^1$ | $G^{10}$ | $G^{11}$ | $R^1$ | $R^2$ | $G^{20}$ | $G^{21}$ | t | $Z^2$ |
|---|---|---|---|---|---|---|---|---|---|---|
| 6-205 | fenarimol | O | O | O | H | H | O | O | 1 | pyrid-2-yl |
| 6-206 | ferimzone | N | O | O | H | H | O | O | 1 | n-propyl |
| 6-207 | ferimzone | N | O | O | H | H | O | O | 1 | C(CH$_3$)$_3$ |
| 6-208 | ferimzone | N | O | O | H | H | O | O | 1 | Ph |
| 6-209 | ferimzone | N | O | O | H | H | O | O | 1 | Ph—CH=CH |
| 6-210 | pyrimethanil | N | O | O | H | H | O | O | 1 | n-propyl |
| 6-211 | pyrimethanil | N | O | O | H | H | O | O | 1 | C(CH$_3$)$_3$ |
| 6-212 | pyrimethanil | N | O | O | H | H | O | O | 1 | Ph |
| 6-213 | pyrimethanil | N | O | O | H | H | O | O | 1 | Ph—CH=CH |
| 6-214 | pyrimethanil | N | O | O | H | H | O | O | 1 | n-propyl |
| 6-215 | pyrimethanil | N | O | O | H | H | O | O | 1 | C(CH$_3$)$_3$ |
| 6-216 | pyrimethanil | N | O | O | H | H | O | O | 1 | Ph |
| 6-217 | pyrimethanil | N | O | O | H | H | O | O | 1 | Ph—CH=CH |
| 6-218 | 8-hydroxyquinoline sufate | O | O | O | H | H | O | O | 1 | C(CH$_3$)$_3$ |
| 6-219 | 8-hydroxyquinoline sufate | O | O | O | H | H | O | O | 1 | Ph |
| 6-220 | metominostrobin | N | O | O | H | H | O | O | 1 | methoxymethyl |
| 6-221 | metominostrobin | N | O | O | H | H | O | O | 1 | n-propyl |
| 6-222 | metominostrobin | N | O | O | H | H | O | O | 1 | 3,3,3-trifluoropropyl |
| 6-223 | metominostrobin | N | O | O | H | H | O | O | 1 | C(CH$_3$)$_3$ |
| 6-224 | metominostrobin | N | O | O | H | H | O | O | 1 | Ph |
| 6-225 | metominostrobin | N | O | O | H | H | O | O | 1 | Ph—CH=CH |
| 6-226 | metominostrobin | N | O | O | H | H | O | O | 1 | (4-Br)PhCH=CH |
| 6-227 | metominostrobin | N | O | O | Me | H | O | O | 1 | C(CH$_3$)$_3$ |
| 6-228 | metominostrobin | N | O | O | Ph | H | O | O | 1 | Ph |
| 6-229 | metominostrobin | N | O | S | H | H | O | O | 1 | C(CH$_3$)$_3$ |
| 6-230 | metominostrobin | N | O | S | H | H | O | O | 1 | Ph |
| 6-231 | metominostrobin | N | O | S | Me | H | O | O | 1 | t-butyl |
| 6-232 | metominostrobin | N | O | S | Me | H | O | O | 1 | (4-Br)PhCH=CH |
| 6-233 | SSF-129* | N | O | O | H | H | O | O | 1 | methoxymethyl |
| 6-234 | SSF-129* | N | O | O | H | H | O | O | 1 | n-propyl |
| 6-235 | SSF-129* | N | O | O | H | H | O | O | 1 | t-butyl |
| 6-236 | SSF-129* | N | O | O | H | H | O | O | 1 | 3,3,3-trifluoropropyl |
| 6-237 | SSF-129* | N | O | O | H | H | O | O | 1 | Ph |
| 6-238 | SSF-129* | N | O | O | H | H | O | O | 1 | 2-Phethenyl |
| 6-239 | SSF-129* | N | O | O | H | H | O | O | 1 | 3-hydroxypyrid-2-yl |
| 6-240 | SSF-129* | N | O | O | H | H | O | O | 1 | 6-hydroxypyrid-2-yl |
| 6-241 | SSF-129* | N | O | S | H | H | O | O | 1 | t-butyl |
| 6-242 | SSF-129* | N | O | S | H | H | O | O | 1 | Ph |
| 6-243 | SSF-129* | N | O | S | H | H | O | O | 1 | Ph—CH=CH |
| 6-244 | SSF-129* | N | O | S | Me | H | O | O | 1 | C(CH$_3$)$_3$ |
| 6-245 | SSF-129* | N | O | S | Me | H | O | O | 1 | Ph |
| 6-246 | SSF-129* | N | O | S | Me | H | O | O | 1 | Ph—CH=CH |
| 6-247 | metsulfovax | N | O | O | H | H | O | O | 1 | methoxymethyl |
| 6-248 | metsulfovax | N | O | O | H | H | O | O | 1 | n-propyl |
| 6-249 | metsulfovax | N | O | O | H | H | O | O | 1 | 3,3,3-trifluoropropyl |
| 6-250 | metsulfovax | N | O | O | H | H | O | O | 1 | C(CH$_3$)$_3$ |
| 6-251 | metsulfovax | N | O | O | H | H | O | O | 1 | Ph |
| 6-252 | zoxamide | N | O | O | H | H | — | — | 0 | Cl |
| 6-253 | zoxamide | N | O | O | H | H | O | O | 1 | methoxymethyl |
| 6-254 | zoxamide | N | O | O | H | H | O | O | 1 | n-propyl |
| 6-255 | zoxamide | N | O | O | H | H | O | O | 1 | 3,3,3-trifluoropropyl |
| 6-256 | zoxamide | N | O | O | H | H | O | O | 1 | C(CH$_3$)$_3$ |
| 6-257 | zoxamide | N | O | O | H | H | O | O | 1 | Ph |
| 6-258 | zoxamide | N | O | O | H | H | O | O | 1 | 3-hydroxypyrid-2-yl |
| 6-259 | zoxamide | N | O | S | H | H | O | O | 1 | n-propyl |
| 6-260 | zoxamide | N | O | S | H | H | O | O | 1 | 3,3,3-trifluoropropyl |
| 6-261 | zoxamide | N | O | S | H | H | O | O | 1 | C(CH$_3$)$_3$ |
| 6-262 | zoxamide | N | O | S | Me | H | O | O | 1 | n-propyl |
| 6-263 | zoxamide | N | O | S | Me | H | O | O | 1 | 3,3,3-trifluoropropyl |
| 6-264 | zoxamide | N | O | S | Me | H | O | O | 1 | C(CH$_3$)$_3$ |
| 6-265 | capropamid | N | O | O | H | H | O | O | 1 | methoxymethyl |
| 6-266 | capropamid | N | O | O | H | H | O | O | 1 | n-propyl |
| 6-267 | capropamid | N | O | O | H | H | O | O | 1 | 3,3,3-trifluoropropyl |
| 6-268 | capropamid | N | O | O | H | H | O | O | 1 | C(CH$_3$)$_3$ |
| 6-269 | capropamid | N | O | O | H | H | O | O | 1 | Ph |
| 6-270 | diclocymet | N | O | O | H | H | O | O | 1 | C(CH$_3$)$_3$ |
| 6-271 | diclocymet | N | O | O | H | H | O | O | 1 | Ph |
| 6-272 | diclocymet | N | O | O | H | H | O | O | 1 | Ph—CH=CH |

TABLE 6-continued $$Z^1(X^1)_m\!-\!\overset{\overset{G^{10}}{\|}}{C}\!-\!G^{11}\!-\!A \quad \text{where A is} \quad \overset{\overset{R^1}{|}}{\underset{R^2}{C}}\!-\!(G^{21}\!-\!\overset{\overset{G^{20}}{\|}}{C})_t\!-\!(X^2)_q Z^2$$

(I)

| Cmpd# | $Z^1(X^1)_m$—H | $X^1$ | $G^{10}$ | $G^{11}$ | $R^1$ | $R^2$ | $G^{20}$ | $G^{21}$ | t | $Z^2$ |
|---|---|---|---|---|---|---|---|---|---|---|
| 6-273 | methasulfocarb | N | O | O | H | H | O | O | 1 | $C(CH_3)_3$ |
| 6-274 | methasulfocarb | N | O | O | H | H | O | O | 1 | Ph |
| 6-275 | methasulfocarb | N | O | O | H | H | O | O | 1 | Ph—CH=CH |
| 6-276 | fenpiclonil | N | O | O | H | H | O | O | 1 | methoxymethyl |
| 6-277 | fenpiclonil | N | O | O | H | H | O | O | 1 | n-propyl |
| 6-278 | fenpiclonil | N | O | O | H | H | O | O | 1 | 3,3-3-trifluoropropyl |
| 6-279 | fenpiclonil | N | O | O | H | H | O | O | 1 | $C(CH_3)_3$ |
| 6-280 | fenpiclonil | N | O | O | H | H | O | O | 1 | Ph |
| 6-281 | fenpiclonil | N | O | O | H | H | O | O | 1 | 3-hydroxypyrid-2-yl |
| 6-282 | fenpiclonil | N | O | O | H | H | O | O | 1 | Ph |
| 6-283 | fenpiclonil | N | O | O | H | H | O | O | 1 | Ph—CH=CH |
| 6-284 | fludioxonil | N | O | O | H | H | O | O | 1 | methoxymethyl |
| 6-285 | fludioxonil | N | O | O | H | H | O | O | 1 | n-propyl |
| 6-286 | fludioxonil | N | O | O | H | H | O | O | 1 | 3,3,3-trifluoropropyl |
| 6-287 | fludioxonil | N | O | O | H | H | O | O | 1 | $C(CH_3)_3$ |
| 6-288 | fludioxonil | N | O | O | H | H | O | O | 1 | Ph |
| 6-289 | F-1* | N | O | O | H | H | O | O | 1 | methoxymethyl |
| 6-290 | F-1* | N | O | O | H | H | O | O | 1 | n-propyl |
| 6-291 | F-1* | N | O | O | H | H | O | O | 1 | t-butyl |
| 6-292 | F-2* | N | O | O | H | H | O | O | 1 | 3,3,3-trifluoropropyl |
| 6-293 | F-2* | N | O | O | H | H | O | O | 1 | Ph |
| 6-294 | F-2* | N | O | O | H | H | O | O | 1 | Ph—CH=CH |
| 6-295 | cymoxanil(A) | N | O | O | H | H | — | — | 0 | $\{N(Et)_3\}^+ Cl^-$ |
| 6-296 | cymoxanil(A) | N | O | O | H | H | — | — | 0 | $\{N(Me)_2Ph\}^+ Cl^-$ |
| 6-297 | cymoxanil(A) | N | O | O | H | H | — | — | 0 | $O\!-\!C(CH_3)_3$ |
| 6-298 | cymoxanil(B) | N | O | O | H | H | — | — | 0 | $\{N(Et)_3\}^+ Cl^-$ |
| 6-299 | cymoxanil(B) | N | O | O | H | H | — | — | 0 | $\{N(Me)_2Ph\}^+ I^-$ |
| 6-300 | cymoxanil(B) | N | O | O | H | H | — | — | 0 | $O\!-\!C(CH_3)_3$ |
| 6-301 | thifluzamide | N | O | O | H | H | — | — | 0 | $\{N(Et)_3\}^+ I^-$ |
| 6-302 | thifluzamide | N | O | O | H | H | — | — | 0 | $\{N(Me)_2Ph\}^+ I^-$ |
| 6-303 | thifluzamide | N | O | O | H | H | — | — | 0 | $O\!-\!C(CH_3)_3$ |
| 6-304 | flutolanil | N | O | O | H | H | — | — | 0 | $\{N(Et)_3\}^+ Cl^-$ |
| 6-305 | flutolanil | N | O | O | H | H | — | — | 0 | $\{N(Me)_2Ph\}^+ Cl^-$ |
| 6-306 | flutolanil | N | O | O | H | H | — | — | 0 | $O\!-\!C(CH_3)_3$ |
| 6-307 | diethofencarb | N | O | O | H | H | — | — | 0 | $\{N(Et)_3\}^+ I^-$ |
| 6-308 | diethofencarb | N | O | O | H | H | — | — | 0 | $\{N(Me)_2Ph\}^+ I^-$ |
| 6-309 | diethofencarb | N | O | O | H | H | — | — | 0 | $O\!-\!C(CH_3)_3$ |
| 6-310 | tebuconazole | O | O | O | H | H | — | — | 0 | $\{N(Et)_3\}^+ Cl^-$ |
| 6-311 | tebuconazole | O | O | O | H | H | — | — | 0 | $\{N(Me)_2Ph\}^+ I^-$ |
| 6-312 | tebuconazole | O | O | O | H | H | — | — | 0 | $O\!-\!C(CH_3)_3$ |
| 6-313 | cyproconazole | O | O | O | H | H | — | — | 0 | $\{N(Et)_3\}^+ Cl^-$ |
| 6-314 | cyproconazole | O | O | O | H | H | — | — | 0 | $\{N(Me)_2Ph\}^+ Cl^-$ |
| 6-315 | cyproconazole | O | O | O | H | H | — | — | 0 | $O\!-\!C(CH_3)_3$ |
| 6-316 | iprodione | N | O | O | H | H | — | — | 0 | $\{N(Et)_3\}^+ I^-$ |
| 6-317 | iprodione | N | O | O | H | H | — | — | 0 | $\{N(Me)_2Ph\}^+ I^-$ |
| 6-318 | iprodione | N | O | O | H | H | — | — | 0 | $O\!-\!C(CH_3)_3$ |
| 6-319 | carboxin | N | O | O | H | H | — | — | 0 | $\{N(Et)_3\}^+ Cl^-$ |
| 6-320 | carboxin | N | O | O | H | H | — | — | 0 | $\{N(Me)_2Ph\}^+ Cl^-$ |
| 6-321 | carboxin | N | O | O | H | H | — | — | 0 | $O\!-\!C(CH_3)_3$ |
| 6-322 | oxycarboxin | N | O | O | H | H | — | — | 0 | $\{N(Et)_3\}^+ Cl^-$ |
| 6-323 | oxycarboxin | N | O | O | H | H | — | — | 0 | $\{N(Me)_2Ph\}^+ Cl^-$ |
| 6-324 | oxycarboxin | N | O | O | H | H | — | — | 0 | $O\!-\!C(CH_3)_3$ |
| 6-325 | famoxadone | N | O | O | H | H | — | — | 0 | $\{N(Et)_3\}^+ Cl^-$ |
| 6-326 | famoxadone | N | O | O | H | H | — | — | 0 | $\{N(Me)_2Ph\}^+ I^-$ |
| 6-327 | famoxadone | N | O | O | H | H | — | — | 0 | $O\!-\!C(CH_3)_3$ |
| 6-328 | fluazinam | N | O | O | H | H | — | — | 0 | $\{N(Et)_3\}^+ I^-$ |
| 6-329 | fluazinam | N | O | O | H | H | — | — | 0 | $\{N(Me)_2Ph\}^+ Cl^-$ |
| 6-330 | fluazinam | N | O | O | H | H | — | — | 0 | O-(4Cl)Ph |
| 6-331 | cyprodinil | N | O | O | H | H | — | — | 0 | $\{N(Et)_3\}^+ Cl^-$ |
| 6-332 | cyprodinil | N | O | O | H | H | — | — | 0 | $\{N(Me)_2Ph\}^+ I^-$ |
| 6-333 | cyprodinil | N | O | O | H | H | — | — | 0 | O-(4Cl)Ph |
| 6-334 | ferimzone | N | O | O | H | H | — | — | 0 | $\{N(Et)_3\}^+ Cl^-$ |
| 6-335 | ferimzone | N | O | O | H | H | — | — | 0 | $\{N(Me)_2Ph\}^+ Cl^-$ |
| 6-336 | ferimzone | N | O | O | H | H | — | — | 0 | O-(4Cl)Ph |
| 6-337 | pyrimethanil | N | O | O | H | H | — | — | 0 | $\{N(Et)_3\}^+ I^-$ |
| 6-338 | pyrimethanil | N | O | O | H | H | — | — | 0 | $\{N(Me)_2Ph\}^+ I^-$ |
| 6-339 | pyrimethanil | N | O | O | H | H | — | — | 0 | O-(4Cl)Ph |
| 6-340 | metominostrobin | N | O | O | H | H | — | — | 0 | $\{N(Et)_3\}^+ Cl^-$ |
| 6-341 | metominostrobin | N | O | O | H | H | — | — | 0 | $\{N(Me)_2Ph\}^+ Cl^-$ |
| 6-342 | metominostrobin | N | O | O | H | H | — | — | 0 | O-(4Cl)Ph |

TABLE 6-continued $$Z^1(X^1)\underset{m}{-}\overset{\overset{G^{10}}{\|}}{C}-G^{11}-A \text{ where A is } \overset{\overset{R^1}{|}}{\underset{R^2}{C}}-(G^{21}-\overset{\overset{G^{20}}{\|}}{C})_t-(X^2)_qZ^2$$

(I)

| Cmpd# | $Z^1(X^1)_m$—H | $X^1$ | $G^{10}$ | $G^{11}$ | $R^1$ | $R^2$ | $G^{20}$ | $G^{21}$ | t | $Z^2$ |
|---|---|---|---|---|---|---|---|---|---|---|
| 6-343 | SSF-129* | N | O | O | H | H | — | — | 0 | {N(Et)$_3$}$^+$ I$^-$ |
| 6-344 | SSF-129* | N | O | O | H | H | — | — | 0 | {N(Me)$_2$Ph}$^+$ I$^-$ |
| 6-345 | SSF-129* | N | O | O | H | H | — | — | 0 | O-(4Cl)Ph |
| 6-346 | metsulfovax | N | O | O | H | H | — | — | 0 | {N(Et)$_3$}$^+$ Cl$^-$ |
| 6-347 | metsulfovax | N | O | O | H | H | — | — | 0 | {N(Me)$_2$Ph}$^+$ Cl$^-$ |
| 6-348 | metsulfovax | N | O | O | H | H | — | — | 0 | O-(4Cl)Ph |
| 6-349 | zoxamide | N | O | O | H | H | — | — | 0 | {N(Et)$_3$}$^+$ I$^-$ |
| 6-350 | zoxamide | N | O | O | H | H | — | — | 0 | {N(Me)$_2$Ph}$^+$ Cl$^-$ |
| 6-351 | zoxamide | N | O | O | H | H | — | — | 0 | O-(4Cl)Ph |
| 6-352 | capropamid | N | O | O | H | H | — | — | 0 | {N(Et)$_3$}$^+$ Cl$^-$ |
| 6-353 | capropamid | N | O | O | H | H | — | — | 0 | {N(Me)$_2$Ph}$^+$ I$^-$ |
| 6-354 | capropamid | N | O | O | H | H | — | — | 0 | O-(4Cl)Ph |
| 6-355 | fenpiclonil | N | O | O | H | H | — | — | 0 | {N(Et)$_3$}$^+$ I$^-$ |
| 6-356 | fenpiclonil | N | O | O | H | H | — | — | 0 | {N(Me)$_2$Ph}$^+$ Cl$^-$ |
| 6-357 | fenpiclonil | N | O | O | H | H | — | — | 0 | O-(4Cl)Ph |
| 6-358 | fludioxonil | N | O | O | H | H | — | — | 0 | {N(Et)$_3$}$^+$ Cl$^-$ |
| 6-359 | fludioxonil | N | O | O | H | H | — | — | 0 | {N(Me)$_2$Ph}$^+$ I$^-$ |
| 6-360 | fludioxonil | N | O | O | H | H | — | — | 0 | O-(4Cl)Ph |
| 6-361 | F-1* | N | O | O | H | H | — | — | 0 | {N(Et)$_3$}$^+$ Cl$^-$ |
| 6-362 | F-1* | N | O | O | H | H | — | — | 0 | {N(Me)$_2$Ph}$^+$ I$^-$ |
| 6-363 | F-1* | N | O | O | H | H | — | — | 0 | O-(4Cl)Ph |
| 6-364 | pronamide | N | O | O | H | H | O | O | 1 | C(CH$_3$)$_3$ |
| 6-365 | pronamide | N | O | O | Me | H | O | O | 1 | C(CH$_3$)$_3$ |
| 6-366 | pronamide | N | O | O | Ph | H | O | O | 1 | C(CH$_3$)$_3$ |
| 6-367 | pronamide | N | O | O | H | H | O | O | 1 | (CH$_2$)$_4$CH$_3$ |
| 6-368 | pronamide | N | O | O | H | H | O | O | 1 | CH$_2$(CH$_3$)CH$_2$CH$_3$ |
| 6-369 | pronamide | N | O | O | H | H | O | O | 1 | Ph |
| 6-370 | pronamide | N | O | O | H | H | O | O | 1 | (p-CH$_3$O)Ph |
| 6-371 | pronamide | N | O | O | H | H | O | O | 1 | (p-NO$_2$)Ph |
| 6-372 | diflufenican | N | O | O | H | H | O | O | 1 | C(CH$_3$)$_3$ |
| 6-373 | flumetsulam | N | O | O | H | H | O | O | 1 | C(CH$_3$)$_3$ |
| 6-374 | propanil | N | O | O | H | H | O | O | 1 | C(CH$_3$)$_3$ |
| 6-375 | asulam (A)* | N | O | O | H | H | O | O | 1 | C(CH$_3$)$_3$ |
| 6-376 | asulam (B)* | N | O | O | H | H | O | O | 1 | C(CH$_3$)$_3$ |
| 6-377 | asulam (A)* | N | O | O | H | H | O | O | 1 | Ph |
| 6-378 | asulam (B)* | N | O | O | H | H | O | O | 1 | Ph |
| 6-379 | chlorpropham | N | O | O | H | H | O | O | 1 | C(CH$_3$)$_3$ |
| 6-380 | desmedipham (A)* | N | O | O | H | H | O | O | 1 | C(CH$_3$)$_3$ |
| 6-381 | desmedipham (B)* | N | O | O | H | H | O | O | 1 | C(CH$_3$)$_3$ |
| 6-382 | desmedipham (A)* | N | O | O | Me | H | O | O | 1 | Ph |
| 6-383 | desmedipham (B)* | N | O | O | Me | H | O | O | 1 | Ph |
| 6-384 | phenmedipham (A)* | N | O | O | H | H | O | O | 1 | C(CH$_3$)$_3$ |
| 6-385 | phenmedipham (B)* | N | O | O | H | H | O | O | 1 | C(CH$_3$)$_3$ |
| 6-386 | phenmedipham (A)* | N | O | O | H | H | O | O | 1 | Ph |
| 6-387 | phenmedipham (B)* | N | O | O | H | H | O | O | 1 | Ph |
| 6-388 | sulcotrione (A)* | O | O | O | H | H | O | O | 1 | C(CH$_3$)$_3$ |
| 6-389 | sulcotrione (B)* | O | O | O | H | H | O | O | 1 | C(CH$_3$)$_3$ |
| 6-390 | sulcotrione (A)* | O | O | O | H | H | O | O | 1 | (CH$_2$)$_4$CH$_3$ |
| 6-391 | sulcotrione (B)* | O | O | O | H | H | O | O | 1 | (CH$_2$)$_4$CH$_3$ |
| 6-392 | sulcotrione (A)* | O | O | O | Me | H | O | O | 1 | Ph |
| 6-393 | sulcotrione (B)* | O | O | O | Me | H | O | O | 1 | Ph |
| 6-394 | sethoxydim | O | O | O | H | H | O | O | 1 | C(CH$_3$)$_3$ |
| 6-395 | sethoxydim | O | O | O | H | H | O | O | 1 | (CH$_2$)$_4$CH$_3$ |
| 6-396 | sethoxydim | O | O | O | H | H | O | O | 1 | Ph |
| 6-397 | sethoxydim | O | O | O | H | H | O | O | 1 | Ph—CH=CH |
| 6-398 | sethoxydim | O | O | O | H | H | O | O | 1 | (4-Br)PhCH=CH |
| 6-399 | sethoxydim | O | O | O | H | H | — | — | 0 | {N(Et)$_3$}$^+$ Cl$^-$ |
| 6-400 | tralkoxydim | O | O | O | H | H | O | O | 1 | C(CH$_3$)$_3$ |
| 6-401 | tralkoxydim | O | O | O | Me | H | O | O | 1 | C(CH$_3$)$_3$ |
| 6-402 | tralkoxydim | O | O | O | H | H | O | O | 1 | (CH$_2$)$_4$CH$_3$ |
| 6-403 | tralkoxydim | O | O | O | H | H | O | O | 1 | Ph |
| 6-404 | tralkoxydim | O | O | O | H | H | O | O | 1 | (p-CH$_3$O)Ph |
| 6-405 | tralkoxydim | O | O | O | H | H | O | O | 1 | Ph—CH=CH |
| 6-406 | tralkoxydim | O | O | O | H | H | O | O | 1 | (4-Br)PhCH=CH |
| 6-407 | tralkoxydim | O | O | O | H | H | — | — | 0 | {N(Et)$_3$}$^+$ I$^-$ |
| 6-408 | pendimethalin | N | O | O | H | H | O | O | 1 | C(CH$_3$)$_3$ |
| 6-409 | pendimethalin | N | O | O | Me | H | O | O | 1 | C(CH$_3$)$_3$ |
| 6-410 | pendimethalin | N | O | O | H | H | O | O | 1 | (CH$_2$)$_4$CH$_3$ |
| 6-411 | pendimethalin | N | O | O | H | H | O | O | 1 | Ph |
| 6-412 | pendimethalin | N | O | O | H | H | O | O | 1 | (p-CH$_3$O)Ph |

TABLE 6-continued $$Z^1(X^1)_{\overline{m}}\overset{G^{10}}{\underset{(I)}{\overset{\|}{C}}}-G^{11}-A \text{ where A is } \overset{R^1}{\underset{R^2}{\overset{|}{C}}}-(G^{21}-\overset{G^{20}}{\overset{\|}{C}})_t-(X^2)_qZ^2$$

| Cmpd# | $Z^1(X^1)_m$—H | $X^1$ | $G^{10}$ | $G^{11}$ | $R^1$ | $R^2$ | $G^{20}$ | $G^{21}$ | t | $Z^2$ |
|---|---|---|---|---|---|---|---|---|---|---|
| 6-413 | pendimethalin | N | O | O | H | H | O | O | 1 | Ph—CH=CH |
| 6-414 | pendimethalin | N | O | O | H | H | O | O | 1 | (4-Br)PhCH=CH |
| 6-415 | pendimethalin | N | O | O | H | H | — | — | 0 | {N(Et)$_3$}$^+$ Cl$^-$ |
| 6-416 | dinoseb | O | O | O | H | H | O | O | 1 | C(CH$_3$)$_3$ |
| 6-417 | dinoseb | O | O | O | H | H | O | O | 1 | Ph |
| 6-418 | aclonifen | N | O | O | H | H | O | O | 1 | C(CH$_3$)$_3$ |
| 6-419 | aclonifen | N | O | O | H | H | O | O | 1 | Ph |
| 6-420 | aclonifen | N | O | O | H | H | O | O | 1 | Ph—CH=CH |
| 6-421 | aclonifen | N | O | O | H | H | O | O | 1 | (4-Br)PhCH=CH |
| 6-422 | fomesafen | N | O | O | H | H | O | O | 1 | C(CH$_3$)$_3$ |
| 6-423 | fomesafen | N | O | O | H | H | O | O | 1 | Ph |
| 6-424 | fomesafen | N | O | O | H | H | O | O | 1 | Ph—CH=CH |
| 6-425 | atrazine (A)* | N | O | O | H | H | O | O | 1 | C(CH$_3$)$_3$ |
| 6-426 | atrazine (B)* | N | O | O | H | H | O | O | 1 | C(CH$_3$)$_3$ |
| 6-427 | atrazine (A)* | N | O | O | Me | H | O | O | 1 | C(CH$_3$)$_3$ |
| 6-428 | atrazine (B)* | N | O | O | Me | H | O | O | 1 | C(CH$_3$)$_3$ |
| 6-429 | atrazine (A)* | N | O | O | H | H | O | O | 1 | Ph |
| 6-430 | atrazine (B)* | N | O | O | H | H | O | O | 1 | Ph |
| 6-431 | atrazine (A)* | N | O | O | Me | H | O | O | 1 | Ph—CH=CH |
| 6-432 | atrazine (B)* | N | O | O | Me | H | O | O | 1 | Ph—CH=CH |
| 6-433 | atrazine (A)* | N | O | O | H | H | O | O | 1 | (4-Br)PhCH=CH |
| 6-434 | atrazine (B)* | N | O | O | H | H | O | O | 1 | (4-Br)PhCH=CH |
| 6-435 | atrazine (A)* | N | O | O | H | H | — | — | 0 | {N(Et)$_3$}$^+$ Cl$^-$ |
| 6-436 | atrazine (B)* | N | O | O | H | H | — | — | 0 | {N(Et)$_3$}$^+$ I$^-$ |
| 6-437 | terbuthylazine (A)* | N | O | O | H | H | O | O | 1 | C(CH$_3$)$_3$ |
| 6-438 | terbuthylazine (B)* | N | O | O | H | H | O | O | 1 | C(CH$_3$)$_3$ |
| 6-439 | terbuthylazine (A)* | N | O | O | H | H | O | O | 1 | Ph |
| 6-440 | terbuthylazine (B)* | N | O | O | H | H | O | O | 1 | Ph |
| 6-441 | terbuthylazine (A)* | N | O | O | H | H | O | O | 1 | Ph—CH=CH |
| 6-442 | terbuthylazine (B)* | N | O | O | H | H | O | O | 1 | Ph—CH=CH |
| 6-443 | terbuthylazine (A)* | N | O | O | H | H | O | O | 1 | (4-Br)PhCH=CH |
| 6-444 | terbuthylazine (B)* | N | O | O | H | H | O | O | 1 | (4-Br)PhCH=CH |
| 6-445 | terbumeton (A)* | N | O | O | H | H | O | O | 1 | C(CH$_3$)$_3$ |
| 6-446 | terbumeton (B)* | N | O | O | H | H | O | O | 1 | C(CH$_3$)$_3$ |
| 6-447 | terbumeton (A)* | N | O | O | H | H | O | O | 1 | Ph |
| 6-448 | terbumeton (B)* | N | O | O | H | H | O | O | 1 | Ph |
| 6-449 | terbumeton (A)* | N | O | O | H | H | O | O | 1 | Ph—CH=CH |
| 6-450 | terbumeton (B)* | N | O | O | H | H | O | O | 1 | Ph—CH=CH |
| 6-451 | ametryn (A)* | N | O | O | H | H | O | O | 1 | C(CH$_3$)$_3$ |
| 6-452 | ametryn (B)* | N | O | O | H | H | O | O | 1 | C(CH$_3$)$_3$ |
| 6-453 | ametryn (A)* | N | O | O | H | H | O | O | 1 | Ph |
| 6-454 | ametryn (B)* | N | O | O | H | H | O | O | 1 | Ph |
| 6-455 | ametryn (A)* | N | O | O | H | H | O | O | 1 | Ph—CH=CH |
| 6-456 | ametryn (B)* | N | O | O | H | H | O | O | 1 | Ph—CH=CH |
| 6-457 | ametryn (A)* | N | O | O | H | H | O | O | 1 | (p-CH$_3$O)Ph |
| 6-458 | ametryn (B)* | N | O | O | H | H | O | O | 1 | (p-CH$_3$O)Ph |
| 6-459 | metribuzin | N | O | O | H | H | O | O | 1 | C(CH$_3$)$_3$ |
| 6-460 | metribuzin | N | O | O | H | H | O | O | 1 | Ph |
| 6-461 | metribuzin | N | O | O | H | H | O | O | 1 | (p-CH$_3$O)Ph |
| 6-462 | metribuzin | N | O | O | H | H | O | O | 1 | Ph—CH=CH |
| 6-463 | metribuzin | N | O | O | H | H | O | O | 1 | (4-Br)PhCH=CH |
| 6-464 | metribuzin | N | O | O | H | H | — | — | 0 | {N(Et)$_3$}$^+$ Cl$^-$ |
| 6-465 | metribuzin | N | O | O | H | H | — | — | 0 | PhO |
| 6-466 | amitrole (A)* | N | O | O | H | H | O | O | 1 | C(CH$_3$)$_3$ |
| 6-467 | amitrole (B)* | N | O | O | H | H | O | O | 1 | C(CH$_3$)$_3$ |
| 6-468 | amitrole (A)* | N | O | O | H | H | O | O | 1 | Ph |
| 6-469 | amitrole (B)* | N | O | O | H | H | O | O | 1 | Ph |
| 6-470 | bentazon | N | O | O | H | H | O | O | 1 | C(CH$_3$)$_3$ |
| 6-471 | bentazon | N | O | O | H | H | O | O | 1 | Ph |
| 6-472 | bentazon | N | O | O | H | H | O | O | 1 | (p-CH$_3$O)Ph |
| 6-473 | bentazon | N | O | O | H | H | O | O | 1 | Ph—CH=CH |
| 6-474 | bentazon | N | O | O | H | H | O | O | 1 | (4-Br)PhCH=CH |
| 6-475 | bentazon | N | O | O | H | H | — | — | 0 | {N(Et)$_3$}$^+$ I$^-$ |
| 6-476 | bromacil | N | O | O | H | H | O | O | 1 | C(CH$_3$)$_3$ |
| 6-477 | bromacil | N | O | O | H | H | O | O | 1 | Ph |
| 6-478 | chlorotoluron | N | O | O | H | H | O | O | 1 | C(CH$_3$)$_3$ |
| 6-479 | chlorotoluron | N | O | O | H | H | O | O | 1 | C(CH$_3$)$_3$ |
| 6-480 | diuron | N | O | O | H | H | O | O | 1 | C(CH$_3$)$_3$ |
| 6-481 | diuron | N | O | O | H | H | O | O | 1 | Ph |
| 6-482 | diuron | N | O | O | H | H | O | O | 1 | (p-CH$_3$O)Ph |

TABLE 6-continued $$Z^1(X^1)_m\overset{\overset{G^{10}}{\|}}{-C}-G^{11}-A \text{ where A is } \overset{\overset{R^1}{|}}{\underset{R^2}{C}}-(G^{21}-\overset{\overset{G^{20}}{\|}}{C})_t-(X^2)_qZ^2$$

(I)

| Cmpd# | Z¹(X¹)ₘ—H | X¹ | G¹⁰ | G¹¹ | R¹ | R² | G²⁰ | G²¹ | t | Z² |
|---|---|---|---|---|---|---|---|---|---|---|
| 6-483 | diuron | N | O | O | H | H | O | O | 1 | Ph—CH=CH |
| 6-484 | diuron | N | O | O | H | H | O | O | 1 | (4-Br)PhCH=CH |
| 6-485 | diuron | N | O | O | H | H | — | — | 0 | {N(Et)₃}⁺ I⁻ |
| 6-486 | diuron | N | O | O | H | H | — | — | 0 | PhO |
| 6-487 | fluometuron | N | O | O | H | H | O | O | 1 | C(CH₃)₃ |
| 6-488 | fluometuron | N | O | O | H | H | O | O | 1 | Ph |
| 6-489 | fluometuron | N | O | O | H | H | O | O | 1 | Ph—CH=CH |
| 6-490 | fluometuron | N | O | O | H | H | — | — | 0 | {N(Et)₃}⁺ Cl⁻ |
| 6-491 | isoproturon | N | O | O | H | H | O | O | 1 | C(CH₃)₃ |
| 6-492 | isoproturon | N | O | O | H | H | O | O | 1 | Ph |
| 6-493 | isoproturon | N | O | O | H | H | O | O | 1 | (p-CH₃O)Ph |
| 6-494 | isoproturon | N | O | O | H | H | O | O | 1 | Ph—CH=CH |
| 6-495 | isoproturon | N | O | O | H | H | O | O | 1 | (4-Br)PhCH=CH |
| 6-496 | isoproturon | N | O | O | H | H | — | — | 0 | {N(Et)₃}⁺ Cl⁻ |
| 6-497 | linuron | N | O | O | H | H | O | O | 1 | Ph |
| 6-498 | linuron | N | O | O | H | H | — | — | 0 | {N(Et)₃}⁺ I⁻ |
| 6-499 | chlorsulfuron | N | O | S | H | H | O | O | 1 | C(CH₃)₃ |
| 6-500 | chlorsulfuron | N | O | O | H | H | O | O | 1 | C(CH₃)₃ |
| 6-501 | chlorsulfuron | N | O | O | H | H | O | O | 1 | Ph |
| 6-502 | chlorsulfuron | N | O | O | H | H | — | — | 0 | {N(Et)₃}⁺ Cl⁻ |
| 6-503 | nicosulfuron | N | O | O | H | H | O | O | 1 | C(CH₃)₃ |
| 6-504 | nicosulfuron | N | O | O | H | H | O | O | 1 | Ph |
| 6-505 | nicosulfuron | N | O | O | H | H | O | O | 1 | Ph—CH=CH |
| 6-506 | nicosulfuron | N | O | O | H | H | — | — | 0 | {N(Et)₃}⁺ I⁻ |
| 6-507 | nicosulfuron | N | O | O | Me | H | O | O | 1 | C(CH₃)₃ |
| 6-508 | nicosulfuron | N | O | O | Me | H | O | O | 1 | Ph |
| 6-509 | nicosulfuron | N | O | O | Me | H | O | O | 1 | Ph—CH=CH |
| 6-510 | rimsulfuron | N | O | O | Me | H | — | — | 0 | {N(Et)₃}⁺ Cl⁻ |
| 6-511 | rimsulfuron | N | O | O | Me | H | O | O | 1 | C(CH₃)₃ |
| 6-512 | rimsulfuron | N | O | O | Me | H | O | O | 1 | Ph |
| 6-513 | rimsulfuron | N | O | O | Me | H | O | O | 1 | (p-CH₃O)Ph |
| 6-514 | rimsulfuron | N | O | O | Me | H | O | O | 1 | Ph—CH=CH |
| 6-515 | rimsulfuron | N | O | O | Me | H | O | O | 1 | (4-Br)PhCH=CH |
| 6-516 | rimsulfuron | N | O | O | Me | H | — | — | 0 | {N(Et)₃}⁺ Cl⁻ |
| 6-517 | chlorfluazuron | N | O | O | H | H | O | O | 1 | C(CH₃)₃ |
| 6-518 | chlorfluazuron | N | O | O | H | H | O | O | 1 | Ph |
| 6-519 | chlorfluazuron | N | O | O | H | H | O | O | 1 | Ph—CH=CH |
| 6-520 | diflubenzuron | N | O | O | H | H | O | O | 1 | C(CH₃)₃ |
| 6-521 | diflubenzuron | N | O | O | H | H | O | O | 1 | Ph |
| 6-522 | diflubenzuron | N | O | O | H | H | O | O | 1 | (p-CH₃O)Ph |
| 6-523 | diflubenzuron | N | O | O | H | H | O | O | 1 | (p-NO₂)Ph |
| 6-524 | diflubenzuron | N | O | O | H | H | O | O | 1 | Ph—CH=CH |
| 6-525 | diflubenzuron | N | O | O | H | H | O | O | 1 | (4-Br)PhCH=CH |
| 6-526 | diflubenzuron | N | O | O | H | H | — | — | 0 | {N(Et)³}⁺ I⁻ |
| 6-527 | diflubenzuron | N | O | O | H | H | — | — | 0 | PhO |
| 6-528 | diflubenzuron | N | O | O | H | H | — | — | 0 | {N(Me)₂Ph}⁺ Cl⁻ |
| 6-529 | diflubenzuron | N | O | O | Me | H | O | O | 1 | C(CH₃)₃ |
| 6-530 | diflubenzuron | N | O | O | Me | H | O | O | 1 | Ph |
| 6-531 | diflubenzuron | N | O | O | Me | H | O | O | 1 | (p-CH₃O)Ph |
| 6-532 | diflubenzuron | N | O | S | H | H | O | O | 1 | C(CH₃)₃ |
| 6-533 | diflubenzuron | N | O | S | H | H | O | O | 1 | Ph |
| 6-534 | diflubenzuron | N | O | S | H | H | O | O | 1 | (p-CH₃O)Ph |
| 6-535 | diflubenzuron | N | O | S | Me | H | O | O | 1 | C(CH₃)₃ |
| 6-536 | diflubenzuron | N | O | S | Me | H | O | O | 1 | Ph |
| 6-537 | diflubenzuron | N | O | S | Me | H | O | O | 1 | (p-CH₃O)Ph |
| 6-538 | flucycloxuron | N | O | O | H | H | O | O | 1 | Ph |
| 6-539 | flucycloxuron | N | O | O | H | H | O | O | 1 | (p-CH₃O)Ph |
| 6-540 | flucycloxuron | N | O | O | H | H | O | O | 1 | C(CH₃)₃ |
| 6-541 | flucycloxuron | N | O | O | H | H | O | O | 1 | C(CH₃)₃ |
| 6-542 | flufenoxuron | N | O | O | H | H | O | O | 1 | Ph |
| 6-543 | flufenoxuron | N | O | O | H | H | O | O | 1 | (p-CH₃O)Ph |
| 6-544 | hexaflumuron | N | O | O | H | H | O | O | 1 | C(CH₃)₃ |
| 6-545 | lufenuron | N | O | O | H | H | O | O | 1 | C(CH₃)₃ |
| 6-546 | novaluron | N | O | O | H | H | O | O | 1 | C(CH₃)₃ |
| 6-547 | teflubenzuron | N | O | O | H | H | O | O | 1 | C(CH₃)₃ |
| 6-548 | triflumuron | N | O | O | H | H | O | O | 1 | C(CH₃)₃ |
| 6-549 | fluazuron | N | O | O | H | H | O | O | 1 | C(CH₃)₃ |
| 6-550 | aldicarb | N | O | O | H | H | O | O | 1 | C(CH₃)₃ |
| 6-551 | bendiocarb | N | O | O | H | H | O | O | 1 | C(CH₃)₃ |
| 6-552 | bendiocarb | N | O | O | H | H | O | O | 1 | Ph |

TABLE 6-continued $$Z^1(X^1)_m\overset{G^{10}}{\underset{(I)}{-C-G^{11}-A}} \text{ where A is } \overset{R^1}{\underset{R^2}{C}}-(G^{21}-\overset{G^{20}}{C})_t-(X^2)_qZ^2$$

| Cmpd# | $Z^1(X^1)_m$—H | $X^1$ | $G^{10}$ | $G^{11}$ | $R^1$ | $R^2$ | $G^{20}$ | $G^{21}$ | t | $Z^2$ |
|---|---|---|---|---|---|---|---|---|---|---|
| 6-553 | BPMC (fenobucarb) | N | O | O | H | H | O | O | 1 | $C(CH_3)_3$ |
| 6-554 | BPMC (fenobucarb) | N | O | O | H | H | O | O | 1 | Ph |
| 6-555 | carbaryl | N | O | O | H | H | O | O | 1 | $C(CH_3)_3$ |
| 6-556 | carbaryl | N | O | O | H | H | O | O | 1 | (4-Cl)PhCH=CH |
| 6-557 | carbaryl | N | O | O | H | H | O | O | 1 | Ph |
| 6-558 | carbaryl | N | O | O | H | H | O | O | 1 | (p-$CH_3$O)Ph |
| 6-559 | carbaryl | N | O | O | H | H | O | O | 1 | (p-$NO_2$)Ph |
| 6-560 | carbaryl | N | O | O | H | H | O | O | 1 | Ph—CH=CH |
| 6-561 | carbaryl | N | O | O | H | H | O | O | 1 | (4-Br)PhCH=CH |
| 6-562 | carbaryl | N | O | O | H | H | — | — | 0 | $\{N(Et)_3\}^+$ $I^-$ |
| 6-563 | carbaryl | N | O | O | H | H | — | — | 0 | PhO |
| 6-564 | carbaryl | N | O | O | H | H | — | — | 0 | $\{N(Me)_2Ph\}^+$ $Cl^-$ |
| 6-565 | carbaryl | N | O | O | Me | H | O | O | 1 | $C(CH_3)_3$ |
| 6-566 | carbaryl | N | O | O | Me | H | O | O | 1 | Ph |
| 6-567 | carbaryl | N | O | O | Me | H | O | O | 1 | (p-$CH_3$O)Ph |
| 6-568 | carbaryl | N | O | S | H | H | O | O | 1 | $C(CH_3)_3$ |
| 6-569 | carbaryl | N | O | S | H | H | O | O | 1 | Ph |
| 6-570 | carbaryl | N | O | S | H | H | O | O | 1 | (p-$CH_3$O)Ph |
| 6-571 | carbaryl | N | O | S | Me | H | O | O | 1 | $C(CH_3)_3$ |
| 6-572 | carbaryl | N | O | S | Me | H | O | O | 1 | Ph |
| 6-573 | carbaryl | N | O | S | Me | H | O | O | 1 | (p-$CH_3$O)Ph |
| 6-574 | carbofuran | N | O | O | H | H | O | O | 1 | $C(CH_3)_3$ |
| 6-575 | cartap | N | O | O | H | H | O | O | 1 | $C(CH_3)_3$ |
| 6-576 | cartap | N | O | O | H | H | O | O | 1 | Ph |
| 6-577 | ethiofencarb | N | O | O | H | H | O | O | 1 | $C(CH_3)_3$ |
| 6-578 | ethiofencarb | N | O | O | H | H | O | O | 1 | Ph |
| 6-579 | fenoxycarb | N | O | O | H | H | O | O | 1 | $C(CH_3)_3$ |
| 6-580 | fenoxycarb | N | O | O | H | H | O | O | 1 | Ph |
| 6-581 | formetanate | N | O | O | H | H | O | O | 1 | $C(CH_3)_3$ |
| 6-582 | formetanate | N | O | O | H | H | O | O | 1 | Ph |
| 6-583 | isoprocarb | N | O | O | H | H | O | O | 1 | $C(CH_3)_3$ |
| 6-584 | isoprocarb | N | O | O | H | H | O | O | 1 | Ph |
| 6-585 | methiocarb | N | O | O | H | H | O | O | 1 | $C(CH_3)_3$ |
| 6-586 | methiocarb | N | O | O | H | H | O | O | 1 | Ph |
| 6-587 | methomyl | N | O | O | H | H | O | O | 1 | $C(CH_3)_3$ |
| 6-588 | methomyl | N | O | O | H | H | O | O | 1 | Ph |
| 6-589 | oxamyl | N | O | O | H | H | O | O | 1 | $C(CH_3)_3$ |
| 6-590 | oxamyl | N | O | O | H | H | O | O | 1 | Ph |
| 6-591 | phosphocarb | N | O | O | H | H | O | O | 1 | $C(CH_3)_3$ |
| 6-592 | phosphocarb | N | O | O | H | H | O | O | 1 | Ph |
| 6-593 | promecarb | N | O | O | H | H | O | O | 1 | $C(CH_3)_3$ |
| 6-594 | promecarb | N | O | O | H | H | O | O | 1 | Ph |
| 6-595 | propoxur | N | O | O | H | H | O | O | 1 | $C(CH_3)_3$ |
| 6-596 | propoxur | N | O | O | H | H | O | O | 1 | Ph |
| 6-597 | tolfenpyrad | N | O | O | H | H | O | O | 1 | $C(CH_3)_3$ |
| 6-598 | tolfenpyrad | N | O | O | H | H | O | O | 1 | Ph |
| 6-599 | xylyl methylcarbamate | N | O | O | H | H | O | O | 1 | $C(CH_3)_3$ |
| 6-600 | xylyl methylcarbamate | N | O | O | H | H | O | O | 1 | Ph |
| 6-601 | xylylcarb | N | O | O | H | H | O | O | 1 | $C(CH_3)_3$ |
| 6-602 | xylylcarb | N | O | O | H | H | O | O | 1 | Ph |
| 6-603 | abamectin | O | O | O | H | H | O | O | 1 | $C(CH_3)_3$ |
| 6-604 | abamectin | O | O | O | H | H | O | O | 1 | Ph |
| 6-605 | abamectin | O | O | O | H | H | O | O | 1 | (p-$CH_3$O)Ph |
| 6-606 | abamectin | O | O | O | H | H | O | O | 1 | (p-$NO_2$)Ph |
| 6-607 | abamectin | O | O | O | H | H | O | O | 1 | Ph—CH=CH |
| 6-608 | abamectin | O | O | O | H | H | O | O | 1 | (4-Br)PhCH=CH |
| 6-609 | abamectin | O | O | O | H | H | — | — | 0 | $\{N(Et)_3\}^+$ $Cl^-$ |
| 6-610 | abamectin | O | O | O | H | H | — | — | 0 | PhO |
| 6-611 | abamectin | O | O | O | H | H | — | — | 0 | $\{N(Me)_2Ph\}^+$ $I^-$ |
| 6-612 | abamectin | O | O | O | Me | H | O | O | 1 | $C(CH_3)_3$ |
| 6-613 | abamectin | O | O | O | Me | H | O | O | 1 | Ph |
| 6-614 | abamectin | O | O | O | Me | H | O | O | 1 | (p-$CH_3$O)Ph |
| 6-615 | abamectin | O | O | S | H | H | O | O | 1 | $C(CH_3)_3$ |
| 6-616 | abamectin | O | O | S | H | H | O | O | 1 | Ph |
| 6-617 | abamectin | O | O | S | H | H | O | O | 1 | (p-$CH_3$O)Ph |
| 6-618 | abamectin | O | O | S | Me | H | O | O | 1 | $C(CH_3)_3$ |
| 6-619 | abamectin | O | O | S | Me | H | O | O | 1 | Ph |
| 6-620 | abamectin | O | O | S | Me | H | O | O | 1 | (p-$CH_3$O)Ph |

TABLE 6-continued $$Z^1(X^1)_{\overline{m}}\overset{G^{10}}{\underset{(I)}{C}}-G^{11}-A \text{ where A is } \overset{R^1}{\underset{R^2}{C}}-(G^{21}-\overset{G^{20}}{C})_t-(X^2)_qZ^2$$

| Cmpd# | $Z^1(X^1)_m$—H | $X^1$ | $G^{10}$ | $G^{11}$ | $R^1$ | $R^2$ | $G^{20}$ | $G^{21}$ | t | $Z^2$ |
|---|---|---|---|---|---|---|---|---|---|---|
| 6-621 | emamectin benzcate | O | O | O | H | H | O | O | 1 | $C(CH_3)_3$ |
| 6-622 | emamectin benzcate | O | O | O | H | H | O | O | 1 | Ph |
| 6-623 | milbemectin | O | O | O | H | H | O | O | 1 | $C(CH_3)_3$ |
| 6-624 | milbemectin | O | O | O | H | H | O | O | 1 | Ph |
| 6-625 | clothianidin | N | O | O | H | H | O | O | 1 | $C(CH_3)_3$ |
| 6-626 | clothianidin | N | O | O | H | H | O | O | 1 | Ph |
| 6-627 | imidacloprid | N | O | O | H | H | O | O | 1 | $C(CH_3)_3$ |
| 6-628 | imidacloprid | N | O | O | H | H | O | O | 1 | Ph |
| 6-629 | imidacloprid | N | O | O | H | H | O | O | 1 | (p-$CH_3O$)Ph |
| 6-630 | imidacloprid | N | O | O | H | H | O | O | 1 | (p-$NO_2$)Ph |
| 6-631 | imidacloprid | N | O | O | H | H | O | O | 1 | Ph—CH=CH |
| 6-632 | imidacloprid | N | O | O | H | H | O | O | 1 | (4-Br)PhCH=CH |
| 6-633 | imidacloprid | N | O | O | H | H | — | — | 0 | $\{N(Et)_3\}^+$ $I^-$ |
| 6-634 | imidacloprid | N | O | O | H | H | — | — | 0 | PhO |
| 6-635 | imidacloprid | N | O | O | H | H | — | — | 0 | $\{N(Me)_2Ph\}^+$ $I^-$ |
| 6-636 | imidacloprid | N | O | O | Me | H | O | O | 1 | $C(CH_3)_3$ |
| 6-637 | imidacloprid | N | O | O | Me | H | O | O | 1 | Ph |
| 6-638 | imidacloprid | N | O | O | Me | H | O | O | 1 | (p-$CH_3O$)Ph |
| 6-639 | imidacloprid | N | O | S | H | H | O | O | 1 | $C(CH_3)_3$ |
| 6-640 | imidacloprid | N | O | S | H | H | O | O | 1 | Ph |
| 6-641 | imidacloprid | N | O | S | H | H | O | O | 1 | (p-$CH_3O$)Ph |
| 6-642 | imidacloprid | N | O | S | Me | H | O | O | 1 | $C(CH_3)_3$ |
| 6-643 | imidacloprid | N | O | S | Me | H | O | O | 1 | Ph |
| 6-644 | imidacloprid | N | O | S | Me | H | O | O | 1 | (p-$CH_3O$)Ph |
| 6-645 | imidacloprid | N | O | O | Ph | H | O | O | 1 | $C(CH_3)_3$ |
| 6-646 | imidacloprid | N | O | O | Ph | H | O | O | 1 | Ph |
| 6-647 | imidacloprid | N | O | O | Ph | H | O | O | 1 | (p-$CH_3O$)Ph |
| 6-648 | imidacloprid | N | O | S | Ph | H | O | O | 1 | $C(CH_3)_3$ |
| 6-649 | imidacloprid | N | O | S | Ph | H | O | O | 1 | Ph |
| 6-650 | imidacloprid | N | O | S | Ph | H | O | O | 1 | (p-$CH_3O$)Ph |
| 6-651 | nidinotefuran | N | O | O | H | H | O | O | 1 | $C(CH_3)_3$ |
| 6-652 | nidinotefuran | N | O | O | H | H | O | O | 1 | Ph |
| 6-653 | nitenpyram | N | O | O | H | H | O | O | 1 | $C(CH_3)_3$ |
| 6-654 | nitenpyram | N | O | O | H | H | O | O | 1 | Ph |
| 6-655 | NTN-32692 | N | O | O | H | H | O | O | 1 | $C(CH_3)_3$ |
| 6-656 | NTN-32692 | N | O | O | H | H | O | O | 1 | Ph |
| 6-657 | acephate | N | O | O | H | H | O | O | 1 | Ph |
| 6-658 | acephate | N | O | O | H | H | O | O | 1 | (p-$CH_3O$)Ph |
| 6-659 | acephate | N | O | O | H | H | O | O | 1 | (p-$NO_2$)Ph |
| 6-660 | acephate | N | O | O | H | H | O | O | 1 | Ph—CH=CH |
| 6-661 | acephate | N | O | O | H | H | O | O | 1 | (4-Br)PhCH=CH |
| 6-662 | acephate | N | O | O | H | H | — | — | 0 | $\{N(Et)_3\}^+$ $Cl^-$ |
| 6-663 | acephate | N | O | O | H | H | — | — | 0 | PhO |
| 6-664 | acephate | N | O | O | H | H | — | — | 0 | $\{N(Me)_2Ph\}^+$ $I^-$ |
| 6-665 | acephate | N | O | O | Me | H | O | O | 1 | $C(CH_3)_3$ |
| 6-666 | acephate | N | O | O | Me | H | O | O | 1 | Ph |
| 6-667 | acephate | N | O | O | Me | H | O | O | 1 | (p-$CH_3O$)Ph |
| 6-668 | acephate | N | O | O | Ph | H | O | O | 1 | $C(CH_3)_3$ |
| 6-669 | acephate | N | O | O | Ph | H | O | O | 1 | Ph |
| 6-670 | acephate | N | O | O | Ph | H | O | O | 1 | (p-$CH_3O$)Ph |
| 6-671 | dimethoate | N | O | O | H | H | O | O | 1 | $C(CH_3)_3$ |
| 6-672 | dimethoate | N | O | O | H | H | O | O | 1 | Ph |
| 6-673 | dimethoate | N | O | O | H | H | O | O | 1 | (p-$CH_3O$)Ph |
| 6-674 | dimethoate | N | O | O | H | H | O | O | 1 | (p-$NO_2$)Ph |
| 6-675 | dimethoate | N | O | O | H | H | O | O | 1 | Ph—CH=CH |
| 6-676 | dimethoate | N | O | O | H | H | O | O | 1 | (4-Br)PhCH=CH |
| 6-677 | dimethoate | N | O | O | H | H | — | — | 0 | $\{N(Et)_3\}^+$ $I^-$ |
| 6-678 | dimethoate | N | O | O | H | H | — | — | 0 | PhO |
| 6-679 | dimethoate | N | O | O | H | H | — | — | 0 | $\{N(Me)_2Ph\}^+$ $Cl^-$ |
| 6-680 | dimethoate | N | O | O | Me | H | O | O | 1 | $C(CH_3)_3$ |
| 6-681 | dimethoate | N | O | O | Me | H | O | O | 1 | Ph |
| 6-682 | dimethoate | N | O | O | Me | H | O | O | 1 | (p-$CH_3O$)Ph |
| 6-683 | dimethoate | N | O | S | H | H | O | O | 1 | $C(CH_3)_3$ |
| 6-684 | dimethoate | N | O | S | H | H | O | O | 1 | Ph |
| 6-685 | dimethoate | N | O | S | H | H | O | O | 1 | (p-$CH_3O$)Ph |
| 6-686 | dimethoate | N | O | S | Me | H | O | O | 1 | $C(CH_3)_3$ |
| 6-687 | dimethoate | N | O | S | Me | H | O | O | 1 | Ph |
| 6-688 | dimethoate | N | O | S | Me | H | O | O | 1 | (p-$CH_3O$)Ph |
| 6-689 | dimethoate | N | O | O | Ph | H | O | O | 1 | $C(CH_3)_3$ |
| 6-690 | dimethoate | N | O | O | Ph | H | O | O | 1 | Ph |

TABLE 6-continued $$Z^1(X^1)_{\overline{m}}\overset{G^{10}}{\underset{(I)}{\overset{\|}{C}}}-G^{11}-A \text{ where A is }\overset{R^1}{\underset{R^2}{\overset{|}{C}}}-(G^{21}-\overset{G^{20}}{\overset{\|}{C}})_t-(X^2)_qZ^2$$

| Cmpd# | $Z^1(X^1)_m$—H | $X^1$ | $G^{10}$ | $G^{11}$ | $R^1$ | $R^2$ | $G^{20}$ | $G^{21}$ | t | $Z^2$ |
|---|---|---|---|---|---|---|---|---|---|---|
| 6-691 | dimethoate | N | O | O | Ph | H | O | O | 1 | (p-CH$_3$O)Ph |
| 6-692 | dimethoate | N | O | S | Ph | H | O | O | 1 | C(CH$_3$)$_3$ |
| 6-693 | dimethoate | N | O | S | Ph | H | O | O | 1 | Ph |
| 6-694 | dimethoate | N | O | S | Ph | H | O | O | 1 | (p-CH$_3$O)Ph |
| 6-695 | fenamiphos | N | O | O | H | H | O | O | 1 | C(CH$_3$)$_3$ |
| 6-696 | fenamiphos | N | O | O | Me | H | O | O | 1 | Ph |
| 6-697 | isofenphos | N | O | O | H | H | O | O | 1 | C(CH$_3$)$_3$ |
| 6-698 | isofenphos | N | O | O | Me | H | O | O | 1 | Ph |
| 6-699 | methamidophos | N | O | O | H | H | O | O | 1 | C(CH$_3$)$_3$ |
| 6-700 | methamidophos | N | O | O | Ph | H | O | O | 1 | Ph |
| 6-701 | monocrotophos | N | O | O | H | H | O | O | 1 | C(CH$_3$)$_3$ |
| 6-702 | monocrotophos | N | O | O | Ph | H | O | O | 1 | Ph |
| 6-703 | omethoate | N | O | O | H | H | O | O | 1 | C(CH$_3$)$_3$ |
| 6-704 | omethoate | N | O | O | H | H | O | O | 1 | Ph |
| 6-705 | vamidothion | N | O | O | H | H | O | O | 1 | C(CH$_3$)$_3$ |
| 6-706 | vamidothion | N | O | O | H | H | O | O | 1 | Ph |
| 6-707 | dicofol | O | O | O | H | H | O | O | 1 | C(CH$_3$)$_3$ |
| 6-708 | dicofol | O | O | O | H | H | O | O | 1 | Ph |
| 6-709 | cyromazine | N | O | O | H | H | O | O | 1 | C(CH$_3$)$_3$ |
| 6-710 | cyromazine | N | O | O | H | H | O | O | 1 | Ph |
| 6-711 | diafenthiuron | N | O | O | H | H | O | O | 1 | C(CH$_3$)$_3$ |
| 6-712 | diafenthiuron | N | O | O | H | H | O | O | 1 | Ph |
| 6-713 | fipronil | N | O | O | H | H | O | O | 1 | C(CH$_3$)$_3$ |
| 6-714 | fipronil | N | O | O | H | H | O | O | 1 | Ph |
| 6-715 | fipronil | N | O | O | H | H | O | O | 1 | (p-CH$_3$O)Ph |
| 6-716 | fipronil | N | O | O | H | H | O | O | 1 | (p-NO$_2$)Ph |
| 6-717 | fipronil | N | O | O | H | H | O | O | 1 | Ph—CH═CH |
| 6-718 | fipronil | N | O | O | H | H | O | O | 1 | (4-Br)PhCH═CH |
| 6-719 | fipronil | N | O | O | H | H | — | — | 0 | {N(Et)$_3$}$^+$ Cl$^-$ |
| 6-720 | fipronil | N | O | O | H | H | — | — | 0 | PhO |
| 6-721 | fipronil | N | O | O | H | H | — | — | 0 | {N(Me)$_2$Ph}$^+$ Cl$^-$ |
| 6-722 | fipronil | N | O | O | Me | H | O | O | 1 | C(CH$_3$)$_3$ |
| 6-723 | fipronil | N | O | O | Me | H | O | O | 1 | Ph |
| 6-724 | fipronil | N | O | O | Me | H | O | O | 1 | (p-CH$_3$O)Ph |
| 6-725 | fipronil | N | O | S | H | H | O | O | 1 | C(CH$_3$)$_3$ |
| 6-726 | fipronil | N | O | S | H | H | O | O | 1 | Ph |
| 6-727 | fipronil | N | O | S | H | H | O | O | 1 | (p-CH$_3$O)Ph |
| 6-728 | fipronil | N | O | S | Me | H | O | O | 1 | C(CH$_3$)$_3$ |
| 6-729 | fipronil | N | O | S | Me | H | O | O | 1 | Ph |
| 6-730 | fipronil | N | O | S | Me | H | O | O | 1 | (p-CH$_3$O)Ph |
| 6-731 | fipronil | N | O | O | Ph | H | O | O | 1 | C(CH$_3$)$_3$ |
| 6-732 | fipronil | N | O | O | Ph | H | O | O | 1 | Ph |
| 6-733 | fipronil | N | O | O | Ph | H | O | O | 1 | (p-CH$_3$O)Ph |
| 6-734 | fipronil | N | O | S | Ph | H | O | O | 1 | C(CH$_3$)$_3$ |
| 6-735 | fipronil | N | O | S | Ph | H | O | O | 1 | Ph |
| 6-736 | fipronil | N | O | S | Ph | H | O | O | 1 | (p-CH$_3$O)Ph |
| 6-737 | pymetrozine | N | O | O | H | H | O | O | 1 | C(CH$_3$)$_3$ |
| 6-738 | pymetrozine | N | O | O | H | H | O | O | 1 | Ph |
| 6-739 | pyrimidifen | N | O | O | H | H | O | O | 1 | C(CH$_3$)$_3$ |
| 6-740 | pyrimidifen | N | O | O | H | H | O | O | 1 | Ph |
| 6-741 | tebufenpyrad | N | O | O | H | H | O | O | 1 | C(CH$_3$)$_3$ |
| 6-742 | tebufenpyrad | N | O | O | H | H | O | O | 1 | Ph |
| 6-743 | bifenazate | N | O | O | H | H | O | O | 1 | C(CH$_3$)$_3$ |
| 6-744 | bifenazate | N | O | O | H | H | O | O | 1 | Ph |
| 6-745 | bromopropylate | O | O | O | H | H | O | O | 1 | C(CH$_3$)$_3$ |
| 6-746 | bromopropylate | O | O | O | H | H | O | O | 1 | Ph |
| 6-747 | chlorobenzilate | O | O | O | H | H | O | O | 1 | C(CH$_3$)$_3$ |
| 6-748 | chlorobenzilate | O | O | O | H | H | O | O | 1 | Ph |
| 6-749 | hexythiazox | N | O | O | H | H | O | O | 1 | C(CH$_3$)$_3$ |
| 6-750 | hexythiazox | N | O | O | H | H | O | O | 1 | Ph |
| 6-751 | fluvalinate | N | O | O | H | H | O | O | 1 | C(CH$_3$)$_3$ |
| 6-752 | fluvalinate | N | O | O | H | H | O | O | 1 | Ph |
| 6-753 | fluvalinate | N | O | O | H | H | O | O | 1 | (p-CH$_3$O)Ph |
| 6-754 | fluvalinate | N | O | O | H | H | O | O | 1 | (p-NO$_2$)Ph |
| 6-755 | fluvalinate | N | O | O | H | H | O | O | 1 | Ph—CH═CH |
| 6-756 | fluvalinate | N | O | O | H | H | O | O | 1 | (4-Br)PhCH═CH |
| 6-757 | fluvalinate | N | O | O | H | H | — | — | 0 | {N(Et)$_3$}$^+$ I$^-$ |
| 6-758 | fluvalinate | N | O | O | H | H | — | — | 0 | PhO |
| 6-759 | fluvalinate | N | O | O | H | H | — | — | 0 | {N(Me)$_2$Ph}$^+$ I$^-$ |
| 6-760 | fluvalinate | N | O | O | Me | H | O | O | 1 | C(CH$_3$)$_3$ |

TABLE 6-continued $$Z^1(X^1)_{\overline{m}} \overset{G^{10}}{\underset{(I)}{\overset{\|}{C}}} - G^{11} - A \text{ where A is } \overset{R^1}{\underset{R^2}{\overset{|}{C}}} - (G^{21} - \overset{G^{20}}{\overset{\|}{C}})_t - (X^2)_q Z^2$$

| Cmpd# | $Z^1(X^1)_m$—H | $X^1$ | $G^{10}$ | $G^{11}$ | $R^1$ | $R^2$ | $G^{20}$ | $G^{21}$ | t | $Z^2$ |
|---|---|---|---|---|---|---|---|---|---|---|
| 6-761 | fluvalinate | N | O | O | Me | H | O | O | 1 | Ph |
| 6-762 | fluvalinate | N | O | O | Me | H | O | O | 1 | (p-CH$_3$O)Ph |
| 6-763 | fluvalinate | N | O | S | H | H | O | O | 1 | C(CH$_3$)$_3$ |
| 6-764 | fluvalinate | N | O | S | H | H | O | O | 1 | Ph |
| 6-765 | fluvalinate | N | O | S | H | H | O | O | 1 | (p-CH$_3$O)Ph |
| 6-766 | fluvalinate | N | O | S | Me | H | O | O | 1 | C(CH$_3$)$_3$ |
| 6-767 | fluvalinate | N | O | S | Me | H | O | O | 1 | Ph |
| 6-768 | fluvalinate | N | O | S | Me | H | O | O | 1 | (p-CH$_3$O)Ph |
| 6-769 | fluvalinate | N | O | O | Ph | H | O | O | 1 | C(CH$_3$)$_3$ |
| 6-770 | fluvalinate | N | O | O | Ph | H | O | O | 1 | Ph |
| 6-771 | fluvalinate | N | O | O | Ph | H | O | O | 1 | (p-CH$_3$O)Ph |
| 6-772 | fluvalinate | N | O | S | Ph | H | O | O | 1 | C(CH$_3$)$_3$ |
| 6-773 | fluvalinate | N | O | S | Ph | H | O | O | 1 | Ph |
| 6-774 | fluvalinate | N | O | S | Ph | H | O | O | 1 | (p-CH$_3$O)Ph |

$Z^1(X^1)_m$—H compounds designated with *, (A), (B) chemical structures are described following Table 8.

Table 7 describes additional examples of compounds of Formula I, when m=0, t=0, q=1 and the pesticides which define the pesticidal moiety of these examples is $Z^2(X^2)$—H or $Z^2(X^2)$, which can be made using the procedures described hereinbefore.

TABLE 7

$$(Z^1(X^1)_{\overline{m}} \overset{G^{10}}{\overset{\|}{C}} - G^{11} - A \text{ where A is } \overset{R^1}{\underset{R^2}{\overset{|}{C}}} - (G^{21} - \overset{G^{20}}{\overset{\|}{C}})_t - (X^2)_q Z^2$$

(I)

| Cmpd# | $Z^1$ | $G^{10}$ | $G^{11}$ | $R^1$ | $R^2$ | $X^2$ | $Z^2(X^2)_q$-H or $Z^2(X^2)_q$ |
|---|---|---|---|---|---|---|---|
| 7-1 | methyl | O | O | H | H | N | fenpropidin |
| 7-2 | methyl | O | O | H | H | N | spiroxamine |
| 7-3 | n-propyl | O | O | H | H | N | fenpropidin |
| 7-4 | n-propyl | O | O | H | H | N | spiroxamine |
| 7-5 | C(CH$_3$)$_3$ | O | O | H | H | N | fenpropidin |
| 7-6 | C(CH$_3$)$_3$ | O | O | H | H | N | spiroxamine |
| 7-7 | Ph | O | O | H | H | N | fenpropidin |
| 7-8 | Ph | O | O | H | H | N | spiroxamine |
| 7-9 | 4 Cl—Ph | O | O | H | H | N | fenpropidin |
| 7-10 | 4 Cl—Ph | O | O | H | H | N | spiroxamine |
| 7-11 | methyl | O | O | H | H | N | propamocarb |
| 7-12 | C(CH$_3$)$_3$ | O | O | H | H | N | propamocarb |
| 7-13 | n-propyl | O | O | H | H | N | propamocarb |
| 7-14 | Ph | O | O | H | H | N | propamocarb |
| 7-15 | pyrid-2-yl | O | O | H | H | N | propamocarb |
| 7-16 | pyrid-3-yl | O | O | H | H | N | propamocarb |
| 7-17 | methyl | O | O | H | H | N | epoxiconazole |
| 7-18 | n-propyl | O | O | H | H | N | epoxiconazole |
| 7-19 | C(CH$_3$)$_3$ | O | O | H | H | N | epoxiconazole |
| 7-20 | Ph | O | O | H | H | N | epoxiconazole |
| 7-21 | PhO | O | O | H | H | N | epoxiconazole |
| 7-22 | Ph—NH | O | O | H | H | N | epoxiconazole |
| 7-23 | (4 Cl)Ph | O | O | H | H | N | epoxiconazole |
| 7-24 | (4 Cl)PhO | O | O | H | H | N | epoxiconazole |
| 7-25 | (4 Cl)PhNH | O | O | H | H | N | epoxiconazole |
| 7-26 | pyrid-2-yl | O | O | H | H | N | epoxiconazole |
| 7-27 | pyrid-4-yl | O | O | H | H | N | epoxiconazole |
| 7-28 | methyl | O | O | Me | H | N | epoxiconazole |
| 7-29 | n-propyl | O | O | Me | H | N | epoxiconazole |
| 7-30 | C(CH$_3$)$_3$ | O | O | Me | H | N | epoxiconazole |
| 7-31 | Ph | O | O | Ph | H | N | epoxiconazole |
| 7-32 | methyl | O | S | H | H | N | epoxiconazole |
| 7-33 | n-propyl | O | S | H | H | N | epoxiconazole |
| 7-34 | C(CH$_3$)$_3$ | O | S | H | H | N | epoxiconazole |

TABLE 7-continued $$(Z^1(X^1)_{\overline{m}} \overset{G^{10}}{\underset{(I)}{\overset{\|}{C}}} - G^{11} - A) \quad \text{where A is } \overset{R^1}{\underset{R^2}{\overset{|}{C}}} - (G^{21} - \overset{G^{20}}{\overset{\|}{C}})_t - (X^2)_q Z^2$$

| Cmpd# | $Z^1$ | $G^{10}$ | $G^{11}$ | $R^1$ | $R^2$ | $X^2$ | $Z^2(X^2)_q$-H or $Z^2(X^2)_q$ |
|---|---|---|---|---|---|---|---|
| 7-35 | Ph | O | S | H | H | N | epoxiconazole |
| 7-36 | methyl | O | S | Me | H | N | epoxiconazole |
| 7-37 | n-propyl | O | S | Me | H | N | epoxiconazole |
| 7-38 | C(CH$_3$)$_3$ | O | S | Me | H | N | epoxiconazole |
| 7-39 | Ph | O | S | Me | H | N | epoxiconazole |
| 7-40 | n-propyl | O | O | H | H | N | flusilazole |
| 7-41 | C(CH$_3$)$_3$ | O | O | H | H | N | flusilazole |
| 7-42 | Ph | O | O | H | H | N | flusilazole |
| 7-43 | PhO | O | O | H | H | N | flusilazole |
| 7-44 | methyl | O | O | H | H | N | propiconazole |
| 7-45 | ethyl | O | O | H | H | N | propiconazole |
| 7-46 | n-propyl | O | O | H | H | N | propiconazole |
| 7-47 | C(CH$_3$)$_3$ | O | O | H | H | N | propiconazole |
| 7-48 | Ph | O | O | H | H | N | propiconazole |
| 7-49 | (4 Cl)PhNH | O | O | H | H | N | propiconazole |
| 7-50 | methyl | O | O | H | H | N | penconazole |
| 7-51 | ethyl | O | O | H | H | N | penconazole |
| 7-52 | n-propyl | O | O | H | H | N | penconazole |
| 7-53 | C(CH$_3$)$_3$ | O | O | H | H | N | penconazole |
| 7-54 | methyl | O | O | H | H | N | fenbuconazole |
| 7-55 | ethyl | O | O | H | H | N | fenbuconazole |
| 7-56 | n-propyl | O | O | H | H | N | fenbuconazole |
| 7-57 | C(CH$_3$)$_3$ | O | O | H | H | N | fenbuconazole |
| 7-58 | Ph | O | O | H | H | N | fenbuconazole |
| 7-59 | PhO | O | O | H | H | N | fenbuconazole |
| 7-60 | (4 Cl)PhNH | O | O | H | H | N | fenbuconazole |
| 7-61 | methyl | O | O | H | H | N | myclobutanil |
| 7-62 | ethyl | O | O | H | H | N | myclobutanil |
| 7-63 | n-propyl | O | O | H | H | N | myclobutanil |
| 7-64 | C(CH$_3$)$_3$ | O | O | H | H | N | myclobutanil |
| 7-65 | Ph | O | O | H | H | N | mydobutanil |
| 7-66 | PhO | O | O | H | H | N | myclobutanil |
| 7-67 | (4 Cl)PhNH | O | O | H | H | N | myclobutanil |
| 7-68 | pyrid-2-yl | O | O | Ph | H | N | myclobutanil |
| 7-69 | pyrid-4-yl | O | O | Ph | H | N | myclobutanil |
| 7-70 | PhO | O | O | H | H | S | mancozeb |
| 7-71 | (4 Cl)PhO | O | O | H | H | S | mancozeb |
| 7-72 | Ph—NH | O | O | H | H | S | mancozeb |
| 7-73 | (4 Cl)PhNH | O | O | H | H | S | mancozeb |
| 7-74 | PhO | O | O | Me | H | S | mancozeb |
| 7-75 | (4 Cl)PhO | O | O | Me | H | S | mancozeb |
| 7-76 | Ph—NH | O | O | Me | H | S | mancozeb |
| 7-77 | (4 Cl)PhNH | O | O | Me | H | S | mancozeb |
| 7-78 | PhO | O | O | H | H | S | maneb |
| 7-79 | (4 Cl)PhO | O | O | H | H | S | maneb |
| 7-80 | Ph—NH | O | O | H | H | S | maneb |
| 7-81 | (4 Cl)PhNH | O | O | H | H | S | maneb |
| 7-82 | PhO | O | O | H | H | S | propineb |
| 7-83 | (4 Cl)PhO | O | O | H | H | S | propineb |
| 7-84 | Ph—NH | O | O | H | H | S | propineb |
| 7-85 | (4 Cl)PhNH | O | O | H | H | S | propineb |
| 7-86 | C(CH$_3$)$_3$ | O | O | H | H | N | fenpropimorph |
| 7-87 | Ph | O | O | H | H | N | fenpropimorph |
| 7-88 | Ph—CH$_2$ | O | O | H | H | N | fenpropimorph |
| 7-89 | Ph—CH$_2$CH$_2$ | O | O | H | H | N | fenpropimorph |
| 7-90 | PhO | O | O | H | H | N | fenpropimorph |
| 7-91 | (4 Cl)PhO | O | O | H | H | N | fenpropimorph |
| 7-92 | 4 Cl—Ph—N | O | O | H | H | N | fenpropimorph |
| 7-93 | PhO | O | O | H | H | O | fosetyl |
| 7-94 | (4 Cl)PhO | O | O | H | H | O | fosetyl |
| 7-95 | Ph—NH | O | O | H | H | O | fosetyl |
| 7-96 | (4 Cl)PhNH | O | O | H | H | O | fosetyl |
| 7-97 | PhO | O | S | H | H | O | fosetyl |
| 7-98 | (4 Cl)PhO | O | S | H | H | O | fosetyl |
| 7-99 | Ph—NH | O | S | H | H | O | fosetyl |
| 7-100 | (4 Cl)PhNH | O | S | H | H | O | fosetyl |
| 7-101 | C(CH$_3$)$_3$ | O | O | H | H | N | quinoxyfen |
| 7-102 | Ph | O | O | H | H | N | quinoxyfen |
| 7-103 | methyl | O | O | H | H | O | tebuconazole |

TABLE 7-continued $$(Z^1(X^1)_{\overline{m}}\overset{G^{10}}{\overset{\|}{C}}-G^{11}-A \text{ where A is } \overset{R^1}{\underset{R^2}{\overset{|}{C}}}-(G^{21}\overset{G^{20}}{\overset{\|}{C}})_t-(X^2)_q Z^2$$

(I)

| Cmpd# | $Z^1$ | $G^{10}$ | $G^{11}$ | $R^1$ | $R^2$ | $X^2$ | $Z^2(X^2)_q$-H or $Z^2(X^2)_q$ |
|---|---|---|---|---|---|---|---|
| 7-104 | n-propyl | O | O | H | H | O | tebuconazole |
| 7-105 | C(CH$_3$)$_3$ | O | O | H | H | O | tebuconazole |
| 7-106 | Ph | O | O | H | H | O | tebuconazole |
| 7-107 | PhO | O | O | H | H | O | tebuconazole |
| 7-108 | Ph—NH | O | O | H | H | O | tebuconazole |
| 7-109 | 4 Cl—Ph | O | O | H | H | O | tebuconazole |
| 7-110 | (4 Cl)PhO | O | O | H | H | O | tebuconazole |
| 7-111 | (4 Cl)PhNH | O | O | H | H | O | tebuconazole |
| 7-112 | pyrid-2-yl | O | O | H | H | O | tebuconazole |
| 7-113 | pyrid-4-yl | O | O | H | H | O | tebuconazole |
| 7-114 | methyl | O | O | Me | H | O | tebuconazole |
| 7-115 | n-propyl | O | O | Me | H | O | tebuconazole |
| 7-116 | C(CH$_3$)$_3$ | O | O | Me | H | O | tebuconazole |
| 7-117 | Ph | O | O | Ph | H | O | tebuconazole |
| 7-118 | methyl | O | S | H | H | O | tebuconazole |
| 7-119 | n-propyl | O | S | H | H | O | tebuconazole |
| 7-120 | C(CH$_3$)$_3$ | O | S | H | H | O | tebuconazole |
| 7-121 | Ph | O | S | H | H | O | tebuconazole |
| 7-122 | methyl | O | S | Me | H | O | tebuconazole |
| 7-123 | n-propyl | O | S | Me | H | O | tebuconazole |
| 7-124 | C(CH$_3$)$_3$ | O | S | Me | H | O | tebuconazole |
| 7-125 | Ph | O | S | Me | H | O | tebuconazole |
| 7-126 | methyl | O | O | H | H | N | zoxamide |
| 7-127 | n-propyl | O | O | H | H | N | zoxamide |
| 7-128 | C(CH$_3$)$_3$ | O | O | H | H | N | zoxamide |
| 7-129 | Ph | O | O | H | H | N | zoxamide |
| 7-130 | PhO | O | O | H | H | N | zoxamide |
| 7-131 | Ph—NH | O | O | H | H | N | zoxamide |
| 7-132 | 4 Cl—Ph | O | O | H | H | N | zoxamide |
| 7-133 | (4 Cl)PhO | O | O | H | H | N | zoxamide |
| 7-134 | (4 Cl)PhNH | O | O | H | H | N | zoxamide |
| 7-135 | pyrid-2-yl | O | O | H | H | N | zoxamide |
| 7-136 | pyrid-4-yl | O | O | H | H | N | zoxamide |
| 7-137 | methyl | O | O | Me | H | N | zoxamide |
| 7-138 | n-propyl | O | O | Me | H | N | zoxamide |
| 7-139 | C(CH$_3$)$_3$ | O | O | Me | H | N | zoxamide |
| 7-140 | Ph | O | O | Ph | H | N | zoxamide |
| 7-141 | methyl | O | S | H | H | N | zoxamide |
| 7-142 | n-propyl | O | S | H | H | N | zoxamide |
| 7-143 | C(CH$_3$)$_3$ | O | S | H | H | N | zoxamide |
| 7-144 | Ph | O | S | H | H | N | zoxamide |
| 7-145 | methyl | O | S | Me | H | N | zoxamide |
| 7-146 | n-propyl | O | S | Me | H | N | zoxamide |
| 7-147 | C(CH$_3$)$_3$ | O | S | Me | H | N | zoxamide |
| 7-148 | Ph | O | S | Me | H | N | zoxamide |
| 7-149 | methyl | O | O | H | H | N | cymoxanil(A) |
| 7-150 | n-propyl | O | O | H | H | N | cymoxanil(A) |
| 7-151 | C(CH$_3$)$_3$ | O | O | H | H | N | cymoxanil(A) |
| 7-152 | t-BuO | O | O | H | H | N | cymoxanil(A) |
| 7-153 | Ph | O | O | H | H | N | cymoxanil(A) |
| 7-154 | PhO | O | O | H | H | N | cymoxanil(A) |
| 7-155 | Ph—NH | O | O | H | H | N | cymoxanil(A) |
| 7-156 | 4 Cl—Ph | O | O | H | H | N | cymoxanil(A) |
| 7-157 | (4 Cl)PhO | O | O | H | H | N | cymoxanil(A) |
| 7-158 | (4 Cl)PhNH | O | O | H | H | N | cymoxanil(A) |
| 7-159 | pyrid-2-yl | O | O | H | H | N | cymoxanil(A) |
| 7-160 | pyrid-4-yl | O | O | H | H | N | cymoxanil(A) |
| 7-161 | methyl | O | O | Me | H | N | cymoxanil(A) |
| 7-162 | n-propyl | O | O | Me | H | N | cymoxanil(A) |
| 7-163 | t-BuO | O | O | Me | H | N | cymoxanil(A) |
| 7-164 | PhO | O | O | Ph | H | N | cymoxanil(A) |
| 7-165 | methyl | O | S | H | H | N | cymoxanil(A) |
| 7-166 | n-propyl | O | S | H | H | N | cymoxanil(A) |
| 7-167 | C(CH$_3$)$_3$ | O | S | H | H | N | cymoxanil(A) |
| 7-168 | PhO | O | S | H | H | N | cymoxanil(A) |
| 7-169 | methyl | O | S | Me | H | N | cymoxanil(A) |
| 7-170 | n-propyl | O | S | Me | H | N | cymoxanil(A) |
| 7-171 | t-BuO | O | S | Me | H | N | cymoxanil(A) |
| 7-172 | PhO | O | S | Me | H | N | cymoxanil(A) |

TABLE 7-continued $$(Z^1(X^1)_m)-\overset{G^{10}}{\underset{\|}{C}}-G^{11}-A \text{ where A is } \overset{R^1}{\underset{R^2}{\overset{|}{C}}}-(G^{21}-\overset{G^{20}}{\underset{\|}{C}})_t-(X^2)_qZ^2$$

(I)

| Cmpd# | $Z^1$ | $G^{10}$ | $G^{11}$ | $R^1$ | $R^2$ | $X^2$ | $Z^2(X^2)_q$-H or $Z^2(X^2)_q$ |
|---|---|---|---|---|---|---|---|
| 7-173 | C(CH$_3$)$_3$-NH | O | O | H | H | O | clopyralid |
| 7-174 | Ph-NH | O | O | H | H | O | clopyralid |
| 7-175 | (p-CH$_3$O)Ph-NH | O | O | H | H | O | clopyralid |
| 7-176 | (p-NO$_2$)Ph-NH | O | O | H | H | O | clopyralid |
| 7-177 | PhO | O | O | H | H | O | clopyralid |
| 7-178 | (p-CH$_3$O)PhO | O | O | H | H | O | clopyralid |
| 7-179 | (p-NO$_2$)PhO | O | O | H | H | O | clopyralid |
| 7-180 | CH$_3$CH$_2$NH | O | O | H | H | O | clopyralid |
| 7-181 | (CH$_3$)$_3$C-NH | O | O | H | H | O | clopyralid |
| 7-182 | CH$_3$CH$_2$O | O | O | H | H | O | clopyralid |
| 7-183 | (CH$_3$)$_3$C-O | O | O | H | H | O | clopyralid |
| 7-184 | (CH$_3$)$_3$C-NH | O | O | H | H | N | trifluralin |
| 7-185 | Ph-NH | O | O | H | H | N | trifluralin |
| 7-186 | (CH$_3$)$_3$C-O | O | O | H | H | N | trifluralin |
| 7-187 | PhO | O | O | H | H | N | trifluralin |
| 7-188 | C(CH$_3$)$_3$ | O | O | H | H | O | acifluorfen |
| 7-189 | Ph-NH | O | O | H | H | O | acifluorfen |
| 7-190 | (CH$_3$)$_3$C-N | O | O | H | H | O | acifluorfen |
| 7-191 | PhO | O | O | H | H | O | acifluorfen |
| 7-192 | (p-NO$_2$)PhO | O | O | H | H | O | acifluorfen |
| 7-193 | CH$_3$CH$_2$-NH | O | O | H | H | O | imazaquin |
| 7-194 | (CH$_3$)$_3$C-NH | O | O | H | H | O | imazaquin |
| 7-195 | CH$_3$CH$_2$O | O | O | H | H | O | imazaquin |
| 7-196 | (CH$_3$)$_3$C-O | O | O | H | H | O | imazaquin |
| 7-197 | PhO | O | O | H | H | O | imazaquin |
| 7-198 | Ph-NH | O | O | H | H | O | imazaquin |
| 7-199 | (p-CH$_3$O)PhO | O | O | H | H | O | imazaquin |
| 7-200 | (p-CH$_3$O)Ph-NH | O | O | H | H | O | imazaquin |
| 7-201 | (p-NO$_2$)PhO | O | O | H | H | O | imazaquin |
| 7-202 | (p-NO$_2$)Ph-NH | O | O | H | H | O | imazaquin |
| 7-203 | CH$_3$CH$_2$-NH | O | O | H | H | O | imazethapyr |
| 7-204 | (CH$_3$)$_3$C-NH | O | O | H | H | O | imazethapyr |
| 7-205 | CH$_3$CH$_2$O | O | O | H | H | O | imazethapyr |
| 7-206 | (CH$_3$)$_3$C-O | O | O | H | H | O | imazethapyr |
| 7-207 | PhO | O | O | H | H | O | imazethapyr |
| 7-208 | Ph-NH | O | O | H | H | O | imazethapyr |
| 7-209 | (p-CH$_3$O)PhO | O | O | H | H | O | imazethapyr |
| 7-210 | (p-CH$_3$O)Ph-NH | O | O | H | H | O | imazethapyr |
| 7-211 | (p-NO$_2$)PhO | O | O | H | H | O | imazethapyr |
| 7-212 | (p-NO$_2$)Ph-N | O | O | H | H | O | imazethapyr |
| 7-213 | CH$_3$CH$_2$-NH | O | O | H | H | O | fenoxaprop |
| 7-214 | (CH$_3$)$_3$C-NH | O | O | H | H | O | fenoxaprop |
| 7-215 | CH$_3$CH$_2$O | O | O | H | H | O | fenoxaprop |
| 7-216 | (CH$_3$)$_3$C-O | O | O | H | H | O | fenoxaprop |
| 7-217 | PhO | O | O | H | H | O | fenoxaprop |
| 7-218 | Ph-NH | O | O | H | H | O | fenoxaprop |
| 7-219 | (p-CH$_3$O)PhO | O | O | H | H | O | fenoxaprop |
| 7-220 | (p-CH$_3$O)Ph-NH | O | O | H | H | O | fenoxaprop |
| 7-221 | (p-NO$_2$)PhO | O | O | H | H | O | fenoxaprop |
| 7-222 | (p-NO$_2$)Ph-N | O | O | H | H | O | fenoxaprop |
| 7-223 | CH$_3$CH$_2$-NH | O | O | H | H | O | fluazifop |
| 7-224 | (CH$_3$)$_3$C-NH | O | O | H | H | O | fluazifop |
| 7-225 | CH$_3$CH$_2$O | O | O | H | H | O | fluazifop |
| 7-226 | (CH$_3$)$_3$C-O | O | O | H | H | O | fluazifop |
| 7-227 | PhO | O | O | H | H | O | fluazifop |
| 7-228 | Ph-NH | O | O | H | H | O | fluazifop |
| 7-229 | (p-CH$_3$O)PhO | O | O | H | H | O | fluazifop |
| 7-230 | (p-CH$_3$O)Ph-NH | O | O | H | H | O | fluazifop |
| 7-231 | (p-NO$_2$)PhO | O | O | H | H | O | fluazifop |
| 7-232 | (p-NO$_2$)Ph-N | O | O | H | H | O | fluazifop |
| 7-233 | PhO | O | O | H | H | O | haloxyfop |
| 7-234 | Ph-NH | O | O | H | H | O | haloxyfop |
| 7-235 | (p-CH$_3$O)PhO | O | O | H | H | O | haloxyfop |
| 7-236 | (p-CH$_3$O)Ph-NH | O | O | H | H | O | haloxyfop |
| 7-237 | (p-NO$_2$)PhO | O | O | H | H | O | haloxyfop |
| 7-238 | C(CH$_3$)$_3$ | O | O | H | H | N | hexazinone |
| 7-239 | Ph | O | O | H | H | N | hexazinone |
| 7-240 | Ph-N | O | O | H | H | N | hexazinone |
| 7-241 | (CH$_3$)$_3$C-O | O | O | H | H | N | pronamide |

TABLE 7-continued $$(Z^1(X^1)_{\overline{m}}\overset{\overset{G^{10}}{\|}}{C}-G^{11}-A \text{ where A is } \overset{R^1}{\underset{R^2}{C}}-(G^{21}-\overset{\overset{G^{20}}{\|}}{C})_t-(X^2)_q Z^2$$

(I)

| Cmpd# | $Z^1$ | $G^{10}$ | $G^{11}$ | $R^1$ | $R^2$ | $X^2$ | $Z^2(X^2)_q$-H or $Z^2(X^2)_q$ |
|---|---|---|---|---|---|---|---|
| 7-242 | PhO | O | O | H | H | N | pronamide |
| 7-243 | Ph—NH | O | O | H | H | N | pronamide |
| 7-244 | (CH$_3$)$_3$C—O | O | O | H | H | N | diflufenican |
| 7-245 | PhO | O | O | H | H | N | flumetsulam |
| 7-246 | PhO | O | O | H | H | N | propanil |
| 7-247 | PhO | O | O | H | H | N | asulam (A)* |
| 7-248 | Ph—NH | O | O | H | H | N | asulam (B)* |
| 7-249 | PhO | O | O | H | H | N | asulam (A)* |
| 7-250 | Ph—NH | O | O | H | H | N | asulam (B)* |
| 7-251 | PhO | O | O | H | H | N | chlorpropham |
| 7-252 | PhO | O | O | H | H | N | desmedipham (A)* |
| 7-253 | Ph—NH | O | O | H | H | N | desmedipham (B)* |
| 7-254 | PhO | O | O | H | H | N | desmedipham (A)* |
| 7-255 | Ph—NH | O | O | H | H | N | desmedipham (B)* |
| 7-256 | PhO | O | O | H | H | N | phenmedipham (A)* |
| 7-257 | Ph—NH | O | O | H | H | N | phenmedipham (B)* |
| 7-258 | PhO | O | O | H | H | N | phenmedipham (A)* |
| 7-259 | Ph—NH | O | O | H | H | N | phenmedipham (B)* |
| 7-260 | PhO | O | O | H | H | O | sulcotrione (A)* |
| 7-261 | Ph—NH | O | O | H | H | O | sulcotrione (B)* |
| 7-262 | PhO | O | O | H | H | O | sulcotrione (A)* |
| 7-263 | Ph—NH | O | O | H | H | O | sulcotrione (B)* |
| 7-264 | PhO | O | S | H | H | O | sulcotrione (A)* |
| 7-265 | Ph—NH | O | S | H | H | O | sulcotrione (B)* |
| 7-266 | C(CH$_3$)$_3$ | O | O | H | H | O | sethoxydim |
| 7-267 | (CH$_3$)$_3$C—O | O | O | H | H | O | sethoxydim |
| 7-268 | PhO | O | O | H | H | O | sethoxydim |
| 7-269 | Ph—N | O | O | H | H | O | sethoxydim |
| 7-270 | (CH$_3$)$_3$C—O | O | S | H | H | O | sethoxydim |
| 7-271 | PhO | O | S | H | H | O | sethoxydim |
| 7-272 | C(CH$_3$)$_3$ | O | O | H | H | O | tralkoxydim |
| 7-273 | (CH$_3$)$_3$C—O | O | O | H | H | O | tralkoxydim |
| 7-274 | PhO | O | O | H | H | O | tralkoxydim |
| 7-275 | Ph—N | O | O | H | H | O | tralkoxydim |
| 7-276 | (CH$_3$)$_3$C—O | O | S | H | H | O | tralkoxydim |
| 7-277 | PhO | O | S | H | H | O | tralkoxydim |
| 7-278 | C(CH$_3$)$_3$ | O | O | H | H | N | pendimethalin |
| 7-279 | (CH$_3$)$_3$C—O | O | O | H | H | N | pendimethalin |
| 7-280 | PhO | O | O | H | H | N | pendimethalin |
| 7-281 | Ph—N | O | O | H | H | N | pendimethalin |
| 7-282 | (CH$_3$)$_3$C—O | O | O | H | H | O | dinoseb |
| 7-283 | PhO | O | O | H | H | O | dinoseb |
| 7-284 | C(CH$_3$)$_3$ | O | O | H | H | N | aclonifen |
| 7-285 | (CH$_3$)$_3$C—O | O | O | H | H | N | aclonifen |
| 7-286 | PhO | O | O | H | H | N | aclonifen |
| 7-287 | Ph—N | O | O | H | H | N | aclonifen |
| 7-288 | (CH$_3$)$_3$C—O | O | O | H | H | N | fomesafen |
| 7-289 | PhO | O | O | H | H | N | fomesafen |
| 7-290 | Ph—N | O | O | H | H | N | fomesafen |
| 7-291 | C(CH$_3$)$_3$ | O | O | H | H | N | atrazine (A)* |
| 7-292 | C(CH$_3$)$_3$ | O | O | H | H | N | atrazine (B)* |
| 7-293 | (CH$_3$)$_3$C—O | O | O | H | H | N | atrazine (A)* |
| 7-294 | (CH$_3$)$_3$C—O | O | O | H | H | N | atrazine (B)* |
| 7-295 | PhO | O | O | H | H | N | atrazine (A)* |
| 7-296 | PhO | O | O | H | H | N | atrazine (B)* |
| 7-297 | Ph—N | O | O | H | H | N | atrazine (A)* |
| 7-298 | Ph—N | O | O | H | H | N | atrazine (B)* |
| 7-299 | C(CH$_3$)$_3$ | O | O | H | H | N | terbuthylazine (A)* |
| 7-300 | C(CH$_3$)$_3$ | O | O | H | H | N | terbuthylazine (B)* |
| 7-301 | (CH$_3$)$_3$C—O | O | O | H | H | N | terbuthylazine (A)* |
| 7-302 | (CH$_3$)$_3$C—O | O | O | H | H | N | terbuthylazine (B)* |
| 7-303 | PhO | O | O | H | H | N | terbuthylazine (A)* |
| 7-304 | PhO | O | O | H | H | N | terbuthylazine (B)* |
| 7-305 | Ph—N | O | O | H | H | N | terbuthylazine (A)* |
| 7-306 | Ph—N | O | O | H | H | N | terbuthylazine (B)* |

TABLE 7-continued $$(Z^1(X^1)_{\overline{m}} \overset{G^{10}}{\underset{(I)}{\|}} -G^{11}-A \text{ where A is } \overset{R^1}{\underset{R^2}{|}} -(G^{21} \overset{G^{20}}{\underset{\|}{C}})_t -(X^2)_q Z^2$$

| Cmpd# | $Z^1$ | $G^{10}$ | $G^{11}$ | $R^1$ | $R^2$ | $X^2$ | $Z^2(X^2)_q$-H or $Z^2(X^2)_q$ |
|---|---|---|---|---|---|---|---|
| 7-307 | C(CH$_3$)$_3$ | O | O | H | H | N | terbumeton (A)* |
| 7-308 | C(CH$_3$)$_3$ | O | O | H | H | N | terbumeton (B)* |
| 7-309 | (CH$_3$)$_3$C—O | O | O | H | H | N | terbumeton (A)* |
| 7-310 | (CH$_3$)$_3$C—O | O | O | H | H | N | terbumeton (B)* |
| 7-311 | PhO | O | O | H | H | N | terbumeton (A)* |
| 7-312 | PhO | O | O | H | H | N | terbumeton (B)* |
| 7-313 | C(CH$_3$)$_3$ | O | O | H | H | N | ametryn (A)* |
| 7-314 | C(CH$_3$)$_3$ | O | O | H | H | N | ametryn (B)* |
| 7-315 | (CH$_3$)$_3$C—O | O | O | H | H | N | ametryn (A)* |
| 7-316 | (CH$_3$)$_3$C—O | O | O | H | H | N | ametryn (B)* |
| 7-317 | PhO | O | O | H | H | N | ametryn (A)* |
| 7-318 | PhO | O | O | H | H | N | ametryn (B)* |
| 7-319 | Ph—N | O | O | H | H | N | ametryn (A)* |
| 7-320 | Ph—N | O | O | H | H | N | ametryn (B)* |
| 7-321 | C(CH$_3$)$_3$ | O | O | H | H | N | metribuzin |
| 7-322 | (CH$_3$)$_3$C—O | O | O | H | H | N | metribuzin |
| 7-323 | PhO | O | O | H | H | N | metribuzin |
| 7-324 | Ph—N | O | O | H | H | N | metribuzin |
| 7-325 | PhO | O | O | H | H | N | amitrole (A)* |
| 7-326 | PhO | O | O | H | H | N | amitrole (B)* |
| 7-327 | Ph—N | O | O | H | H | N | amitrole (A)* |
| 7-328 | Ph—N | O | O | H | H | N | amitrole (B)* |
| 7-329 | C(CH$_3$)$_3$ | O | O | H | H | N | bentazon |
| 7-330 | (CH$_3$)$_3$C—O | O | O | H | H | N | bentazon |
| 7-331 | PhO | O | O | H | H | N | bentazon |
| 7-332 | Ph—N | O | O | H | H | N | bentazon |
| 7-333 | (CH$_3$)$_3$C—O | O | O | H | H | N | bentazon |
| 7-334 | PhO | O | O | H | H | N | bromacil |
| 7-335 | (CH$_3$)$_3$C—O | O | O | H | H | N | bromacil |
| 7-336 | PhO | O | O | H | H | N | chlorotoluron |
| 7-337 | C(CH$_3$)$_3$ | O | O | H | H | N | chlorotoluron |
| 7-338 | (CH$_3$)$_3$C—O | O | O | H | H | N | diuron |
| 7-339 | PhO | O | O | H | H | N | diuron |
| 7-340 | Ph—N | O | O | H | H | N | diuron |
| 7-341 | C(CH$_3$)$_3$ | O | O | H | H | N | fluometuron |
| 7-342 | (CH$_3$)$_3$C—O | O | O | H | H | N | fluometuron |
| 7-343 | PhO | O | O | H | H | N | fluometuron |
| 7-344 | Ph—N | O | O | H | H | N | fluometuron |
| 7-345 | C(CH$_3$)$_3$ | O | O | H | H | N | isoproturon |
| 7-346 | (CH$_3$)$_3$C—O | O | O | H | H | N | isoproturon |
| 7-347 | PhO | O | O | H | H | N | isoproturon |
| 7-348 | Ph—N | O | O | H | H | N | isoproturon |
| 7-349 | (CH$_3$)$_3$C—S | O | O | H | H | N | isoproturon |
| 7-350 | Ph—S | O | O | H | H | N | isoproturon |
| 7-351 | (CH$_3$)$_3$C—S | O | O | H | H | N | linuron |
| 7-352 | Ph—S | O | O | H | H | N | linuron |
| 7-353 | C(CH$_3$)$_3$ | O | O | H | H | N | chlorsulfuron |
| 7-354 | (CH$_3$)$_3$C—O | O | O | H | H | N | chlorsulfuron |
| 7-355 | PhO | O | O | H | H | N | chlorsulfuron |
| 7-356 | Ph—N | O | O | H | H | N | chlorsulfuron |
| 7-357 | C(CH$_3$)$_3$ | O | O | H | H | N | nicosulfuron |
| 7-358 | (CH$_3$)$_3$C—O | O | O | H | H | N | nicosulfuron |
| 7-359 | (CH$_3$)$_3$C—N | O | O | H | H | N | nicosulfuron |
| 7-360 | (CH$_3$)$_3$C—S | O | O | H | H | N | nicosulfuron |
| 7-361 | PhO | O | O | H | H | N | nicosulfuron |
| 7-362 | Ph—N | O | O | H | H | N | nicosulfuron |
| 7-363 | Ph—S | O | O | H | H | N | nicosulfuron |
| 7-364 | C(CH$_3$)$_3$ | O | O | H | H | N | rimsulfuron |
| 7-365 | (CH$_3$)$_3$C—O | O | O | H | H | N | rimsulfuron |
| 7-366 | (CH$_3$)$_3$C—N | O | O | H | H | N | rimsulfuron |
| 7-367 | (CH$_3$)$_3$C—S | O | O | H | H | N | rimsulfuron |
| 7-368 | PhO | O | O | H | H | N | rimsulfuron |
| 7-369 | Ph—N | O | O | H | H | N | rimsulfuron |
| 7-370 | Ph—S | O | O | H | H | N | rimsulfuron |
| 7-371 | C(CH$_3$)$_3$ | O | O | H | H | N | chlorfluazuron |
| 7-372 | (CH$_3$)$_3$C—O | O | O | H | H | N | chlorfluazuron |
| 7-373 | (CH$_3$)$_3$C—N | O | O | H | H | N | chlorfluazuron |
| 7-374 | C(CH$_3$)$_3$ | O | O | H | H | N | diflubenzuron |
| 7-375 | (CH$_3$)$_3$C—O | O | O | H | H | N | diflubenzuron |

TABLE 7-continued $$(Z^1(X^1)_{\overline{m}}\overset{G^{10}}{\underset{(I)}{\overset{\|}{C}}}-G^{11}-A \text{ where A is } \overset{R^1}{\underset{R^2}{\overset{|}{C}}}-(G^{21}\overset{G^{20}}{\overset{\|}{-C}})_t-(X^2)_qZ^2$$

| Cmpd# | $Z^1$ | $G^{10}$ | $G^{11}$ | $R^1$ | $R^2$ | $X^2$ | $Z^2(X^2)_q$-H or $Z^2(X^2)_q$ |
|---|---|---|---|---|---|---|---|
| 7-376 | $(CH_3)_3C$—N | O | O | H | H | N | diflubenzuron |
| 7-377 | $(CH_3)_3C$—S | O | O | H | H | N | diflubenzuron |
| 7-378 | PhO | O | O | H | H | N | diflubenzuron |
| 7-379 | Ph—N | O | O | H | H | N | diflubenzuron |
| 7-380 | Ph—S | O | O | H | H | N | diflubenzuron |
| 7-381 | $(CH_3)_3C$—O | O | O | H | H | N | flucycloxuron |
| 7-382 | $(CH_3)_3C$—N | O | O | H | H | N | flucycloxuron |
| 7-383 | $(CH_3)_3C$—S | O | O | H | H | N | flucycloxuron |
| 7-384 | PhO | O | O | H | H | N | flucycloxuron |
| 7-385 | Ph—N | O | O | H | H | N | flufenoxuron |
| 7-386 | Ph—S | O | O | H | H | N | flufenoxuron |
| 7-387 | PhO | O | O | H | H | N | hexaflumuron |
| 7-388 | PhO | O | O | H | H | N | lufenuron |
| 7-389 | PhO | O | O | H | H | N | novaluron |
| 7-390 | PhO | O | O | H | H | N | teflubenzuron |
| 7-391 | PhO | O | O | H | H | N | triflumuron |
| 7-392 | PhO | O | O | H | H | N | fluazuron |
| 7-393 | PhO | O | O | H | H | N | aldicarb |
| 7-394 | $(CH_3)_3C$—O | O | O | H | H | N | bendiocarb |
| 7-395 | $(CH_3)_3C$—N | O | O | H | H | N | bendiocarb |
| 7-396 | $(CH_3)_3C$—O | O | O | H | H | N | BPMC (fenobucarb) |
| 7-397 | $(CH_3)_3C$—N | O | O | H | H | N | BPMC (fenobucarb) |
| 7-398 | $C(CH_3)_3$ | O | O | H | H | N | carbaryl |
| 7-399 | $(CH_3)_3C$—O | O | O | H | H | N | carbaryl |
| 7-400 | $(CH_3)_3C$—N | O | O | H | H | N | carbaryl |
| 7-401 | $(CH_3)_3C$—S | O | O | H | H | N | carbaryl |
| 7-402 | PhO | O | O | H | H | N | carbaryl |
| 7-403 | Ph—N | O | O | H | H | N | carbaryl |
| 7-404 | Ph—S | O | O | H | H | N | carbaryl |
| 7-405 | $C(CH_3)_3$ | O | O | Me | H | N | carbaryl |
| 7-406 | $(CH_3)_3C$—O | O | O | Me | H | N | carbaryl |
| 7-407 | $(CH_3)_3C$—N | O | O | Me | H | N | carbaryl |
| 7-408 | $(CH_3)_3C$—S | O | O | Me | H | N | carbaryl |
| 7-409 | PhO | O | O | Ph | H | N | carbaryl |
| 7-410 | Ph—N | O | O | Ph | H | N | carbaryl |
| 7-411 | Ph—S | O | O | Ph | H | N | carbaryl |
| 7-412 | $C(CH_3)_3$ | O | S | H | H | N | carbaryl |
| 7-413 | $(CH_3)_3C$—O | O | S | H | H | N | carbaryl |
| 7-414 | $(CH_3)_3C$—N | O | S | H | H | N | carbaryl |
| 7-415 | $(CH_3)_3C$—S | O | S | H | H | N | carbaryl |
| 7-416 | $(CH_3)_3C$—O | O | S | Ph | H | N | carbaryl |
| 7-417 | $(CH_3)_3C$—O | O | S | Ph | H | N | carbofuran |
| 7-418 | $(CH_3)_3C$—N | O | S | H | H | N | cartap |
| 7-419 | $(CH_3)_3C$—S | O | S | H | H | N | cartap |
| 7-420 | $(CH_3)_3C$—N | O | S | Ph | H | N | ethiofencarb |
| 7-421 | $(CH_3)_3C$—S | O | S | Ph | H | N | ethiofencarb |
| 7-422 | $(CH_3)_3C$—N | O | S | Ph | H | N | fenoxycarb |
| 7-423 | $(CH_3)_3C$—S | O | S | Ph | H | N | fenoxycarb |
| 7-424 | $(CH_3)_3C$—N | O | S | Ph | H | N | formetanate |
| 7-425 | $(CH_3)_3C$—S | O | S | Ph | H | N | formetanate |
| 7-426 | $(CH_3)_3C$—N | O | O | Ph | H | N | isoprocarb |
| 7-427 | $(CH_3)_3C$—S | O | O | Ph | H | N | isoprocarb |
| 7-428 | PhO | O | O | H | H | N | methiocarb |
| 7-429 | Ph—N | O | O | H | H | N | methiocarb |
| 7-430 | PhO | O | O | H | H | N | methomyl |
| 7-431 | Ph—N | O | O | H | H | N | methomyl |
| 7-432 | PhO | O | O | H | H | N | oxamyl |
| 7-433 | Ph—N | O | O | H | H | N | oxamyl |
| 7-434 | PhO | O | O | H | H | N | phosphocarb |
| 7-435 | Ph—N | O | O | H | H | N | phosphocarb |
| 7-436 | PhO | O | O | H | H | N | promecarb |
| 7-437 | Ph—N | O | O | H | H | N | promecarb |
| 7-438 | PhO | O | O | H | H | N | propoxur |
| 7-439 | Ph—N | O | O | H | H | N | propoxur |
| 7-440 | PhO | O | O | H | H | N | tolfenpyrad |
| 7-441 | Ph—N | O | O | H | H | N | tolfenpyrad |
| 7-442 | PhO | O | O | H | H | N | xylyl methylcarbamate |

TABLE 7-continued $$(Z^1(X^1)_{\overline{m}} \overset{G^{10}}{\underset{\|}{C}} - G^{11} - A \text{ where A is } \overset{R^1}{\underset{R^2}{C}} - (G^{21} - \overset{G^{20}}{\underset{\|}{C}})_t - (X^2)_q Z^2$$
(I)

| Cmpd# | $Z^1$ | $G^{10}$ | $G^{11}$ | $R^1$ | $R^2$ | $X^2$ | $Z^2(X^2)_q$-H or $Z^2(X^2)_q$ |
|---|---|---|---|---|---|---|---|
| 7-443 | Ph—N | O | O | H | H | N | xylyl methylcarbamate |
| 7-444 | PhO | O | O | H | H | N | xylylcarb |
| 7-445 | Ph—N | O | O | H | H | N | xylylcarb |
| 7-446 | C(CH$_3$)$_3$ | O | O | H | H | O | abamectin |
| 7-447 | (CH$_3$)$_3$C—O | O | O | H | H | O | abamectin |
| 7-448 | (CH$_3$)$_3$C—N | O | O | H | H | O | abamectin |
| 7-449 | (CH$_3$)$_3$C—S | O | O | H | H | O | abamectin |
| 7-450 | PhO | O | O | H | H | O | abamectin |
| 7-451 | Ph—N | O | O | H | H | O | abamectin |
| 7-452 | Ph—S | O | O | H | H | O | abamectin |
| 7-453 | C(CH$_3$)$_3$ | O | O | Me | H | O | abamectin |
| 7-454 | (CH$_3$)$_3$C—O | O | O | Me | H | O | abamectin |
| 7-455 | (CH$_3$)$_3$C—N | O | O | Me | H | O | abamectin |
| 7-456 | (CH$_3$)$_3$C—S | O | O | Me | H | O | abamectin |
| 7-457 | PhO | O | O | Me | H | O | abamectin |
| 7-458 | Ph—N | O | O | Me | H | O | abamectin |
| 7-459 | Ph—S | O | O | Me | H | O | abamectin |
| 7-460 | C(CH$_3$)$_3$ | O | O | Ph | H | O | abamectin |
| 7-461 | (CH$_3$)$_3$C—O | O | O | Ph | H | O | abamectin |
| 7-462 | (CH$_3$)$_3$C—N | O | O | Ph | H | O | abamectin |
| 7-463 | (CH$_3$)$_3$C—S | O | O | Ph | H | O | abamectin |
| 7-464 | (CH$_3$)$_3$C—O | O | O | Ph | H | O | emamectin benzoate |
| 7-465 | (CH$_3$)$_3$C—N | O | O | Ph | H | O | emamectin benzoate |
| 7-466 | (CH$_3$)$_3$C—O | O | O | Ph | H | O | milbemectin |
| 7-467 | (CH$_3$)$_3$C—N | O | O | Ph | H | O | milbemectin |
| 7-468 | (CH$_3$)$_3$C—O | O | O | Ph | H | N | clothianidin |
| 7-469 | (CH$_3$)$_3$C—N | O | O | Ph | H | N | clothianidin |
| 7-470 | C(CH$_3$)$_3$ | O | O | H | H | N | imidacloprid |
| 7-471 | (CH$_3$)$_3$C—O | O | O | H | H | N | imidacloprid |
| 7-472 | (CH$_3$)$_3$C—N | O | O | H | H | N | imidacloprid |
| 7-473 | (CH$_3$)$_3$C—S | O | O | H | H | N | imidacloprid |
| 7-474 | PhO | O | O | H | H | N | imidacloprid |
| 7-475 | Ph—N | O | O | H | H | N | imidacloprid |
| 7-476 | Ph—S | O | O | H | H | N | imidacloprid |
| 7-477 | C(CH$_3$)$_3$ | O | O | Me | H | N | imidacloprid |
| 7-478 | (CH$_3$)$_3$C—O | O | O | Me | H | N | imidacloprid |
| 7-479 | (CH$_3$)$_3$C—N | O | O | Me | H | N | imidacloprid |
| 7-480 | (CH$_3$)$_3$C—S | O | O | Me | H | N | imidacloprid |
| 7-481 | PhO | O | O | Me | H | N | imidacloprid |
| 7-482 | Ph—N | O | O | Me | H | N | imidacloprid |
| 7-483 | Ph—S | O | O | Me | H | N | imidacloprid |
| 7-484 | C(CH$_3$)$_3$ | O | O | Ph | H | N | imidacloprid |
| 7-485 | (CH$_3$)$_3$C—O | O | O | Ph | H | N | imidacloprid |
| 7-486 | (CH$_3$)$_3$C—N | O | O | Ph | H | N | imidacloprid |
| 7-487 | (CH$_3$)$_3$C—S | O | O | Ph | H | N | imidacloprid |
| 7-488 | PhO | O | O | Ph | H | N | imidacloprid |
| 7-489 | Ph—N | O | O | Ph | H | N | imidacloprid |
| 7-490 | Ph—S | O | O | Ph | H | N | imidacloprid |
| 7-491 | C(CH$_3$)$_3$ | O | S | H | H | N | imidacloprid |
| 7-492 | (CH$_3$)$_3$C—O | O | S | H | H | N | imidacloprid |
| 7-493 | (CH$_3$)$_3$C—N | O | S | H | H | N | imidacloprid |
| 7-494 | C(CH$_3$)$_3$ | O | O | H | H | N | nidinotefuran |
| 7-495 | (CH$_3$)$_3$C—O | O | O | H | H | N | nidinotefuran |
| 7-496 | C(CH$_3$)$_3$ | O | O | H | H | N | nitenpyram |
| 7-497 | (CH$_3$)$_3$C—O | O | O | H | H | N | nitenpyram |
| 7-498 | C(CH$_3$)$_3$ | O | O | H | H | N | NTN-32692 |
| 7-499 | (CH$_3$)$_3$C—O | O | O | H | H | N | NTN-32692 |
| 7-500 | C(CH$_3$)$_3$ | O | O | H | H | N | acephate |
| 7-501 | (CH$_3$)$_3$C—O | O | O | H | H | N | acephate |
| 7-502 | (CH$_3$)$_3$C—N | O | O | H | H | N | acephate |
| 7-503 | (CH$_3$)$_3$C—S | O | O | H | H | N | acephate |
| 7-504 | PhO | O | O | H | H | N | acephate |
| 7-505 | Ph—N | O | O | H | H | N | acephate |
| 7-506 | Ph—S | O | O | H | H | N | acephate |
| 7-507 | C(CH$_3$)$_3$ | O | O | Me | H | N | acephate |
| 7-508 | (CH$_3$)$_3$C—O | O | O | Me | H | N | acephate |

TABLE 7-continued $$(Z^1(X^1)_m){-}\overset{\overset{G^{10}}{\|}}{C}{-}G^{11}{-}A \text{ where A is } \overset{R^1}{\underset{R^2}{C}}{-}(G^{21}{-}\overset{\overset{G^{20}}{\|}}{C})_t{-}(X^2)_q Z^2$$
(I)

| Cmpd# | $Z^1$ | $G^{10}$ | $G^{11}$ | $R^1$ | $R^2$ | $X^2$ | $Z^2(X^2)_q$-H or $Z^2(X^2)_q$ |
|---|---|---|---|---|---|---|---|
| 7-509 | $(CH_3)_3C{-}N$ | O | O | Me | H | N | acephate |
| 7-510 | $(CH_3)_3C{-}S$ | O | O | Me | H | N | acephate |
| 7-511 | PhO | O | O | Me | H | N | acephate |
| 7-512 | Ph—N | O | O | Me | H | N | acephate |
| 7-513 | Ph—S | O | O | Me | H | N | acephate |
| 7-514 | $C(CH_3)_3$ | O | O | H | H | N | dimethoate |
| 7-515 | $(CH_3)_3C{-}O$ | O | O | H | H | N | dimethoate |
| 7-516 | $(CH_3)_3C{-}N$ | O | O | H | H | N | dimethoate |
| 7-517 | $(CH_3)_3C{-}S$ | O | O | H | H | N | dimethoate |
| 7-518 | PhO | O | O | H | H | N | dimethoate |
| 7-519 | Ph—N | O | O | H | H | N | dimethoate |
| 7-520 | Ph—S | O | O | H | H | N | dimethoate |
| 7-521 | $C(CH_3)_3$ | O | O | Me | H | N | dimethoate |
| 7-522 | $(CH_3)_3C{-}O$ | O | O | Me | H | N | dimethoate |
| 7-523 | $(CH_3)_3C{-}N$ | O | O | Me | H | N | dimethoate |
| 7-524 | $(CH_3)_3C{-}S$ | O | O | Me | H | N | dimethoate |
| 7-525 | PhO | O | O | Me | H | N | dimethoate |
| 7-526 | Ph—N | O | O | Me | H | N | dimethoate |
| 7-527 | Ph—S | O | O | Me | H | N | dimethoate |
| 7-528 | $C(CH_3)_3$ | O | O | Ph | H | N | dimethoate |
| 7-529 | $(CH_3)_3C{-}O$ | O | O | Ph | H | N | dimethoate |
| 7-530 | $(CH_3)_3C{-}N$ | O | O | Ph | H | N | dimethoate |
| 7-531 | $(CH_3)_3C{-}S$ | O | O | Ph | H | N | dimethoate |
| 7-532 | PhO | O | O | Ph | H | N | dimethoate |
| 7-533 | Ph—N | O | O | Ph | H | N | dimethoate |
| 7-534 | Ph—S | O | O | Ph | H | N | dimethoate |
| 7-535 | PhO | O | S | H | H | N | dimethoate |
| 7-536 | Ph—N | O | S | H | H | N | dimethoate |
| 7-537 | Ph—S | O | S | H | H | N | dimethoate |
| 7-538 | PhO | O | O | H | H | N | fenamiphos |
| 7-539 | Ph—N | O | O | H | H | N | fenamiphos |
| 7-540 | PhO | O | O | H | H | N | isofenphos |
| 7-541 | Ph—N | O | O | H | H | N | isofenphos |
| 7-542 | PhO | O | O | H | H | N | methamidophos |
| 7-543 | Ph—N | O | O | H | H | N | methamidophos |
| 7-544 | PhO | O | O | H | H | N | monocrotophos |
| 7-545 | Ph—N | O | O | H | H | N | monocrotophos |
| 7-546 | PhO | O | O | H | H | N | omethoate |
| 7-547 | Ph—N | O | O | H | H | N | omethoate |
| 7-548 | PhO | O | O | H | H | N | vamidothion |
| 7-549 | Ph—N | O | O | H | H | N | vamidothion |
| 7-550 | PhO | O | O | H | H | O | dicofol |
| 7-551 | Ph—N | O | O | H | H | O | dicofol |
| 7-552 | PhO | O | O | H | H | N | cyromazine |
| 7-553 | Ph—N | O | O | H | H | N | cyromazine |
| 7-554 | PhO | O | O | H | H | N | diafenthiuron |
| 7-555 | Ph—N | O | O | H | H | N | diafenthiuron |
| 7-556 | $C(CH_3)_3$ | O | O | H | H | N | fipronil |
| 7-557 | $(CH_3)_3C{-}O$ | O | O | H | H | N | fipronil |
| 7-558 | $(CH_3)_3C{-}N$ | O | O | H | H | N | fipronil |
| 7-559 | $(CH_3)_3C{-}S$ | O | O | H | H | N | fipronil |
| 7-560 | PhO | O | O | H | H | N | fipronil |
| 7-561 | Ph—N | O | O | H | H | N | fipronil |
| 7-562 | Ph—S | O | O | H | H | N | fipronil |
| 7-563 | $C(CH_3)_3$ | O | O | Me | H | N | fipronil |
| 7-564 | $(CH_3)_3C{-}O$ | O | O | Me | H | N | fipronil |
| 7-565 | $(CH_3)_3C{-}N$ | O | O | Me | H | N | fipronil |
| 7-566 | $(CH_3)_3C{-}S$ | O | O | Me | H | N | fipronil |
| 7-567 | PhO | O | O | Me | H | N | fipronil |
| 7-568 | Ph—N | O | O | Me | H | N | fipronil |
| 7-569 | Ph—S | O | O | Me | H | N | fipronil |
| 7-570 | $C(CH_3)_3$ | O | O | Ph | H | N | fipronil |
| 7-571 | $(CH_3)_3C{-}O$ | O | O | Ph | H | N | fipronil |
| 7-572 | $(CH_3)_3C{-}N$ | O | O | Ph | H | N | fipronil |
| 7-573 | $(CH_3)_3C{-}S$ | O | O | Ph | H | N | fipronil |
| 7-574 | PhO | O | O | Ph | H | N | fipronil |
| 7-575 | Ph—N | O | O | Ph | H | N | fipronil |
| 7-576 | Ph—S | O | O | Ph | H | N | fipronil |
| 7-577 | PhO | O | S | H | H | N | fipronil |

TABLE 7-continued $$(Z^1(X^1)_{\overline{m}}\overset{\overset{G^{10}}{\|}}{C}-G^{11}-A) \quad \text{where A is } \overset{R^1}{\underset{R^2}{\overset{|}{C}}}-(G^{21}-\overset{\overset{G^{20}}{\|}}{C})_t-(X^2)_qZ^2$$

(I)

| Cmpd# | $Z^1$ | $G^{10}$ | $G^{11}$ | $R^1$ | $R^2$ | $X^2$ | $Z^2(X^2)_q$-H or $Z^2(X^2)_q$ |
|---|---|---|---|---|---|---|---|
| 7-578 | Ph—N | O | S | H | H | N | fipronil |
| 7-579 | Ph—S | O | S | H | H | N | fipronil |
| 7-580 | PhO | O | O | H | H | N | pymetrozine |
| 7-581 | Ph—N | O | O | H | H | N | pymetrozine |
| 7-582 | PhO | O | O | H | H | N | pyrimidifen |
| 7-583 | Ph—N | O | O | H | H | N | pyrimidifen |
| 7-584 | PhO | O | O | H | H | N | tebufenpyrad |
| 7-585 | Ph—N | O | O | H | H | N | tebufenpyrad |
| 7-586 | PhO | O | O | H | H | N | bifenazate |
| 7-587 | Ph—N | O | O | H | H | N | bifenazate |
| 7-588 | PhO | O | O | H | H | O | bromopropylate |
| 7-589 | Ph—N | O | O | H | H | O | bromopropylate |
| 7-590 | PhO | O | O | H | H | O | chlorobenzilate |
| 7-591 | Ph—N | O | O | H | H | O | chlorobenzilate |
| 7-592 | PhO | O | O | H | H | N | hexythiazox |
| 7-593 | Ph—N | O | O | H | H | N | hexythiazox |
| 7-594 | $C(CH_3)_3$ | O | O | H | H | N | fluvalinate |
| 7-595 | $(CH_3)_3C$—O | O | O | H | H | N | fluvalinate |
| 7-596 | $(CH_3)_3C$—N | O | O | H | H | N | fluvalinate |
| 7-597 | $(CH_3)_3C$—S | O | O | H | H | N | fluvalinate |
| 7-598 | PhO | O | O | H | H | N | fluvalinate |
| 7-599 | Ph—N | O | O | H | H | N | fluvalinate |
| 7-600 | Ph—S | O | O | H | H | N | fluvalinate |
| 7-601 | $C(CH_3)_3$ | O | O | Me | H | N | fluvalinate |
| 7-602 | $(CH_3)_3C$—O | O | O | Me | H | N | fluvalinate |
| 7-603 | $(CH_3)_3C$—N | O | O | Me | H | N | fluvalinate |
| 7-604 | $(CH_3)_3C$—S | O | O | Me | H | N | fluvalinate |
| 7-605 | PhO | O | O | Me | H | N | fluvalinate |
| 7-606 | Ph—N | O | O | Me | H | N | fluvalinate |
| 7-607 | Ph—S | O | O | Me | H | N | fluvalinate |
| 7-608 | $C(CH_3)_3$ | O | O | Ph | H | N | fluvalinate |
| 7-609 | $(CH_3)_3C$—O | O | O | Ph | H | N | fluvalinate |
| 7-610 | $(CH_3)_3C$—N | O | O | Ph | H | N | fluvalinate |
| 7-611 | $(CH_3)_3C$—S | O | O | Ph | H | N | fluvalinate |
| 7-612 | PhO | O | O | Ph | H | N | fluvalinate |
| 7-613 | Ph—N | O | O | Ph | H | N | fluvalinate |
| 7-614 | Ph—S | O | O | Ph | H | N | fluvalinate |
| 7-615 | PhO | O | S | H | H | N | fluvalinate |
| 7-616 | Ph—N | O | S | H | H | N | fluvalinate |
| 7-617 | Ph—S | O | S | H | H | N | fluvalinate |

$Z^2(X^2)$—H or $Z^2(X^2)$ compounds designated with *, (A), (B) chemical structures are described following Table 8.

Table 8 describes additional examples of compounds of Formula I, when m=1, t=0, q=1 and the pesticides which define the pesticidal moiety of these examples are $Z^1(X^1)$—H and $Z^2(X^2)$—H or $Z^2(X^2)$, which can be made using the procedures described hereinbefore.

TABLE 8

$$Z^1(X^1)_m\overset{\overset{G^{10}}{\|}}{-C}-G^{11}-A$$

where A is $$\overset{R^1}{\underset{R^2}{\overset{|}{C}}}-(G^{21}-\overset{\overset{G^{20}}{\|}}{C})_t-(X^2)_qZ^2$$

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-1 | cymoxanil(A) | N | O | O | H | H | N | myclobutanil |
| 8-2 | cymoxanil(A) | N | O | O | H | H | N | fenbuconazole |

TABLE 8-continued

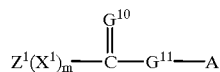

where A is

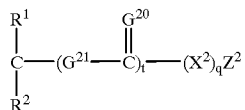

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-3 | cymoxanil(A) | N | O | O | H | H | N | epoxiconazole |
| 8-4 | cymoxanil(A) | N | O | O | H | H | N | propiconazole |
| 8-5 | cymoxanil(A) | N | O | O | H | H | N | tebuconazole |
| 8-6 | cymoxanil(A) | N | O | O | H | H | O | tebuconazole |
| 8-7 | cymoxanil(A) | N | O | O | H | H | N | zoxamide |
| 8-8 | cymoxanil(A) | N | O | O | H | H | S | mancozeb |
| 8-9 | cymoxanil(A) | N | O | O | H | H | N | famoxadone |
| 8-10 | cymoxanil(A) | N | O | O | H | H | N | fenamidone |
| 8-11 | cymoxanil(A) | N | O | O | H | H | N | propamocarb |
| 8-12 | cymoxanil(A) | N | O | O | H | H | N | fluazinam |
| 8-13 | cymoxanil(A) | N | O | O | H | H | O | fosetyl |
| 8-14 | cymoxanil(B) | N | O | O | H | H | N | myclobutanil |
| 8-15 | cymoxanil(B) | N | O | O | H | H | N | fenbuconazole |
| 8-16 | cymoxanil(B) | N | O | O | H | H | N | epoxiconazole |
| 8-17 | cymoxanil(B) | N | O | O | H | H | N | propiconazole |
| 8-18 | cymoxanil(B) | N | O | O | H | H | N | tebuconazole |
| 8-19 | cymoxanil(B) | N | O | O | H | H | O | tebuconazole |
| 8-20 | cymoxanil(B) | N | O | O | H | H | N | zoxamide |
| 8-21 | cymoxanil(B) | N | O | O | H | H | S | mancozeb |
| 8-22 | cymoxanil(B) | N | O | O | H | H | N | famoxadone |
| 8-23 | cymoxanil(B) | N | O | O | H | H | N | fenamidone |
| 8-24 | cymoxanil(B) | N | O | O | H | H | N | propamocarb |
| 8-25 | cymoxanil(B) | N | O | O | H | H | N | fluazinam |
| 8-26 | cymoxanil(B) | N | O | O | H | H | O | fosetyl |
| 8-27 | thifluzamide | N | O | O | H | H | N | ferimzone |
| 8-28 | thifluzamide | N | O | O | H | H | N | capropamid |
| 8-29 | thifluzamide | N | O | O | H | H | N | myclobutanil |
| 8-30 | thifluzamide | N | O | O | H | H | N | fenbuconazole |
| 8-31 | thifluzamide | N | O | O | H | H | N | epoxiconazole |
| 8-32 | thifluzamide | N | O | O | H | H | N | propiconazole |
| 8-33 | thifluzamide | N | O | O | H | H | N | tebuconazole |
| 8-34 | thifluzamide | N | O | O | H | H | O | tebuconazole |
| 8-35 | thifluzamide | N | O | O | H | H | N | ferimzone |
| 8-36 | thifluzamide | N | O | O | Me | H | N | capropamid |
| 8-37 | thifluzamide | N | O | O | Me | H | N | myclobutanil |
| 8-38 | thifluzamide | N | O | O | Me | H | N | fenbuconazole |
| 8-39 | thifluzamide | N | O | O | Me | H | N | epoxiconazole |
| 8-40 | thifluzamide | N | O | O | Me | H | N | propiconazole |
| 8-41 | thifluzamide | N | O | O | Me | H | N | tebuconazole |
| 8-42 | thifluzamide | N | O | O | Me | H | O | tebuconazole |
| 8-43 | thifluzamide | N | O | O | H | H | N | fenpiclonil |
| 8-44 | thifluzamide | N | O | O | H | H | N | fludioxonil |
| 8-45 | thifluzamide | N | O | O | H | H | N | metominostrobin |
| 8-46 | thifluzamide | N | O | O | H | H | N | SSF-129* |
| 8-47 | thifluzamide | N | O | O | H | H | N | F-1* |
| 8-48 | thifluzamide | N | O | O | H | H | N | fluazinam |
| 8-49 | flutolanil | N | O | O | H | H | N | ferimzone |
| 8-50 | flutolanil | N | O | O | H | H | N | capropamid |
| 8-51 | flutolanil | N | O | O | H | H | N | myclobutanil |
| 8-52 | flutolanil | N | O | O | H | H | N | fenbuconazole |
| 8-53 | flutolanil | N | O | O | H | H | N | epoxiconazole |
| 8-54 | flutolanil | N | O | O | H | H | N | propiconazole |
| 8-55 | flutolanil | N | O | O | H | H | N | tebuconazole |
| 8-56 | flutolanil | N | O | O | H | H | O | tebuconazole |
| 8-57 | flutolanil | N | O | O | H | H | N | metominostrobin |
| 8-58 | flutolanil | N | O | O | H | H | N | SSF-129* |
| 8-59 | flutolanil | N | O | O | H | H | N | F-1* |
| 8-60 | flutolanil | N | O | O | H | H | N | ferimzone |
| 8-61 | propamocarb | N | O | O | H | H | N | myclobutanil |
| 8-62 | propamocarb | N | O | O | H | H | N | fenbuconazole |
| 8-63 | propamocarb | N | O | O | H | H | N | epoxiconazole |
| 8-64 | propamocarb | N | O | O | H | H | N | propiconazole |
| 8-65 | propamocarb | N | O | O | H | H | N | tebuconazole |
| 8-66 | propamocarb | N | O | O | H | H | O | tebuconazole |

TABLE 8-continued

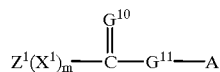

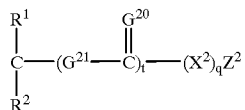

where A is

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-67 | propamocarb | N | O | O | H | H | N | zoxamide |
| 8-68 | propamocarb | N | O | O | H | H | S | mancozeb |
| 8-69 | propamocarb | N | O | O | H | H | N | famoxadone |
| 8-70 | propamocarb | N | O | O | H | H | N | fenamidone |
| 8-71 | propamocarb | N | O | O | H | H | N | fluazinam |
| 8-72 | propamocarb | N | O | O | H | H | N | metominostrobin |
| 8-73 | propamocarb | N | O | O | H | H | N | SSF-129* |
| 8-74 | propamocarb | N | O | O | H | H | N | F-1* |
| 8-75 | propamocarb | N | O | O | H | H | O | fosetyl |
| 8-76 | tebuconazole | O | O | O | H | H | N | zoxamide |
| 8-77 | tebuconazole | O | O | O | H | H | S | mancozeb |
| 8-78 | tebuconazole | O | O | O | H | H | N | famoxadone |
| 8-79 | tebuconazole | O | O | O | H | H | N | fenamidone |
| 8-80 | tebuconazole | O | O | O | H | H | N | ferimzone |
| 8-81 | tebuconazole | O | O | O | H | H | N | capropamid |
| 8-82 | tebuconazole | O | O | O | H | H | N | metominostrobin |
| 8-83 | tebuconazole | O | O | O | H | H | N | SSF-129* |
| 8-84 | tebuconazole | O | O | O | H | H | N | F-1* |
| 8-85 | tebuconazole | O | O | O | H | H | N | fluazinam |
| 8-86 | tebuconazole | O | O | O | H | H | N | cyprodinil |
| 8-87 | tebuconazole | O | O | O | H | H | N | pyrimethanil |
| 8-88 | tebuconazole | O | O | O | H | H | N | epoxiconazole |
| 8-89 | tebuconazole | O | O | O | H | H | N | propiconazole |
| 8-90 | tebuconazole | O | O | O | Ph | H | N | metominostrobin |
| 8-91 | tebuconazole | O | O | O | Ph | H | N | F-1* |
| 8-92 | tebuconazole | O | O | O | Ph | H | N | F-2* |
| 8-93 | tebuconazole | O | O | O | Ph | H | N | fluazinam |
| 8-94 | tebuconazole | O | O | O | Me | H | N | cyprodinil |
| 8-95 | tebuconazole | O | O | O | Me | H | N | pyrimethanil |
| 8-96 | tebuconazole | O | O | O | Me | H | N | epoxiconazole |
| 8-97 | tebuconazole | O | O | O | Me | H | N | propiconazole |
| 8-98 | tebuconazole | O | O | O | H | H | N | myclobutanil |
| 8-99 | tebuconazole | O | O | O | H | H | N | fenbuconazole |
| 8-100 | tebuconazole | O | O | O | H | H | N | cyproconazole |
| 8-101 | tebuconazole | O | O | O | H | H | O | cyproconazole |
| 8-102 | tebuconazole | O | O | O | H | H | N | fenpropimorph |
| 8-103 | tebuconazole | O | O | O | H | H | O | fosetyl |
| 8-104 | tebuconazole | O | O | S | H | H | N | myclobutanil |
| 8-105 | tebuconazole | O | O | S | H | H | N | fenbuconazole |
| 8-106 | tebuconazole | O | O | S | H | H | N | cyproconazole |
| 8-107 | tebuconazole | O | O | S | H | H | O | cyproconazole |
| 8-108 | tebuconazole | O | O | S | H | H | N | fenpropimorph |
| 8-109 | tebuconazole | O | O | S | H | H | O | fosetyl |
| 8-110 | cyproconazole | O | O | O | H | H | N | zoxamide |
| 8-111 | cyproconazole | O | O | O | H | H | S | mancozeb |
| 8-112 | cyproconazole | O | O | O | H | H | N | famoxadone |
| 8-113 | cyproconazole | O | O | O | H | H | N | fenamidone |
| 8-114 | cyproconazole | O | O | O | H | H | N | ferimzone |
| 8-115 | cyproconazole | O | O | O | H | H | N | capropamid |
| 8-116 | cyproconazole | O | O | O | H | H | N | metominostrobin |
| 8-117 | cyproconazole | O | O | O | H | H | N | SSF-129* |
| 8-118 | cyproconazole | O | O | O | H | H | N | F-1* |
| 8-119 | cyproconazole | O | O | O | H | H | N | fluazinam |
| 8-120 | cyproconazole | O | O | O | H | H | N | cyprodinil |
| 8-121 | cyproconazole | O | O | O | H | H | N | pyrimethanil |
| 8-122 | cyproconazole | O | O | O | H | H | N | epoxiconazole |
| 8-123 | cyproconazole | O | O | O | H | H | N | propiconazole |
| 8-124 | cyproconazole | O | O | O | H | H | N | myclobutanil |
| 8-125 | cyproconazole | O | O | O | H | H | N | fenbuconazole |
| 8-126 | cyproconazole | O | O | O | H | H | N | tebuconazole |
| 8-127 | cyproconazole | O | O | O | H | H | O | tebuconazole |
| 8-128 | cyproconazole | O | O | O | H | H | N | fenpropimorph |
| 8-129 | cyproconazole | O | O | O | H | H | O | fosetyl |
| 8-130 | fenamidone | N | O | O | H | H | N | myclobutanil |

TABLE 8-continued

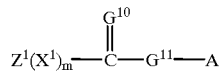

where A is

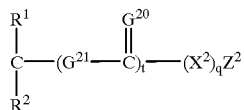

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-131 | fenamidone | N | O | O | H | H | N | fenbuconazole |
| 8-132 | fenamidone | N | O | O | H | H | N | epoxiconazole |
| 8-133 | fenamidone | N | O | O | H | H | N | propiconazole |
| 8-134 | fenamidone | N | O | O | H | H | N | tebuconazole |
| 8-135 | fenamidone | N | O | O | H | H | O | tebuconazole |
| 8-136 | fenamidone | N | O | O | H | H | N | zoxamide |
| 8-137 | fenamidone | N | O | O | H | H | N | mancozeb |
| 8-138 | fenamidone | N | O | O | H | H | N | famoxadone |
| 8-139 | fenamidone | N | O | O | H | H | N | cyprodinil |
| 8-140 | fenamidone | N | O | O | H | H | N | pyrimethanil |
| 8-141 | fenamidone | N | O | O | H | H | N | fluazinam |
| 8-142 | fenamidone | N | O | O | H | H | N | metominostrobin |
| 8-143 | fenamidone | N | O | O | H | H | N | SSF-129* |
| 8-144 | fenamidone | N | O | O | H | H | N | F-1* |
| 8-145 | fenamidone | N | O | O | H | H | O | fosetyl |
| 8-146 | fenamidone | N | O | S | H | H | O | fosetyl |
| 8-147 | iprodione | N | O | O | H | H | N | zoxamide |
| 8-148 | iprodione | N | O | O | H | H | O | fosetyl |
| 8-149 | iprodione | N | O | O | H | H | N | mancozeb |
| 8-150 | iprodione | N | O | O | H | H | N | famoxadone |
| 8-151 | iprodione | N | O | O | H | H | N | fenamidone |
| 8-152 | iprodione | N | O | O | H | H | N | ferimzone |
| 8-153 | iprodione | N | O | O | H | H | N | capropamid |
| 8-154 | iprodione | N | O | O | H | H | N | metominostrobin |
| 8-155 | iprodione | N | O | O | H | H | N | SSF-129* |
| 8-156 | iprodione | N | O | O | H | H | N | F-1* |
| 8-157 | iprodione | N | O | O | H | H | N | fluazinam |
| 8-158 | iprodione | N | O | O | H | H | N | cyprodinil |
| 8-159 | iprodione | N | O | O | H | H | N | pyrimethanil |
| 8-160 | iprodione | N | O | O | H | H | N | epoxiconazole |
| 8-161 | iprodione | N | O | O | H | H | N | propiconazole |
| 8-162 | iprodione | N | O | O | H | H | N | myclobutanil |
| 8-163 | iprodione | N | O | O | H | H | N | fenbuconazole |
| 8-164 | iprodione | N | O | O | H | H | O | cyproconazole |
| 8-165 | iprodione | N | O | O | H | H | N | tebuconazole |
| 8-166 | iprodione | N | O | S | H | H | N | tebuconazole |
| 8-167 | iprodione | N | O | O | Ph | H | N | tebuconazole |
| 8-168 | iprodione | N | O | S | Ph | H | N | tebuconazole |
| 8-169 | iprodione | N | O | O | H | H | O | tebuconazole |
| 8-170 | iprodione | N | O | S | H | H | O | tebuconazole |
| 8-171 | iprodione | N | O | O | Ph | H | O | tebuconazole |
| 8-172 | iprodione | N | O | S | Ph | H | O | tebuconazole |
| 8-173 | fosetyl | O | O | O | H | H | N | myclobutanil |
| 8-174 | fosetyl | O | O | O | H | H | N | fenbuconazole |
| 8-175 | fosetyl | O | O | O | H | H | N | epoxiconazole |
| 8-176 | fosetyl | O | O | O | H | H | N | propiconazole |
| 8-177 | fosetyl | O | O | O | H | H | N | tebuconazole |
| 8-178 | fosetyl | O | O | O | H | H | O | tebuconazole |
| 8-179 | fosetyl | O | O | O | H | H | N | fenpropimorph |
| 8-180 | fosetyl | O | O | O | H | H | N | zoxamide |
| 8-181 | fosetyl | O | O | O | H | H | S | mancozeb |
| 8-182 | fosetyl | O | O | O | H | H | N | famoxadone |
| 8-183 | fosetyl | O | O | O | H | H | N | fenamidone |
| 8-184 | fosetyl | O | O | O | H | H | N | zoxamide |
| 8-185 | fosetyl | O | O | O | Me | H | S | mancozeb |
| 8-186 | fosetyl | O | O | O | Me | H | N | famoxadone |
| 8-187 | fosetyl | O | O | O | Me | H | N | fenamidone |
| 8-188 | fosetyl | O | O | S | H | H | N | zoxamide |
| 8-189 | fosetyl | O | O | S | H | H | S | mancozeb |
| 8-190 | fosetyl | O | O | S | H | H | N | famoxadone |
| 8-191 | fosetyl | O | O | S | H | H | N | fenamidone |
| 8-192 | fosetyl | O | O | S | Me | H | N | zoxamide |
| 8-193 | fosetyl | O | O | S | Me | H | S | mancozeb |
| 8-194 | fosetyl | O | O | S | Me | H | N | famoxadone |

TABLE 8-continued

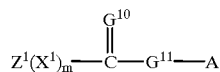

where A is

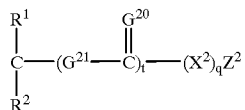

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-195 | fosetyl | O | O | S | Me | H | N | fenamidone |
| 8-196 | fosetyl | O | O | O | H | H | N | cyprodinil |
| 8-197 | fosetyl | O | O | O | H | H | N | pyrimethanil |
| 8-198 | fosetyl | O | O | O | H | H | N | fluazinam |
| 8-199 | fosetyl | O | O | O | H | H | N | metominostrobin |
| 8-200 | fosetyl | O | O | O | H | H | N | SSF-129* |
| 8-201 | fosetyl | O | O | O | H | H | N | F-1* |
| 8-202 | fosetyl | O | O | O | H | H | N | thifluzamide |
| 8-203 | carboxin | N | O | O | H | H | N | myclobutanil |
| 8-204 | carboxin | N | O | O | H | H | N | fenbuconazole |
| 8-205 | carboxin | N | O | O | H | H | N | epoxiconazole |
| 8-206 | carboxin | N | O | O | H | H | N | propiconazole |
| 8-207 | carboxin | N | O | O | H | H | N | tebuconazole |
| 8-208 | carboxin | N | O | O | H | H | O | tebuconazole |
| 8-209 | carboxin | N | O | O | H | H | N | zoxamide |
| 8-210 | carboxin | N | O | O | H | H | S | mancozeb |
| 8-211 | carboxin | N | O | O | H | H | N | famoxadone |
| 8-212 | carboxin | N | O | O | H | H | N | fenamidone |
| 8-213 | carboxin | N | O | O | H | H | N | cyprodinil |
| 8-214 | carboxin | N | O | O | H | H | N | pyrimethanil |
| 8-215 | carboxin | N | O | O | H | H | N | fluazinam |
| 8-216 | carboxin | N | O | O | H | H | N | metominostrobin |
| 8-217 | carboxin | N | O | O | H | H | N | SSF-129* |
| 8-218 | carboxin | N | O | O | H | H | N | F-1* |
| 8-219 | carboxin | N | O | O | H | H | N | thifluzamide |
| 8-220 | carboxin | N | O | O | H | H | O | fosetyl |
| 8-221 | famoxadone | N | O | O | H | H | N | myclobutanil |
| 8-222 | famoxadone | N | O | O | H | H | N | fenbuconazole |
| 8-223 | famoxadone | N | O | O | H | H | N | epoxiconazole |
| 8-224 | famoxadone | N | O | O | H | H | N | propiconazole |
| 8-225 | famoxadone | N | O | O | H | H | N | tebuconazole |
| 8-226 | famoxadone | N | O | O | H | H | O | tebuconazole |
| 8-227 | famoxadone | N | O | O | H | H | N | zoxamide |
| 8-228 | famoxadone | N | O | O | H | H | S | mancozeb |
| 8-229 | famoxadone | N | O | O | H | H | N | cyprodinil |
| 8-230 | famoxadone | N | O | O | H | H | N | pyrimethanil |
| 8-231 | famoxadone | N | O | O | H | H | N | fluazinam |
| 8-232 | famoxadone | N | O | O | H | H | N | metominostrobin |
| 8-233 | famoxadone | N | O | O | H | H | N | SSF-129* |
| 8-234 | famoxadone | N | O | O | H | H | N | F-1* |
| 8-235 | famoxadone | N | O | O | H | H | N | thifluzamide |
| 8-236 | famoxadone | N | O | O | H | H | O | fosetyl |
| 8-237 | fluazinam | N | O | O | H | H | N | myclobutanil |
| 8-238 | fluazinam | N | O | O | H | H | N | fenbuconazole |
| 8-239 | fluazinam | N | O | O | H | H | N | epoxiconazole |
| 8-240 | fluazinam | N | O | O | H | H | N | propiconazole |
| 8-241 | fluazinam | N | O | O | H | H | N | tebuconazole |
| 8-242 | fluazinam | N | O | O | H | H | O | tebuconazole |
| 8-243 | fluazinam | N | O | O | H | H | N | zoxamide |
| 8-244 | fluazinam | N | O | O | H | H | S | mancozeb |
| 8-245 | fluazinam | N | O | O | H | H | N | cyprodinil |
| 8-246 | fluazinam | N | O | O | H | H | N | pyrimethanil |
| 8-247 | fluazinam | N | O | O | H | H | N | fluazinam |
| 8-248 | fluazinam | N | O | O | H | H | N | metominostrobin |
| 8-249 | fluazinam | N | O | O | H | H | N | SSF-129* |
| 8-250 | fluazinam | N | O | O | H | H | N | F-1* |
| 8-251 | fluazinam | N | O | O | H | H | N | thifluzamide |
| 8-252 | fluazinam | N | O | O | H | H | O | fosetyl |
| 8-253 | cyprodinil | N | O | O | H | H | N | zoxamide |
| 8-254 | cyprodinil | N | O | O | H | H | S | mancozeb |
| 8-255 | cyprodinil | N | O | O | H | H | N | famoxadone |
| 8-256 | cyprodinil | N | O | O | H | H | N | fenamidone |
| 8-257 | cyprodinil | N | O | O | H | H | N | ferimzone |
| 8-258 | cyprodinil | N | O | O | H | H | N | capropamid |

TABLE 8-continued

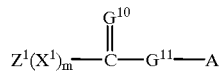

where A is

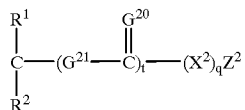

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-259 | cyprodinil | N | O | O | H | H | N | metominostrobin |
| 8-260 | cyprodinil | N | O | O | H | H | N | SSF-129* |
| 8-261 | cyprodinil | N | O | O | H | H | N | F-1* |
| 8-262 | cyprodinil | N | O | O | H | H | N | fluazinam |
| 8-263 | cyprodinil | N | O | O | H | H | N | pyrimethanil |
| 8-264 | cyprodinil | N | O | O | H | H | N | epoxiconazole |
| 8-265 | cyprodinil | N | O | O | H | H | N | propiconazole |
| 8-266 | cyprodinil | N | O | O | H | H | N | tebuconazole |
| 8-267 | cyprodinil | N | O | O | H | H | O | tebuconazole |
| 8-268 | cyprodinil | N | O | O | H | H | N | cyproconazole |
| 8-269 | cyprodinil | N | O | O | H | H | O | cyproconazole |
| 8-270 | cyprodinil | N | O | O | H | H | N | myclobutanil |
| 8-271 | cyprodinil | N | O | O | H | H | N | fenbuconazole |
| 8-272 | cyprodinil | N | O | O | H | H | N | fenpropimorph |
| 8-273 | cyprodinil | N | O | O | H | H | O | fosetyl |
| 8-274 | fenarimol | O | O | O | H | H | N | zoxamide |
| 8-275 | fenarimol | O | O | O | H | H | S | mancozeb |
| 8-276 | fenarimol | O | O | O | H | H | N | famoxadone |
| 8-277 | fenarimol | O | O | O | H | H | N | fenamidone |
| 8-278 | fenarimol | O | O | O | H | H | N | SSF-129* |
| 8-279 | fenarimol | O | O | O | H | H | N | F-1* |
| 8-280 | fenarimol | O | O | O | H | H | N | fluazinam |
| 8-281 | fenarimol | O | O | O | H | H | N | pyrimethanil |
| 8-282 | ferimzone | N | O | O | H | H | N | capropamid |
| 8-283 | ferimzone | N | O | O | H | H | N | myclobutanil |
| 8-284 | ferimzone | N | O | O | H | H | N | fenbuconazole |
| 8-285 | ferimzone | N | O | O | H | H | N | epoxiconazole |
| 8-286 | ferimzone | N | O | O | H | H | N | propiconazole |
| 8-287 | ferimzone | N | O | O | H | H | N | tebuconazole |
| 8-288 | ferimzone | N | O | O | H | H | O | tebuconazole |
| 8-289 | ferimzone | N | O | O | H | H | N | metominostrobin |
| 8-290 | ferimzone | N | O | O | H | H | N | SSF-129* |
| 8-291 | ferimzone | N | O | O | H | H | N | F-1* |
| 8-292 | ferimzone | N | O | O | H | H | N | flutolanil |
| 8-293 | ferimzone | N | O | O | H | H | N | thifluzamide |
| 8-294 | ferimzone | N | O | O | H | H | N | pencycuron |
| 8-295 | pyrimethanil | N | O | O | H | H | N | zoxamide |
| 8-296 | pyrimethanil | N | O | O | H | H | S | mancozeb |
| 8-297 | pyrimethanil | N | O | O | H | H | N | famoxadone |
| 8-298 | pyrimethanil | N | O | O | H | H | N | fenamidone |
| 8-299 | pyrimethanil | N | O | O | H | H | N | SSF-129* |
| 8-300 | pyrimethanil | N | O | O | H | H | N | F-1* |
| 8-301 | pyrimethanil | N | O | O | H | H | N | fluazinam |
| 8-302 | pyrimethanil | N | O | O | H | H | N | cyprodinil |
| 8-303 | pyrimethanil | N | O | O | H | H | N | myclobutanil |
| 8-304 | pyrimethanil | N | O | O | H | H | N | fenbuconazole |
| 8-305 | pyrimethanil | N | O | O | H | H | N | epoxiconazole |
| 8-306 | ferimzone | N | O | O | H | H | N | tebuconazole |
| 8-307 | ferimzone | N | O | O | H | H | O | tebuconazole |
| 8-308 | pyrimethanil | N | O | O | H | H | O | fosetyl |
| 8-309 | metominostrobin | N | O | O | H | H | S | mancozeb |
| 8-310 | metominostrobin | N | O | O | H | H | N | ferimzone |
| 8-311 | metominostrobin | N | O | O | H | H | N | capropamid |
| 8-312 | metominostrobin | N | O | O | H | H | N | myclobutanil |
| 8-313 | metominostrobin | N | O | O | H | H | N | fenbuconazole |
| 8-314 | metominostrobin | N | O | O | H | H | N | tebuconazole |
| 8-315 | metominostrobin | N | O | O | H | H | O | tebuconazole |
| 8-316 | metominostrobin | N | O | O | H | H | N | epoxiconazole |
| 8-317 | metominostrobin | N | O | O | H | H | N | SSF-129* |
| 8-318 | metominostrobin | N | O | O | H | H | N | F-1* |
| 8-319 | metominostrobin | N | O | O | H | H | N | flutolanil |
| 8-320 | metominostrobin | N | O | O | H | H | N | pencycuron |
| 8-321 | metominostrobin | N | O | O | H | H | N | fosetyl |
| 8-322 | metominostrobin | N | O | O | H | H | N | pencycuron |

TABLE 8-continued

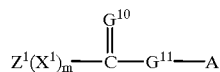

where A is

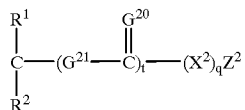

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-323 | zoxamide | N | O | O | H | H | N | myclobutanil |
| 8-324 | zoxamide | N | O | O | H | H | N | fenbuconazole |
| 8-325 | zoxamide | N | O | O | H | H | N | epoxiconazole |
| 8-326 | zoxamide | N | O | O | H | H | N | propiconazole |
| 8-327 | zoxamide | N | O | O | H | H | N | tebuconazole |
| 8-328 | zoxamide | N | O | O | H | H | O | tebuconazole |
| 8-329 | zoxamide | N | O | O | H | H | N | cyproconazole |
| 8-330 | zoxamide | N | O | O | H | H | O | cyproconazole |
| 8-331 | zoxamide | N | O | O | H | H | N | fenpropimorph |
| 8-332 | zoxamide | N | O | O | H | H | S | maneb |
| 8-333 | zoxamide | N | O | O | H | H | S | mancozeb |
| 8-334 | zoxamide | N | O | O | H | H | N | famoxadone |
| 8-335 | zoxamide | N | O | O | H | H | N | fenamidone |
| 8-336 | zoxamide | N | O | O | Me | H | S | mancozeb |
| 8-337 | zoxamide | N | O | O | Me | H | N | famoxadone |
| 8-338 | zoxamide | N | O | O | Me | H | N | fenamidone |
| 8-339 | zoxamide | N | O | O | Me | H | O | fosetyl |
| 8-340 | zoxamide | N | O | S | H | H | S | mancozeb |
| 8-341 | zoxamide | N | O | S | H | H | N | famoxadone |
| 8-342 | zoxamide | N | O | S | H | H | N | fenamidone |
| 8-343 | zoxamide | N | O | S | H | H | O | fosetyl |
| 8-344 | zoxamide | N | O | S | Me | H | S | mancozeb |
| 8-345 | zoxamide | N | O | S | Me | H | N | famoxadone |
| 8-346 | zoxamide | N | O | S | Me | H | N | fenamidone |
| 8-347 | zoxamide | N | O | S | Me | H | O | fosetyl |
| 8-348 | zoxamide | N | O | O | H | H | N | cyprodinil |
| 8-349 | zoxamide | N | O | O | H | H | N | pyrimethanil |
| 8-350 | zoxamide | N | O | O | H | H | N | fluazinam |
| 8-351 | zoxamide | N | O | O | H | H | N | metominostrobin |
| 8-352 | zoxamide | N | O | O | H | H | N | SSF-129* |
| 8-353 | zoxamide | N | O | O | H | H | N | F-1* |
| 8-354 | zoxamide | N | O | O | H | H | N | thifluzamide |
| 8-355 | capropamid | N | O | O | H | H | N | myclobutanil |
| 8-356 | capropamid | N | O | O | H | H | N | fenbuconazole |
| 8-357 | capropamid | N | O | O | H | H | N | epoxiconazole |
| 8-358 | capropamid | N | O | O | H | H | N | propiconazole |
| 8-359 | capropamid | N | O | O | H | H | N | tebuconazole |
| 8-360 | capropamid | N | O | O | H | H | O | tebuconazole |
| 8-361 | capropamid | N | O | O | H | H | N | metominostrobin |
| 8-362 | capropamid | N | O | O | H | H | N | SSF-129* |
| 8-363 | capropamid | N | O | O | H | H | N | F-1* |
| 8-364 | capropamid | N | O | O | H | H | N | flutolanil |
| 8-365 | capropamid | N | O | O | H | H | N | thifluzamide |
| 8-366 | capropamid | N | O | O | H | H | N | pencycuron |
| 8-367 | capropamid | N | O | O | H | H | N | flutolanil |
| 8-368 | capropamid | N | O | O | H | H | N | thifluzamide |
| 8-369 | capropamid | N | O | O | H | H | N | pencycuron |
| 8-370 | fenpiclonil | N | O | O | H | H | N | myclobutanil |
| 8-371 | fenpiclonil | N | O | O | H | H | N | tebuconazole |
| 8-372 | fenpiclonil | N | O | O | H | H | O | tebuconazole |
| 8-373 | fenpiclonil | N | O | O | H | H | N | epoxiconazole |
| 8-374 | fenpiclonil | N | O | O | H | H | N | thifluzamide |
| 8-375 | fludioxonil | N | O | O | H | H | N | myclobutanil |
| 8-376 | fludioxonil | N | O | O | H | H | N | tebuconazole |
| 8-377 | fludioxonil | N | O | O | H | H | O | tebuconazole |
| 8-378 | fludioxonil | N | O | O | H | H | N | epoxiconazole |
| 8-379 | fludioxonil | N | O | O | H | H | N | thifluzamide |
| 8-380 | SSF-129* | N | O | O | H | H | N | zoxamide |
| 8-381 | SSF-129* | N | O | O | H | H | S | mancozeb |
| 8-382 | SSF-129* | N | O | O | H | H | N | famoxadone |
| 8-383 | SSF-129* | N | O | O | H | H | N | fenamidone |
| 8-384 | SSF-129* | N | O | O | H | H | N | ferimzone |
| 8-385 | SSF-129* | N | O | O | H | H | N | capropamid |
| 8-386 | SSF-129* | N | O | O | H | H | N | metominostrobin |

TABLE 8-continued

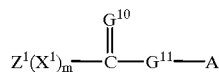

where A is

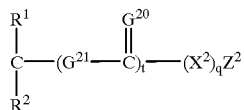

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-387 | SSF-129* | N | O | O | H | H | N | F-1* |
| 8-388 | SSF-129* | N | O | O | H | H | N | fluazinam |
| 8-389 | SSF-129* | N | O | O | H | H | N | cyprodinil |
| 8-390 | SSF-129* | N | O | O | H | H | N | pyrimethanil |
| 8-391 | SSF-129* | N | O | O | H | H | N | epoxiconazole |
| 8-392 | SSF-129* | N | O | O | H | H | N | propiconazole |
| 8-393 | SSF-129* | N | O | O | Me | H | N | metominostrobin |
| 8-394 | SSF-129* | N | O | O | Me | H | N | F-1* |
| 8-395 | SSF-129* | N | O | O | Me | H | N | fluazinam |
| 8-396 | SSF-129* | N | O | O | Me | H | N | cyprodinil |
| 8-397 | SSF-129* | N | O | O | Me | H | N | pyrimethanil |
| 8-398 | SSF-129* | N | O | O | Me | H | N | epoxiconazole |
| 8-399 | SSF-129* | N | O | O | Me | H | N | propiconazole |
| 8-400 | SSF-129* | N | O | O | H | H | N | myclobutanil |
| 8-401 | SSF-129* | N | O | O | H | H | N | fenbuconazole |
| 8-402 | SSF-129* | N | O | O | H | H | N | tebuconazole |
| 8-403 | SSF-129* | N | O | O | H | H | O | tebuconazole |
| 8-404 | SSF-129* | N | O | O | H | H | N | cyproconazole |
| 8-405 | SSF-129* | N | O | O | H | H | O | cyproconazole |
| 8-406 | SSF-129* | N | O | O | H | H | N | fenpropimorph |
| 8-407 | SSF-129* | N | O | S | H | H | O | fosetyl |
| 8-408 | SSF-129* | N | O | S | H | H | N | myclobutanil |
| 8-409 | SSF-129* | N | O | S | H | H | N | fenbuconazole |
| 8-410 | SSF-129* | N | O | S | H | H | N | cyproconazole |
| 8-411 | SSF-129* | N | O | S | H | H | N | fenpropimorph |
| 8-412 | SSF-129* | N | O | S | H | H | O | fosetyl |
| 8-413 | F-1* | N | O | O | H | H | N | zoxamide |
| 8-414 | F-1* | N | O | O | H | H | S | mancozeb |
| 8-415 | F-1* | N | O | O | H | H | N | famoxadone |
| 8-416 | F-1* | N | O | O | H | H | N | fenamidone |
| 8-417 | F-1* | N | O | O | H | H | N | ferimzone |
| 8-418 | F-1* | N | O | O | H | H | N | capropamid |
| 8-419 | F-1* | N | O | O | H | H | N | metominostrobin |
| 8-420 | F-1* | N | O | O | H | H | N | SSF-129* |
| 8-421 | F-1* | N | O | O | H | H | N | fluazinam |
| 8-422 | F-1* | N | O | O | H | H | N | cyprodinil |
| 8-423 | F-1* | N | O | O | H | H | N | pyrimethanil |
| 8-424 | F-1* | N | O | O | H | H | N | epoxiconazole |
| 8-425 | F-1* | N | O | O | H | H | N | propiconazole |
| 8-426 | F-2* | N | O | O | Ph | H | N | metominostrobin |
| 8-427 | F-2* | N | O | O | Ph | H | N | SSF-129* |
| 8-428 | F-2* | N | O | O | Ph | H | N | fluazinam |
| 8-429 | F-2* | N | O | O | Ph | H | N | cyprodinil |
| 8-430 | F-2* | N | O | O | Ph | H | N | pyrimethanil |
| 8-431 | F-2* | N | O | O | Ph | H | N | epoxiconazole |
| 8-432 | F-2* | N | O | O | Ph | H | N | propiconazole |
| 8-433 | F-2* | N | O | O | H | H | N | myclobutanil |
| 8-434 | F-2* | N | O | O | H | H | N | fenbuconazole |
| 8-435 | F-2* | N | O | O | H | H | N | tebuconazole |
| 8-436 | F-2* | N | O | O | H | H | O | tebuconazole |
| 8-437 | F-2* | N | O | O | H | H | N | cyproconazole |
| 8-438 | F-2* | N | O | O | H | H | N | fenpropimorph |
| 8-439 | F-2* | N | O | S | H | H | O | fosetyl |
| 8-440 | F-2* | N | O | S | H | H | N | myclobutanil |
| 8-441 | F-2* | N | O | S | H | H | N | fenbuconazole |
| 8-442 | F-2* | N | O | S | H | H | N | cyproconazole |
| 8-443 | F-2* | N | O | S | H | H | N | fenpropimorph |
| 8-444 | F-2* | N | O | S | H | H | O | fosetyl |
| 8-445 | pronamide | N | O | O | H | H | O | clopyralid |
| 8-446 | diflufenican | N | O | O | H | H | O | clopyralid |
| 8-447 | flumetsulam | N | O | O | H | H | O | clopyralid |
| 8-448 | propanil | N | O | O | H | H | O | clopyralid |
| 8-449 | asulam (A) * | N | O | O | H | H | O | clopyralid |
| 8-450 | asulam (B) * | N | O | O | H | H | O | clopyralid |

TABLE 8-continued

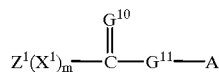

where A is

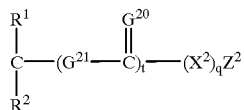

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-451 | chlorpropham | N | O | O | H | H | O | clopyralid |
| 8-452 | desmedipham (A) * | N | O | O | H | H | O | clopyralid |
| 8-453 | desmedipham (B) * | N | O | O | H | H | O | clopyralid |
| 8-454 | phenmedipham (A) * | N | O | O | H | H | O | clopyralid |
| 8-455 | phenmedipham (B) * | N | O | O | H | H | O | clopyralid |
| 8-456 | sulcotrione (A) * | O | O | O | H | H | O | clopyralid |
| 8-457 | sulcotrione (B) * | O | O | O | H | H | O | clopyralid |
| 8-458 | sethoxydim | O | O | O | H | H | O | clopyralid |
| 8-459 | tralkoxydim | O | O | O | H | H | O | clopyralid |
| 8-460 | pendimethalin | N | O | O | H | H | O | clopyralid |
| 8-461 | dinoseb | O | O | O | H | H | O | clopyralid |
| 8-462 | aclonifen | N | O | O | H | H | O | clopyralid |
| 8-463 | fomesafen | N | O | O | H | H | O | clopyralid |
| 8-464 | atrazine (A) * | N | O | O | H | H | O | clopyralid |
| 8-465 | atrazine (B) * | N | O | O | H | H | O | clopyralid |
| 8-466 | terbuthylazine (A) * | N | O | O | H | H | O | clopyralid |
| 8-467 | terbuthylazine (B) * | N | O | O | H | H | O | clopyralid |
| 8-468 | terbumeton (A) * | N | O | O | H | H | O | clopyralid |
| 8-469 | terbumeton (B) * | N | O | O | H | H | O | clopyralid |
| 8-470 | ametryn (A) * | N | O | O | H | H | O | clopyralid |
| 8-471 | ametryn (B) * | N | O | O | H | H | O | clopyralid |
| 8-472 | metribuzin | N | O | O | H | H | O | clopyralid |
| 8-473 | amitrole (A) * | N | O | O | H | H | O | clopyralid |
| 8-474 | amitrole (B) * | N | O | O | H | H | O | clopyralid |
| 8-475 | bentazon | N | O | O | H | H | O | clopyralid |
| 8-476 | bromacil | N | O | O | H | H | O | clopyralid |
| 8-477 | chlorotoluron | N | O | O | H | H | O | clopyralid |
| 8-478 | diuron | N | O | O | H | H | O | clopyralid |
| 8-479 | fluometuron | N | O | O | H | H | O | clopyralid |
| 8-480 | isoproturon | N | O | O | H | H | O | clopyralid |
| 8-481 | linuron | N | O | O | H | H | O | clopyralid |
| 8-482 | chlorsulfuron | N | O | O | H | H | O | clopyralid |
| 8-483 | nicosulfuron | N | O | O | H | H | O | clopyralid |
| 8-484 | rimsulfuron | N | O | O | H | H | O | clopyralid |
| 8-485 | pronamide | N | O | O | H | H | O | acifluorfen |
| 8-486 | diflufenican | N | O | O | H | H | O | acifluorfen |
| 8-487 | flumetsulam | N | O | O | H | H | O | acifluorfen |
| 8-488 | propanil | N | O | O | H | H | O | acifluorfen |
| 8-489 | asulam (A) * | N | O | O | H | H | O | acifluorfen |
| 8-490 | asulam (B) * | N | O | O | H | H | O | acifluorfen |
| 8-491 | chlorpropham | N | O | O | H | H | O | acifluorfen |
| 8-492 | desmedipham (A) * | N | O | O | H | H | O | acifluorfen |
| 8-493 | desmedipham (B) * | N | O | O | H | H | O | acifluorfen |
| 8-494 | phenmedipham (A) * | N | O | O | H | H | O | acifluorfen |
| 8-495 | phenmedipham (B) * | N | O | O | H | H | O | acifluorfen |
| 8-496 | sulcotrione (A) * | O | O | O | H | H | O | acifluorfen |
| 8-497 | sulcotrione (B) * | O | O | O | H | H | O | acifluorfen |
| 8-498 | sethoxydim | O | O | O | H | H | O | acifluorfen |
| 8-499 | tralkoxydim | O | O | O | H | H | O | acifluorfen |
| 8-500 | pendimethalin | N | O | O | H | H | O | acifluorfen |
| 8-501 | dinoseb | O | O | O | H | H | O | acifluorfen |
| 8-502 | aclonifen | N | O | O | H | H | O | acifluorfen |
| 8-503 | fomesafen | N | O | O | H | H | O | acifluorfen |
| 8-504 | atrazine (A) * | N | O | O | H | H | O | acifluorfen |
| 8-505 | atrazine (B) * | N | O | O | H | H | O | acifluorfen |
| 8-506 | terbuthylazine (A) * | N | O | O | H | H | O | acifluorfen |
| 8-507 | terbuthylazine (B) * | N | O | O | H | H | O | acifluorfen |
| 8-508 | terbumeton (A) * | N | O | O | H | H | O | acifluorfen |
| 8-509 | terbumeton (B) * | N | O | O | H | H | O | acifluorfen |
| 8-510 | ametryn (A) * | N | O | O | H | H | O | acifluorfen |
| 8-511 | ametryn (B) * | N | O | O | H | H | O | acifluorfen |
| 8-512 | metribuzin | N | O | O | H | H | O | acifluorfen |
| 8-513 | amitrole (A) * | N | O | O | H | H | O | acifluorfen |
| 8-514 | amitrole (B) * | N | O | O | H | H | O | acifluorfen |

TABLE 8-continued

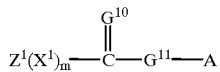

where A is

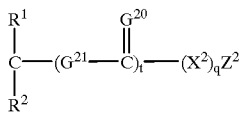

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-515 | bentazon | N | O | O | H | H | O | acifluorfen |
| 8-516 | bromacil | N | O | O | H | H | O | acifluorfen |
| 8-517 | chlorotoluron | N | O | O | H | H | O | acifluorfen |
| 8-518 | diuron | N | O | O | H | H | O | acifluorfen |
| 8-519 | fluometuron | N | O | O | H | H | O | acifluorfen |
| 8-520 | isoproturon | N | O | O | H | H | O | acifluorfen |
| 8-521 | linuron | N | O | O | H | H | O | acifluorfen |
| 8-522 | chlorsulfuron | N | O | O | H | H | O | acifluorfen |
| 8-523 | nicosulfuron | N | O | O | H | H | O | acifluorfen |
| 8-524 | rimsulfuron | N | O | O | H | H | O | acifluorfen |
| 8-525 | pronamide | N | O | O | H | H | O | imazaquin |
| 8-526 | diflufenican | N | O | O | H | H | O | imazaquin |
| 8-527 | flumetsulam | N | O | O | H | H | O | imazaquin |
| 8-528 | propanil | N | O | O | H | H | O | imazaquin |
| 8-529 | asulam (A) * | N | O | O | H | H | O | imazaquin |
| 8-530 | asulam (B) * | N | O | O | H | H | O | imazaquin |
| 8-531 | chlorpropham | N | O | O | H | H | O | imazaquin |
| 8-532 | desmedipham (A) * | N | O | O | H | H | O | imazaquin |
| 8-533 | desmedipham (B) * | N | O | O | H | H | O | imazaquin |
| 8-534 | phenmedipham (A) * | N | O | O | H | H | O | imazaquin |
| 8-535 | phenmedipham (B) * | N | O | O | H | H | O | imazaquin |
| 8-536 | sulcotrione (A) * | O | O | O | H | H | O | imazaquin |
| 8-537 | sulcotrione (B) * | O | O | O | H | H | O | imazaquin |
| 8-538 | sethoxydim | O | O | O | H | H | O | imazaquin |
| 8-539 | tralkoxydim | O | O | O | H | H | O | imazaquin |
| 8-540 | pendimethalin | N | O | O | H | H | O | imazaquin |
| 8-541 | dinoseb | O | O | O | H | H | O | imazaquin |
| 8-542 | aclonifen | N | O | O | H | H | O | imazaquin |
| 8-543 | fomesafen | N | O | O | H | H | O | imazaquin |
| 8-544 | atrazine (A) * | N | O | O | H | H | O | imazaquin |
| 8-545 | atrazine (B) * | N | O | O | H | H | O | imazaquin |
| 8-546 | terbuthylazine (A) * | N | O | O | H | H | O | imazaquin |
| 8-547 | terbuthylazine (B) * | N | O | O | H | H | O | imazaquin |
| 8-548 | terbumeton (A) * | N | O | O | H | H | O | imazaquin |
| 8-549 | terbumeton (B) * | N | O | O | H | H | O | imazaquin |
| 8-550 | ametryn (A) * | N | O | O | H | H | O | imazaquin |
| 8-551 | ametryn (B) * | N | O | O | H | H | O | imazaquin |
| 8-552 | metribuzin | N | O | O | H | H | O | imazaquin |
| 8-553 | amitrole (A) * | N | O | O | H | H | O | imazaquin |
| 8-554 | amitrole (B) * | N | O | O | H | H | O | imazaquin |
| 8-555 | bentazon | N | O | O | H | H | O | imazaquin |
| 8-556 | bromacil | N | O | O | H | H | O | imazaquin |
| 8-557 | chlorotoluron | N | O | O | H | H | O | imazaquin |
| 8-558 | diuron | N | O | O | H | H | O | imazaquin |
| 8-559 | fluometuron | N | O | O | H | H | O | imazaquin |
| 8-560 | isoproturon | N | O | O | H | H | O | imazaquin |
| 8-561 | linuron | N | O | O | H | H | O | imazaquin |
| 8-562 | chlorsulfuron | N | O | O | H | H | O | imazaquin |
| 8-563 | nicosulfuron | N | O | O | H | H | O | imazaquin |
| 8-564 | rimsulfuron | N | O | O | H | H | O | imazaquin |
| 8-565 | pronamide | N | O | O | H | H | O | imazethapyr |
| 8-566 | diflufenican | N | O | O | H | H | O | imazethapyr |
| 8-567 | flumetsulam | N | O | O | H | H | O | imazethapyr |
| 8-568 | propanil | N | O | O | H | H | O | imazethapyr |
| 8-569 | asulam (A) * | N | O | O | H | H | O | imazethapyr |
| 8-570 | asulam (B) * | N | O | O | H | H | O | imazethapyr |
| 8-571 | chlorpropham | N | O | O | H | H | O | imazethapyr |
| 8-572 | desmedipham (A) * | N | O | O | H | H | O | imazethapyr |
| 8-573 | desmedipham (B) * | N | O | O | H | H | O | imazethapyr |
| 8-574 | phenmedipham (A) * | N | O | O | H | H | O | imazethapyr |
| 8-575 | phenmedipham (B) * | N | O | O | H | H | O | imazethapyr |
| 8-576 | sulcotrione (A) * | O | O | O | H | H | O | imazethapyr |
| 8-577 | sulcotrione (B) * | O | O | O | H | H | O | imazethapyr |
| 8-578 | sethoxydim | O | O | O | H | H | O | imazethapyr |

TABLE 8-continued

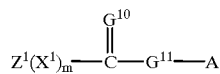

where A is

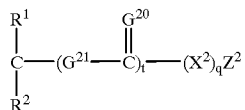

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-579 | tralkoxydim | O | O | O | H | H | O | imazethapyr |
| 8-580 | pendimethalin | N | O | O | H | H | O | imazethapyr |
| 8-581 | dinoseb | O | O | O | H | H | O | imazethapyr |
| 8-582 | aclonifen | N | O | O | H | H | O | imazethapyr |
| 8-583 | fomesafen | N | O | O | H | H | O | imazethapyr |
| 8-584 | oisoxaben | N | O | O | H | H | O | imazethapyr |
| 8-585 | pyrazon | N | O | O | H | H | O | imazethapyr |
| 8-586 | atrazine (A) * | N | O | O | H | H | O | imazethapyr |
| 8-587 | atrazine (B) * | N | O | O | H | H | O | imazethapyr |
| 8-588 | terbuthylazine (A) * | N | O | O | H | H | O | imazethapyr |
| 8-589 | terbuthylazine (B) * | N | O | O | H | H | O | imazethapyr |
| 8-590 | terbumeton (A) * | N | O | O | H | H | O | imazethapyr |
| 8-591 | terbumeton (B) * | N | O | O | H | H | O | imazethapyr |
| 8-592 | ametryn (A) * | N | O | O | H | H | O | imazethapyr |
| 8-593 | ametryn (B) * | N | O | O | H | H | O | imazethapyr |
| 8-594 | metribuzin | N | O | O | H | H | O | imazethapyr |
| 8-595 | amitrole (A) * | N | O | O | H | H | O | imazethapyr |
| 8-596 | amitrole (B) * | N | O | O | H | H | O | imazethapyr |
| 8-597 | bentazon | N | O | O | H | H | O | imazethapyr |
| 8-598 | bromacil | N | O | O | H | H | O | imazethapyr |
| 8-599 | chlorotoluron | N | O | O | H | H | O | imazethapyr |
| 8-600 | diuron | N | O | O | H | H | O | imazethapyr |
| 8-601 | fluometuron | N | O | O | H | H | O | imazethapyr |
| 8-602 | isoproturon | N | O | O | H | H | O | imazethapyr |
| 8-603 | linuron | N | O | O | H | H | O | imazethapyr |
| 8-604 | chlorsulfuron | N | O | O | H | H | O | imazethapyr |
| 8-605 | nicosulfuron | N | O | O | H | H | O | imazethapyr |
| 8-606 | rimsulfuron | N | O | O | H | H | O | imazethapyr |
| 8-607 | tribenuron | N | O | O | H | H | O | fenoxaprop |
| 8-608 | thifensulfuron | N | O | O | H | H | O | fenoxaprop |
| 8-609 | pronamide | N | O | O | H | H | O | fenoxaprop |
| 8-610 | diflufenican | N | O | O | H | H | O | fenoxaprop |
| 8-611 | flumetsulam | N | O | O | H | H | O | fenoxaprop |
| 8-612 | propanil | N | O | O | H | H | O | fenoxaprop |
| 8-613 | asulam (A) * | N | O | O | H | H | O | fenoxaprop |
| 8-614 | asulam (B) * | N | O | O | H | H | O | fenoxaprop |
| 8-615 | chlorpropham | N | O | O | H | H | O | fenoxaprop |
| 8-616 | desmedipham (A) * | N | O | O | H | H | O | fenoxaprop |
| 8-617 | desmedipham (B) * | N | O | O | H | H | O | fenoxaprop |
| 8-618 | phenmedipham (A) * | N | O | O | H | H | O | fenoxaprop |
| 8-619 | phenmedipham (B) * | N | O | O | H | H | O | fenoxaprop |
| 8-620 | sulcotrione (A) * | O | O | O | H | H | O | fenoxaprop |
| 8-621 | sulcotrione (B) * | O | O | O | H | H | O | fenoxaprop |
| 8-622 | sethoxydim | O | O | O | H | H | O | fenoxaprop |
| 8-623 | tralkoxydim | O | O | O | H | H | O | fenoxaprop |
| 8-624 | pendimethalin | N | O | O | H | H | O | fenoxaprop |
| 8-625 | dinoseb | O | O | O | H | H | O | fenoxaprop |
| 8-626 | aclonifen | N | O | O | H | H | O | fenoxaprop |
| 8-627 | fomesafen | N | O | O | H | H | O | fenoxaprop |
| 8-628 | atrazine (A) * | N | O | O | H | H | O | fenoxaprop |
| 8-629 | atrazine (B) * | N | O | O | H | H | O | fenoxaprop |
| 8-630 | terbuthylazine (A) * | N | O | O | H | H | O | fenoxaprop |
| 8-631 | terbuthylazine (B) * | N | O | O | H | H | O | fenoxaprop |
| 8-632 | terbumeton (A) * | N | O | O | H | H | O | fenoxaprop |
| 8-633 | terbumeton (B) * | N | O | O | H | H | O | fenoxaprop |
| 8-634 | ametryn (A) * | N | O | O | H | H | O | fenoxaprop |
| 8-635 | ametryn (B) * | N | O | O | H | H | O | fenoxaprop |
| 8-636 | metribuzin | N | O | O | H | H | O | fenoxaprop |
| 8-637 | amitrole (A) * | N | O | O | H | H | O | fenoxaprop |
| 8-638 | amitrole (B) * | N | O | O | H | H | O | fenoxaprop |
| 8-639 | bentazon | N | O | O | H | H | O | fenoxaprop |
| 8-640 | bromacil | N | O | O | H | H | O | fenoxaprop |
| 8-641 | chlorotoluron | N | O | O | H | H | O | fenoxaprop |
| 8-642 | diuron | N | O | O | H | H | O | fenoxaprop |

TABLE 8-continued

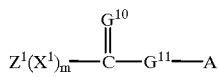

where A is

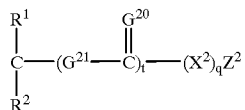

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-643 | fluometuron | N | O | O | H | H | O | fenoxaprop |
| 8-644 | isoproturon | N | O | O | H | H | O | fenoxaprop |
| 8-645 | linuron | N | O | O | H | H | O | fenoxaprop |
| 8-646 | chlorsulfuron | N | O | O | H | H | O | fenoxaprop |
| 8-647 | nicosulfuron | N | O | O | H | H | O | fenoxaprop |
| 8-648 | rimsulfuron | N | O | O | H | H | O | fenoxaprop |
| 8-649 | pronamide | N | O | O | H | H | O | fluazifop |
| 8-650 | diflufenican | N | O | O | H | H | O | fluazifop |
| 8-651 | flumetsulam | N | O | O | H | H | O | fluazifop |
| 8-652 | propanil | N | O | O | H | H | O | fluazifop |
| 8-653 | asulam (A) * | N | O | O | H | H | O | fluazifop |
| 8-654 | asulam (B) * | N | O | O | H | H | O | fluazifop |
| 8-655 | chlorpropham | N | O | O | H | H | O | fluazifop |
| 8-656 | desmedipham (A) * | N | O | O | H | H | O | fluazifop |
| 8-657 | desmedipham (B) * | N | O | O | H | H | O | fluazifop |
| 8-658 | phenmedipham (A) * | N | O | O | H | H | O | fluazifop |
| 8-659 | phenmedipham (B) * | N | O | O | H | H | O | fluazifop |
| 8-660 | sulcotrione (A) * | O | O | O | H | H | O | fluazifop |
| 8-661 | sulcotrione (B) * | O | O | O | H | H | O | fluazifop |
| 8-662 | sethoxydim | O | O | O | H | H | O | fluazifop |
| 8-663 | tralkoxydim | O | O | O | H | H | O | fluazifop |
| 8-664 | pendimethalin | N | O | O | H | H | O | fluazifop |
| 8-665 | dinoseb | O | O | O | H | H | O | fluazifop |
| 8-666 | aclonifen | N | O | O | H | H | O | fluazifop |
| 8-667 | fomesafen | N | O | O | H | H | O | fluazifop |
| 8-668 | atrazine (A) * | N | O | O | H | H | O | fluazifop |
| 8-669 | atrazine (B) * | N | O | O | H | H | O | fluazifop |
| 8-670 | terbuthylazine (A) * | N | O | O | H | H | O | fluazifop |
| 8-671 | terbuthylazine (B) * | N | O | O | H | H | O | fluazifop |
| 8-672 | terbumeton (A) * | N | O | O | H | H | O | fluazifop |
| 8-673 | terbumeton (B) * | N | O | O | H | H | O | fluazifop |
| 8-674 | ametryn (A) * | N | O | O | H | H | O | fluazifop |
| 8-675 | ametryn (B) * | N | O | O | H | H | O | fluazifop |
| 8-676 | metribuzin | N | O | O | H | H | O | fluazifop |
| 8-677 | amitrole (A) * | N | O | O | H | H | O | fluazifop |
| 8-678 | amitrole (B) * | N | O | O | H | H | O | fluazifop |
| 8-679 | bentazon | N | O | O | H | H | O | fluazifop |
| 8-680 | bromacil | N | O | O | H | H | O | fluazifop |
| 8-681 | chlorotoluron | N | O | O | H | H | O | fluazifop |
| 8-682 | diuron | N | O | O | H | H | O | fluazifop |
| 8-683 | fluometuron | N | O | O | H | H | O | fluazifop |
| 8-684 | isoproturon | N | O | O | H | H | O | fluazifop |
| 8-685 | linuron | N | O | O | H | H | O | fluazifop |
| 8-686 | chlorsulfuron | N | O | O | H | H | O | fluazifop |
| 8-687 | nicosulfuron | N | O | O | H | H | O | fluazifop |
| 8-688 | rimsulfuron | N | O | O | H | H | O | fluazifop |
| 8-689 | pronamide | N | O | O | H | H | O | haloxyfop |
| 8-690 | diflufenican | N | O | O | H | H | O | haloxyfop |
| 8-691 | flumetsulam | N | O | O | H | H | O | haloxyfop |
| 8-692 | propanil | N | O | O | H | H | O | haloxyfop |
| 8-693 | asulam (A) * | N | O | O | H | H | O | haloxyfop |
| 8-694 | asulam (B) * | N | O | O | H | H | O | haloxyfop |
| 8-695 | chlorpropham | N | O | O | H | H | O | haloxyfop |
| 8-696 | desmedipham (A) * | N | O | O | H | H | O | haloxyfop |
| 8-697 | desmedipham (B) * | N | O | O | H | H | O | haloxyfop |
| 8-698 | phenmedipham (A) * | N | O | O | H | H | O | haloxyfop |
| 8-699 | phenmedipham (B) * | N | O | O | H | H | O | haloxyfop |
| 8-700 | sulcotrione (A) * | O | O | O | H | H | O | haloxyfop |
| 8-701 | sulcotrione (B) * | O | O | O | H | H | O | haloxyfop |
| 8-702 | sethoxydim | O | O | O | H | H | O | haloxyfop |
| 8-703 | tralkoxydim | O | O | O | H | H | O | haloxyfop |
| 8-704 | pendimethalin | N | O | O | H | H | O | haloxyfop |
| 8-705 | dinoseb | O | O | O | H | H | O | haloxyfop |
| 8-706 | aclonifen | N | O | O | H | H | O | haloxyfop |

TABLE 8-continued

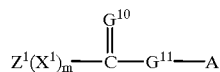

where A is

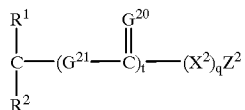

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-707 | fomesafen | N | O | O | H | H | O | haloxyfop |
| 8-708 | oisoxaben | N | O | O | H | H | O | haloxyfop |
| 8-709 | pyrazon | N | O | O | H | H | O | haloxyfop |
| 8-710 | atrazine (A) * | N | O | O | H | H | O | haloxyfop |
| 8-711 | atrazine (B) * | N | O | O | H | H | O | haloxyfop |
| 8-712 | terbuthylazine (A) * | N | O | O | H | H | O | haloxyfop |
| 8-713 | terbuthylazine (B) * | N | O | O | H | H | O | haloxyfop |
| 8-714 | terbumeton (A) * | N | O | O | H | H | O | haloxyfop |
| 8-715 | terbumeton (B) * | N | O | O | H | H | O | haloxyfop |
| 8-716 | ametryn (A) * | N | O | O | H | H | O | haloxyfop |
| 8-717 | ametryn (B) * | N | O | O | H | H | O | haloxyfop |
| 8-718 | metribuzin | N | O | O | H | H | O | haloxyfop |
| 8-719 | amitrole (A) * | N | O | O | H | H | O | haloxyfop |
| 8-720 | amitrole (B) * | N | O | O | H | H | O | haloxyfop |
| 8-721 | bentazon | N | O | O | H | H | O | haloxyfop |
| 8-722 | bromacil | N | O | O | H | H | O | haloxyfop |
| 8-723 | chlorotoluron | N | O | O | H | H | O | haloxyfop |
| 8-724 | diuron | N | O | O | H | H | O | haloxyfop |
| 8-725 | fluometuron | N | O | O | H | H | O | haloxyfop |
| 8-726 | isoproturon | N | O | O | H | H | O | haloxyfop |
| 8-727 | linuron | N | O | O | H | H | O | haloxyfop |
| 8-728 | chlorsulfuron | N | O | O | H | H | O | haloxyfop |
| 8-729 | nicosulfuron | N | O | O | H | H | O | haloxyfop |
| 8-730 | rimsulfuron | N | O | O | H | H | O | haloxyfop |
| 8-731 | diflufenican | N | O | O | H | H | O | 2,4-D |
| 8-732 | pendimethalin | N | O | O | H | H | O | 2,4-D |
| 8-733 | nicosulfuron | N | O | O | H | H | O | 2,4-D |
| 8-734 | rimsulfuron | N | O | O | H | H | O | 2,4-D |
| 8-735 | diflufenican | N | O | O | H | H | O | 2,4-DB |
| 8-736 | pendimethalin | N | O | O | H | H | O | 2,4-DB |
| 8-737 | nicosulfuron | N | O | O | H | H | O | 2,4-DB |
| 8-738 | diflufenican | N | O | O | H | H | O | triclopyr |
| 8-739 | pendimethalin | N | O | O | H | H | O | triclopyr |
| 8-740 | nicosulfuron | N | O | O | H | H | O | triclopyr |
| 8-741 | diflufenican | N | O | O | H | H | O | dicamba |
| 8-742 | pendimethalin | N | O | O | H | H | O | dicamba |
| 8-743 | nicosulfuron | N | O | O | H | H | O | dicamba |
| 8-744 | clothianidin | N | O | O | H | H | N | chromafenozide |
| 8-745 | imidacloprid | N | O | O | H | H | N | chromafenozide |
| 8-746 | nidinotefuran | N | O | O | H | H | N | chromafenozide |
| 8-747 | nitenpyram | N | O | O | H | H | N | chromafenozide |
| 8-748 | NTN-32692 | N | O | O | H | H | N | chromafenozide |
| 8-749 | chromafenozide | N | O | O | H | H | N | clothianidin |
| 8-750 | chromafenozide | N | O | O | H | H | N | imidacloprid |
| 8-751 | chromafenozide | N | O | O | H | H | N | nidinotefluan |
| 8-752 | chromafenozide | N | O | O | H | H | N | nitenpyram |
| 8-753 | chromafenozide | N | O | O | H | H | N | NTN-32692 |
| 8-754 | chromafenozide | N | O | O | Me | H | N | fluvalinate |
| 8-755 | chromafenozide | N | O | O | Me | H | N | clothianidin |
| 8-756 | chromafenozide | N | O | O | Ph | H | N | imidacloprid |
| 8-757 | chromafenozide | N | O | O | Ph | H | N | nidinotefuran |
| 8-758 | chromafenozide | N | O | O | Ph | H | N | nitenpyram |
| 8-759 | chromafenozide | N | O | O | Ph | H | N | NTN-32692 |
| 8-760 | chromafenozide | N | O | S | H | H | N | fluvalinate |
| 8-761 | chromafenozide | N | O | S | H | H | N | clothianidin |
| 8-762 | chromafenozide | N | O | S | H | H | N | imidacloprid |
| 8-763 | chromafenozide | N | O | S | H | H | N | nidinotefuran |
| 8-764 | chromafenozide | N | O | S | H | H | N | nitenpyram |
| 8-765 | chromafenozide | N | O | S | H | H | N | NTN-32692 |
| 8-766 | clothianidin | N | O | O | H | H | N | halofenozide |
| 8-767 | imidacloprid | N | O | O | H | H | N | halofenozide |
| 8-768 | nidinotefuran | N | O | O | H | H | N | halofenozide |
| 8-769 | nitenpyram | N | O | O | H | H | N | halofenozide |
| 8-770 | NTN-32692 | N | O | O | H | H | N | halofenozide |

TABLE 8-continued

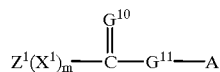

where A is

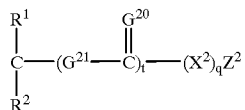

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-771 | clothianidin | N | O | O | Me | H | N | halofenozide |
| 8-772 | imidacloprid | N | O | O | Me | H | N | halofenozide |
| 8-773 | nidinotefuran | N | O | O | Me | H | N | halofenozide |
| 8-774 | nitenpyram | N | O | O | Me | H | N | halofenozide |
| 8-775 | NTN-32692 | N | O | O | Me | H | N | halofenozide |
| 8-776 | halofenozide | N | O | O | H | H | N | clothianidin |
| 8-777 | halofenozide | N | O | O | H | H | N | imidacloprid |
| 8-778 | halofenozide | N | O | O | H | H | N | nictinotefuran |
| 8-779 | halofenozide | N | O | O | H | H | N | nitenpyram |
| 8-780 | halofenozide | N | O | O | H | H | N | NTN-32692 |
| 8-781 | halofenozide | N | O | O | Me | H | N | clothianidin |
| 8-782 | halofenozide | N | O | O | Me | H | N | imidacloprid |
| 8-783 | halofenozide | N | O | O | Me | H | N | nidinotefuran |
| 8-784 | halofenozide | N | O | O | Me | H | N | nitenpyram |
| 8-785 | halofenozide | N | O | O | Me | H | N | NTN-32692 |
| 8-786 | halofenozide | N | O | O | Ph | H | N | clothianidin |
| 8-787 | halofenozide | N | O | O | Ph | H | N | imidacloprid |
| 8-788 | halofenozide | N | O | O | Ph | H | N | nidinotefuran |
| 8-789 | halofenozide | N | O | O | Ph | H | N | nitenpyram |
| 8-790 | halofenozide | N | O | O | Ph | H | N | NTN-32692 |
| 8-791 | clothianidin | N | O | O | H | H | N | methoxyfenozide |
| 8-792 | imidacloprid | N | O | O | H | H | N | methoxyfenozide |
| 8-793 | nidinotefuran | N | O | O | H | H | N | methoxyfenozide |
| 8-794 | nitenpyram | N | O | O | H | H | N | methoxyfenozide |
| 8-795 | NTN-32692 | N | O | O | Me | H | N | methoxyfenozide |
| 8-796 | clothianidin | N | O | O | Me | H | N | methoxyfenozide |
| 8-797 | imidacloprid | N | O | O | Me | H | N | methoxyfenozide |
| 8-798 | nidinotefuran | N | O | O | Me | H | N | methoxyfenozide |
| 8-799 | nitenpyram | N | O | O | Me | H | N | methoxyfenozide |
| 8-800 | methoxyfenozide | N | O | O | H | H | N | clothianidin |
| 8-801 | methoxyfenozide | N | O | O | H | H | N | imidacloprid |
| 8-802 | methoxyfenozide | N | O | O | H | H | N | nidinotefuran |
| 8-803 | methoxyfenozide | N | O | O | H | H | N | nitenpyram |
| 8-804 | methoxyfenozide | N | O | O | H | H | N | NTN-32692 |
| 8-805 | methoxyfenozide | N | O | O | Me | H | N | clothianidin |
| 8-806 | methoxyfenozide | N | O | O | Me | H | N | imidacloprid |
| 8-807 | methoxyfenozide | N | O | O | Me | H | N | nidinotefuran |
| 8-808 | methoxyfenozide | N | O | O | Me | H | N | nitenpyram |
| 8-809 | methoxyfenozide | N | O | O | Me | H | N | NTN-32692 |
| 8-810 | methoxyfenozide | N | O | O | Ph | H | N | imidacloprid |
| 8-811 | methoxyfenozide | N | O | O | Ph | H | N | clothianidin |
| 8-812 | methoxyfenozide | N | O | O | Ph | H | N | nidinotefuran |
| 8-813 | methoxyfenozide | N | O | O | Ph | H | N | nitenpyram |
| 8-814 | methoxyfenozide | N | O | O | Ph | H | N | NTN-32692 |
| 8-815 | methoxyfenozide | N | O | S | H | H | N | clothianidin |
| 8-816 | methoxyfenozide | N | O | S | H | H | N | imidacloprid |
| 8-817 | methoxyfenozide | N | O | S | H | H | N | nidinotefuran |
| 8-818 | methoxyfenozide | N | O | S | H | H | N | nitenpyram |
| 8-819 | methoxyfenozide | N | O | S | H | H | N | NTN-32692 |
| 8-820 | clothianidin | N | O | O | H | H | N | tebufenozide |
| 8-821 | imidacloprid | N | O | O | H | H | N | tebufenozide |
| 8-822 | nidinotefuran | N | O | O | H | H | N | tebufenozide |
| 8-823 | nitenpyram | N | O | O | H | H | N | tebufenozide |
| 8-824 | NTN-32692 | N | O | O | H | H | N | tebufenozide |
| 8-825 | clothianidin | N | O | O | Ph | H | N | tebufenozide |
| 8-826 | imidacloprid | N | O | O | Ph | H | N | tebufenozide |
| 8-827 | nidinotefuran | N | O | O | Ph | H | N | tebufenozide |
| 8-828 | nitenpyram | N | O | O | Ph | H | N | tebufenozide |
| 8-829 | NTN-32692 | N | O | O | Ph | H | N | tebufenozide |
| 8-830 | tebufenozide | N | O | O | H | H | N | clothianidin |
| 8-831 | tebufenozide | N | O | O | H | H | N | imidacloprid |
| 8-832 | tebufenozide | N | O | O | H | H | N | nidinotefuran |
| 8-833 | tebufenozide | N | O | O | H | H | N | nitenpyram |
| 8-834 | tebufenozide | N | O | O | H | H | N | NTN-32692 |

TABLE 8-continued

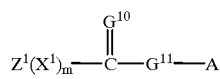

where A is

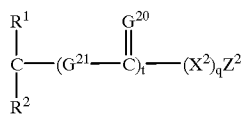

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-835 | tebufenozide | N | O | O | Ph | H | N | clothianidin |
| 8-836 | tebufenozide | N | O | O | Ph | H | N | imidacloprid |
| 8-837 | tebufenozide | N | O | O | Ph | H | N | nidinotefuran |
| 8-838 | tebufenozide | N | O | O | Ph | H | N | nitenpyram |
| 8-839 | tebufenozide | N | O | O | Ph | H | N | NTN-32692 |
| 8-840 | tebufenozide | N | O | S | H | H | N | clothianidin |
| 8-841 | tebufenozide | N | O | S | H | H | N | imidacloprid |
| 8-842 | tebufenozide | N | O | S | H | H | N | nidinotefuran |
| 8-843 | tebufenozide | N | O | S | H | H | N | nitenpyram |
| 8-844 | tebufenozide | N | O | S | H | H | N | NTN-32692 |
| 8-845 | tebufenozide | N | O | S | Me | H | N | clothianidin |
| 8-846 | tebufenozide | N | O | S | Me | H | N | imidacloprid |
| 8-847 | tebufenozide | N | O | S | Me | H | N | nidinotefuran |
| 8-848 | tebufenozide | N | O | S | Me | H | N | nitenpyram |
| 8-849 | tebufenozide | N | O | S | Me | H | N | NTN-32692 |
| 8-850 | chlorfluazuron | N | O | O | H | H | N | clothianidin |
| 8-851 | diflubenzuron | N | O | O | H | H | N | clothianidin |
| 8-852 | flucycloxuron | N | O | O | H | H | N | clothianidin |
| 8-853 | flufenoxuron | N | O | O | H | H | N | clothianidin |
| 8-854 | hexaflumuron | N | O | O | H | H | N | clothianidin |
| 8-855 | lufenuron | N | O | O | H | H | N | clothianidin |
| 8-856 | novaluron | N | O | O | H | H | N | clothianidin |
| 8-857 | teflubenzuron | N | O | O | H | H | N | clothianidin |
| 8-858 | triflumuron | N | O | O | H | H | N | clothianidin |
| 8-859 | clothianidin | N | O | O | Me | H | N | chlorfluazuron |
| 8-860 | clothianidin | N | O | O | Me | H | N | diflubenzuron |
| 8-861 | clothianidin | N | O | O | Me | H | N | flucycloxuron |
| 8-862 | clothianidin | N | O | O | Me | H | N | flufenoxuron |
| 8-863 | clothianidin | N | O | O | Ph | H | N | hexaflumuron |
| 8-864 | clothianidin | N | O | O | Ph | H | N | lufenuron |
| 8-865 | clothianidin | N | O | O | Ph | H | N | novaluron |
| 8-866 | clothianidin | N | O | O | Ph | H | N | teflubenzuron |
| 8-867 | clothianidin | N | O | O | Ph | H | N | triflumuron |
| 8-868 | chlorfluazuron | N | O | O | H | H | N | imidacloprid |
| 8-869 | diflubenzuron | N | O | O | H | H | N | imidacloprid |
| 8-870 | flucycloxuron | N | O | O | H | H | N | imidacloprid |
| 8-871 | flufenoxuron | N | O | O | H | H | N | imidacloprid |
| 8-872 | hexaflumuron | N | O | O | H | H | N | imidacloprid |
| 8-873 | lufenuron | N | O | O | H | H | N | imidacloprid |
| 8-874 | novaluron | N | O | O | H | H | N | imidacloprid |
| 8-875 | teflubenzuron | N | O | O | H | H | N | imidacloprid |
| 8-876 | triflumuron | N | O | O | H | H | N | imidacloprid |
| 8-877 | imidacloprid | N | O | O | H | H | N | chlorfluazuron |
| 8-878 | imidacloprid | N | O | O | H | H | N | diflubenzuron |
| 8-879 | imidacloprid | N | O | O | H | H | N | flucycloxuron |
| 8-880 | imidacloprid | N | O | O | H | H | N | flufenoxuron |
| 8-881 | imidacloprid | N | O | O | H | H | N | hexaflumuron |
| 8-882 | imidacloprid | N | O | O | H | H | N | lufenuron |
| 8-883 | imidacloprid | N | O | O | H | H | N | novaluron |
| 8-884 | imidacloprid | N | O | O | H | H | N | teflubenzuron |
| 8-885 | imidacloprid | N | O | O | H | H | N | triflumuron |
| 8-886 | chlorfluazuron | N | O | O | H | H | N | nidinotefuran |
| 8-887 | diflubenzuron | N | O | O | H | H | N | nidinotefuran |
| 8-888 | flucycloxuron | N | O | O | H | H | N | nidinotefuran |
| 8-889 | flufenoxuron | N | O | O | H | H | N | nidinotefuran |
| 8-890 | hexaflumuron | N | O | O | H | H | N | nidinotefuran |
| 8-891 | novaluron | N | O | O | H | H | N | nidinotefuran |
| 8-892 | teflubenzuron | N | O | O | H | H | N | nidinotefuran |
| 8-893 | triflumuron | N | O | O | H | H | N | nidinotefuran |
| 8-894 | nidinotefuran | N | O | O | H | H | N | chlorfluazuron |
| 8-895 | nidinotefuran | N | O | O | H | H | N | diflubenzuron |
| 8-896 | nidinotefuran | N | O | O | H | H | N | flucycloxuron |
| 8-897 | nidinotefuran | N | O | O | H | H | N | flufenoxuron |
| 8-898 | nidinotefuran | N | O | O | H | H | N | hexaflumuron |

TABLE 8-continued

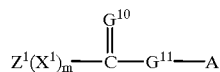

$$Z^1(X^1)_m—C—G^{11}—A$$

where A is

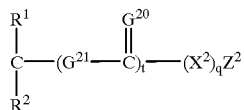

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-899 | nidinotefuran | N | O | O | H | H | N | novaluron |
| 8-900 | nidinotefuran | N | O | O | H | H | N | teflubenzuron |
| 8-901 | nidinotefuran | N | O | O | H | H | N | triflumuron |
| 8-902 | diflubenzuron | N | O | O | H | H | N | nitenpyram |
| 8-903 | flucycloxuron | N | O | O | H | H | N | nitenpyram |
| 8-904 | flufenoxuron | N | O | O | H | H | N | nitenpyram |
| 8-905 | hexaflumuron | N | O | O | H | H | N | nitenpyram |
| 8-906 | lufenuron | N | O | O | H | H | N | nitenpyram |
| 8-907 | novaluron | N | O | O | H | H | N | nitenpyram |
| 8-908 | teflubenzuron | N | O | O | H | H | N | nitenpyram |
| 8-909 | triflumuron | N | O | O | H | H | N | nitenpyram |
| 8-910 | nitenpyram | N | O | O | H | H | N | diflubenzuron |
| 8-911 | nitenpyram | N | O | O | H | H | N | flucycloxuron |
| 8-912 | nitenpyram | N | O | O | H | H | N | flufenoxuron |
| 8-913 | nitenpyram | N | O | O | H | H | N | flexaflumuron |
| 8-914 | nitenpyram | N | O | O | H | H | N | lufenuron |
| 8-915 | nitenpyram | N | O | O | H | H | N | novaluron |
| 8-916 | nitenpyram | N | O | O | H | H | N | teflubenzuron |
| 8-917 | nitenpyram | N | O | O | H | H | N | triflumuron |
| 8-918 | chlorfluazuron | N | O | O | H | H | N | NTN-32692 |
| 8-919 | diflubenzuron | N | O | O | H | H | N | NTN-32692 |
| 8-920 | flucycloxuron | N | O | O | H | H | N | NTN-32692 |
| 8-921 | flufenoxuron | N | O | O | H | H | N | NTN-32692 |
| 8-922 | hexaflumuron | N | O | O | H | H | N | NTN-32692 |
| 8-923 | lufenuron | N | O | O | H | H | N | NTN-32692 |
| 8-924 | novaluron | N | O | O | H | H | N | NTN-32692 |
| 8-925 | teflubenzuron | N | O | O | H | H | N | NTN-32692 |
| 8-926 | triflumuron | N | O | O | H | H | N | NTN-32692 |
| 8-927 | NTN-32692 | N | O | O | H | H | N | chlorfluazuron |
| 8-928 | NTN-32692 | N | O | O | H | H | N | diflubenzuron |
| 8-929 | NTN-32692 | N | O | O | H | H | N | flucycloxuron |
| 8-930 | NTN-32692 | N | O | O | H | H | N | flufenoxuron |
| 8-931 | NTN-32692 | N | O | O | H | H | N | hexaflumuron |
| 8-932 | NTN-32692 | N | O | O | H | H | N | lufenuron |
| 8-933 | NTN-32692 | N | O | O | H | H | N | novaluron |
| 8-934 | NTN-32692 | N | O | O | H | H | N | teflubenzuron |
| 8-935 | NTN-32692 | N | O | O | H | H | N | triflumuron |
| 8-936 | chlorfluazuron | N | O | O | H | H | N | acephate |
| 8-937 | diflubenzuron | N | O | O | H | H | N | acephate |
| 8-938 | flucycloxuron | N | O | O | H | H | N | acephate |
| 8-939 | flufenoxuron | N | O | O | H | H | N | acephate |
| 8-940 | hexaflumuron | N | O | O | H | H | N | acephate |
| 8-941 | lufenuron | N | O | O | H | H | N | acephate |
| 8-942 | novaluron | N | O | O | H | H | N | acephate |
| 8-943 | teflubenzuron | N | O | O | H | H | N | acephate |
| 8-944 | triflumuron | N | O | O | H | H | N | acephate |
| 8-945 | chromafenozide | N | O | O | H | H | N | acephate |
| 8-946 | halofenozide | N | O | O | H | H | N | acephate |
| 8-947 | methoxyfenozide | N | O | O | H | H | N | acephate |
| 8-948 | tebufenozide | N | O | O | H | H | N | acephate |
| 8-949 | acephate | N | O | O | H | H | N | chlorfluazuron |
| 8-950 | acephate | N | O | O | H | H | N | diflubenzuron |
| 8-951 | acephate | N | O | O | H | H | N | flucycloxuron |
| 8-952 | acephate | N | O | O | H | H | N | flufenoxuron |
| 8-953 | acephate | N | O | O | H | H | N | hexaflumuron |
| 8-954 | acephate | N | O | O | H | H | N | lufenuron |
| 8-955 | acephate | N | O | O | H | H | N | novaluron |
| 8-956 | acephate | N | O | O | H | H | N | teflubenzuron |
| 8-957 | acephate | N | O | O | H | H | N | triflumuron |
| 8-958 | acephate | N | O | O | H | H | N | chromafenozide |
| 8-959 | acephate | N | O | O | H | H | N | halofenozide |
| 8-960 | acephate | N | O | O | H | H | N | methoxyfenozide |
| 8-961 | tebufenozide | N | O | O | H | H | N | tebufenozide |
| 8-962 | chromafenozide | N | O | O | H | H | N | fluvalinate |

TABLE 8-continued

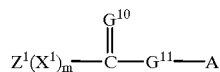

where A is

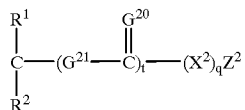

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-963 | halofenozide | N | O | O | H | H | N | fluvalinate |
| 8-964 | methoxyfenozide | N | O | O | H | H | N | fluvalinate |
| 8-965 | tebufenozide | N | O | O | H | H | N | fluvalinate |
| 8-966 | halofenozide | N | O | O | Me | H | N | fluvalinate |
| 8-967 | methoxyfenozide | N | O | O | Me | H | N | fluvalinate |
| 8-968 | tebufenozide | N | O | O | Me | H | N | fluvalinate |
| 8-969 | halofenozide | N | O | S | H | H | N | fluvalinate |
| 8-970 | methoxyfenozide | N | O | S | H | H | N | fluvalinate |
| 8-971 | tebufenozide | N | O | S | H | H | N | fluvalinate |
| 8-972 | halofenozide | N | O | S | Me | H | N | fluvalinate |
| 8-973 | methoxyfenozide | N | O | S | Me | H | N | fluvalinate |
| 8-974 | tebufenozide | N | O | S | Me | H | N | fluvalinate |
| 8-975 | halofenozide | N | O | O | Ph | H | N | fluvalinate |
| 8-976 | methoxyfenozide | N | O | O | Ph | H | N | fluvalinate |
| 8-977 | tebufenozide | N | O | O | Ph | H | N | fluvalinate |
| 8-978 | halofenozide | N | O | S | Ph | H | N | fluvalinate |
| 8-979 | methoxyfenozide | N | O | S | Ph | H | N | fluvalinate |
| 8-980 | tebufenozide | N | O | S | Ph | H | N | fluvalinate |
| 8-981 | chromafenozide | N | O | O | H | H | N | fluazuron |
| 8-982 | halofenozide | N | O | O | H | H | N | fluazuron |
| 8-983 | methoxyfenozide | N | O | O | H | H | N | fluazuron |
| 8-984 | tebufenozide | N | O | O | H | H | N | fluazuron |
| 8-985 | chromafenozide | N | O | O | H | H | N | fipronil |
| 8-986 | halofenozide | N | O | O | H | H | N | fipronil |
| 8-987 | methoxyfenozide | N | O | O | H | H | N | fipronil |
| 8-988 | tebufenozide | N | O | O | H | H | N | fipronil |
| 8-989 | chromafenozide | N | O | O | Me | H | N | fipronil |
| 8-990 | halofenozide | N | O | O | Me | H | N | fipronil |
| 8-991 | methoxyfenozide | N | O | O | Me | H | N | fipronil |
| 8-992 | tebufenozide | N | O | O | Me | H | N | fipronil |
| 8-993 | chromafenozide | N | O | O | Ph | H | N | fipronil |
| 8-994 | halofenozide | N | O | O | Ph | H | N | fipronil |
| 8-995 | methoxyfenozide | N | O | O | Ph | H | N | fipronil |
| 8-996 | tebufenozide | N | O | O | Ph | H | N | fipronil |
| 8-997 | fipronil | N | O | O | H | H | N | chromafenozide |
| 8-998 | fipronil | N | O | O | H | H | N | halofenozide |
| 8-999 | fipronil | N | O | O | H | H | N | methoxyfenozide |
| 8-1000 | fipronil | N | O | O | H | H | N | tebufenozide |
| 8-1001 | fipronil | N | O | O | Me | H | N | chromafenozide |
| 8-1002 | fipronil | N | O | O | Me | H | N | halofenozide |
| 8-1003 | fipronil | N | O | O | Me | H | N | methoxyfenozide |
| 8-1004 | fipronil | N | O | O | Me | H | N | tebufenozide |
| 8-1005 | fipronil | N | O | O | Ph | H | N | chromafenozide |
| 8-1006 | fipronil | N | O | O | Ph | H | N | halofenozide |
| 8-1007 | fipronil | N | O | O | Ph | H | N | methoxyfenozide |
| 8-1008 | fipronil | N | O | O | Ph | H | N | tebufenozide |
| 8-1009 | chromafenozide | N | O | O | H | H | N | pyrimidifen |
| 8-1010 | halofenozide | N | O | O | H | H | N | pyrimidifen |
| 8-1011 | methoxyfenozide | N | O | O | H | H | N | pyrimidifen |
| 8-1012 | tebufenozide | N | O | O | H | H | N | pyrimidifen |
| 8-1013 | chlorfluazuron | N | O | O | H | H | N | pyrimidifen |
| 8-1014 | diflubenzuron | N | O | O | H | H | N | pyrimidifen |
| 8-1015 | flucycloxuron | N | O | O | H | H | N | pyrimidifen |
| 8-1016 | flufenoxuron | N | O | O | H | H | N | pyrimidifen |
| 8-1017 | hexaflumuron | N | O | O | H | H | N | pyrimidifen |
| 8-1018 | lufenuron | N | O | O | H | H | N | pyrimidifen |
| 8-1019 | novaluron | N | O | O | H | H | N | pyrimidifen |
| 8-1020 | teflubenzuron | N | O | O | H | H | N | pyrimidifen |
| 8-1021 | triflumuron | N | O | O | H | H | N | pyrimidifen |
| 8-1022 | chlorfluazuron | N | O | O | H | H | O | dicofol |
| 8-1023 | diflubenzuron | N | O | O | H | H | O | dicofol |
| 8-1024 | flucycloxuron | N | O | O | H | H | O | dicofol |
| 8-1025 | flufenoxuron | N | O | O | H | H | O | dicofol |
| 8-1026 | hexaflumuron | N | O | O | H | H | O | dicofol |

TABLE 8-continued

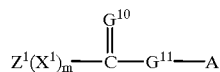

where A is

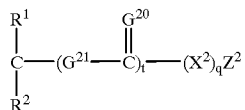

| Cmpd# | $Z^1(X^1)_m$—H | $X^1$ | $G^{10}$ | $G^{11}$ | $R^1$ | $R^2$ | $X^2$ | $Z^2(X^2)_q$ or $Z^2(X^2)_q$—H |
|---|---|---|---|---|---|---|---|---|
| 8-1027 | lufenuron | N | O | O | H | H | O | dicofol |
| 8-1028 | novaluron | N | O | O | H | H | O | dicofol |
| 8-1029 | teflubenzuron | N | O | O | H | H | O | dicofol |
| 8-1030 | triflumuron | N | O | O | H | H | O | dicofol |
| 8-1031 | dicofol | O | O | O | H | H | O | chlorfluazuron |
| 8-1032 | dicofol | O | O | O | H | H | O | diflubenzuron |
| 8-1033 | dicofol | O | O | O | H | H | O | flucycloxuron |
| 8-1034 | dicofol | O | O | O | H | H | O | flufenoxuron |
| 8-1035 | dicofol | O | O | O | H | H | O | hexaflumuron |
| 8-1036 | dicofol | O | O | O | H | H | O | lufenuron |
| 8-1037 | dicofol | O | O | O | H | H | O | novaluron |
| 8-1038 | dicofol | O | O | O | H | H | O | teflubenzuron |
| 8-1039 | dicofol | O | O | O | H | H | O | triflumuron |
| 8-1040 | chromafenozide | N | O | O | H | H | N | tebuconazole |
| 8-1041 | methoxyfenozide | N | O | O | H | H | N | tebuconazole |
| 8-1042 | tebufenozide | N | O | O | H | H | N | tebuconazole |
| 8-1043 | bifenazate | N | O | O | H | H | O | tebuconazole |
| 8-1044 | pyrimidifen | N | O | O | H | H | O | tebuconazole |
| 8-1045 | tebuconazole | O | O | O | H | H | N | chromafenozide |
| 8-1046 | tebuconazole | O | O | O | H | H | N | methoxyfenozide |
| 8-1047 | tebuconazole | O | O | O | H | H | N | tebufenozide |
| 8-1048 | tebuconazole | O | O | O | H | H | N | bifenazate |
| 8-1049 | tebuconazole | O | O | O | H | H | N | pyrimidifen |
| 8-1050 | chromafenozide | N | O | O | H | H | N | fenbuconazole |
| 8-1051 | methoxyfenozide | N | O | O | H | H | N | fenbuconazole |
| 8-1052 | tebufenozide | N | O | O | H | H | N | fenbuconazole |
| 8-1053 | bifenazate | N | O | O | H | H | N | fenbuconazole |
| 8-1054 | pyrimidifen | N | O | O | H | H | N | fenbuconazole |
| 8-1055 | cyproconazole | O | O | O | H | H | N | chromafenozide |
| 8-1056 | cyproconazole | O | O | O | H | H | N | methoxyfenozide |
| 8-1057 | cyproconazole | O | O | O | H | H | N | tebufenozide |
| 8-1058 | cyproconazole | O | O | O | H | H | N | bifenazate |
| 8-1059 | cyproconazole | O | O | O | H | H | N | pyrimidifen |
| 8-1060 | halofenozide | N | O | O | H | H | N | fenpiclonil |
| 8-1061 | fenpiclonil | N | O | O | H | H | N | halofenozide |
| 8-1062 | chromafenozide | N | O | O | H | H | N | fluazinam |
| 8-1063 | halofenozide | N | O | O | H | H | N | fluazinam |
| 8-1064 | methoxyfenozide | N | O | O | H | H | N | fluazinam |
| 8-1065 | tebufenozide | N | O | O | H | H | N | fluazinam |
| 8-1066 | chlorfluazuron | N | O | O | H | H | N | fluazinam |
| 8-1067 | diflubenzuron | N | O | O | H | H | N | fluazinam |
| 8-1068 | flucycloxuron | N | O | O | H | H | N | fluazinam |
| 8-1069 | flufenoxuron | N | O | O | H | H | N | fluazinam |
| 8-1070 | hexaflumuron | N | O | O | H | H | N | fluazinam |
| 8-1071 | lufenuron | N | O | O | H | H | N | fluazinam |
| 8-1072 | novaluron | N | O | O | H | H | N | fluazinam |
| 8-1073 | teflubenzuron | N | O | O | H | H | N | fluazinam |
| 8-1074 | triflumuron | N | O | O | H | H | N | fluazinam |
| 8-1075 | fluazinam | N | O | O | H | H | N | chromafenozide |
| 8-1076 | fluazinam | N | O | O | H | H | N | halofenozide |
| 8-1077 | fluazinam | N | O | O | H | H | N | methoxyfenozide |
| 8-1078 | fluazinam | N | O | O | H | H | N | tebufenozide |
| 8-1079 | fluazinam | N | O | O | H | H | N | chlorfluazuron |
| 8-1080 | fluazinam | N | O | O | H | H | N | diflubenzuron |
| 8-1081 | fluazinam | N | O | O | H | H | N | flucycloxuron |
| 8-1082 | fluazinam | N | O | O | H | H | N | flufenoxuron |
| 8-1083 | fluazinam | N | O | O | H | H | N | hexaflumuron |
| 8-1084 | fluazinam | N | O | O | H | H | N | lufenuron |
| 8-1085 | fluazinam | N | O | O | H | H | N | novaluron |
| 8-1086 | fluazinam | N | O | O | H | H | N | teflubenzuron |
| 8-1087 | fluazinam | N | O | O | H | H | N | triflumuron |

The following Table 9 provides the chemical structures of the compounds of Tables 6,7,8 indicated with the designation *, (A) or (B).
TABLE 9
| Common Name | Structures (point of attachment indicated for A and B) |
|---|---|
| F-1* | 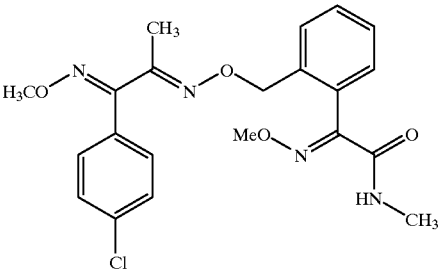 |
| F-2** | 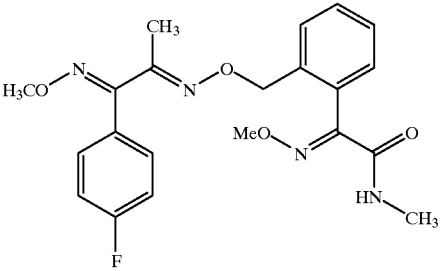 |
| cymoxanil (A) | 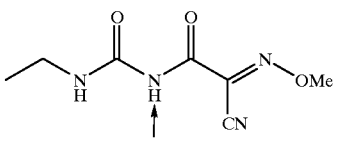 |
| cymoxanil (B) | 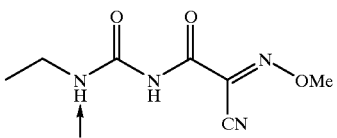 |
| dodine (A) | 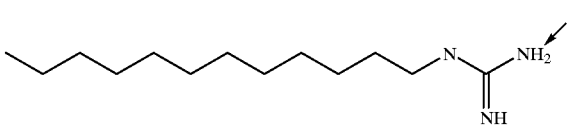 |
| dodine (B) | 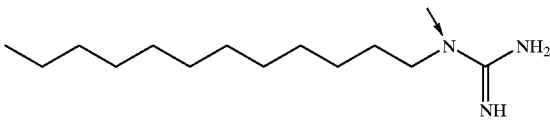 |
| benomyl (A) | 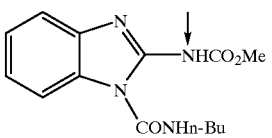 |

TABLE 9-continued
| Common Name | Structures (point of attachment indicated for A and B) |
|---|---|
| benomyl (B) | 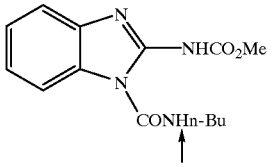 |
| carbendazim (A) | 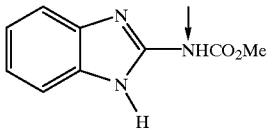 |
| carbendazim (B) | 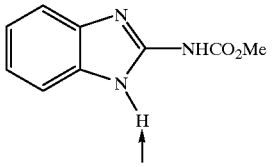 |
| thiophanate methyl (A) | 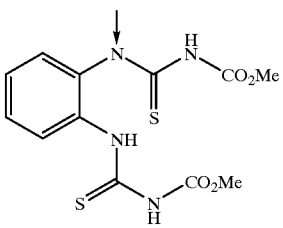 |
| thiophanate methyl (B) | 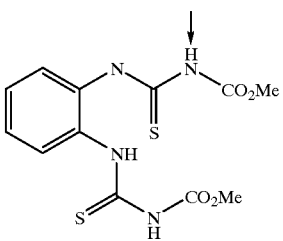 |
| SSF129 | 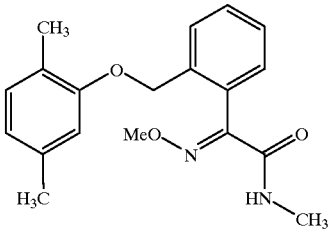 |
| asulam (A) | 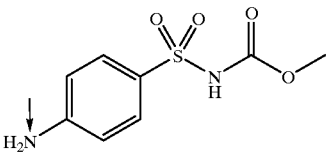 |

TABLE 9-continued
| Common Name | Structures (point of attachment indicated for A and B) |
|---|---|
| asulam (B) | 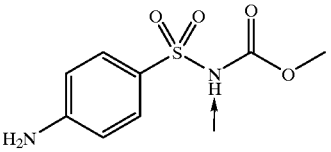 |
| desmedipham (A) | 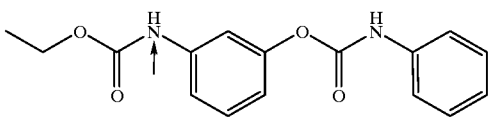 |
| desmedipham (B) | 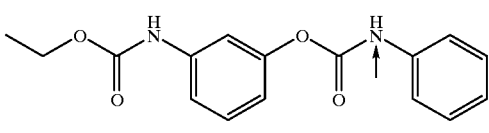 |
| phenmedipham (A) | 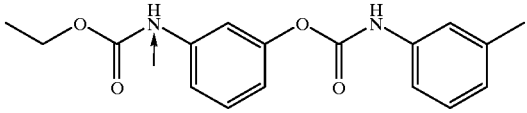 |
| phenmedipham (B) | 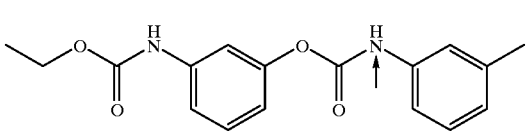 |
| sulcotrione (A) | 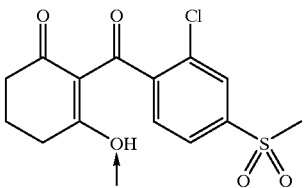 |
| sulcotrione (B) | 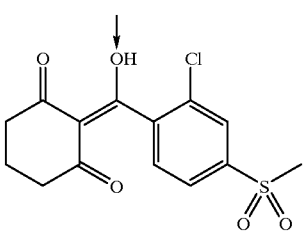 |
| atrazine (A) | 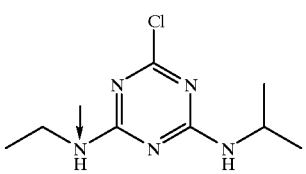 |
| atrazine (B) | 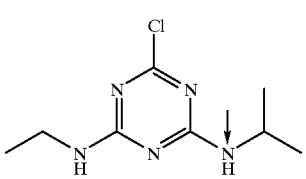 |

TABLE 9-continued

| Common Name | Structures (point of attachment indicated for A and B) |
|---|---|
| terbuthylazine (A) | |
| terbuthylazine (B) | |
| terbumeton (A) | |
| terbumeton (B) | |
| ametryn (A) | |
| ametryn (B) | |
| amitrole (A) | |
| amitrole (B) | |

*F-1 is 2-[5-(4-chlorophenyl)-4-methyl-2,7-dioxa-3,6-diazaocta-3,5-dien-1-yl]-α-(methoxyimino)-N-methyl-benzeneacetamide
**F-2 is 2-[5-(4-fluorophenyl)-4-methyl-2,7-dioxa-3,6-diazaocta-3,5-dien-1-yl]-α-(methoxyimino)-N-methyl-benzeneacetamide.

Insecticide Test Methods and Results

Numerous compounds of this invention were tested for insecticidal activity in vivo against the insects described below. The following test procedures were employed.

The compound to be evaluated was dissolved in an appropriate solvent, usually a mix of acetone, methanol, water. A test solution was made, usually containing between 7 and 15 ppm concentration of test compound. Analogous solutions were made by serially diluting the test solution with acetone, methanol, water to give concentrations between 0.7 and 1.5 ppm. Initial evaluations were made at one or more concentrations on one or more of the following insects:

| Code Symbol | Common Name | Latin Name |
| --- | --- | --- |
| BAW | Beet Armyworm | Spodoptera exigua |
| CL | Cabbage Looper | Trichoplusia ni |
| TBW | Tobacco Budworm | Heliothis virescens |

Feeding bioassays were conducted in 128-well bioassay trays containing insect diet. Treatments were made by applying 50 microliters of test solution to the surface of the diet in each of 5 wells. After the test solution dried, each well was infested with a single neonate larva. The trays were held for six days, then the mortality rating was determined for each treatment. If the result was <50% mortality, the rating was "0", if mortality was between 50% and 90%, the rating was "1", and if mortality was >90% the rating was "2".

Contact bioassays were conducted by applying 2 ml of each test compound to the bottom and top a Petri dish. The solution was allowed to air-dry, then each dish was infested with twelve 2nd instar BAW, and held overnight. Ten larvae from each treatment were transferred to 32-well bioassay trays. The trays were held for four days, then the mortality rating was determined for each treatment. If the result was <10% mortality, the rating was "0", if mortality was between 10% and 80% mortality the rating was "1", and if mortality was >80% the rating was "2".

Plant systemic bioassays were conducted on rice seedlings in soil. Intact seedlings were exposed to test compounds by soaking them for two days in the test solutions. The foliage was removed from the seedlings of each treatment and placed in a well of a 32-well bioassay tray. Each well was infested with 10 neonate BAW. The trays were held for four days, then the mortality rating was determined for each treatment. If the result was <10% mortality, the rating was "0", if mortality was between 10% and 70% mortality the rating was "1", and if mortality was >70% the rating was "2".

Foliar bioassays were conducted on cotton seedlings in soil. Intact seedlings were sprayed to run-off with test compounds using a hand-held sprayer. After the spray dried, the treated plants were held at 100% relative humidity for 6–8 hours, then transferred to the greenhouse for 6 days. The foliage was removed from each treated seedling and placed in a Petri dish. Each Petri dish was infested with 10 neonate BAW and held for six days, then the feeding damage rating was determined for each treatment. If the result was <50% reduction in feeding damage compared to the check, the rating was "0", if feeding damage was reduced between 50% and 90%, the rating was "1", and if feeding damage reduction was >90% the rating was "2". The results of the testing are listed in Table 10.

TABLE 10

INSECTICIDAL CONTROL DATA

| | Diet Assay | | | Contact | Systemic | Foliar |
| --- | --- | --- | --- | --- | --- | --- |
| Cmpd # | 0.7–1.5 ppm BAW | 0.4–0.8 ppm CL | 7–15 ppm TBW | 0.5–1 ppm BAW | 2–4 ppm BAW | 1–2 ppm BAW |
| 1-6 | 2 | 2 | 2 | 1 | 0 | 2 |
| 1-7 | 2 | 2 | 2 | 0 | 1 | 0 |
| 1-10 | 2 | 1 | 1 | 1 | 0 | NT[1] |
| 1-11 | 1 | 0 | 2 | 1 | 0 | NT |
| 1-12 | 2 | 2 | 2 | 1 | 1 | NT |
| 1-13 | 2 | 2 | 1 | 1 | 1 | NT |
| 1-14 | 2 | 2 | 1 | 1 | 0 | NT |
| 1-15 | 2 | 1 | 1 | 1 | 0 | NT |
| 1-16 | 0 | 0 | 2 | 1 | 0 | NT |
| 1-18 | 1 | 0 | 0 | 0 | 0 | 2 |
| 1-19 | 1 | 2 | 1 | 0 | 1 | 0 |
| 1-20 | 1 | 2 | 1 | 1 | 1 | 2 |
| 1-21 | 0 | 0 | 0 | 0 | 0 | 1 |
| 1-22 | 1 | 0 | 0 | 1 | 0 | 0 |
| 1-23 | 1 | 0 | 1 | 0 | 1 | 0 |
| 1-26 | 2 | 2 | 2 | 1 | 1 | 2 |
| 1-27 | 2 | 2 | 2 | 0 | 1 | 0 |
| 1-28 | 2 | 2 | 2 | 0 | 1 | 0 |
| 1-29 | 2 | 2 | 2 | 0 | 0 | 2 |
| 1-50 | 2 | 2 | 2 | 0 | 1 | 2 |
| 1-51 | 2 | 2 | 2 | 0 | 1 | 2 |
| 1-52 | 2 | 2 | 1 | 0 | 1 | 0 |
| 1-65 | 0 | 0 | 0 | 1 | 0 | 0 |
| 1-76 | 1 | 1 | 2 | 1 | 0 | 1 |
| 1-77 | 2 | 1 | 0 | 1 | 0 | 1 |
| 1-78 | 1 | 0 | 0 | 0 | 0 | 2 |
| 1-83 | 0 | 0 | 0 | 1 | 0 | 0 |
| 1-84 | 0 | 0 | 0 | 1 | 0 | 0 |
| 1-86 | 0 | 1 | 2 | 1 | 0 | 2 |
| 1-87 | 0 | 0 | 0 | 1 | 0 | 1 |
| 1-89 | 0 | 0 | 0 | 1 | 0 | 2 |
| 1-90 | 0 | 0 | 0 | 0 | 0 | 2 |
| 1-93 | 0 | 0 | 2 | 1 | 0 | 0 |
| 1-94 | 0 | 0 | 1 | 0 | 0 | 2 |
| 1-95 | 2 | 1 | 0 | 0 | 0 | 0 |
| 1-96 | 1 | 1 | 0 | 1 | 0 | 2 |
| 1-97 | 1 | 0 | 1 | 0 | 0 | 0 |
| 1-98 | 2 | 1 | 0 | 0 | 0 | 0 |
| 1-100 | 0 | 0 | 0 | 1 | 0 | 0 |
| 1-102 | 0 | 0 | 0 | 1 | 0 | 0 |
| 1-103 | 1 | 2 | 2 | 1 | 0 | 2 |
| 1-104 | 2 | 1 | 1 | 2 | 0 | 2 |
| 1-105 | 0 | 0 | 1 | 1 | 0 | 2 |
| 1-106 | 0 | 1 | 0 | 1 | 0 | 0 |
| 1-107 | 0 | 0 | 1 | 1 | 0 | 0 |
| 1-108 | 1 | 1 | 1 | 1 | 0 | 0 |
| 1-109 | 0 | 0 | 1 | 1 | 0 | 0 |
| 1-110 | 1 | 2 | 2 | 1 | 0 | 0 |
| 1-111 | 1 | 0 | 2 | 0 | 0 | 0 |
| 1-114 | 0 | 0 | 0 | 1 | 0 | 0 |
| 1-115 | 0 | 1 | 1 | 1 | 0 | 0 |
| 1-116 | 0 | 0 | 0 | 1 | 1 | 0 |
| 1-117 | 0 | 0 | 0 | 1 | 0 | 0 |
| 1-118 | 1 | 0 | 1 | 1 | 0 | 0 |
| 1-119 | 0 | 1 | 2 | 0 | 0 | 0 |
| 1-120 | 0 | 0 | 0 | 1 | 0 | 0 |
| 1-121 | 1 | 1 | 2 | 1 | 0 | 0 |
| 1-123 | 1 | 1 | 1 | 0 | 0 | 0 |
| 1-124 | 2 | 1 | 1 | 0 | 0 | 0 |
| 1-125 | 2 | 1 | 2 | 1 | 0 | 2 |
| 1-126 | 1 | 0 | 1 | 0 | 0 | 0 |
| 1-127 | 1 | 1 | 1 | 1 | 0 | 0 |
| 1-128 | 0 | 0 | 0 | 1 | 0 | 0 |
| 1-129 | 1 | 0 | 1 | 1 | 0 | 0 |
| 1-130 | 0 | 0 | 1 | 0 | 0 | 2 |
| 1-132 | 0 | 0 | 0 | 1 | 0 | 0 |
| 1-133 | 0 | 1 | 0 | 0 | 0 | 0 |
| 1-134 | 1 | 1 | 2 | 1 | 0 | 0 |
| 1-135 | 1 | 1 | 2 | 1 | 0 | 0 |
| 1-136 | 0 | 0 | 0 | 1 | 0 | 2 |
| 1-137 | 1 | 1 | 2 | 1 | 0 | 1 |

TABLE 10-continued

INSECTICIDAL CONTROL DATA

| | Diet Assay | | | Contact | Systemic | Foliar |
|---|---|---|---|---|---|---|
| Cmpd # | 0.7–1.5 ppm BAW | 0.4–0.8 ppm CL | 7–15 ppm TBW | 0.5–1 ppm BAW | 2–4 ppm BAW | 1–2 ppm BAW |
| 1-141 | 0 | 0 | 0 | 1 | 0 | 2 |
| 1-144 | 2 | 2 | 1 | 1 | 1 | NT |
| 1-145 | 2 | 2 | 2 | 1 | 0 | NT |
| 1-146 | 2 | 2 | 2 | 1 | 0 | NT |
| 1-147 | 2 | 1 | 2 | 0 | 0 | NT |
| 1-148 | 2 | 2 | 2 | 1 | 1 | NT |
| 1-149 | 2 | 2 | 2 | 1 | 0 | NT |
| 1-150 | 2 | 2 | 2 | 1 | 1 | NT |
| 1-151 | 2 | 2 | 2 | 1 | 1 | NT |
| 1-152 | 2 | 2 | 2 | 0 | 1 | NT |
| 1-153 | 2 | 2 | 2 | 1 | 1 | NT |
| 1-154 | 2 | 2 | 2 | 1 | 0 | NT |
| 1-155 | 2 | 2 | 2 | 0 | 1 | NT |
| 1-156 | 2 | 2 | 2 | 0 | 0 | NT |
| 1-157 | 2 | 2 | 2 | 0 | 1 | NT |
| 1-158 | 2 | 2 | 1 | 0 | 1 | NT |
| 1-160 | 2 | 2 | 1 | 0 | 1 | NT |
| 1-161 | 2 | 2 | 2 | 0 | 1 | NT |
| 1-162 | 2 | 2 | 2 | 0 | 1 | NT |
| 1-163 | 2 | 2 | 2 | 0 | 0 | NT |
| 1-164 | 2 | 2 | 2 | 0 | 1 | NT |
| 1-165 | 2 | 2 | 2 | 1 | 1 | NT |
| 1-166 | 2 | 2 | 2 | 1 | 0 | NT |
| 1-167 | 2 | 1 | 2 | 1 | 0 | NT |
| 1-168 | 2 | 2 | 2 | 0 | 1 | NT |
| 1-169 | 2 | 2 | 2 | 0 | 1 | NT |
| 1-170 | 2 | 2 | 2 | 0 | 0 | NT |
| 1-171 | 2 | 2 | 2 | 0 | 1 | NT |
| 1-172 | 2 | 2 | 2 | 0 | 1 | NT |
| 1-173 | 2 | 2 | 2 | 1 | 1 | NT |
| 1-174 | 2 | 2 | 2 | 0 | 1 | NT |
| 1-175 | 2 | 2 | 2 | 1 | 0 | NT |
| 1-176 | 2 | 2 | 2 | 1 | 1 | NT |
| 1-177 | 2 | 2 | 2 | 1 | 1 | NT |
| 1-178 | 2 | 2 | 2 | 1 | 1 | NT |
| 1-179 | 2 | 2 | 2 | 0 | 1 | NT |
| 1-180 | 2 | 2 | 2 | NT | NT | NT |
| 1-181 | 2 | 2 | 2 | 0 | 0 | NT |
| 1-182 | 2 | 2 | 2 | 1 | 0 | NT |
| 1-183 | 2 | 2 | 2 | 1 | 0 | NT |
| 1-184 | 2 | 2 | 2 | 0 | 0 | NT |
| 1-185 | 2 | 2 | 2 | 0 | 0 | NT |
| 1-186 | 2 | 2 | 2 | 0 | 1 | NT |
| 1-187 | 2 | 2 | 2 | 1 | 1 | NT |
| 1-188 | 2 | 2 | 2 | 1 | 0 | NT |
| 1-189 | 2 | 2 | 2 | 0 | 0 | NT |
| 1-190 | 2 | 2 | 2 | 1 | 0 | NT |
| 1-191 | 2 | 2 | 2 | 0 | 1 | NT |
| 1-192 | 2 | 2 | 2 | 0 | 0 | NT |
| 1-193 | 2 | 2 | 2 | 1 | 0 | NT |
| 1-194 | 2 | 2 | 2 | 0 | 1 | NT |
| 1-195 | 2 | 2 | 2 | 0 | 0 | NT |
| 1-196 | 2 | 2 | 2 | 0 | 1 | NT |
| 1-197 | 2 | 2 | 2 | 0 | 1 | NT |

[1]NT means "not tested".

Herbicide Test Methods and Results

The preemergence tests were run using plastic pots manufactured by Kord Products Ltd. from Bramalea, Ontario Canada, measuring 20 cm in diameter×10 cm in height. The soil was locally obtained, Pennsylvania top soil (silty loam with 1.0 to 1.5% organic matter). The sub-soil (soil below the seed) in the tray was amended with Redi-earth® Plug and Seedling Mix in a one to one ratio. Cover soil (soil above the seed) was amended with sand in a two soil and one sand mix. The test weed seeds were sown 3.5 cm deep. The preemergence tray was usually sprayed within 4 hours after planting.

Postemergence test weeds in the primary screens were on plants grown in the same pots as used in the preemergence test. Some weed seeds were sown at a different time to obtain equality in the plants development at the time of spraying. The soil used was amended with Redi-earth® Plug and Seedling Mix in a one to one ratio. Generally, postemergence plants were 7 to 21 days old (from planting) when sprayed. Grasses were in the 2–4 leaf stage and broadleaf weeds were in the 1–2 true leaf stage.

Redi-Earth® Plug and Seedling Mix is a registered trademark of the Scotts Company.

The typical planting design for the primary screen test consisted of four monocot weeds, four dicot weeds and one sedge weed.

| Common Name | Key to Weed Species | Scientific Name |
|---|---|---|
| Grasses | | |
| Barnyardgrass | BYG | Echinochloa crusgalli |
| Crabgrass (large) | CRB | Digitaria sanguinalis |
| Foxtail, (green) | FOX | Setaria viridis |
| Perennial Ryegrass | RYE | Lolium perenne |
| Sedges | | |
| Nutsedge, (yellow) | NUT | Cyperus esculentus |
| Broad Leaf Weeds | | |
| Hairy Beggarticks | BID | Bidens pilosa |
| Nightshade, (black) | NS | Solanum nigrum |
| Smartweed, (pale) | SMT | Polygonum lapathifolium |
| Velvetleaf | VEL | Abutilon theophrasti |

Rates of application (grams per hectare) and spray volume varied depending on the individual test requirement. Technical samples were usually dissolved in acetone. Formulations were suspended in water. Spray adjuvants were sometimes added to formulations to improve or modify biological activity. All applications were made using a trolley belt sprayer. The test plants were placed on the belt inside the spray hood. Then the spray nozzle which is attached to the trolley, was placed mechanically over the top of the plants. The spray nozzle delivered a full cone spray pattern of application.

After the spray application, the test plants were placed in a vented cabinet until dry, then placed in the greenhouse. The preemergence tests were watered overhead and postemergence tests were watered by subirrigation for a period of 48 hours so that the water did not contact the foliage.

| TROLLEY SPRAYER SETTINGS | |
|---|---|
| NOZZLE | Full Cone-TG-0.3 |
| PRESSURE | 29 PSIG |
| HEIGHT | 29.2 cm above target for a 20 cm diameter treated area. |

Test observations were made 11 to 14 days after treatment using a 0 (no effect) to 100% (complete control) rating system. The percent injury values were a composite value which entails chlorosis, necrosis, inhibition of growth or tip burning. All ratings were made compared to an untreated check and are shown in Tables 11, 12A and 12B.

TABLE 11

Preemergence Control at 1200 g/ha, 14 Days After Treatment

| Cmpd # | BID | NS | SMT | VEL | BYG | CRB | FOX | NUT | RYE |
|---|---|---|---|---|---|---|---|---|---|
| 4-6 | 100 | 100 | 40 | 30 | 100 | 90 | 90 | 0 | 40 |
| 4-7 | 100 | 90 | 40 | 40 | 0 | 100 | 90 | 0 | 0 |
| 4-8 | 100 | 95 | 95 | 95 | 100 | 100 | 100 | 100 | 0 |
| 4-9 | 100 | 60 | 30 | 0 | 0 | 90 | 90 | 0 | 40 |

TABLE 12A

Postemergence Activity at 1200 g/ha ai, 14 Days After Treatment

| Cmpd # | BID | NS | SMT | VEL | BYG | CRB | FOX | NUT | RYE |
|---|---|---|---|---|---|---|---|---|---|
| 4-2 | 100 | 100 | 100 | 100 | 70 | 0 | 30 | 0 | 0 |
| 4-3 | 100 | 100 | 100 | 100 | 100 | 0 | 100 | 0 | 80 |
| 4-4 | 100 | 100 | 100 | 100 | 60 | 0 | 95 | 0 | 0 |
| 4-5 | 100 | 100 | 100 | 95 | 95 | 90 | 100 | 40 | 95 |
| 4-6 | 100 | 100 | 60 | 100 | 0 | 0 | 0 | 0 | 0 |
| 4-7 | 60 | 100 | 80 | 90 | 0 | 0 | 0 | 0 | 0 |
| 4-8 | 90 | 100 | 90 | 95 | 70 | 0 | 0 | 0 | 0 |
| 4-9 | 100 | 100 | 100 | 100 | 60 | 0 | 80 | 0 | 0 |

TABLE 12B

Postemergence Activity at 1200 g/ha ai, 11 Days After Treatment

| Cmpd # | BID | NS | SMT | VEL | BYG | CRB | FOX | NUT | RYE |
|---|---|---|---|---|---|---|---|---|---|
| 2-1 | 100 | 80 | 75 | 75 | 100 | 95 | 100 | 50 | 80 |
| 2-2 | 75 | 85 | 80 | 85 | 100 | 100 | 100 | 60 | 80 |
| 2-4 | 100 | 80 | 75 | 50 | 100 | 80 | 100 | 40 | 50 |
| 2-5 | 100 | 50 | 50 | 60 | 98 | 80 | 98 | 60 | 75 |
| 2-6 | 100 | 100 | 100 | 90 | 100 | 100 | 100 | 80 | 50 |
| 2-7 | 100 | 95 | 85 | 98 | 100 | 100 | 100 | 50 | 90 |
| 2-11 | 100 | 95 | 50 | 95 | 100 | 100 | 100 | 50 | 100 |
| 2-12 | 95 | 85 | 60 | 50 | 100 | 90 | 100 | 70 | 90 |
| 2-13 | 95 | 80 | 75 | 90 | 100 | 100 | 100 | 60 | 95 |
| 2-14 | 100 | 50 | 60 | 50 | 100 | 85 | 98 | 50 | 80 |
| 2-15 | 100 | 75 | 60 | 50 | 100 | 98 | 95 | 60 | 50 |
| 2-16 | 100 | 80 | 50 | 85 | 100 | 95 | 100 | 60 | 90 |
| 2-17 | 50 | 80 | 30 | 40 | 100 | 95 | 98 | 50 | 80 |
| 2-18 | 30 | 30 | 0 | 0 | 95 | 50 | 85 | 40 | 20 |
| 2-19 | 0 | 0 | 0 | 20 | 70 | 85 | 70 | 30 | 20 |
| 2-20 | 60 | 50 | 30 | 30 | 100 | 75 | 90 | 50 | 50 |
| 2-21 | 60 | 60 | 30 | 60 | 100 | 100 | 100 | 50 | 50 |
| 2-22 | 100 | 95 | 90 | 80 | 100 | 100 | 100 | 80 | 100 |
| 2-23 | 90 | 90 | 75 | 85 | 100 | 100 | 100 | 60 | 80 |
| 2-24 | 60 | 80 | 50 | 50 | 100 | 50 | 100 | 50 | 60 |
| 2-25 | 70 | 80 | 50 | 50 | 100 | 100 | 100 | 50 | 90 |
| 2-26 | 100 | 75 | 75 | 85 | 100 | 90 | 98 | 75 | 75 |
| 2-38 | 100 | 85 | 90 | 85 | 100 | 100 | 100 | 60 | 100 |

We claim:

1. A pesticidal compound represented by formula (II)

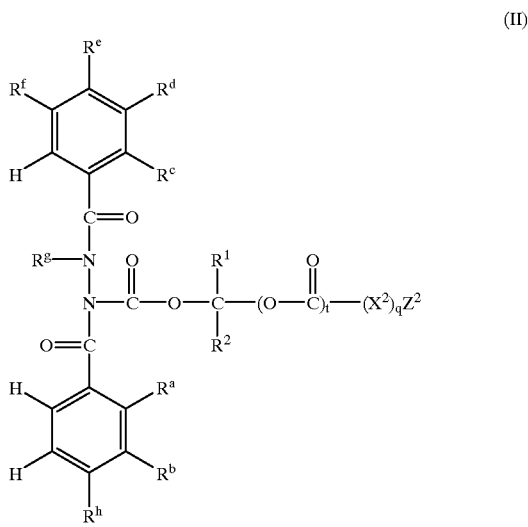

(II)

wherein $R^a$ is a hydrogen atom, halo or $(C_1-C_4)$alkyl, $R^b$ is a hydrogen atom or $(C_1-C_4)$alkoxy, optionally substituted with halo, $R^c$ is selected from a hydrogen atom, halo, $(C_1-C_4)$alkyl, $(C_1-C_4)$alkoxy, $(C_1-C_4)$alkoxy$(C_1-C_4)$alkyl and nitro, $R^d$, $R^e$ and $R^f$ are each independently selected from a hydrogen atom, halo, $(C_1-C_4)$alkyl, $(C_1-C_4)$alkoxy, and $(C_1-C_4)$alkoxy$(C_1-C_4)$alkyl, $R^g$ is a branched $(C_4-C_6)$alkyl, $R^h$ is a hydrogen atom, halo, $(C_1-C_4)$alkoxy, $(C_1-C_4)$alkyl, or when taken together with $R^b$ is methylenedioxy, 1,2-ethylenedioxy, or 1,2-ethyleneoxy or 1,3-propyleneoxy wherein the oxo atom is located at either the $R^b$ or $R^h$ position, the substituents $R^c$ and $R^d$, or $R^d$ and $R^e$, or $R^e$ and $R^f$ when taken together can be methylenedioxy or 1,2-ethylenedioxy, $R^1$ and $R^2$ are each independently a hydrogen atom, $(C_1-C_{20})$alkyl, $(C_2-C_{10})$alkenyl, $(C_2-C_{10})$alkynyl, $(C_1-C_{10})$alkoxy$(C_1-C_{10})$alkyl, $(C_1-C_{10})$alkoxy$(C_2-C_{10})$alkenyl, $(C_1-C_{10})$alkoxy$(C_2-C_{10})$alkynyl, $(C_1-C_{10})$alkylthio$(C_1-C_{10})$alkyl, $(C_1-C_{10})$alkylthio$(C_2-C_{10})$alkenyl, $(C_1-C_{10})$alkylthio$(C_2-C_{10})$alkynyl, carboxy, carboxy$(C_1-C_{20})$alkyl, carboxy$(C_2-C_{20})$alkenyl, carboxy$(C_2-C_{20})$alkynyl, $(C_1-C_{20})$alkoxycarbonyl, $(C_1-C_{10})$alkoxycarbonyl$(C_1-C_{10})$alkyl, $(C_1-C_{10})$alkoxycarbonyl$(C_2-C_{10})$alkenyl, $(C_1-C_{10})$alkoxycarbonyl$(C_2-C_{10})$alkynyl, $(C_1-C_{20})$alkylcarbonyl, $(C_2-C_{20})$alkenylcarbonyl, $(C_2-C_{20})$alkynylcarbonyl, cyclo$(C_3-C_8)$alkyl, cyclo$(C_3-C_8)$alkenyl, cyclo$(C_3-C_8)$alkyl$(C_1-C_{10})$alkyl, cyclo$(C_3-C_8)$alkenyl$(C_1-C_{10})$alkyl, cyclo$(C_3-C_8)$alkyl$(C_2-C_{10})$alkenyl, cyclo$(C_3-C_8$alkenyl$(C_2-C_{10})$alkenyl, cyclo$(C_3-C_8)$alkyl$(C_2-C_{10})$alkynyl, cyclo$(C_3-C_8$alkenyl$(C_2-C_{10})$alkynyl, heterocyclyl, heterocyclyl$(C_1-C_{10})$alkyl, heterocyclyl$(C_2-C_{10})$alkenyl, heterocyclyl$(C_2-C_{10})$alkynyl, aryl, aryl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$alkoxy, halo ($C_1$–$C_{10}$)alkoxy, $SO_2NR^3R^4$ and $NR^3R^4$, ar($C_1$–$C_{10}$) alkyl, ar($C_2$–$C_{10}$)alkenyl ar($C_2$–$C_{10}$)alkynyl, or ar($C_1$–$C_{10}$)alkyl, ar($C_2$–$C_{10}$)alkenyl, ar($C_2$–$C_{10}$) alkynyl substituted with one or more substituents independently selected from halo, ($C_1$–$C_{10}$)alkyl, ($C_2$–$C_{10}$) alkenyl, ($C_2$–$C_{10}$)alkynyl, halo($C_1$–$C_{10}$)alkyl, halo ($C_2$–$C_{10}$)alkenyl, halo($C_2$–$C_{10}$)alkynyl, ($C_1$–$C_{10}$) alkoxy, halo($C_1$–$C_{10}$)alkoxy, $SO_2NR^3R^4$ and $NR^3R^4$, heteroaryl, heteroaryl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo ($C_2$–$C_{10}$)alkynyl, ($C_1$–$C_{10}$)alkoxy, halo($C_1$–$C_{10}$)alkoxy and $NR^3R^4$, heteroar($C_1$–$C_{10}$)alkyl, heteroar($C_2$–$C_{10}$) alkenyl, heteroar($C_2$–$C_{10}$)alkynyl or heteroar($C_1$–$C_{10}$) alkyl, heteroar($C_2$–$C_{10}$)alkenyl, heteroar($C_2$–$C_{10}$) alkynyl substituted with one or more substituents independently selected from halo, ($C_1$–$C_{10}$)alkyl, ($C_2$–$C_{10}$)alkenyl, ($C_2$–$C_{10}$)alkynyl, halo($C_1$–$C_{10}$)alkyl, halo($C_2$–$C_{10}$)alkenyl, halo($C_2$–$C_{10}$)alkynyl, ($C_1$–$C_{10}$) alkoxy, halo ($C_1$–$C_{10}$)alkoxy, $SO_2NR^3R^4$ and $NR^3R^4$, or $R^1$ and $R^2$ taken together with the carbon atom to which they are attached form a 5–7 membered saturated or unsaturated ring, or $R^1$ may be a pesticidal moiety if $R^2$ is a hydrogen atom, q and t are each independently 0 or 1, $Z^2(X^2)_q$ is halo, $NR^3R^4$, $\{(NR^3R^4R^5)^+M^-\}$, $OR^3$, $S(O)_jR^3$ or $SO_2NR^3R^4$ when both q and t are 0 wherein $M^-$ is halo, hydroxy, ($C_1$–$C_8$)alkoxy or the anion of a carboxylic acid and j is 0, 1 or 2, $R^3$, $R^4$ and $R^5$ are each independently a hydrogen atom, ($C_1$–$C_{20}$)alkyl, cyclo($C_3$–$C_8$)alkyl, cyclo($C_3$–$C_8$) alkenyl, cyclo($C_3$–$C_8$)alkyl($C_1$–$C_{10}$)alkyl, cyclo ($C_3$–$C_8$)alkyl($C_2$–$C_{10}$)alkenyl, cyclo($C_3$–$C_8$)alkyl ($C_2$–$C_{10}$)alkynyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$) alkenyl($C_2$–$C_{10}$)alkynyl, heterocyclyl, heterocyclyl ($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy ($C_1$–$C_{10}$)alkyl, ($C_2$–$C_{10}$)alkenyl, ($C_2$–$C_{10}$)alkynyl, or ($C_1$–$C_{10}$)alkyl, cyclo($C_3$–$C_8$)alkyl, cyclo($C_3$–$C_8$) alkenyl, cyclo($C_3$–$C_8$)alkyl($C_1$–$C_{10}$)alkyl, cyclo ($C_3$–$C_8$)alkyl($C_2$–$C_{10}$)alkenyl, cyclo($C_3$–$C_8$)alkyl ($C_2$–$C_{10}$)alkynyl, cyclo($C_3$–$C_8$)alkenyl($C_1$–$C_{10}$)alkyl, cyclo($C_3$–$C_8$)alkenyl($C_2$–$C_{10}$)alkenyl, cyclo($C_3$–$C_8$) alkenyl($C_2$–$C_{10}$)alkynyl, heterocyclyl, heterocyclyl ($C_1$–$C_{10}$)alkyl, heterocyclyl($C_2$–$C_{10}$)alkenyl, heterocyclyl($C_2$–$C_{10}$)alkynyl, ($C_1$–$C_{10}$)alkoxy ($C_1$–$C_{10}$)alkyl, ($C_2$–$C_{10}$)alkenyl or ($C_2$–$C_{10}$)alkynyl substituted with one or more halo, aryl, ar($C_1$–$C_{10}$) alkyl, ar($C_2$–$C_{10}$)alkenyl, ar($C_2$–$C_{10}$)alkynyl or aryl, ar($C_1$–$C_{10}$)alkyl, ar($C_2$–$C_{10}$)alkenyl, ar($C_2$–$C_{10}$) alkynyl substituted with one or more substituents independently selected from halo, ($C_1$–$C_{10}$)alkyl, ($C_2$–$C_{10}$) alkenyl, ($C_2$–$C_{10}$)alkynyl, halo($C_1$–$C_{10}$)alkyl, halo ($C_2$–$C_{10}$)alkenyl, halo($C_2$–$C_{10}$)alkynyl, ($C_1$–$C_{10}$) alkoxy and halo($C_1$–$C_{10}$)alkoxy, heteroaryl, heteroar ($C_1$–$C_{10}$)alkyl, heteroar($C_2$–$C_{10}$)alkenyl, heteroar ($C_2$–$C_{10}$)alkynyl or heteroaryl, heteroar($C_1$–$C_{10}$)alkyl, heteroar($C_2$–$C_{10}$)alkenyl, heteroar($C_2$–$C_{10}$)alkynyl substituted with one or more substituents independently selected from halo, ($C_1$–$C_{10}$)alkyl, ($C_2$–$C_{10}$) alkenyl, ($C_2$–$C_{10}$)alkynyl, halo($C_1$–$C_{10}$)alkyl, halo ($C_2$–$C_{10}$)alkenyl, halo($C_2$–$C_{10}$)alkynyl, ($C_1$–$C_{10}$) alkoxy and halo($C_1$–$C_{10}$)alkoxy, or $R^3$ and $R^4$ taken together with the nitrogen atom to which they are attached form a 5- or 6-membered saturated or unsaturated heterocyclic ring, and $M^-$ is halo, hydroxy, alkoxy or the anion of a carboxylic acid, $Z^2(X^2)_q$ is a hydrogen atom, methyl, tert-butyl, isobutyl, acetamidomethyl, α-carboxybenzyl, methoxycarbonylaminomethyl, diethylphosphorylmethyl, 2-hydroxy-2-propyl, 1-(isopropylidenyliminooxy)ethyl, 4,4,4-trifluoro-2-butyl, 2-(trifluoromethyl)propyl, 2,2,2-trifluoroethyl, ethynyl, 5-pyrrolidinyl-2-one, 1-(benzyloxycarbonylamino)-1-methylethyl, methylcarbonyl, 3-rhodaninylmethyl, 2-pyrazinyl, 4-pyrazolyl, 2-furylcarbonylaminomethyl, 2-(2,5-dihydropyrrolidion-1-yl)ethyl, 2-(methoxy) ethoxymethyl, mesylmethyl, 4-heptyloxyphenyl, 2,6-dichlorophenyl, 1-(3,5-diiodopyridin-4-one)ylmethyl, 3-pyridyl, 2,3-dichloro-5-pyridyl, 4-pyridyl, 2,6-dichloro-4-pyridyl, 4-mesylphenyl, 2-chloro-4-nitrophenyl, 2-nitro-4-chlorophenyl, 2-nitro-5-chlorophenyl, 2-ethoxyphenyl, cyclohexyl, cyclopropyl, 5-methyl-2-pyrazinyl, 2-tetrahydrofuryl, 3-(2-thienyl)propyl, 1-phenyl-1-cyclopentyl, α-cyclopentylbenzyl, 1-methylcyclohexyl, 2-chloro-3-pyridyl, cyclopentyl, 1-methyl-2-pyrrolyl, 2,6-dimethoxyphenyl, 2,6-dimethoxy-3-pyridyl, 2-(2-thienyl)vinyl, 2-nitro-5-thiocyanatophenyl, 2-(tert-butoxycarbonylamino)-2-propyl, 1-(tert-butoxycarbonyl)piperidin-4-yl, 2-methyl-3-pyridyl, 1-(acetylamino)-2-methylpropyl, 1-acetyl-4-hydroxypyrrolidin-2-yl, 1,3-dihydroxy-2-methyl-2-propyl, 3-methylthio-1-acetylaminopropyl, 2,6-dimethoxy-4-hydroxyphenyl, 4-nitro-3-pyrazolyl, 4-sulfamoylphenyl, 1-acetylaminovinyl, 2-(benzyloxycarbonyl)-1-(tert-butoxycarbonylamino) ethyl, 4-(1-hexyloxy)phenyl, 1-(2-chlorophenoxy)-1-methylethyl, 3-hydroxy-4-methoxyphenyl, 3,5-dinitro-4-hydroxyphenyl, 4-piperidinyl hydrochloride, 2-carboxy-1-(tert-butoxycarbonylamino)ethyl, 2-(benzyloxycarbonyl)-1-aminoethyl hydrochloride, 2-carboxy-1-aminoethyl hydrochloride, 2-methyl-3-pyridyl hydrochloride, 2,4-dinitrophenyl, 1-hydroxy-1-phenylethyl, 2-nitro-3-hydroxy-4-methylphenyl, 2-methylcyclopropyl, 1-phenylpropyl, 1,2,3,4-tetrahydronaphth-2-yl, 1-benzyl-2,2-dimethylpropyl, 2,2,3,3-tetramethylcyclopropyl, acetoxymethyl, 2,2,2-trifluoro-1-methoxy-1-phenylethyl, 2-hexyl, 1-heptynyl, 3-tetrahydrofuryl, 2-methyl-2-butyl, 2-methylcyclohexyl, 2-methyl-4-penten-2-yl, 4-heptyl, 2-pentyl, 1-phenylethyl, phenoxymethyl, 2,3,4,5,6-pentafluorophenoxymethyl, 1-(methoxyimino)-1-((2-formylamino)-4-thiazolyl)methyl, 3-hydroxy-3-pentyl, 2-methoxyphenoxymethyl, mesityl, 2-methyl-1,4-cyclohexadien-3-yl, 2-(4-chlorophenoxy)-2-propyl, 2-hydroxy-2-butyl, 3-heptyl, 1-phenyl-2-methylbutyl, sec-butyl, cyclobutyl, 3-pentyl, α-(3,5-dinitrobenzoylamino)benzyl, 2,2-dichloro-1-methylcyclopropyl, 1,1,1-trifluoro-2-hydroxy-2-butyl, 3-nitro-4-hydroxyphenyl, 4,8-dihydroxy-2-quinolinyl, 2-hydroxy-1-phenylethyl, 4-hydroxyphenyl, neopentyl, 1-(3,5-dinitrobenzoylamino)-3-methylbutyl, 2-hydroxybenzoylaminomethyl, 3,3,3-trifluoropropyl, 2-pyridyl-N-oxide, 6-hydroxy-2-pyridyl, 3-hydroxy-2-pyridyl, benzoylaminomethyl, 1-methyl-2-oxo-5-(3-pyridyl)pyrrolidin-4-yl, 1,3,4,5-tetrahydroxycyclohexyl, 1-acetamido-2-methylpropyl, 1-acetamido-3-methylthiopropyl, 1-(tert-butoxycarbonylamino)-2-methylpropyl, 2-(2-chlorophenyl)vinyl, benzofuran-2-yl, 3-thienyl, 3-methylinden-2-yl, 3,4,5-trihydroxy-1-cyclohexenyl, 2-(2-(trifluoromethyl)phenyl)vinyl, 2-(4-methylphenyl)vinyl, cyclohexenyl, 2-(4-(trifluoromethyl)phenyl)vinyl, cyclopentenyl, 2-penten-2-yl, 2-(trifuoromethyl)-1-propenyl, 2-(2-fluorophenyl)vinyl, vinyl, 2-(4-(dimethylamino)phenyl)vinyl, 2-(2-methoxyphenyl)vinyl, 2-(3-hydroxy-4-methoxyphenyl)vinyl, 2-(3-(trifluoromethyl)phenyl)vinyl, 1-fluoro-2-phenylvinyl, 3-methyl-2-thienyl, 1-cyano-2-(4-hydroxyphenyl) vinyl, 2-(4-fluorophenyl)vinyl, isobutylidene, 7-methyl-1-ethyl-3-naphthyridinyl-4-one, 2-(3-methoxy-4-hydroxyphenyl)vinyl, 2-(5-(1,3-benzodioxolanyl))vinyl, 1-methylcyclopropyl, 2-furyl, 2-phenylvinyl, 2-(4-bromophenyl)vinyl, 3-furyl, 2-(4-methoxyphenyl)vinyl, 1-methyl-2-indolyl, 2-(3-pyridyl)vinyl, 2-(3-fluorophenyl)vinyl, 5-methyl-2-thienyl, 3-isoquinolinyl-1-one, 2,6-dimethyl-1,5-heptadienyl, 1-pentenyl, 2-(2,3-dimethoxyphenyl) vinyl, 1,3-pentadienyl, 2-(3-nitrophenyl)vinyl, 2-(4-chlorophenyl)vinyl, 2-(4-nitrophenyl)vinyl, 2-(3,4-dimethoxyphenyl)vinyl, 2-pentafluorophenylvinyl, 1-methyl-2-phenylvinyl, 2-(4-hydroxyphenyl)vinyl, 2-(3-hydroxyphenyl)vinyl, 2-(2-furyl)vinyl, 2-(3,4-dichlorophenyl)vinyl, 2-(2,4-dichlorophenyl)vinyl, 2-(2-nitrophenyl)vinyl, 1,1,1,3,3,3-hexafluoro-2-methyl-2-propyl, 1-(tert-butoxycarbonyl)-2-pyrrolidinyl, 1-(di-n-propylamino)ethyl, 2-amino-2-propyl hydrochloride or 2-pyrrolidinyl hydrochloride, when q is 0 and t is 1, $Z^2(X^2)_q$ is 3,5,6-trichloro-2-pyridyloxymethyl, 3,6-dichloro-2-pyridyl, 3-(4,6-dimethoxy-2-pyrimidinyloxy)-2-pyridyl or

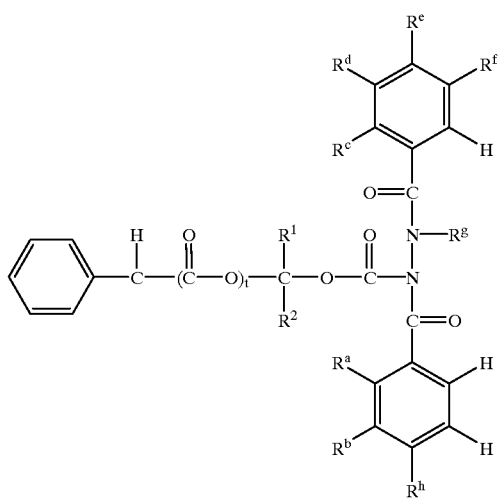

when both q and t are 1, or
the pesticidally acceptable salts, isomers and enantiomers thereof.

2. The compound of claim 1 wherein $R^g$ is tert-butyl.
3. The compound of claim 2 wherein $R^h$ is halo and $R^a$, $R^b$, $R^c$, $R^d$, $R^e$ and $R^f$ are hydrogen atoms.
4. The compound of claim 3 wherein $R^h$ is chloro.
5. The compound of claim 2 wherein $R^h$ is methyl or ethyl, $R^a$, $R^b$, $R^c$ and $R^e$ are hydrogen atoms, and $R^d$ and $R^f$ are independently selected from methyl, ethyl, halo and cyano.
6. The compound of claim 5 wherein $R^h$ is ethyl.
7. The compound of claim 6 wherein $R^d$ and $R^f$ are methyl.

8. The compound of claim 2 wherein $R^a$ is halo, methyl or ethyl, $R^b$ is methoxy or ethoxy, $R^c$, $R^e$ and $R^h$ are hydrogen atoms, and $R^d$ and $R^f$ are independently selected from methyl, ethyl, halo and cyano.
9. The compound of claim 8 wherein $R^a$ is methyl.
10. The compound of claim 9 wherein $R^b$ is methoxy.
11. The compound of claim 10 wherein $R^d$ and $R^f$ are methyl.
12. The compound of claim 2 wherein $R^a$ is halo, methyl or ethyl, $R^b$ and $R^h$ are taken together to form a methylenedioxy, a 1,2-ethylenedioxy, or a 1,2-ethyleneoxy or 1,3-propyleneoxy link wherein the oxo atom is located at either the $R^b$ or $R^h$ position, $R^c$ and $R^f$ are hydrogen atoms, and $R^d$ and $R^f$ are independently selected from methyl, ethyl, halo and cyano.
13. The compound of claim 12 wherein $R^a$ is methyl.
14. The compound of claim 13 wherein $R^b$ and $R^h$ are taken together to form a 1,3-propyleneoxy link.
15. The compound of claim 14 wherein the oxo atom is located at $R^h$.
16. The compound of claim 15 wherein $R^d$ and $R^f$ are methyl.

17. A pesticidal compound represented by formula (II)

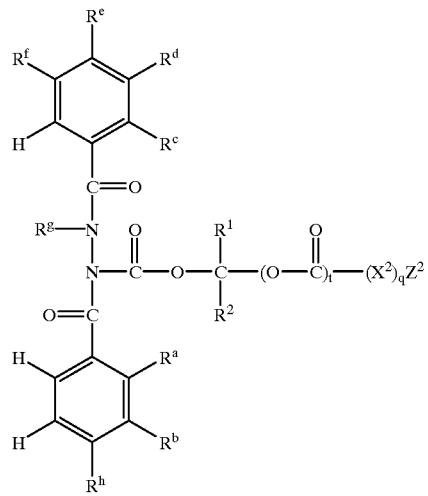

(II)

wherein $R^a$ is a hydrogen atom, halo or $(C_1-C_4)$alkyl, $R^b$ is a hydrogen atom or $(C_1-C_4)$alkoxy, optionally substituted with halo, $R^c$ is selected from a hydrogen atom, halo, $(C_1-C_4)$alkyl, $(C_1-C_4)$alkoxy, $(C_1-C_4)$alkoxy$(C_1-C_4)$alkyl and nitro, $R^d$, $R^e$ and $R^f$ are each independently selected from a hydrogen atom, halo, $(C_1-C_4)$alkyl, $(C_1-C_4)$alkoxy, and $(C_1-C_4)$alkoxy$(C_1-C_4)$alkyl, $R^g$ is a branched $(C_4-C_6)$alkyl, $R^h$ is a hydrogen atom, halo, $(C_1-C_4)$alkoxy, $(C_1-C_4)$alkyl, or when taken together with $R^b$ is methylenedioxy ($-OCH_2O-$), 1,2-ethylenedioxy ($-OCH_2CH_2O-$), or 1,2-ethyleneoxy ($-CH_2CH_2O-$) or 1,3-propyleneoxy ($-CH_2CH_2CH_2O-$) wherein the oxo atom is located at either the $R^b$ or $R^h$ position, the substituents $R^c$ and $R^d$, or $R^d$ and $R^e$, or $R^e$ and $R^f$ when taken together can be methylenedioxy or 1,2-ethylenedioxy, $R^1$ and $R^2$ are each independently a hydrogen atom, $(C_1-C_{20})$alkyl, $(C_2-C_{10})$alkenyl, $(C_2-C_{10})$alkynyl, $(C_1-C_{10})$alkoxy$(C_1-C_{10})$alkyl, $(C_1-C_{10})$alkoxy $(C_2-C_{10})$alkenyl, $(C_1-C_{10})$alkoxy$(C_2-C_{10})$alkynyl, $(C_1-C_{10})$alkylthio$(C_1-C_{10})$alkyl, $(C_1-C_{10})$alkylthio $(C_2-C_{10})$alkenyl, $(C_1-C_{10})$alkylthio$(C_2-C_{10})$alkynyl, carboxy, carboxy$(C_1-C_{20})$alkyl, carboxy$(C_2-C_{20})$ alkenyl, carboxy$(C_2-C_{20})$alkynyl, $(C_1-C_{20})$ alkoxycarbonyl, $(C_1-C_{10})$alkoxycarbonyl$(C_1-C_{10})$ alkyl, $(C_1-C_{10})$alkoxycarbonyl$(C_2-C_{10})$alkenyl, $(C_1-C_{10})$alkoxycarbonyl$(C_2-C_{10})$alkynyl, $(C_1-C_{20})$ alkylcarbonyl, $(C_2-C_{20})$alkenylcarbonyl, $(C_2-C_{20})$ alkynylcarbonyl, cyclo$(C_3-C_8)$alkyl, cyclo$(C_3-C_8)$ alkenyl, cyclo$(C_3-C_8)$alkyl$(C_1-C_{10})$alkyl, cyclo $(C_3-C_8)$alkenyl$(C_1-C_{10})$alkyl, cyclo$(C_3-C_8)$alkyl $(C_2-C_{10})$alkenyl, cyclo$(C_3-C_8)$alkenyl$(C_2-C_{10})$ alkenyl, cyclo$(C_3-C_8)$alkyl$(C_2-C_{10})$alkynyl, cyclo $(C_3-C_8)$alkenyl$(C_2-C_{10})$alkynyl, heterocyclyl, heterocyclyl$(C_1-C_{10})$alkyl, heterocyclyl$(C_2-C_{10})$ alkenyl, heterocyclyl$(C_2-C_{10})$alkynyl, aryl, aryl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$ alkenyl, halo$(C_2-C_{10})$alkynyl, $(C_1-C_{10})$alkoxy, halo $(C_1-C_{10})$alkoxy, $SO_2NR^3R^4$ and $NR^3R^4$, ar$(C_1-C_{10})$ alkyl, ar$(C_2-C_{10})$alkenyl, ar$(C_2-C_{10})$alkynyl, or ar$(C_1-C_{10})$alkyl, ar$(C_2-C_{10})$alkenyl, ar$(C_2-C_{10})$ alkynyl substituted with one or more substituents independently selected from halo, $(C_1-C_{10})$alkyl, $(C_2-C_{10})$ alkenyl, $(C_2-C_{10})$alkynyl, halo$(C_1-C_{10})$alkyl, halo $(C_2-C_{10})$alkenyl, halo$(C_2-C_{10})$alkynyl, $(C_1-C_{10})$ alkoxy, halo$(C_1-C_{10})$alkoxy, $SO_2NR^3R^4$ and $NR^3R^4$, heteroaryl, heteroaryl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo $(C_2-C_{10})$alkynyl, $(C_1-C_{10})$alkoxy, halo$(C_1-C_{10})$alkoxy and $NR^3R^4$, heteroar$(C_1-C_{10})$alkyl, heteroar$(C_2-C_{10})$ alkenyl, heteroar$(C_2-C_{10})$alkynyl or heteroar$(C_1-C_{10})$ alkyl, heteroar$(C_2-C_{10})$alkenyl, heteroar$(C_2-C_{10})$ alkynyl substituted with one or more substituents independently selected from halo, $(C_1-C_{10})$alkyl, $(C_2-C_{10})$alkenyl, $(C_2-C_{10})$alkynyl, halo$(C_1-C_{10})$alkyl, halo$(C_2-C_{10})$alkenyl, halo$(C_2-C_{10})$alkynyl, $(C_1-C_{10})$ alkoxy, halo$(C_1-C_{10})$alkoxy, $SO_2NR^3R^4$ and $NR^3R^4$, or $R^1$ and $R^2$ taken together with the carbon atom to which they are attached form a 5–7 membered saturated or unsaturated ring, or $R^1$ may be a pesticidal moiety if $R^2$ is a hydrogen atom, $Z^2(X^2)_q$ is halo, $NR^3R^4$, $\{(NR^3R^4R^5)^+M^-\}$, $OR^3$, $S(O)_jR^3$ or $SO_2NR^3R^4$ when both q and t are 0 wherein $M^-$ is halo, hydroxy, $(C_1-C_8)$alkoxy or the anion of a carboxylic acid and j is 0, 1 or 2, $R^3$, $R^4$ and $R^5$ are each independently a hydrogen atom, $(C_1-C_{20})$alkyl, cyclo$(C_3-C_8)$alkyl, cyclo$(C_3-C_8)$ alkenyl, cyclo$(C_3-C_8)$alkyl$(C_1-C_{10})$alkyl, cyclo $(C_3-C_8)$alkyl$(C_2-C_{10})$alkenyl, cyclo$(C_3-C_8)$alkyl $(C_2-C_{10})$alkynyl, cyclo$(C_3-C_8)$alkenyl$(C_1-C_{10})$alkyl, cyclo$(C_3-C_8)_{alkenyl(C2}-C_{10})$alkenyl, cyclo$(C_3-C_8)$ alkenyl$(C_2-C_{10})$alkynyl, heterocyclyl, heterocyclyl $(C_1-C_{10})$alkyl, heterocyclyl$(C_2-C_{10})$alkenyl, heterocyclyl$(C_2-C_{10})$alkynyl, $(C_1-C_{10})$alkoxy $(C_1-C_{10})$alkyl, $(C_2-C_{10})$alkenyl, $(C_2-C_{10})$alkynyl, or $(C_1-C_{10})$alkyl, cyclo$(C_3-C_8)$alkyl, cyclo$(C_3-C_8)$ alkenyl, cyclo$(C_3-C_8)$alkyl$(C_1-C_{10})$alkyl, cyclo $(C_3-C_8)$alkyl$(C_2-C_{10})$alkenyl, cyclo$(C_3-C_8)$alkyl $(C_2-C_{10})$alkynyl, cyclo$(C_3-C_8)$alkenyl$(C_1-C_{10})$alkyl, cyclo$(C_3-C_8)$alkenyl$(C_2-C_{10})$alkenyl, cyclo$(C_3-C_8)$ alkenyl$(C_2-C_{10})$alkynyl, heterocyclyl, heterocyclyl $(C_1-C_{10})$alkyl, heterocyclyl$(C_2-C_{10})$alkenyl, heterocyclyl$(C_2-C_{10})$alkynyl, $(C_1-C_{10})$alkoxy $(C_1-C_{10})$alkyl, $(C_2-C_{10})$alkenyl or $(C_2-C_{10})$alkynyl substituted with one or more halo, aryl, ar$(C_1-C_{10})$ alkyl, ar$(C_2-C_{10})$alkenyl, ar$(C_2-C_{10})$alkynyl or aryl, ar$(C_1-C_{10})$alkyl, ar$(C_2-C_{10})$alkenyl, ar$(C_2-C_{10})$ alkynyl substituted with one or more substituents independently selected from halo, $(C_1-C_{10})$alkyl, $(C_2-C_{10})$ alkenyl, $(C_2-C_{10})$alkynyl, halo$(C_1-C_{10})$alkyl, halo $(C_2-C_{10})$alkenyl, halo$(C_2-C_{10})$alkynyl, $(C_1-C_{10})$ alkoxy and halo$(C_1-C_{10})$alkoxy, heteroaryl, heteroar $(C_1-C_{10})$alkyl, heteroar$(C_2-C_{10})$alkenyl, heteroar $(C_2-C_{10})$alkynyl or heteroaryl, heteroar$(C_1-C_{10})$alkyl, heteroar$(C_2-C_{10})$alkenyl, heteroar$(C_2-C_{10})$alkynyl substituted with one or more substituents independently selected from halo, $(C_1-C_{10})$alkyl, $(C_2-C_{10})$ alkenyl, $(C_2-C_{10})$alkynyl, halo$(C_1-C_{10})$alkyl, halo $(C_2-C_{10})$alkenyl, halo$(C_2-C_{10})$alkynyl, $(C_1-C_{10})$ alkoxy and halo$(C_1-C_{10})$alkoxy, or $R^3$ and $R^4$ taken together with the nitrogen atom to which they are attached form a 5- or 6-membered saturated or unsaturated heterocyclic ring, $Z^2(X^2)_q$ is a pesticidal moiety selected from the group consisting of E,E)-8,10-dodecadienoxy, dodecane-1-oxy, (E)-11-tetradecen-1-oxy, (Z)-9-tetradecen-1-oxy, (Z)-11-hexadecene-1-oxy, when q is 1 and t is 0, or the pesticidally acceptable salts, isomers and enantiomers thereof.

18. A pesticidal compound represented by formula (IIA)

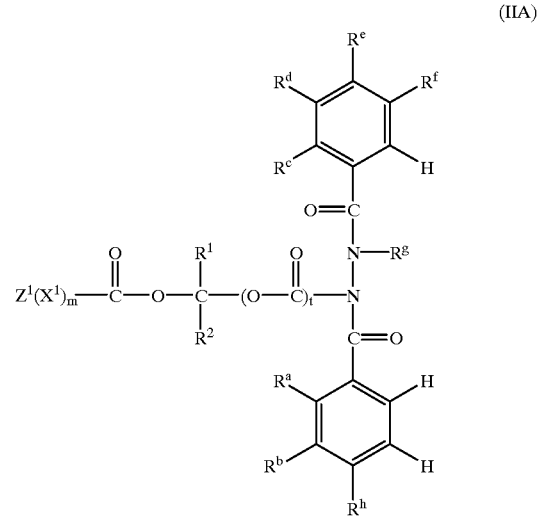

(IIA)

wherein $R^a$ is a hydrogen atom, halo or $(C_1-C_4)$alkyl, $R^b$ is a hydrogen atom or $(C_1-C_4)$alkoxy, optionally substituted with halo, $R^c$ is selected from a hydrogen atom, halo, $(C_1-C_4)$alkyl, $(C_1-C_4)$alkoxy, $(C_1-C_4)$alkoxy$(C_1-C_4)$alkyl and nitro, $R^d$, $R^e$ and $R^f$ are each independently selected from a hydrogen atom, halo, $(C_1-C_4)$alkyl, $(C_1-C_4)$alkoxy, and $(C_1-C_4)$alkoxy$(C_1-C_4)$alkyl, $R^g$ is a branched $(C_4-C_6)$alkyl, $R^h$ is a hydrogen atom, halo, $(C_1-C_4)$alkoxy, $(C_1-C_4)$ alkyl, or when taken together with $R^b$ is methylenedioxy ($-OCH_2O-$), 1,2-ethylenedioxy ($-OCH_2CH_2O-$), or 1,2-ethyleneoxy ($-CH_2CH_2O-$) or 1,3-propyleneoxy (—CH$_2$CH$_2$CH$_2$O—) wherein the oxo atom is located at either the R$^b$ or R$^h$ position, the substituents R$^c$ and R$^d$, or R$^d$ and R$^e$, or R$^e$ and R$^f$ when taken together can be methylenedioxy or 1,2-ethylenedioxy, R$^1$ and R$^2$ are each independently a hydrogen atom, (C$_1$–C$_{20}$)alkyl, (C$_2$–C$_{10}$)alkenyl, (C$_2$–C$_{10}$)alkynyl, (C$_1$–C$_{10}$)alkoxy(C$_1$–C$_{10}$)alkyl, (C$_1$–C$_{10}$)alkoxy (C$_2$–C$_{10}$)alkenyl, (C$_1$–C$_{10}$)alkoxy(C$_2$–C$_{10}$)alkynyl, (C$_1$–C$_{10}$)alkylthio(C$_1$–C$_{10}$)alkyl, (C$_1$–C$_{10}$)alkylthio (C$_2$–C$_{10}$)alkenyl, (C$_1$–C$_{10}$)alkylthio(C$_2$–C$_{10}$)alkynyl, carboxy, carboxy(C$_1$–C$_{20}$)alkyl, carboxy(C$_2$–C$_{20}$) alkenyl, carboxy(C$_2$–C$_{20}$)alkynyl, (C$_1$–C$_{20}$) alkoxycarbonyl, (C$_1$–C$_{10}$)alkoxycarbonyl(C$_1$–C$_{10}$) alkyl, (C$_1$–C$_{10}$)alkoxycarbonyl(C$_2$–C$_{10}$)alkenyl, (C$_1$–C$_{10}$)alkoxycarbonyl(C$_2$–C$_{10}$)alkynyl, (C$_1$–C$_{20}$) alkylcarbonyl, (C$_2$–C$_{20}$)alkenylcarbonyl, (C$_2$–C$_{20}$) alkynylcarbonyl, cyclo(C$_3$–C$_8$)alkyl, cyclo(C$_3$–C$_8$) alkenyl, cyclo(C$_3$–C$_8$)alkyl(C$_1$–C$_{10}$)alkyl, cyclo (C$_3$–C$_8$)alkenyl(C$_1$–C$_{10}$)alkyl, cyclo(C$_3$–C$_8$)alkyl (C$_2$–C$_{10}$)alkenyl, cyclo(C$_3$–C$_8$)alkenyl(C$_2$–C$_{10}$) alkenyl, cyclo(C$_3$–C$_8$)alkyl(C$_2$–C$_{10}$)alkynyl, cyclo (C$_3$–C$_8$)alkenyl(C$_2$–C$_{10}$)alkynyl, heterocyclyl, heterocyclyl(C$_1$–C$_{10}$)alkyl, heterocyclyl(C$_2$–C$_{10}$) alkenyl, heterocyclyl(C$_2$–C$_{10}$)alkynyl, aryl, aryl substituted with one or more substituents independently selected from halo, (C$_1$–C$_{10}$)alkyl, (C$_2$–C$_{10}$)alkenyl, (C$_2$–C$_{10}$)alkynyl, halo(C$_1$–C$_{10}$)alkyl, halo(C$_2$–C$_{10}$) alkenyl, halo(C$_2$–C$_{10}$)alkynyl, (C$_1$–C$_{10}$)alkoxy, halo (C$_1$–C$_{10}$)alkoxy, SO$_2$NR$^3$R$^4$ and NR$^3$R$^4$, ar(C$_1$–C$_{10}$) alkyl, ar(C$_2$–C$_{10}$)alkenyl, ar(C$_2$–C$_{10}$)alkynyl, or ar(C$_1$–C$_{10}$)alkyl, ar(C$_2$–C$_{10}$)alkenyl, ar(C$_2$–C$_{10}$) alkynyl substituted with one or more substituents independently selected from halo, (C$_1$–C$_{10}$)alkyl, (C$_2$–C$_{10}$) alkenyl, (C$_2$–C$_{10}$)alkynyl, halo(C$_1$–C$_{10}$)alkyl, halo (C$_2$–C$_{10}$)alkenyl, halo(C$_2$–C$_{10}$)alkynyl, (C$_1$–C$_{10}$) alkoxy, halo(C$_1$–C$_{10}$)alkoxy, SO$_2$NR$^3$R$^4$ and NR$^3$R$^4$, heteroaryl, heteroaryl substituted with one or more substituents independently selected from halo, (C$_1$–C$_{10}$)alkyl, (C$_2$–C$_{10}$)alkenyl, (C$_2$–C$_{10}$)alkynyl, halo(C$_1$–C$_{10}$)alkyl, halo(C$_2$–C$_{10}$)alkenyl, halo (C$_2$–C$_{10}$)alkynyl, (C$_1$–C$_{10}$)alkoxy, halo(C$_1$–C$_{10}$)alkoxy and NR$^3$R$^4$, heteroar(C$_1$–C$_{10}$)alkyl, heteroar(C$_2$–C$_{10}$) alkenyl, heteroar(C$_2$–C$_{10}$)alkynyl or heteroar(C$_1$–C$_{10}$) alkyl, heteroar(C$_2$–C$_{10}$)alkenyl, heteroar(C$_2$–C$_{10}$) alkynyl substituted with one or more substituents independently selected from halo, (C$_1$–C$_{10}$)alkyl, (C$_2$–C$_{10}$)alkenyl, (C$_2$–C$_{10}$)alkynyl, halo(C$_1$–C$_{10}$)alkyl, halo(C$_2$–C$_{10}$)alkenyl, halo(C$_2$–C$_{10}$)alkynyl, (C$_1$–C$_{10}$) alkoxy, halo(C$_1$–C$_{10}$)alkoxy, SO$_2$NR$^3$R$^4$ and NR$^3$R$^4$, or R$^1$ and R$^2$ taken together with the carbon atom to which they are attached form a 5–7 membered saturated or unsaturated ring, or R$^1$ may be a pesticidal moiety if R$^2$ is a hydrogen atom, m is 0 or 1, t is 0, Z$^1$(X$^1$)$_m$ is NR$^3$R$^4$, OR$^3$, S(O)$_j$R$^3$ or SO$_2$NR$^3$R$^4$ when m is 0 and j is 0, 1 or 2, R$^3$, R$^4$ and R$^5$ are each independently a hydrogen atom, (C$_1$–C$_{20}$)alkyl, cyclo(C$_3$–C$_8$)alkyl, cyclo(C$_3$–C$_8$) alkenyl, cyclo(C$_3$–C$_8$)alkyl(C$_1$–C$_{10}$)alkyl, cyclo (C$_3$–C$_8$)alkyl(C$_2$–C$_{10}$)alkenyl, cyclo(C$_3$–C$_8$)alkyl (C$_2$–C$_{10}$)alkynyl, cyclo(C$_3$–C$_8$)alkenyl(C$_1$–C$_{10}$)alkyl, cyclo(C$_3$–C$_8$)alkenyl(C$_2$–C$_{10}$)alkenyl, cyclo(C$_3$–C$_8$) alkenyl(C$_2$–C$_{10}$)alkynyl, heterocyclyl, heterocyclyl (C$_1$–C$_{10}$)alkyl, heterocyclyl(C$_2$–C$_{10}$)alkenyl, heterocyclyl(C$_2$–C$_{10}$)alkynyl, (C$_1$–C$_{10}$)alkoxy (C$_1$–C$_{10}$)alkyl, (C$_2$–C$_{10}$)alkenyl, (C$_2$–C$_{10}$)alkynyl, or (C$_1$–C$_{10}$)alkyl, cyclo(C$_3$–C$_8$)alkyl, cyclo(C$_3$–C$_8$) alkenyl, cyclo(C$_3$–C$_8$)alkyl(C$_1$–C$_{10}$)alkyl, cyclo (C$_3$–C$_8$)alkyl(C$_2$–C$_{10}$)alkenyl, cyclo(C$_3$–C$_8$)alkyl (C$_2$–C$_{10}$)alkynyl, cyclo(C$_3$–C$_8$)alkenyl(C$_1$–C$_{10}$)alkyl, cyclo(C$_3$–C$_8$)alkenyl(C$_2$–C$_{10}$)alkenyl, cyclo(C$_3$–C$_8$) alkenyl(C$_2$–C$_{10}$)alkynyl, heterocyclyl, heterocyclyl (C$_1$–C$_{10}$)alkyl, heterocyclyl(C$_2$–C$_{10}$)alkenyl, heterocyclyl(C$_2$–C$_{10}$)alkynyl, (C$_1$–C$_{10}$)alkoxy (C$_1$–C$_{10}$)alkyl, (C$_2$–C$_{10}$)alkenyl or (C$_2$–C$_{10}$)alkynyl substituted with one or more halo, aryl, ar(C$_1$–C$_{10}$) alkyl, ar(C$_2$–C$_{10}$)alkenyl, ar(C$_2$–C$_{10}$)alkynyl or aryl, ar(C$_1$–C$_{10}$)alkyl, ar(C$_2$–C$_{10}$)alkenyl, ar(C$_2$–C$_{10}$) alkynyl substituted with one or more substituents independently selected from halo, (C$_1$–C$_{10}$)alkyl, (C$_2$–C$_{10}$) alkenyl, (C$_2$–C$_{10}$)alkynyl, halo(C$_1$–C$_{10}$)alkyl, halo (C$_2$–C$_{10}$)alkenyl, halo(C$_2$–C$_{10}$)alkynyl, (C$_1$–C$_{10}$) alkoxy and halo(C$_1$–C$_{10}$)alkoxy, heteroaryl, heteroar (C$_1$–C$_{10}$)alkyl, heteroar(C$_2$–C$_{10}$)alkenyl, heteroar (C$_2$–C$_{10}$)alkynyl or heteroaryl, heteroar(C$_1$–C$_{10}$)alkyl, heteroar(C$_2$–C$_{10}$)alkenyl, heteroar(C$_2$–C$_{10}$)alkynyl substituted with one or more substituents independently selected from halo, (C$_1$–C$_{10}$)alkyl, (C$_2$–C$_{10}$) alkenyl, (C$_2$–C$_{10}$)alkynyl, halo(C$_1$–C$_{10}$)alkyl, halo (C$_2$–C$_{10}$)alkenyl, halo(C$_2$–C$_{10}$)alkynyl, (C$_1$–C$_{10}$) alkoxy and halo(C$_1$–C$_{10}$)alkoxy, or R$^3$ and R$^4$ taken together with the nitrogen atom to which they are attached form a 5- or 6-membered saturated or unsaturated heterocyclic ring, Z$^1$(X$^1$)$_m$ is a pesticidal moiety selected from the group consisting of (E,E)-8,10-dodecadienoxy, dodecane-1-oxy, (E)-11-tetradecen-1-oxy, (Z)-9-tetradecen-1-oxy, (Z)-11-hexadecene-1-oxy, or the pesticidally acceptable salts, isomers and enantiomers thereof.

19. A pesticidal composition comprising a compound as in any one of claims 1–16 and 17–18 and a pesticidally acceptable carrier.

20. The composition of claim 19 which contains from about 0.1% to about 99% by weight of said compound.

21. A method of controlling a pest comprising applying a pesticidally effective amount of a compound as in any one of claims 1–16 and 17–18 to the pest, to the locus of the pest or to the growth medium of said pest.

22. A method of controlling a pest comprising applying a pesticidally effective amount of a composition of claim 20 and a pesticidally acceptable carrier to the pest, to the locus of the pest or to the growth medium of said pest.

* * * * *